US010676721B2

(12) United States Patent
Collins et al.

(10) Patent No.: US 10,676,721 B2
(45) Date of Patent: Jun. 9, 2020

(54) BACTERIOPHAGES EXPRESSING ANTIMICROBIAL PEPTIDES AND USES THEREOF

(75) Inventors: James J. Collins, Newton, MA (US); Michael Koeris, Natick, MA (US); Timothy Kuan-Ta Lu, Charlestown, MA (US); Tanguy My Chau, Palo Alto, CA (US); Gregory Stephanopoulos, Winchester, MA (US); Christopher Jongsoo Yoon, Seoul (KR)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 2166 days.

(21) Appl. No.: 13/224,776

(22) Filed: Sep. 2, 2011
(Under 37 CFR 1.47)

(65) Prior Publication Data

US 2015/0050717 A1 Feb. 19, 2015

Related U.S. Application Data

(63) Continuation of application No. PCT/US2010/026357, filed on Mar. 5, 2010.

(60) Provisional application No. 61/157,773, filed on Mar. 5, 2009.

(51) Int. Cl.

| | |
|---|---|
| ***C12N 7/00*** | (2006.01) |
| ***A61K 35/76*** | (2015.01) |
| ***A61K 38/17*** | (2006.01) |
| ***C07K 14/435*** | (2006.01) |
| ***C07K 14/46*** | (2006.01) |
| ***C12N 9/50*** | (2006.01) |

(52) U.S. Cl.

CPC ................ *C12N 7/00* (2013.01); *A61K 35/76* (2013.01); *A61K 38/1767* (2013.01); *C07K 14/43504* (2013.01); *C07K 14/43563* (2013.01); *C07K 14/463* (2013.01); *C12N 9/503* (2013.01); *C12N 2795/10221* (2013.01); *C12N 2795/10231* (2013.01); *C12N 2795/10232* (2013.01); *C12N 2795/12032* (2013.01); *C12N 2795/12043* (2013.01); *C12N 2795/14132* (2013.01); *C12N 2795/14143* (2013.01)

(58) Field of Classification Search

None

See application file for complete search history.

(56) References Cited

U.S. PATENT DOCUMENTS

| | | | |
|---|---|---|---|
| 4,678,750 A | 7/1987 | Vandenbergh et al. | |
| 6,335,012 B1 | 1/2002 | Fischetti et al. | |
| 6,699,701 B1 | 3/2004 | Sulakvelidze et al. | |
| 6,759,229 B2 * | 7/2004 | Schaak | 435/235.1 |
| 7,211,426 B2 | 5/2007 | Bruessow et al. | |
| 8,153,119 B2 | 4/2012 | Collins et al. | |
| 8,182,804 B1 | 5/2012 | Collins et al. | |
| 2001/0026795 A1 | 10/2001 | Merril et al. | |
| 2002/0013671 A1 | 1/2002 | Ananthaiyer et al. | |
| 2004/0161141 A1 | 8/2004 | Dewaele | |
| 2005/0004030 A1 | 1/2005 | Fischetti et al. | |
| 2007/0020240 A1 | 1/2007 | Jayasheela et al. | |
| 2007/0134207 A1 | 6/2007 | Bruessow et al. | |
| 2007/0207209 A1 * | 9/2007 | Murphy | A61K 9/06 424/484 |
| 2007/0248724 A1 | 10/2007 | Sulakvelidze et al. | |
| 2008/0194000 A1 | 8/2008 | Pasternack et al. | |
| 2008/0247997 A1 | 10/2008 | Reber et al. | |
| 2008/0311643 A1 | 12/2008 | Sulakvelidze et al. | |
| 2008/0318867 A1 | 12/2008 | Loessner et al. | |

FOREIGN PATENT DOCUMENTS

| | | | |
|---|---|---|---|
| EP | 0403458 A1 * | 12/1990 | C07K 7/10 |
| WO | 2002/034892 A1 | 5/2002 | |
| WO | 2004/046319 A2 | 6/2004 | |
| WO | 2004/062677 A1 | 7/2004 | |
| WO | 2005/009451 A1 | 2/2005 | |
| WO | 2005/071088 A1 | 8/2005 | |
| WO | 2006/137847 A2 | 12/2006 | |
| WO | 2008/110840 A1 | 9/2008 | |
| WO | 2009/108406 A2 | 9/2009 | |

OTHER PUBLICATIONS

Westwater et al., Antimicrobial Agents and Chemotherapy, 2003, vol. 47, pp. 1301-1307.*

Westwater et al., Antimicrobial Agents and Chemotherapy, 2003, Vo147, pp. 1301-1307.*

Horgan et al., Applied and Environmental Microbiology, 2008, vol. 75, pp. 872-874.*

Chap, Genbank accession No. YP_241096.1, published May 20, 2007.*

Clark et al., Trends in Biotechnology, 2006, vol. 24., pp. 212-218.*

Takahara et al., The Journal of Biological Chemistry, 1985, vol. 260, pp. 2670-2674.*

Sargent et al., FEMS, 2006, vol. 254, pp. 198-207.*

(Continued)

*Primary Examiner* — Mindy G Brown

(74) *Attorney, Agent, or Firm* — Nixon Peabody LLP

(57) ABSTRACT

The present invention is generally related to engineered bacteriophages expressing antimicrobial peptides or lytic enzymes or fragments thereof for targeting a broad spectrum of bacterial hosts, and for the long-term suppression of bacterial phage resistance for reducing bacterial infections. In some embodiments, bacteriophages express antimicrobial peptides or antimicrobial polypeptides (e.g. phage lytic enzymes) which are secreted from the host bacteria, or alternatively released upon lysis of the bacterial host cell. Aspects of the present invention also relate to the use of the engineered bacteriophages for the reduction of bacterial infections, both in a subject or for bioremediation purposes, in clinical settings and wound healing.

19 Claims, 30 Drawing Sheets

Specification includes a Sequence Listing.

(56) References Cited

OTHER PUBLICATIONS

Stein, et al., "Two Different Lantibiotic-Like Peptides Originate from the Ericin Gene Cluster of Bacillus subtills A 1/3," J. Bacteriol 2002, 184(6):1703-1711.

Obeso, et al., "Lytic activity of the recombinant staphylococcal Bacteriophage PhiH5 endolysin active against *Staphylococcus aureus* in milk," Int J Food Microbiol. 2008, 128(2):212-218.

Becker et al., FEMS Microbiol Lett., 287(2):185-91 (2008). "The phage K lytic enzyme LysK and lysostaphin act synergistically to kill MRSA."

Brogden,K.A., Nat Rev Microbiol., 3(3):238-50 (2005). "Antimicrobial peptides: pore formers or metabolic inhibitors in bacteria?".

Lutz and Bujard, Nucleic Acids Res., 25(6):1203-10 (1997). "Independent and tight regulation of transcriptional in units *Escherichia coli* via the LacR/O, the TetR/O and AraC/I1-I2 regulatory elements."

Cegelski et al., Nat Rev Microbiol. , 6(1):17-27 (2008). "The biology and future prospects of antivirulence therapies."

Curtin et al., Antimicrob Agents Chemother. , 50(4):1268-75 (2006). "Using bacteriophages to reduce formation of catheter-associated biofilms by *Staphylococcus epidermidis*."

Dai et al., Proc Natl Acad Sci U S A., 107(9):4347-52 (2010). "Three-dimensional structure of tropism-switching Bordetella bacteriophage."

Deresinski, S., Clin Infect Dis., 48(8):1096-101 (2009). "Bacteriophage therapy: exploiting smaller fleas."

D'Herelle, F. Comptes Rendus Hebdomadaires des Seances de L'academie des Sciences ( 165): 373-5. (1917). "An invisible antagonist microbe of dysentery bacillus".

Fischetti, V.A., Nat Biotechnol., 19(8):734-5 (2001). "Phage antibacterials make a comeback."

Hagens et al., Microb Drug Resist., 12(3):164-8 (2006). "Augmentation of the antimicrobial efficacy of antibiotics by filamentous phage."

Hancock et al., Nat Biotechnol., 24(12):1551-7 (2006). "Antimicrobial and host-defense peptides as new anti-infective therapeutic strategies."

Horgan et al., Appl Environ Microbiol., 75(3):872-4 (2009). "Phage lysin LysK can be truncated to its CHAP domain and retain lytic activity against live antibiotic-resistant staphylococci."

Huff et al., Poultry Science, 83:1944-1947, (2004). "Therapeutic efficacy of bacteriophage and Baytril (enrofloxacin) individually and in combination to treat colibacillosis in broilers."

Jensen et al., Appl Environ Microbiol., 64(2):575-80 (1998). "Prevalence of broad-host-range lytic bacteriophages of Sphaerotilus natans, *Escherichia coli*, and Pseudomonas aeruginosa."

Keller et al., Nat Rev Microbiol., 4(4):249-58 (2006). "Communication in bacteria: an ecological and evolutionary perspective."

Lederberg, J., Proc Natl Acad Sci U S A., 93(8):3167-8, (1996). "Smaller fleas . . . ad infinitum: therapeutic bacteriophage redux."

Liu et al., Science., 295(5562):2091-4 (2002). "Reverse transcriptase-mediated tropism switching in Bordetella bacteriophage."

Loose et al., Nature., 443(7113):867-9 (2006). "A linguistic model for the rational design of antimicrobial peptides."

Lorch, A., Biotechnology and Development Monitor, 39:14-17, (1999). "Bacteriophages: An alternative to antibiotics?".

Lu et al., Proc Natl Acad Sci U S A., 104(27):11197-202 (2007). "Dispersing biofilms with engineered enzymatic bacteriophage."

Lu et al., Proc Natl Acad Sci U S A., 106(12):4629-34, (2009). "Engineered bacteriophage targeting gene networks as adjuvants for antibiotic therapy."

Merril et al., Nat Rev Drug Discov., 2(6):489-97 (2003) "The prospect for bacteriophage therapy in Western medicine."

Movva et al., J Biol Chem., 255(1):27-9, (1980) "Amino acid sequence of the signal peptide of ompA protein, a major outer membrane protein of *Escherichia coli*."

O'Flaherty et al., Journal of Bacteriology, 187(20):7161-7164, (2005). "The recombinant phage lysin LysK has a broad spectrum of lytic activity against clinically relevant staphylococci, including methicillin-resistant *Staphylococcus aureus*."

Skurnik et al., Int J Med Microbiol., 296(1):5-14 (2006). "Phage therapy: facts and fiction."

Stone, R., Science., 298(5594):728-31 (2002). "Bacteriophage therapy. Stalin's forgotten cure."

Twort, F. W., Lancet, 2:1241-1243, (1915). "An investigation on the nature of ultra-microscopic viruses."

Westwater et al., Antimicrob Agents Chemother. , 47(4):1301-7 (2003). "Use of genetically engineered phage to deliver antimicrobial agents to bacteria: an alternative therapy for treatment of bacterial infections."

Wise, R., J Antimicrob Chemother., 54(2):306-10, (2004). "The relentless rise of resistance?"

Yacoby et al., Antimicrob Agents Chemother., 50(6):2087-97, (2006). "Targeting antibacterial agents by using drug-carrying filamentous bacteriophages."

Yacoby et al., Antimicrob Agents Chemother., 51(6):2156-63, (2007). "Targeted drug-carrying bacteriophages as antibacterial nanomedicines."

* cited by examiner

FIG. 18
1% TAE, 150V, 30MIN
R8903 DIGESTED Nde I, Bam HI
2-LOG LADDER
2
3

SEQUENCE LISTING

<160> NUMBER OF SEQ ID NOS: 122

<210> SEQ ID NO 1
<211> LENGTH: 5408
<212> TYPE: DNA
<213> ORGANISM: Bos taurus

<400> SEQUENCE: 1

```
ggtcccaaga tggcgtcgtg gctgccggag actctgttcg aaattgtagg acaaggccca     60

gcgccgagca aagactatta ccagttattg gtcacccggt tccaggtaat ttttagatgg    120

tggaagatct ctctgaggag tgagtatcga tcaacaaaac ctggagaaac aaaagaaact    180

catgaagact tcctagagaa gtcacatctt caggttcaaa ttgccttaat atttggttca    240

agaatattag actatgtctt caatttatgt gaaggtaaat ttgacttcct tgaacggctc    300

tcagacagtt tgctgctgaa tatcatttct tacctggatc ttgaagacat tgccaggctt    360

tctcaaacat cacgcagatt tgcaaagttg tgcatgtcgg acgaactgtg ggagcagatc    420

gtccggagct cctgtgacca catcaccccc gacatgcgag ccttggccca ggacatgggt    480

tggagacaga tgtacttcac caacaagctg cagctccagc ggcacctccg caagaggaag    540

cagcggcagg gaagccagcg aagcagtcag ctctagatgc acaagttccc gccgccgggg    600

agtaggaggc acggctgtgt tttccttctg tgtcagacct cttccgctgc cttcccttaa    660

gggaaccgct gccgattcaa ggtgtcatag agtacttgca cacgcacgca gcaccctgcc    720

tgcctctgcc aggtcttttg cctgaaccac agtctcggct acaggagcag tatcatcaac    780

ctaaaatgct gtaagacatc agcaacctca gtggtcgatc attctgcctc tctctcccgc    840

ctccatgggg aggcgatggt ggttttgcct ctccgcctct gctgacagtt tttatgtgga    900

cagataaatc tgcttcgttc atgacacatc gtttcagagt gaaatgccac agcagtttat    960

acttttgtct ctttttgtct tttcactcaa aagtgcttct acccggctat cactcaccat   1020

tgtaactgta aaagtaaaat gctgatattc tccaatgact catatgttta gtgttataaa   1080

aataatttat taacagtcgc atatgtgaat atttaattta taaactaaag aaatatgtat   1140

attttactcc atgtcaactt ctattactgc tttttattct tgaagaggtt agtatattac   1200

aagcattaaa ctttgattat atggaatctg caatttttaa aaaaataatt ttatttattt   1260

ttggctttgc tggatcttgg ttactgcaca ggcttttctc caggtgagcg ggtgctactg   1320

tctaattgca gtgcacgggc ttctcattgt ggagcttctg ttcaagggct tctgttgttg   1380

gggcgcacag gctctaggca cacaggctca ggactttggt tcacgggccc tagagtgagc   1440

aggctccagt aattgtggcg gacaggctta gctgctccgt agcatgtgga atcttcctgg   1500

accagggatg gaacccatgt cccctgcact ggcagatgca tttcttatcc actgtgccac   1560

cagggaagtc cctgttccaa gcctttgacg aactggatta ttgcccactt ttccataagc   1620

atactattat atgtgcatgt gtgcgtgctc agtcgctcag tcgtgtccac agactgtacc   1680

ccaccaggct cctctgtcca tgggatttcc caggcaagaa tactggagtg gcttgccatt   1740

ttcccctcca agggatcttc ccaacccagg gattaaaccc atgtctcctg tgtctcctgt   1800

attggcaggt agattcttta ccactgcgcc acctgggaag caagcatact actatacatt   1860
```

-continued

```
tatttaaata ataataagca tattcttctt caaggccctc acatgctcta agagcaagcc   1920
aagtaaagga ttgagttacg gagtggacca tgtctcactg gcaccttccc aaattcagtc   1980
ctctcttctt cctgctactt tcctccacca aagaccaggc cttcccaaga actcgcacct   2040
cttcccactt tacctgacat tggaagaggc tccccagtgc cagtttgaga ccctcagccc   2100
aatcctgctt tgactgctgg aggtccacac aattcattta tggcatcttt aatgtattgc   2160
cagtgatctg ctctctgccc tgactcagtt ttcctttcct gatgccaaat gctgctgctt   2220
ccatctttgc aattcaacat cagccttttc tcccccacca ctgttccccc aacattttgg   2280
ctttacaacc ctccattcag tgttacgttt aagtcacact ccatttactg ttatatttaa   2340
gcaaggatca ttaactttca gggagattag aaatcttgtt tccttggttc acagctgtac   2400
catctaattg caaagatgct gaaaaagatg aatctaaaat ctactgaaaa aaagtataga   2460
tttgaaacaa aatatgactt aaaagctacc tattccttgg ctttacaatg ttaaaatttt   2520
acctttgtgt tacctcataa gttgtggcat catgttaaga gaaatcattc agagtctaaa   2580
gaaaaaggaa ttgaatattt caaatgcaga tgtgatgaat tcattaaatg ccaaaaattg   2640
ttcattatag cttttcaacc caggaaggca aagccactgg agtccctgca ggtaggcaac   2700
ttgtgcagtg tgtgccatca cagaaagttc ctctggcaga aaggcatgtg agccttcgag   2760
ttgacactgc cgactgctgg ctggccagag agtcagaaga agacgtcaca gtggcaccac   2820
tttataatca tacaggagct ggtgaaagca aagactaagc tgcaaacagg aaggctaagt   2880
caataccttc tctgcagaat ggtacttctg tctcacaaac aggcaaatca acggatgtgt   2940
ccagactcgc cattttgctt gtgttcatcc agtgttacac caactagaca aagatctttt   3000
atgtgaatgc ttagaagcaa acacaagggg tgctgaaacg ttcaaaatac tgaataactt   3060
cattcagtct catggttgat cctggagtca ctgtgttgag gtttgtactg atgatgcagg   3120
gcaatggtgg ctgctgttag tgccttggca ccagtcagag cagggccact caaatgtacc   3180
agaagtcact gtatttttca ttggcatgct tgtagtcaaa taagggccag attcacttaa   3240
ggacatcctt gatgaaacag taaaaatgat cacttttatg aaatctttac tcttgatttc   3300
acatcttttt gaatatcctg tgtgacaaaa ttgttaccaa atcaaacttg agtctgatag   3360
agcagcaaag ccaatctact gatacctggt tgtggtgaag gaaaatacag tatttattgc   3420
agggtgcaag gaatacaggc agctcatgct taaaagaccc aaattcttct agctttccag   3480
ggaggttttt aaaaaaagtg tgaggtaaca gattgcatgc agaaacaaac atgagaaccc   3540
tatctgttct caaacatgag aaccccccaac tgtcttctgt taatccaaat attaaagaaa   3600
tttgcaaaaa tgtaaaacaa tgtcactact cttactaaaa ttttttggg gaaatgtggt   3660
tacttttcaa aaaatgtttt aaacgagtgt gagttcattg ttattttaga atgaagtaat   3720
aacataaata tttttttaat tttcttagtt ttgtttccta atatggtaaa tatcaacaag   3780
atatagccta taaaaacaga agatctttgg gacttcattg gggacctgag acccaagagt   3840
ctgagaactc taagtctagg atttgtagtc ggtgtctttc atttgacaag cagacgtacc   3900
tagggatggt tcttcaattg tcttcttgag cctctatgta ttttacatta ttaattacaa   3960
tttcatttaa gcaggtcaca ggtctaattt ccccttagcgt cctaatcaaa ttgtcacttt   4020
tagcaacagt agcttccttt gcgtgcaggc aagcgctttg catgagctgg ccttgttcta   4080
ttaggagccc agtttacatc tgttgagtgg aaaggaacta tggaaggaca cagtggaata   4140
aaaatactgt gtactaggaa tgctccatag gtagtgatcg accagaattt catcctgaaa   4200
aaaggaaata atcaaagcaa gggagtcagg gtgagcactt gaaactgatt ggaggttgag   4260
```

```
agaagtattt atcacaacat tacacattat ggttaaaaat cagaaacaac ctaagtggcc   4320

aacaatcagg agtttgtttt tattttttta aaaaaagatt tatttatttt tggttattct   4380

tcattggctg ggacttcgtt gctttgcttg gatttttccc acgttgtggt gagcaggggc   4440

ttcctcccta gctgcagtgc acaggcttct cagtgtagca gcttctcttg ggcagagtat   4500

agcctctagc atgggcttca gtagctgtgc tcgtgggctc tacagtgcaa gctcagtggt   4560

tgtggcacat gggcttattt gctccgtggc atgtgggatc ctcctggatc agggatcgaa   4620

tctgtgtctc ctgcattgac aggtggattc tttaccactg agctgccagg gaagtttgtt   4680

tttaaaacat tataatttat acaatcatta aaagtgatat tgcagatagg tatttgtcac   4740

atggaatttt tttggacata aattgaccat tttttctccc tctccttgcc ccttaaaaaa   4800

gagttgaaat agaataccat tatcaaaact atgttaatcc ctcagttgtg ctggagtgaa   4860

aaagctggtt gagaccactg gactgaagat gcgtatcaac tgatacagag aaatgtcact   4920

gacacagtgt tcatgcaaag aacacattat aatttgcttt ataataacat ttaattatac   4980

attgtaattt aaagtataaa agtgattttt gtgaaacaca caaaaagtaa gaagatataa   5040

aagattgcaa tctctgtatc agagtattgg aattacatta aaattttttt tcttgttgct   5100

tatttttatt ctattttcag tatactaata catacttata tgcttatcaa attcagtata   5160

tcaatgaaca tataacaata cttttctaac aggaaaacaa aattattttt aatttgttaa   5220

aatacaataa taactcacaa gtttctcttt attaaagtgt tacactggta gcgatttagc   5280

aaaaggaaaa aaccatgcta ataaactcac tgttgctttt tcaaaaaaaa aaaaaaaaaa   5340

aaaaaaaaaa aaaaaaaaaa aaaaaaaaaa aaaaaaaaaa aaaaaaaaaa aaaaaaaaaa   5400

aaaaaaaa                                                            5408
```

<210> SEQ ID NO 2
<211> LENGTH: 550
<212> TYPE: DNA
<213> ORGANISM: Bos taurus

<400> SEQUENCE: 2

```
agactgggga ccatgcagac ccagagggcc agcctctcac tggggcggtg gtcgctgtgg     60

ctactgctgc tgggactagt ggtgccctcg gccagcgccc aagccctcag ctacagggag    120

gccgtgcttc gtgctgtgga tcagctcaat gagctgtcct cagaagctaa tctctaccgc    180

ctcctggagc tagacccacc tcccaaggat aatgaagatc tgggcactcg aaagcctgtg    240

agcttcacgg tgaaggagac tgtgtgcccc aggacgattc agcagcccgc ggagcagtgt    300

gacttcaagg agaaagggcg ggtgaaacag tgtgtgggga cagtcaccct ggacccatcc    360

aatgaccagt ttgacctaaa ctgtaatgag ctccagagtg tcatcctacc ctggaaatgg    420

ccatggtggc cttggcgcag aggttgatgg agaagagctg tcagatcctg agcctcggga    480

agagtcttaa gtgtctgatt tgttcagatt cgggcttctg gacagtgaaa ataaattctt    540

gtgaaaacgg                                                           550
```

<210> SEQ ID NO 3
<211> LENGTH: 144
<212> TYPE: PRT
<213> ORGANISM: Bos taurus

<400> SEQUENCE: 3

```
Met Gln Thr Gln Arg Ala Ser Leu Ser Leu Gly Arg Trp Ser Leu Trp
1               5                   10                  15
```

```
Leu Leu Leu Leu Gly Leu Val Val Pro Ser Ala Ser Ala Gln Ala Leu
            20                  25                  30

Ser Tyr Arg Glu Ala Val Leu Arg Ala Val Asp Gln Leu Asn Glu Leu
        35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
            100                 105                 110

Leu Asp Pro Ser Asn Asp Gln Phe Asp Leu Asn Cys Asn Glu Leu Gln
        115                 120                 125

Ser Val Ile Leu Pro Trp Lys Trp Pro Trp Trp Pro Trp Arg Arg Gly
    130                 135                 140


<210> SEQ ID NO 4
<211> LENGTH: 144
<212> TYPE: PRT
<213> ORGANISM: Bos taurus

<400> SEQUENCE: 4

Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Gln Leu Asn Glu Leu
        35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
            100                 105                 110

Leu Asp Pro Ser Asn Asp Gln Phe Asp Leu Asn Cys Asn Glu Leu Gln
        115                 120                 125

Ser Val Ile Leu Pro Trp Lys Trp Pro Trp Trp Pro Trp Arg Arg Gly
    130                 135                 140


<210> SEQ ID NO 5
<211> LENGTH: 29
<212> TYPE: PRT
<213> ORGANISM: Bos taurus

<400> SEQUENCE: 5

Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala
            20                  25


<210> SEQ ID NO 6
<211> LENGTH: 14
<212> TYPE: PRT
<213> ORGANISM: Bos taurus
```

<400> SEQUENCE: 6

Ile Leu Pro Trp Lys Trp Pro Trp Trp Pro Trp Arg Arg Gly
1 5 10

<210> SEQ ID NO 7
<211> LENGTH: 472
<212> TYPE: DNA
<213> ORGANISM: Ascaris suum

<400> SEQUENCE: 7
gatcactcgt tgcatcgtta tttcatttgt taagttcttg cgatctactc gtcatgtttg 60
ctacacgtcg tgctttactg tgtatgttcc tcatatatct gttcgtgcaa acggcagaaa 120
gcagctggct cagcaaaact gccaagaaac ttgagaactc agcaaagaaa cgcatatctg 180
aaggaattgc aatcgctata caaggcggtc cgcgccgacg tcgtttcgtc gcagagcagg 240
acgcgattca ctctcgtgtt agccgagaag tgcctaccct gtccgactca gtttgattgc 300
ttttgcaact attggtgacg atgatatatg cttctacata tgacttcacg gtgggcttgg 360
actggattca gtgaatttgt aacggatttt tatggattta tgcatatatg acgccttcat 420
atttgtgcaa tctggtgata ttaacgtata tgtataaatc tgcctttggt ct 472

<210> SEQ ID NO 8
<211> LENGTH: 70
<212> TYPE: PRT
<213> ORGANISM: Ascaris suum

<400> SEQUENCE: 8

Met Phe Leu Ile Tyr Leu Phe Val Gln Thr Ala Glu Ser Ser Trp Leu
1 5 10 15

Ser Lys Thr Ala Lys Lys Leu Glu Asn Ser Ala Lys Lys Arg Ile Ser
20 25 30

Glu Gly Ile Ala Ile Ala Ile Gln Gly Gly Pro Arg Arg Arg Arg Phe
35 40 45

Val Ala Glu Gln Asp Ala Ile His Ser Arg Val Ser Arg Glu Val Pro
50 55 60

Thr Leu Ser Asp Ser Val
65 70

<210> SEQ ID NO 9
<211> LENGTH: 13
<212> TYPE: PRT
<213> ORGANISM: Ascaris suum

<400> SEQUENCE: 9

Met Phe Leu Ile Tyr Leu Phe Val Gln Thr Ala Glu Ser
1 5 10

<210> SEQ ID NO 10
<211> LENGTH: 12
<212> TYPE: PRT
<213> ORGANISM: Bos taurus

<400> SEQUENCE: 10

Arg Leu Cys Arg Ile Val Val Ile Arg Val Cys Arg
1 5 10

<210> SEQ ID NO 11
<211> LENGTH: 31
<212> TYPE: PRT

<213> ORGANISM: Ascaris suum

<400> SEQUENCE: 11

Ser Trp Leu Ser Lys Thr Ala Lys Lys Leu Glu Asn Ser Ala Lys Lys
1 5 10 15

Arg Ile Ser Glu Gly Ile Ala Ile Ala Ile Gln Gly Gly Pro Arg
20 25 30

<210> SEQ ID NO 12
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
gcgctgtgga aaaccatgct gaaaaaactg ggcaccatgg cgctgcatgc gggcaaagcg 60
gcgctgggcg cggcggcgga taccattagc cagggcaccc ag 102

<210> SEQ ID NO 13
<211> LENGTH: 34
<212> TYPE: PRT
<213> ORGANISM: Phyllomedusa sauvagii

<400> SEQUENCE: 13

Ala Leu Trp Lys Thr Met Leu Lys Lys Leu Gly Thr Met Ala Leu His
1 5 10 15

Ala Gly Lys Ala Ala Leu Gly Ala Ala Ala Asp Thr Ile Ser Gln Gly
20 25 30

Thr Gln

<210> SEQ ID NO 14
<211> LENGTH: 34
<212> TYPE: PRT
<213> ORGANISM: Phyllomedusa sauvagii

<400> SEQUENCE: 14

Ala Leu Trp Lys Thr Met Leu Lys Lys Leu Gly Thr Met Ala Leu His
1 5 10 15

Ala Gly Lys Ala Ala Leu Gly Ala Ala Ala Asp Thr Ile Ser Gln Gly
20 25 30

Thr Gln

<210> SEQ ID NO 15
<211> LENGTH: 25
<212> TYPE: PRT
<213> ORGANISM: Pachycondyla goeldii

<400> SEQUENCE: 15

Trp Leu Gly Ser Ala Leu Lys Ile Gly Ala Lys Leu Leu Pro Ser Val
1 5 10 15

Val Gly Leu Phe Lys Lys Lys Lys Gln
20 25

<210> SEQ ID NO 16
<211> LENGTH: 25
<212> TYPE: PRT
<213> ORGANISM: Pachycondyla goeldii

<400> SEQUENCE: 16

-continued

```
Trp Leu Gly Ser Ala Leu Lys Ile Gly Ala Lys Leu Leu Pro Ser Val
1               5                   10                  15

Val Gly Leu Phe Lys Lys Lys Lys Gln
            20                  25


<210> SEQ ID NO 17
<211> LENGTH: 26
<212> TYPE: PRT
<213> ORGANISM: Pachycondyla goeldii

<400> SEQUENCE: 17

Gly Ile Trp Gly Thr Ala Leu Lys Trp Gly Val Lys Leu Leu Pro Lys
1               5                   10                  15

Leu Val Gly Met Ala Gln Thr Lys Lys Gln
            20                  25


<210> SEQ ID NO 18
<211> LENGTH: 26
<212> TYPE: PRT
<213> ORGANISM: Pachycondyla goeldii

<400> SEQUENCE: 18

Gly Ile Trp Gly Thr Ala Leu Lys Trp Gly Val Lys Leu Leu Pro Lys
1               5                   10                  15

Leu Val Gly Met Ala Gln Thr Lys Lys Gln
            20                  25


<210> SEQ ID NO 19
<211> LENGTH: 24
<212> TYPE: PRT
<213> ORGANISM: Pachycondyla goeldii

<400> SEQUENCE: 19

Phe Trp Gly Ala Leu Ile Lys Gly Ala Ala Lys Leu Ile Pro Ser Val
1               5                   10                  15

Val Gly Leu Phe Lys Lys Lys Gln
            20


<210> SEQ ID NO 20
<211> LENGTH: 24
<212> TYPE: PRT
<213> ORGANISM: Pachycondyla goeldii

<400> SEQUENCE: 20

Phe Trp Gly Ala Leu Ile Lys Gly Ala Ala Lys Leu Ile Pro Ser Val
1               5                   10                  15

Val Gly Leu Phe Lys Lys Lys Gln
            20


<210> SEQ ID NO 21
<211> LENGTH: 20
<212> TYPE: PRT
<213> ORGANISM: Pachycondyla goeldii

<400> SEQUENCE: 21

Phe Ile Gly Thr Ala Leu Gly Ile Ala Ser Ala Ile Pro Ala Ile Val
1               5                   10                  15

Lys Leu Phe Lys
            20


<210> SEQ ID NO 22
<211> LENGTH: 20
```

<212> TYPE: PRT
<213> ORGANISM: Pachycondyla goeldii

<400> SEQUENCE: 22

Phe Ile Gly Thr Ala Leu Gly Ile Ala Ser Ala Ile Pro Ala Ile Val
1 5 10 15

Lys Leu Phe Lys
20

<210> SEQ ID NO 23
<211> LENGTH: 24
<212> TYPE: PRT
<213> ORGANISM: Listeria monocytogenes

<400> SEQUENCE: 23

Met Lys Lys Ile Met Leu Val Ile Thr Leu Ile Leu Val Ser Pro Ile
1 5 10 15

Ala Gln Gln Thr Glu Ala Lys Asp
20

<210> SEQ ID NO 24
<211> LENGTH: 29
<212> TYPE: PRT
<213> ORGANISM: Lactococcus lactis

<400> SEQUENCE: 24

Met Lys Lys Lys Ile Ile Ser Ala Ile Leu Met Ser Thr Val Ile Leu
1 5 10 15

Ser Ala Ala Ala Pro Leu Ser Gly Val Tyr Ala Asp Thr
20 25

<210> SEQ ID NO 25
<211> LENGTH: 31
<212> TYPE: PRT
<213> ORGANISM: Bacillus anthracis

<400> SEQUENCE: 25

Met Lys Lys Arg Lys Val Leu Ile Pro Leu Met Ala Leu Ser Thr Ile
1 5 10 15

Leu Val Ser Ser Thr Gly Asn Leu Glu Val Ile Gln Ala Glu Val
20 25 30

<210> SEQ ID NO 26
<211> LENGTH: 29
<212> TYPE: PRT
<213> ORGANISM: Listeria monocytogenes

<400> SEQUENCE: 26

Met Asn Met Lys Lys Ala Thr Ile Ala Ala Thr Ala Gly Ile Ala Val
1 5 10 15

Thr Ala Phe Ala Ala Pro Thr Ile Ala Ser Ala Ser Thr
20 25

<210> SEQ ID NO 27
<211> LENGTH: 54
<212> TYPE: PRT
<213> ORGANISM: Listeria monocytogenes

<400> SEQUENCE: 27

Met Gln Lys Thr Arg Lys Glu Arg Ile Leu Glu Ala Leu Gln Glu Glu
1 5 10 15

Lys Lys Asn Lys Lys Ser Lys Lys Phe Lys Thr Gly Ala Thr Ile Ala

-continued

```
            20                  25                  30

Gly Val Thr Ala Ile Ala Thr Ser Ile Thr Val Pro Gly Ile Glu Val
        35                  40                  45

Ile Val Ser Ala Asp Glu
    50


<210> SEQ ID NO 28
<211> LENGTH: 28
<212> TYPE: PRT
<213> ORGANISM: Bacillus anthracis

<400> SEQUENCE: 28

Met Lys Lys Leu Lys Met Ala Ser Cys Ala Leu Val Ala Gly Leu Met
1               5                   10                  15

Phe Ser Gly Leu Thr Pro Asn Ala Phe Ala Glu Asp
            20                  25


<210> SEQ ID NO 29
<211> LENGTH: 31
<212> TYPE: PRT
<213> ORGANISM: Staphylococcus aureus

<400> SEQUENCE: 29

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu
            20                  25                  30


<210> SEQ ID NO 30
<211> LENGTH: 59
<212> TYPE: PRT
<213> ORGANISM: Listeria monocytogenes

<400> SEQUENCE: 30

Met Thr Asp Lys Lys Ser Glu Asn Gln Thr Glu Lys Thr Glu Thr Lys
1               5                   10                  15

Glu Asn Lys Gly Met Thr Arg Arg Glu Met Leu Lys Leu Ser Ala Val
            20                  25                  30

Ala Gly Thr Gly Ile Ala Val Gly Ala Thr Gly Leu Gly Thr Ile Leu
        35                  40                  45

Asn Val Val Asp Gln Val Asp Lys Ala Leu Thr
    50                  55


<210> SEQ ID NO 31
<211> LENGTH: 53
<212> TYPE: PRT
<213> ORGANISM: Bacillus subtillis

<400> SEQUENCE: 31

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Gly Leu Gly Leu Thr Ile Ala Gln Ser
        35                  40                  45

Val Gly Ala Phe Gly
    50


<210> SEQ ID NO 32
<211> LENGTH: 84
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

gcatgctccc tatcagtgat agagattgac atccctatca gtgatagaga tactgagcac     60

atcagcagga cgcactgacc agga                                            84


<210> SEQ ID NO 33
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccata                  286


<210> SEQ ID NO 34
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

ccatcgaatg gctgaaatga gctgttgaca attaatcatc cggctcgtat aatgtgtgga     60

attgtgagcg gataacaatt tcacacagga                                      90


<210> SEQ ID NO 35
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

gcatgcacag ataaccatct gcggtgataa attatctctg gcggtgttga cataaatacc     60

actggcggtt ataatgagca catcagcagg gtatgcaaag ga                       102


<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Leu Leu Phe Leu Leu Lys Lys Arg Lys Lys Arg Lys Tyr
1               5                   10


<210> SEQ ID NO 37
```

<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Phe Phe His His Ile Phe Arg Gly Ile Val His Val Gly Lys Thr Ile
1               5                   10                  15

His Lys Leu Val Thr Gly
            20
```

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Trp Leu Gly Ser Ala Leu Lys Ile Gly Ala Lys Leu Leu Pro Ser Val
1               5                   10                  15

Val Gly Leu Phe Gln Lys Lys Lys Lys
            20                  25
```

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Phe Phe Gly Trp Leu Ile Lys Gly Ala Ile His Ala Gly Lys Ala Ile
1               5                   10                  15

His Gly Leu Ile His Arg Arg Arg His
            20                  25
```

<210> SEQ ID NO 40
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Ile Trp Gly Thr Leu Ala Lys Ile Gly Ile Lys Ala Val Pro Arg
1               5                   10                  15

Val Ile Ser Met Leu Lys Lys Lys Lys Gln
            20                  25
```

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Lys Trp Lys Leu Phe Lys Lys Ile Leu Lys Phe Leu His Leu Ala Lys
1               5                   10                  15
```

Lys Phe

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Phe Trp Gly Ala Leu Ile Lys Gly Ala Ala Lys Leu Ile Pro Ser Val
1 5 10 15

Val Gly Leu Phe Lys Lys Lys Gln
20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Phe Leu Gly Ala Leu Phe Lys Val Ala Ser Lys Val Leu Pro Ser Val
1 5 10 15

Phe Cys Ala Ile Thr Lys Lys Cys
20

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Trp Leu Gly Ser Ala Leu Lys Ile Gly Ala Lys Leu Leu Pro Ser Val
1 5 10 15

Val Gly Leu Phe Lys Lys Lys Lys Gln
20 25

<210> SEQ ID NO 45
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
agtaaacata tgggcatttg gggcaccctg gcgaaaattg gcattaaagc ggtgccgcgc 60
gtgattagca tgctgaaaaa aaaaaaacag taaggatcct cgat 104

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
atcgaggatc cttactgttt tttttttttc agcatgctaa tcacg 45

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
agtaaacata tgggcatttg gggcaccctg gcgaaa 36

<210> SEQ ID NO 48
<211> LENGTH: 98
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
agtaaacata tgttttgggg cgcgctgatt aaaggcgcgg cgaaactgat tccgagcgtg 60
gtgggcctgt ttaaaaaaaa acagtaagga tcctcgat 98

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
agtaaacata tgttttgggg cgcgctgatt aaag 34

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
atcgaggatc cttactgttt ttttttttta aacaggccca ccacg 45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
atcgaggatc cttactgttt ttttttaaac aggcccacca cgctc 45

<210> SEQ ID NO 52
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
agtaaacata tgtggctggg cagcgcgctg aaaattggcg cgaaactgct gccgagcgtg 60
gtgggcctgt ttaaaaaaaa aaaacagtaa ggatcctcga t 101

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
atcgaggatc cttactgttt ttttttttta aacaggccca ccacg 45

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
agtaaacata tgtggctggg cagcgcgctg aaaattgg 38

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tactcgaatt cttaagtaac taacgaaatt aatacgactc 40

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
aaatataagc ttcgggcttt gttagcagcc 30

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
agtaaacata tggctaagac tcaagcagaa ata 33

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tagctggatc ctttgaatac tccccaggca 30

<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
atgaaaaaga cagctatcgc gattgcagtg gcactggctg gtttcgctac cgtagcgcag 60
gcc 63

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
cgtagcgcag gccatggcta agactcaagc agaaata 37

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gcactggctg gtttcgctac cgtagcgcag gccatggcta ag 42

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
cagctatcgc gattgcagtg gcactggctg gtttcgctac 40

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
agtaaacata tgaaaaagac agctatcgcg attgcagtg 39

<210> SEQ ID NO 64
<211> LENGTH: 37921
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 64
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg ggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920
cgctacgaag acgtttacat gcctgaggtg tacaaagcga ttaacattgc gcaaaacacc 1980
gcatggaaaa tcaacaagaa agtcctagcg gtcgccaacg taatcaccaa gtggaagcat 2040
tgtccggtcg aggacatccc tgcgattgag cgtgaagaac tcccgatgaa accggaagac 2100
atcgacatga atcctgaggc tctcaccgcg tggaaacgtg ctgccgctgc tgtgtaccgc 2160
aaggacaagg ctcgcaagtc tcgccgtatc agccttgagt tcatgcttga gcaagccaat 2220
aagtttgcta accataaggc catctggttc ccttacaaca tggactggcg cggtcgtgtt 2280

-continued

```
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
tctctaggag tggccttagt catttaacca ataggagata aacattatga tgaacattaa   4320
gactaacccg tttaaagccg tgtctttcgt agagtctgcc attaagaagg ctctggataa   4380
cgctgggtat cttatcgctg aaatcaagta cgatggtgta cgcgggaaca tctgcgtaga   4440
caatactgct aacagttact ggctctctcg tgtatctaaa acgattccgg cactggagca   4500
cttaaacggg tttgatgttc gctggaagcg tctactgaac gatgaccgtt gcttctacaa   4560
agatggcttt atgcttgatg gggaactcat ggtcaagggc gtagacttta acacagggtc   4620
```

cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400
cttcgggtgg gcctttctgc gtttataagg agacacttta tgtttaagaa ggttggtaaa 5460
ttccttgcgg ctttggcagc tatcctgacg cttgcgtata ttcttgcggt ataccctcaa 5520
gtagcactag tagtagttgg cgcttgttac ttagcggcag tgtgtgcttg cgtgtggagt 5580
atagttaact ggtaatacga ctcactaaag gaggtacaca ccatgatgta cttaatgcca 5640
ttactcatcg tcattgtagg atgccttgcg ctccactgta gcgatgatga tatgccagat 5700
ggtcacgctt aatacgactc actaaaggag acactatatg tttcgacttc attacaacaa 5760
aagcgttaag aatttcacgg ttcgccgtgc tgaccgttca atcgtatgtg cgagcgagcg 5820
ccgagctaag atacctctta ttggtaacac agttcctttg gcaccgagcg tccacatcat 5880
tatcacccgt ggtgactttg agaaagcaat agacaagaaa cgtccggttc ttagtgtggc 5940
agtgacccgc ttcccgttcg tccgtctgtt actcaaacga atcaaggagg tgttctgatg 6000
ggactgttag atggtgaagc ctgggaaaaa gaaaacccgc cagtacaagc aactgggtgt 6060
atagcttgct tagagaaaga tgaccgttat ccacacacct gtaacaaagg agctaacgat 6120
atgaccgaac gtgaacaaga gatgatcatt aagttgatag acaataatga aggtcgccca 6180
gatgatttga atggctgcgg tattctctgc tccaatgtcc cttgccacct ctgccccgca 6240
aataacgatc aaaagataac cttaggtgaa atccgagcga tggacccacg taaaccacat 6300
ctgaataaac ctgaggtaac tcctacagat gaccagcctt ccgctgagac aatcgaaggt 6360
gtcactaagc cttcccacta catgctgttt gacgacattg aggctatcga agtgattgct 6420
cgttcaatga ccgttgagca gttcaaggga tactgcttcg gtaacatctt aaagtacaga 6480
ctacgtgctg gtaagaagtc agagttagcg tacttagaga aagacctagc gaaagcagac 6540
ttctataaag aactctttga gaaacataag gataaatgtt atgcataact tcaagtcaac 6600
cccacctgcc gacagcctat ctgatgactt cacatcttgc tcagagtggt gccgaaagat 6660
gtgggaagag acattcgacg atgcgtacat caagctgtat gaactttgga aatcgagagg 6720
tcaatgacta tgtcaaacgt aaatacaggt tcacttagtg tggacaataa gaagttttgg 6780
gctaccgtag agtcctcgga gcattccttc gaggttccaa tctacgctga gaccctagac 6840
gaagctctgg agttagccga atggcaatac gttccggctg gctttgaggt tactcgtgtg 6900
cgtccttgtg tagcaccgaa gtaatacgac tcactattag ggaagactcc ctctgagaaa 6960
ccaaacgaaa cctaaaggag attaacatta tggctaagaa gattttcacc tctgcgctgg 7020

```
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac tacctttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
ttggaagtcg ttgcgtggat ttatagaact aggagggaat tgcatggaca attcgcacga   9060
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
```

-continued

```
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
ttaccatgcg tgaccctaaa gttatccaag cagaaatcgc taaactggaa gctgaactgg  11460
aggacgttaa gtaccatgaa gctaagactc gctccgctgt tcacatcttg aagaacttag  11520
gctggacttg gacaagacag actggctgga agaaaccaga agttaccaag ctgagtcata  11580
aggtgttcga taaggacact atgacccaca tcaaggctgg tgattgggtt aaggttgaca  11640
tgggagttgt tggtggatac ggctacgtcc gctcagttag tggcaaatat gcacaagtgt  11700
catacatcac aggtgttact ccacgcggtg caatcgttgc cgataagacc aacatgattc  11760
```

-continued acacaggttt cttgacagtt gtttcatatg aagagattgt taagtcacga taatcaatag 11820
gagaaatcaa tatgatcgtt tctgacatcg aagctaacgc cctcttagag agcgtcacta 11880
agttccactg cggggttatc tacgactact ccaccgctga gtacgtaagc taccgtccga 11940
gtgacttcgg tgcgtatctg gatgcgctgg aagccgaggt tgcacgaggc ggtcttattg 12000
tgttccacaa cggtcacaag tatgacgttc ctgcattgac caaactggca aagttgcaat 12060
tgaaccgaga gttccacctt cctcgtgaga actgtattga cacccttgtg ttgtcacgtt 12120
tgattcattc caacctcaag gacaccgata tgggtcttct gcgttccggc aagttgcccg 12180
gaaaacgctt tgggtctcac gctttggagg cgtggggtta tcgcttaggc gagatgaagg 12240
gtgaatacaa agacgacttt aagcgtatgc ttgaagagca gggtgaagaa tacgttgacg 12300
gaatggagtg gtggaacttc aacgaagaga tgatggacta taacgttcag gacgttgtgg 12360
taactaaagc tctccttgag aagctactct ctgacaaaca ttacttccct cctgagattg 12420
actttacgga cgtaggatac actacgttct ggtcagaatc ccttgaggcc gttgacattg 12480
aacatcgtgc tgcatggctg ctcgctaaac aagagcgcaa cgggttcccg tttgacacaa 12540
aagcaatcga agagttgtac gtagagttag ctgctcgccg ctctgagttg ctccgtaaat 12600
tgaccgaaac gttcggctcg tggtatcagc ctaaaggtgg cactgagatg ttctgccatc 12660
cgcgaacagg taagccacta cctaaatacc ctcgcattaa gacacctaaa gttggtggta 12720
tctttaagaa gcctaagaac aaggcacagc gagaaggccg tgagccttgc gaacttgata 12780
cccgcgagta cgttgctggt gctccttaca ccccagttga acatgttgtg tttaaccctt 12840
cgtctcgtga ccacattcag aagaaactcc aagaggctgg gtgggtcccg accaagtaca 12900
ccgataaggg tgctcctgtg gtggacgatg aggtactcga aggagtacgt gtagatgacc 12960
ctgagaagca agccgctatc gacctcatta aagagtactt gatgattcag aagcgaatcg 13020
gacagtctgc tgagggagac aaagcatggc ttcgttatgt tgctgaggat ggtaagattc 13080
atggttctgt taaccctaat ggagcagtta cgggtcgtgc gacccatgcg ttcccaaacc 13140
ttgcgcaaat tccgggtgta cgttctcctt atggagagca gtgtcgcgct gcttttggcg 13200
ctgagcacca tttggatggg ataactggta agccttgggt tcaggctggc atcgacgcat 13260
ccggtcttga gctacgctgc ttggctcact tcatggctcg ctttgataac ggcgagtacg 13320
ctcacgagat tcttaacggc gacatccaca ctaagaacca gatagctgct gaactaccta 13380
cccgagataa cgctaagacg ttcatctatg ggttcctcta tggtgctggt gatgagaaga 13440
ttggacagat tgttggtgct ggtaaagagc gcggtaagga actcaagaag aaattccttg 13500
agaacacccc cgcgattgca gcactccgcg agtctatcca acagacactt gtcgagtcct 13560
ctcaatgggt agctggtgag caacaagtca agtggaaacg ccgctggatt aaaggtctgg 13620
atggtcgtaa ggtacacgtt cgtagtcctc acgctgcctt gaatacccta ctgcaatctg 13680
ctggtgctct catctgcaaa ctgtggatta tcaagaccga agagatgctc gtagagaaag 13740
gcttgaagca tggctgggat ggggactttg cgtacatggc atgggtacat gatgaaatcc 13800
aagtaggctg ccgtaccgaa gagattgctc aggtggtcat tgagaccgca caagaagcga 13860
tgcgctgggt tggagaccac tggaacttcc ggtgtcttct ggataccgaa ggtaagatgg 13920
gtcctaattg ggcgatttgc cactgataca ggaggctact catgaacgaa agacacttaa 13980
caggtgctgc ttctgaaatg ctagtagcct acaaatttac caaagctggg tacactgtct 14040
attaccctat gctgactcag agtaaagagg acttggttgt atgtaaggat ggtaaattta 14100
gtaaggttca ggttaaaaca gccacaacgg ttcaaaccaa cacaggagat gccaagcagg 14160
ttaggctagg tggatgcggt aggtccgaat ataaggatgg agactttgac attcttgcgg 14220
ttgtggttga cgaagatgtg cttattttca catgggacga agtaaaaggt aagacatcca 14280
tgtgtgtcgg caagagaaac aaaggcataa aactatagga gaaattatta tggctatgac 14340
aaagaaattt aaagtgtcct tcgacgttac cgcaaagatg tcgtctgacg ttcaggcaat 14400
cttagagaaa gatatgctgc atctatgtaa gcaggtcggc tcaggtgcga ttgtccccaa 14460
tggtaaacag aaggaaatga ttgtccagtt cctgacacac ggtatggaag gattgatgac 14520
attcgtagta cgtacatcat ttcgtgaggc cattaaggac atgcacgaag agtatgcaga 14580
taaggactct ttcaaacaat ctcctgcaac agtacgggag gtgttctgat gtctgactac 14640
ctgaaagtgc tgcaagcaat caaaagttgc cctaagactt tccagtccaa ctatgtacgg 14700
aacaatgcga gcctcgtagc ggaggccgct tcccgtggtc acatctcgtg cctgactact 14760
agtggacgta acggtggcgc ttgggaaatc actgcttccg gtactcgctt tctgaaacga 14820
atgggaggat gtgtctaatg tctcgtgacc ttgtgactat tccacgcgat gtgtggaacg 14880
atatacaggg ctacatcgac tctctggaac gtgagaacga tagccttaag aatcaactaa 14940
tggaagctga cgaatacgta gcggaactag aggagaaact taatggcact tcttgacctt 15000
aaacaattct atgagttacg tgaaggctgc gacgacaagg gtatccttgt gatggacggc 15060
gactggctgg tcttccaagc tatgagtgct gctgagtttg atgcctcttg ggaggaagag 15120
atttggcacc gatgctgtga ccacgctaag gcccgtcaga ttcttgagga ttccattaag 15180
tcctacgaga cccgtaagaa ggcttgggca ggtgctccaa ttgtccttgc gttcaccgat 15240
agtgttaact ggcgtaaaga actggttgac ccgaactata aggctaaccg taaggccgtg 15300
aagaaacctg tagggtactt tgagttcctt gatgctctct ttgagcgcga agagttctat 15360
tgcatccgtg agcctatgct tgagggtgat gacgttatgg gagttattgc ttccaatccg 15420
tctgccttcg gtgctcgtaa ggctgtaatc atctcttgcg ataaggactt taagaccatc 15480
cctaactgtg acttcctgtg gtgtaccact ggtaacatcc tgactcagac cgaagagtcc 15540
gctgactggt ggcacctctt ccagaccatc aagggtgaca tcactgatgg ttactcaggg 15600
attgctggat ggggtgatac cgccgaggac ttcttgaata acccgttcat aaccgagcct 15660
aaaacgtctg tgcttaagtc cggtaagaac aaaggccaag aggttactaa atgggttaaa 15720
cgcgaccctg agcctcatga gacgctttgg gactgcatta agtccattgg cgcgaaggct 15780
ggtatgaccg aagaggatat tatcaagcag ggccaaatgg ctcgaatcct acggttcaac 15840
gagtacaact ttattgacaa ggagatttac ctgtggagac cgtagcgtat attggtctgg 15900
gtctttgtgt tctcggagtg tgcctcattt cgtggggcct ttgggactta gccagaataa 15960
tcaagtcgtt acacgacact aagtgataaa ctcaaggtcc ctaaattaat acgactcact 16020
atagggagat aggggccttt acgattatta ctttaagatt taactctaag aggaatcttt 16080
attatgttaa cacctattaa ccaattactt aagaacccta acgatattcc agatgtacct 16140
cgtgcaaccg ctgagtatct acaggttcga ttcaactatg cgtacctcga agcgtctggt 16200
catataggac ttatgcgtgc taatggttgt agtgaggccc acatcttggg tttcattcag 16260
ggcctacagt atgcctctaa cgtcattgac gagattgagt tacgcaagga acaactaaga 16320
gatgatgggg aggattgaca ctatgtgttt ctcaccgaaa attaaaactc cgaagatgga 16380
taccaatcag attcgagccg ttgagccagc gcctctgacc caagaagtgt caagcgtgga 16440
gttcggtggg tcttctgatg agacggatac cgagggcacc gaagtgtctg gacgcaaagg 16500
cctcaaggtc gaacgtgatg attccgtagc gaagtctaaa gccagcggca atggctccgc 16560
tcgtatgaaa tcttccatcc gtaagtccgc atttggaggt aagaagtgat gtctgagttc 16620
acatgtgtgg aggctaagag tcgcttccgt gcaatccggt ggactgtgga acaccttggg 16680
ttgcctaaag gattcgaagg acactttgtg ggctacagcc tctacgtaga cgaagtgatg 16740
gacatgtctg gttgccgtga agagtacatt ctggactcta ccggaaaaca tgtagcgtac 16800
ttcgcgtggt gcgtaagctg tgacattcac cacaaaggag acattctgga tgtaacgtcc 16860
gttgtcatta atcctgaggc agactctaag ggcttacagc gattcctagc gaaacgcttt 16920
aagtaccttg cggaactcca cgattgcgat tgggtgtctc gttgtaagca tgaaggcgag 16980
acaatgcgtg tatactttaa ggaggtataa gttatgggta agaaagttaa gaaggccgtg 17040
aagaaagtca ccaagtccgt taagaaagtc gttaaggaag gggctcgtcc ggttaaacag 17100
gttgctggcg gtctagctgg tctggctggt ggtactggtg aagcacagat ggtggaagta 17160
ccacaagctg ccgcacagat tgttgacgta cctgagaaag aggtttccac tgaggacgaa 17220
gcacagacag aaagcggacg caagaaagct cgtgctggcg gtaagaaatc cttgagtgta 17280
gcccgtagct ccggtggcgg tatcaacatt taatcaggag gttatcgtgg aagactgcat 17340
tgaatggacc ggaggtgtca actctaaggg ttatggtcgt aagtgggtta atggtaaact 17400
tgtgactcca cataggcaca tctatgagga gacatatggt ccagttccaa caggaattgt 17460
ggtgatgcat atctgcgata accctaggtg ctataacata aagcacctta cgcttggaac 17520
tccaaaggat aattccgagg acatggttac caaaggtaga caggctaaag gagaggaact 17580
aagcaagaaa cttacagagt cagacgttct cgctatacgc tcttcaacct taagccaccg 17640
ctccttagga gaactgtatg gagtcagtca atcaaccata acgcgaatac tacagcgtaa 17700
gacatggaga cacatttaat ggctgagaaa cgaacaggac ttgcggagga tggcgcaaag 17760
tctgtctatg agcgtttaaa gaacgaccgt gctccctatg agacacgcgc tcagaattgc 17820
gctcaatata ccatcccatc attgttccct aaggactccg ataacgcctc tacagattat 17880
caaactccgt ggcaagccgt gggcgctcgt ggtctgaaca atctagcctc taagctcatg 17940
ctggctctat tccctatgca gacttggatg cgacttacta tatctgaata tgaagcaaag 18000
cagttactga gcgaccccga tggactcgct aaggtcgatg agggcctctc gatggtagag 18060
cgtatcatca tgaactacat tgagtctaac agttaccgcg tgactctctt tgaggctctc 18120
aaacagttag tcgtagctgg taacgtcctg ctgtacctac cggaaccgga agggtcaaac 18180
tataatccca tgaagctgta ccgattgtct tcttatgtgg tccaacgaga cgcattcggc 18240
aacgttctgc aaatggtgac tcgtgaccag atagcttttg gtgctctccc tgaggacatc 18300
cgtaaggctg tagaaggtca aggtggtgag aagaaagctg atgagacaat cgacgtgtac 18360
actcacatct atctggatga ggactcaggt gaatacctcc gatacgaaga ggtcgagggt 18420
atggaagtcc aaggctccga tggggacttat cctaaagagg cttgcccata catcccgatt 18480
cggatggtca gactagatgg tgaatcctac ggtcgttcgt acattgagga atacttaggt 18540
gacttacggt cccttgaaaa tctccaagag gctatcgtca agatgtccat gattagctct 18600
aaggttatcg gcttagtgaa tcctgctggt atcacccagc cacgccgact gaccaaagct 18660
cagactggtg acttcgttac tggtcgtcca gaagacatct cgttcctcca actggagaag 18720
caagcagact ttactgtagc taaagccgta agtgacgcta tcgaggctcg cctttcgttt 18780
gcctttatgt tgaactctgc ggttcagcgt acaggtgaac gtgtgaccgc cgaagagatt 18840

-continued

```
cggtatgtag cttctgaact tgaagatact ttaggtggtg tctactctat cctttctcaa  18900
gaattacaat tgcctctggt acgagtgctc ttgaagcaac tacaagccac gcaacagatt  18960
cctgagttac ctaaggaagc cgtagagcca accattagta caggtctgga agcaattggt  19020
cgaggacaag accttgataa gctggagcgg tgtgtcactg cgtgggctgc actggcacct  19080
atgcgggacg accctgatat taaccttgcg atgattaagt tacgtattgc caacgctatc  19140
ggtattgaca cttctggtat tctactcacc gaagaacaga agcaacagaa gatggcccaa  19200
cagtctatgc aaatgggtat ggataatggt gctgctgcgc tggctcaagg tatggctgca  19260
caagctacag cttcacctga ggctatggct gctgccgctg attccgtagg tttacagccg  19320
ggaatttaat acgactcact atagggagac ctcatctttg aaatgagcga tgacaagagg  19380
ttggagtcct cggtcttcct gtagttcaac tttaaggaga caataataat ggctgaatct  19440
aatgcagacg tatatgcatc ttttggcgtg aactccgctg tgatgtctgg tggttccgtt  19500
gaggaacatg agcagaacat gctggctctt gatgttgctg cccgtgatgg cgatgatgca  19560
atcgagttag cgtcagacga agtggaaaca gaacgtgacc tgtatgacaa ctctgacccg  19620
ttcggtcaag aggatgacga aggccgcatt caggttcgta tcggtgatgg ctctgagccg  19680
accgatgtgg acactggaga agaaggcgtt gagggcaccg aaggttccga agagtttacc  19740
ccactgggcg agactccaga agaactggta gctgcctctg agcaacttgg tgagcacgaa  19800
gagggcttcc aagagatgat taacattgct gctgagcgtg gcatgagtgt cgagaccatt  19860
gaggctatcc agcgtgagta cgaggagaac gaagagttgt ccgccgagtc ctacgctaag  19920
ctggctgaaa ttggctacac gaaggctttc attgactcgt atatccgtgg tcaagaagct  19980
ctggtggagc agtacgtaaa cagtgtcatt gagtacgctg gtggtcgtga acgttttgat  20040
gcactgtata accaccttga gacgcacaac cctgaggctg cacagtcgct ggataatgcg  20100
ttgaccaatc gtgacttagc gaccgttaag gctatcatca acttggctgg tgagtctcgc  20160
gctaaggcgt tcggtcgtaa gccaactcgt agtgtgacta atcgtgctat tccggctaaa  20220
cctcaggcta ccaagcgtga aggctttgcg gaccgtagcg agatgattaa agctatgagt  20280
gaccctcggt atcgcacaga tgccaactat cgtcgtcaag tcgaacagaa agtaatcgat  20340
tcgaacttct gatagacttc gaaattaata cgactcacta tagggagacc acaacggttt  20400
ccctctagaa ataattttgt ttaactttaa gaaggagata tacatatggc tagcatgact  20460
ggtggacagc aaatgggtac taaccaaggt aaaggtgtag ttgctgctgg agataaactg  20520
gcgttgttct tgaaggtatt tggcggtgaa gtcctgactg cgttcgctcg tacctccgtg  20580
accacttctc gccacatggt acgttccatc tccagcggta aatccgctca gttccctgtt  20640
ctgggtcgca ctcaggcagc gtatctggct ccgggcgaga acctcgacga taaacgtaag  20700
gacatcaaac acaccgagaa ggtaatcacc attgacggtc tcctgacggc tgacgttctg  20760
atttatgata ttgaggacgc gatgaaccac tacgacgttc gctctgagta tacctctcag  20820
ttgggtgaat ctctggcgat ggctgcggat ggtgcggttc tggctgagat tgccggtctg  20880
tgtaacgtgg aaagcaaata taatgagaac atcgagggct taggtactgc taccgtaatt  20940
gagaccactc agaacaaggc cgcacttacc gaccaagttg cgctgggtaa ggagattatt  21000
gcggctctga ctaaggctcg tgcggctctg accaagaact atgttccggc tgctgaccgt  21060
gtgttctact gtgacccaga tagctactct gcgattctgg cagcactgat gccgaacgca  21120
gcaaactacg ctgctctgat tgaccctgag aagggttcta tccgcaacgt tatgggcttt  21180
gaggttgtag aagttccgca cctcaccgct ggtggtgctg gtaccgctcg tgagggcact  21240
```

```
actggtcaga agcacgtctt ccctgccaat aaaggtgagg gtaatgtcaa ggttgctaag  21300
gacaacgtta tcggcctgtt catgcaccgc tctgcggtag gtactgttaa gctgcgtgac  21360
ttggctctgg agcgcgctcg ccgtgctaac ttccaagcgg accagattat cgctaagtac  21420
gcaatgggcc acggtggtct tcgcccagaa gctgcaggag ctgtcgtatt ccagtcaggt  21480
gtgatgctcg gggatccgaa ttcttaagta actaacgaaa ttaatacgac tcactatagg  21540
gagaccacaa cggtttccct ctagaaataa ttttgtttaa ctttaagaag gagatataca  21600
tatggctaag actcaagcag aaataaataa acgtttagat gcttatgcaa aaggaacagt  21660
agatagccct tacagagtta aaaaagctac aagttatgac ccatcatttg gtgtaatgga  21720
agcaggagcc attgatgcag atggttacta tcacgctcag tgtcaagacc ttattacaga  21780
ctatgtttta tggttaacag ataataaagt tagaacttgg ggtaatgcta aagaccaaat  21840
taaacagagt tatggtactg gatttaaaat acatgaaaat aaaccttcta ctgtacctaa  21900
aaaaggttgg attgcggtat ttacatccgg tagttatgaa cagtggggtc acataggtat  21960
tgtatatgat ggaggtaata cttctacatt tactatttta gagcaaaact ggaatggtta  22020
tgctaataaa aaacctacaa aacgtgtaga taattattac ggattaactc acttcattga  22080
aatacctgta aaagcatagg gatccggctg ctaacaaagc ccgaaagctt cggccgcact  22140
cgagtaacta gttaacccct tggggcctct aaacgggtct tgaggggttt tttgctgaaa  22200
ggaggaacta tatgcgctca tacgatatga acgttgagac tgccgctgag ttatcagctg  22260
tgaacgacat tctggcgtct atcggtgaac ctccggtatc aacgctggaa ggtgacgcta  22320
acgcagatgc agcgaacgct cggcgtattc tcaacaagat taaccgacag attcaatctc  22380
gtggatggac gttcaacatt gaggaaggca taacgctact acctgatgtt tactccaacc  22440
tgattgtata cagtgacgac tatttatccc taatgtctac ttccggtcaa tccatctacg  22500
ttaaccgagg tggctatgtg tatgaccgaa cgagtcaatc agaccgcttt gactctggta  22560
ttactgtgaa cattattcgt ctccgcgact acgatgagat gcctgagtgc ttccgttact  22620
ggattgtcac caaggcttcc cgtcagttca acaaccgatt ctttggggca ccggaagtag  22680
agggtgtact ccaagaagag gaagatgagg ctagacgtct ctgcatggag tatgagatgg  22740
actacggtgg gtacaatatg ctggatggag atgcgttcac ttctggtcta ctgactcgct  22800
aacattaata aataaggagg ctctaatggc actcattagc caatcaatca agaacttgaa  22860
gggtggtatc agccaacagc ctgacatcct tcgttatcca gaccaagggt cacgccaagt  22920
taacggttgg tcttcggaga ccgagggcct ccaaaagcgt ccacctcttg ttttcttaaa  22980
tacacttgga gacaacggtg cgttaggtca agctccgtac atccacctga ttaaccgaga  23040
tgagcacgaa cagtattacg ctgtgttcac tggtagcgga atccgagtgt tcgacctttc  23100
tggtaacgag aagcaagtta ggtatcctaa cggttccaac tacatcaaga ccgctaatcc  23160
acgtaacgac ctgcgaatgg ttactgtagc agactatacg ttcatcgtta accgtaacgt  23220
tgttgcacag aagaacacaa agtctgtcaa cttaccgaat tacaacccta atcaagacgg  23280
attgattaac gttcgtggtg gtcagtatgg tagggaacta attgtacaca ttaacggtaa  23340
agacgttgcg aagtataaga taccagatgg tagtcaacct gaacacgtaa acaatacgga  23400
tgcccaatgg ttagctgaag agttagccaa gcagatgcgc actaacttgt ctgattggac  23460
tgtaaatgta gggcaagggt tcatccatgt gaccgcacct agtggtcaac agattgactc  23520
cttcacgact aaagatggct acgcagacca gttgattaac cctgtgaccc actacgctca  23580
```

gtcgttctct aagctgccac ctaatgctcc taacggctac atggtgaaaa tcgtagggga 23640
cgcctctaag tctgccgacc agtattacgt tcggtatgac gctgagcgga aagtttggac 23700
tgagacttta ggttggaaca ctgaggacca agttctatgg gaaaccatgc cacacgctct 23760
tgtgcgagcc gctgacggta atttcgactt caagtggctt gagtggtctc ctaagtcttg 23820
tggtgacgtt gacaccaacc cttggccttc ttttgttggt tcaagtatta acgatgtgtt 23880
cttcttccgt aaccgcttag gattccttag tggggagaac atcatattga gtcgtacagc 23940
caaatacttc aacttctacc ctgcgtccat tgcgaacctt agtgatgacg accctataga 24000
cgtagctgtg agtaccaacc gaatagcaat ccttaagtac gccgttccgt tctcagaaga 24060
gttactcatc tggtccgatg aagcacaatt cgtcctgact gcctcgggta ctctcacatc 24120
taagtcggtt gagttgaacc taacgaccca gtttgacgta caggaccgag cgagaccttt 24180
tgggattggg cgtaatgtct actttgctag tccgaggtcc agcttcacgt ccatccacag 24240
gtactacgct gtgcaggatg tcagttccgt taagaatgct gaggacatta catcacacgt 24300
tcctaactac atccctaatg gtgtgttcag tatttgcgga agtggtacgg aaaacttctg 24360
ttcggtacta tctcacgggg accctagtaa aatcttcatg tacaaattcc tgtacctgaa 24420
cgaagagtta aggcaacagt cgtggtctca ttgggacttt ggggaaaacg tacaggttct 24480
agcttgtcag agtatcagct cagatatgta tgtgattctt cgcaatgagt tcaatacgtt 24540
cctagctaga atctctttca ctaagaacgc cattgactta cagggagaac cctatcgtgc 24600
ctttatggac atgaagattc gatacacgat tcctagtgga acatacaacg atgacacatt 24660
cactacctct attcatattc caacaattta tggtgcaaac ttcgggaggg gcaaaatcac 24720
tgtattggag cctgatggta agataaccgt gtttgagcaa cctacggctg ggtggaatag 24780
cgacccttgg ctgagactca gcggtaactt ggagggacgc atggtgtaca ttgggttcaa 24840
cattaacttc gtatatgagt tctctaagtt cctcatcaag cagactgccg acgacgggtc 24900
tacctccacg gaagacattg ggcgcttaca gttacgccga gcgtgggtta actacgagaa 24960
ctctggtacg tttgacattt atgttgagaa ccaatcgtct aactggaagt acacaatggc 25020
tggtgcccga ttaggctcta acactctgag ggctgggaga ctgaacttag ggaccggaca 25080
atatcgattc cctgtggttg gtaacgccaa gttcaacact gtatacatct tgtcagatga 25140
gactacccct ctgaacatca ttgggtgtgg ctgggaaggt aactacttac ggagaagttc 25200
cggtatttaa ttaaatattc tccctgtggt ggctcgaaat taatacgact cactataggg 25260
agaacaatac gactacggga gggttttctt atgatgacta taagacctac taaaagtaca 25320
gactttgagg tattcactcc ggctcaccat gacattcttg aagctaaggc tgctggtatt 25380
gagccgagtt tccctgatgc ttccgagtgt gtcacgttga gcctctatgg gttccctcta 25440
gctatcggtg gtaactgcgg ggaccagtgc tggttcgtta cgagcgacca agtgtggcga 25500
cttagtggaa aggctaagcg aaagttccgt aagttaatca tggagtatcg cgataagatg 25560
cttgagaagt atgatactct ttggaattac gtatgggtag gcaatacgtc ccacattcgt 25620
ttcctcaaga ctatcggtgc ggtattccat gaagagtaca cacgagatgg tcaatttcag 25680
ttatttacaa tcacgaaagg aggataacca tatgtgttgg gcagccgcaa tacctatcgc 25740
tatatctggc gctcaggcta tcagtggtca gaacgctcag gccaaaatga ttgccgctca 25800
gaccgctgct ggtcgtcgtc aagctatgga aatcatgagg cagacgaaca tccagaatgc 25860
tgacctatcg ttgcaagctc gaagtaaact tgaggaagcg tccgccgagt tgacctcaca 25920
gaacatgcag aaggtccaag ctattgggtc tatccgagcg gctatcggag agagtatgct 25980

-continued

```
tgaaggttcc tcaatggacc gcattaagcg agtcacagaa ggacagttca ttcgggaagc  26040
caatatggta actgagaact atcgccgtga ctaccaagca atcttcgcac agcaacttgg  26100
tggtactcaa agtgctgcaa gtcagattga cgaaatctat aagagcgaac agaaacagaa  26160
gagtaagcta cagatggttc tggacccact ggctatcatg gggtcttccg ctgcgagtgc  26220
ttacgcatcc ggtgcgttcg actctaagtc cacaactaag gcacctattg ttgccgctaa  26280
aggaaccaag acggggaggt aatgagctat gagtaaaatt gaatctgccc ttcaagcggc  26340
acaaccggga ctctctcggt tacgtggtgg tgctggaggt atgggctatc gtgcagcaac  26400
cactcaggcc gaacagccaa ggtcaagcct attggacacc attggtcggt tcgctaaggc  26460
tggtgccgat atgtataccg ctaaggaaca acgagcacga gacctagctg atgaacgctc  26520
taacgagatt atccgtaagc tgacccctga gcaacgtcga gaagctctca acaacgggac  26580
ccttctgtat caggatgacc catacgctat ggaagcactc cgagtcaaga ctggtcgtaa  26640
cgctgcgtat cttgtggacg atgacgttat gcagaagata aaagagggtg tcttccgtac  26700
tcgcgaagag atggaagagt atcgccatag tcgccttcaa gagggcgcta aggtatacgc  26760
tgagcagttc ggcatcgacc ctgaggacgt tgattatcag cgtggtttca acggggacat  26820
taccgagcgt aacatctcgc tgtatggtgc gcatgataac ttcttgagcc agcaagctca  26880
gaagggcgct atcatgaaca gccgagtgga actcaacggt gtccttcaag accctgatat  26940
gctgcgtcgt ccagactctg ctgacttctt tgagaagtat atcgacaacg gtctggttac  27000
tggcgcaatc ccatctgatg ctcaagccac acagcttata agccaagcgt tcagtgacgc  27060
ttctagccgt gctggtggtg ctgacttcct gatgcgagtc ggtgacaaga aggtaacact  27120
taacggagcc actacgactt accgagagtt gattggtgag gaacagtgga acgctctcat  27180
ggtcacagca caacgttctc agtttgagac tgacgcgaag ctgaacgagc agtatcgctt  27240
gaagattaac tctgcgctga accaagagga cccaaggaca gcttgggaga tgcttcaagg  27300
tatcaaggct gaactagata aggtccaacc tgatgagcag atgacaccac aacgtgagtg  27360
gctaatctcc gcacaggaac aagttcagaa tcagatgaac gcatggacga aagctcaggc  27420
caaggctctg gacgattcca tgaagtcaat gaacaaactt gacgtaatcg acaagcaatt  27480
ccagaagcga atcaacggtg agtgggtctc aacggatttt aaggatatgc cagtcaacga  27540
gaacactggt gagttcaagc atagcgatat ggttaactac gccaataaga agctcgctga  27600
gattgacagt atggacattc cagacggtgc caaggatgct atgaagttga agtaccttca  27660
agcggactct aaggacggag cattccgtac agccatcgga accatggtca ctgacgctgg  27720
tcaagagtgg tctgccgctg tgattaacgg taagttacca gaacgaaccc cagctatgga  27780
tgctctgcgc agaatccgca atgctgaccc tcagttgatt gctgcgctat acccagacca  27840
agctgagcta ttcctgacga tggacatgat ggacaagcag ggtattgacc ctcaggttat  27900
tcttgatgcc gaccgactga ctgttaagcg gtccaaagag caacgctttg aggatgataa  27960
agcattcgag tctgcactga atgcatctaa ggctcctgag attgcccgta tgccagcgtc  28020
actgcgcgaa tctgcacgta agatttatga ctccgttaag tatcgctcgg ggaacgaaag  28080
catggctatg gagcagatga ccaagttcct taaggaatct acctacacgt tcactggtga  28140
tgatgttgac ggtgataccg ttggtgtgat tcctaagaat atgatgcagg ttaactctga  28200
cccgaaatca tgggagcaag gtcgggatat tctggaggaa gcacgtaagg gaatcattgc  28260
gagcaaccct tggataacca ataagcaact gaccatgtat tctcaaggtg actccattta  28320
```

-continued

```
ccttatggac accacaggtc aagtcagagt ccgatacgac aaagagttac tctcgaaggt  28380
ctggagtgag aaccagaaga aactcgaaga gaaagctcgt gagaaggctc tggctgatgt  28440
gaacaagcga gcacctatag ttgccgctac gaaggcccgt gaagctgctg ctaaacgagt  28500
ccgagagaaa cgtaaacaga ctcctaagtt catctacgga cgtaaggagt aactaaaggc  28560
tacataagga ggccctaaat ggataagtac gataagaacg taccaagtga ttatgatggt  28620
ctgttccaaa aggctgctga tgccaacggg gtctcttatg accttttacg taaagtcgct  28680
tggacagaat cacgatttgt gcctacagca aaatctaaga ctggaccatt aggcatgatg  28740
caatttacca aggcaaccgc taaggccctc ggtctgcgag ttaccgatgg tccagacgac  28800
gaccgactga accctgagtt agctattaat gctgccgcta agcaacttgc aggtctggta  28860
gggaagtttg atggcgatga actcaaagct gcccttgcgt acaaccaagg cgagggacgc  28920
ttgggtaatc cacaacttga ggcgtactct aagggagact tcgcatcaat ctctgaggag  28980
ggacgtaact acatgcgtaa ccttctggat gttgctaagt cacctatggc tggacagttg  29040
gaaacttttg gtggcataac cccaaagggt aaaggcattc cggctgaggt aggattggct  29100
ggaattggtc acaagcagaa agtaacacag gaacttcctg agtccacaag ttttgacgtt  29160
aagggtatcg aacaggaggc tacggcgaaa ccattcgcca aggacttttg ggagacccac  29220
ggagaaacac ttgacgagta caacagtcgt tcaaccttct tcggattcaa aaatgctgcc  29280
gaagctgaac tctccaactc agtcgctggg atggctttcc gtgctggtcg tctcgataat  29340
ggttttgatg tgtttaaaga caccattacg ccgactcgct ggaactctca catctggact  29400
ccagaggagt tagagaagat tcgaacagag gttaagaacc ctgcgtacat caacgttgta  29460
actggtggtt cccctgagaa cctcgatgac ctcattaaat tggctaacga gaactttgag  29520
aatgactccc gcgctgccga ggctggccta ggtgccaaac tgagtgctgg tattattggt  29580
gctggtgtgg acccgcttag ctatgttcct atggtcggtg tcactggtaa gggctttaag  29640
ttaatcaata aggctcttgt agttggtgcc gaaagtgctg ctctgaacgt tgcatccgaa  29700
ggtctccgta cctccgtagc tggtggtgac gcagactatg cgggtgctgc cttaggtggc  29760
tttgtgtttg gcgcaggcat gtctgcaatc agtgacgctg tagctgctgg actgaaacgc  29820
agtaaaccag aagctgagtt cgacaatgag ttcatcggtc ctatgatgcg attggaagcc  29880
cgtgagacag cacgaaacgc caactctgcg gacctctctc ggatgaacac tgagaacatg  29940
aagtttgaag gtgaacataa tggtgtccct tatgaggact taccaacaga gagaggtgcc  30000
gtggtgttac atgatggctc cgttctaagt gcaagcaacc caatcaaccc taagactcta  30060
aaagagttct ccgaggttga ccctgagaag gctgcgcgag gaatcaaact ggctgggttc  30120
accgagattg gcttgaagac cttggggtct gacgatgctg acatccgtag agtggctatc  30180
gacctcgttc gctctcctac tggtatgcag tctggtgcct caggtaagtt cggtgcaaca  30240
gcttctgaca tccatgagag acttcatggt actgaccagc gtacttataa tgacttgtac  30300
aaagcaatgt ctgacgctat gaaagaccct gagttctcta ctggcggcgc taagatgtcc  30360
cgtgaagaaa ctcgatacac tatctaccgt agagcggcac tagctattga gcgtccagaa  30420
ctacagaagg cactcactcc gtctgagaga atcgttatgg acatcattaa gcgtcacttt  30480
gacaccaagc gtgaacttat ggaaaaccca gcaatattcg gtaacacaaa ggctgtgagt  30540
atcttccctg agagtcgcca caaaggtact tacgttcctc acgtatatga ccgtcatgcc  30600
aaggcgctga tgattcaacg ctacggtgcc gaaggtttgc aggaagggat tgcccgctca  30660
tggatgaaca gctacgtctc cagacctgag gtcaaggcca gagtcgatga gatgcttaag  30720
```

gaattacacg gggtgaagga agtaacacca gagatggtag agaagtacgc tatggataag 30780
gcttatggta tctcccactc agaccagttc accaacagtt ccataataga agagaacatt 30840
gagggcttag taggtatcga gaataactca ttccttgagg cacgtaactt gtttgattcg 30900
gacctatcca tcactatgcc agacggacag caattctcag tgaatgacct aagggacttc 30960
gatatgttcc gcatcatgcc agcgtatgac cgccgtgtca atggtgacat cgccatcatg 31020
gggtctactg gtaaaaccac taaggaactt aaggatgaga ttttggctct caaagcgaaa 31080
gctgagggag acggtaagaa gactggcgag gtacatgctt taatggatac cgttaagatt 31140
cttactggtc gtgctagacg caatcaggac actgtgtggg aaacctcact gcgtgccatc 31200
aatgacctag ggttcttcgc taagaacgcc tacatgggtg ctcagaacat tacggagatt 31260
gctgggatga ttgtcactgg taacgttcgt gctctagggc atggtatccc aattctgcgt 31320
gatacactct acaagtctaa accagtttca gctaaggaac tcaaggaact ccatgcgtct 31380
ctgttcggga aggaggtgga ccagttgatt cggcctaaac gtgctgacat tgtgcagcgc 31440
ctaagggaag caactgatac cggacctgcc gtggcgaaca tcgtagggac cttgaagtat 31500
tcaacacagg aactggctgc tcgctctccg tggactaagc tactgaacgg aaccactaac 31560
taccttctgg atgctgcgcg tcaaggtatg cttggggatg ttattagtgc caccctaaca 31620
ggtaagacta cccgctggga gaaagaaggc ttccttcgtg gtgcctccgt aactcctgag 31680
cagatggctg gcatcaagtc tctcatcaag gaacatatgg tacgcggtga ggacgggaag 31740
tttaccgtta aggacaagca agcgttctct atggacccac gggctatgga cttatggaga 31800
ctggctgaca aggtagctga tgaggcaatg ctgcgtccac ataaggtgtc cttacaggat 31860
tcccatgcgt tcggagcact aggtaagatg gttatgcagt ttaagtcttt cactatcaag 31920
tcccttaact ctaagttcct gcgaaccttc tatgatggat acaagaacaa ccgagcgatt 31980
gacgctgcgc tgagcatcat cacctctatg ggtctcgctg gtggtttcta tgctatggct 32040
gcacacgtca aagcatacgc tctgcctaag gagaaacgta aggagtactt ggagcgtgca 32100
ctggacccaa ccatgattgc ccacgctgcg ttatctcgta gttctcaatt gggtgctcct 32160
ttggctatgg ttgacctagt tggtggtgtt ttagggttcg agtcctccaa gatggctcgc 32220
tctacgattc tacctaagga caccgtgaag gaacgtgacc caaacaaacc gtacacctct 32280
agagaggtaa tgggcgctat gggttcaaac cttctggaac agatgccttc ggctggcttt 32340
gtggctaacg taggggctac cttaatgaat gctgctggcg tggtcaactc acctaataaa 32400
gcaaccgagc aggacttcat gactggtctt atgaactcca caaaagagtt agtaccgaac 32460
gacccattga ctcaacagct tgtgttgaag atttatgagg cgaacggtgt taacttgagg 32520
gagcgtagga aataatacga ctcactatag ggagaggcga aataatcttc tccctgtagt 32580
ctcttagatt tactttaagg aggtcaaatg gctaacgtaa ttaaaaccgt tttgacttac 32640
cagttagatg gctccaatcg tgattttaat atcccgtttg agtatctagc ccgtaagttc 32700
gtagtggtaa ctcttattgg tgtagaccga aaggtcctta cgattaatac agactatcgc 32760
tttgctacac gtactactat ctctctgaca aaggcttggg gtccagccga tggctacacg 32820
accatcgagt tacgtcgagt aacctccact accgaccgat tggttgactt tacggatggt 32880
tcaatcctcc gcgcgtatga ccttaacgtc gctcagattc aaacgatgca cgtagcggaa 32940
gaggcccgtg acctcactac ggatactatc ggtgtcaata acgatggtca cttggatgct 33000
cgtggtcgtc gaattgtgaa cctagcgaac gccgtggatg accgcgatgc tgttccgttt 33060

-continued

```
ggtcaactaa agaccatgaa ccagaactca tggcaagcac gtaatgaagc cttacagttc  33120
cgtaatgagg ctgagacttt cagaaaccaa gcggagggct ttaagaacga gtccagtacc  33180
aacgctacga acacaaagca gtggcgcgat gagaccaagg gtttccgaga cgaagccaag  33240
cggttcaaga atacggctgg tcaatacgct acatctgctg ggaactctgc ttccgctgcg  33300
catcaatctg aggtaaacgc tgagaactct gccacagcat ccgctaactc tgctcatttg  33360
gcagaacagc aagcagaccg tgcggaacgt gaggcagaca agctggaaaa ttacaatgga  33420
ttggctggtg caattgataa ggtagatgga accaatgtgt actggaaagg aaatattcac  33480
gctaacgggc gcctttacat gaccacaaac ggttttgact gtggccagta tcaacagttc  33540
tttggtggtg tcactaatcg ttactctgtc atggagtggg gagatgagaa cggatggctg  33600
atgtatgttc aacgtagaga gtggacaaca gcgataggcg gtaacatcca gttagtagta  33660
aacggacaga tcatcaccca aggtggagcc atgaccggtc agctaaaatt gcagaatggg  33720
catgttcttc aattagagtc cgcatccgac aaggcgcact atattctatc taaagatggt  33780
aacaggaata actggtacat tggtagaggg tcagataaca acaatgactg taccttccac  33840
tcctatgtac atggtacgac cttaacactc aagcaggact atgcagtagt taacaaacac  33900
ttccacgtag gtcaggccgt tgtggccact gatggtaata ttcaaggtac taagtgggga  33960
ggtaaatggc tggatgctta cctacgtgac agcttcgttg cgaagtccaa ggcgtggact  34020
caggtgtggt ctggtagtgc tggcggtggg gtaagtgtga ctgtttcaca ggatctccgc  34080
ttccgcaata tctggattaa gtgtgccaac aactcttgga acttcttccg tactggcccc  34140
gatggaatct acttcatagc ctctgatggt ggatggttac gattccaaat acactccaac  34200
ggtctcggat tcaagaatat tgcagacagt cgttcagtac ctaatgcaat catggtggag  34260
aacgagtaat tggtaaatca caaggaaaga cgtgtagtcc acggatggac tctcaaggag  34320
gtacaaggtg ctatcattag actttaacaa cgaattgatt aaggctgctc caattgttgg  34380
gacgggtgta gcagatgtta gtgctcgact gttctttggg ttaagcctta acgaatggtt  34440
ctacgttgct gctatcgcct acacagtggt tcagattggt gccaaggtag tcgataagat  34500
gattgactgg aagaaagcca ataaggagtg atatgtatgg aaaaggataa gagccttatt  34560
acattcttag agatgttgga cactgcgatg gctcagcgta tgcttgcgga cctttcggac  34620
catgagcgtc gctctccgca actctataat gctattaaca aactgttaga ccgccacaag  34680
ttccagattg gtaagttgca gccggatgtt cacatcttag gtggccttgc tggtgctctt  34740
gaagagtaca aagagaaagt cggtgataac ggtcttacgg atgatgatat ttacacatta  34800
cagtgatata ctcaaggcca ctacagatag tggtctttat ggatgtcatt gtctatacga  34860
gatgctccta cgtgaaatct gaaagttaac gggaggcatt atgctagaat ttttacgtaa  34920
gctaatccct tgggttctcg ctgggatgct attcgggtta ggatggcatc tagggtcaga  34980
ctcaatggac gctaaatgga aacaggaggt acacaatgag tacgttaaga gagttgaggc  35040
tgcgaagagc actcaaagag caatcgatgc ggtatctgct aagtatcaag aagaccttgc  35100
cgcgctggaa gggagcactg ataggattat ttctgatttg cgtagcgaca ataagcggtt  35160
gcgcgtcaga gtcaaaacta ccggaacctc cgatggtcag tgtggattcg agcctgatgg  35220
tcgagccgaa cttgacgacc gagatgctaa acgtattctc gcagtgaccc agaagggtga  35280
cgcatggatt cgtgcgttac aggatactat tcgtgaactg caacgtaagt aggaaatcaa  35340
gtaaggaggc aatgtgtcta ctcaatccaa tcgtaatgcg ctcgtagtgg cgcaactgaa  35400
aggagacttc gtggcgttcc tattcgtctt atggaaggcg ctaaacctac cggtgcccac  35460
```

-continued

```
taagtgtcag attgacatgg ctaaggtgct ggcgaatgga gacaacaaga agttcatctt  35520
acaggctttc cgtggtatcg gtaagtcgtt catcacatgt gcgttcgttg tgtggtcctt  35580
atggagagac cctcagttga agatacttat cgtatcagcc tctaaggagc gtgcagacgc  35640
taactccatc tttattaaga acatcattga cctgctgcca ttcctatctg agttaaagcc  35700
aagacccgga cagcgtgact cggtaatcag ctttgatgta ggcccagcca atcctgacca  35760
ctctcctagt gtgaaatcag taggtatcac tggtcagtta actggtagcc gtgctgacat  35820
tatcattgcg gatgacgttg agattccgtc taacagcgca actatgggtg cccgtgagaa  35880
gctatggact ctggttcagg agttcgctgc gttacttaaa ccgctgcctt cctctcgcgt  35940
tatctacctt ggtacacctc agacagagat gactctctat aaggaacttg aggataaccg  36000
tgggtacaca accattatct ggcctgctct gtacccaagg acacgtgaag agaacctcta  36060
ttactcacag cgtcttgctc ctatgttacg cgctgagtac gatgagaacc ctgaggcact  36120
tgctgggact ccaacagacc cagtgcgctt tgaccgtgat gacctgcgcg agcgtgagtt  36180
ggaatacggt aaggctggct ttacgctaca gttcatgctt aaccctaacc ttagtgatgc  36240
cgagaagtac ccgctgaggc ttcgtgacgc tatcgtagcg gccttagact tagagaaggc  36300
cccaatgcat taccagtggc ttccgaaccg tcagaacatc attgaggacc ttcctaacgt  36360
tggccttaag ggtgatgacc tgcatacgta ccacgattgt tccaacaact caggtcagta  36420
ccaacagaag attctggtca ttgaccctag tggtcgcggt aaggacgaaa caggttacgc  36480
tgtgctgtac acactgaacg gttacatcta ccttatggaa gctggaggtt tccgtgatgg  36540
ctactccgat aagacccttg agttactcgc taagaaggca aagcaatggg gagtccagac  36600
ggttgtctac gagagtaact tcggtgacgg tatgttcggt aaggtattca gtcctatcct  36660
tcttaaacac cacaactgtg cgatggaaga gattcgtgcc cgtggtatga aagagatgcg  36720
tatttgcgat acccttgagc cagtcatgca gactcaccgc cttgtaattc gtgatgaggt  36780
cattagggcc gactaccagt ccgctcgtga cgtagacggt aagcatgacg ttaagtactc  36840
gttgttctac cagatgaccc gtatcactcg tgagaaaggc gctctggctc atgatgaccg  36900
attggatgcc cttgcgttag gcattgagta tctccgtgag tccatgcagt tggattccgt  36960
taaggtcgag ggtgaagtac ttgctgactt ccttgaggaa cacatgatgc gtcctacggt  37020
tgctgctacg catatcattg agatgtctgt gggaggagtt gatgtgtact ctgaggacga  37080
tgagggttac ggtacgtctt tcattgagtg gtgatttatg cattaggact gcatagggat  37140
gcactataga ccacggatgg tcagttcttt aagttactga aaagacacga taaattaata  37200
cgactcacta tagggagagg agggacgaaa ggttactata tagatactga atgaatactt  37260
atagagtgca taaagtatgc ataatggtgt acctagagtg acctctaaga atggtgatta  37320
tattgtatta gtatcacctt aacttaagga ccaacataaa gggaggagac tcatgttccg  37380
cttattgttg aacctactgc ggcatagagt cacctaccga tttcttgtgg tactttgtgc  37440
tgcccttggg tacgcatctc ttactggaga cctcagttca ctggagtctg tcgtttgctc  37500
tatactcact tgtagcgatt agggtcttcc tgaccgactg atggctcacc gagggattca  37560
gcggtatgat tgcatcacac cacttcatcc ctatagagtc aagtcctaag gtatacccat  37620
aaagagcctc taatggtcta tcctaaggtc tatacctaaa gataggccat cctatcagtg  37680
tcacctaaag agggtcttag agagggccta tggagttcct atagggtcct ttaaaatata  37740
ccataaaaat ctgagtgact atctcacagt gtacggacct aaagttcccc catagggggt  37800
```

acctaaagcc cagccaatca cctaaagtca accttcggtt gaccttgagg gttccctaag 37860
ggttggggat gacccttggg tttgtctttg ggtgttacct tgagtgtctc tctgtgtccc 37920
t 37921

<210> SEQ ID NO 65
<211> LENGTH: 37501
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
tctcacagtg tacggaccta aagttccccc ataggggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg ggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860

-continued tgggctaacg gtcgtcgtcc tctggcgctg gtgcgtactc acagtaagaa agcactgatg 1920
cgctacgaag acgtttacat gcctgaggtg tacaaagcga ttaacattgc gcaaaacacc 1980
gcatggaaaa tcaacaagaa agtcctagcg gtcgccaacg taatcaccaa gtggaagcat 2040
tgtccggtcg aggacatccc tgcgattgag cgtgaagaac tcccgatgaa accggaagac 2100
atcgacatga atcctgaggc tctcaccgcg tggaaacgtg ctgccgctgc tgtgtaccgc 2160
aaggacaagg ctcgcaagtc tcgccgtatc agccttgagt tcatgcttga gcaagccaat 2220
aagtttgcta accataaggc catctggttc ccttacaaca tggactggcg cggtcgtgtt 2280
tacgctgtgt caatgttcaa cccgcaaggt aacgatatga ccaaaggact gcttacgctg 2340
gcgaaaggta aaccaatcgg taaggaaggt tactactggc tgaaaatcca cggtgcaaac 2400
tgtgcgggtg tcgataaggt tccgttccct gagcgcatca agttcattga ggaaaaccac 2460
gagaacatca tggcttgcgc taagtctcca ctggagaaca cttggtgggc tgagcaagat 2520
tctccgttct gcttccttgc gttctgcttt gagtacgctg gggtacagca ccacggcctg 2580
agctataact gctcccttcc gctggcgttt gacgggtctt gctctggcat ccagcacttc 2640
tccgcgatgc tccgagatga ggtaggtggt cgcgcggtta acttgcttcc tagtgaaacc 2700
gttcaggaca tctacgggat tgttgctaag aaagtcaacg agattctaca agcagacgca 2760
atcaatggga ccgataacga agtagttacc gtgaccgatg agaacactgg tgaaatctct 2820
gagaaagtca agctgggcac taaggcactg gctggtcaat ggctggctta cggtgttact 2880
cgcagtgtga ctaagcgttc agtcatgacg ctggcttacg ggtccaaaga gttcggcttc 2940
cgtcaacaag tgctggaaga taccattcag ccagctattg attccggcaa gggtctgatg 3000
ttcactcagc cgaatcaggc tgctggatac atggctaagc tgatttggga atctgtgagc 3060
gtgacggtgg tagctgcggt tgaagcaatg aactggctta agtctgctgc taagctgctg 3120
gctgctgagg tcaaagataa gaagactgga gagattcttc gcaagcgttg cgctgtgcat 3180
tgggtaactc ctgatggttt ccctgtgtgg caggaataca agaagcctat tcagacgcgc 3240
ttgaacctga tgttcctcgg tcagttccgc ttacagccta ccattaacac caacaaagat 3300
agcgagattg atgcacacaa acaggagtct ggtatcgctc ctaactttgt acacagccaa 3360
gacggtagcc accttcgtaa gactgtagtg tgggcacacg agaagtacgg aatcgaatct 3420
tttgcactga ttcacgactc cttcggtacc attccggctg acgctgcgaa cctgttcaaa 3480
gcagtgcgcg aaactatggt tgacacatat gagtcttgtg atgtactggc tgatttctac 3540
gaccagttcg ctgaccagtt gcacgagtct caattggaca aaatgccagc acttccggct 3600
aaaggtaact tgaacctccg tgacatctta gagtcggact tcgcgttcgc gtaacgccaa 3660
atcaatacga ctcactatag agggacaaac tcaaggtcat tcgcaagagt ggcctttatg 3720
attgaccttc ttccggttaa tacgactcac tataggagaa ccttaaggtt taactttaag 3780
acccttaagt gttaattaga gatttaaatt aaagaattac taagagagga ctttaagtat 3840
gcgtaacttc gaaaagatga ccaaacgttc taaccgtaat gctcgtgact tcgaggcaac 3900
caaaggtcgc aagttgaata agactaagcg tgaccgctct cacaagcgta gctgggaggg 3960
tcagtaagat gggacgttta tatagtggta atctggcagc attcaaggca gcaacaaaca 4020
agctgttcca gttagactta gcggtcattt atgatgactg gtatgatgcc tatacaagaa 4080
aagattgcat acggttacgt attgaggaca ggagtggaaa cctgattgat actagcacct 4140
tctaccacca cgacgaggac gttctgttca atatgtgtac tgattggttg aaccatatgt 4200
atgaccagtt gaaggactgg aagtaatacg actcagtata gggacaatgc ttaaggtcgc 4260

-continued tctctaggag tggccttagt catttaacca ataggagata aacattatga tgaacattaa 4320
gactaacccg tttaaagccg tgtctttcgt agagtctgcc attaagaagg ctctggataa 4380
cgctgggtat cttatcgctg aaatcaagta cgatggtgta cgcgggaaca tctgcgtaga 4440
caatactgct aacagttact ggctctctcg tgtatctaaa acgattccgg cactggagca 4500
cttaaacggg tttgatgttc gctggaagcg tctactgaac gatgaccgtt gcttctacaa 4560
agatggcttt atgcttgatg gggaactcat ggtcaagggc gtagacttta acacagggtc 4620
cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400
cttcgggtgg gcctttctgc gtttataagg agacacttta tgtttaagaa ggttggtaaa 5460
ttccttgcgg ctttggcagc tatcctgacg cttgcgtata ttcttgcggt ataccctcaa 5520
gtagcactag tagtagttgg cgcttgttac ttagcggcag tgtgtgcttg cgtgtggagt 5580
atagttaact ggtaatacga ctcactaaag gaggtacaca ccatgatgta cttaatgcca 5640
ttactcatcg tcattgtagg atgccttgcg ctccactgta gcgatgatga tatgccagat 5700
ggtcacgctt aatacgactc actaaaggag acactatatg tttcgacttc attacaacaa 5760
aagcgttaag aatttcacgg ttcgccgtgc tgaccgttca atcgtatgtg cgagcgagcg 5820
ccgagctaag atacctctta ttggtaacac agttcctttg gcaccgagcg tccacatcat 5880
tatcacccgt ggtgactttg agaaagcaat agacaagaaa cgtccggttc ttagtgtggc 5940
agtgacccgc ttcccgttcg tccgtctgtt actcaaacga atcaaggagg tgttctgatg 6000
ggactgttag atggtgaagc ctgggaaaaa gaaaacccgc cagtacaagc aactgggtgt 6060
atagcttgct tagagaaaga tgaccgttat ccacacacct gtaacaaagg agctaacgat 6120
atgaccgaac gtgaacaaga gatgatcatt aagttgatag acaataatga aggtcgccca 6180
gatgatttga atggctgcgg tattctctgc tccaatgtcc cttgccacct ctgccccgca 6240
aataacgatc aaaagataac cttaggtgaa atccgagcga tggacccacg taaaccacat 6300
ctgaataaac ctgaggtaac tcctacagat gaccagcctt ccgctgagac aatcgaaggt 6360
gtcactaagc cttcccacta catgctgttt gacgacattg aggctatcga agtgattgct 6420
cgttcaatga ccgttgagca gttcaaggga tactgcttcg gtaacatctt aaagtacaga 6480
ctacgtgctg gtaagaagtc agagttagcg tacttagaga aagacctagc gaaagcagac 6540
ttctataaag aactctttga gaaacataag gataaatgtt atgcataact tcaagtcaac 6600

-continued

```
cccacctgcc gacagcctat ctgatgactt cacatcttgc tcagagtggt gccgaaagat   6660
gtgggaagag acattcgacg atgcgtacat caagctgtat gaactttgga aatcgagagg   6720
tcaatgacta tgtcaaacgt aaatacaggt tcacttagtg tggacaataa gaagttttgg   6780
gctaccgtag agtcctcgga gcattccttc gaggttccaa tctacgctga gaccctagac   6840
gaagctctgg agttagccga atggcaatac gttccggctg gctttgaggt tactcgtgtg   6900
cgtccttgtg tagcaccgaa gtaatacgac tcactattag ggaagactcc ctctgagaaa   6960
ccaaacgaaa cctaaaggag attaacatta tggctaagaa gattttcacc tctgcgctgg   7020
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac tacctttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
```

-continued ttggaagtcg ttgcgtggat ttatagaact aggagggaat tgcatggaca attcgcacga 9060
ttccgatagt gtatttcttt accacattcc ttgtgacaac tgtgggagta gtgatgggaa 9120
ctcgctgttc tctgacggac acacgttctg ctacgtatgc gagaagtgga ctgctggtaa 9180
tgaagacact aaagagaggg cttcaaaacg gaaaccctca ggaggtaaac caatgactta 9240
caacgtgtgg aacttcgggg aatccaatgg acgctactcc gcgttaactg cgagaggaat 9300
ctccaaggaa acctgtcaga aggctggcta ctggattgcc aaagtagacg gtgtgatgta 9360
ccaagtggct gactatcggg accagaacgg caacattgtg agtcagaagg ttcgagataa 9420
agataagaac tttaagacca ctggtagtca caagagtgac gctctgttcg ggaagcactt 9480
gtggaatggt ggtaagaaga ttgtcgttac agaaggtgaa atcgacatgc ttaccgtgat 9540
ggaacttcaa gactgtaagt atcctgtagt gtcgttgggt cacggtgcct ctgccgctaa 9600
gaagacatgc gctgccaact acgaatactt tgaccagttc gaacagatta tcttaatgtt 9660
cgatatggac gaagcagggc gcaaagcagt cgaagaggct gcacaggttc tacctgctgg 9720
taaggtacga gtggcagttc ttccgtgtaa ggatgcaaac gagtgtcacc taaatggtca 9780
cgaccgtgaa atcatggagc aagtgtggaa tgctggtcct tggattcctg atggtgtggt 9840
atcggctctt tcgttacgtg aacgaatccg tgagcaccta tcgtccgagg aatcagtagg 9900
tttacttttc agtggctgca ctggtatcaa cgataagacc ttaggtgccc gtggtggtga 9960
agtcattatg gtcacttccg gttccggtat gggtaagtca acgttcgtcc gtcaacaagc 10020
tctacaatgg ggcacagcga tgggcaagaa ggtaggctta gcgatgcttg aggagtccgt 10080
tgaggagacc gctgaggacc ttataggtct acacaaccgt gtccgactga gacaatccga 10140
ctcactaaag agagagatta ttgagaacgg taagttcgac caatggttcg atgaactgtt 10200
cggcaacgat acgttccatc tatatgactc attcgccgag gctgagacgg atagactgct 10260
cgctaagctg gcctacatgc gctcaggctt gggctgtgac gtaatcattc tagaccacat 10320
ctcaatcgtc gtatccgctt ctggtgaatc cgatgagcgt aagatgattg acaacctgat 10380
gaccaagctc aaagggttcg ctaagtcaac tggggtggtg ctggtcgtaa tttgtcacct 10440
taagaaccca gacaaaggta aagcacatga ggaaggtcgc cccgtttcta ttactgacct 10500
acgtggttct ggcgcactac gccaactatc tgatactatt attgcccttg agcgtaatca 10560
gcaaggcgat atgcctaacc ttgtcctcgt tcgtattctc aagtgccgct ttactggtga 10620
tactggtatc gctggctaca tggaatacaa caaggaaacc ggatggcttg aaccatcaag 10680
ttactcaggg gaagaagagt cacactcaga gtcaacagac tggtccaacg acactgactt 10740
ctgacaggat tcttgatgac tttccagacg actacgagaa gtttcgctgg agagtcccat 10800
tctaatacga ctcactaaag gagacacacc atgttcaaac tgattaagaa gttaggccaa 10860
ctgctggttc gtatgtacaa cgtggaagcc aagcgactga acgatgaggc tcgtaaagag 10920
gccacacagt cacgcgctct ggcgattcgc tccaacgaac tggctgacag tgcatccact 10980
aaagttaccg aggctgcccg tgtggcaaac caagctcaac agctttccaa attctttgag 11040
taatcaaaca ggagaaacca ttatgtctaa cgtagctgaa actatccgtc tatccgatac 11100
agctgaccag tggaaccgtc gagtccacat caacgttcgc aacggtaagg cgactatggt 11160
ttaccgctgg aaggactcta agtcctctaa gaatcacact cagcgtatga cgttgacaga 11220
tgagcaagca ctgcgtctgg tcaatgcgct taccaaagct gccgtgacag caattcatga 11280
agctggtcgc gtcaatgaag ctatggctat cctcgacaag attgataact aagagtggta 11340

-continued

```
tcctcaaggt cgccaaagtg gtggccttca tgaatactat tcgactcact ataggagata  11400
ttaccatgcg tgaccctaaa gttatccaag cagaaatcgc taaactggaa gctgaactgg  11460
aggacgttaa gtaccatgaa gctaagactc gctccgctgt tcacatcttg aagaacttag  11520
gctggacttg gacaagacag actggctgga agaaaccaga agttaccaag ctgagtcata  11580
aggtgttcga taaggacact atgacccaca tcaaggctgg tgattgggtt aaggttgaca  11640
tgggagttgt tggtggatac ggctacgtcc gctcagttag tggcaaatat gcacaagtgt  11700
catacatcac aggtgttact ccacgcggtg caatcgttgc cgataagacc aacatgattc  11760
acacaggttt cttgacagtt gtttcatatg aagagattgt taagtcacga taatcaatag  11820
gagaaatcaa tatgatcgtt tctgacatcg aagctaacgc cctcttagag agcgtcacta  11880
agttccactg cggggttatc tacgactact ccaccgctga gtacgtaagc taccgtccga  11940
gtgacttcgg tgcgtatctg gatgcgctgg aagccgaggt tgcacgaggc ggtcttattg  12000
tgttccacaa cggtcacaag tatgacgttc ctgcattgac caaactggca aagttgcaat  12060
tgaaccgaga gttccacctt cctcgtgaga actgtattga cacccttgtg ttgtcacgtt  12120
tgattcattc caacctcaag gacaccgata tgggtcttct gcgttccggc aagttgcccg  12180
gaaaacgctt tgggtctcac gctttggagg cgtggggtta tcgcttaggc gagatgaagg  12240
gtgaatacaa agacgacttt aagcgtatgc ttgaagagca gggtgaagaa tacgttgacg  12300
gaatggagtg gtggaacttc aacgaagaga tgatggacta taacgttcag gacgttgtgg  12360
taactaaagc tctccttgag aagctactct ctgacaaaca ttacttccct cctgagattg  12420
actttacgga cgtaggatac actacgttct ggtcagaatc ccttgaggcc gttgacattg  12480
aacatcgtgc tgcatggctg ctcgctaaac aagagcgcaa cgggttcccg tttgacacaa  12540
aagcaatcga agagttgtac gtagagttag ctgctcgccg ctctgagttg ctccgtaaat  12600
tgaccgaaac gttcggctcg tggtatcagc ctaaaggtgg cactgagatg ttctgccatc  12660
cgcgaacagg taagccacta cctaaatacc ctcgcattaa gacacctaaa gttggtggta  12720
tctttaagaa gcctaagaac aaggcacagc gagaaggccg tgagccttgc gaacttgata  12780
cccgcgagta cgttgctggt gctccttaca ccccagttga acatgttgtg tttaaccctt  12840
cgtctcgtga ccacattcag aagaaactcc aagaggctgg gtgggtcccg accaagtaca  12900
ccgataaggg tgctcctgtg gtggacgatg aggtactcga aggagtacgt gtagatgacc  12960
ctgagaagca agccgctatc gacctcatta aagagtactt gatgattcag aagcgaatcg  13020
gacagtctgc tgagggagac aaagcatggc ttcgttatgt tgctgaggat ggtaagattc  13080
atggttctgt taaccctaat ggagcagtta cgggtcgtgc gacccatgcg ttcccaaacc  13140
ttgcgcaaat tccgggtgta cgttctcctt atggagagca gtgtcgcgct gcttttggcg  13200
ctgagcacca tttggatggg ataactggta agccttgggt tcaggctggc atcgacgcat  13260
ccggtcttga gctacgctgc ttggctcact tcatggctcg ctttgataac ggcgagtacg  13320
ctcacgagat tcttaacggc gacatccaca ctaagaacca gatagctgct gaactaccta  13380
cccgagataa cgctaagacg ttcatctatg ggttcctcta tggtgctggt gatgagaaga  13440
ttggacagat tgttggtgct ggtaaagagc gcggtaagga actcaagaag aaattccttg  13500
agaacacccc cgcgattgca gcactccgcg agtctatcca acagacactt gtcgagtcct  13560
ctcaatgggt agctggtgag caacaagtca agtggaaacg ccgctggatt aaaggtctgg  13620
atggtcgtaa ggtacacgtt cgtagtcctc acgctgcctt gaatacccta ctgcaatctg  13680
ctggtgctct catctgcaaa ctgtggatta tcaagaccga agagatgctc gtagagaaag  13740
```

gcttgaagca tggctgggat ggggactttg cgtacatggc atgggtacat gatgaaatcc 13800
aagtaggctg ccgtaccgaa gagattgctc aggtggtcat tgagaccgca caagaagcga 13860
tgcgctgggt tggagaccac tggaacttcc ggtgtcttct ggataccgaa ggtaagatgg 13920
gtcctaattg ggcgatttgc cactgataca ggaggctact catgaacgaa agacacttaa 13980
caggtgctgc ttctgaaatg ctagtagcct acaaatttac caaagctggg tacactgtct 14040
attaccctat gctgactcag agtaaagagg acttggttgt atgtaaggat ggtaaattta 14100
gtaaggttca ggttaaaaca gccacaacgg ttcaaaccaa cacaggagat gccaagcagg 14160
ttaggctagg tggatgcggt aggtccgaat ataaggatgg agactttgac attcttgcgg 14220
ttgtggttga cgaagatgtg cttattttca catgggacga agtaaaaggt aagacatcca 14280
tgtgtgtcgg caagagaaac aaaggcataa aactatagga gaaattatta tggctatgac 14340
aaagaaattt aaagtgtcct tcgacgttac cgcaaagatg tcgtctgacg ttcaggcaat 14400
cttagagaaa gatatgctgc atctatgtaa gcaggtcggc tcaggtgcga ttgtccccaa 14460
tggtaaacag aaggaaatga ttgtccagtt cctgacacac ggtatggaag gattgatgac 14520
attcgtagta cgtacatcat ttcgtgaggc cattaaggac atgcacgaag agtatgcaga 14580
taaggactct ttcaaacaat ctcctgcaac agtacgggag gtgttctgat gtctgactac 14640
ctgaaagtgc tgcaagcaat caaaagttgc cctaagactt tccagtccaa ctatgtacgg 14700
aacaatgcga gcctcgtagc ggaggccgct tcccgtggtc acatctcgtg cctgactact 14760
agtggacgta acggtggcgc ttgggaaatc actgcttccg gtactcgctt tctgaaacga 14820
atgggaggat gtgtctaatg tctcgtgacc ttgtgactat tccacgcgat gtgtggaacg 14880
atatacaggg ctacatcgac tctctggaac gtgagaacga tagccttaag aatcaactaa 14940
tggaagctga cgaatacgta gcggaactag aggagaaact taatggcact tcttgacctt 15000
aaacaattct atgagttacg tgaaggctgc gacgacaagg gtatccttgt gatggacggc 15060
gactggctgg tcttccaagc tatgagtgct gctgagtttg atgcctcttg ggaggaagag 15120
atttggcacc gatgctgtga ccacgctaag gcccgtcaga ttcttgagga ttccattaag 15180
tcctacgaga cccgtaagaa ggcttgggca ggtgctccaa ttgtccttgc gttcaccgat 15240
agtgttaact ggcgtaaaga actggttgac ccgaactata aggctaaccg taaggccgtg 15300
aagaaacctg tagggtactt tgagttcctt gatgctctct ttgagcgcga agagttctat 15360
tgcatccgtg agcctatgct tgagggtgat gacgttatgg gagttattgc ttccaatccg 15420
tctgccttcg gtgctcgtaa ggctgtaatc atctcttgcg ataaggactt taagaccatc 15480
cctaactgtg acttcctgtg gtgtaccact ggtaacatcc tgactcagac cgaagagtcc 15540
gctgactggt ggcacctctt ccagaccatc aagggtgaca tcactgatgg ttactcaggg 15600
attgctggat ggggtgatac cgccgaggac ttcttgaata acccgttcat aaccgagcct 15660
aaaacgtctg tgcttaagtc cggtaagaac aaaggccaag aggttactaa atgggttaaa 15720
cgcgaccctg agcctcatga gacgctttgg gactgcatta agtccattgg cgcgaaggct 15780
ggtatgaccg aagaggatat tatcaagcag ggccaaatgg ctcgaatcct acggttcaac 15840
gagtacaact ttattgacaa ggagatttac ctgtggagac cgtagcgtat attggtctgg 15900
gtctttgtgt tctcggagtg tgcctcattt cgtggggcct ttgggactta gccagaataa 15960
tcaagtcgtt acacgacact aagtgataaa ctcaaggtcc ctaaattaat acgactcact 16020
atagggagat aggggccttt acgattatta ctttaagatt taactctaag aggaatcttt 16080

-continued

```
attatgttaa cacctattaa ccaattactt aagaacccta acgatattcc agatgtacct  16140
cgtgcaaccg ctgagtatct acaggttcga ttcaactatg cgtacctcga agcgtctggt  16200
catataggac ttatgcgtgc taatggttgt agtgaggccc acatcttggg tttcattcag  16260
ggcctacagt atgcctctaa cgtcattgac gagattgagt tacgcaagga acaactaaga  16320
gatgatgggg aggattgaca ctatgtgttt ctcaccgaaa attaaaactc cgaagatgga  16380
taccaatcag attcgagccg ttgagccagc gcctctgacc caagaagtgt caagcgtgga  16440
gttcggtggg tcttctgatg agacggatac cgagggcacc gaagtgtctg gacgcaaagg  16500
cctcaaggtc gaacgtgatg attccgtagc gaagtctaaa gccagcggca atggctccgc  16560
tcgtatgaaa tcttccatcc gtaagtccgc atttggaggt aagaagtgat gtctgagttc  16620
acatgtgtgg aggctaagag tcgcttccgt gcaatccggt ggactgtgga acaccttggg  16680
ttgcctaaag gattcgaagg acactttgtg ggctacagcc tctacgtaga cgaagtgatg  16740
gacatgtctg gttgccgtga agagtacatt ctggactcta ccggaaaaca tgtagcgtac  16800
ttcgcgtggt gcgtaagctg tgacattcac cacaaaggag acattctgga tgtaacgtcc  16860
gttgtcatta atcctgaggc agactctaag ggcttacagc gattcctagc gaaacgcttt  16920
aagtaccttg cggaactcca cgattgcgat tgggtgtctc gttgtaagca tgaaggcgag  16980
acaatgcgtg tatactttaa ggaggtataa gttatgggta agaaagttaa gaaggccgtg  17040
aagaaagtca ccaagtccgt taagaaagtc gttaaggaag gggctcgtcc ggttaaacag  17100
gttgctggcg gtctagctgg tctggctggt ggtactggtg aagcacagat ggtggaagta  17160
ccacaagctg ccgcacagat tgttgacgta cctgagaaag aggtttccac tgaggacgaa  17220
gcacagacag aaagcggacg caagaaagct cgtgctggcg gtaagaaatc cttgagtgta  17280
gcccgtagct ccggtggcgg tatcaacatt taatcaggag gttatcgtgg aagactgcat  17340
tgaatggacc ggaggtgtca actctaaggg ttatggtcgt aagtgggtta atggtaaact  17400
tgtgactcca cataggcaca tctatgagga gacatatggt ccagttccaa caggaattgt  17460
ggtgatgcat atctgcgata accctaggtg ctataacata aagcacctta cgcttggaac  17520
tccaaaggat aattccgagg acatggttac caaaggtaga caggctaaag gagaggaact  17580
aagcaagaaa cttacagagt cagacgttct cgctatacgc tcttcaacct taagccaccg  17640
ctccttagga gaactgtatg gagtcagtca atcaacccata acgcgaatac tacagcgtaa  17700
gacatggaga cacatttaat ggctgagaaa cgaacaggac ttgcggagga tggcgcaaag  17760
tctgtctatg agcgtttaaa gaacgaccgt gctccctatg agacacgcgc tcagaattgc  17820
gctcaatata ccatcccatc attgttccct aaggactccg ataacgcctc tacagattat  17880
caaactccgt ggcaagccgt gggcgctcgt ggtctgaaca atctagcctc taagctcatg  17940
ctggctctat tccctatgca gacttggatg cgacttacta tatctgaata tgaagcaaag  18000
cagttactga gcgaccccga tggactcgct aaggtcgatg agggcctctc gatggtagag  18060
cgtatcatca tgaactacat tgagtctaac agttaccgcg tgactctctt tgaggctctc  18120
aaacagttag tcgtagctgg taacgtcctg ctgtacctac cggaaccgga agggtcaaac  18180
tataatccca tgaagctgta ccgattgtct tcttatgtgg tccaacgaga cgcattcggc  18240
aacgttctgc aaatggtgac tcgtgaccag atagcttttg gtgctctccc tgaggacatc  18300
cgtaaggctg tagaaggtca aggtggtgag aagaaagctg atgagacaat cgacgtgtac  18360
actcacatct atctggatga ggactcaggt gaatacctcc gatacgaaga ggtcgagggt  18420
atggaagtcc aaggctccga tgggacttat cctaaagagg cttgcccata catcccgatt  18480
```

```
cggatggtca gactagatgg tgaatcctac ggtcgttcgt acattgagga atacttaggt  18540
gacttacggt cccttgaaaa tctccaagag gctatcgtca agatgtccat gattagctct  18600
aaggttatcg gcttagtgaa tcctgctggt atcacccagc cacgccgact gaccaaagct  18660
cagactggtg acttcgttac tggtcgtcca gaagacatct cgttcctcca actggagaag  18720
caagcagact ttactgtagc taaagccgta agtgacgcta tcgaggctcg cctttcgttt  18780
gcctttatgt tgaactctgc ggttcagcgt acaggtgaac gtgtgaccgc cgaagagatt  18840
cggtatgtag cttctgaact tgaagatact ttaggtggtg tctactctat cctttctcaa  18900
gaattacaat tgcctctggt acgagtgctc ttgaagcaac tacaagccac gcaacagatt  18960
cctgagttac ctaaggaagc cgtagagcca accattagta caggtctgga agcaattggt  19020
cgaggacaag accttgataa gctggagcgg tgtgtcactg cgtgggctgc actggcacct  19080
atgcgggacg accctgatat taaccttgcg atgattaagt tacgtattgc caacgctatc  19140
ggtattgaca cttctggtat tctactcacc gaagaacaga agcaacagaa gatggcccaa  19200
cagtctatgc aaatgggtat ggataatggt gctgctgcgc tggctcaagg tatggctgca  19260
caagctacag cttcacctga ggctatggct gctgccgctg attccgtagg tttacagccg  19320
ggaatttaat acgactcact atagggagac ctcatctttg aaatgagcga tgacaagagg  19380
ttggagtcct cggtcttcct gtagttcaac tttaaggaga caataataat ggctgaatct  19440
aatgcagacg tatatgcatc ttttggcgtg aactccgctg tgatgtctgg tggttccgtt  19500
gaggaacatg agcagaacat gctggctctt gatgttgctg cccgtgatgg cgatgatgca  19560
atcgagttag cgtcagacga agtggaaaca gaacgtgacc tgtatgacaa ctctgacccg  19620
ttcggtcaag aggatgacga aggccgcatt caggttcgta tcggtgatgg ctctgagccg  19680
accgatgtgg acactggaga agaaggcgtt gagggcaccg aaggttccga agagtttacc  19740
ccactgggcg agactccaga agaactggta gctgcctctg agcaacttgg tgagcacgaa  19800
gagggcttcc aagagatgat taacattgct gctgagcgtg gcatgagtgt cgagaccatt  19860
gaggctatcc agcgtgagta cgaggagaac gaagagttgt ccgccgagtc ctacgctaag  19920
ctggctgaaa ttggctacac gaaggctttc attgactcgt atatccgtgg tcaagaagct  19980
ctggtggagc agtacgtaaa cagtgtcatt gagtacgctg gtggtcgtga acgttttgat  20040
gcactgtata accaccttga gacgcacaac cctgaggctg cacagtcgct ggataatgcg  20100
ttgaccaatc gtgacttagc gaccgttaag gctatcatca acttggctgg tgagtctcgc  20160
gctaaggcgt tcggtcgtaa gccaactcgt agtgtgacta atcgtgctat tccggctaaa  20220
cctcaggcta ccaagcgtga aggctttgcg gaccgtagcg agatgattaa agctatgagt  20280
gaccctcggt atcgcacaga tgccaactat cgtcgtcaag tcgaacagaa agtaatcgat  20340
tcgaacttct gatagacttc gaaattaata cgactcacta tagggagacc acaacggttt  20400
ccctctagaa ataattttgt ttaactttaa gaaggagata tacatatggc tagcatgact  20460
ggtggacagc aaatgggtac taaccaaggt aaaggtgtag ttgctgctgg agataaactg  20520
gcgttgttct tgaaggtatt tggcggtgaa gtcctgactg cgttcgctcg tacctccgtg  20580
accacttctc gccacatggt acgttccatc tccagcggta aatccgctca gttccctgtt  20640
ctgggtcgca ctcaggcagc gtatctggct ccgggcgaga acctcgacga taaacgtaag  20700
gacatcaaac acaccgagaa ggtaatcacc attgacggtc tcctgacggc tgacgttctg  20760
atttatgata ttgaggacgc gatgaaccac tacgacgttc gctctgagta tacctctcag  20820
```

ttgggtgaat ctctggcgat ggctgcggat ggtgcggttc tggctgagat tgccggtctg 20880
tgtaacgtgg aaagcaaata taatgagaac atcgagggct taggtactgc taccgtaatt 20940
gagaccactc agaacaaggc cgcacttacc gaccaagttg cgctgggtaa ggagattatt 21000
gcggctctga ctaaggctcg tgcggctctg accaagaact atgttccggc tgctgaccgt 21060
gtgttctact gtgacccaga tagctactct gcgattctgg cagcactgat gccgaacgca 21120
gcaaactacg ctgctctgat tgaccctgag aagggttcta tccgcaacgt tatgggcttt 21180
gaggttgtag aagttccgca cctcaccgct ggtggtgctg gtaccgctcg tgagggcact 21240
actggtcaga agcacgtctt ccctgccaat aaaggtgagg gtaatgtcaa ggttgctaag 21300
gacaacgtta tcggcctgtt catgcaccgc tctgcggtag gtactgttaa gctgcgtgac 21360
ttggctctgg agcgcgctcg ccgtgctaac ttccaagcgg accagattat cgctaagtac 21420
gcaatgggcc acggtggtct tcgcccagaa gctgcaggag ctgtcgtatt ccagtcaggt 21480
gtgatgctcg gggatccgaa ttcttaagta actaacgaaa ttaatacgac tcactatagg 21540
gagaccacaa cggtttccct ctagaaataa ttttgtttaa ctttaagaag gagatataca 21600
tatgttttgg ggcgcgctga ttaaaggcgc ggcgaaactg attccgagcg tggtgggcct 21660
gtttaaaaaa aaacagtaag gatccggctg ctaacaaagc ccgaagcttg cggccgcact 21720
cgagtaacta gttaacccct tggggcctct aaacgggtct tgaggggttt tttgctgaaa 21780
ggaggaacta tatgcgctca tacgatatga acgttgagac tgccgctgag ttatcagctg 21840
tgaacgacat tctggcgtct atcggtgaac ctccggtatc aacgctggaa ggtgacgcta 21900
acgcagatgc agcgaacgct cggcgtattc tcaacaagat taaccgacag attcaatctc 21960
gtggatggac gttcaacatt gaggaaggca taacgctact acctgatgtt tactccaacc 22020
tgattgtata cagtgacgac tatttatccc taatgtctac ttccggtcaa tccatctacg 22080
ttaaccgagg tggctatgtg tatgaccgaa cgagtcaatc agaccgcttt gactctggta 22140
ttactgtgaa cattattcgt ctccgcgact acgatgagat gcctgagtgc ttccgttact 22200
ggattgtcac caaggcttcc cgtcagttca acaaccgatt ctttggggca ccggaagtag 22260
agggtgtact ccaagaagag gaagatgagg ctagacgtct ctgcatggag tatgagatgg 22320
actacggtgg gtacaatatg ctggatggag atgcgttcac ttctggtcta ctgactcgct 22380
aacattaata aataaggagg ctctaatggc actcattagc caatcaatca agaacttgaa 22440
gggtggtatc agccaacagc ctgacatcct tcgttatcca gaccaagggt cacgccaagt 22500
taacggttgg tcttcggaga ccgagggcct ccaaaagcgt ccacctcttg ttttcttaaa 22560
tacacttgga gacaacggtg cgttaggtca agctccgtac atccacctga ttaaccgaga 22620
tgagcacgaa cagtattacg ctgtgttcac tggtagcgga atccgagtgt tcgacctttc 22680
tggtaacgag aagcaagtta ggtatcctaa cggttccaac tacatcaaga ccgctaatcc 22740
acgtaacgac ctgcgaatgg ttactgtagc agactatacg ttcatcgtta accgtaacgt 22800
tgttgcacag aagaacacaa agtctgtcaa cttaccgaat tacaacccta atcaagacgg 22860
attgattaac gttcgtggtg gtcagtatgg tagggaacta attgtacaca ttaacggtaa 22920
agacgttgcg aagtataaga taccagatgg tagtcaacct gaacacgtaa acaatacgga 22980
tgcccaatgg ttagctgaag agttagccaa gcagatgcgc actaacttgt ctgattggac 23040
tgtaaatgta gggcaagggt tcatccatgt gaccgcacct agtggtcaac agattgactc 23100
cttcacgact aaagatggct acgcagacca gttgattaac cctgtgaccc actacgctca 23160
gtcgttctct aagctgccac ctaatgctcc taacggctac atggtgaaaa tcgtagggga 23220

```
cgcctctaag tctgccgacc agtattacgt tcggtatgac gctgagcgga aagtttggac  23280
tgagacttta ggttggaaca ctgaggacca agttctatgg gaaaccatgc cacacgctct  23340
tgtgcgagcc gctgacggta atttcgactt caagtggctt gagtggtctc ctaagtcttg  23400
tggtgacgtt gacaccaacc cttggccttc ttttgttggt tcaagtatta acgatgtgtt  23460
cttcttccgt aaccgcttag gattccttag tggggagaac atcatattga gtcgtacagc  23520
caaatacttc aacttctacc ctgcgtccat tgcgaacctt agtgatgacg accctataga  23580
cgtagctgtg agtaccaacc gaatagcaat ccttaagtac gccgttccgt tctcagaaga  23640
gttactcatc tggtccgatg aagcacaatt cgtcctgact gcctcgggta ctctcacatc  23700
taagtcggtt gagttgaacc taacgaccca gtttgacgta caggaccgag cgagaccttt  23760
tgggattggg cgtaatgtct actttgctag tccgaggtcc agcttcacgt ccatccacag  23820
gtactacgct gtgcaggatg tcagttccgt taagaatgct gaggacatta catcacacgt  23880
tcctaactac atccctaatg gtgtgttcag tatttgcgga agtggtacgg aaaacttctg  23940
ttcggtacta tctcacgggg accctagtaa aatcttcatg tacaaattcc tgtacctgaa  24000
cgaagagtta aggcaacagt cgtggtctca ttgggacttt ggggaaaacg tacaggttct  24060
agcttgtcag agtatcagct cagatatgta tgtgattctt cgcaatgagt tcaatacgtt  24120
cctagctaga atctctttca ctaagaacgc cattgactta cagggagaac cctatcgtgc  24180
ctttatggac atgaagattc gatacacgat tcctagtgga acatacaacg atgacacatt  24240
cactacctct attcatattc caacaattta tggtgcaaac ttcgggaggg gcaaaatcac  24300
tgtattggag cctgatggta agataaccgt gtttgagcaa cctacggctg ggtggaatag  24360
cgacccttgg ctgagactca gcggtaactt ggagggacgc atggtgtaca ttgggttcaa  24420
cattaacttc gtatatgagt tctctaagtt cctcatcaag cagactgccg acgacgggtc  24480
tacctccacg gaagacattg ggcgcttaca gttacgccga gcgtgggtta actacgagaa  24540
ctctggtacg tttgacattt atgttgagaa ccaatcgtct aactggaagt acacaatggc  24600
tggtgcccga ttaggctcta acactctgag ggctgggaga ctgaacttag ggaccggaca  24660
atatcgattc cctgtggttg gtaacgccaa gttcaacact gtatacatct tgtcagatga  24720
gactacccct ctgaacatca ttgggtgtgg ctgggaaggt aactacttac ggagaagttc  24780
cggtatttaa ttaaatattc tccctgtggt ggctcgaaat taatacgact cactataggg  24840
agaacaatac gactacggga gggttttctt atgatgacta taagacctac taaaagtaca  24900
gactttgagg tattcactcc ggctcaccat gacattcttg aagctaaggc tgctggtatt  24960
gagccgagtt tccctgatgc ttccgagtgt gtcacgttga gcctctatgg gttccctcta  25020
gctatcggtg gtaactgcgg ggaccagtgc tggttcgtta cgagcgacca agtgtggcga  25080
cttagtggaa aggctaagcg aaagttccgt aagttaatca tggagtatcg cgataagatg  25140
cttgagaagt atgatactct ttggaattac gtatgggtag gcaatacgtc ccacattcgt  25200
ttcctcaaga ctatcggtgc ggtattccat gaagagtaca cacgagatgg tcaatttcag  25260
ttatttacaa tcacgaaagg aggataacca tatgtgttgg gcagccgcaa tacctatcgc  25320
tatatctggc gctcaggcta tcagtggtca gaacgctcag gccaaaatga ttgccgctca  25380
gaccgctgct ggtcgtcgtc aagctatgga aatcatgagg cagacgaaca tccagaatgc  25440
tgacctatcg ttgcaagctc gaagtaaact tgaggaagcg tccgccgagt tgacctcaca  25500
gaacatgcag aaggtccaag ctattgggtc tatccgagcg gctatcggag agagtatgct  25560
```

-continued

```
tgaaggttcc tcaatggacc gcattaagcg agtcacagaa ggacagttca ttcgggaagc  25620
caatatggta actgagaact atcgccgtga ctaccaagca atcttcgcac agcaacttgg  25680
tggtactcaa agtgctgcaa gtcagattga cgaaatctat aagagcgaac agaaacagaa  25740
gagtaagcta cagatggttc tggacccact ggctatcatg gggtcttccg ctgcgagtgc  25800
ttacgcatcc ggtgcgttcg actctaagtc cacaactaag gcacctattg ttgccgctaa  25860
aggaaccaag acggggaggt aatgagctat gagtaaaatt gaatctgccc ttcaagcggc  25920
acaaccggga ctctctcggt tacgtggtgg tgctggaggt atgggctatc gtgcagcaac  25980
cactcaggcc gaacagccaa ggtcaagcct attggacacc attggtcggt tcgctaaggc  26040
tggtgccgat atgtataccg ctaaggaaca acgagcacga gacctagctg atgaacgctc  26100
taacgagatt atccgtaagc tgacccctga gcaacgtcga gaagctctca acaacgggac  26160
ccttctgtat caggatgacc catacgctat ggaagcactc cgagtcaaga ctggtcgtaa  26220
cgctgcgtat cttgtggacg atgacgttat gcagaagata aaagagggtg tcttccgtac  26280
tcgcgaagag atggaagagt atcgccatag tcgccttcaa gagggcgcta aggtatacgc  26340
tgagcagttc ggcatcgacc ctgaggacgt tgattatcag cgtggtttca acggggacat  26400
taccgagcgt aacatctcgc tgtatggtgc gcatgataac ttcttgagcc agcaagctca  26460
gaagggcgct atcatgaaca gccgagtgga actcaacggt gtccttcaag accctgatat  26520
gctgcgtcgt ccagactctg ctgacttctt tgagaagtat atcgacaacg gtctggttac  26580
tggcgcaatc ccatctgatg ctcaagccac acagcttata agccaagcgt tcagtgacgc  26640
ttctagccgt gctggtggtg ctgacttcct gatgcgagtc ggtgacaaga aggtaacact  26700
taacggagcc actacgactt accgagagtt gattggtgag gaacagtgga acgctctcat  26760
ggtcacagca caacgttctc agtttgagac tgacgcgaag ctgaacgagc agtatcgctt  26820
gaagattaac tctgcgctga accaagagga cccaaggaca gcttgggaga tgcttcaagg  26880
tatcaaggct gaactagata aggtccaacc tgatgagcag atgacaccac aacgtgagtg  26940
gctaatctcc gcacaggaac aagttcagaa tcagatgaac gcatggacga aagctcaggc  27000
caaggctctg gacgattcca tgaagtcaat gaacaaactt gacgtaatcg acaagcaatt  27060
ccagaagcga atcaacggtg agtgggtctc aacggatttt aaggatatgc cagtcaacga  27120
gaacactggt gagttcaagc atagcgatat ggttaactac gccaataaga agctcgctga  27180
gattgacagt atggacattc cagacggtgc caaggatgct atgaagttga agtaccttca  27240
agcggactct aaggacggag cattccgtac agccatcgga accatggtca ctgacgctgg  27300
tcaagagtgg tctgccgctg tgattaacgg taagttacca gaacgaaccc cagctatgga  27360
tgctctgcgc agaatccgca atgctgaccc tcagttgatt gctgcgctat acccagacca  27420
agctgagcta ttcctgacga tggacatgat ggacaagcag ggtattgacc ctcaggttat  27480
tcttgatgcc gaccgactga ctgttaagcg gtccaaagag caacgctttg aggatgataa  27540
agcattcgag tctgcactga atgcatctaa ggctcctgag attgcccgta tgccagcgtc  27600
actgcgcgaa tctgcacgta agatttatga ctccgttaag tatcgctcgg ggaacgaaag  27660
catggctatg gagcagatga ccaagttcct taaggaatct acctacacgt tcactggtga  27720
tgatgttgac ggtgataccg ttggtgtgat tcctaagaat atgatgcagg ttaactctga  27780
cccgaaatca tgggagcaag gtcgggatat tctggaggaa gcacgtaagg gaatcattgc  27840
gagcaaccct tggataacca ataagcaact gaccatgtat tctcaaggtg actccattta  27900
ccttatggac accacaggtc aagtcagagt ccgatacgac aaagagttac tctcgaaggt  27960
```

```
ctggagtgag aaccagaaga aactcgaaga gaaagctcgt gagaaggctc tggctgatgt  28020
gaacaagcga gcacctatag ttgccgctac gaaggcccgt gaagctgctg ctaaacgagt  28080
ccgagagaaa cgtaaacaga ctcctaagtt catctacgga cgtaaggagt aactaaaggc  28140
tacataagga ggccctaaat ggataagtac gataagaacg taccaagtga ttatgatggt  28200
ctgttccaaa aggctgctga tgccaacggg gtctcttatg accttttacg taaagtcgct  28260
tggacagaat cacgatttgt gcctacagca aaatctaaga ctggaccatt aggcatgatg  28320
caatttacca aggcaaccgc taaggccctc ggtctgcgag ttaccgatgg tccagacgac  28380
gaccgactga accctgagtt agctattaat gctgccgcta agcaacttgc aggtctggta  28440
gggaagtttg atggcgatga actcaaagct gcccttgcgt acaaccaagg cgagggacgc  28500
ttgggtaatc cacaacttga ggcgtactct aagggagact tcgcatcaat ctctgaggag  28560
ggacgtaact acatgcgtaa ccttctggat gttgctaagt cacctatggc tggacagttg  28620
gaaacttttg gtggcataac cccaaagggt aaaggcattc cggctgaggt aggattggct  28680
ggaattggtc acaagcagaa agtaacacag gaacttcctg agtccacaag ttttgacgtt  28740
aagggtatcg aacaggaggc tacggcgaaa ccattcgcca aggacttttg ggagacccac  28800
ggagaaacac ttgacgagta caacagtcgt tcaaccttct tcggattcaa aaatgctgcc  28860
gaagctgaac tctccaactc agtcgctggg atggctttcc gtgctggtcg tctcgataat  28920
ggttttgatg tgtttaaaga caccattacg ccgactcgct ggaactctca catctggact  28980
ccagaggagt tagagaagat tcgaacagag gttaagaacc ctgcgtacat caacgttgta  29040
actggtggtt cccctgagaa cctcgatgac ctcattaaat tggctaacga gaactttgag  29100
aatgactccc gcgctgccga ggctggccta ggtgccaaac tgagtgctgg tattattggt  29160
gctggtgtgg acccgcttag ctatgttcct atggtcggtg tcactggtaa gggctttaag  29220
ttaatcaata aggctcttgt agttggtgcc gaaagtgctg ctctgaacgt tgcatccgaa  29280
ggtctccgta cctccgtagc tggtggtgac gcagactatg cgggtgctgc cttaggtggc  29340
tttgtgtttg gcgcaggcat gtctgcaatc agtgacgctg tagctgctgg actgaaacgc  29400
agtaaaccag aagctgagtt cgacaatgag ttcatcggtc ctatgatgcg attggaagcc  29460
cgtgagacag cacgaaacgc caactctgcg gacctctctc ggatgaacac tgagaacatg  29520
aagtttgaag gtgaacataa tggtgtccct tatgaggact taccaacaga gagaggtgcc  29580
gtggtgttac atgatggctc cgttctaagt gcaagcaacc caatcaaccc taagactcta  29640
aaagagttct ccgaggttga ccctgagaag gctgcgcgag gaatcaaact ggctgggttc  29700
accgagattg gcttgaagac cttggggtct gacgatgctg acatccgtag agtggctatc  29760
gacctcgttc gctctcctac tggtatgcag tctggtgcct caggtaagtt cggtgcaaca  29820
gcttctgaca tccatgagag acttcatggt actgaccagc gtacttataa tgacttgtac  29880
aaagcaatgt ctgacgctat gaaagaccct gagttctcta ctggcggcgc taagatgtcc  29940
cgtgaagaaa ctcgatacac tatctaccgt agagcggcac tagctattga gcgtccagaa  30000
ctacagaagg cactcactcc gtctgagaga atcgttatgg acatcattaa gcgtcacttt  30060
gacaccaagc gtgaacttat ggaaaaccca gcaatattcg gtaacacaaa ggctgtgagt  30120
atcttccctg agagtcgcca caaaggtact tacgttcctc acgtatatga ccgtcatgcc  30180
aaggcgctga tgattcaacg ctacggtgcc gaaggtttgc aggaagggat tgcccgctca  30240
tggatgaaca gctacgtctc cagacctgag gtcaaggcca gagtcgatga gatgcttaag  30300
```

-continued

```
gaattacacg gggtgaagga agtaacacca gagatggtag agaagtacgc tatggataag  30360
gcttatggta tctcccactc agaccagttc accaacagtt ccataataga agagaacatt  30420
gagggcttag taggtatcga gaataactca ttccttgagg cacgtaactt gtttgattcg  30480
gacctatcca tcactatgcc agacggacag caattctcag tgaatgacct aagggacttc  30540
gatatgttcc gcatcatgcc agcgtatgac cgccgtgtca atggtgacat cgccatcatg  30600
gggtctactg gtaaaaccac taaggaactt aaggatgaga ttttggctct caaagcgaaa  30660
gctgagggag acggtaagaa gactggcgag gtacatgctt taatggatac cgttaagatt  30720
cttactggtc gtgctagacg caatcaggac actgtgtggg aaacctcact gcgtgccatc  30780
aatgacctag ggttcttcgc taagaacgcc tacatgggtg ctcagaacat tacggagatt  30840
gctgggatga ttgtcactgg taacgttcgt gctctagggc atggtatccc aattctgcgt  30900
gatacactct acaagtctaa accagtttca gctaaggaac tcaaggaact ccatgcgtct  30960
ctgttcggga aggaggtgga ccagttgatt cggcctaaac gtgctgacat tgtgcagcgc  31020
ctaagggaag caactgatac cggacctgcc gtggcgaaca tcgtagggac cttgaagtat  31080
tcaacacagg aactggctgc tcgctctccg tggactaagc tactgaacgg aaccactaac  31140
taccttctgg atgctgcgcg tcaaggtatg cttggggatg ttattagtgc caccctaaca  31200
ggtaagacta cccgctggga gaaagaaggc ttccttcgtg gtgcctccgt aactcctgag  31260
cagatggctg gcatcaagtc tctcatcaag gaacatatgg tacgcggtga ggacgggaag  31320
tttaccgtta aggacaagca agcgttctct atggacccac gggctatgga cttatggaga  31380
ctggctgaca aggtagctga tgaggcaatg ctgcgtccac ataaggtgtc cttacaggat  31440
tcccatgcgt tcggagcact aggtaagatg gttatgcagt ttaagtcttt cactatcaag  31500
tcccttaact ctaagttcct gcgaaccttc tatgatggat acaagaacaa ccgagcgatt  31560
gacgctgcgc tgagcatcat cacctctatg ggtctcgctg gtggtttcta tgctatggct  31620
gcacacgtca aagcatacgc tctgcctaag gagaaacgta aggagtactt ggagcgtgca  31680
ctggacccaa ccatgattgc ccacgctgcg ttatctcgta gttctcaatt gggtgctcct  31740
ttggctatgg ttgacctagt tggtggtgtt ttagggttcg agtcctccaa gatggctcgc  31800
tctacgattc tacctaagga caccgtgaag gaacgtgacc caaacaaacc gtacacctct  31860
agagaggtaa tgggcgctat gggttcaaac cttctggaac agatgccttc ggctggcttt  31920
gtggctaacg taggggctac cttaatgaat gctgctggcg tggtcaactc acctaataaa  31980
gcaaccgagc aggacttcat gactggtctt atgaactcca caaaagagtt agtaccgaac  32040
gacccattga ctcaacagct tgtgttgaag atttatgagg cgaacggtgt taacttgagg  32100
gagcgtagga aataatacga ctcactatag ggagaggcga aataatcttc tccctgtagt  32160
ctcttagatt tactttaagg aggtcaaatg gctaacgtaa ttaaaaccgt tttgacttac  32220
cagttagatg gctccaatcg tgattttaat atcccgtttg agtatctagc ccgtaagttc  32280
gtagtggtaa ctcttattgg tgtagaccga aaggtcctta cgattaatac agactatcgc  32340
tttgctacac gtactactat ctctctgaca aaggcttggg gtccagccga tggctacacg  32400
accatcgagt tacgtcgagt aacctccact accgaccgat tggttgactt tacggatggt  32460
tcaatcctcc gcgcgtatga ccttaacgtc gctcagattc aaacgatgca cgtagcggaa  32520
gaggcccgtg acctcactac ggatactatc ggtgtcaata acgatggtca cttggatgct  32580
cgtggtcgtc gaattgtgaa cctagcgaac gccgtggatg accgcgatgc tgttccgttt  32640
ggtcaactaa agaccatgaa ccagaactca tggcaagcac gtaatgaagc cttacagttc  32700
```

cgtaatgagg ctgagacttt cagaaaccaa gcggagggct ttaagaacga gtccagtacc 32760
aacgctacga acacaaagca gtggcgcgat gagaccaagg gtttccgaga cgaagccaag 32820
cggttcaaga atacggctgg tcaatacgct acatctgctg ggaactctgc ttccgctgcg 32880
catcaatctg aggtaaacgc tgagaactct gccacagcat ccgctaactc tgctcatttg 32940
gcagaacagc aagcagaccg tgcggaacgt gaggcagaca agctggaaaa ttacaatgga 33000
ttggctggtg caattgataa ggtagatgga accaatgtgt actggaaagg aaatattcac 33060
gctaacgggc gcctttacat gaccacaaac ggttttgact gtggccagta tcaacagttc 33120
tttggtggtg tcactaatcg ttactctgtc atggagtggg gagatgagaa cggatggctg 33180
atgtatgttc aacgtagaga gtggacaaca gcgataggcg gtaacatcca gttagtagta 33240
aacggacaga tcatcaccca aggtggagcc atgaccggtc agctaaaatt gcagaatggg 33300
catgttcttc aattagagtc cgcatccgac aaggcgcact atattctatc taaagatggt 33360
aacaggaata actggtacat tggtagaggg tcagataaca acaatgactg taccttccac 33420
tcctatgtac atggtacgac cttaacactc aagcaggact atgcagtagt taacaaacac 33480
ttccacgtag gtcaggccgt tgtggccact gatggtaata ttcaaggtac taagtgggga 33540
ggtaaatggc tggatgctta cctacgtgac agcttcgttg cgaagtccaa ggcgtggact 33600
caggtgtggt ctggtagtgc tggcggtggg gtaagtgtga ctgtttcaca ggatctccgc 33660
ttccgcaata tctggattaa gtgtgccaac aactcttgga acttcttccg tactggcccc 33720
gatggaatct acttcatagc ctctgatggt ggatggttac gattccaaat acactccaac 33780
ggtctcggat tcaagaatat tgcagacagt cgttcagtac ctaatgcaat catggtggag 33840
aacgagtaat tggtaaatca caaggaaaga cgtgtagtcc acggatggac tctcaaggag 33900
gtacaaggtg ctatcattag actttaacaa cgaattgatt aaggctgctc caattgttgg 33960
gacgggtgta gcagatgtta gtgctcgact gttctttggg ttaagcctta acgaatggtt 34020
ctacgttgct gctatcgcct acacagtggt tcagattggt gccaaggtag tcgataagat 34080
gattgactgg aagaaagcca ataaggagtg atatgtatgg aaaaggataa gagccttatt 34140
acattcttag agatgttgga cactgcgatg gctcagcgta tgcttgcgga cctttcggac 34200
catgagcgtc gctctccgca actctataat gctattaaca aactgttaga ccgccacaag 34260
ttccagattg gtaagttgca gccggatgtt cacatcttag gtggccttgc tggtgctctt 34320
gaagagtaca aagagaaagt cggtgataac ggtcttacgg atgatgatat ttacacatta 34380
cagtgatata ctcaaggcca ctacagatag tggtctttat ggatgtcatt gtctatacga 34440
gatgctccta cgtgaaatct gaaagttaac gggaggcatt atgctagaat ttttacgtaa 34500
gctaatccct tgggttctcg ctgggatgct attcgggtta ggatggcatc tagggtcaga 34560
ctcaatggac gctaaatgga aacaggaggt acacaatgag tacgttaaga gagttgaggc 34620
tgcgaagagc actcaaagag caatcgatgc ggtatctgct aagtatcaag aagaccttgc 34680
cgcgctggaa gggagcactg ataggattat ttctgatttg cgtagcgaca ataagcggtt 34740
gcgcgtcaga gtcaaaacta ccggaacctc cgatggtcag tgtggattcg agcctgatgg 34800
tcgagccgaa cttgacgacc gagatgctaa acgtattctc gcagtgaccc agaagggtga 34860
cgcatggatt cgtgcgttac aggatactat tcgtgaactg caacgtaagt aggaaatcaa 34920
gtaaggaggc aatgtgtcta ctcaatccaa tcgtaatgcg ctcgtagtgg cgcaactgaa 34980
aggagacttc gtggcgttcc tattcgtctt atggaaggcg ctaaacctac cggtgcccac 35040

-continued taagtgtcag attgacatgg ctaaggtgct ggcgaatgga gacaacaaga agttcatctt 35100
acaggctttc cgtggtatcg gtaagtcgtt catcacatgt gcgttcgttg tgtggtcctt 35160
atggagagac cctcagttga agatacttat cgtatcagcc tctaaggagc gtgcagacgc 35220
taactccatc tttattaaga acatcattga cctgctgcca ttcctatctg agttaaagcc 35280
aagacccgga cagcgtgact cggtaatcag ctttgatgta ggcccagcca atcctgacca 35340
ctctcctagt gtgaaatcag taggtatcac tggtcagtta actggtagcc gtgctgacat 35400
tatcattgcg gatgacgttg agattccgtc taacagcgca actatgggtg cccgtgagaa 35460
gctatggact ctggttcagg agttcgctgc gttacttaaa ccgctgcctt cctctcgcgt 35520
tatctacctt ggtacacctc agacagagat gactctctat aaggaacttg aggataaccg 35580
tgggtacaca accattatct ggcctgctct gtacccaagg acacgtgaag agaacctcta 35640
ttactcacag cgtcttgctc ctatgttacg cgctgagtac gatgagaacc ctgaggcact 35700
tgctgggact ccaacagacc cagtgcgctt tgaccgtgat gacctgcgcg agcgtgagtt 35760
ggaatacggt aaggctggct ttacgctaca gttcatgctt aaccctaacc ttagtgatgc 35820
cgagaagtac ccgctgaggc ttcgtgacgc tatcgtagcg gccttagact tagagaaggc 35880
cccaatgcat taccagtggc ttccgaaccg tcagaacatc attgaggacc ttcctaacgt 35940
tggccttaag ggtgatgacc tgcatacgta ccacgattgt tccaacaact caggtcagta 36000
ccaacagaag attctggtca ttgaccctag tggtcgcggt aaggacgaaa caggttacgc 36060
tgtgctgtac acactgaacg gttacatcta ccttatggaa gctggaggtt tccgtgatgg 36120
ctactccgat aagacccttg agttactcgc taagaaggca aagcaatggg gagtccagac 36180
ggttgtctac gagagtaact tcggtgacgg tatgttcggt aaggtattca gtcctatcct 36240
tcttaaacac cacaactgtg cgatggaaga gattcgtgcc cgtggtatga aagagatgcg 36300
tatttgcgat acccttgagc cagtcatgca gactcaccgc cttgtaattc gtgatgaggt 36360
cattagggcc gactaccagt ccgctcgtga cgtagacggt aagcatgacg ttaagtactc 36420
gttgttctac cagatgaccc gtatcactcg tgagaaaggc gctctggctc atgatgaccg 36480
attggatgcc cttgcgttag gcattgagta tctccgtgag tccatgcagt tggattccgt 36540
taaggtcgag ggtgaagtac ttgctgactt ccttgaggaa cacatgatgc gtcctacggt 36600
tgctgctacg catatcattg agatgtctgt gggaggagtt gatgtgtact ctgaggacga 36660
tgagggttac ggtacgtctt tcattgagtg gtgatttatg cattaggact gcatagggat 36720
gcactataga ccacggatgg tcagttcttt aagttactga aaagacacga taaattaata 36780
cgactcacta tagggagagg agggacgaaa ggttactata tagatactga atgaatactt 36840
atagagtgca taaagtatgc ataatggtgt acctagagtg acctctaaga atggtgatta 36900
tattgtatta gtatcacctt aacttaagga ccaacataaa gggaggagac tcatgttccg 36960
cttattgttg aacctactgc ggcatagagt cacctaccga tttcttgtgg tactttgtgc 37020
tgcccttggg tacgcatctc ttactggaga cctcagttca ctggagtctg tcgtttgctc 37080
tatactcact tgtagcgatt agggtcttcc tgaccgactg atggctcacc gagggattca 37140
gcggtatgat tgcatcacac cacttcatcc ctatagagtc aagtcctaag gtatacccat 37200
aaagagcctc taatggtcta tcctaaggtc tatacctaaa gataggccat cctatcagtg 37260
tcacctaaag agggtcttag agagggccta tggagttcct atagggtcct ttaaaatata 37320
ccataaaaat ctgagtgact atctcacagt gtacggacct aaagttcccc catagggggt 37380
acctaaagcc cagccaatca cctaaagtca accttcggtt gaccttgagg gttccctaag 37440
ggttggggat gacccttggg tttgtctttg ggtgttacct tgagtgtctc tctgtgtccc 37500
t 37501

<210> SEQ ID NO 66
<211> LENGTH: 37507
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg ggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920

-continued

```
cgctacgaag acgtttacat gcctgaggtg tacaaagcga ttaacattgc gcaaaacacc   1980
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
```

-continued

```
tctctaggag tggccttagt catttaacca ataggagata aacattatga tgaacattaa   4320
gactaacccg tttaaagccg tgtctttcgt agagtctgcc attaagaagg ctctggataa   4380
cgctgggtat cttatcgctg aaatcaagta cgatggtgta cgcgggaaca tctgcgtaga   4440
caatactgct aacagttact ggctctctcg tgtatctaaa acgattccgg cactggagca   4500
cttaaacggg tttgatgttc gctggaagcg tctactgaac gatgaccgtt gcttctacaa   4560
agatggcttt atgcttgatg gggaactcat ggtcaagggc gtagacttta acacagggtc   4620
cggcctactg cgtaccaaat ggactgacac gaagaaccaa gagttccatg aagagttatt   4680
cgttgaacca atccgtaaga aagataaagt tccctttaag ctgcacactg gacaccttca   4740
cataaaactg tacgctatcc tcccgctgca catcgtggag tctggagaag actgtgatgt   4800
catgacgttg ctcatgcagg aacacgttaa gaacatgctg cctctgctac aggaatactt   4860
ccctgaaatc gaatggcaag cggctgaatc ttacgaggtc tacgatatgg tagaactaca   4920
gcaactgtac gagcagaagc gagcagaagg ccatgagggt ctcattgtga aagacccgat   4980
gtgtatctat aagcgcggta agaaatctgg ctggtggaaa atgaaacctg agaacgaagc   5040
tgacggtatc attcagggtc tggtatgggg tacaaaaggt ctggctaatg aaggtaaagt   5100
gattggtttt gaggtgcttc ttgagagtgg tcgtttagtt aacgccacga atatctctcg   5160
cgccttaatg gatgagttca ctgagacagt aaaagaggcc accctaagtc aatggggatt   5220
ctttagccca tacggtattg gcgacaacga tgcttgtact attaaccctt acgatggctg   5280
ggcgtgtcaa attagctaca tggaggaaac acctgatggc tctttgcggc acccatcgtt   5340
cgtaatgttc cgtggcaccg aggacaaccc tcaagagaaa atgtaatcac actggctcac   5400
cttcgggtgg gcctttctgc gtttataagg agacacttta tgtttaagaa ggttggtaaa   5460
ttccttgcgg ctttggcagc tatcctgacg cttgcgtata ttcttgcggt ataccctcaa   5520
gtagcactag tagtagttgg cgcttgttac ttagcggcag tgtgtgcttg cgtgtggagt   5580
atagttaact ggtaatacga ctcactaaag gaggtacaca ccatgatgta cttaatgcca   5640
ttactcatcg tcattgtagg atgccttgcg ctccactgta gcgatgatga tatgccagat   5700
ggtcacgctt aatacgactc actaaaggag acactatatg tttcgacttc attacaacaa   5760
aagcgttaag aatttcacgg ttcgccgtgc tgaccgttca atcgtatgtg cgagcgagcg   5820
ccgagctaag atacctctta ttggtaacac agttcctttg gcaccgagcg tccacatcat   5880
tatcacccgt ggtgactttg agaaagcaat agacaagaaa cgtccggttc ttagtgtggc   5940
agtgacccgc ttcccgttcg tccgtctgtt actcaaacga atcaaggagg tgttctgatg   6000
ggactgttag atggtgaagc ctgggaaaaa gaaaacccgc cagtacaagc aactgggtgt   6060
atagcttgct tagagaaaga tgaccgttat ccacacacct gtaacaaagg agctaacgat   6120
atgaccgaac gtgaacaaga gatgatcatt aagttgatag acaataatga aggtcgccca   6180
gatgatttga atggctgcgg tattctctgc tccaatgtcc cttgccacct ctgccccgca   6240
aataacgatc aaaagataac cttaggtgaa atccgagcga tggacccacg taaaccacat   6300
ctgaataaac ctgaggtaac tcctacagat gaccagcctt ccgctgagac aatcgaaggt   6360
gtcactaagc cttcccacta catgctgttt gacgacattg aggctatcga agtgattgct   6420
cgttcaatga ccgttgagca gttcaaggga tactgcttcg gtaacatctt aaagtacaga   6480
ctacgtgctg gtaagaagtc agagttagcg tacttagaga aagacctagc gaaagcagac   6540
ttctataaag aactctttga gaaacataag gataaatgtt atgcataact tcaagtcaac   6600
cccacctgcc gacagcctat ctgatgactt cacatcttgc tcagagtggt gccgaaagat   6660
```

-continued

```
gtgggaagag acattcgacg atgcgtacat caagctgtat gaactttgga aatcgagagg   6720
tcaatgacta tgtcaaacgt aaatacaggt tcacttagtg tggacaataa gaagttttgg   6780
gctaccgtag agtcctcgga gcattccttc gaggttccaa tctacgctga gaccctagac   6840
gaagctctgg agttagccga atggcaatac gttccggctg gctttgaggt tactcgtgtg   6900
cgtccttgtg tagcaccgaa gtaatacgac tcactattag ggaagactcc ctctgagaaa   6960
ccaaacgaaa cctaaaggag attaacatta tggctaagaa gattttcacc tctgcgctgg   7020
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac tacctttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
```

-continued

```
ttggaagtcg ttgcgtggat ttatagaact aggagggaat tgcatggaca attcgcacga   9060
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
```

ttaccatgcg tgaccctaaa gttatccaag cagaaatcgc taaactggaa gctgaactgg 11460
aggacgttaa gtaccatgaa gctaagactc gctccgctgt tcacatcttg aagaacttag 11520
gctggacttg gacaagacag actggctgga agaaaccaga agttaccaag ctgagtcata 11580
aggtgttcga taaggacact atgacccaca tcaaggctgg tgattgggtt aaggttgaca 11640
tgggagttgt tggtggatac ggctacgtcc gctcagttag tggcaaatat gcacaagtgt 11700
catacatcac aggtgttact ccacgcggtg caatcgttgc cgataagacc aacatgattc 11760
acacaggttt cttgacagtt gtttcatatg aagagattgt taagtcacga taatcaatag 11820
gagaaatcaa tatgatcgtt tctgacatcg aagctaacgc cctcttagag agcgtcacta 11880
agttccactg cggggttatc tacgactact ccaccgctga gtacgtaagc taccgtccga 11940
gtgacttcgg tgcgtatctg gatgcgctgg aagccgaggt tgcacgaggc ggtcttattg 12000
tgttccacaa cggtcacaag tatgacgttc ctgcattgac caaactggca aagttgcaat 12060
tgaaccgaga gttccacctt cctcgtgaga actgtattga cacccttgtg ttgtcacgtt 12120
tgattcattc caacctcaag gacaccgata tgggtcttct gcgttccggc aagttgcccg 12180
gaaaacgctt tgggtctcac gctttggagg cgtggggtta tcgcttaggc gagatgaagg 12240
gtgaatacaa agacgacttt aagcgtatgc ttgaagagca gggtgaagaa tacgttgacg 12300
gaatggagtg gtggaacttc aacgaagaga tgatggacta taacgttcag gacgttgtgg 12360
taactaaagc tctccttgag aagctactct ctgacaaaca ttacttccct cctgagattg 12420
actttacgga cgtaggatac actacgttct ggtcagaatc ccttgaggcc gttgacattg 12480
aacatcgtgc tgcatggctg ctcgctaaac aagagcgcaa cgggttcccg tttgacacaa 12540
aagcaatcga agagttgtac gtagagttag ctgctcgccg ctctgagttg ctccgtaaat 12600
tgaccgaaac gttcggctcg tggtatcagc ctaaaggtgg cactgagatg ttctgccatc 12660
cgcgaacagg taagccacta cctaaatacc ctcgcattaa gacacctaaa gttggtggta 12720
tctttaagaa gcctaagaac aaggcacagc gagaaggccg tgagccttgc gaacttgata 12780
cccgcgagta cgttgctggt gctccttaca ccccagttga acatgttgtg tttaaccctt 12840
cgtctcgtga ccacattcag aagaaactcc aagaggctgg gtgggtcccg accaagtaca 12900
ccgataaggg tgctcctgtg gtggacgatg aggtactcga aggagtacgt gtagatgacc 12960
ctgagaagca agccgctatc gacctcatta aagagtactt gatgattcag aagcgaatcg 13020
gacagtctgc tgagggagac aaagcatggc ttcgttatgt tgctgaggat ggtaagattc 13080
atggttctgt taaccctaat ggagcagtta cgggtcgtgc gacccatgcg ttcccaaacc 13140
ttgcgcaaat tccgggtgta cgttctcctt atggagagca gtgtcgcgct gcttttggcg 13200
ctgagcacca tttggatggg ataactggta agccttgggt tcaggctggc atcgacgcat 13260
ccggtcttga gctacgctgc ttggctcact tcatggctcg ctttgataac ggcgagtacg 13320
ctcacgagat tcttaacggc gacatccaca ctaagaacca gatagctgct gaactaccta 13380
cccgagataa cgctaagacg ttcatctatg ggttcctcta tggtgctggt gatgagaaga 13440
ttggacagat tgttggtgct ggtaaagagc gcggtaagga actcaagaag aaattccttg 13500
agaacacccc cgcgattgca gcactccgcg agtctatcca acagacactt gtcgagtcct 13560
ctcaatgggt agctggtgag caacaagtca agtggaaacg ccgctggatt aaaggtctgg 13620
atggtcgtaa ggtacacgtt cgtagtcctc acgctgcctt gaatacccta ctgcaatctg 13680
ctggtgctct catctgcaaa ctgtggatta tcaagaccga agagatgctc gtagagaaag 13740

```
gcttgaagca tggctgggat ggggactttg cgtacatggc atgggtacat gatgaaatcc  13800
aagtaggctg ccgtaccgaa gagattgctc aggtggtcat tgagaccgca caagaagcga  13860
tgcgctgggt tggagaccac tggaacttcc ggtgtcttct ggataccgaa ggtaagatgg  13920
gtcctaattg ggcgatttgc cactgataca ggaggctact catgaacgaa agacacttaa  13980
caggtgctgc ttctgaaatg ctagtagcct acaaatttac caaagctggg tacactgtct  14040
attaccctat gctgactcag agtaaagagg acttggttgt atgtaaggat ggtaaattta  14100
gtaaggttca ggttaaaaca gccacaacgg ttcaaaccaa cacaggagat gccaagcagg  14160
ttaggctagg tggatgcggt aggtccgaat ataaggatgg agactttgac attcttgcgg  14220
ttgtggttga cgaagatgtg cttattttca catgggacga agtaaaaggt aagacatcca  14280
tgtgtgtcgg caagagaaac aaaggcataa aactatagga gaaattatta tggctatgac  14340
aaagaaattt aaagtgtcct tcgacgttac cgcaaagatg tcgtctgacg ttcaggcaat  14400
cttagagaaa gatatgctgc atctatgtaa gcaggtcggc tcaggtgcga ttgtccccaa  14460
tggtaaacag aaggaaatga ttgtccagtt cctgacacac ggtatggaag gattgatgac  14520
attcgtagta cgtacatcat ttcgtgaggc cattaaggac atgcacgaag agtatgcaga  14580
taaggactct ttcaaacaat ctcctgcaac agtacgggag gtgttctgat gtctgactac  14640
ctgaaagtgc tgcaagcaat caaaagttgc cctaagactt tccagtccaa ctatgtacgg  14700
aacaatgcga gcctcgtagc ggaggccgct tcccgtggtc acatctcgtg cctgactact  14760
agtggacgta acggtggcgc ttgggaaatc actgcttccg gtactcgctt tctgaaacga  14820
atgggaggat gtgtctaatg tctcgtgacc ttgtgactat tccacgcgat gtgtggaacg  14880
atatacaggg ctacatcgac tctctggaac gtgagaacga tagccttaag aatcaactaa  14940
tggaagctga cgaatacgta gcggaactag aggagaaact taatggcact tcttgacctt  15000
aaacaattct atgagttacg tgaaggctgc gacgacaagg gtatccttgt gatggacggc  15060
gactggctgg tcttccaagc tatgagtgct gctgagtttg atgcctcttg ggaggaagag  15120
atttggcacc gatgctgtga ccacgctaag gcccgtcaga ttcttgagga ttccattaag  15180
tcctacgaga cccgtaagaa ggcttgggca ggtgctccaa ttgtccttgc gttcaccgat  15240
agtgttaact ggcgtaaaga actggttgac ccgaactata aggctaaccg taaggccgtg  15300
aagaaacctg tagggtactt tgagttcctt gatgctctct ttgagcgcga agagttctat  15360
tgcatccgtg agcctatgct tgagggtgat gacgttatgg gagttattgc ttccaatccg  15420
tctgccttcg gtgctcgtaa ggctgtaatc atctcttgcg ataaggactt taagaccatc  15480
cctaactgtg acttcctgtg gtgtaccact ggtaacatcc tgactcagac cgaagagtcc  15540
gctgactggt ggcacctctt ccagaccatc aagggtgaca tcactgatgg ttactcaggg  15600
attgctggat ggggtgatac cgccgaggac ttcttgaata acccgttcat aaccgagcct  15660
aaaacgtctg tgcttaagtc cggtaagaac aaaggccaag aggttactaa atgggttaaa  15720
cgcgaccctg agcctcatga gacgctttgg gactgcatta agtccattgg cgcgaaggct  15780
ggtatgaccg aagaggatat tatcaagcag ggccaaatgg ctcgaatcct acggttcaac  15840
gagtacaact ttattgacaa ggagatttac ctgtggagac cgtagcgtat attggtctgg  15900
gtctttgtgt tctcggagtg tgcctcattt cgtggggcct ttgggactta gccagaataa  15960
tcaagtcgtt acacgacact aagtgataaa ctcaaggtcc ctaaattaat acgactcact  16020
atagggagat aggggccttt acgattatta ctttaagatt taactctaag aggaatcttt  16080
attatgttaa cacctattaa ccaattactt aagaacccta acgatattcc agatgtacct  16140
```

```
cgtgcaaccg ctgagtatct acaggttcga ttcaactatg cgtacctcga agcgtctggt  16200
catataggac ttatgcgtgc taatggttgt agtgaggccc acatcttggg tttcattcag  16260
ggcctacagt atgcctctaa cgtcattgac gagattgagt tacgcaagga acaactaaga  16320
gatgatgggg aggattgaca ctatgtgttt ctcaccgaaa attaaaactc cgaagatgga  16380
taccaatcag attcgagccg ttgagccagc gcctctgacc caagaagtgt caagcgtgga  16440
gttcggtggg tcttctgatg agacggatac cgagggcacc gaagtgtctg gacgcaaagg  16500
cctcaaggtc gaacgtgatg attccgtagc gaagtctaaa gccagcggca atggctccgc  16560
tcgtatgaaa tcttccatcc gtaagtccgc atttggaggt aagaagtgat gtctgagttc  16620
acatgtgtgg aggctaagag tcgcttccgt gcaatccggt ggactgtgga acaccttggg  16680
ttgcctaaag gattcgaagg acactttgtg ggctacagcc tctacgtaga cgaagtgatg  16740
gacatgtctg gttgccgtga agagtacatt ctggactcta ccggaaaaca tgtagcgtac  16800
ttcgcgtggt gcgtaagctg tgacattcac cacaaaggag acattctgga tgtaacgtcc  16860
gttgtcatta atcctgaggc agactctaag ggcttacagc gattcctagc gaaacgcttt  16920
aagtaccttg cggaactcca cgattgcgat tgggtgtctc gttgtaagca tgaaggcgag  16980
acaatgcgtg tatactttaa ggaggtataa gttatgggta agaaagttaa gaaggccgtg  17040
aagaaagtca ccaagtccgt taagaaagtc gttaaggaag gggctcgtcc ggttaaacag  17100
gttgctggcg gtctagctgg tctggctggt ggtactggtg aagcacagat ggtggaagta  17160
ccacaagctg ccgcacagat tgttgacgta cctgagaaag aggtttccac tgaggacgaa  17220
gcacagacag aaagcggacg caagaaagct cgtgctggcg gtaagaaatc cttgagtgta  17280
gcccgtagct ccggtggcgg tatcaacatt taatcaggag gttatcgtgg aagactgcat  17340
tgaatggacc ggaggtgtca actctaaggg ttatggtcgt aagtgggtta atggtaaact  17400
tgtgactcca cataggcaca tctatgagga gacatatggt ccagttccaa caggaattgt  17460
ggtgatgcat atctgcgata accctaggtg ctataacata aagcacctta cgcttggaac  17520
tccaaaggat aattccgagg acatggttac caaaggtaga caggctaaag gagaggaact  17580
aagcaagaaa cttacagagt cagacgttct cgctatacgc tcttcaacct taagccaccg  17640
ctccttagga gaactgtatg gagtcagtca atcaaccata acgcgaatac tacagcgtaa  17700
gacatggaga cacatttaat ggctgagaaa cgaacaggac ttgcggagga tggcgcaaag  17760
tctgtctatg agcgtttaaa gaacgaccgt gctccctatg agacacgcgc tcagaattgc  17820
gctcaatata ccatcccatc attgttccct aaggactccg ataacgcctc tacagattat  17880
caaactccgt ggcaagccgt gggcgctcgt ggtctgaaca atctagcctc taagctcatg  17940
ctggctctat tccctatgca gacttggatg cgacttacta tatctgaata tgaagcaaag  18000
cagttactga gcgaccccga tggactcgct aaggtcgatg agggcctctc gatggtagag  18060
cgtatcatca tgaactacat tgagtctaac agttaccgcg tgactctctt tgaggctctc  18120
aaacagttag tcgtagctgg taacgtcctg ctgtacctac cggaaccgga agggtcaaac  18180
tataatccca tgaagctgta ccgattgtct tcttatgtgg tccaacgaga cgcattcggc  18240
aacgttctgc aaatggtgac tcgtgaccag atagcttttg gtgctctccc tgaggacatc  18300
cgtaaggctg tagaaggtca aggtggtgag aagaaagctg atgagacaat cgacgtgtac  18360
actcacatct atctggatga ggactcaggt gaatacctcc gatacgaaga ggtcgagggt  18420
atggaagtcc aaggctccga tgggacttat cctaaagagg cttgcccata catcccgatt  18480
```

-continued cggatggtca gactagatgg tgaatcctac ggtcgttcgt acattgagga atacttaggt 18540
gacttacggt cccttgaaaa tctccaagag gctatcgtca agatgtccat gattagctct 18600
aaggttatcg gcttagtgaa tcctgctggt atcacccagc cacgccgact gaccaaagct 18660
cagactggtg acttcgttac tggtcgtcca gaagacatct cgttcctcca actggagaag 18720
caagcagact ttactgtagc taaagccgta agtgacgcta tcgaggctcg cctttcgttt 18780
gcctttatgt tgaactctgc ggttcagcgt acaggtgaac gtgtgaccgc cgaagagatt 18840
cggtatgtag cttctgaact tgaagatact ttaggtggtg tctactctat cctttctcaa 18900
gaattacaat tgcctctggt acgagtgctc ttgaagcaac tacaagccac gcaacagatt 18960
cctgagttac ctaaggaagc cgtagagcca accattagta caggtctgga agcaattggt 19020
cgaggacaag accttgataa gctggagcgg tgtgtcactg cgtgggctgc actggcacct 19080
atgcgggacg accctgatat taaccttgcg atgattaagt tacgtattgc caacgctatc 19140
ggtattgaca cttctggtat tctactcacc gaagaacaga agcaacagaa gatggcccaa 19200
cagtctatgc aaatgggtat ggataatggt gctgctgcgc tggctcaagg tatggctgca 19260
caagctacag cttcacctga ggctatggct gctgccgctg attccgtagg tttacagccg 19320
ggaatttaat acgactcact atagggagac ctcatctttg aaatgagcga tgacaagagg 19380
ttggagtcct cggtcttcct gtagttcaac tttaaggaga caataataat ggctgaatct 19440
aatgcagacg tatatgcatc ttttggcgtg aactccgctg tgatgtctgg tggttccgtt 19500
gaggaacatg agcagaacat gctggctctt gatgttgctg cccgtgatgg cgatgatgca 19560
atcgagttag cgtcagacga agtggaaaca gaacgtgacc tgtatgacaa ctctgacccg 19620
ttcggtcaag aggatgacga aggccgcatt caggttcgta tcggtgatgg ctctgagccg 19680
accgatgtgg acactggaga agaaggcgtt gagggcaccg aaggttccga agagtttacc 19740
ccactgggcg agactccaga agaactggta gctgcctctg agcaacttgg tgagcacgaa 19800
gagggcttcc aagagatgat taacattgct gctgagcgtg gcatgagtgt cgagaccatt 19860
gaggctatcc agcgtgagta cgaggagaac gaagagttgt ccgccgagtc ctacgctaag 19920
ctggctgaaa ttggctacac gaaggctttc attgactcgt atatccgtgg tcaagaagct 19980
ctggtggagc agtacgtaaa cagtgtcatt gagtacgctg gtggtcgtga acgttttgat 20040
gcactgtata accaccttga gacgcacaac cctgaggctg cacagtcgct ggataatgcg 20100
ttgaccaatc gtgacttagc gaccgttaag gctatcatca acttggctgg tgagtctcgc 20160
gctaaggcgt tcggtcgtaa gccaactcgt agtgtgacta atcgtgctat tccggctaaa 20220
cctcaggcta ccaagcgtga aggctttgcg gaccgtagcg agatgattaa agctatgagt 20280
gaccctcggt atcgcacaga tgccaactat cgtcgtcaag tcgaacagaa agtaatcgat 20340
tcgaacttct gatagacttc gaaattaata cgactcacta tagggagacc acaacggttt 20400
ccctctagaa ataattttgt ttaactttaa gaaggagata tacatatggc tagcatgact 20460
ggtggacagc aaatgggtac taaccaaggt aaaggtgtag ttgctgctgg agataaactg 20520
gcgttgttct tgaaggtatt tggcggtgaa gtcctgactg cgttcgctcg tacctccgtg 20580
accacttctc gccacatggt acgttccatc tccagcggta aatccgctca gttccctgtt 20640
ctgggtcgca ctcaggcagc gtatctggct ccgggcgaga acctcgacga taaacgtaag 20700
gacatcaaac acaccgagaa ggtaatcacc attgacggtc tcctgacggc tgacgttctg 20760
atttatgata ttgaggacgc gatgaaccac tacgacgttc gctctgagta tacctctcag 20820
ttgggtgaat ctctggcgat ggctgcggat ggtgcggttc tggctgagat tgccggtctg 20880

```
tgtaacgtgg aaagcaaata taatgagaac atcgagggct taggtactgc taccgtaatt  20940
gagaccactc agaacaaggc cgcacttacc gaccaagttg cgctgggtaa ggagattatt  21000
gcggctctga ctaaggctcg tgcggctctg accaagaact atgttccggc tgctgaccgt  21060
gtgttctact gtgacccaga tagctactct gcgattctgg cagcactgat gccgaacgca  21120
gcaaactacg ctgctctgat tgaccctgag aagggttcta tccgcaacgt tatgggcttt  21180
gaggttgtag aagttccgca cctcaccgct ggtggtgctg gtaccgctcg tgagggcact  21240
actggtcaga agcacgtctt ccctgccaat aaaggtgagg gtaatgtcaa ggttgctaag  21300
gacaacgtta tcggcctgtt catgcaccgc tctgcggtag gtactgttaa gctgcgtgac  21360
ttggctctgg agcgcgctcg ccgtgctaac ttccaagcgg accagattat cgctaagtac  21420
gcaatgggcc acggtggtct tcgcccagaa gctgcaggag ctgtcgtatt ccagtcaggt  21480
gtgatgctcg gggatccgaa ttcttaagta actaacgaaa ttaatacgac tcactatagg  21540
gagaccacaa cggtttccct ctagaaataa ttttgtttaa ctttaagaag gagatataca  21600
tatgggcatt tggggcaccc tggcgaaaat tggcattaaa gcggtgccgc gcgtgattag  21660
catgctgaaa aaaaaaaaac agtaaggatc cggctgctaa caaagcccga agcttgcggc  21720
cgcactcgag taactagtta accccttggg gcctctaaac gggtcttgag gggttttttg  21780
ctgaaaggag gaactatatg cgctcatacg atatgaacgt tgagactgcc gctgagttat  21840
cagctgtgaa cgacattctg gcgtctatcg gtgaacctcc ggtatcaacg ctggaaggtg  21900
acgctaacgc agatgcagcg aacgctcggc gtattctcaa caagattaac cgacagattc  21960
aatctcgtgg atggacgttc aacattgagg aaggcataac gctactacct gatgtttact  22020
ccaacctgat tgtatacagt gacgactatt tatccctaat gtctacttcc ggtcaatcca  22080
tctacgttaa ccgaggtggc tatgtgtatg accgaacgag tcaatcagac cgctttgact  22140
ctggtattac tgtgaacatt attcgtctcc gcgactacga tgagatgcct gagtgcttcc  22200
gttactggat tgtcaccaag gcttcccgtc agttcaacaa ccgattcttt ggggcaccgg  22260
aagtagaggg tgtactccaa gaagaggaag atgaggctag acgtctctgc atggagtatg  22320
agatggacta cggtgggtac aatatgctgg atggagatgc gttcacttct ggtctactga  22380
ctcgctaaca ttaataaata aggaggctct aatggcactc attagccaat caatcaagaa  22440
cttgaagggt ggtatcagcc aacagcctga catccttcgt tatccagacc aagggtcacg  22500
ccaagttaac ggttggtctt cggagaccga gggcctccaa aagcgtccac ctcttgtttt  22560
cttaaataca cttggagaca acggtgcgtt aggtcaagct ccgtacatcc acctgattaa  22620
ccgagatgag cacgaacagt attacgctgt gttcactggt agcggaatcc gagtgttcga  22680
cctttctggt aacgagaagc aagttaggta tcctaacggt tccaactaca tcaagaccgc  22740
taatccacgt aacgacctgc gaatggttac tgtagcagac tatacgttca tcgttaaccg  22800
taacgttgtt gcacagaaga acacaaagtc tgtcaactta ccgaattaca accctaatca  22860
agacggattg attaacgttc gtggtggtca gtatggtagg gaactaattg tacacattaa  22920
cggtaaagac gttgcgaagt ataagatacc agatggtagt caacctgaac acgtaaacaa  22980
tacggatgcc caatggttag ctgaagagtt agccaagcag atgcgcacta acttgtctga  23040
ttggactgta aatgtagggc aagggttcat ccatgtgacc gcacctagtg gtcaacagat  23100
tgactccttc acgactaaag atggctacgc agaccagttg attaaccctg tgacccacta  23160
cgctcagtcg ttctctaagc tgccacctaa tgctcctaac ggctacatgg tgaaaatcgt  23220
```

-continued

```
aggggacgcc tctaagtctg ccgaccagta ttacgttcgg tatgacgctg agcggaaagt  23280
ttggactgag actttaggtt ggaacactga ggaccaagtt ctatgggaaa ccatgccaca  23340
cgctcttgtg cgagccgctg acggtaattt cgacttcaag tggcttgagt ggtctcctaa  23400
gtcttgtggt gacgttgaca ccaacccttg gccttctttt gttggttcaa gtattaacga  23460
tgtgttcttc ttccgtaacc gcttaggatt ccttagtggg gagaacatca tattgagtcg  23520
tacagccaaa tacttcaact tctaccctgc gtccattgcg aaccttagtg atgacgaccc  23580
tatagacgta gctgtgagta ccaaccgaat agcaatcctt aagtacgccg ttccgttctc  23640
agaagagtta ctcatctggt ccgatgaagc acaattcgtc ctgactgcct cgggtactct  23700
cacatctaag tcggttgagt tgaacctaac gacccagttt gacgtacagg accgagcgag  23760
accttttggg attgggcgta atgtctactt tgctagtccg aggtccagct tcacgtccat  23820
ccacaggtac tacgctgtgc aggatgtcag ttccgttaag aatgctgagg acattacatc  23880
acacgttcct aactacatcc ctaatggtgt gttcagtatt tgcggaagtg gtacggaaaa  23940
cttctgttcg gtactatctc acggggaccc tagtaaaatc ttcatgtaca aattcctgta  24000
cctgaacgaa gagttaaggc aacagtcgtg gtctcattgg gactttgggg aaaacgtaca  24060
ggttctagct tgtcagagta tcagctcaga tatgtatgtg attcttcgca atgagttcaa  24120
tacgttccta gctagaatct ctttcactaa gaacgccatt gacttacagg gagaacccta  24180
tcgtgccttt atggacatga agattcgata cacgattcct agtggaacat acaacgatga  24240
cacattcact acctctattc atattccaac aatttatggt gcaaacttcg ggaggggcaa  24300
aatcactgta ttggagcctg atggtaagat aaccgtgttt gagcaaccta cggctgggtg  24360
gaatagcgac ccttggctga gactcagcgg taacttggag ggacgcatgg tgtacattgg  24420
gttcaacatt aacttcgtat atgagttctc taagttcctc atcaagcaga ctgccgacga  24480
cgggtctacc tccacggaag acattgggcg cttacagtta cgccgagcgt gggttaacta  24540
cgagaactct ggtacgtttg acatttatgt tgagaaccaa tcgtctaact ggaagtacac  24600
aatggctggt gcccgattag gctctaacac tctgagggct gggagactga acttagggac  24660
cggacaatat cgattccctg tggttggtaa cgccaagttc aacactgtat acatcttgtc  24720
agatgagact acccctctga acatcattgg gtgtggctgg gaaggtaact acttacggag  24780
aagttccggt atttaattaa atattctccc tgtggtggct cgaaattaat acgactcact  24840
atagggagaa caatacgact acgggagggt tttcttatga tgactataag acctactaaa  24900
agtacagact ttgaggtatt cactccggct caccatgaca ttcttgaagc taaggctgct  24960
ggtattgagc cgagtttccc tgatgcttcc gagtgtgtca cgttgagcct ctatgggttc  25020
cctctagcta tcggtggtaa ctgcggggac cagtgctggt tcgttacgag cgaccaagtg  25080
tggcgactta gtggaaaggc taagcgaaag ttccgtaagt taatcatgga gtatcgcgat  25140
aagatgcttg agaagtatga tactctttgg aattacgtat gggtaggcaa tacgtcccac  25200
attcgtttcc tcaagactat cggtgcggta ttccatgaag agtacacacg agatggtcaa  25260
tttcagttat ttacaatcac gaaaggagga taaccatatg tgttgggcag ccgcaatacc  25320
tatcgctata tctggcgctc aggctatcag tggtcagaac gctcaggcca aaatgattgc  25380
cgctcagacc gctgctggtc gtcgtcaagc tatggaaatc atgaggcaga cgaacatcca  25440
gaatgctgac ctatcgttgc aagctcgaag taaacttgag gaagcgtccg ccgagttgac  25500
ctcacagaac atgcagaagg tccaagctat tgggtctatc cgagcggcta tcggagagag  25560
tatgcttgaa ggttcctcaa tggaccgcat taagcgagtc acagaaggac agttcattcg  25620
```

```
ggaagccaat atggtaactg agaactatcg ccgtgactac caagcaatct tcgcacagca  25680
acttggtggt actcaaagtg ctgcaagtca gattgacgaa atctataaga gcgaacagaa  25740
acagaagagt aagctacaga tggttctgga cccactggct atcatggggt cttccgctgc  25800
gagtgcttac gcatccggtg cgttcgactc taagtccaca actaaggcac ctattgttgc  25860
cgctaaagga accaagacgg ggaggtaatg agctatgagt aaaattgaat ctgcccttca  25920
agcggcacaa ccgggactct ctcggttacg tggtggtgct ggaggtatgg gctatcgtgc  25980
agcaaccact caggccgaac agccaaggtc aagcctattg gacaccattg gtcggttcgc  26040
taaggctggt gccgatatgt ataccgctaa ggaacaacga gcacgagacc tagctgatga  26100
acgctctaac gagattatcc gtaagctgac ccctgagcaa cgtcgagaag ctctcaacaa  26160
cgggaccctt ctgtatcagg atgacccata cgctatggaa gcactccgag tcaagactgg  26220
tcgtaacgct gcgtatcttg tggacgatga cgttatgcag aagataaaag agggtgtctt  26280
ccgtactcgc gaagagatgg aagagtatcg ccatagtcgc cttcaagagg gcgctaaggt  26340
atacgctgag cagttcggca tcgaccctga ggacgttgat tatcagcgtg gtttcaacgg  26400
ggacattacc gagcgtaaca tctcgctgta tggtgcgcat gataacttct tgagccagca  26460
agctcagaag ggcgctatca tgaacagccg agtggaactc aacggtgtcc ttcaagaccc  26520
tgatatgctg cgtcgtccag actctgctga cttctttgag aagtatatcg acaacggtct  26580
ggttactggc gcaatcccat ctgatgctca agccacacag cttataagcc aagcgttcag  26640
tgacgcttct agccgtgctg gtggtgctga cttcctgatg cgagtcggtg acaagaaggt  26700
aacacttaac ggagccacta cgacttaccg agagttgatt ggtgaggaac agtggaacgc  26760
tctcatggtc acagcacaac gttctcagtt tgagactgac gcgaagctga acgagcagta  26820
tcgcttgaag attaactctg cgctgaacca agaggaccca aggacagctt gggagatgct  26880
tcaaggtatc aaggctgaac tagataaggt ccaacctgat gagcagatga caccacaacg  26940
tgagtggcta atctccgcac aggaacaagt tcagaatcag atgaacgcat ggacgaaagc  27000
tcaggccaag gctctggacg attccatgaa gtcaatgaac aaacttgacg taatcgacaa  27060
gcaattccag aagcgaatca acggtgagtg ggtctcaacg gattttaagg atatgccagt  27120
caacgagaac actggtgagt tcaagcatag cgatatggtt aactacgcca ataagaagct  27180
cgctgagatt gacagtatgg acattccaga cggtgccaag gatgctatga agttgaagta  27240
ccttcaagcg gactctaagg acggagcatt ccgtacagcc atcggaacca tggtcactga  27300
cgctggtcaa gagtggtctg ccgctgtgat taacggtaag ttaccagaac gaaccccagc  27360
tatggatgct ctgcgcagaa tccgcaatgc tgaccctcag ttgattgctg cgctataccc  27420
agaccaagct gagctattcc tgacgatgga catgatggac aagcagggta ttgaccctca  27480
ggttattctt gatgccgacc gactgactgt taagcggtcc aaagagcaac gctttgagga  27540
tgataaagca ttcgagtctg cactgaatgc atctaaggct cctgagattg cccgtatgcc  27600
agcgtcactg cgcgaatctg cacgtaagat ttatgactcc gttaagtatc gctcggggaa  27660
cgaaagcatg gctatggagc agatgaccaa gttccttaag gaatctacct acacgttcac  27720
tggtgatgat gttgacggtg ataccgttgg tgtgattcct aagaatatga tgcaggttaa  27780
ctctgacccg aaatcatggg agcaaggtcg ggatattctg gaggaagcac gtaagggaat  27840
cattgcgagc aacccttgga taaccaataa gcaactgacc atgtattctc aaggtgactc  27900
catttacctt atggacacca caggtcaagt cagagtccga tacgacaaag agttactctc  27960
```

-continued gaaggtctgg agtgagaacc agaagaaact cgaagagaaa gctcgtgaga aggctctggc 28020
tgatgtgaac aagcgagcac ctatagttgc cgctacgaag gcccgtgaag ctgctgctaa 28080
acgagtccga gagaaacgta aacagactcc taagttcatc tacggacgta aggagtaact 28140
aaaggctaca taaggaggcc ctaaatggat aagtacgata agaacgtacc aagtgattat 28200
gatggtctgt tccaaaaggc tgctgatgcc aacggggtct cttatgacct tttacgtaaa 28260
gtcgcttgga cagaatcacg atttgtgcct acagcaaaat ctaagactgg accattaggc 28320
atgatgcaat ttaccaaggc aaccgctaag gccctcggtc tgcgagttac cgatggtcca 28380
gacgacgacc gactgaaccc tgagttagct attaatgctg ccgctaagca acttgcaggt 28440
ctggtaggga agtttgatgg cgatgaactc aaagctgccc ttgcgtacaa ccaaggcgag 28500
ggacgcttgg gtaatccaca acttgaggcg tactctaagg gagacttcgc atcaatctct 28560
gaggagggac gtaactacat gcgtaacctt ctggatgttg ctaagtcacc tatggctgga 28620
cagttggaaa cttttggtgg cataacccca aagggtaaag gcattccggc tgaggtagga 28680
ttggctggaa ttggtcacaa gcagaaagta acacaggaac ttcctgagtc cacaagtttt 28740
gacgttaagg gtatcgaaca ggaggctacg gcgaaaccat tcgccaagga cttttgggag 28800
acccacggag aaacacttga cgagtacaac agtcgttcaa ccttcttcgg attcaaaaat 28860
gctgccgaag ctgaactctc caactcagtc gctgggatgg ctttccgtgc tggtcgtctc 28920
gataatggtt ttgatgtgtt taaagacacc attacgccga ctcgctggaa ctctcacatc 28980
tggactccag aggagttaga gaagattcga acagaggtta agaaccctgc gtacatcaac 29040
gttgtaactg gtggttcccc tgagaacctc gatgacctca ttaaattggc taacgagaac 29100
tttgagaatg actcccgcgc tgccgaggct ggcctaggtg ccaaactgag tgctggtatt 29160
attggtgctg gtgtggaccc gcttagctat gttcctatgg tcggtgtcac tggtaagggc 29220
tttaagttaa tcaataaggc tcttgtagtt ggtgccgaaa gtgctgctct gaacgttgca 29280
tccgaaggtc tccgtacctc cgtagctggt ggtgacgcag actatgcggg tgctgcctta 29340
ggtggctttg tgtttggcgc aggcatgtct gcaatcagtg acgctgtagc tgctggactg 29400
aaacgcagta aaccagaagc tgagttcgac aatgagttca tcggtcctat gatgcgattg 29460
gaagcccgtg agacagcacg aaacgccaac tctgcggacc tctctcggat gaacactgag 29520
aacatgaagt ttgaaggtga acataatggt gtcccttatg aggacttacc aacagagaga 29580
ggtgccgtgg tgttacatga tggctccgtt ctaagtgcaa gcaacccaat caaccctaag 29640
actctaaaag agttctccga ggttgaccct gagaaggctg cgcgaggaat caaactggct 29700
gggttcaccg agattggctt gaagaccttg gggtctgacg atgctgacat ccgtagagtg 29760
gctatcgacc tcgttcgctc tcctactggt atgcagtctg gtgcctcagg taagttcggt 29820
gcaacagctt ctgacatcca tgagagactt catggtactg accagcgtac ttataatgac 29880
ttgtacaaag caatgtctga cgctatgaaa gaccctgagt tctctactgg cggcgctaag 29940
atgtcccgtg aagaaactcg atacactatc taccgtagag cggcactagc tattgagcgt 30000
ccagaactac agaaggcact cactccgtct gagagaatcg ttatggacat cattaagcgt 30060
cactttgaca ccaagcgtga acttatggaa aacccagcaa tattcggtaa cacaaaggct 30120
gtgagtatct tccctgagag tcgccacaaa ggtacttacg ttcctcacgt atatgaccgt 30180
catgccaagg cgctgatgat tcaacgctac ggtgccgaag gtttgcagga agggattgcc 30240
cgctcatgga tgaacagcta cgtctccaga cctgaggtca aggccagagt cgatgagatg 30300
cttaaggaat tacacggggt gaaggaagta acaccagaga tggtagagaa gtacgctatg 30360

-continued gataaggctt atggtatctc ccactcagac cagttcacca acagttccat aatagaagag 30420
aacattgagg gcttagtagg tatcgagaat aactcattcc ttgaggcacg taacttgttt 30480
gattcggacc tatccatcac tatgccagac ggacagcaat tctcagtgaa tgacctaagg 30540
gacttcgata tgttccgcat catgccagcg tatgaccgcc gtgtcaatgg tgacatcgcc 30600
atcatggggt ctactggtaa aaccactaag gaacttaagg atgagatttt ggctctcaaa 30660
gcgaaagctg agggagacgg taagaagact ggcgaggtac atgctttaat ggataccgtt 30720
aagattctta ctggtcgtgc tagacgcaat caggacactg tgtgggaaac ctcactgcgt 30780
gccatcaatg acctagggtt cttcgctaag aacgcctaca tgggtgctca gaacattacg 30840
gagattgctg ggatgattgt cactggtaac gttcgtgctc tagggcatgg tatcccaatt 30900
ctgcgtgata cactctacaa gtctaaacca gtttcagcta aggaactcaa ggaactccat 30960
gcgtctctgt tcgggaagga ggtggaccag ttgattcggc ctaaacgtgc tgacattgtg 31020
cagcgcctaa gggaagcaac tgataccgga cctgccgtgg cgaacatcgt agggaccttg 31080
aagtattcaa cacaggaact ggctgctcgc tctccgtgga ctaagctact gaacggaacc 31140
actaactacc ttctggatgc tgcgcgtcaa ggtatgcttg gggatgttat tagtgccacc 31200
ctaacaggta agactacccg ctgggagaaa gaaggcttcc ttcgtggtgc ctccgtaact 31260
cctgagcaga tggctggcat caagtctctc atcaaggaac atatggtacg cggtgaggac 31320
gggaagttta ccgttaagga caagcaagcg ttctctatgg acccacgggc tatggactta 31380
tggagactgg ctgacaaggt agctgatgag gcaatgctgc gtccacataa ggtgtcctta 31440
caggattccc atgcgttcgg agcactaggt aagatggtta tgcagtttaa gtctttcact 31500
atcaagtccc ttaactctaa gttcctgcga accttctatg atggatacaa gaacaaccga 31560
gcgattgacg ctgcgctgag catcatcacc tctatgggtc tcgctggtgg tttctatgct 31620
atggctgcac acgtcaaagc atacgctctg cctaaggaga aacgtaagga gtacttggag 31680
cgtgcactgg acccaaccat gattgcccac gctgcgttat ctcgtagttc tcaattgggt 31740
gctcctttgg ctatggttga cctagttggt ggtgttttag ggttcgagtc ctccaagatg 31800
gctcgctcta cgattctacc taaggacacc gtgaaggaac gtgacccaaa caaaccgtac 31860
acctctagag aggtaatggg cgctatgggt tcaaaccttc tggaacagat gccttcggct 31920
ggctttgtgg ctaacgtagg ggctacctta atgaatgctg ctggcgtggt caactcacct 31980
aataaagcaa ccgagcagga cttcatgact ggtcttatga actccacaaa agagttagta 32040
ccgaacgacc cattgactca acagcttgtg ttgaagattt atgaggcgaa cggtgttaac 32100
ttgagggagc gtaggaaata atacgactca ctatagggag aggcgaaata atcttctccc 32160
tgtagtctct tagatttact ttaaggaggt caaatggcta acgtaattaa aaccgttttg 32220
acttaccagt tagatggctc caatcgtgat tttaatatcc cgtttgagta tctagcccgt 32280
aagttcgtag tggtaactct tattggtgta gaccgaaagg tccttacgat taatacagac 32340
tatcgctttg ctacacgtac tactatctct ctgacaaagg cttggggtcc agccgatggc 32400
tacacgacca tcgagttacg tcgagtaacc tccactaccg accgattggt tgactttacg 32460
gatggttcaa tcctccgcgc gtatgacctt aacgtcgctc agattcaaac gatgcacgta 32520
gcggaagagg cccgtgacct cactacggat actatcggtg tcaataacga tggtcacttg 32580
gatgctcgtg gtcgtcgaat tgtgaaccta gcgaacgccg tggatgaccg cgatgctgtt 32640
ccgtttggtc aactaaagac catgaaccag aactcatggc aagcacgtaa tgaagcctta 32700

-continued

```
cagttccgta atgaggctga gactttcaga aaccaagcgg agggctttaa gaacgagtcc  32760
agtaccaacg ctacgaacac aaagcagtgg cgcgatgaga ccaagggttt ccgagacgaa  32820
gccaagcggt tcaagaatac ggctggtcaa tacgctacat ctgctgggaa ctctgcttcc  32880
gctgcgcatc aatctgaggt aaacgctgag aactctgcca cagcatccgc taactctgct  32940
catttggcag aacagcaagc agaccgtgcg gaacgtgagg cagacaagct ggaaaattac  33000
aatggattgg ctggtgcaat tgataaggta gatggaacca atgtgtactg gaaaggaaat  33060
attcacgcta acgggcgcct ttacatgacc acaaacggtt ttgactgtgg ccagtatcaa  33120
cagttctttg gtggtgtcac taatcgttac tctgtcatgg agtggggaga tgagaacgga  33180
tggctgatgt atgttcaacg tagagagtgg acaacagcga taggcggtaa catccagtta  33240
gtagtaaacg gacagatcat cacccaaggt ggagccatga ccggtcagct aaaattgcag  33300
aatgggcatg ttcttcaatt agagtccgca tccgacaagg cgcactatat tctatctaaa  33360
gatggtaaca ggaataactg gtacattggt agagggtcag ataacaacaa tgactgtacc  33420
ttccactcct atgtacatgg tacgacctta acactcaagc aggactatgc agtagttaac  33480
aaacacttcc acgtaggtca ggccgttgtg gccactgatg gtaatattca aggtactaag  33540
tggggaggta aatggctgga tgcttaccta cgtgacagct tcgttgcgaa gtccaaggcg  33600
tggactcagg tgtggtctgg tagtgctggc ggtggggtaa gtgtgactgt ttcacaggat  33660
ctccgcttcc gcaatatctg gattaagtgt gccaacaact cttggaactt cttccgtact  33720
ggccccgatg gaatctactt catagcctct gatggtggat ggttacgatt ccaaatacac  33780
tccaacggtc tcggattcaa gaatattgca gacagtcgtt cagtacctaa tgcaatcatg  33840
gtggagaacg agtaattggt aaatcacaag gaaagacgtg tagtccacgg atggactctc  33900
aaggaggtac aaggtgctat cattagactt taacaacgaa ttgattaagg ctgctccaat  33960
tgttgggacg ggtgtagcag atgttagtgc tcgactgttc tttgggttaa gccttaacga  34020
atggttctac gttgctgcta tcgcctacac agtggttcag attggtgcca aggtagtcga  34080
taagatgatt gactggaaga aagccaataa ggagtgatat gtatggaaaa ggataagagc  34140
cttattacat tcttagagat gttggacact gcgatggctc agcgtatgct tgcggacctt  34200
tcggaccatg agcgtcgctc tccgcaactc tataatgcta ttaacaaact gttagaccgc  34260
cacaagttcc agattggtaa gttgcagccg gatgttcaca tcttaggtgg ccttgctggt  34320
gctcttgaag agtacaaaga gaaagtcggt gataacggtc ttacggatga tgatatttac  34380
acattacagt gatatactca aggccactac agatagtggt ctttatggat gtcattgtct  34440
atacgagatg ctcctacgtg aaatctgaaa gttaacggga ggcattatgc tagaattttt  34500
acgtaagcta atcccttggg ttctcgctgg gatgctattc gggttaggat ggcatctagg  34560
gtcagactca atggacgcta aatggaaaca ggaggtacac aatgagtacg ttaagagagt  34620
tgaggctgcg aagagcactc aaagagcaat cgatgcggta tctgctaagt atcaagaaga  34680
ccttgccgcg ctggaaggga gcactgatag gattatttct gatttgcgta gcgacaataa  34740
gcggttgcgc gtcagagtca aaactaccgg aacctccgat ggtcagtgtg gattcgagcc  34800
tgatggtcga gccgaacttg acgaccgaga tgctaaacgt attctcgcag tgacccagaa  34860
gggtgacgca tggattcgtg cgttacagga tactattcgt gaactgcaac gtaagtagga  34920
aatcaagtaa ggaggcaatg tgtctactca atccaatcgt aatgcgctcg tagtggcgca  34980
actgaaagga gacttcgtgg cgttcctatt cgtcttatgg aaggcgctaa acctaccggt  35040
gcccactaag tgtcagattg acatggctaa ggtgctggcg aatggagaca acaagaagtt  35100
```

catcttacag gctttccgtg gtatcggtaa gtcgttcatc acatgtgcgt tcgttgtgtg 35160
gtccttatgg agagaccctc agttgaagat acttatcgta tcagcctcta aggagcgtgc 35220
agacgctaac tccatcttta ttaagaacat cattgacctg ctgccattcc tatctgagtt 35280
aaagccaaga cccggacagc gtgactcggt aatcagcttt gatgtaggcc cagccaatcc 35340
tgaccactct cctagtgtga aatcagtagg tatcactggt cagttaactg gtagccgtgc 35400
tgacattatc attgcggatg acgttgagat tccgtctaac agcgcaacta tgggtgcccg 35460
tgagaagcta tggactctgg ttcaggagtt cgctgcgtta cttaaaccgc tgccttcctc 35520
tcgcgttatc taccttggta cacctcagac agagatgact ctctataagg aacttgagga 35580
taaccgtggg tacacaacca ttatctggcc tgctctgtac ccaaggacac gtgaagagaa 35640
cctctattac tcacagcgtc ttgctcctat gttacgcgct gagtacgatg agaaccctga 35700
ggcacttgct gggactccaa cagacccagt gcgctttgac cgtgatgacc tgcgcgagcg 35760
tgagttggaa tacggtaagg ctggctttac gctacagttc atgcttaacc ctaaccttag 35820
tgatgccgag aagtacccgc tgaggcttcg tgacgctatc gtagcggcct tagacttaga 35880
gaaggcccca atgcattacc agtggcttcc gaaccgtcag aacatcattg aggaccttcc 35940
taacgttggc cttaagggtg atgacctgca tacgtaccac gattgttcca acaactcagg 36000
tcagtaccaa cagaagattc tggtcattga ccctagtggt cgcggtaagg acgaaacagg 36060
ttacgctgtg ctgtacacac tgaacggtta catctacctt atggaagctg gaggtttccg 36120
tgatggctac tccgataaga cccttgagtt actcgctaag aaggcaaagc aatggggagt 36180
ccagacggtt gtctacgaga gtaacttcgg tgacggtatg ttcggtaagg tattcagtcc 36240
tatccttctt aaacaccaca actgtgcgat ggaagagatt cgtgcccgtg gtatgaaaga 36300
gatgcgtatt tgcgataccc ttgagccagt catgcagact caccgccttg taattcgtga 36360
tgaggtcatt agggccgact accagtccgc tcgtgacgta gacggtaagc atgacgttaa 36420
gtactcgttg ttctaccaga tgacccgtat cactcgtgag aaaggcgctc tggctcatga 36480
tgaccgattg gatgcccttg cgttaggcat tgagtatctc cgtgagtcca tgcagttgga 36540
ttccgttaag gtcgagggtg aagtacttgc tgacttcctt gaggaacaca tgatgcgtcc 36600
tacggttgct gctacgcata tcattgagat gtctgtggga ggagttgatg tgtactctga 36660
ggacgatgag ggttacggta cgtctttcat tgagtggtga tttatgcatt aggactgcat 36720
agggatgcac tatagaccac ggatggtcag ttctttaagt tactgaaaag acacgataaa 36780
ttaatacgac tcactatagg gagaggaggg acgaaaggtt actatataga tactgaatga 36840
atacttatag agtgcataaa gtatgcataa tggtgtacct agagtgacct ctaagaatgg 36900
tgattatatt gtattagtat caccttaact taaggaccaa cataaaggga ggagactcat 36960
gttccgctta ttgttgaacc tactgcggca tagagtcacc taccgatttc ttgtggtact 37020
ttgtgctgcc cttgggtacg catctcttac tggagacctc agttcactgg agtctgtcgt 37080
ttgctctata ctcacttgta gcgattaggg tcttcctgac cgactgatgg ctcaccgagg 37140
gattcagcgg tatgattgca tcacaccact tcatccctat agagtcaagt cctaaggtat 37200
acccataaag agcctctaat ggtctatcct aaggtctata cctaaagata ggccatccta 37260
tcagtgtcac ctaaagaggg tcttagagag ggcctatgga gttcctatag ggtcctttaa 37320
aatataccat aaaaatctga gtgactatct cacagtgtac ggacctaaag ttcccccata 37380
gggggtacct aaagcccagc caatcaccta aagtcaacct tcggttgacc ttgagggttc 37440
cctaagggtt ggggatgacc cttgggtttg tctttgggtg ttaccttgag tgtctctctg 37500
tgtccct 37507

<210> SEQ ID NO 67
<211> LENGTH: 37504
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg gggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920

-continued

```
cgctacgaag acgtttacat gcctgaggtg tacaaagcga ttaacattgc gcaaaacacc   1980
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
tctctaggag tggccttagt catttaacca ataggagata aacattatga tgaacattaa   4320
```

gactaacccg tttaaagccg tgtctttcgt agagtctgcc attaagaagg ctctggataa 4380
cgctgggtat cttatcgctg aaatcaagta cgatggtgta cgcgggaaca tctgcgtaga 4440
caatactgct aacagttact ggctctctcg tgtatctaaa acgattccgg cactggagca 4500
cttaaacggg tttgatgttc gctggaagcg tctactgaac gatgaccgtt gcttctacaa 4560
agatggcttt atgcttgatg gggaactcat ggtcaagggc gtagacttta acacagggtc 4620
cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400
cttcgggtgg gcctttctgc gtttataagg agacacttta tgtttaagaa ggttggtaaa 5460
ttccttgcgg ctttggcagc tatcctgacg cttgcgtata ttcttgcggt ataccctcaa 5520
gtagcactag tagtagttgg cgcttgttac ttagcggcag tgtgtgcttg cgtgtggagt 5580
atagttaact ggtaatacga ctcactaaag gaggtacaca ccatgatgta cttaatgcca 5640
ttactcatcg tcattgtagg atgccttgcg ctccactgta gcgatgatga tatgccagat 5700
ggtcacgctt aatacgactc actaaaggag acactatatg tttcgacttc attacaacaa 5760
aagcgttaag aatttcacgg ttcgccgtgc tgaccgttca atcgtatgtg cgagcgagcg 5820
ccgagctaag atacctctta ttggtaacac agttcctttg gcaccgagcg tccacatcat 5880
tatcacccgt ggtgactttg agaaagcaat agacaagaaa cgtccggttc ttagtgtggc 5940
agtgacccgc ttcccgttcg tccgtctgtt actcaaacga atcaaggagg tgttctgatg 6000
ggactgttag atggtgaagc ctgggaaaaa gaaaacccgc cagtacaagc aactgggtgt 6060
atagcttgct tagagaaaga tgaccgttat ccacacacct gtaacaaagg agctaacgat 6120
atgaccgaac gtgaacaaga gatgatcatt aagttgatag acaataatga aggtcgccca 6180
gatgatttga atggctgcgg tattctctgc tccaatgtcc cttgccacct ctgccccgca 6240
aataacgatc aaaagataac cttaggtgaa atccgagcga tggacccacg taaaccacat 6300
ctgaataaac ctgaggtaac tcctacagat gaccagcctt ccgctgagac aatcgaaggt 6360
gtcactaagc cttcccacta catgctgttt gacgacattg aggctatcga agtgattgct 6420
cgttcaatga ccgttgagca gttcaaggga tactgcttcg gtaacatctt aaagtacaga 6480
ctacgtgctg gtaagaagtc agagttagcg tacttagaga aagacctagc gaaagcagac 6540
ttctataaag aactctttga gaaacataag gataaatgtt atgcataact tcaagtcaac 6600
cccacctgcc gacagcctat ctgatgactt cacatcttgc tcagagtggt gccgaaagat 6660

-continued gtgggaagag acattcgacg atgcgtacat caagctgtat gaactttgga aatcgagagg 6720
tcaatgacta tgtcaaacgt aaatacaggt tcacttagtg tggacaataa gaagttttgg 6780
gctaccgtag agtcctcgga gcattccttc gaggttccaa tctacgctga gaccctagac 6840
gaagctctgg agttagccga atggcaatac gttccggctg gctttgaggt tactcgtgtg 6900
cgtccttgtg tagcaccgaa gtaatacgac tcactattag ggaagactcc ctctgagaaa 6960
ccaaacgaaa cctaaaggag attaacatta tggctaagaa gattttcacc tctgcgctgg 7020
gtaccgctga accttacgct tacatcgcca agccggacta cggcaacgaa gagcgtggct 7080
ttgggaaccc tcgtggtgtc tataaagttg acctgactat tcccaacaaa gacccgcgct 7140
gccagcgtat ggtcgatgaa atcgtgaagt gtcacgaaga ggcttatgct gctgccgttg 7200
aggaatacga agctaatcca cctgctgtag ctcgtggtaa gaaaccgctg aaaccgtatg 7260
agggtgacat gccgttcttc gataacggtg acggtacgac tacctttaag ttcaaatgct 7320
acgcgtcttt ccaagacaag aagaccaaag agaccaagca catcaatctg gttgtggttg 7380
actcaaaagg taagaagatg gaagacgttc cgattatcgg tggtggctct aagctgaaag 7440
ttaaatattc tctggttcca tacaagtgga acactgctgt aggtgcgagc gttaagctgc 7500
aactggaatc cgtgatgctg gtcgaactgg ctacctttgg tggcggtgaa gacgattggg 7560
ctgacgaagt tgaagagaac ggctatgttg cctctggttc tgccaaagcg agcaaaccac 7620
gcgacgaaga aagctgggac gaagacgacg aagagtccga ggaagcagac gaagacggag 7680
acttctaagt ggaactgcgg gagaaaatcc ttgagcgaat caaggtgact tcctctgggt 7740
gttgggagtg gcagggcgct acgaacaata aagggtacgg gcaggtgtgg tgcagcaata 7800
ccggaaaggt tgtctactgt catcgcgtaa tgtctaatgc tccgaaaggt tctaccgtcc 7860
tgcactcctg tgataatcca ttatgttgta accctgaaca cctatccata ggaactccaa 7920
aagagaactc cactgacatg gtaaataagg gtcgctcaca caaggggtat aaactttcag 7980
acgaagacgt aatggcaatc atggagtcca gcgagtccaa tgtatcctta gctcgcacct 8040
atggtgtctc ccaacagact atttgtgata tacgcaaagg gaggcgacat ggcaggttac 8100
ggcgctaaag gaatccgaaa ggttggagcg tttcgctctg gcctagagga caaggtttca 8160
aagcagttgg aatcaaaagg tattaaattc gagtatgaag agtggaaagt gccttatgta 8220
attccggcga gcaatcacac ttacactcca gacttcttac ttccaaacgg tatattcgtt 8280
gagacaaagg gtctgtggga aagcgatgat agaaagaagc acttattaat tagggagcag 8340
caccccgagc tagacatccg tattgtcttc tcaagctcac gtactaagtt atacaaaggt 8400
tctccaacgt cttatggaga gttctgcgaa aagcatggta ttaagttcgc tgataaactg 8460
atacctgctg agtggataaa ggaacccaag aaggaggtcc cctttgatag attaaaaagg 8520
aaaggaggaa agaaataatg gctcgtgtac agtttaaaca acgtgaatct actgacgcaa 8580
tctttgttca ctgctcggct accaagccaa gtcagaatgt tggtgtccgt gagattcgcc 8640
agtggcacaa agagcagggt tggctcgatg tgggatacca ctttatcatc aagcgagacg 8700
gtactgtgga ggcaggacga gatgagatgg ctgtaggctc tcacgctaag ggttacaacc 8760
acaactctat cggcgtctgc cttgttggtg gtatcgacga taaaggtaag ttcgacgcta 8820
actttacgcc agcccaaatg caatcccttc gctcactgct tgtcacactg ctggctaagt 8880
acgaaggcgc tggtcttcgc gcccatcatg aggtggcgcc gaaggcttgc ccttcgttcg 8940
accttaagcg ttggtgggag aagaacgaac tggtcacttc tgaccgtgga taatgatcta 9000
ttggaagtcg ttgcgtggat ttatagaact aggagggaat tgcatggaca attcgcacga 9060

```
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
```

-continued

```
ttaccatgcg tgaccctaaa gttatccaag cagaaatcgc taaactggaa gctgaactgg  11460
aggacgttaa gtaccatgaa gctaagactc gctccgctgt tcacatcttg aagaacttag  11520
gctggacttg gacaagacag actggctgga agaaaccaga agttaccaag ctgagtcata  11580
aggtgttcga taaggacact atgacccaca tcaaggctgg tgattgggtt aaggttgaca  11640
tgggagttgt tggtggatac ggctacgtcc gctcagttag tggcaaatat gcacaagtgt  11700
catacatcac aggtgttact ccacgcggtg caatcgttgc cgataagacc aacatgattc  11760
acacaggttt cttgacagtt gtttcatatg aagagattgt taagtcacga taatcaatag  11820
gagaaatcaa tatgatcgtt tctgacatcg aagctaacgc cctcttagag agcgtcacta  11880
agttccactg cggggttatc tacgactact ccaccgctga gtacgtaagc taccgtccga  11940
gtgacttcgg tgcgtatctg gatgcgctgg aagccgaggt tgcacgaggc ggtcttattg  12000
tgttccacaa cggtcacaag tatgacgttc ctgcattgac caaactggca aagttgcaat  12060
tgaaccgaga gttccacctt cctcgtgaga actgtattga cacccttgtg ttgtcacgtt  12120
tgattcattc caacctcaag gacaccgata tgggtcttct gcgttccggc aagttgcccg  12180
gaaaacgctt tgggtctcac gctttggagg cgtggggtta tcgcttaggc gagatgaagg  12240
gtgaatacaa agacgacttt aagcgtatgc ttgaagagca gggtgaagaa tacgttgacg  12300
gaatggagtg gtggaacttc aacgaagaga tgatggacta taacgttcag gacgttgtgg  12360
taactaaagc tctccttgag aagctactct ctgacaaaca ttacttccct cctgagattg  12420
actttacgga cgtaggatac actacgttct ggtcagaatc ccttgaggcc gttgacattg  12480
aacatcgtgc tgcatggctg ctcgctaaac aagagcgcaa cgggttcccg tttgacacaa  12540
aagcaatcga agagttgtac gtagagttag ctgctcgccg ctctgagttg ctccgtaaat  12600
tgaccgaaac gttcggctcg tggtatcagc ctaaaggtgg cactgagatg ttctgccatc  12660
cgcgaacagg taagccacta cctaaatacc ctcgcattaa gacacctaaa gttggtggta  12720
tctttaagaa gcctaagaac aaggcacagc gagaaggccg tgagccttgc gaacttgata  12780
cccgcgagta cgttgctggt gctccttaca ccccagttga acatgttgtg tttaaccctt  12840
cgtctcgtga ccacattcag aagaaactcc aagaggctgg gtgggtcccg accaagtaca  12900
ccgataaggg tgctcctgtg gtggacgatg aggtactcga aggagtacgt gtagatgacc  12960
ctgagaagca agccgctatc gacctcatta aagagtactt gatgattcag aagcgaatcg  13020
gacagtctgc tgagggagac aaagcatggc ttcgttatgt tgctgaggat ggtaagattc  13080
atggttctgt taaccctaat ggagcagtta cgggtcgtgc gacccatgcg ttcccaaacc  13140
ttgcgcaaat tccgggtgta cgttctcctt atggagagca gtgtcgcgct gcttttggcg  13200
ctgagcacca tttggatggg ataactggta agccttgggt tcaggctggc atcgacgcat  13260
ccggtcttga gctacgctgc ttggctcact tcatggctcg ctttgataac ggcgagtacg  13320
ctcacgagat tcttaacggc gacatccaca ctaagaacca gatagctgct gaactaccta  13380
cccgagataa cgctaagacg ttcatctatg ggttcctcta tggtgctggt gatgagaaga  13440
ttggacagat tgttggtgct ggtaaagagc gcggtaagga actcaagaag aaattccttg  13500
agaacacccc cgcgattgca gcactccgcg agtctatcca acagacactt gtcgagtcct  13560
ctcaatgggt agctggtgag caacaagtca agtggaaacg ccgctggatt aaaggtctgg  13620
atggtcgtaa ggtacacgtt cgtagtcctc acgctgcctt gaatacccta ctgcaatctg  13680
ctggtgctct catctgcaaa ctgtggatta tcaagaccga agagatgctc gtagagaaag  13740
gcttgaagca tggctgggat ggggactttg cgtacatggc atgggtacat gatgaaatcc  13800
```

-continued

```
aagtaggctg ccgtaccgaa gagattgctc aggtggtcat tgagaccgca caagaagcga  13860
tgcgctgggt tggagaccac tggaacttcc ggtgtcttct ggataccgaa ggtaagatgg  13920
gtcctaattg ggcgatttgc cactgataca ggaggctact catgaacgaa agacacttaa  13980
caggtgctgc ttctgaaatg ctagtagcct acaaatttac caaagctggg tacactgtct  14040
attaccctat gctgactcag agtaaagagg acttggttgt atgtaaggat ggtaaattta  14100
gtaaggttca ggttaaaaca gccacaacgg ttcaaaccaa cacaggagat gccaagcagg  14160
ttaggctagg tggatgcggt aggtccgaat ataaggatgg agactttgac attcttgcgg  14220
ttgtggttga cgaagatgtg cttattttca catgggacga agtaaaaggt aagacatcca  14280
tgtgtgtcgg caagagaaac aaaggcataa aactatagga gaaattatta tggctatgac  14340
aaagaaattt aaagtgtcct tcgacgttac cgcaaagatg tcgtctgacg ttcaggcaat  14400
cttagagaaa gatatgctgc atctatgtaa gcaggtcggc tcaggtgcga ttgtccccaa  14460
tggtaaacag aaggaaatga ttgtccagtt cctgacacac ggtatggaag gattgatgac  14520
attcgtagta cgtacatcat ttcgtgaggc cattaaggac atgcacgaag agtatgcaga  14580
taaggactct ttcaaacaat ctcctgcaac agtacgggag gtgttctgat gtctgactac  14640
ctgaaagtgc tgcaagcaat caaaagttgc cctaagactt tccagtccaa ctatgtacgg  14700
aacaatgcga gcctcgtagc ggaggccgct tcccgtggtc acatctcgtg cctgactact  14760
agtggacgta acggtggcgc ttgggaaatc actgcttccg gtactcgctt tctgaaacga  14820
atgggaggat gtgtctaatg tctcgtgacc ttgtgactat tccacgcgat gtgtggaacg  14880
atatacaggg ctacatcgac tctctggaac gtgagaacga tagccttaag aatcaactaa  14940
tggaagctga cgaatacgta gcggaactag aggagaaact taatggcact tcttgacctt  15000
aaacaattct atgagttacg tgaaggctgc gacgacaagg gtatccttgt gatggacggc  15060
gactggctgg tcttccaagc tatgagtgct gctgagtttg atgcctcttg ggaggaagag  15120
atttggcacc gatgctgtga ccacgctaag gcccgtcaga ttcttgagga ttccattaag  15180
tcctacgaga cccgtaagaa ggcttgggca ggtgctccaa ttgtccttgc gttcaccgat  15240
agtgttaact ggcgtaaaga actggttgac ccgaactata aggctaaccg taaggccgtg  15300
aagaaacctg tagggtactt tgagttcctt gatgctctct ttgagcgcga agagttctat  15360
tgcatccgtg agcctatgct tgagggtgat gacgttatgg gagttattgc ttccaatccg  15420
tctgccttcg gtgctcgtaa ggctgtaatc atctcttgcg ataaggactt taagaccatc  15480
cctaactgtg acttcctgtg gtgtaccact ggtaacatcc tgactcagac cgaagagtcc  15540
gctgactggt ggcacctctt ccagaccatc aagggtgaca tcactgatgg ttactcaggg  15600
attgctggat ggggtgatac cgccgaggac ttcttgaata acccgttcat aaccgagcct  15660
aaaacgtctg tgcttaagtc cggtaagaac aaaggccaag aggttactaa atgggttaaa  15720
cgcgaccctg agcctcatga gacgctttgg gactgcatta agtccattgg cgcgaaggct  15780
ggtatgaccg aagaggatat tatcaagcag ggccaaatgg ctcgaatcct acggttcaac  15840
gagtacaact ttattgacaa ggagatttac ctgtggagac cgtagcgtat attggtctgg  15900
gtctttgtgt tctcggagtg tgcctcattt cgtggggcct ttgggactta gccagaataa  15960
tcaagtcgtt acacgacact aagtgataaa ctcaaggtcc ctaaattaat acgactcact  16020
atagggagat aggggccttt acgattatta ctttaagatt taactctaag aggaatcttt  16080
attatgttaa cacctattaa ccaattactt aagaacccta acgatattcc agatgtacct  16140
```

-continued

```
cgtgcaaccg ctgagtatct acaggttcga ttcaactatg cgtacctcga agcgtctggt  16200
catataggac ttatgcgtgc taatggttgt agtgaggccc acatcttggg tttcattcag  16260
ggcctacagt atgcctctaa cgtcattgac gagattgagt tacgcaagga acaactaaga  16320
gatgatgggg aggattgaca ctatgtgttt ctcaccgaaa attaaaactc cgaagatgga  16380
taccaatcag attcgagccg ttgagccagc gcctctgacc caagaagtgt caagcgtgga  16440
gttcggtggg tcttctgatg agacggatac cgagggcacc gaagtgtctg gacgcaaagg  16500
cctcaaggtc gaacgtgatg attccgtagc gaagtctaaa gccagcggca atggctccgc  16560
tcgtatgaaa tcttccatcc gtaagtccgc atttggaggt aagaagtgat gtctgagttc  16620
acatgtgtgg aggctaagag tcgcttccgt gcaatccggt ggactgtgga acaccttggg  16680
ttgcctaaag gattcgaagg acactttgtg ggctacagcc tctacgtaga cgaagtgatg  16740
gacatgtctg gttgccgtga agagtacatt ctggactcta ccggaaaaca tgtagcgtac  16800
ttcgcgtggt gcgtaagctg tgacattcac cacaaaggag acattctgga tgtaacgtcc  16860
gttgtcatta atcctgaggc agactctaag ggcttacagc gattcctagc gaaacgcttt  16920
aagtaccttg cggaactcca cgattgcgat tgggtgtctc gttgtaagca tgaaggcgag  16980
acaatgcgtg tatactttaa ggaggtataa gttatgggta agaaagttaa gaaggccgtg  17040
aagaaagtca ccaagtccgt taagaaagtc gttaaggaag gggctcgtcc ggttaaacag  17100
gttgctggcg gtctagctgg tctggctggt ggtactggtg aagcacagat ggtggaagta  17160
ccacaagctg ccgcacagat tgttgacgta cctgagaaag aggtttccac tgaggacgaa  17220
gcacagacag aaagcggacg caagaaagct cgtgctggcg gtaagaaatc cttgagtgta  17280
gcccgtagct ccggtggcgg tatcaacatt taatcaggag gttatcgtgg aagactgcat  17340
tgaatggacc ggaggtgtca actctaaggg ttatggtcgt aagtgggtta atggtaaact  17400
tgtgactcca cataggcaca tctatgagga gacatatggt ccagttccaa caggaattgt  17460
ggtgatgcat atctgcgata accctaggtg ctataacata aagcacctta cgcttggaac  17520
tccaaaggat aattccgagg acatggttac caaaggtaga caggctaaag gagaggaact  17580
aagcaagaaa cttacagagt cagacgttct cgctatacgc tcttcaacct taagccaccg  17640
ctccttagga gaactgtatg gagtcagtca atcaaccata acgcgaatac tacagcgtaa  17700
gacatggaga cacatttaat ggctgagaaa cgaacaggac ttgcggagga tggcgcaaag  17760
tctgtctatg agcgtttaaa gaacgaccgt gctccctatg agacacgcgc tcagaattgc  17820
gctcaatata ccatcccatc attgttccct aaggactccg ataacgcctc tacagattat  17880
caaactccgt ggcaagccgt gggcgctcgt ggtctgaaca atctagcctc taagctcatg  17940
ctggctctat tccctatgca gacttggatg cgacttacta tatctgaata tgaagcaaag  18000
cagttactga gcgaccccga tggactcgct aaggtcgatg agggcctctc gatggtagag  18060
cgtatcatca tgaactacat tgagtctaac agttaccgcg tgactctctt tgaggctctc  18120
aaacagttag tcgtagctgg taacgtcctg ctgtacctac cggaaccgga agggtcaaac  18180
tataatccca tgaagctgta ccgattgtct tcttatgtgg tccaacgaga cgcattcggc  18240
aacgttctgc aaatggtgac tcgtgaccag atagcttttg gtgctctccc tgaggacatc  18300
cgtaaggctg tagaaggtca aggtggtgag aagaaagctg atgagacaat cgacgtgtac  18360
actcacatct atctggatga ggactcaggt gaatacctcc gatacgaaga ggtcgagggt  18420
atggaagtcc aaggctccga tgggacttat cctaaagagg cttgcccata catcccgatt  18480
cggatggtca gactagatgg tgaatcctac ggtcgttcgt acattgagga atacttaggt  18540
```

```
gacttacggt cccttgaaaa tctccaagag gctatcgtca agatgtccat gattagctct  18600
aaggttatcg gcttagtgaa tcctgctggt atcacccagc cacgccgact gaccaaagct  18660
cagactggtg acttcgttac tggtcgtcca gaagacatct cgttcctcca actggagaag  18720
caagcagact ttactgtagc taaagccgta agtgacgcta tcgaggctcg cctttcgttt  18780
gcctttatgt tgaactctgc ggttcagcgt acaggtgaac gtgtgaccgc cgaagagatt  18840
cggtatgtag cttctgaact tgaagatact ttaggtggtg tctactctat cctttctcaa  18900
gaattacaat tgcctctggt acgagtgctc ttgaagcaac tacaagccac gcaacagatt  18960
cctgagttac ctaaggaagc cgtagagcca accattagta caggtctgga agcaattggt  19020
cgaggacaag accttgataa gctggagcgg tgtgtcactg cgtgggctgc actggcacct  19080
atgcgggacg accctgatat taaccttgcg atgattaagt tacgtattgc caacgctatc  19140
ggtattgaca cttctggtat tctactcacc gaagaacaga agcaacagaa gatggcccaa  19200
cagtctatgc aaatgggtat ggataatggt gctgctgcgc tggctcaagg tatggctgca  19260
caagctacag cttcacctga ggctatggct gctgccgctg attccgtagg tttacagccg  19320
ggaatttaat acgactcact atagggagac ctcatctttg aaatgagcga tgacaagagg  19380
ttggagtcct cggtcttcct gtagttcaac tttaaggaga caataataat ggctgaatct  19440
aatgcagacg tatatgcatc ttttggcgtg aactccgctg tgatgtctgg tggttccgtt  19500
gaggaacatg agcagaacat gctggctctt gatgttgctg cccgtgatgg cgatgatgca  19560
atcgagttag cgtcagacga agtggaaaca gaacgtgacc tgtatgacaa ctctgacccg  19620
ttcggtcaag aggatgacga aggccgcatt caggttcgta tcggtgatgg ctctgagccg  19680
accgatgtgg acactggaga agaaggcgtt gagggcaccg aaggttccga agagtttacc  19740
ccactgggcg agactccaga agaactggta gctgcctctg agcaacttgg tgagcacgaa  19800
gagggcttcc aagagatgat taacattgct gctgagcgtg gcatgagtgt cgagaccatt  19860
gaggctatcc agcgtgagta cgaggagaac gaagagttgt ccgccgagtc ctacgctaag  19920
ctggctgaaa ttggctacac gaaggctttc attgactcgt atatccgtgg tcaagaagct  19980
ctggtggagc agtacgtaaa cagtgtcatt gagtacgctg gtggtcgtga acgttttgat  20040
gcactgtata accaccttga gacgcacaac cctgaggctg cacagtcgct ggataatgcg  20100
ttgaccaatc gtgacttagc gaccgttaag gctatcatca acttggctgg tgagtctcgc  20160
gctaaggcgt tcggtcgtaa gccaactcgt agtgtgacta atcgtgctat tccggctaaa  20220
cctcaggcta ccaagcgtga aggctttgcg gaccgtagcg agatgattaa agctatgagt  20280
gaccctcggt atcgcacaga tgccaactat cgtcgtcaag tcgaacagaa agtaatcgat  20340
tcgaacttct gatagacttc gaaattaata cgactcacta tagggagacc acaacggttt  20400
ccctctagaa ataattttgt ttaactttaa gaaggagata tacatatggc tagcatgact  20460
ggtggacagc aaatgggtac taaccaaggt aaaggtgtag ttgctgctgg agataaactg  20520
gcgttgttct tgaaggtatt tggcggtgaa gtcctgactg cgttcgctcg tacctccgtg  20580
accacttctc gccacatggt acgttccatc tccagcggta aatccgctca gttccctgtt  20640
ctgggtcgca ctcaggcagc gtatctggct ccgggcgaga acctcgacga taaacgtaag  20700
gacatcaaac acaccgagaa ggtaatcacc attgacggtc tcctgacggc tgacgttctg  20760
atttatgata ttgaggacgc gatgaaccac tacgacgttc gctctgagta tacctctcag  20820
ttgggtgaat ctctggcgat ggctgcggat ggtgcggttc tggctgagat tgccggtctg  20880
```

tgtaacgtgg aaagcaaata taatgagaac atcgagggct taggtactgc taccgtaatt 20940
gagaccactc agaacaaggc cgcacttacc gaccaagttg cgctgggtaa ggagattatt 21000
gcggctctga ctaaggctcg tgcggctctg accaagaact atgttccggc tgctgaccgt 21060
gtgttctact gtgacccaga tagctactct gcgattctgg cagcactgat gccgaacgca 21120
gcaaactacg ctgctctgat tgaccctgag aagggttcta tccgcaacgt tatgggcttt 21180
gaggttgtag aagttccgca cctcaccgct ggtggtgctg gtaccgctcg tgagggcact 21240
actggtcaga agcacgtctt ccctgccaat aaaggtgagg gtaatgtcaa ggttgctaag 21300
gacaacgtta tcggcctgtt catgcaccgc tctgcggtag gtactgttaa gctgcgtgac 21360
ttggctctgg agcgcgctcg ccgtgctaac ttccaagcgg accagattat cgctaagtac 21420
gcaatgggcc acggtggtct tcgcccagaa gctgcaggag ctgtcgtatt ccagtcaggt 21480
gtgatgctcg ggatccgaa ttcttaagta actaacgaaa ttaatacgac tcactatagg 21540
gagaccacaa cggtttccct ctagaaataa ttttgtttaa ctttaagaag gagatataca 21600
tatgtggctg ggcagcgcgc tgaaaattgg cgcgaaactg ctgccgagcg tggtgggcct 21660
gtttaaaaaa aaaaaacagt aaggatccgg ctgctaacaa agcccgaagc ttgcggccgc 21720
actcgagtaa ctagttaacc ccttggggcc tctaaacggg tcttgagggg tttttgctg 21780 aaaggaggaa ctatatgcgc tcatacgata tgaacgttga gactgccgct gagttatcag 21840
ctgtgaacga cattctggcg tctatcggtg aacctccggt atcaacgctg gaaggtgacg 21900
ctaacgcaga tgcagcgaac gctcggcgta ttctcaacaa gattaaccga cagattcaat 21960
ctcgtggatg gacgttcaac attgaggaag gcataacgct actacctgat gtttactcca 22020
acctgattgt atacagtgac gactatttat ccctaatgtc tacttccggt caatccatct 22080
acgttaaccg aggtggctat gtgtatgacc gaacgagtca atcagaccgc tttgactctg 22140
gtattactgt gaacattatt cgtctccgcg actacgatga gatgcctgag tgcttccgtt 22200
actggattgt caccaaggct tcccgtcagt tcaacaaccg attctttggg gcaccggaag 22260
tagagggtgt actccaagaa gaggaagatg aggctagacg tctctgcatg gagtatgaga 22320
tggactacgg tgggtacaat atgctggatg gagatgcgtt cacttctggt ctactgactc 22380
gctaacatta ataaataagg aggctctaat ggcactcatt agccaatcaa tcaagaactt 22440
gaagggtggt atcagccaac agcctgacat ccttcgttat ccagaccaag ggtcacgcca 22500
agttaacggt tggtcttcgg agaccgaggg cctccaaaag cgtccacctc ttgttttctt 22560
aaatacactt ggagacaacg gtgcgttagg tcaagctccg tacatccacc tgattaaccg 22620
agatgagcac gaacagtatt acgctgtgtt cactggtagc ggaatccgag tgttcgacct 22680
ttctggtaac gagaagcaag ttaggtatcc taacggttcc aactacatca agaccgctaa 22740
tccacgtaac gacctgcgaa tggttactgt agcagactat acgttcatcg ttaaccgtaa 22800
cgttgttgca cagaagaaca caaagtctgt caacttaccg aattacaacc ctaatcaaga 22860
cggattgatt aacgttcgtg gtggtcagta tggtagggaa ctaattgtac acattaacgg 22920
taaagacgtt gcgaagtata agataccaga tggtagtcaa cctgaacacg taaacaatac 22980
ggatgcccaa tggttagctg aagagttagc caagcagatg cgcactaact tgtctgattg 23040
gactgtaaat gtagggcaag ggttcatcca tgtgaccgca cctagtggtc aacagattga 23100
ctccttcacg actaaagatg gctacgcaga ccagttgatt aaccctgtga cccactacgc 23160
tcagtcgttc tctaagctgc cacctaatgc tcctaacggc tacatggtga aaatcgtagg 23220
ggacgcctct aagtctgccg accagtatta cgttcggtat gacgctgagc ggaaagtttg 23280

```
gactgagact ttaggttgga acactgagga ccaagttcta tgggaaacca tgccacacgc  23340
tcttgtgcga gccgctgacg gtaatttcga cttcaagtgg cttgagtggt ctcctaagtc  23400
ttgtggtgac gttgacacca acccttggcc ttcttttgtt ggttcaagta ttaacgatgt  23460
gttcttcttc cgtaaccgct taggattcct tagtggggag aacatcatat tgagtcgtac  23520
agccaaatac ttcaacttct accctgcgtc cattgcgaac cttagtgatg acgaccctat  23580
agacgtagct gtgagtacca accgaatagc aatccttaag tacgccgttc cgttctcaga  23640
agagttactc atctggtccg atgaagcaca attcgtcctg actgcctcgg gtactctcac  23700
atctaagtcg gttgagttga acctaacgac ccagtttgac gtacaggacc gagcgagacc  23760
ttttgggatt gggcgtaatg tctactttgc tagtccgagg tccagcttca cgtccatcca  23820
caggtactac gctgtgcagg atgtcagttc cgttaagaat gctgaggaca ttacatcaca  23880
cgttcctaac tacatcccta atggtgtgtt cagtatttgc ggaagtggta cggaaaactt  23940
ctgttcggta ctatctcacg gggaccctag taaaatcttc atgtacaaat tcctgtacct  24000
gaacgaagag ttaaggcaac agtcgtggtc tcattgggac tttggggaaa acgtacaggt  24060
tctagcttgt cagagtatca gctcagatat gtatgtgatt cttcgcaatg agttcaatac  24120
gttcctagct agaatctctt tcactaagaa cgccattgac ttacagggag aaccctatcg  24180
tgcctttatg gacatgaaga ttcgatacac gattcctagt ggaacataca acgatgacac  24240
attcactacc tctattcata ttccaacaat ttatggtgca aacttcggga ggggcaaaat  24300
cactgtattg gagcctgatg gtaagataac cgtgtttgag caacctacgg ctgggtggaa  24360
tagcgaccct tggctgagac tcagcggtaa cttggaggga cgcatggtgt acattgggtt  24420
caacattaac ttcgtatatg agttctctaa gttcctcatc aagcagactg ccgacgacgg  24480
gtctacctcc acggaagaca ttgggcgctt acagttacgc cgagcgtggg ttaactacga  24540
gaactctggt acgtttgaca tttatgttga gaaccaatcg tctaactgga agtacacaat  24600
ggctggtgcc cgattaggct ctaacactct gagggctggg agactgaact tagggaccgg  24660
acaatatcga ttccctgtgg ttggtaacgc caagttcaac actgtataca tcttgtcaga  24720
tgagactacc cctctgaaca tcattgggtg tggctgggaa ggtaactact tacggagaag  24780
ttccggtatt taattaaata ttctccctgt ggtggctcga aattaatacg actcactata  24840
gggagaacaa tacgactacg ggagggtttt cttatgatga ctataagacc tactaaaagt  24900
acagactttg aggtattcac tccggctcac catgacattc ttgaagctaa ggctgctggt  24960
attgagccga gtttccctga tgcttccgag tgtgtcacgt tgagcctcta tgggttccct  25020
ctagctatcg gtggtaactg cggggaccag tgctggttcg ttacgagcga ccaagtgtgg  25080
cgacttagtg gaaaggctaa gcgaaagttc cgtaagttaa tcatggagta tcgcgataag  25140
atgcttgaga agtatgatac tctttggaat tacgtatggg taggcaatac gtcccacatt  25200
cgtttcctca agactatcgg tgcggtattc catgaagagt acacacgaga tggtcaattt  25260
cagttattta caatcacgaa aggaggataa ccatatgtgt tgggcagccg caatacctat  25320
cgctatatct ggcgctcagg ctatcagtgg tcagaacgct caggccaaaa tgattgccgc  25380
tcagaccgct gctggtcgtc gtcaagctat ggaaatcatg aggcagacga acatccagaa  25440
tgctgaccta tcgttgcaag ctcgaagtaa acttgaggaa gcgtccgccg agttgacctc  25500
acagaacatg cagaaggtcc aagctattgg gtctatccga gcggctatcg gagagagtat  25560
gcttgaaggt tcctcaatgg accgcattaa gcgagtcaca gaaggacagt tcattcggga  25620
```

-continued

```
agccaatatg gtaactgaga actatcgccg tgactaccaa gcaatcttcg cacagcaact  25680
tggtggtact caaagtgctg caagtcagat tgacgaaatc tataagagcg aacagaaaca  25740
gaagagtaag ctacagatgg ttctggaccc actggctatc atggggtctt ccgctgcgag  25800
tgcttacgca tccggtgcgt tcgactctaa gtccacaact aaggcaccta ttgttgccgc  25860
taaaggaacc aagacgggga ggtaatgagc tatgagtaaa attgaatctg cccttcaagc  25920
ggcacaaccg ggactctctc ggttacgtgg tggtgctgga ggtatgggct atcgtgcagc  25980
aaccactcag gccgaacagc caaggtcaag cctattggac accattggtc ggttcgctaa  26040
ggctggtgcc gatatgtata ccgctaagga acaacgagca cgagacctag ctgatgaacg  26100
ctctaacgag attatccgta agctgacccc tgagcaacgt cgagaagctc tcaacaacgg  26160
gacccttctg tatcaggatg acccatacgc tatggaagca ctccgagtca agactggtcg  26220
taacgctgcg tatcttgtgg acgatgacgt tatgcagaag ataaaagagg gtgtcttccg  26280
tactcgcgaa gagatggaag agtatcgcca tagtcgcctt caagagggcg ctaaggtata  26340
cgctgagcag ttcggcatcg accctgagga cgttgattat cagcgtggtt tcaacgggga  26400
cattaccgag cgtaacatct cgctgtatgg tgcgcatgat aacttcttga gccagcaagc  26460
tcagaagggc gctatcatga acagccgagt ggaactcaac ggtgtccttc aagaccctga  26520
tatgctgcgt cgtccagact ctgctgactt ctttgagaag tatatcgaca acggtctggt  26580
tactggcgca atcccatctg atgctcaagc cacacagctt ataagccaag cgttcagtga  26640
cgcttctagc cgtgctggtg gtgctgactt cctgatgcga gtcggtgaca agaaggtaac  26700
acttaacgga gccactacga cttaccgaga gttgattggt gaggaacagt ggaacgctct  26760
catggtcaca gcacaacgtt ctcagtttga gactgacgcg aagctgaacg agcagtatcg  26820
cttgaagatt aactctgcgc tgaaccaaga ggacccaagg acagcttggg agatgcttca  26880
aggtatcaag gctgaactag ataaggtcca acctgatgag cagatgacac cacaacgtga  26940
gtggctaatc tccgcacagg aacaagttca gaatcagatg aacgcatgga cgaaagctca  27000
ggccaaggct ctggacgatt ccatgaagtc aatgaacaaa cttgacgtaa tcgacaagca  27060
attccagaag cgaatcaacg gtgagtgggt ctcaacggat tttaaggata tgccagtcaa  27120
cgagaacact ggtgagttca agcatagcga tatggttaac tacgccaata agaagctcgc  27180
tgagattgac agtatggaca ttccagacgg tgccaaggat gctatgaagt tgaagtacct  27240
tcaagcggac tctaaggacg gagcattccg tacagccatc ggaaccatgg tcactgacgc  27300
tggtcaagag tggtctgccg ctgtgattaa cggtaagtta ccagaacgaa ccccagctat  27360
ggatgctctg cgcagaatcc gcaatgctga ccctcagttg attgctgcgc tatacccaga  27420
ccaagctgag ctattcctga cgatggacat gatggacaag cagggtattg accctcaggt  27480
tattcttgat gccgaccgac tgactgttaa gcggtccaaa gagcaacgct ttgaggatga  27540
taaagcattc gagtctgcac tgaatgcatc taaggctcct gagattgccc gtatgccagc  27600
gtcactgcgc gaatctgcac gtaagattta tgactccgtt aagtatcgct cggggaacga  27660
aagcatggct atggagcaga tgaccaagtt ccttaaggaa tctacctaca cgttcactgg  27720
tgatgatgtt gacggtgata ccgttggtgt gattcctaag aatatgatgc aggttaactc  27780
tgacccgaaa tcatgggagc aaggtcggga tattctggag gaagcacgta agggaatcat  27840
tgcgagcaac ccttggataa ccaataagca actgaccatg tattctcaag gtgactccat  27900
ttaccttatg gacaccacag gtcaagtcag agtccgatac gacaaagagt tactctcgaa  27960
ggtctggagt gagaaccaga agaaactcga agagaaagct cgtgagaagg ctctggctga  28020
```

tgtgaacaag cgagcaccta tagttgccgc tacgaaggcc cgtgaagctg ctgctaaacg 28080
agtccgagag aaacgtaaac agactcctaa gttcatctac ggacgtaagg agtaactaaa 28140
ggctacataa ggaggcccta aatggataag tacgataaga acgtaccaag tgattatgat 28200
ggtctgttcc aaaaggctgc tgatgccaac ggggtctctt atgacctttt acgtaaagtc 28260
gcttggacag aatcacgatt tgtgcctaca gcaaaatcta agactggacc attaggcatg 28320
atgcaattta ccaaggcaac cgctaaggcc ctcggtctgc gagttaccga tggtccagac 28380
gacgaccgac tgaaccctga gttagctatt aatgctgccg ctaagcaact tgcaggtctg 28440
gtagggaagt ttgatggcga tgaactcaaa gctgcccttg cgtacaacca aggcgaggga 28500
cgcttgggta atccacaact tgaggcgtac tctaagggag acttcgcatc aatctctgag 28560
gagggacgta actacatgcg taaccttctg gatgttgcta agtcacctat ggctggacag 28620
ttggaaactt ttggtggcat aaccccaaag ggtaaaggca ttccggctga ggtaggattg 28680
gctggaattg gtcacaagca gaaagtaaca caggaacttc ctgagtccac aagttttgac 28740
gttaagggta tcgaacagga ggctacggcg aaaccattcg ccaaggactt ttgggagacc 28800
cacggagaaa cacttgacga gtacaacagt cgttcaacct tcttcggatt caaaaatgct 28860
gccgaagctg aactctccaa ctcagtcgct gggatggctt tccgtgctgg tcgtctcgat 28920
aatggttttg atgtgtttaa agacaccatt acgccgactc gctggaactc tcacatctgg 28980
actccagagg agttagagaa gattcgaaca gaggttaaga accctgcgta catcaacgtt 29040
gtaactggtg gttcccctga gaacctcgat gacctcatta aattggctaa cgagaacttt 29100
gagaatgact cccgcgctgc cgaggctggc ctaggtgcca aactgagtgc tggtattatt 29160
ggtgctggtg tggacccgct tagctatgtt cctatggtcg gtgtcactgg taagggcttt 29220
aagttaatca ataaggctct tgtagttggt gccgaaagtg ctgctctgaa cgttgcatcc 29280
gaaggtctcc gtacctccgt agctggtggt gacgcagact atgcgggtgc tgccttaggt 29340
ggctttgtgt ttggcgcagg catgtctgca atcagtgacg ctgtagctgc tggactgaaa 29400
cgcagtaaac cagaagctga gttcgacaat gagttcatcg gtcctatgat gcgattggaa 29460
gcccgtgaga cagcacgaaa cgccaactct gcggacctct ctcggatgaa cactgagaac 29520
atgaagtttg aaggtgaaca taatggtgtc ccttatgagg acttaccaac agagagaggt 29580
gccgtggtgt tacatgatgg ctccgttcta agtgcaagca acccaatcaa ccctaagact 29640
ctaaaagagt tctccgaggt tgaccctgag aaggctgcgc gaggaatcaa actggctggg 29700
ttcaccgaga ttggcttgaa gaccttgggg tctgacgatg ctgacatccg tagagtggct 29760
atcgacctcg ttcgctctcc tactggtatg cagtctggtg cctcaggtaa gttcggtgca 29820
acagcttctg acatccatga gagacttcat ggtactgacc agcgtactta taatgacttg 29880
tacaaagcaa tgtctgacgc tatgaaagac cctgagttct ctactggcgg cgctaagatg 29940
tcccgtgaag aaactcgata cactatctac cgtagagcgg cactagctat tgagcgtcca 30000
gaactacaga aggcactcac tccgtctgag agaatcgtta tggacatcat taagcgtcac 30060
tttgacacca agcgtgaact tatggaaaac ccagcaatat tcggtaacac aaaggctgtg 30120
agtatcttcc ctgagagtcg ccacaaaggt acttacgttc ctcacgtata tgaccgtcat 30180
gccaaggcgc tgatgattca acgctacggt gccgaaggtt tgcaggaagg gattgcccgc 30240
tcatggatga acagctacgt ctccagacct gaggtcaagg ccagagtcga tgagatgctt 30300
aaggaattac acggggtgaa ggaagtaaca ccagagatgg tagagaagta cgctatggat 30360

-continued

```
aaggcttatg gtatctccca ctcagaccag ttcaccaaca gttccataat agaagagaac  30420
attgagggct tagtaggtat cgagaataac tcattccttg aggcacgtaa cttgtttgat  30480
tcggacctat ccatcactat gccagacgga cagcaattct cagtgaatga cctaagggac  30540
ttcgatatgt tccgcatcat gccagcgtat gaccgccgtg tcaatggtga catcgccatc  30600
atggggtcta ctggtaaaac cactaaggaa cttaaggatg agattttggc tctcaaagcg  30660
aaagctgagg gagacggtaa gaagactggc gaggtacatg ctttaatgga taccgttaag  30720
attcttactg gtcgtgctag acgcaatcag gacactgtgt gggaaacctc actgcgtgcc  30780
atcaatgacc tagggttctt cgctaagaac gcctacatgg gtgctcagaa cattacggag  30840
attgctggga tgattgtcac tggtaacgtt cgtgctctag ggcatggtat cccaattctg  30900
cgtgatacac tctacaagtc taaaccagtt tcagctaagg aactcaagga actccatgcg  30960
tctctgttcg ggaaggaggt ggaccagttg attcggccta aacgtgctga cattgtgcag  31020
cgcctaaggg aagcaactga taccggacct gccgtggcga acatcgtagg gaccttgaag  31080
tattcaacac aggaactggc tgctcgctct ccgtggacta agctactgaa cggaaccact  31140
aactaccttc tggatgctgc gcgtcaaggt atgcttgggg atgttattag tgccacccta  31200
acaggtaaga ctacccgctg ggagaaagaa ggcttccttc gtggtgcctc cgtaactcct  31260
gagcagatgg ctggcatcaa gtctctcatc aaggaacata tggtacgcgg tgaggacggg  31320
aagtttaccg ttaaggacaa gcaagcgttc tctatggacc cacgggctat ggacttatgg  31380
agactggctg acaaggtagc tgatgaggca atgctgcgtc cacataaggt gtccttacag  31440
gattcccatg cgttcggagc actaggtaag atggttatgc agtttaagtc tttcactatc  31500
aagtccctta actctaagtt cctgcgaacc ttctatgatg gatacaagaa caaccgagcg  31560
attgacgctg cgctgagcat catcacctct atgggtctcg ctggtggttt ctatgctatg  31620
gctgcacacg tcaaagcata cgctctgcct aaggagaaac gtaaggagta cttggagcgt  31680
gcactggacc caaccatgat tgcccacgct gcgttatctc gtagttctca attgggtgct  31740
cctttggcta tggttgacct agttggtggt gttttagggt tcgagtcctc caagatggct  31800
cgctctacga ttctacctaa ggacaccgtg aaggaacgtg acccaaacaa accgtacacc  31860
tctagagagg taatgggcgc tatgggttca aaccttctgg aacagatgcc ttcggctggc  31920
tttgtggcta acgtaggggc taccttaatg aatgctgctg gcgtggtcaa ctcacctaat  31980
aaagcaaccg agcaggactt catgactggt cttatgaact ccacaaaaga gttagtaccg  32040
aacgacccat tgactcaaca gcttgtgttg aagatttatg aggcgaacgg tgttaacttg  32100
agggagcgta ggaaataata cgactcacta tagggagagg cgaaataatc ttctccctgt  32160
agtctcttag atttacttta aggaggtcaa atggctaacg taattaaaac cgttttgact  32220
taccagttag atggctccaa tcgtgatttt aatatcccgt ttgagtatct agcccgtaag  32280
ttcgtagtgg taactcttat tggtgtagac cgaaaggtcc ttacgattaa tacagactat  32340
cgctttgcta cacgtactac tatctctctg acaaaggctt ggggtccagc cgatggctac  32400
acgaccatcg agttacgtcg agtaacctcc actaccgacc gattggttga ctttacggat  32460
ggttcaatcc tccgcgcgta tgaccttaac gtcgctcaga ttcaaacgat gcacgtagcg  32520
gaagaggccc gtgacctcac tacggatact atcggtgtca ataacgatgg tcacttggat  32580
gctcgtggtc gtcgaattgt gaacctagcg aacgccgtgg atgaccgcga tgctgttccg  32640
tttggtcaac taaagaccat gaaccagaac tcatggcaag cacgtaatga agccttacag  32700
ttccgtaatg aggctgagac tttcagaaac caagcggagg gctttaagaa cgagtccagt  32760
```

```
accaacgcta cgaacacaaa gcagtggcgc gatgagacca agggtttccg agacgaagcc  32820
aagcggttca agaatacggc tggtcaatac gctacatctg ctgggaactc tgcttccgct  32880
gcgcatcaat ctgaggtaaa cgctgagaac tctgccacag catccgctaa ctctgctcat  32940
ttggcagaac agcaagcaga ccgtgcggaa cgtgaggcag acaagctgga aaattacaat  33000
ggattggctg gtgcaattga taaggtagat ggaaccaatg tgtactggaa aggaaatatt  33060
cacgctaacg ggcgccttta catgaccaca aacggttttg actgtggcca gtatcaacag  33120
ttctttggtg gtgtcactaa tcgttactct gtcatggagt ggggagatga gaacggatgg  33180
ctgatgtatg ttcaacgtag agagtggaca acagcgatag gcggtaacat ccagttagta  33240
gtaaacggac agatcatcac ccaaggtgga gccatgaccg gtcagctaaa attgcagaat  33300
gggcatgttc ttcaattaga gtccgcatcc gacaaggcgc actatattct atctaaagat  33360
ggtaacagga ataactggta cattggtaga gggtcagata acaacaatga ctgtaccttc  33420
cactcctatg tacatggtac gaccttaaca ctcaagcagg actatgcagt agttaacaaa  33480
cacttccacg taggtcaggc cgttgtggcc actgatggta atattcaagg tactaagtgg  33540
ggaggtaaat ggctggatgc ttacctacgt gacagcttcg ttgcgaagtc caaggcgtgg  33600
actcaggtgt ggtctggtag tgctggcggt ggggtaagtg tgactgtttc acaggatctc  33660
cgcttccgca atatctggat taagtgtgcc aacaactctt ggaacttctt ccgtactggc  33720
cccgatggaa tctacttcat agcctctgat ggtggatggt tacgattcca aatacactcc  33780
aacggtctcg gattcaagaa tattgcagac agtcgttcag tacctaatgc aatcatggtg  33840
gagaacgagt aattggtaaa tcacaaggaa agacgtgtag tccacggatg gactctcaag  33900
gaggtacaag gtgctatcat tagactttaa caacgaattg attaaggctg ctccaattgt  33960
tgggacgggt gtagcagatg ttagtgctcg actgttcttt gggttaagcc ttaacgaatg  34020
gttctacgtt gctgctatcg cctacacagt ggttcagatt ggtgccaagg tagtcgataa  34080
gatgattgac tggaagaaag ccaataagga gtgatatgta tggaaaagga taagagcctt  34140
attacattct tagagatgtt ggacactgcg atggctcagc gtatgcttgc ggacctttcg  34200
gaccatgagc gtcgctctcc gcaactctat aatgctatta acaaactgtt agaccgccac  34260
aagttccaga ttggtaagtt gcagccggat gttcacatct taggtggcct tgctggtgct  34320
cttgaagagt acaaagagaa agtcggtgat aacggtctta cggatgatga tatttacaca  34380
ttacagtgat atactcaagg ccactacaga tagtggtctt tatggatgtc attgtctata  34440
cgagatgctc ctacgtgaaa tctgaaagtt aacgggaggc attatgctag aatttttacg  34500
taagctaatc ccttgggttc tcgctgggat gctattcggg ttaggatggc atctagggtc  34560
agactcaatg gacgctaaat ggaaacagga ggtacacaat gagtacgtta agagagttga  34620
ggctgcgaag agcactcaaa gagcaatcga tgcggtatct gctaagtatc aagaagacct  34680
tgccgcgctg gaagggagca ctgataggat tatttctgat ttgcgtagcg acaataagcg  34740
gttgcgcgtc agagtcaaaa ctaccggaac ctccgatggt cagtgtggat tcgagcctga  34800
tggtcgagcc gaacttgacg accgagatgc taaacgtatt ctcgcagtga cccagaaggg  34860
tgacgcatgg attcgtgcgt tacaggatac tattcgtgaa ctgcaacgta agtaggaaat  34920
caagtaagga ggcaatgtgt ctactcaatc caatcgtaat gcgctcgtag tggcgcaact  34980
gaaaggagac ttcgtggcgt tcctattcgt cttatggaag gcgctaaacc taccggtgcc  35040
cactaagtgt cagattgaca tggctaaggt gctggcgaat ggagacaaca agaagttcat  35100
```

-continued

```
cttacaggct ttccgtggta tcggtaagtc gttcatcaca tgtgcgttcg ttgtgtggtc  35160
cttatggaga gaccctcagt tgaagatact tatcgtatca gcctctaagg agcgtgcaga  35220
cgctaactcc atctttatta agaacatcat tgacctgctg ccattcctat ctgagttaaa  35280
gccaagaccc ggacagcgtg actcggtaat cagctttgat gtaggcccag ccaatcctga  35340
ccactctcct agtgtgaaat cagtaggtat cactggtcag ttaactggta gccgtgctga  35400
cattatcatt gcggatgacg ttgagattcc gtctaacagc gcaactatgg gtgcccgtga  35460
gaagctatgg actctggttc aggagttcgc tgcgttactt aaaccgctgc cttcctctcg  35520
cgttatctac cttggtacac ctcagacaga gatgactctc tataaggaac ttgaggataa  35580
ccgtgggtac acaaccatta tctggcctgc tctgtaccca aggacacgtg aagagaacct  35640
ctattactca cagcgtcttg ctcctatgtt acgcgctgag tacgatgaga accctgaggc  35700
acttgctggg actccaacag acccagtgcg ctttgaccgt gatgacctgc gcgagcgtga  35760
gttggaatac ggtaaggctg gctttacgct acagttcatg cttaacccta accttagtga  35820
tgccgagaag tacccgctga ggcttcgtga cgctatcgta gcggccttag acttagagaa  35880
ggccccaatg cattaccagt ggcttccgaa ccgtcagaac atcattgagg accttcctaa  35940
cgttggcctt aagggtgatg acctgcatac gtaccacgat tgttccaaca actcaggtca  36000
gtaccaacag aagattctgg tcattgaccc tagtggtcgc ggtaaggacg aaacaggtta  36060
cgctgtgctg tacacactga acggttacat ctaccttatg gaagctggag gtttccgtga  36120
tggctactcc gataagaccc ttgagttact cgctaagaag gcaaagcaat ggggagtcca  36180
gacggttgtc tacgagagta acttcggtga cggtatgttc ggtaaggtat tcagtcctat  36240
ccttcttaaa caccacaact gtgcgatgga agagattcgt gcccgtggta tgaaagagat  36300
gcgtatttgc gataccctttg agccagtcat gcagactcac cgccttgtaa ttcgtgatga  36360
ggtcattagg gccgactacc agtccgctcg tgacgtagac ggtaagcatg acgttaagta  36420
ctcgttgttc taccagatga cccgtatcac tcgtgagaaa ggcgctctgg ctcatgatga  36480
ccgattggat gcccttgcgt taggcattga gtatctccgt gagtccatgc agttggattc  36540
cgttaaggtc gagggtgaag tacttgctga cttccttgag gaacacatga tgcgtcctac  36600
ggttgctgct acgcatatca ttgagatgtc tgtgggagga gttgatgtgt actctgagga  36660
cgatgagggt tacggtacgt ctttcattga gtggtgattt atgcattagg actgcatagg  36720
gatgcactat agaccacgga tggtcagttc tttaagttac tgaaaagaca cgataaatta  36780
atacgactca ctatagggag aggagggacg aaaggttact atatagatac tgaatgaata  36840
cttatagagt gcataaagta tgcataatgg tgtacctaga gtgacctcta agaatggtga  36900
ttatattgta ttagtatcac cttaacttaa ggaccaacat aaagggagga gactcatgtt  36960
ccgcttattg ttgaacctac tgcggcatag agtcacctac cgatttcttg tggtactttg  37020
tgctgccctt gggtacgcat ctcttactgg agacctcagt tcactggagt ctgtcgtttg  37080
ctctatactc acttgtagcg attagggtct tcctgaccga ctgatggctc accgagggat  37140
tcagcggtat gattgcatca caccacttca tccctataga gtcaagtcct aaggtatacc  37200
cataaagagc ctctaatggt ctatcctaag gtctatacct aaagataggc catcctatca  37260
gtgtcaccta aagagggtct tagagagggc ctatggagtt cctatagggt cctttaaaat  37320
ataccataaa aatctgagtg actatctcac agtgtacgga cctaaagttc ccccataggg  37380
ggtacctaaa gcccagccaa tcacctaaag tcaaccttcg gttgaccttg agggttccct  37440
aagggttggg gatgaccctt gggtttgtct ttgggtgtta ccttgagtgt ctctctgtgt  37500
```

ccct 37504

<210> SEQ ID NO 68
<211> LENGTH: 37567
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg gggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920
cgctacgaag acgtttacat gcctgaggtg tacaaagcga ttaacattgc gcaaaacacc 1980

-continued

```
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
tctctaggag tggccttagt catttaacca ataggagata aacattatga tgaacattaa   4320
```

-continued gactaacccg tttaaagccg tgtctttcgt agagtctgcc attaagaagg ctctggataa 4380
cgctgggtat cttatcgctg aaatcaagta cgatggtgta cgcgggaaca tctgcgtaga 4440
caatactgct aacagttact ggctctctcg tgtatctaaa acgattccgg cactggagca 4500
cttaaacggg tttgatgttc gctggaagcg tctactgaac gatgaccgtt gcttctacaa 4560
agatggcttt atgcttgatg gggaactcat ggtcaagggc gtagacttta acacagggtc 4620
cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400
cttcgggtgg gcctttctgc gtttataagg agacacttta tgtttaagaa ggttggtaaa 5460
ttccttgcgg ctttggcagc tatcctgacg cttgcgtata ttcttgcggt ataccctcaa 5520
gtagcactag tagtagttgg cgcttgttac ttagcggcag tgtgtgcttg cgtgtggagt 5580
atagttaact ggtaatacga ctcactaaag gaggtacaca ccatgatgta cttaatgcca 5640
ttactcatcg tcattgtagg atgccttgcg ctccactgta gcgatgatga tatgccagat 5700
ggtcacgctt aatacgactc actaaaggag acactatatg tttcgacttc attacaacaa 5760
aagcgttaag aatttcacgg ttcgccgtgc tgaccgttca atcgtatgtg cgagcgagcg 5820
ccgagctaag atacctctta ttggtaacac agttcctttg gcaccgagcg tccacatcat 5880
tatcacccgt ggtgactttg agaaagcaat agacaagaaa cgtccggttc ttagtgtggc 5940
agtgacccgc ttcccgttcg tccgtctgtt actcaaacga atcaaggagg tgttctgatg 6000
ggactgttag atggtgaagc ctgggaaaaa gaaaacccgc cagtacaagc aactgggtgt 6060
atagcttgct tagagaaaga tgaccgttat ccacacacct gtaacaaagg agctaacgat 6120
atgaccgaac gtgaacaaga gatgatcatt aagttgatag acaataatga aggtcgccca 6180
gatgatttga atggctgcgg tattctctgc tccaatgtcc cttgccacct ctgccccgca 6240
aataacgatc aaaagataac cttaggtgaa atccgagcga tggacccacg taaaccacat 6300
ctgaataaac ctgaggtaac tcctacagat gaccagcctt ccgctgagac aatcgaaggt 6360
gtcactaagc cttcccacta catgctgttt gacgacattg aggctatcga agtgattgct 6420
cgttcaatga ccgttgagca gttcaaggga tactgcttcg gtaacatctt aaagtacaga 6480
ctacgtgctg gtaagaagtc agagttagcg tacttagaga aagacctagc gaaagcagac 6540
ttctataaag aactctttga gaaacataag gataaatgtt atgcataact tcaagtcaac 6600
cccacctgcc gacagcctat ctgatgactt cacatcttgc tcagagtggt gccgaaagat 6660
gtgggaagag acattcgacg atgcgtacat caagctgtat gaactttgga aatcgagagg 6720
tcaatgacta tgtcaaacgt aaatacaggt tcacttagtg tggacaataa gaagttttgg 6780
gctaccgtag agtcctcgga gcattccttc gaggttccaa tctacgctga gaccctagac 6840
gaagctctgg agttagccga atggcaatac gttccggctg gctttgaggt tactcgtgtg 6900
cgtccttgtg tagcaccgaa gtaatacgac tcactattag ggaagactcc ctctgagaaa 6960
ccaaacgaaa cctaaaggag attaacatta tggctaagaa gattttcacc tctgcgctgg 7020
gtaccgctga accttacgct tacatcgcca agccggacta cggcaacgaa gagcgtggct 7080
ttgggaaccc tcgtggtgtc tataaagttg acctgactat tcccaacaaa gacccgcgct 7140
gccagcgtat ggtcgatgaa atcgtgaagt gtcacgaaga ggcttatgct gctgccgttg 7200
aggaatacga agctaatcca cctgctgtag ctcgtggtaa gaaaccgctg aaaccgtatg 7260
agggtgacat gccgttcttc gataacggtg acggtacgac tacctttaag ttcaaatgct 7320
acgcgtcttt ccaagacaag aagaccaaag agaccaagca catcaatctg gttgtggttg 7380
actcaaaagg taagaagatg gaagacgttc cgattatcgg tggtggctct aagctgaaag 7440
ttaaatattc tctggttcca tacaagtgga acactgctgt aggtgcgagc gttaagctgc 7500
aactggaatc cgtgatgctg gtcgaactgg ctacctttgg tggcggtgaa gacgattggg 7560
ctgacgaagt tgaagagaac ggctatgttg cctctggttc tgccaaagcg agcaaaccac 7620
gcgacgaaga aagctgggac gaagacgacg aagagtccga ggaagcagac gaagacggag 7680
acttctaagt ggaactgcgg gagaaaatcc ttgagcgaat caaggtgact tcctctgggt 7740
gttgggagtg gcagggcgct acgaacaata aagggtacgg gcaggtgtgg tgcagcaata 7800
ccggaaaggt tgtctactgt catcgcgtaa tgtctaatgc tccgaaaggt tctaccgtcc 7860
tgcactcctg tgataatcca ttatgttgta accctgaaca cctatccata ggaactccaa 7920
aagagaactc cactgacatg gtaaataagg gtcgctcaca caaggggtat aaactttcag 7980
acgaagacgt aatggcaatc atggagtcca gcgagtccaa tgtatcctta gctcgcacct 8040
atggtgtctc ccaacagact atttgtgata tacgcaaagg gaggcgacat ggcaggttac 8100
ggcgctaaag gaatccgaaa ggttggagcg tttcgctctg gcctagagga caaggtttca 8160
aagcagttgg aatcaaaagg tattaaattc gagtatgaag agtggaaagt gccttatgta 8220
attccggcga gcaatcacac ttacactcca gacttcttac ttccaaacgg tatattcgtt 8280
gagacaaagg gtctgtggga aagcgatgat agaaagaagc acttattaat tagggagcag 8340
caccccgagc tagacatccg tattgtcttc tcaagctcac gtactaagtt atacaaaggt 8400
tctccaacgt cttatggaga gttctgcgaa aagcatggta ttaagttcgc tgataaactg 8460
atacctgctg agtggataaa ggaacccaag aaggaggtcc cctttgatag attaaaaagg 8520
aaaggaggaa agaaataatg gctcgtgtac agtttaaaca acgtgaatct actgacgcaa 8580
tctttgttca ctgctcggct accaagccaa gtcagaatgt tggtgtccgt gagattcgcc 8640
agtggcacaa agagcagggt tggctcgatg tgggatacca ctttatcatc aagcgagacg 8700
gtactgtgga ggcaggacga gatgagatgg ctgtaggctc tcacgctaag ggttacaacc 8760
acaactctat cggcgtctgc cttgttggtg gtatcgacga taaaggtaag ttcgacgcta 8820
actttacgcc agcccaaatg caatcccttc gctcactgct tgtcacactg ctggctaagt 8880
acgaaggcgc tggtcttcgc gcccatcatg aggtggcgcc gaaggcttgc ccttcgttcg 8940
accttaagcg ttggtgggag aagaacgaac tggtcacttc tgaccgtgga taatgatcta 9000
ttggaagtcg ttgcgtggat ttatagaact aggagggaat tgcatggaca attcgcacga 9060

-continued

```
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
ttaccatgcg tgaccctaaa gttatccaag cagaaatcgc taaactggaa gctgaactgg  11460
```

```
aggacgttaa gtaccatgaa gctaagactc gctccgctgt tcacatcttg aagaacttag  11520
gctggacttg gacaagacag actggctgga agaaaccaga agttaccaag ctgagtcata  11580
aggtgttcga taaggacact atgacccaca tcaaggctgg tgattgggtt aaggttgaca  11640
tgggagttgt tggtggatac ggctacgtcc gctcagttag tggcaaatat gcacaagtgt  11700
catacatcac aggtgttact ccacgcggtg caatcgttgc cgataagacc aacatgattc  11760
acacaggttt cttgacagtt gtttcatatg aagagattgt taagtcacga taatcaatag  11820
gagaaatcaa tatgatcgtt tctgacatcg aagctaacgc cctcttagag agcgtcacta  11880
agttccactg cggggttatc tacgactact ccaccgctga gtacgtaagc taccgtccga  11940
gtgacttcgg tgcgtatctg gatgcgctgg aagccgaggt tgcacgaggc ggtcttattg  12000
tgttccacaa cggtcacaag tatgacgttc ctgcattgac caaactggca aagttgcaat  12060
tgaaccgaga gttccacctt cctcgtgaga actgtattga cacccttgtg ttgtcacgtt  12120
tgattcattc caacctcaag gacaccgata tgggtcttct gcgttccggc aagttgcccg  12180
gaaaacgctt tgggtctcac gctttggagg cgtggggtta tcgcttaggc gagatgaagg  12240
gtgaatacaa agacgacttt aagcgtatgc ttgaagagca gggtgaagaa tacgttgacg  12300
gaatggagtg gtggaacttc aacgaagaga tgatggacta taacgttcag gacgttgtgg  12360
taactaaagc tctccttgag aagctactct ctgacaaaca ttacttccct cctgagattg  12420
actttacgga cgtaggatac actacgttct ggtcagaatc ccttgaggcc gttgacattg  12480
aacatcgtgc tgcatggctg ctcgctaaac aagagcgcaa cgggttcccg tttgacacaa  12540
aagcaatcga agagttgtac gtagagttag ctgctcgccg ctctgagttg ctccgtaaat  12600
tgaccgaaac gttcggctcg tggtatcagc ctaaaggtgg cactgagatg ttctgccatc  12660
cgcgaacagg taagccacta cctaaatacc ctcgcattaa gacacctaaa gttggtggta  12720
tctttaagaa gcctaagaac aaggcacagc gagaaggccg tgagccttgc gaacttgata  12780
cccgcgagta cgttgctggt gctccttaca ccccagttga acatgttgtg tttaaccctt  12840
cgtctcgtga ccacattcag aagaaactcc aagaggctgg gtgggtcccg accaagtaca  12900
ccgataaggg tgctcctgtg gtggacgatg aggtactcga aggagtacgt gtagatgacc  12960
ctgagaagca agccgctatc gacctcatta aagagtactt gatgattcag aagcgaatcg  13020
gacagtctgc tgagggagac aaagcatggc ttcgttatgt tgctgaggat ggtaagattc  13080
atggttctgt taaccctaat ggagcagtta cgggtcgtgc gacccatgcg ttcccaaacc  13140
ttgcgcaaat tccgggtgta cgttctcctt atggagagca gtgtcgcgct gcttttggcg  13200
ctgagcacca tttggatggg ataactggta agccttgggt tcaggctggc atcgacgcat  13260
ccggtcttga gctacgctgc ttggctcact tcatggctcg ctttgataac ggcgagtacg  13320
ctcacgagat tcttaacggc gacatccaca ctaagaacca gatagctgct gaactaccta  13380
cccgagataa cgctaagacg ttcatctatg ggttcctcta tggtgctggt gatgagaaga  13440
ttggacagat tgttggtgct ggtaaagagc gcggtaagga actcaagaag aaattccttg  13500
agaacacccc cgcgattgca gcactccgcg agtctatcca acagacactt gtcgagtcct  13560
ctcaatgggt agctggtgag caacaagtca agtggaaacg ccgctggatt aaaggtctgg  13620
atggtcgtaa ggtacacgtt cgtagtcctc acgctgcctt gaatacccta ctgcaatctg  13680
ctggtgctct catctgcaaa ctgtggatta tcaagaccga agagatgctc gtagagaaag  13740
gcttgaagca tggctgggat ggggactttg cgtacatggc atgggtacat gatgaaatcc  13800
```

aagtaggctg ccgtaccgaa gagattgctc aggtggtcat tgagaccgca caagaagcga 13860
tgcgctgggt tggagaccac tggaacttcc ggtgtcttct ggataccgaa ggtaagatgg 13920
gtcctaattg ggcgatttgc cactgataca ggaggctact catgaacgaa agacacttaa 13980
caggtgctgc ttctgaaatg ctagtagcct acaaatttac caaagctggg tacactgtct 14040
attaccctat gctgactcag agtaaagagg acttggttgt atgtaaggat ggtaaattta 14100
gtaaggttca ggttaaaaca gccacaacgg ttcaaaccaa cacaggagat gccaagcagg 14160
ttaggctagg tggatgcggt aggtccgaat ataaggatgg agactttgac attcttgcgg 14220
ttgtggttga cgaagatgtg cttattttca catgggacga agtaaaaggt aagacatcca 14280
tgtgtgtcgg caagagaaac aaaggcataa aactatagga gaaattatta tggctatgac 14340
aaagaaattt aaagtgtcct tcgacgttac cgcaaagatg tcgtctgacg ttcaggcaat 14400
cttagagaaa gatatgctgc atctatgtaa gcaggtcggc tcaggtgcga ttgtccccaa 14460
tggtaaacag aaggaaatga ttgtccagtt cctgacacac ggtatggaag gattgatgac 14520
attcgtagta cgtacatcat ttcgtgaggc cattaaggac atgcacgaag agtatgcaga 14580
taaggactct ttcaaacaat ctcctgcaac agtacgggag gtgttctgat gtctgactac 14640
ctgaaagtgc tgcaagcaat caaaagttgc cctaagactt tccagtccaa ctatgtacgg 14700
aacaatgcga gcctcgtagc ggaggccgct tcccgtggtc acatctcgtg cctgactact 14760
agtggacgta acggtggcgc ttgggaaatc actgcttccg gtactcgctt tctgaaacga 14820
atgggaggat gtgtctaatg tctcgtgacc ttgtgactat tccacgcgat gtgtggaacg 14880
atatacaggg ctacatcgac tctctggaac gtgagaacga tagccttaag aatcaactaa 14940
tggaagctga cgaatacgta gcggaactag aggagaaact taatggcact tcttgacctt 15000
aaacaattct atgagttacg tgaaggctgc gacgacaagg gtatccttgt gatggacggc 15060
gactggctgg tcttccaagc tatgagtgct gctgagtttg atgcctcttg ggaggaagag 15120
atttggcacc gatgctgtga ccacgctaag gcccgtcaga ttcttgagga ttccattaag 15180
tcctacgaga cccgtaagaa ggcttgggca ggtgctccaa ttgtccttgc gttcaccgat 15240
agtgttaact ggcgtaaaga actggttgac ccgaactata aggctaaccg taaggccgtg 15300
aagaaacctg tagggtactt tgagttcctt gatgctctct ttgagcgcga agagttctat 15360
tgcatccgtg agcctatgct tgagggtgat gacgttatgg gagttattgc ttccaatccg 15420
tctgccttcg gtgctcgtaa ggctgtaatc atctcttgcg ataaggactt taagaccatc 15480
cctaactgtg acttcctgtg gtgtaccact ggtaacatcc tgactcagac cgaagagtcc 15540
gctgactggt ggcacctctt ccagaccatc aagggtgaca tcactgatgg ttactcaggg 15600
attgctggat ggggtgatac cgccgaggac ttcttgaata acccgttcat aaccgagcct 15660
aaaacgtctg tgcttaagtc cggtaagaac aaaggccaag aggttactaa atgggttaaa 15720
cgcgaccctg agcctcatga gacgctttgg gactgcatta agtccattgg cgcgaaggct 15780
ggtatgaccg aagaggatat tatcaagcag ggccaaatgg ctcgaatcct acggttcaac 15840
gagtacaact ttattgacaa ggagatttac ctgtggagac cgtagcgtat attggtctgg 15900
gtctttgtgt tctcggagtg tgcctcattt cgtggggcct ttgggactta gccagaataa 15960
tcaagtcgtt acacgacact aagtgataaa ctcaaggtcc ctaaattaat acgactcact 16020
atagggagat aggggccttt acgattatta ctttaagatt taactctaag aggaatcttt 16080
attatgttaa cacctattaa ccaattactt aagaacccta acgatattcc agatgtacct 16140
cgtgcaaccg ctgagtatct acaggttcga ttcaactatg cgtacctcga agcgtctggt 16200

```
catataggac ttatgcgtgc taatggttgt agtgaggccc acatcttggg tttcattcag  16260
ggcctacagt atgcctctaa cgtcattgac gagattgagt tacgcaagga acaactaaga  16320
gatgatgggg aggattgaca ctatgtgttt ctcaccgaaa attaaaactc cgaagatgga  16380
taccaatcag attcgagccg ttgagccagc gcctctgacc caagaagtgt caagcgtgga  16440
gttcggtggg tcttctgatg agacggatac cgagggcacc gaagtgtctg gacgcaaagg  16500
cctcaaggtc gaacgtgatg attccgtagc gaagtctaaa gccagcggca atggctccgc  16560
tcgtatgaaa tcttccatcc gtaagtccgc atttggaggt aagaagtgat gtctgagttc  16620
acatgtgtgg aggctaagag tcgcttccgt gcaatccggt ggactgtgga acaccttggg  16680
ttgcctaaag gattcgaagg acactttgtg ggctacagcc tctacgtaga cgaagtgatg  16740
gacatgtctg gttgccgtga agagtacatt ctggactcta ccggaaaaca tgtagcgtac  16800
ttcgcgtggt gcgtaagctg tgacattcac cacaaaggag acattctgga tgtaacgtcc  16860
gttgtcatta atcctgaggc agactctaag ggcttacagc gattcctagc gaaacgcttt  16920
aagtaccttg cggaactcca cgattgcgat tgggtgtctc gttgtaagca tgaaggcgag  16980
acaatgcgtg tatactttaa ggaggtataa gttatgggta agaaagttaa gaaggccgtg  17040
aagaaagtca ccaagtccgt taagaaagtc gttaaggaag gggctcgtcc ggttaaacag  17100
gttgctggcg gtctagctgg tctggctggt ggtactggtg aagcacagat ggtggaagta  17160
ccacaagctg ccgcacagat tgttgacgta cctgagaaag aggtttccac tgaggacgaa  17220
gcacagacag aaagcggacg caagaaagct cgtgctggcg gtaagaaatc cttgagtgta  17280
gcccgtagct ccggtggcgg tatcaacatt taatcaggag gttatcgtgg aagactgcat  17340
tgaatggacc ggaggtgtca actctaaggg ttatggtcgt aagtgggtta atggtaaact  17400
tgtgactcca cataggcaca tctatgagga gacatatggt ccagttccaa caggaattgt  17460
ggtgatgcat atctgcgata accctaggtg ctataacata aagcacctta cgcttggaac  17520
tccaaaggat aattccgagg acatggttac caaaggtaga caggctaaag gagaggaact  17580
aagcaagaaa cttacagagt cagacgttct cgctatacgc tcttcaacct taagccaccg  17640
ctccttagga gaactgtatg gagtcagtca atcaaccata acgcgaatac tacagcgtaa  17700
gacatggaga cacatttaat ggctgagaaa cgaacaggac ttgcggagga tggcgcaaag  17760
tctgtctatg agcgtttaaa gaacgaccgt gctccctatg agacacgcgc tcagaattgc  17820
gctcaatata ccatcccatc attgttccct aaggactccg ataacgcctc tacagattat  17880
caaactccgt ggcaagccgt gggcgctcgt ggtctgaaca atctagcctc taagctcatg  17940
ctggctctat tccctatgca gacttggatg cgacttacta tatctgaata tgaagcaaag  18000
cagttactga gcgaccccga tggactcgct aaggtcgatg agggcctctc gatggtagag  18060
cgtatcatca tgaactacat tgagtctaac agttaccgcg tgactctctt tgaggctctc  18120
aaacagttag tcgtagctgg taacgtcctg ctgtacctac cggaaccgga agggtcaaac  18180
tataatccca tgaagctgta ccgattgtct tcttatgtgg tccaacgaga cgcattcggc  18240
aacgttctgc aaatggtgac tcgtgaccag atagcttttg gtgctctccc tgaggacatc  18300
cgtaaggctg tagaaggtca aggtggtgag aagaaagctg atgagacaat cgacgtgtac  18360
actcacatct atctggatga ggactcaggt gaatacctcc gatacgaaga ggtcgagggt  18420
atggaagtcc aaggctccga tgggacttat cctaaagagg cttgcccata catcccgatt  18480
cggatggtca gactagatgg tgaatcctac ggtcgttcgt acattgagga atacttaggt  18540
```

-continued gacttacggt cccttgaaaa tctccaagag gctatcgtca agatgtccat gattagctct 18600
aaggttatcg gcttagtgaa tcctgctggt atcacccagc cacgccgact gaccaaagct 18660
cagactggtg acttcgttac tggtcgtcca gaagacatct cgttcctcca actggagaag 18720
caagcagact ttactgtagc taaagccgta agtgacgcta tcgaggctcg cctttcgttt 18780
gcctttatgt tgaactctgc ggttcagcgt acaggtgaac gtgtgaccgc cgaagagatt 18840
cggtatgtag cttctgaact tgaagatact ttaggtggtg tctactctat cctttctcaa 18900
gaattacaat tgcctctggt acgagtgctc ttgaagcaac tacaagccac gcaacagatt 18960
cctgagttac ctaaggaagc cgtagagcca accattagta caggtctgga agcaattggt 19020
cgaggacaag accttgataa gctggagcgg tgtgtcactg cgtgggctgc actggcacct 19080
atgcgggacg accctgatat taaccttgcg atgattaagt tacgtattgc caacgctatc 19140
ggtattgaca cttctggtat tctactcacc gaagaacaga agcaacagaa gatggcccaa 19200
cagtctatgc aaatgggtat ggataatggt gctgctgcgc tggctcaagg tatggctgca 19260
caagctacag cttcacctga ggctatggct gctgccgctg attccgtagg tttacagccg 19320
ggaatttaat acgactcact atagggagac ctcatctttg aaatgagcga tgacaagagg 19380
ttggagtcct cggtcttcct gtagttcaac tttaaggaga caataataat ggctgaatct 19440
aatgcagacg tatatgcatc ttttggcgtg aactccgctg tgatgtctgg tggttccgtt 19500
gaggaacatg agcagaacat gctggctctt gatgttgctg cccgtgatgg cgatgatgca 19560
atcgagttag cgtcagacga agtggaaaca gaacgtgacc tgtatgacaa ctctgacccg 19620
ttcggtcaag aggatgacga aggccgcatt caggttcgta tcggtgatgg ctctgagccg 19680
accgatgtgg acactggaga agaaggcgtt gagggcaccg aaggttccga agagtttacc 19740
ccactgggcg agactccaga agaactggta gctgcctctg agcaacttgg tgagcacgaa 19800
gagggcttcc aagagatgat taacattgct gctgagcgtg gcatgagtgt cgagaccatt 19860
gaggctatcc agcgtgagta cgaggagaac gaagagttgt ccgccgagtc ctacgctaag 19920
ctggctgaaa ttggctacac gaaggctttc attgactcgt atatccgtgg tcaagaagct 19980
ctggtggagc agtacgtaaa cagtgtcatt gagtacgctg gtggtcgtga acgttttgat 20040
gcactgtata accaccttga gacgcacaac cctgaggctg cacagtcgct ggataatgcg 20100
ttgaccaatc gtgacttagc gaccgttaag gctatcatca acttggctgg tgagtctcgc 20160
gctaaggcgt tcggtcgtaa gccaactcgt agtgtgacta atcgtgctat tccggctaaa 20220
cctcaggcta ccaagcgtga aggctttgcg gaccgtagcg agatgattaa agctatgagt 20280
gaccctcggt atcgcacaga tgccaactat cgtcgtcaag tcgaacagaa agtaatcgat 20340
tcgaacttct gatagacttc gaaattaata cgactcacta tagggagacc acaacggttt 20400
ccctctagaa ataattttgt ttaactttaa gaaggagata tacatatggc tagcatgact 20460
ggtggacagc aaatgggtac taaccaaggt aaaggtgtag ttgctgctgg agataaactg 20520
gcgttgttct tgaaggtatt tggcggtgaa gtcctgactg cgttcgctcg tacctccgtg 20580
accacttctc gccacatggt acgttccatc tccagcggta aatccgctca gttccctgtt 20640
ctgggtcgca ctcaggcagc gtatctggct ccgggcgaga acctcgacga taaacgtaag 20700
gacatcaaac acaccgagaa ggtaatcacc attgacggtc tcctgacggc tgacgttctg 20760
atttatgata ttgaggacgc gatgaaccac tacgacgttc gctctgagta tacctctcag 20820
ttgggtgaat ctctggcgat ggctgcggat ggtgcggttc tggctgagat tgccggtctg 20880
tgtaacgtgg aaagcaaata taatgagaac atcgagggct taggtactgc taccgtaatt 20940

```
gagaccactc agaacaaggc cgcacttacc gaccaagttg cgctgggtaa ggagattatt    21000

gcggctctga ctaaggctcg tgcggctctg accaagaact atgttccggc tgctgaccgt    21060

gtgttctact gtgacccaga tagctactct gcgattctgg cagcactgat gccgaacgca    21120

gcaaactacg ctgctctgat tgaccctgag aagggttcta tccgcaacgt tatgggcttt    21180

gaggttgtag aagttccgca cctcaccgct ggtggtgctg gtaccgctcg tgagggcact    21240

actggtcaga agcacgtctt ccctgccaat aaaggtgagg gtaatgtcaa ggttgctaag    21300

gacaacgtta tcggcctgtt catgcaccgc tctgcggtag gtactgttaa gctgcgtgac    21360

ttggctctgg agcgcgctcg ccgtgctaac ttccaagcgg accagattat cgctaagtac    21420

gcaatgggcc acggtggtct tcgcccagaa gctgcaggag ctgtcgtatt ccagtcaggt    21480

gtgatgctcg gggatccgaa ttcttaagta actaacgaaa ttaatacgac tcactatagg    21540

gagaccacaa cggtttccct ctagaaataa ttttgtttaa ctttaagaag agatataca    21600

tatgaaaaag acagctatcg cgattgcagt ggcactggct ggtttcgcta ccgtagcgca    21660

ggccggcatt tggggcaccc tggcgaaaat tggcattaaa gcggtgccgc gcgtgattag    21720

catgctgaaa aaaaaaaaac agtaaggatc cggctgctaa caaagcccga agcttgcggc    21780

cgcactcgag taactagtta accccttggg gcctctaaac gggtcttgag gggttttttg    21840

ctgaaaggag gaactatatg cgctcatacg atatgaacgt tgagactgcc gctgagttat    21900

cagctgtgaa cgacattctg gcgtctatcg gtgaacctcc ggtatcaacg ctggaaggtg    21960

acgctaacgc agatgcagcg aacgctcggc gtattctcaa caagattaac cgacagattc    22020

aatctcgtgg atggacgttc aacattgagg aaggcataac gctactacct gatgtttact    22080

ccaacctgat tgtatacagt gacgactatt tatccctaat gtctacttcc ggtcaatcca    22140

tctacgttaa ccgaggtggc tatgtgtatg accgaacgag tcaatcagac cgctttgact    22200

ctggtattac tgtgaacatt attcgtctcc gcgactacga tgagatgcct gagtgcttcc    22260

gttactggat tgtcaccaag gcttcccgtc agttcaacaa ccgattcttt ggggcaccgg    22320

aagtagaggg tgtactccaa gaagaggaag atgaggctag acgtctctgc atggagtatg    22380

agatggacta cggtgggtac aatatgctgg atggagatgc gttcacttct ggtctactga    22440

ctcgctaaca ttaataaata aggaggctct aatggcactc attagccaat caatcaagaa    22500

cttgaagggt ggtatcagcc aacagcctga catccttcgt tatccagacc aagggtcacg    22560

ccaagttaac ggttggtctt cggagaccga gggcctccaa aagcgtccac ctcttgtttt    22620

cttaaataca cttggagaca acggtgcgtt aggtcaagct ccgtacatcc acctgattaa    22680

ccgagatgag cacgaacagt attacgctgt gttcactggt agcggaatcc gagtgttcga    22740

cctttctggt aacgagaagc aagttaggta tcctaacggt tccaactaca tcaagaccgc    22800

taatccacgt aacgacctgc gaatggttac tgtagcagac tatacgttca tcgttaaccg    22860

taacgttgtt gcacagaaga acacaaagtc tgtcaactta ccgaattaca accctaatca    22920

agacggattg attaacgttc gtggtggtca gtatggtagg gaactaattg tacacattaa    22980

cggtaaagac gttgcgaagt ataagatacc agatggtagt caacctgaac acgtaaacaa    23040

tacggatgcc caatggttag ctgaagagtt agccaagcag atgcgcacta acttgtctga    23100

ttggactgta aatgtagggc aagggttcat ccatgtgacc gcacctagtg gtcaacagat    23160

tgactccttc acgactaaag atggctacga agaccagttg attaaccctg tgacccacta    23220

cgctcagtcg ttctctaagc tgccacctaa tgctcctaac ggctacatgg tgaaaatcgt    23280
```

-continued

```
aggggacgcc tctaagtctg ccgaccagta ttacgttcgg tatgacgctg agcggaaagt  23340
ttggactgag actttaggtt ggaacactga ggaccaagtt ctatgggaaa ccatgccaca  23400
cgctcttgtg cgagccgctg acggtaattt cgacttcaag tggcttgagt ggtctcctaa  23460
gtcttgtggt gacgttgaca ccaacccttg gccttctttt gttggttcaa gtattaacga  23520
tgtgttcttc ttccgtaacc gcttaggatt ccttagtggg gagaacatca tattgagtcg  23580
tacagccaaa tacttcaact tctaccctgc gtccattgcg aaccttagtg atgacgaccc  23640
tatagacgta gctgtgagta ccaaccgaat agcaatcctt aagtacgccg ttccgttctc  23700
agaagagtta ctcatctggt ccgatgaagc acaattcgtc ctgactgcct cgggtactct  23760
cacatctaag tcggttgagt tgaacctaac gacccagttt gacgtacagg accgagcgag  23820
accttttggg attgggcgta atgtctactt tgctagtccg aggtccagct tcacgtccat  23880
ccacaggtac tacgctgtgc aggatgtcag ttccgttaag aatgctgagg acattacatc  23940
acacgttcct aactacatcc ctaatggtgt gttcagtatt tgcggaagtg gtacggaaaa  24000
cttctgttcg gtactatctc acggggaccc tagtaaaatc ttcatgtaca aattcctgta  24060
cctgaacgaa gagttaaggc aacagtcgtg gtctcattgg gactttgggg aaaacgtaca  24120
ggttctagct tgtcagagta tcagctcaga tatgtatgtg attcttcgca atgagttcaa  24180
tacgttccta gctagaatct ctttcactaa gaacgccatt gacttacagg gagaacccta  24240
tcgtgccttt atggacatga agattcgata cacgattcct agtggaacat acaacgatga  24300
cacattcact acctctattc atattccaac aatttatggt gcaaacttcg ggaggggcaa  24360
aatcactgta ttggagcctg atggtaagat aaccgtgttt gagcaaccta cggctgggtg  24420
gaatagcgac ccttggctga gactcagcgg taacttggag ggacgcatgg tgtacattgg  24480
gttcaacatt aacttcgtat atgagttctc taagttcctc atcaagcaga ctgccgacga  24540
cgggtctacc tccacggaag acattgggcg cttacagtta cgccgagcgt gggttaacta  24600
cgagaactct ggtacgtttg acatttatgt tgagaaccaa tcgtctaact ggaagtacac  24660
aatggctggt gcccgattag gctctaacac tctgagggct gggagactga acttagggac  24720
cggacaatat cgattccctg tggttggtaa cgccaagttc aacactgtat acatcttgtc  24780
agatgagact acccctctga acatcattgg gtgtggctgg gaaggtaact acttacggag  24840
aagttccggt atttaattaa atattctccc tgtggtggct cgaaattaat acgactcact  24900
atagggagaa caatacgact acgggagggt tttcttatga tgactataag acctactaaa  24960
agtacagact ttgaggtatt cactccggct caccatgaca ttcttgaagc taaggctgct  25020
ggtattgagc cgagtttccc tgatgcttcc gagtgtgtca cgttgagcct ctatgggttc  25080
cctctagcta tcggtggtaa ctgcggggac cagtgctggt tcgttacgag cgaccaagtg  25140
tggcgactta gtggaaaggc taagcgaaag ttccgtaagt taatcatgga gtatcgcgat  25200
aagatgcttg agaagtatga tactctttgg aattacgtat gggtaggcaa tacgtcccac  25260
attcgtttcc tcaagactat cggtgcggta ttccatgaag agtacacacg agatggtcaa  25320
tttcagttat ttacaatcac gaaaggagga taaccatatg tgttgggcag ccgcaatacc  25380
tatcgctata tctggcgctc aggctatcag tggtcagaac gctcaggcca aaatgattgc  25440
cgctcagacc gctgctggtc gtcgtcaagc tatggaaatc atgaggcaga cgaacatcca  25500
gaatgctgac ctatcgttgc aagctcgaag taaacttgag gaagcgtccg ccgagttgac  25560
ctcacagaac atgcagaagg tccaagctat tgggtctatc cgagcggcta tcggagagag  25620
tatgcttgaa ggttcctcaa tggaccgcat taagcgagtc acagaaggac agttcattcg  25680
```

```
ggaagccaat atggtaactg agaactatcg ccgtgactac caagcaatct tcgcacagca  25740
acttggtggt actcaaagtg ctgcaagtca gattgacgaa atctataaga gcgaacagaa  25800
acagaagagt aagctacaga tggttctgga cccactggct atcatggggt cttccgctgc  25860
gagtgcttac gcatccggtg cgttcgactc taagtccaca actaaggcac ctattgttgc  25920
cgctaaagga accaagacgg ggaggtaatg agctatgagt aaaattgaat ctgcccttca  25980
agcggcacaa ccgggactct ctcggttacg tggtggtgct ggaggtatgg gctatcgtgc  26040
agcaaccact caggccgaac agccaaggtc aagcctattg gacaccattg gtcggttcgc  26100
taaggctggt gccgatatgt ataccgctaa ggaacaacga gcacgagacc tagctgatga  26160
acgctctaac gagattatcc gtaagctgac ccctgagcaa cgtcgagaag ctctcaacaa  26220
cgggaccctt ctgtatcagg atgacccata cgctatggaa gcactccgag tcaagactgg  26280
tcgtaacgct gcgtatcttg tggacgatga cgttatgcag aagataaaag agggtgtctt  26340
ccgtactcgc gaagagatgg aagagtatcg ccatagtcgc cttcaagagg gcgctaaggt  26400
atacgctgag cagttcggca tcgaccctga ggacgttgat tatcagcgtg gtttcaacgg  26460
ggacattacc gagcgtaaca tctcgctgta tggtgcgcat gataacttct tgagccagca  26520
agctcagaag ggcgctatca tgaacagccg agtggaactc aacggtgtcc ttcaagaccc  26580
tgatatgctg cgtcgtccag actctgctga cttctttgag aagtatatcg acaacggtct  26640
ggttactggc gcaatcccat ctgatgctca agccacacag cttataagcc aagcgttcag  26700
tgacgcttct agccgtgctg gtggtgctga cttcctgatg cgagtcggtg acaagaaggt  26760
aacacttaac ggagccacta cgacttaccg agagttgatt ggtgaggaac agtggaacgc  26820
tctcatggtc acagcacaac gttctcagtt tgagactgac gcgaagctga acgagcagta  26880
tcgcttgaag attaactctg cgctgaacca agaggaccca aggacagctt gggagatgct  26940
tcaaggtatc aaggctgaac tagataaggt ccaacctgat gagcagatga caccacaacg  27000
tgagtggcta atctccgcac aggaacaagt tcagaatcag atgaacgcat ggacgaaagc  27060
tcaggccaag gctctggacg attccatgaa gtcaatgaac aaacttgacg taatcgacaa  27120
gcaattccag aagcgaatca acggtgagtg ggtctcaacg gattttaagg atatgccagt  27180
caacgagaac actggtgagt tcaagcatag cgatatggtt aactacgcca ataagaagct  27240
cgctgagatt gacagtatgg acattccaga cggtgccaag gatgctatga agttgaagta  27300
ccttcaagcg gactctaagg acggagcatt ccgtacagcc atcggaacca tggtcactga  27360
cgctggtcaa gagtggtctg ccgctgtgat taacggtaag ttaccagaac gaaccccagc  27420
tatggatgct ctgcgcagaa tccgcaatgc tgaccctcag ttgattgctg cgctataccc  27480
agaccaagct gagctattcc tgacgatgga catgatggac aagcagggta ttgaccctca  27540
ggttattctt gatgccgacc gactgactgt taagcggtcc aaagagcaac gctttgagga  27600
tgataaagca ttcgagtctg cactgaatgc atctaaggct cctgagattg cccgtatgcc  27660
agcgtcactg cgcgaatctg cacgtaagat ttatgactcc gttaagtatc gctcggggaa  27720
cgaaagcatg gctatggagc agatgaccaa gttccttaag gaatctacct acacgttcac  27780
tggtgatgat gttgacggtg ataccgttgg tgtgattcct aagaatatga tgcaggttaa  27840
ctctgacccg aaatcatggg agcaaggtcg ggatattctg gaggaagcac gtaagggaat  27900
cattgcgagc aacccttgga taaccaataa gcaactgacc atgtattctc aaggtgactc  27960
catttacctt atggacacca caggtcaagt cagagtccga tacgacaaag agttactctc  28020
```

```
gaaggtctgg agtgagaacc agaagaaact cgaagagaaa gctcgtgaga aggctctggc  28080
tgatgtgaac aagcgagcac ctatagttgc cgctacgaag gcccgtgaag ctgctgctaa  28140
acgagtccga gagaaacgta aacagactcc taagttcatc tacggacgta aggagtaact  28200
aaaggctaca taaggaggcc ctaaatggat aagtacgata agaacgtacc aagtgattat  28260
gatggtctgt tccaaaaggc tgctgatgcc aacggggtct cttatgacct tttacgtaaa  28320
gtcgcttgga cagaatcacg atttgtgcct acagcaaaat ctaagactgg accattaggc  28380
atgatgcaat ttaccaaggc aaccgctaag gccctcggtc tgcgagttac cgatggtcca  28440
gacgacgacc gactgaaccc tgagttagct attaatgctg ccgctaagca acttgcaggt  28500
ctggtaggga agtttgatgg cgatgaactc aaagctgccc ttgcgtacaa ccaaggcgag  28560
ggacgcttgg gtaatccaca acttgaggcg tactctaagg gagacttcgc atcaatctct  28620
gaggagggac gtaactacat gcgtaacctt ctggatgttg ctaagtcacc tatggctgga  28680
cagttggaaa cttttggtgg cataacccca aagggtaaag gcattccggc tgaggtagga  28740
ttggctggaa ttggtcacaa gcagaaagta acacaggaac ttcctgagtc cacaagtttt  28800
gacgttaagg gtatcgaaca ggaggctacg gcgaaaccat tcgccaagga cttttgggag  28860
acccacggag aaacacttga cgagtacaac agtcgttcaa ccttcttcgg attcaaaaat  28920
gctgccgaag ctgaactctc caactcagtc gctgggatgg ctttccgtgc tggtcgtctc  28980
gataatggtt ttgatgtgtt taaagacacc attacgccga ctcgctggaa ctctcacatc  29040
tggactccag aggagttaga gaagattcga acagaggtta agaaccctgc gtacatcaac  29100
gttgtaactg gtggttcccc tgagaacctc gatgacctca ttaaattggc taacgagaac  29160
tttgagaatg actcccgcgc tgccgaggct ggcctaggtg ccaaactgag tgctggtatt  29220
attggtgctg gtgtggaccc gcttagctat gttcctatgg tcggtgtcac tggtaagggc  29280
tttaagttaa tcaataaggc tcttgtagtt ggtgccgaaa gtgctgctct gaacgttgca  29340
tccgaaggtc tccgtacctc cgtagctggt ggtgacgcag actatgcggg tgctgcctta  29400
ggtggctttg tgtttggcgc aggcatgtct gcaatcagtg acgctgtagc tgctggactg  29460
aaacgcagta aaccagaagc tgagttcgac aatgagttca tcggtcctat gatgcgattg  29520
gaagcccgtg agacagcacg aaacgccaac tctgcggacc tctctcggat gaacactgag  29580
aacatgaagt ttgaaggtga acataatggt gtcccttatg aggacttacc aacagagaga  29640
ggtgccgtgg tgttacatga tggctccgtt ctaagtgcaa gcaacccaat caaccctaag  29700
actctaaaag agttctccga ggttgaccct gagaaggctg cgcgaggaat caaactggct  29760
gggttcaccg agattggctt gaagaccttg gggtctgacg atgctgacat ccgtagagtg  29820
gctatcgacc tcgttcgctc tcctactggt atgcagtctg gtgcctcagg taagttcggt  29880
gcaacagctt ctgacatcca tgagagactt catggtactg accagcgtac ttataatgac  29940
ttgtacaaag caatgtctga cgctatgaaa gaccctgagt tctctactgg cggcgctaag  30000
atgtcccgtg aagaaactcg atacactatc taccgtagag cggcactagc tattgagcgt  30060
ccagaactac agaaggcact cactccgtct gagagaatcg ttatggacat cattaagcgt  30120
cactttgaca ccaagcgtga acttatggaa aacccagcaa tattcggtaa cacaaaggct  30180
gtgagtatct tccctgagag tcgccacaaa ggtacttacg ttcctcacgt atatgaccgt  30240
catgccaagg cgctgatgat tcaacgctac ggtgccgaag gtttgcagga agggattgcc  30300
cgctcatgga tgaacagcta cgtctccaga cctgaggtca aggccagagt cgatgagatg  30360
cttaaggaat tacacggggt gaaggaagta acaccagaga tggtagagaa gtacgctatg  30420
```

gataaggctt atggtatctc ccactcagac cagttcacca acagttccat aatagaagag 30480
aacattgagg gcttagtagg tatcgagaat aactcattcc ttgaggcacg taacttgttt 30540
gattcggacc tatccatcac tatgccagac ggacagcaat tctcagtgaa tgacctaagg 30600
gacttcgata tgttccgcat catgccagcg tatgaccgcc gtgtcaatgg tgacatcgcc 30660
atcatggggt ctactggtaa aaccactaag gaacttaagg atgagatttt ggctctcaaa 30720
gcgaaagctg agggagacgg taagaagact ggcgaggtac atgctttaat ggataccgtt 30780
aagattctta ctggtcgtgc tagacgcaat caggacactg tgtgggaaac ctcactgcgt 30840
gccatcaatg acctagggtt cttcgctaag aacgcctaca tgggtgctca gaacattacg 30900
gagattgctg ggatgattgt cactggtaac gttcgtgctc tagggcatgg tatcccaatt 30960
ctgcgtgata cactctacaa gtctaaacca gtttcagcta aggaactcaa ggaactccat 31020
gcgtctctgt tcgggaagga ggtggaccag ttgattcggc ctaaacgtgc tgacattgtg 31080
cagcgcctaa gggaagcaac tgataccgga cctgccgtgg cgaacatcgt agggaccttg 31140
aagtattcaa cacaggaact ggctgctcgc tctccgtgga ctaagctact gaacggaacc 31200
actaactacc ttctggatgc tgcgcgtcaa ggtatgcttg gggatgttat tagtgccacc 31260
ctaacaggta agactacccg ctgggagaaa gaaggcttcc ttcgtggtgc ctccgtaact 31320
cctgagcaga tggctggcat caagtctctc atcaaggaac atatggtacg cggtgaggac 31380
gggaagttta ccgttaagga caagcaagcg ttctctatgg acccacgggc tatggactta 31440
tggagactgg ctgacaaggt agctgatgag gcaatgctgc gtccacataa ggtgtcctta 31500
caggattccc atgcgttcgg agcactaggt aagatggtta tgcagtttaa gtctttcact 31560
atcaagtccc ttaactctaa gttcctgcga accttctatg atggatacaa gaacaaccga 31620
gcgattgacg ctgcgctgag catcatcacc tctatgggtc tcgctggtgg tttctatgct 31680
atggctgcac acgtcaaagc atacgctctg cctaaggaga aacgtaagga gtacttggag 31740
cgtgcactgg acccaaccat gattgcccac gctgcgttat ctcgtagttc tcaattgggt 31800
gctcctttgg ctatggttga cctagttggt ggtgttttag ggttcgagtc ctccaagatg 31860
gctcgctcta cgattctacc taaggacacc gtgaaggaac gtgacccaaa caaaccgtac 31920
acctctagag aggtaatggg cgctatgggt tcaaaccttc tggaacagat gccttcggct 31980
ggctttgtgg ctaacgtagg ggctacctta atgaatgctg ctggcgtggt caactcacct 32040
aataaagcaa ccgagcagga cttcatgact ggtcttatga actccacaaa agagttagta 32100
ccgaacgacc cattgactca acagcttgtg ttgaagattt atgaggcgaa cggtgttaac 32160
ttgagggagc gtaggaaata atacgactca ctatagggag aggcgaaata atcttctccc 32220
tgtagtctct tagatttact ttaaggaggt caaatggcta acgtaattaa aaccgttttg 32280
acttaccagt tagatggctc caatcgtgat tttaatatcc cgtttgagta tctagcccgt 32340
aagttcgtag tggtaactct tattggtgta gaccgaaagg tccttacgat taatacagac 32400
tatcgctttg ctacacgtac tactatctct ctgacaaagg cttggggtcc agccgatggc 32460
tacacgacca tcgagttacg tcgagtaacc tccactaccg accgattggt tgactttacg 32520
gatggttcaa tcctccgcgc gtatgacctt aacgtcgctc agattcaaac gatgcacgta 32580
gcggaagagg cccgtgacct cactacggat actatcggtg tcaataacga tggtcacttg 32640
gatgctcgtg gtcgtcgaat tgtgaaccta gcgaacgccg tggatgaccg cgatgctgtt 32700
ccgtttggtc aactaaagac catgaaccag aactcatggc aagcacgtaa tgaagcctta 32760

```
cagttccgta atgaggctga gactttcaga aaccaagcgg agggctttaa gaacgagtcc  32820
agtaccaacg ctacgaacac aaagcagtgg cgcgatgaga ccaagggttt ccgagacgaa  32880
gccaagcggt tcaagaatac ggctggtcaa tacgctacat ctgctgggaa ctctgcttcc  32940
gctgcgcatc aatctgaggt aaacgctgag aactctgcca cagcatccgc taactctgct  33000
catttggcag aacagcaagc agaccgtgcg gaacgtgagg cagacaagct ggaaaattac  33060
aatggattgg ctggtgcaat tgataaggta gatggaacca atgtgtactg gaaaggaaat  33120
attcacgcta acgggcgcct ttacatgacc acaaacggtt ttgactgtgg ccagtatcaa  33180
cagttctttg gtggtgtcac taatcgttac tctgtcatgg agtggggaga tgagaacgga  33240
tggctgatgt atgttcaacg tagagagtgg acaacagcga taggcggtaa catccagtta  33300
gtagtaaacg gacagatcat cacccaaggt ggagccatga ccggtcagct aaaattgcag  33360
aatgggcatg ttcttcaatt agagtccgca tccgacaagg cgcactatat tctatctaaa  33420
gatggtaaca ggaataactg gtacattggt agagggtcag ataacaacaa tgactgtacc  33480
ttccactcct atgtacatgg tacgacctta acactcaagc aggactatgc agtagttaac  33540
aaacacttcc acgtaggtca ggccgttgtg gccactgatg gtaatattca aggtactaag  33600
tggggaggta aatggctgga tgcttaccta cgtgacagct tcgttgcgaa gtccaaggcg  33660
tggactcagg tgtggtctgg tagtgctggc ggtggggtaa gtgtgactgt ttcacaggat  33720
ctccgcttcc gcaatatctg gattaagtgt gccaacaact cttggaactt cttccgtact  33780
ggccccgatg gaatctactt catagcctct gatggtggat ggttacgatt ccaaatacac  33840
tccaacggtc tcggattcaa gaatattgca gacagtcgtt cagtacctaa tgcaatcatg  33900
gtggagaacg agtaattggt aaatcacaag gaaagacgtg tagtccacgg atggactctc  33960
aaggaggtac aaggtgctat cattagactt taacaacgaa ttgattaagg ctgctccaat  34020
tgttgggacg ggtgtagcag atgttagtgc tcgactgttc tttgggttaa gccttaacga  34080
atggttctac gttgctgcta tcgcctacac agtggttcag attggtgcca aggtagtcga  34140
taagatgatt gactggaaga aagccaataa ggagtgatat gtatggaaaa ggataagagc  34200
cttattacat tcttagagat gttggacact gcgatggctc agcgtatgct tgcggacctt  34260
tcggaccatg agcgtcgctc tccgcaactc tataatgcta ttaacaaact gttagaccgc  34320
cacaagttcc agattggtaa gttgcagccg gatgttcaca tcttaggtgg ccttgctggt  34380
gctcttgaag agtacaaaga gaaagtcggt gataacggtc ttacggatga tgatatttac  34440
acattacagt gatatactca aggccactac agatagtggt ctttatggat gtcattgtct  34500
atacgagatg ctcctacgtg aaatctgaaa gttaacggga ggcattatgc tagaattttt  34560
acgtaagcta atcccttggg ttctcgctgg gatgctattc gggttaggat ggcatctagg  34620
gtcagactca atggacgcta aatggaaaca ggaggtacac aatgagtacg ttaagagagt  34680
tgaggctgcg aagagcactc aaagagcaat cgatgcggta tctgctaagt atcaagaaga  34740
ccttgccgcg ctggaaggga gcactgatag gattatttct gatttgcgta gcgacaataa  34800
gcggttgcgc gtcagagtca aaactaccgg aacctccgat ggtcagtgtg gattcgagcc  34860
tgatggtcga gccgaacttg acgaccgaga tgctaaacgt attctcgcag tgacccagaa  34920
gggtgacgca tggattcgtg cgttacagga tactattcgt gaactgcaac gtaagtagga  34980
aatcaagtaa ggaggcaatg tgtctactca atccaatcgt aatgcgctcg tagtggcgca  35040
actgaaagga gacttcgtgg cgttcctatt cgtcttatgg aaggcgctaa acctaccggt  35100
gcccactaag tgtcagattg acatggctaa ggtgctggcg aatggagaca acaagaagtt  35160
```

catcttacag gctttccgtg gtatcggtaa gtcgttcatc acatgtgcgt tcgttgtgtg 35220
gtccttatgg agagaccctc agttgaagat acttatcgta tcagcctcta aggagcgtgc 35280
agacgctaac tccatcttta ttaagaacat cattgacctg ctgccattcc tatctgagtt 35340
aaagccaaga cccggacagc gtgactcggt aatcagcttt gatgtaggcc cagccaatcc 35400
tgaccactct cctagtgtga aatcagtagg tatcactggt cagttaactg gtagccgtgc 35460
tgacattatc attgcggatg acgttgagat tccgtctaac agcgcaacta tgggtgcccg 35520
tgagaagcta tggactctgg ttcaggagtt cgctgcgtta cttaaaccgc tgccttcctc 35580
tcgcgttatc taccttggta cacctcagac agagatgact ctctataagg aacttgagga 35640
taaccgtggg tacacaacca ttatctggcc tgctctgtac ccaaggacac gtgaagagaa 35700
cctctattac tcacagcgtc ttgctcctat gttacgcgct gagtacgatg agaaccctga 35760
ggcacttgct gggactccaa cagacccagt gcgctttgac cgtgatgacc tgcgcgagcg 35820
tgagttggaa tacggtaagg ctggctttac gctacagttc atgcttaacc ctaaccttag 35880
tgatgccgag aagtacccgc tgaggcttcg tgacgctatc gtagcggcct tagacttaga 35940
gaaggcccca atgcattacc agtggcttcc gaaccgtcag aacatcattg aggaccttcc 36000
taacgttggc cttaagggtg atgacctgca tacgtaccac gattgttcca acaactcagg 36060
tcagtaccaa cagaagattc tggtcattga ccctagtggt cgcggtaagg acgaaacagg 36120
ttacgctgtg ctgtacacac tgaacggtta catctacctt atggaagctg gaggtttccg 36180
tgatggctac tccgataaga cccttgagtt actcgctaag aaggcaaagc aatggggagt 36240
ccagacggtt gtctacgaga gtaacttcgg tgacggtatg ttcggtaagg tattcagtcc 36300
tatccttctt aaacaccaca actgtgcgat ggaagagatt cgtgcccgtg gtatgaaaga 36360
gatgcgtatt tgcgataccc ttgagccagt catgcagact caccgccttg taattcgtga 36420
tgaggtcatt agggccgact accagtccgc tcgtgacgta gacggtaagc atgacgttaa 36480
gtactcgttg ttctaccaga tgacccgtat cactcgtgag aaaggcgctc tggctcatga 36540
tgaccgattg gatgcccttg cgttaggcat tgagtatctc cgtgagtcca tgcagttgga 36600
ttccgttaag gtcgagggtg aagtacttgc tgacttcctt gaggaacaca tgatgcgtcc 36660
tacggttgct gctacgcata tcattgagat gtctgtggga ggagttgatg tgtactctga 36720
ggacgatgag ggttacggta cgtctttcat tgagtggtga tttatgcatt aggactgcat 36780
agggatgcac tatagaccac ggatggtcag ttctttaagt tactgaaaag acacgataaa 36840
ttaatacgac tcactatagg gagaggaggg acgaaaggtt actatataga tactgaatga 36900
atacttatag agtgcataaa gtatgcataa tggtgtacct agagtgacct ctaagaatgg 36960
tgattatatt gtattagtat caccttaact taaggaccaa cataaaggga ggagactcat 37020
gttccgctta ttgttgaacc tactgcggca tagagtcacc taccgatttc ttgtggtact 37080
ttgtgctgcc cttgggtacg catctcttac tggagacctc agttcactgg agtctgtcgt 37140
ttgctctata ctcacttgta gcgattaggg tcttcctgac cgactgatgg ctcaccgagg 37200
gattcagcgg tatgattgca tcacaccact tcatccctat agagtcaagt cctaaggtat 37260
acccataaag agcctctaat ggtctatcct aaggtctata cctaaagata ggccatccta 37320
tcagtgtcac ctaaagaggg tcttagagag ggcctatgga gttcctatag ggtcctttaa 37380
aatataccat aaaaatctga gtgactatct cacagtgtac ggacctaaag ttcccccata 37440
gggggtacct aaagcccagc caatcaccta aagtcaacct tcggttgacc ttgagggttc 37500
cctaagggtt ggggatgacc cttgggtttg tctttgggtg ttaccttgag tgtctctctg 37560
tgtccct 37567

<210> SEQ ID NO 69
<211> LENGTH: 37561
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg gggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920

-continued

```
cgctacgaag acgtttacat gcctgaggtg tacaaagcga ttaacattgc gcaaaacacc   1980
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
tctctaggag tggccttagt catttaacca ataggagata aacattatga tgaacattaa   4320
```

gactaacccg tttaaagccg tgtctttcgt agagtctgcc attaagaagg ctctggataa 4380
cgctgggtat cttatcgctg aaatcaagta cgatggtgta cgcgggaaca tctgcgtaga 4440
caatactgct aacagttact ggctctctcg tgtatctaaa acgattccgg cactggagca 4500
cttaaacggg tttgatgttc gctggaagcg tctactgaac gatgaccgtt gcttctacaa 4560
agatggcttt atgcttgatg gggaactcat ggtcaagggc gtagacttta acacagggtc 4620
cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400
cttcgggtgg gcctttctgc gtttataagg agacacttta tgtttaagaa ggttggtaaa 5460
ttccttgcgg ctttggcagc tatcctgacg cttgcgtata ttcttgcggt ataccctcaa 5520
gtagcactag tagtagttgg cgcttgttac ttagcggcag tgtgtgcttg cgtgtggagt 5580
atagttaact ggtaatacga ctcactaaag gaggtacaca ccatgatgta cttaatgcca 5640
ttactcatcg tcattgtagg atgccttgcg ctccactgta gcgatgatga tatgccagat 5700
ggtcacgctt aatacgactc actaaaggag acactatatg tttcgacttc attacaacaa 5760
aagcgttaag aatttcacgg ttcgccgtgc tgaccgttca atcgtatgtg cgagcgagcg 5820
ccgagctaag atacctctta ttggtaacac agttcctttg gcaccgagcg tccacatcat 5880
tatcacccgt ggtgactttg agaaagcaat agacaagaaa cgtccggttc ttagtgtggc 5940
agtgacccgc ttcccgttcg tccgtctgtt actcaaacga atcaaggagg tgttctgatg 6000
ggactgttag atggtgaagc ctgggaaaaa gaaaacccgc cagtacaagc aactgggtgt 6060
atagcttgct tagagaaaga tgaccgttat ccacacacct gtaacaaagg agctaacgat 6120
atgaccgaac gtgaacaaga gatgatcatt aagttgatag acaataatga aggtcgccca 6180
gatgatttga atggctgcgg tattctctgc tccaatgtcc cttgccacct ctgccccgca 6240
aataacgatc aaaagataac cttaggtgaa atccgagcga tggacccacg taaaccacat 6300
ctgaataaac ctgaggtaac tcctacagat gaccagcctt ccgctgagac aatcgaaggt 6360
gtcactaagc cttcccacta catgctgttt gacgacattg aggctatcga agtgattgct 6420
cgttcaatga ccgttgagca gttcaaggga tactgcttcg gtaacatctt aaagtacaga 6480
ctacgtgctg gtaagaagtc agagttagcg tacttagaga aagacctagc gaaagcagac 6540
ttctataaag aactctttga gaaacataag gataaatgtt atgcataact tcaagtcaac 6600
cccacctgcc gacagcctat ctgatgactt cacatcttgc tcagagtggt gccgaaagat 6660

-continued

```
gtgggaagag acattcgacg atgcgtacat caagctgtat gaactttgga aatcgagagg   6720
tcaatgacta tgtcaaacgt aaatacaggt tcacttagtg tggacaataa gaagttttgg   6780
gctaccgtag agtcctcgga gcattccttc gaggttccaa tctacgctga gaccctagac   6840
gaagctctgg agttagccga atggcaatac gttccggctg gctttgaggt tactcgtgtg   6900
cgtccttgtg tagcaccgaa gtaatacgac tcactattag ggaagactcc ctctgagaaa   6960
ccaaacgaaa cctaaaggag attaacatta tggctaagaa gattttcacc tctgcgctgg   7020
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac taccttttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
ttggaagtcg ttgcgtggat ttatagaact aggagggaat tgcatggaca attcgcacga   9060
```

-continued

```
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
```

-continued ttaccatgcg tgaccctaaa gttatccaag cagaaatcgc taaactggaa gctgaactgg 11460
aggacgttaa gtaccatgaa gctaagactc gctccgctgt tcacatcttg aagaacttag 11520
gctggacttg gacaagacag actggctgga agaaaccaga agttaccaag ctgagtcata 11580
aggtgttcga taaggacact atgacccaca tcaaggctgg tgattgggtt aaggttgaca 11640
tgggagttgt tggtggatac ggctacgtcc gctcagttag tggcaaatat gcacaagtgt 11700
catacatcac aggtgttact ccacgcggtg caatcgttgc cgataagacc aacatgattc 11760
acacaggttt cttgacagtt gtttcatatg aagagattgt taagtcacga taatcaatag 11820
gagaaatcaa tatgatcgtt tctgacatcg aagctaacgc cctcttagag agcgtcacta 11880
agttccactg cggggttatc tacgactact ccaccgctga gtacgtaagc taccgtccga 11940
gtgacttcgg tgcgtatctg gatgcgctgg aagccgaggt tgcacgaggc ggtcttattg 12000
tgttccacaa cggtcacaag tatgacgttc ctgcattgac caaactggca aagttgcaat 12060
tgaaccgaga gttccacctt cctcgtgaga actgtattga cacccttgtg ttgtcacgtt 12120
tgattcattc caacctcaag gacaccgata tgggtcttct gcgttccggc aagttgcccg 12180
gaaaacgctt tgggtctcac gctttggagg cgtggggtta tcgcttaggc gagatgaagg 12240
gtgaatacaa agacgacttt aagcgtatgc ttgaagagca gggtgaagaa tacgttgacg 12300
gaatggagtg gtggaacttc aacgaagaga tgatggacta taacgttcag gacgttgtgg 12360
taactaaagc tctccttgag aagctactct ctgacaaaca ttacttccct cctgagattg 12420
actttacgga cgtaggatac actacgttct ggtcagaatc ccttgaggcc gttgacattg 12480
aacatcgtgc tgcatggctg ctcgctaaac aagagcgcaa cgggttcccg tttgacacaa 12540
aagcaatcga agagttgtac gtagagttag ctgctcgccg ctctgagttg ctccgtaaat 12600
tgaccgaaac gttcggctcg tggtatcagc ctaaaggtgg cactgagatg ttctgccatc 12660
cgcgaacagg taagccacta cctaaatacc ctcgcattaa gacacctaaa gttggtggta 12720
tctttaagaa gcctaagaac aaggcacagc gagaaggccg tgagccttgc gaacttgata 12780
cccgcgagta cgttgctggt gctccttaca ccccagttga acatgttgtg tttaaccctt 12840
cgtctcgtga ccacattcag aagaaactcc aagaggctgg gtgggtcccg accaagtaca 12900
ccgataaggg tgctcctgtg gtggacgatg aggtactcga aggagtacgt gtagatgacc 12960
ctgagaagca agccgctatc gacctcatta aagagtactt gatgattcag aagcgaatcg 13020
gacagtctgc tgagggagac aaagcatggc ttcgttatgt tgctgaggat ggtaagattc 13080
atggttctgt taaccctaat ggagcagtta cgggtcgtgc gacccatgcg ttcccaaacc 13140
ttgcgcaaat tccgggtgta cgttctcctt atggagagca gtgtcgcgct gcttttggcg 13200
ctgagcacca tttggatggg ataactggta agccttgggt tcaggctggc atcgacgcat 13260
ccggtcttga gctacgctgc ttggctcact tcatggctcg ctttgataac ggcgagtacg 13320
ctcacgagat tcttaacggc gacatccaca ctaagaacca gatagctgct gaactaccta 13380
cccgagataa cgctaagacg ttcatctatg ggttcctcta tggtgctggt gatgagaaga 13440
ttggacagat tgttggtgct ggtaaagagc gcggtaagga actcaagaag aaattccttg 13500
agaacacccc cgcgattgca gcactccgcg agtctatcca acagacactt gtcgagtcct 13560
ctcaatgggt agctggtgag caacaagtca agtggaaacg ccgctggatt aaaggtctgg 13620
atggtcgtaa ggtacacgtt cgtagtcctc acgctgcctt gaatacccta ctgcaatctg 13680
ctggtgctct catctgcaaa ctgtggatta tcaagaccga agagatgctc gtagagaaag 13740
gcttgaagca tggctgggat ggggactttg cgtacatggc atgggtacat gatgaaatcc 13800
aagtaggctg ccgtaccgaa gagattgctc aggtggtcat tgagaccgca caagaagcga 13860
tgcgctgggt tggagaccac tggaacttcc ggtgtcttct ggataccgaa ggtaagatgg 13920
gtcctaattg ggcgatttgc cactgataca ggaggctact catgaacgaa agacacttaa 13980
caggtgctgc ttctgaaatg ctagtagcct acaaatttac caaagctggg tacactgtct 14040
attaccctat gctgactcag agtaaagagg acttggttgt atgtaaggat ggtaaattta 14100
gtaaggttca ggttaaaaca gccacaacgg ttcaaaccaa cacaggagat gccaagcagg 14160
ttaggctagg tggatgcggt aggtccgaat ataaggatgg agactttgac attcttgcgg 14220
ttgtggttga cgaagatgtg cttattttca catgggacga agtaaaaggt aagacatcca 14280
tgtgtgtcgg caagagaaac aaaggcataa aactatagga gaaattatta tggctatgac 14340
aaagaaattt aaagtgtcct tcgacgttac cgcaaagatg tcgtctgacg ttcaggcaat 14400
cttagagaaa gatatgctgc atctatgtaa gcaggtcggc tcaggtgcga ttgtccccaa 14460
tggtaaacag aaggaaatga ttgtccagtt cctgacacac ggtatggaag gattgatgac 14520
attcgtagta cgtacatcat ttcgtgaggc cattaaggac atgcacgaag agtatgcaga 14580
taaggactct ttcaaacaat ctcctgcaac agtacgggag gtgttctgat gtctgactac 14640
ctgaaagtgc tgcaagcaat caaaagttgc cctaagactt tccagtccaa ctatgtacgg 14700
aacaatgcga gcctcgtagc ggaggccgct tcccgtggtc acatctcgtg cctgactact 14760
agtggacgta acggtggcgc ttgggaaatc actgcttccg gtactcgctt tctgaaacga 14820
atgggaggat gtgtctaatg tctcgtgacc ttgtgactat tccacgcgat gtgtggaacg 14880
atatacaggg ctacatcgac tctctggaac gtgagaacga tagccttaag aatcaactaa 14940
tggaagctga cgaatacgta gcggaactag aggagaaact taatggcact tcttgacctt 15000
aaacaattct atgagttacg tgaaggctgc gacgacaagg gtatccttgt gatggacggc 15060
gactggctgg tcttccaagc tatgagtgct gctgagtttg atgcctcttg ggaggaagag 15120
atttggcacc gatgctgtga ccacgctaag gcccgtcaga ttcttgagga ttccattaag 15180
tcctacgaga cccgtaagaa ggcttgggca ggtgctccaa ttgtccttgc gttcaccgat 15240
agtgttaact ggcgtaaaga actggttgac ccgaactata aggctaaccg taaggccgtg 15300
aagaaacctg tagggtactt tgagttcctt gatgctctct ttgagcgcga agagttctat 15360
tgcatccgtg agcctatgct tgagggtgat gacgttatgg gagttattgc ttccaatccg 15420
tctgccttcg gtgctcgtaa ggctgtaatc atctcttgcg ataaggactt taagaccatc 15480
cctaactgtg acttcctgtg gtgtaccact ggtaacatcc tgactcagac cgaagagtcc 15540
gctgactggt ggcacctctt ccagaccatc aagggtgaca tcactgatgg ttactcaggg 15600
attgctggat ggggtgatac cgccgaggac ttcttgaata acccgttcat aaccgagcct 15660
aaaacgtctg tgcttaagtc cggtaagaac aaaggccaag aggttactaa atgggttaaa 15720
cgcgaccctg agcctcatga gacgctttgg gactgcatta agtccattgg cgcgaaggct 15780
ggtatgaccg aagaggatat tatcaagcag ggccaaatgg ctcgaatcct acggttcaac 15840
gagtacaact ttattgacaa ggagatttac ctgtggagac cgtagcgtat attggtctgg 15900
gtctttgtgt tctcggagtg tgcctcattt cgtggggcct ttgggactta gccagaataa 15960
tcaagtcgtt acacgacact aagtgataaa ctcaaggtcc ctaaattaat acgactcact 16020
atagggagat aggggccttt acgattatta ctttaagatt taactctaag aggaatcttt 16080
attatgttaa cacctattaa ccaattactt aagaacccta acgatattcc agatgtacct 16140

```
cgtgcaaccg ctgagtatct acaggttcga ttcaactatg cgtacctcga agcgtctggt  16200
catataggac ttatgcgtgc taatggttgt agtgaggccc acatcttggg tttcattcag  16260
ggcctacagt atgcctctaa cgtcattgac gagattgagt tacgcaagga acaactaaga  16320
gatgatgggg aggattgaca ctatgtgttt ctcaccgaaa attaaaactc cgaagatgga  16380
taccaatcag attcgagccg ttgagccagc gcctctgacc caagaagtgt caagcgtgga  16440
gttcggtggg tcttctgatg agacggatac cgagggcacc gaagtgtctg gacgcaaagg  16500
cctcaaggtc gaacgtgatg attccgtagc gaagtctaaa gccagcggca atggctccgc  16560
tcgtatgaaa tcttccatcc gtaagtccgc atttggaggt aagaagtgat gtctgagttc  16620
acatgtgtgg aggctaagag tcgcttccgt gcaatccggt ggactgtgga acaccttggg  16680
ttgcctaaag gattcgaagg acactttgtg ggctacagcc tctacgtaga cgaagtgatg  16740
gacatgtctg gttgccgtga agagtacatt ctggactcta ccggaaaaca tgtagcgtac  16800
ttcgcgtggt gcgtaagctg tgacattcac cacaaaggag acattctgga tgtaacgtcc  16860
gttgtcatta atcctgaggc agactctaag ggcttacagc gattcctagc gaaacgcttt  16920
aagtaccttg cggaactcca cgattgcgat tgggtgtctc gttgtaagca tgaaggcgag  16980
acaatgcgtg tatactttaa ggaggtataa gttatgggta agaaagttaa gaaggccgtg  17040
aagaaagtca ccaagtccgt taagaaagtc gttaaggaag gggctcgtcc ggttaaacag  17100
gttgctggcg gtctagctgg tctggctggt ggtactggtg aagcacagat ggtggaagta  17160
ccacaagctg ccgcacagat tgttgacgta cctgagaaag aggtttccac tgaggacgaa  17220
gcacagacag aaagcggacg caagaaagct cgtgctggcg gtaagaaatc cttgagtgta  17280
gcccgtagct ccggtggcgg tatcaacatt taatcaggag gttatcgtgg aagactgcat  17340
tgaatggacc ggaggtgtca actctaaggg ttatggtcgt aagtgggtta atggtaaact  17400
tgtgactcca cataggcaca tctatgagga gacatatggt ccagttccaa caggaattgt  17460
ggtgatgcat atctgcgata accctaggtg ctataacata aagcacctta cgcttggaac  17520
tccaaaggat aattccgagg acatggttac caaaggtaga caggctaaag gagaggaact  17580
aagcaagaaa cttacagagt cagacgttct cgctatacgc tcttcaacct taagccaccg  17640
ctccttagga gaactgtatg gagtcagtca atcaaccata acgcgaatac tacagcgtaa  17700
gacatggaga cacatttaat ggctgagaaa cgaacaggac ttgcggagga tggcgcaaag  17760
tctgtctatg agcgtttaaa gaacgaccgt gctccctatg agacacgcgc tcagaattgc  17820
gctcaatata ccatcccatc attgttccct aaggactccg ataacgcctc tacagattat  17880
caaactccgt ggcaagccgt gggcgctcgt ggtctgaaca atctagcctc taagctcatg  17940
ctggctctat tccctatgca gacttggatg cgacttacta tatctgaata tgaagcaaag  18000
cagttactga gcgaccccga tggactcgct aaggtcgatg agggcctctc gatggtagag  18060
cgtatcatca tgaactacat tgagtctaac agttaccgcg tgactctctt tgaggctctc  18120
aaacagttag tcgtagctgg taacgtcctg ctgtacctac cggaaccgga agggtcaaac  18180
tataatccca tgaagctgta ccgattgtct tcttatgtgg tccaacgaga cgcattcggc  18240
aacgttctgc aaatggtgac tcgtgaccag atagcttttg gtgctctccc tgaggacatc  18300
cgtaaggctg tagaaggtca aggtggtgag aagaaagctg atgagacaat cgacgtgtac  18360
actcacatct atctggatga ggactcaggt gaatacctcc gatacgaaga ggtcgagggt  18420
atggaagtcc aaggctccga tgggacttat cctaaagagg cttgcccata catcccgatt  18480
cggatggtca gactagatgg tgaatcctac ggtcgttcgt acattgagga atacttaggt  18540
```

gacttacggt cccttgaaaa tctccaagag gctatcgtca agatgtccat gattagctct 18600
aaggttatcg gcttagtgaa tcctgctggt atcacccagc cacgccgact gaccaaagct 18660
cagactggtg acttcgttac tggtcgtcca gaagacatct cgttcctcca actggagaag 18720
caagcagact ttactgtagc taaagccgta agtgacgcta tcgaggctcg cctttcgttt 18780
gcctttatgt tgaactctgc ggttcagcgt acaggtgaac gtgtgaccgc cgaagagatt 18840
cggtatgtag cttctgaact tgaagatact ttaggtggtg tctactctat cctttctcaa 18900
gaattacaat tgcctctggt acgagtgctc ttgaagcaac tacaagccac gcaacagatt 18960
cctgagttac ctaaggaagc cgtagagcca accattagta caggtctgga agcaattggt 19020
cgaggacaag accttgataa gctggagcgg tgtgtcactg cgtgggctgc actggcacct 19080
atgcgggacg accctgatat taaccttgcg atgattaagt tacgtattgc caacgctatc 19140
ggtattgaca cttctggtat tctactcacc gaagaacaga agcaacagaa gatggcccaa 19200
cagtctatgc aaatgggtat ggataatggt gctgctgcgc tggctcaagg tatggctgca 19260
caagctacag cttcacctga ggctatggct gctgccgctg attccgtagg tttacagccg 19320
ggaatttaat acgactcact atagggagac ctcatctttg aaatgagcga tgacaagagg 19380
ttggagtcct cggtcttcct gtagttcaac tttaaggaga caataataat ggctgaatct 19440
aatgcagacg tatatgcatc ttttggcgtg aactccgctg tgatgtctgg tggttccgtt 19500
gaggaacatg agcagaacat gctggctctt gatgttgctg cccgtgatgg cgatgatgca 19560
atcgagttag cgtcagacga agtggaaaca gaacgtgacc tgtatgacaa ctctgacccg 19620
ttcggtcaag aggatgacga aggccgcatt caggttcgta tcggtgatgg ctctgagccg 19680
accgatgtgg acactggaga agaaggcgtt gagggcaccg aaggttccga agagtttacc 19740
ccactgggcg agactccaga agaactggta gctgcctctg agcaacttgg tgagcacgaa 19800
gagggcttcc aagagatgat taacattgct gctgagcgtg gcatgagtgt cgagaccatt 19860
gaggctatcc agcgtgagta cgaggagaac gaagagttgt ccgccgagtc ctacgctaag 19920
ctggctgaaa ttggctacac gaaggctttc attgactcgt atatccgtgg tcaagaagct 19980
ctggtggagc agtacgtaaa cagtgtcatt gagtacgctg gtggtcgtga acgttttgat 20040
gcactgtata accaccttga gacgcacaac cctgaggctg cacagtcgct ggataatgcg 20100
ttgaccaatc gtgacttagc gaccgttaag gctatcatca acttggctgg tgagtctcgc 20160
gctaaggcgt tcggtcgtaa gccaactcgt agtgtgacta atcgtgctat tccggctaaa 20220
cctcaggcta ccaagcgtga aggctttgcg gaccgtagcg agatgattaa agctatgagt 20280
gaccctcggt atcgcacaga tgccaactat cgtcgtcaag tcgaacagaa agtaatcgat 20340
tcgaacttct gatagacttc gaaattaata cgactcacta tagggagacc acaacggttt 20400
ccctctagaa ataattttgt ttaactttaa gaaggagata tacatatggc tagcatgact 20460
ggtggacagc aaatgggtac taaccaaggt aaaggtgtag ttgctgctgg agataaactg 20520
gcgttgttct tgaaggtatt tggcggtgaa gtcctgactg cgttcgctcg tacctccgtg 20580
accacttctc gccacatggt acgttccatc tccagcggta aatccgctca gttccctgtt 20640
ctgggtcgca ctcaggcagc gtatctggct ccgggcgaga acctcgacga taaacgtaag 20700
gacatcaaac acaccgagaa ggtaatcacc attgacggtc tcctgacggc tgacgttctg 20760
atttatgata ttgaggacgc gatgaaccac tacgacgttc gctctgagta tacctctcag 20820
ttgggtgaat ctctggcgat ggctgcggat ggtgcggttc tggctgagat tgccggtctg 20880

-continued

```
tgtaacgtgg aaagcaaata taatgagaac atcgagggct taggtactgc taccgtaatt  20940
gagaccactc agaacaaggc cgcacttacc gaccaagttg cgctgggtaa ggagattatt  21000
gcggctctga ctaaggctcg tgcggctctg accaagaact atgttccggc tgctgaccgt  21060
gtgttctact gtgacccaga tagctactct gcgattctgg cagcactgat gccgaacgca  21120
gcaaactacg ctgctctgat tgaccctgag aagggttcta tccgcaacgt tatgggcttt  21180
gaggttgtag aagttccgca cctcaccgct ggtggtgctg gtaccgctcg tgagggcact  21240
actggtcaga agcacgtctt ccctgccaat aaaggtgagg gtaatgtcaa ggttgctaag  21300
gacaacgtta tcggcctgtt catgcaccgc tctgcggtag gtactgttaa gctgcgtgac  21360
ttggctctgg agcgcgctcg ccgtgctaac ttccaagcgg accagattat cgctaagtac  21420
gcaatgggcc acggtggtct tcgcccagaa gctgcaggag ctgtcgtatt ccagtcaggt  21480
gtgatgctcg gggatccgaa ttcttaagta actaacgaaa ttaatacgac tcactatagg  21540
gagaccacaa cggtttccct ctagaaataa ttttgtttaa ctttaagaag gagatataca  21600
tatgaaaaag acagctatcg cgattgcagt ggcactggct ggtttcgcta ccgtagcgca  21660
ggccttttgg ggcgcgctga ttaaaggcgc ggcgaaactg attccgagcg tggtgggcct  21720
gtttaaaaaa aaacagtaag gatccggctg ctaacaaagc ccgaagcttg cggccgcact  21780
cgagtaacta gttaacccct tggggcctct aaacgggtct tgaggggttt tttgctgaaa  21840
ggaggaacta tatgcgctca tacgatatga acgttgagac tgccgctgag ttatcagctg  21900
tgaacgacat tctggcgtct atcggtgaac ctccggtatc aacgctggaa ggtgacgcta  21960
acgcagatgc agcgaacgct cggcgtattc tcaacaagat taaccgacag attcaatctc  22020
gtggatggac gttcaacatt gaggaaggca taacgctact acctgatgtt tactccaacc  22080
tgattgtata cagtgacgac tatttatccc taatgtctac ttccggtcaa tccatctacg  22140
ttaaccgagg tggctatgtg tatgaccgaa cgagtcaatc agaccgcttt gactctggta  22200
ttactgtgaa cattattcgt ctccgcgact acgatgagat gcctgagtgc ttccgttact  22260
ggattgtcac caaggcttcc cgtcagttca acaaccgatt ctttggggca ccggaagtag  22320
agggtgtact ccaagaagag gaagatgagg ctagacgtct ctgcatggag tatgagatgg  22380
actacggtgg gtacaatatg ctggatggag atgcgttcac ttctggtcta ctgactcgct  22440
aacattaata aataaggagg ctctaatggc actcattagc caatcaatca agaacttgaa  22500
gggtggtatc agccaacagc ctgacatcct tcgttatcca gaccaagggt cacgccaagt  22560
taacggttgg tcttcggaga ccgagggcct ccaaaagcgt ccacctcttg ttttcttaaa  22620
tacacttgga gacaacggtg cgttaggtca agctccgtac atccacctga ttaaccgaga  22680
tgagcacgaa cagtattacg ctgtgttcac tggtagcgga atccgagtgt tcgacctttc  22740
tggtaacgag aagcaagtta ggtatcctaa cggttccaac tacatcaaga ccgctaatcc  22800
acgtaacgac ctgcgaatgg ttactgtagc agactatacg ttcatcgtta accgtaacgt  22860
tgttgcacag aagaacacaa agtctgtcaa cttaccgaat tacaacccta atcaagacgg  22920
attgattaac gttcgtggtg gtcagtatgg tagggaacta attgtacaca ttaacggtaa  22980
agacgttgcg aagtataaga taccagatgg tagtcaacct gaacacgtaa acaatacgga  23040
tgcccaatgg ttagctgaag agttagccaa gcagatgcgc actaacttgt ctgattggac  23100
tgtaaatgta gggcaagggt tcatccatgt gaccgcacct agtggtcaac agattgactc  23160
cttcacgact aaagatggct acgcagacca gttgattaac cctgtgaccc actacgctca  23220
gtcgttctct aagctgccac ctaatgctcc taacggctac atggtgaaaa tcgtagggga  23280
```

```
cgcctctaag tctgccgacc agtattacgt tcggtatgac gctgagcgga aagtttggac  23340
tgagacttta ggttggaaca ctgaggacca agttctatgg gaaaccatgc cacacgctct  23400
tgtgcgagcc gctgacggta atttcgactt caagtggctt gagtggtctc ctaagtcttg  23460
tggtgacgtt gacaccaacc cttggccttc ttttgttggt tcaagtatta acgatgtgtt  23520
cttcttccgt aaccgcttag gattccttag tggggagaac atcatattga gtcgtacagc  23580
caaatacttc aacttctacc ctgcgtccat tgcgaacctt agtgatgacg accctataga  23640
cgtagctgtg agtaccaacc gaatagcaat ccttaagtac gccgttccgt tctcagaaga  23700
gttactcatc tggtccgatg aagcacaatt cgtcctgact gcctcgggta ctctcacatc  23760
taagtcggtt gagttgaacc taacgaccca gtttgacgta caggaccgag cgagaccttt  23820
tgggattggg cgtaatgtct actttgctag tccgaggtcc agcttcacgt ccatccacag  23880
gtactacgct gtgcaggatg tcagttccgt taagaatgct gaggacatta catcacacgt  23940
tcctaactac atccctaatg gtgtgttcag tatttgcgga agtggtacgg aaaacttctg  24000
ttcggtacta tctcacgggg accctagtaa aatcttcatg tacaaattcc tgtacctgaa  24060
cgaagagtta aggcaacagt cgtggtctca ttgggacttt ggggaaaacg tacaggttct  24120
agcttgtcag agtatcagct cagatatgta tgtgattctt cgcaatgagt tcaatacgtt  24180
cctagctaga atctctttca ctaagaacgc cattgactta cagggagaac cctatcgtgc  24240
ctttatggac atgaagattc gatacacgat tcctagtgga acatacaacg atgacacatt  24300
cactacctct attcatattc caacaattta tggtgcaaac ttcgggaggg gcaaaatcac  24360
tgtattggag cctgatggta agataaccgt gtttgagcaa cctacggctg ggtggaatag  24420
cgacccttgg ctgagactca gcggtaactt ggagggacgc atggtgtaca ttgggttcaa  24480
cattaacttc gtatatgagt tctctaagtt cctcatcaag cagactgccg acgacgggtc  24540
tacctccacg gaagacattg ggcgcttaca gttacgccga gcgtgggtta actacgagaa  24600
ctctggtacg tttgacattt atgttgagaa ccaatcgtct aactggaagt acacaatggc  24660
tggtgcccga ttaggctcta acactctgag ggctgggaga ctgaacttag ggaccggaca  24720
atatcgattc cctgtggttg gtaacgccaa gttcaacact gtatacatct tgtcagatga  24780
gactacccct ctgaacatca ttgggtgtgg ctgggaaggt aactacttac ggagaagttc  24840
cggtatttaa ttaaatattc tccctgtggt ggctcgaaat taatacgact cactataggg  24900
agaacaatac gactacggga gggttttctt atgatgacta taagacctac taaaagtaca  24960
gactttgagg tattcactcc ggctcaccat gacattcttg aagctaaggc tgctggtatt  25020
gagccgagtt tccctgatgc ttccgagtgt gtcacgttga gcctctatgg gttccctcta  25080
gctatcggtg gtaactgcgg ggaccagtgc tggttcgtta cgagcgacca agtgtggcga  25140
cttagtggaa aggctaagcg aaagttccgt aagttaatca tggagtatcg cgataagatg  25200
cttgagaagt atgatactct ttggaattac gtatgggtag gcaatacgtc ccacattcgt  25260
ttcctcaaga ctatcggtgc ggtattccat gaagagtaca cacgagatgg tcaatttcag  25320
ttatttacaa tcacgaaagg aggataacca tatgtgttgg gcagccgcaa tacctatcgc  25380
tatatctggc gctcaggcta tcagtggtca gaacgctcag gccaaaatga ttgccgctca  25440
gaccgctgct ggtcgtcgtc aagctatgga aatcatgagg cagacgaaca tccagaatgc  25500
tgacctatcg ttgcaagctc gaagtaaact tgaggaagcg tccgccgagt tgacctcaca  25560
gaacatgcag aaggtccaag ctattgggtc tatccgagcg gctatcggag agagtatgct  25620
```

-continued

```
tgaaggttcc tcaatggacc gcattaagcg agtcacagaa ggacagttca ttcgggaagc  25680
caatatggta actgagaact atcgccgtga ctaccaagca atcttcgcac agcaacttgg  25740
tggtactcaa agtgctgcaa gtcagattga cgaaatctat aagagcgaac agaaacagaa  25800
gagtaagcta cagatggttc tggacccact ggctatcatg gggtcttccg ctgcgagtgc  25860
ttacgcatcc ggtgcgttcg actctaagtc cacaactaag gcacctattg ttgccgctaa  25920
aggaaccaag acggggaggt aatgagctat gagtaaaatt gaatctgccc ttcaagcggc  25980
acaaccggga ctctctcggt tacgtggtgg tgctggaggt atgggctatc gtgcagcaac  26040
cactcaggcc gaacagccaa ggtcaagcct attggacacc attggtcggt tcgctaaggc  26100
tggtgccgat atgtataccg ctaaggaaca acgagcacga gacctagctg atgaacgctc  26160
taacgagatt atccgtaagc tgacccctga gcaacgtcga gaagctctca acaacgggac  26220
ccttctgtat caggatgacc catacgctat ggaagcactc cgagtcaaga ctggtcgtaa  26280
cgctgcgtat cttgtggacg atgacgttat gcagaagata aaagagggtg tcttccgtac  26340
tcgcgaagag atggaagagt atcgccatag tcgccttcaa gagggcgcta aggtatacgc  26400
tgagcagttc ggcatcgacc ctgaggacgt tgattatcag cgtggtttca acggggacat  26460
taccgagcgt aacatctcgc tgtatggtgc gcatgataac ttcttgagcc agcaagctca  26520
gaagggcgct atcatgaaca gccgagtgga actcaacggt gtccttcaag accctgatat  26580
gctgcgtcgt ccagactctg ctgacttctt tgagaagtat atcgacaacg gtctggttac  26640
tggcgcaatc ccatctgatg ctcaagccac acagcttata agccaagcgt tcagtgacgc  26700
ttctagccgt gctggtggtg ctgacttcct gatgcgagtc ggtgacaaga aggtaacact  26760
taacggagcc actacgactt accgagagtt gattggtgag gaacagtgga acgctctcat  26820
ggtcacagca caacgttctc agtttgagac tgacgcgaag ctgaacgagc agtatcgctt  26880
gaagattaac tctgcgctga accaagagga cccaaggaca gcttgggaga tgcttcaagg  26940
tatcaaggct gaactagata aggtccaacc tgatgagcag atgacaccac aacgtgagtg  27000
gctaatctcc gcacaggaac aagttcagaa tcagatgaac gcatggacga aagctcaggc  27060
caaggctctg gacgattcca tgaagtcaat gaacaaactt gacgtaatcg acaagcaatt  27120
ccagaagcga atcaacggtg agtgggtctc aacggatttt aaggatatgc cagtcaacga  27180
gaacactggt gagttcaagc atagcgatat ggttaactac gccaataaga agctcgctga  27240
gattgacagt atggacattc cagacggtgc caaggatgct atgaagttga agtaccttca  27300
agcggactct aaggacggag cattccgtac agccatcgga accatggtca ctgacgctgg  27360
tcaagagtgg tctgccgctg tgattaacgg taagttacca gaacgaaccc cagctatgga  27420
tgctctgcgc agaatccgca atgctgaccc tcagttgatt gctgcgctat acccagacca  27480
agctgagcta ttcctgacga tggacatgat ggacaagcag ggtattgacc ctcaggttat  27540
tcttgatgcc gaccgactga ctgttaagcg gtccaaagag caacgctttg aggatgataa  27600
agcattcgag tctgcactga atgcatctaa ggctcctgag attgcccgta tgccagcgtc  27660
actgcgcgaa tctgcacgta agatttatga ctccgttaag tatcgctcgg ggaacgaaag  27720
catggctatg gagcagatga ccaagttcct taaggaatct acctacacgt tcactggtga  27780
tgatgttgac ggtgataccg ttggtgtgat tcctaagaat atgatgcagg ttaactctga  27840
cccgaaatca tgggagcaag gtcgggatat tctggaggaa gcacgtaagg gaatcattgc  27900
gagcaaccct tggataacca ataagcaact gaccatgtat tctcaaggtg actccattta  27960
ccttatggac accacaggtc aagtcagagt ccgatacgac aaagagttac tctcgaaggt  28020
```

ctggagtgag aaccagaaga aactcgaaga gaaagctcgt gagaaggctc tggctgatgt 28080
gaacaagcga gcacctatag ttgccgctac gaaggcccgt gaagctgctg ctaaacgagt 28140
ccgagagaaa cgtaaacaga ctcctaagtt catctacgga cgtaaggagt aactaaaggc 28200
tacataagga ggccctaaat ggataagtac gataagaacg taccaagtga ttatgatggt 28260
ctgttccaaa aggctgctga tgccaacggg gtctcttatg accttttacg taaagtcgct 28320
tggacagaat cacgatttgt gcctacagca aaatctaaga ctggaccatt aggcatgatg 28380
caatttacca aggcaaccgc taaggccctc ggtctgcgag ttaccgatgg tccagacgac 28440
gaccgactga accctgagtt agctattaat gctgccgcta agcaacttgc aggtctggta 28500
gggaagtttg atggcgatga actcaaagct gcccttgcgt acaaccaagg cgagggacgc 28560
ttgggtaatc cacaacttga ggcgtactct aagggagact tcgcatcaat ctctgaggag 28620
ggacgtaact acatgcgtaa ccttctggat gttgctaagt cacctatggc tggacagttg 28680
gaaacttttg gtggcataac cccaaagggt aaaggcattc cggctgaggt aggattggct 28740
ggaattggtc acaagcagaa agtaacacag gaacttcctg agtccacaag ttttgacgtt 28800
aagggtatcg aacaggaggc tacggcgaaa ccattcgcca aggacttttg ggagacccac 28860
ggagaaacac ttgacgagta caacagtcgt tcaaccttct tcggattcaa aaatgctgcc 28920
gaagctgaac tctccaactc agtcgctggg atggctttcc gtgctggtcg tctcgataat 28980
ggttttgatg tgtttaaaga caccattacg ccgactcgct ggaactctca catctggact 29040
ccagaggagt tagagaagat tcgaacagag gttaagaacc ctgcgtacat caacgttgta 29100
actggtggtt cccctgagaa cctcgatgac ctcattaaat tggctaacga gaactttgag 29160
aatgactccc gcgctgccga ggctggccta ggtgccaaac tgagtgctgg tattattggt 29220
gctggtgtgg acccgcttag ctatgttcct atggtcggtg tcactggtaa gggctttaag 29280
ttaatcaata aggctcttgt agttggtgcc gaaagtgctg ctctgaacgt tgcatccgaa 29340
ggtctccgta cctccgtagc tggtggtgac gcagactatg cgggtgctgc cttaggtggc 29400
tttgtgtttg gcgcaggcat gtctgcaatc agtgacgctg tagctgctgg actgaaacgc 29460
agtaaaccag aagctgagtt cgacaatgag ttcatcggtc ctatgatgcg attggaagcc 29520
cgtgagacag cacgaaacgc caactctgcg gacctctctc ggatgaacac tgagaacatg 29580
aagtttgaag gtgaacataa tggtgtccct tatgaggact taccaacaga gagaggtgcc 29640
gtggtgttac atgatggctc cgttctaagt gcaagcaacc caatcaaccc taagactcta 29700
aaagagttct ccgaggttga ccctgagaag gctgcgcgag gaatcaaact ggctgggttc 29760
accgagattg gcttgaagac cttggggtct gacgatgctg acatccgtag agtggctatc 29820
gacctcgttc gctctcctac tggtatgcag tctggtgcct caggtaagtt cggtgcaaca 29880
gcttctgaca tccatgagag acttcatggt actgaccagc gtacttataa tgacttgtac 29940
aaagcaatgt ctgacgctat gaaagaccct gagttctcta ctggcggcgc taagatgtcc 30000
cgtgaagaaa ctcgatacac tatctaccgt agagcggcac tagctattga gcgtccagaa 30060
ctacagaagg cactcactcc gtctgagaga atcgttatgg acatcattaa gcgtcacttt 30120
gacaccaagc gtgaacttat ggaaaaccca gcaatattcg gtaacacaaa ggctgtgagt 30180
atcttccctg agagtcgcca caaaggtact tacgttcctc acgtatatga ccgtcatgcc 30240
aaggcgctga tgattcaacg ctacggtgcc gaaggtttgc aggaagggat tgcccgctca 30300
tggatgaaca gctacgtctc cagacctgag gtcaaggcca gagtcgatga gatgcttaag 30360

-continued

```
gaattacacg gggtgaagga agtaacacca gagatggtag agaagtacgc tatggataag  30420
gcttatggta tctcccactc agaccagttc accaacagtt ccataataga agagaacatt  30480
gagggcttag taggtatcga gaataactca ttccttgagg cacgtaactt gtttgattcg  30540
gacctatcca tcactatgcc agacggacag caattctcag tgaatgacct aagggacttc  30600
gatatgttcc gcatcatgcc agcgtatgac cgccgtgtca atggtgacat cgccatcatg  30660
gggtctactg gtaaaaccac taaggaactt aaggatgaga ttttggctct caaagcgaaa  30720
gctgagggag acggtaagaa gactggcgag gtacatgctt taatggatac cgttaagatt  30780
cttactggtc gtgctagacg caatcaggac actgtgtggg aaacctcact gcgtgccatc  30840
aatgacctag ggttcttcgc taagaacgcc tacatgggtg ctcagaacat tacggagatt  30900
gctgggatga ttgtcactgg taacgttcgt gctctagggc atggtatccc aattctgcgt  30960
gatacactct acaagtctaa accagtttca gctaaggaac tcaaggaact ccatgcgtct  31020
ctgttcggga aggaggtgga ccagttgatt cggcctaaac gtgctgacat tgtgcagcgc  31080
ctaagggaag caactgatac cggacctgcc gtggcgaaca tcgtagggac cttgaagtat  31140
tcaacacagg aactggctgc tcgctctccg tggactaagc tactgaacgg aaccactaac  31200
taccttctgg atgctgcgcg tcaaggtatg cttggggatg ttattagtgc caccctaaca  31260
ggtaagacta cccgctggga gaaagaaggc ttccttcgtg gtgcctccgt aactcctgag  31320
cagatggctg gcatcaagtc tctcatcaag gaacatatgg tacgcggtga ggacgggaag  31380
tttaccgtta aggacaagca agcgttctct atggacccac gggctatgga cttatggaga  31440
ctggctgaca aggtagctga tgaggcaatg ctgcgtccac ataaggtgtc cttacaggat  31500
tcccatgcgt tcggagcact aggtaagatg gttatgcagt ttaagtcttt cactatcaag  31560
tcccttaact ctaagttcct gcgaaccttc tatgatggat acaagaacaa ccgagcgatt  31620
gacgctgcgc tgagcatcat cacctctatg ggtctcgctg gtggtttcta tgctatggct  31680
gcacacgtca aagcatacgc tctgcctaag gagaaacgta aggagtactt ggagcgtgca  31740
ctggacccaa ccatgattgc ccacgctgcg ttatctcgta gttctcaatt gggtgctcct  31800
ttggctatgg ttgacctagt tggtggtgtt ttagggttcg agtcctccaa gatggctcgc  31860
tctacgattc tacctaagga caccgtgaag gaacgtgacc caaacaaacc gtacacctct  31920
agagaggtaa tgggcgctat gggttcaaac cttctggaac agatgccttc ggctggcttt  31980
gtggctaacg taggggctac cttaatgaat gctgctggcg tggtcaactc acctaataaa  32040
gcaaccgagc aggacttcat gactggtctt atgaactcca caaaagagtt agtaccgaac  32100
gacccattga ctcaacagct tgtgttgaag atttatgagg cgaacggtgt taacttgagg  32160
gagcgtagga aataatacga ctcactatag ggagaggcga aataatcttc tccctgtagt  32220
ctcttagatt tactttaagg aggtcaaatg gctaacgtaa ttaaaaccgt tttgacttac  32280
cagttagatg gctccaatcg tgattttaat atcccgtttg agtatctagc ccgtaagttc  32340
gtagtggtaa ctcttattgg tgtagaccga aaggtcctta cgattaatac agactatcgc  32400
tttgctacac gtactactat ctctctgaca aaggcttggg gtccagccga tggctacacg  32460
accatcgagt tacgtcgagt aacctccact accgaccgat tggttgactt tacggatggt  32520
tcaatcctcc gcgcgtatga ccttaacgtc gctcagattc aaacgatgca cgtagcggaa  32580
gaggcccgtg acctcactac ggatactatc ggtgtcaata acgatggtca cttggatgct  32640
cgtggtcgtc gaattgtgaa cctagcgaac gccgtggatg accgcgatgc tgttccgttt  32700
ggtcaactaa agaccatgaa ccagaactca tggcaagcac gtaatgaagc cttacagttc  32760
```

```
cgtaatgagg ctgagacttt cagaaaccaa gcggagggct ttaagaacga gtccagtacc  32820
aacgctacga acacaaagca gtggcgcgat gagaccaagg gtttccgaga cgaagccaag  32880
cggttcaaga atacggctgg tcaatacgct acatctgctg ggaactctgc ttccgctgcg  32940
catcaatctg aggtaaacgc tgagaactct gccacagcat ccgctaactc tgctcatttg  33000
gcagaacagc aagcagaccg tgcggaacgt gaggcagaca agctggaaaa ttacaatgga  33060
ttggctggtg caattgataa ggtagatgga accaatgtgt actggaaagg aaatattcac  33120
gctaacgggc gcctttacat gaccacaaac ggttttgact gtggccagta tcaacagttc  33180
tttggtggtg tcactaatcg ttactctgtc atggagtggg gagatgagaa cggatggctg  33240
atgtatgttc aacgtagaga gtggacaaca gcgataggcg gtaacatcca gttagtagta  33300
aacggacaga tcatcaccca aggtggagcc atgaccggtc agctaaaatt gcagaatggg  33360
catgttcttc aattagagtc cgcatccgac aaggcgcact atattctatc taaagatggt  33420
aacaggaata actggtacat tggtagaggg tcagataaca acaatgactg taccttccac  33480
tcctatgtac atggtacgac cttaacactc aagcaggact atgcagtagt taacaaacac  33540
ttccacgtag gtcaggccgt tgtggccact gatggtaata ttcaaggtac taagtgggga  33600
ggtaaatggc tggatgctta cctacgtgac agcttcgttg cgaagtccaa ggcgtggact  33660
caggtgtggt ctggtagtgc tggcggtggg gtaagtgtga ctgtttcaca ggatctccgc  33720
ttccgcaata tctggattaa gtgtgccaac aactcttgga acttcttccg tactggcccc  33780
gatggaatct acttcatagc ctctgatggt ggatggttac gattccaaat acactccaac  33840
ggtctcggat tcaagaatat tgcagacagt cgttcagtac ctaatgcaat catggtggag  33900
aacgagtaat tggtaaatca caaggaaaga cgtgtagtcc acggatggac tctcaaggag  33960
gtacaaggtg ctatcattag actttaacaa cgaattgatt aaggctgctc caattgttgg  34020
gacgggtgta gcagatgtta gtgctcgact gttctttggg ttaagcctta acgaatggtt  34080
ctacgttgct gctatcgcct acacagtggt tcagattggt gccaaggtag tcgataagat  34140
gattgactgg aagaaagcca ataaggagtg atatgtatgg aaaaggataa gagccttatt  34200
acattcttag agatgttgga cactgcgatg gctcagcgta tgcttgcgga cctttcggac  34260
catgagcgtc gctctccgca actctataat gctattaaca aactgttaga ccgccacaag  34320
ttccagattg gtaagttgca gccggatgtt cacatcttag gtggccttgc tggtgctctt  34380
gaagagtaca aagagaaagt cggtgataac ggtcttacgg atgatgatat ttacacatta  34440
cagtgatata ctcaaggcca ctacagatag tggtctttat ggatgtcatt gtctatacga  34500
gatgctccta cgtgaaatct gaaagttaac gggaggcatt atgctagaat ttttacgtaa  34560
gctaatccct tgggttctcg ctgggatgct attcgggtta ggatggcatc tagggtcaga  34620
ctcaatggac gctaaatgga aacaggaggt acacaatgag tacgttaaga gagttgaggc  34680
tgcgaagagc actcaaagag caatcgatgc ggtatctgct aagtatcaag aagaccttgc  34740
cgcgctggaa gggagcactg ataggattat ttctgatttg cgtagcgaca ataagcggtt  34800
gcgcgtcaga gtcaaaacta ccggaacctc cgatggtcag tgtggattcg agcctgatgg  34860
tcgagccgaa cttgacgacc gagatgctaa acgtattctc gcagtgaccc agaagggtga  34920
cgcatggatt cgtgcgttac aggatactat tcgtgaactg caacgtaagt aggaaatcaa  34980
gtaaggaggc aatgtgtcta ctcaatccaa tcgtaatgcg ctcgtagtgg cgcaactgaa  35040
aggagacttc gtggcgttcc tattcgtctt atggaaggcg ctaaacctac cggtgcccac  35100
```

taagtgtcag attgacatgg ctaaggtgct ggcgaatgga gacaacaaga agttcatctt 35160
acaggctttc cgtggtatcg gtaagtcgtt catcacatgt gcgttcgttg tgtggtcctt 35220
atggagagac cctcagttga agatacttat cgtatcagcc tctaaggagc gtgcagacgc 35280
taactccatc tttattaaga acatcattga cctgctgcca ttcctatctg agttaaagcc 35340
aagacccgga cagcgtgact cggtaatcag ctttgatgta ggcccagcca atcctgacca 35400
ctctcctagt gtgaaatcag taggtatcac tggtcagtta actggtagcc gtgctgacat 35460
tatcattgcg gatgacgttg agattccgtc taacagcgca actatgggtg cccgtgagaa 35520
gctatggact ctggttcagg agttcgctgc gttacttaaa ccgctgcctt cctctcgcgt 35580
tatctacctt ggtacacctc agacagagat gactctctat aaggaacttg aggataaccg 35640
tgggtacaca accattatct ggcctgctct gtacccaagg acacgtgaag agaacctcta 35700
ttactcacag cgtcttgctc ctatgttacg cgctgagtac gatgagaacc ctgaggcact 35760
tgctgggact ccaacagacc cagtgcgctt tgaccgtgat gacctgcgcg agcgtgagtt 35820
ggaatacggt aaggctggct ttacgctaca gttcatgctt aaccctaacc ttagtgatgc 35880
cgagaagtac ccgctgaggc ttcgtgacgc tatcgtagcg gccttagact tagagaaggc 35940
cccaatgcat taccagtggc ttccgaaccg tcagaacatc attgaggacc ttcctaacgt 36000
tggccttaag ggtgatgacc tgcatacgta ccacgattgt tccaacaact caggtcagta 36060
ccaacagaag attctggtca ttgaccctag tggtcgcggt aaggacgaaa caggttacgc 36120
tgtgctgtac acactgaacg gttacatcta ccttatggaa gctggaggtt tccgtgatgg 36180
ctactccgat aagacccttg agttactcgc taagaaggca aagcaatggg gagtccagac 36240
ggttgtctac gagagtaact tcggtgacgg tatgttcggt aaggtattca gtcctatcct 36300
tcttaaacac cacaactgtg cgatggaaga gattcgtgcc cgtggtatga aagagatgcg 36360
tatttgcgat acccttgagc cagtcatgca gactcaccgc cttgtaattc gtgatgaggt 36420
cattagggcc gactaccagt ccgctcgtga cgtagacggt aagcatgacg ttaagtactc 36480
gttgttctac cagatgaccc gtatcactcg tgagaaaggc gctctggctc atgatgaccg 36540
attggatgcc cttgcgttag gcattgagta tctccgtgag tccatgcagt tggattccgt 36600
taaggtcgag ggtgaagtac ttgctgactt ccttgaggaa cacatgatgc gtcctacggt 36660
tgctgctacg catatcattg agatgtctgt gggaggagtt gatgtgtact ctgaggacga 36720
tgagggttac ggtacgtctt tcattgagtg gtgatttatg cattaggact gcatagggat 36780
gcactataga ccacggatgg tcagttcttt aagttactga aaagacacga taaattaata 36840
cgactcacta tagggagagg agggacgaaa ggttactata tagatactga atgaatactt 36900
atagagtgca taaagtatgc ataatggtgt acctagagtg acctctaaga atggtgatta 36960
tattgtatta gtatcacctt aacttaagga ccaacataaa gggaggagac tcatgttccg 37020
cttattgttg aacctactgc ggcatagagt cacctaccga tttcttgtgg tactttgtgc 37080
tgcccttggg tacgcatctc ttactggaga cctcagttca ctggagtctg tcgtttgctc 37140
tatactcact tgtagcgatt agggtcttcc tgaccgactg atggctcacc gagggattca 37200
gcggtatgat tgcatcacac cacttcatcc ctatagagtc aagtcctaag gtatacccat 37260
aaagagcctc taatggtcta tcctaaggtc tatacctaaa gataggccat cctatcagtg 37320
tcacctaaag agggtcttag agagggccta tggagttcct atagggtcct ttaaaatata 37380
ccataaaaat ctgagtgact atctcacagt gtacggacct aaagttcccc catagggggt 37440
acctaaagcc cagccaatca cctaaagtca accttcggtt gaccttgagg gttccctaag 37500
ggttggggat gacccttggg tttgtctttg ggtgttacct tgagtgtctc tctgtgtccc 37560
t 37561

<210> SEQ ID NO 70
<211> LENGTH: 37564
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
tctcacagtg tacggaccta aagttccccc atagggggta cctaaagccc agccaatcac 60
ctaaagtcaa ccttcggttg accttgaggg ttccctaagg gttggggatg acccttgggt 120
ttgtctttgg gtgttacctt gagtgtctct ctgtgtccct atctgttaca gtctcctaaa 180
gtatcctcct aaagtcacct cctaacgtcc atcctaaagc caacacctaa agcctacacc 240
taaagaccca tcaagtcaac gcctatctta aagtttaaac ataaagacca gacctaaaga 300
ccagacctaa agacactaca taaagaccag acctaaagac gccttgttgt tagccataaa 360
gtgataacct ttaatcattg tctttattaa tacaactcac tataaggaga gacaacttaa 420
agagacttaa aagattaatt taaaatttat caaaaagagt attgacttaa agtctaacct 480
ataggatact tacagccatc gagagggaca cggcgaatag ccatcccaat cgacaccggg 540
gtcaaccgga taagtagaca gcctgataag tcgcacgaca gaaagaaatt gaccgcgcta 600
aggcccgtaa agaacgtcac gaggggcgct tagaggcacg cagattcaaa cgtcgcaacc 660
gcaaggcacg taaagcacac aaagctaagc gcgaaagaat gcttgctgcg tggcgatggg 720
ctgaacgtca agaacggcgt aaccatgagg tagctgtaga tgtactagga agaaccaata 780
acgctatgct ctgggtcaac atgttctctg ggactttaa ggcgcttgag gaacgaatcg 840
cgctgcactg gcgtaatgct gaccggatgg ctatcgctaa tggtcttacg ctcaacattg 900
ataagcaact tgacgcaatg ttaatgggct gatagtctta tcttacaggt catctgcggg 960
tggcctgaat aggtacgatt tactaactgg aagaggcact aaatgaacac gattaacatc 1020
gctaagaacg acttctctga catcgaactg gctgctatcc cgttcaacac tctggctgac 1080
cattacggtg agcgtttagc tcgcgaacag ttggcccttg agcatgagtc ttacgagatg 1140
ggtgaagcac gcttccgcaa gatgtttgag cgtcaactta aagctggtga ggttgcggat 1200
aacgctgccg ccaagcctct catcactacc ctactcccta agatgattgc acgcatcaac 1260
gactggtttg aggaagtgaa agctaagcgc ggcaagcgcc cgacagcctt ccagttcctg 1320
caagaaatca agccggaagc cgtagcgtac atcaccatta agaccactct ggcttgccta 1380
accagtgctg acaatacaac cgttcaggct gtagcaagcg caatcggtcg ggccattgag 1440
gacgaggctc gcttcggtcg tatccgtgac cttgaagcta agcacttcaa gaaaaacgtt 1500
gaggaacaac tcaacaagcg cgtagggcac gtctacaaga aagcatttat gcaagttgtc 1560
gaggctgaca tgctctctaa gggtctactc ggtggcgagg cgtggtcttc gtggcataag 1620
gaagactcta ttcatgtagg agtacgctgc atcgagatgc tcattgagtc aaccggaatg 1680
gttagcttac accgccaaaa tgctggcgta gtaggtcaag actctgagac tatcgaactc 1740
gcacctgaat acgctgaggc tatcgcaacc cgtgcaggtg cgctggctgg catctctccg 1800
atgttccaac cttgcgtagt tcctcctaag ccgtggactg gcattactgg tggtggctat 1860
tgggctaacg gtcgtcgtcc tctggcgctg gtgcgtactc acagtaagaa agcactgatg 1920

-continued

```
cgctacgaag acgtttacat gcctgaggtg tacaaagcga ttaacattgc gcaaaacacc   1980
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
gtgacggtgg tagctgcggt tgaagcaatg aactggctta agtctgctgc taagctgctg   3120
gctgctgagg tcaaagataa gaagactgga gagattcttc gcaagcgttg cgctgtgcat   3180
tgggtaactc ctgatggttt ccctgtgtgg caggaataca agaagcctat tcagacgcgc   3240
ttgaacctga tgttcctcgg tcagttccgc ttacagccta ccattaacac caacaaagat   3300
agcgagattg atgcacacaa acaggagtct ggtatcgctc ctaactttgt acacagccaa   3360
gacggtagcc accttcgtaa gactgtagtg tgggcacacg agaagtacgg aatcgaatct   3420
tttgcactga ttcacgactc cttcggtacc attccggctg acgctgcgaa cctgttcaaa   3480
gcagtgcgcg aaactatggt tgacacatat gagtcttgtg atgtactggc tgatttctac   3540
gaccagttcg ctgaccagtt gcacgagtct caattggaca aaatgccagc acttccggct   3600
aaaggtaact tgaacctccg tgacatctta gagtcggact tcgcgttcgc gtaacgccaa   3660
atcaatacga ctcactatag agggacaaac tcaaggtcat tcgcaagagt ggcctttatg   3720
attgaccttc ttccggttaa tacgactcac tataggagaa ccttaaggtt taactttaag   3780
acccttaagt gttaattaga gatttaaatt aaagaattac taagagagga ctttaagtat   3840
gcgtaacttc gaaaagatga ccaaacgttc taaccgtaat gctcgtgact tcgaggcaac   3900
caaaggtcgc aagttgaata agactaagcg tgaccgctct cacaagcgta gctgggaggg   3960
tcagtaagat gggacgttta tatagtggta atctggcagc attcaaggca gcaacaaaca   4020
agctgttcca gttagactta gcggtcattt atgatgactg gtatgatgcc tatacaagaa   4080
aagattgcat acggttacgt attgaggaca ggagtggaaa cctgattgat actagcacct   4140
tctaccacca cgacgaggac gttctgttca atatgtgtac tgattggttg aaccatatgt   4200
atgaccagtt gaaggactgg aagtaatacg actcagtata gggacaatgc ttaaggtcgc   4260
```

-continued

```
tctctaggag tggccttagt catttaacca ataggagata aacattatga tgaacattaa   4320
gactaacccg tttaaagccg tgtctttcgt agagtctgcc attaagaagg ctctggataa   4380
cgctgggtat cttatcgctg aaatcaagta cgatggtgta cgcgggaaca tctgcgtaga   4440
caatactgct aacagttact ggctctctcg tgtatctaaa acgattccgg cactggagca   4500
cttaaacggg tttgatgttc gctggaagcg tctactgaac gatgaccgtt gcttctacaa   4560
agatggcttt atgcttgatg gggaactcat ggtcaagggc gtagacttta acacagggtc   4620
cggcctactg cgtaccaaat ggactgacac gaagaaccaa gagttccatg aagagttatt   4680
cgttgaacca atccgtaaga aagataaagt tccctttaag ctgcacactg gacaccttca   4740
cataaaactg tacgctatcc tcccgctgca catcgtggag tctggagaag actgtgatgt   4800
catgacgttg ctcatgcagg aacacgttaa gaacatgctg cctctgctac aggaatactt   4860
ccctgaaatc gaatggcaag cggctgaatc ttacgaggtc tacgatatgg tagaactaca   4920
gcaactgtac gagcagaagc gagcagaagg ccatgagggt ctcattgtga aagacccgat   4980
gtgtatctat aagcgcggta agaaatctgg ctggtggaaa atgaaacctg agaacgaagc   5040
tgacggtatc attcagggtc tggtatgggg tacaaaaggt ctggctaatg aaggtaaagt   5100
gattggtttt gaggtgcttc ttgagagtgg tcgtttagtt aacgccacga atatctctcg   5160
cgccttaatg gatgagttca ctgagacagt aaaagaggcc accctaagtc aatggggatt   5220
ctttagccca tacggtattg gcgacaacga tgcttgtact attaaccctt acgatggctg   5280
ggcgtgtcaa attagctaca tggaggaaac acctgatggc tctttgcggc acccatcgtt   5340
cgtaatgttc cgtggcaccg aggacaaccc tcaagagaaa atgtaatcac actggctcac   5400
cttcgggtgg gcctttctgc gtttataagg agacacttta tgtttaagaa ggttggtaaa   5460
ttccttgcgg ctttggcagc tatcctgacg cttgcgtata ttcttgcggt ataccctcaa   5520
gtagcactag tagtagttgg cgcttgttac ttagcggcag tgtgtgcttg cgtgtggagt   5580
atagttaact ggtaatacga ctcactaaag gaggtacaca ccatgatgta cttaatgcca   5640
ttactcatcg tcattgtagg atgccttgcg ctccactgta gcgatgatga tatgccagat   5700
ggtcacgctt aatacgactc actaaaggag acactatatg tttcgacttc attacaacaa   5760
aagcgttaag aatttcacgg ttcgccgtgc tgaccgttca atcgtatgtg cgagcgagcg   5820
ccgagctaag atacctctta ttggtaacac agttcctttg gcaccgagcg tccacatcat   5880
tatcacccgt ggtgactttg agaaagcaat agacaagaaa cgtccggttc ttagtgtggc   5940
agtgacccgc ttcccgttcg tccgtctgtt actcaaacga atcaaggagg tgttctgatg   6000
ggactgttag atggtgaagc ctgggaaaaa gaaaacccgc cagtacaagc aactgggtgt   6060
atagcttgct tagagaaaga tgaccgttat ccacacacct gtaacaaagg agctaacgat   6120
atgaccgaac gtgaacaaga gatgatcatt aagttgatag acaataatga aggtcgccca   6180
gatgatttga atggctgcgg tattctctgc tccaatgtcc cttgccacct ctgccccgca   6240
aataacgatc aaaagataac cttaggtgaa atccgagcga tggacccacg taaaccacat   6300
ctgaataaac ctgaggtaac tcctacagat gaccagcctt ccgctgagac aatcgaaggt   6360
gtcactaagc cttcccacta catgctgttt gacgacattg aggctatcga agtgattgct   6420
cgttcaatga ccgttgagca gttcaaggga tactgcttcg gtaacatctt aaagtacaga   6480
ctacgtgctg gtaagaagtc agagttagcg tacttagaga aagacctagc gaaagcagac   6540
ttctataaag aactctttga gaaacataag gataaatgtt atgcataact tcaagtcaac   6600
cccacctgcc gacagcctat ctgatgactt cacatcttgc tcagagtggt gccgaaagat   6660
```

```
gtgggaagag acattcgacg atgcgtacat caagctgtat gaactttgga aatcgagagg   6720
tcaatgacta tgtcaaacgt aaatacaggt tcacttagtg tggacaataa gaagttttgg   6780
gctaccgtag agtcctcgga gcattccttc gaggttccaa tctacgctga gaccctagac   6840
gaagctctgg agttagccga atggcaatac gttccggctg gctttgaggt tactcgtgtg   6900
cgtccttgtg tagcaccgaa gtaatacgac tcactattag ggaagactcc ctctgagaaa   6960
ccaaacgaaa cctaaaggag attaacatta tggctaagaa gattttcacc tctgcgctgg   7020
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac tacctttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
```

-continued

```
ttggaagtcg ttgcgtggat ttatagaact aggagggaat tgcatggaca attcgcacga   9060
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgatgac tttccagacg actacgagaa gtttcgctgg agagtcccat  10800
tctaatacga ctcactaaag gagacacacc atgttcaaac tgattaagaa gttaggccaa  10860
ctgctggttc gtatgtacaa cgtggaagcc aagcgactga acgatgaggc tcgtaaagag  10920
gccacacagt cacgcgctct ggcgattcgc tccaacgaac tggctgacag tgcatccact  10980
aaagttaccg aggctgcccg tgtggcaaac caagctcaac agctttccaa attctttgag  11040
taatcaaaca ggagaaacca ttatgtctaa cgtagctgaa actatccgtc tatccgatac  11100
agctgaccag tggaaccgtc gagtccacat caacgttcgc aacggtaagg cgactatggt  11160
ttaccgctgg aaggactcta agtcctctaa gaatcacact cagcgtatga cgttgacaga  11220
tgagcaagca ctgcgtctgg tcaatgcgct taccaaagct gccgtgacag caattcatga  11280
agctggtcgc gtcaatgaag ctatggctat cctcgacaag attgataact aagagtggta  11340
tcctcaaggt cgccaaagtg gtggccttca tgaatactat tcgactcact ataggagata  11400
```

ttaccatgcg tgaccctaaa gttatccaag cagaaatcgc taaactggaa gctgaactgg 11460
aggacgttaa gtaccatgaa gctaagactc gctccgctgt tcacatcttg aagaacttag 11520
gctggacttg gacaagacag actggctgga agaaaccaga agttaccaag ctgagtcata 11580
aggtgttcga taaggacact atgacccaca tcaaggctgg tgattgggtt aaggttgaca 11640
tgggagttgt tggtggatac ggctacgtcc gctcagttag tggcaaatat gcacaagtgt 11700
catacatcac aggtgttact ccacgcggtg caatcgttgc cgataagacc aacatgattc 11760
acacaggttt cttgacagtt gtttcatatg aagagattgt taagtcacga taatcaatag 11820
gagaaatcaa tatgatcgtt tctgacatcg aagctaacgc cctcttagag agcgtcacta 11880
agttccactg cggggttatc tacgactact ccaccgctga gtacgtaagc taccgtccga 11940
gtgacttcgg tgcgtatctg gatgcgctgg aagccgaggt tgcacgaggc ggtcttattg 12000
tgttccacaa cggtcacaag tatgacgttc ctgcattgac caaactggca aagttgcaat 12060
tgaaccgaga gttccacctt cctcgtgaga actgtattga cacccttgtg ttgtcacgtt 12120
tgattcattc caacctcaag gacaccgata tgggtcttct gcgttccggc aagttgcccg 12180
gaaaacgctt tgggtctcac gctttggagg cgtggggtta tcgcttaggc gagatgaagg 12240
gtgaatacaa agacgacttt aagcgtatgc ttgaagagca gggtgaagaa tacgttgacg 12300
gaatggagtg gtggaacttc aacgaagaga tgatggacta taacgttcag gacgttgtgg 12360
taactaaagc tctccttgag aagctactct ctgacaaaca ttacttccct cctgagattg 12420
actttacgga cgtaggatac actacgttct ggtcagaatc ccttgaggcc gttgacattg 12480
aacatcgtgc tgcatggctg ctcgctaaac aagagcgcaa cgggttcccg tttgacacaa 12540
aagcaatcga agagttgtac gtagagttag ctgctcgccg ctctgagttg ctccgtaaat 12600
tgaccgaaac gttcggctcg tggtatcagc ctaaaggtgg cactgagatg ttctgccatc 12660
cgcgaacagg taagccacta cctaaatacc ctcgcattaa gacacctaaa gttggtggta 12720
tctttaagaa gcctaagaac aaggcacagc gagaaggccg tgagccttgc gaacttgata 12780
cccgcgagta cgttgctggt gctccttaca ccccagttga acatgttgtg tttaaccctt 12840
cgtctcgtga ccacattcag aagaaactcc aagaggctgg gtgggtcccg accaagtaca 12900
ccgataaggg tgctcctgtg gtggacgatg aggtactcga aggagtacgt gtagatgacc 12960
ctgagaagca agccgctatc gacctcatta aagagtactt gatgattcag aagcgaatcg 13020
gacagtctgc tgagggagac aaagcatggc ttcgttatgt tgctgaggat ggtaagattc 13080
atggttctgt taaccctaat ggagcagtta cgggtcgtgc gacccatgcg ttcccaaacc 13140
ttgcgcaaat tccgggtgta cgttctcctt atggagagca gtgtcgcgct gcttttggcg 13200
ctgagcacca tttggatggg ataactggta agccttgggt tcaggctggc atcgacgcat 13260
ccggtcttga gctacgctgc ttggctcact tcatggctcg ctttgataac ggcgagtacg 13320
ctcacgagat tcttaacggc gacatccaca ctaagaacca gatagctgct gaactaccta 13380
cccgagataa cgctaagacg ttcatctatg ggttcctcta tggtgctggt gatgagaaga 13440
ttggacagat tgttggtgct ggtaaagagc gcggtaagga actcaagaag aaattccttg 13500
agaacacccc cgcgattgca gcactccgcg agtctatcca acagacactt gtcgagtcct 13560
ctcaatgggt agctggtgag caacaagtca agtggaaacg ccgctggatt aaaggtctgg 13620
atggtcgtaa ggtacacgtt cgtagtcctc acgctgcctt gaatacccta ctgcaatctg 13680
ctggtgctct catctgcaaa ctgtggatta tcaagaccga agagatgctc gtagagaaag 13740
gcttgaagca tggctgggat ggggactttg cgtacatggc atgggtacat gatgaaatcc 13800
aagtaggctg ccgtaccgaa gagattgctc aggtggtcat tgagaccgca caagaagcga 13860
tgcgctgggt tggagaccac tggaacttcc ggtgtcttct ggataccgaa ggtaagatgg 13920
gtcctaattg ggcgatttgc cactgataca ggaggctact catgaacgaa agacacttaa 13980
caggtgctgc ttctgaaatg ctagtagcct acaaatttac caaagctggg tacactgtct 14040
attaccctat gctgactcag agtaaagagg acttggttgt atgtaaggat ggtaaattta 14100
gtaaggttca ggttaaaaca gccacaacgg ttcaaaccaa cacaggagat gccaagcagg 14160
ttaggctagg tggatgcggt aggtccgaat ataaggatgg agactttgac attcttgcgg 14220
ttgtggttga cgaagatgtg cttattttca catgggacga agtaaaaggt aagacatcca 14280
tgtgtgtcgg caagagaaac aaaggcataa aactatagga gaaattatta tggctatgac 14340
aaagaaattt aaagtgtcct tcgacgttac cgcaaagatg tcgtctgacg ttcaggcaat 14400
cttagagaaa gatatgctgc atctatgtaa gcaggtcggc tcaggtgcga ttgtccccaa 14460
tggtaaacag aaggaaatga ttgtccagtt cctgacacac ggtatggaag gattgatgac 14520
attcgtagta cgtacatcat ttcgtgaggc cattaaggac atgcacgaag agtatgcaga 14580
taaggactct ttcaaacaat ctcctgcaac agtacgggag gtgttctgat gtctgactac 14640
ctgaaagtgc tgcaagcaat caaaagttgc cctaagactt tccagtccaa ctatgtacgg 14700
aacaatgcga gcctcgtagc ggaggccgct tcccgtggtc acatctcgtg cctgactact 14760
agtggacgta acggtggcgc ttgggaaatc actgcttccg gtactcgctt tctgaaacga 14820
atgggaggat gtgtctaatg tctcgtgacc ttgtgactat tccacgcgat gtgtggaacg 14880
atatacaggg ctacatcgac tctctggaac gtgagaacga tagccttaag aatcaactaa 14940
tggaagctga cgaatacgta gcggaactag aggagaaact taatggcact tcttgacctt 15000
aaacaattct atgagttacg tgaaggctgc gacgacaagg gtatccttgt gatggacggc 15060
gactggctgg tcttccaagc tatgagtgct gctgagtttg atgcctcttg ggaggaagag 15120
atttggcacc gatgctgtga ccacgctaag gcccgtcaga ttcttgagga ttccattaag 15180
tcctacgaga cccgtaagaa ggcttgggca ggtgctccaa ttgtccttgc gttcaccgat 15240
agtgttaact ggcgtaaaga actggttgac ccgaactata aggctaaccg taaggccgtg 15300
aagaaacctg tagggtactt tgagttcctt gatgctctct ttgagcgcga agagttctat 15360
tgcatccgtg agcctatgct tgagggtgat gacgttatgg gagttattgc ttccaatccg 15420
tctgccttcg gtgctcgtaa ggctgtaatc atctcttgcg ataaggactt taagaccatc 15480
cctaactgtg acttcctgtg gtgtaccact ggtaacatcc tgactcagac cgaagagtcc 15540
gctgactggt ggcacctctt ccagaccatc aagggtgaca tcactgatgg ttactcaggg 15600
attgctggat ggggtgatac cgccgaggac ttcttgaata acccgttcat aaccgagcct 15660
aaaacgtctg tgcttaagtc cggtaagaac aaaggccaag aggttactaa atgggttaaa 15720
cgcgaccctg agcctcatga gacgctttgg gactgcatta agtccattgg cgcgaaggct 15780
ggtatgaccg aagaggatat tatcaagcag ggccaaatgg ctcgaatcct acggttcaac 15840
gagtacaact ttattgacaa ggagatttac ctgtggagac cgtagcgtat attggtctgg 15900
gtctttgtgt tctcggagtg tgcctcattt cgtggggcct ttgggactta gccagaataa 15960
tcaagtcgtt acacgacact aagtgataaa ctcaaggtcc ctaaattaat acgactcact 16020
atagggagat aggggccttt acgattatta ctttaagatt taactctaag aggaatcttt 16080
attatgttaa cacctattaa ccaattactt aagaacccta acgatattcc agatgtacct 16140
cgtgcaaccg ctgagtatct acaggttcga ttcaactatg cgtacctcga agcgtctggt 16200
catataggac ttatgcgtgc taatggttgt agtgaggccc acatcttggg tttcattcag 16260
ggcctacagt atgcctctaa cgtcattgac gagattgagt tacgcaagga acaactaaga 16320
gatgatgggg aggattgaca ctatgtgttt ctcaccgaaa attaaaactc cgaagatgga 16380
taccaatcag attcgagccg ttgagccagc gcctctgacc caagaagtgt caagcgtgga 16440
gttcggtggg tcttctgatg agacggatac cgagggcacc gaagtgtctg gacgcaaagg 16500
cctcaaggtc gaacgtgatg attccgtagc gaagtctaaa gccagcggca atggctccgc 16560
tcgtatgaaa tcttccatcc gtaagtccgc atttggaggt aagaagtgat gtctgagttc 16620
acatgtgtgg aggctaagag tcgcttccgt gcaatccggt ggactgtgga acaccttggg 16680
ttgcctaaag gattcgaagg acactttgtg ggctacagcc tctacgtaga cgaagtgatg 16740
gacatgtctg gttgccgtga agagtacatt ctggactcta ccggaaaaca tgtagcgtac 16800
ttcgcgtggt gcgtaagctg tgacattcac cacaaaggag acattctgga tgtaacgtcc 16860
gttgtcatta atcctgaggc agactctaag ggcttacagc gattcctagc gaaacgcttt 16920
aagtaccttg cggaactcca cgattgcgat tgggtgtctc gttgtaagca tgaaggcgag 16980
acaatgcgtg tatactttaa ggaggtataa gttatgggta agaaagttaa gaaggccgtg 17040
aagaaagtca ccaagtccgt taagaaagtc gttaaggaag gggctcgtcc ggttaaacag 17100
gttgctggcg gtctagctgg tctggctggt ggtactggtg aagcacagat ggtggaagta 17160
ccacaagctg ccgcacagat tgttgacgta cctgagaaag aggtttccac tgaggacgaa 17220
gcacagacag aaagcggacg caagaaagct cgtgctggcg gtaagaaatc cttgagtgta 17280
gcccgtagct ccggtggcgg tatcaacatt taatcaggag gttatcgtgg aagactgcat 17340
tgaatggacc ggaggtgtca actctaaggg ttatggtcgt aagtgggtta atggtaaact 17400
tgtgactcca cataggcaca tctatgagga gacatatggt ccagttccaa caggaattgt 17460
ggtgatgcat atctgcgata accctaggtg ctataacata aagcacctta cgcttggaac 17520
tccaaaggat aattccgagg acatggttac caaaggtaga caggctaaag gagaggaact 17580
aagcaagaaa cttacagagt cagacgttct cgctatacgc tcttcaacct taagccaccg 17640
ctccttagga gaactgtatg gagtcagtca atcaaccata acgcgaatac tacagcgtaa 17700
gacatggaga cacatttaat ggctgagaaa cgaacaggac ttgcggagga tggcgcaaag 17760
tctgtctatg agcgtttaaa gaacgaccgt gctccctatg agacacgcgc tcagaattgc 17820
gctcaatata ccatcccatc attgttccct aaggactccg ataacgcctc tacagattat 17880
caaactccgt ggcaagccgt gggcgctcgt ggtctgaaca atctagcctc taagctcatg 17940
ctggctctat tccctatgca gacttggatg cgacttacta tatctgaata tgaagcaaag 18000
cagttactga gcgaccccga tggactcgct aaggtcgatg agggcctctc gatggtagag 18060
cgtatcatca tgaactacat tgagtctaac agttaccgcg tgactctctt tgaggctctc 18120
aaacagttag tcgtagctgg taacgtcctg ctgtacctac cggaaccgga agggtcaaac 18180
tataatccca tgaagctgta ccgattgtct tcttatgtgg tccaacgaga cgcattcggc 18240
aacgttctgc aaatggtgac tcgtgaccag atagcttttg gtgctctccc tgaggacatc 18300
cgtaaggctg tagaaggtca aggtggtgag aagaaagctg atgagacaat cgacgtgtac 18360
actcacatct atctggatga ggactcaggt gaatacctcc gatacgaaga ggtcgagggt 18420
atggaagtcc aaggctccga tgggacttat cctaaagagg cttgcccata catcccgatt 18480

-continued

```
cggatggtca gactagatgg tgaatcctac ggtcgttcgt acattgagga atacttaggt  18540
gacttacggt cccttgaaaa tctccaagag gctatcgtca agatgtccat gattagctct  18600
aaggttatcg gcttagtgaa tcctgctggt atcacccagc cacgccgact gaccaaagct  18660
cagactggtg acttcgttac tggtcgtcca gaagacatct cgttcctcca actggagaag  18720
caagcagact ttactgtagc taaagccgta agtgacgcta tcgaggctcg cctttcgttt  18780
gcctttatgt tgaactctgc ggttcagcgt acaggtgaac gtgtgaccgc cgaagagatt  18840
cggtatgtag cttctgaact tgaagatact ttaggtggtg tctactctat cctttctcaa  18900
gaattacaat tgcctctggt acgagtgctc ttgaagcaac tacaagccac gcaacagatt  18960
cctgagttac ctaaggaagc cgtagagcca accattagta caggtctgga agcaattggt  19020
cgaggacaag accttgataa gctggagcgg tgtgtcactg cgtgggctgc actggcacct  19080
atgcgggacg accctgatat taaccttgcg atgattaagt tacgtattgc caacgctatc  19140
ggtattgaca cttctggtat tctactcacc gaagaacaga agcaacagaa gatggcccaa  19200
cagtctatgc aaatgggtat ggataatggt gctgctgcgc tggctcaagg tatggctgca  19260
caagctacag cttcacctga ggctatggct gctgccgctg attccgtagg tttacagccg  19320
ggaatttaat acgactcact atagggagac ctcatctttg aaatgagcga tgacaagagg  19380
ttggagtcct cggtcttcct gtagttcaac tttaaggaga caataataat ggctgaatct  19440
aatgcagacg tatatgcatc ttttggcgtg aactccgctg tgatgtctgg tggttccgtt  19500
gaggaacatg agcagaacat gctggctctt gatgttgctg cccgtgatgg cgatgatgca  19560
atcgagttag cgtcagacga agtggaaaca gaacgtgacc tgtatgacaa ctctgacccg  19620
ttcggtcaag aggatgacga aggccgcatt caggttcgta tcggtgatgg ctctgagccg  19680
accgatgtgg acactggaga agaaggcgtt gagggcaccg aaggttccga agagtttacc  19740
ccactgggcg agactccaga agaactggta gctgcctctg agcaacttgg tgagcacgaa  19800
gagggcttcc aagagatgat taacattgct gctgagcgtg gcatgagtgt cgagaccatt  19860
gaggctatcc agcgtgagta cgaggagaac gaagagttgt ccgccgagtc ctacgctaag  19920
ctggctgaaa ttggctacac gaaggctttc attgactcgt atatccgtgg tcaagaagct  19980
ctggtggagc agtacgtaaa cagtgtcatt gagtacgctg gtggtcgtga acgttttgat  20040
gcactgtata accaccttga gacgcacaac cctgaggctg cacagtcgct ggataatgcg  20100
ttgaccaatc gtgacttagc gaccgttaag gctatcatca acttggctgg tgagtctcgc  20160
gctaaggcgt tcggtcgtaa gccaactcgt agtgtgacta atcgtgctat tccggctaaa  20220
cctcaggcta ccaagcgtga aggctttgcg gaccgtagcg agatgattaa agctatgagt  20280
gaccctcggt atcgcacaga tgccaactat cgtcgtcaag tcgaacagaa agtaatcgat  20340
tcgaacttct gatagacttc gaaattaata cgactcacta tagggagacc acaacggttt  20400
ccctctagaa ataattttgt ttaactttaa gaaggagata tacatatggc tagcatgact  20460
ggtggacagc aaatgggtac taaccaaggt aaaggtgtag ttgctgctgg agataaactg  20520
gcgttgttct tgaaggtatt tggcggtgaa gtcctgactg cgttcgctcg tacctccgtg  20580
accacttctc gccacatggt acgttccatc tccagcggta aatccgctca gttccctgtt  20640
ctgggtcgca ctcaggcagc gtatctggct ccgggcgaga acctcgacga taaacgtaag  20700
gacatcaaac acaccgagaa ggtaatcacc attgacggtc tcctgacggc tgacgttctg  20760
atttatgata ttgaggacgc gatgaaccac tacgacgttc gctctgagta tacctctcag  20820
ttgggtgaat ctctggcgat ggctgcggat ggtgcggttc tggctgagat tgccggtctg  20880
```

-continued

```
tgtaacgtgg aaagcaaata taatgagaac atcgagggct taggtactgc taccgtaatt  20940
gagaccactc agaacaaggc cgcacttacc gaccaagttg cgctgggtaa ggagattatt  21000
gcggctctga ctaaggctcg tgcggctctg accaagaact atgttccggc tgctgaccgt  21060
gtgttctact gtgacccaga tagctactct gcgattctgg cagcactgat gccgaacgca  21120
gcaaactacg ctgctctgat tgaccctgag aagggttcta tccgcaacgt tatgggcttt  21180
gaggttgtag aagttccgca cctcaccgct ggtggtgctg gtaccgctcg tgagggcact  21240
actggtcaga agcacgtctt ccctgccaat aaaggtgagg gtaatgtcaa ggttgctaag  21300
gacaacgtta tcggcctgtt catgcaccgc tctgcggtag gtactgttaa gctgcgtgac  21360
ttggctctgg agcgcgctcg ccgtgctaac ttccaagcgg accagattat cgctaagtac  21420
gcaatgggcc acggtggtct tcgcccagaa gctgcaggag ctgtcgtatt ccagtcaggt  21480
gtgatgctcg gggatccgaa ttcttaagta actaacgaaa ttaatacgac tcactatagg  21540
gagaccacaa cggtttccct ctagaaataa ttttgtttaa ctttaagaag gagatataca  21600
tatgaaaaag acagctatcg cgattgcagt ggcactggct ggtttcgcta ccgtagcgca  21660
ggcctggctg ggcagcgcgc tgaaaattgg cgcgaaactg ctgccgagcg tggtgggcct  21720
gtttaaaaaa aaaaaacagt aaggatccgg ctgctaacaa agcccgaagc ttgcggccgc  21780
actcgagtaa ctagttaacc ccttggggcc tctaaacggg tcttgagggg ttttttgctg  21840
aaaggaggaa ctatatgcgc tcatacgata tgaacgttga gactgccgct gagttatcag  21900
ctgtgaacga cattctggcg tctatcggtg aacctccggt atcaacgctg gaaggtgacg  21960
ctaacgcaga tgcagcgaac gctcggcgta ttctcaacaa gattaaccga cagattcaat  22020
ctcgtggatg gacgttcaac attgaggaag gcataacgct actacctgat gtttactcca  22080
acctgattgt atacagtgac gactatttat ccctaatgtc tacttccggt caatccatct  22140
acgttaaccg aggtggctat gtgtatgacc gaacgagtca atcagaccgc tttgactctg  22200
gtattactgt gaacattatt cgtctccgcg actacgatga gatgcctgag tgcttccgtt  22260
actggattgt caccaaggct tcccgtcagt tcaacaaccg attctttggg gcaccggaag  22320
tagagggtgt actccaagaa gaggaagatg aggctagacg tctctgcatg gagtatgaga  22380
tggactacgg tgggtacaat atgctggatg gagatgcgtt cacttctggt ctactgactc  22440
gctaacatta ataaataagg aggctctaat ggcactcatt agccaatcaa tcaagaactt  22500
gaagggtggt atcagccaac agcctgacat ccttcgttat ccagaccaag ggtcacgcca  22560
agttaacggt tggtcttcgg agaccgaggg cctccaaaag cgtccacctc ttgttttctt  22620
aaatacactt ggagacaacg gtgcgttagg tcaagctccg tacatccacc tgattaaccg  22680
agatgagcac gaacagtatt acgctgtgtt cactggtagc ggaatccgag tgttcgacct  22740
ttctggtaac gagaagcaag ttaggtatcc taacggttcc aactacatca agaccgctaa  22800
tccacgtaac gacctgcgaa tggttactgt agcagactat acgttcatcg ttaaccgtaa  22860
cgttgttgca cagaagaaca caaagtctgt caacttaccg aattacaacc ctaatcaaga  22920
cggattgatt aacgttcgtg gtggtcagta tggtagggaa ctaattgtac acattaacgg  22980
taaagacgtt gcgaagtata agataccaga tggtagtcaa cctgaacacg taaacaatac  23040
ggatgcccaa tggttagctg aagagttagc caagcagatg cgcactaact tgtctgattg  23100
gactgtaaat gtagggcaag ggttcatcca tgtgaccgca cctagtggtc aacagattga  23160
ctccttcacg actaaagatg gctacgcaga ccagttgatt aaccctgtga cccactacgc  23220
```

-continued

```
tcagtcgttc tctaagctgc cacctaatgc tcctaacggc tacatggtga aaatcgtagg  23280
ggacgcctct aagtctgccg accagtatta cgttcggtat gacgctgagc ggaaagtttg  23340
gactgagact ttaggttgga acactgagga ccaagttcta tgggaaacca tgccacacgc  23400
tcttgtgcga gccgctgacg gtaatttcga cttcaagtgg cttgagtggt ctcctaagtc  23460
ttgtggtgac gttgacacca acccttggcc ttcttttgtt ggttcaagta ttaacgatgt  23520
gttcttcttc cgtaaccgct taggattcct tagtggggag aacatcatat tgagtcgtac  23580
agccaaatac ttcaacttct accctgcgtc cattgcgaac cttagtgatg acgaccctat  23640
agacgtagct gtgagtacca accgaatagc aatccttaag tacgccgttc cgttctcaga  23700
agagttactc atctggtccg atgaagcaca attcgtcctg actgcctcgg gtactctcac  23760
atctaagtcg gttgagttga acctaacgac ccagtttgac gtacaggacc gagcgagacc  23820
ttttgggatt gggcgtaatg tctactttgc tagtccgagg tccagcttca cgtccatcca  23880
caggtactac gctgtgcagg atgtcagttc cgttaagaat gctgaggaca ttacatcaca  23940
cgttcctaac tacatcccta atggtgtgtt cagtatttgc ggaagtggta cggaaaactt  24000
ctgttcggta ctatctcacg ggaccctag taaaatcttc atgtacaaat tcctgtacct  24060
gaacgaagag ttaaggcaac agtcgtggtc tcattgggac tttggggaaa acgtacaggt  24120
tctagcttgt cagagtatca gctcagatat gtatgtgatt cttcgcaatg agttcaatac  24180
gttcctagct agaatctctt tcactaagaa cgccattgac ttacagggag aaccctatcg  24240
tgcctttatg gacatgaaga ttcgatacac gattcctagt ggaacataca acgatgacac  24300
attcactacc tctattcata ttccaacaat ttatggtgca aacttcggga ggggcaaaat  24360
cactgtattg gagcctgatg gtaagataac cgtgtttgag caacctacgg ctgggtggaa  24420
tagcgaccct tggctgagac tcagcggtaa cttggaggga cgcatggtgt acattgggtt  24480
caacattaac ttcgtatatg agttctctaa gttcctcatc aagcagactg ccgacgacgg  24540
gtctacctcc acggaagaca ttgggcgctt acagttacgc cgagcgtggg ttaactacga  24600
gaactctggt acgtttgaca tttatgttga gaaccaatcg tctaactgga agtacacaat  24660
ggctggtgcc cgattaggct ctaacactct gagggctggg agactgaact tagggaccgg  24720
acaatatcga ttccctgtgg ttggtaacgc caagttcaac actgtataca tcttgtcaga  24780
tgagactacc cctctgaaca tcattgggtg tggctgggaa ggtaactact tacggagaag  24840
ttccggtatt taattaaata ttctccctgt ggtggctcga aattaatacg actcactata  24900
gggagaacaa tacgactacg ggagggtttt cttatgatga ctataagacc tactaaaagt  24960
acagactttg aggtattcac tccggctcac catgacattc ttgaagctaa ggctgctggt  25020
attgagccga gtttccctga tgcttccgag tgtgtcacgt tgagcctcta tgggttccct  25080
ctagctatcg gtggtaactg cggggaccag tgctggttcg ttacgagcga ccaagtgtgg  25140
cgacttagtg gaaaggctaa gcgaaagttc cgtaagttaa tcatggagta tcgcgataag  25200
atgcttgaga agtatgatac tctttggaat tacgtatggg taggcaatac gtcccacatt  25260
cgtttcctca agactatcgg tgcggtattc catgaagagt acacacgaga tggtcaattt  25320
cagttattta caatcacgaa aggaggataa ccatatgtgt tgggcagccg caatacctat  25380
cgctatatct ggcgctcagg ctatcagtgg tcagaacgct caggccaaaa tgattgccgc  25440
tcagaccgct gctggtcgtc gtcaagctat ggaaatcatg aggcagacga acatccagaa  25500
tgctgaccta tcgttgcaag ctcgaagtaa acttgaggaa gcgtccgccg agttgacctc  25560
acagaacatg cagaaggtcc aagctattgg gtctatccga gcggctatcg gagagagtat  25620
```

```
gcttgaaggt tcctcaatgg accgcattaa gcgagtcaca gaaggacagt tcattcggga  25680
agccaatatg gtaactgaga actatcgccg tgactaccaa gcaatcttcg cacagcaact  25740
tggtggtact caaagtgctg caagtcagat tgacgaaatc tataagagcg aacagaaaca  25800
gaagagtaag ctacagatgg ttctggaccc actggctatc atggggtctt ccgctgcgag  25860
tgcttacgca tccggtgcgt tcgactctaa gtccacaact aaggcaccta ttgttgccgc  25920
taaaggaacc aagacgggga ggtaatgagc tatgagtaaa attgaatctg cccttcaagc  25980
ggcacaaccg ggactctctc ggttacgtgg tggtgctgga ggtatgggct atcgtgcagc  26040
aaccactcag gccgaacagc caaggtcaag cctattggac accattggtc ggttcgctaa  26100
ggctggtgcc gatatgtata ccgctaagga acaacgagca cgagacctag ctgatgaacg  26160
ctctaacgag attatccgta agctgacccc tgagcaacgt cgagaagctc tcaacaacgg  26220
gacccttctg tatcaggatg acccatacgc tatggaagca ctccgagtca agactggtcg  26280
taacgctgcg tatcttgtgg acgatgacgt tatgcagaag ataaaagagg gtgtcttccg  26340
tactcgcgaa gagatggaag agtatcgcca tagtcgcctt caagagggcg ctaaggtata  26400
cgctgagcag ttcggcatcg accctgagga cgttgattat cagcgtggtt tcaacgggga  26460
cattaccgag cgtaacatct cgctgtatgg tgcgcatgat aacttcttga gccagcaagc  26520
tcagaagggc gctatcatga acagccgagt ggaactcaac ggtgtccttc aagaccctga  26580
tatgctgcgt cgtccagact ctgctgactt ctttgagaag tatatcgaca acggtctggt  26640
tactggcgca atcccatctg atgctcaagc cacacagctt ataagccaag cgttcagtga  26700
cgcttctagc cgtgctggtg gtgctgactt cctgatgcga gtcggtgaca agaaggtaac  26760
acttaacgga gccactacga cttaccgaga gttgattggt gaggaacagt ggaacgctct  26820
catggtcaca gcacaacgtt ctcagtttga gactgacgcg aagctgaacg agcagtatcg  26880
cttgaagatt aactctgcgc tgaaccaaga ggacccaagg acagcttggg agatgcttca  26940
aggtatcaag gctgaactag ataaggtcca acctgatgag cagatgacac cacaacgtga  27000
gtggctaatc tccgcacagg aacaagttca gaatcagatg aacgcatgga cgaaagctca  27060
ggccaaggct ctggacgatt ccatgaagtc aatgaacaaa cttgacgtaa tcgacaagca  27120
attccagaag cgaatcaacg gtgagtgggt ctcaacggat tttaaggata tgccagtcaa  27180
cgagaacact ggtgagttca agcatagcga tatggttaac tacgccaata agaagctcgc  27240
tgagattgac agtatggaca ttccagacgg tgccaaggat gctatgaagt tgaagtacct  27300
tcaagcggac tctaaggacg gagcattccg tacagccatc ggaaccatgg tcactgacgc  27360
tggtcaagag tggtctgccg ctgtgattaa cggtaagtta ccagaacgaa ccccagctat  27420
ggatgctctg cgcagaatcc gcaatgctga ccctcagttg attgctgcgc tatacccaga  27480
ccaagctgag ctattcctga cgatggacat gatggacaag cagggtattg accctcaggt  27540
tattcttgat gccgaccgac tgactgttaa gcggtccaaa gagcaacgct ttgaggatga  27600
taaagcattc gagtctgcac tgaatgcatc taaggctcct gagattgccc gtatgccagc  27660
gtcactgcgc gaatctgcac gtaagattta tgactccgtt aagtatcgct cggggaacga  27720
aagcatggct atggagcaga tgaccaagtt ccttaaggaa tctacctaca cgttcactgg  27780
tgatgatgtt gacggtgata ccgttggtgt gattcctaag aatatgatgc aggttaactc  27840
tgacccgaaa tcatgggagc aaggtcggga tattctggag gaagcacgta agggaatcat  27900
tgcgagcaac ccttggataa ccaataagca actgaccatg tattctcaag gtgactccat  27960
```

-continued ttaccttatg gacaccacag gtcaagtcag agtccgatac gacaaagagt tactctcgaa 28020
ggtctggagt gagaaccaga agaaactcga agagaaagct cgtgagaagg ctctggctga 28080
tgtgaacaag cgagcaccta tagttgccgc tacgaaggcc cgtgaagctg ctgctaaacg 28140
agtccgagag aaacgtaaac agactcctaa gttcatctac ggacgtaagg agtaactaaa 28200
ggctacataa ggaggcccta aatggataag tacgataaga acgtaccaag tgattatgat 28260
ggtctgttcc aaaaggctgc tgatgccaac ggggtctctt atgacctttt acgtaaagtc 28320
gcttggacag aatcacgatt tgtgcctaca gcaaaatcta agactggacc attaggcatg 28380
atgcaattta ccaaggcaac cgctaaggcc ctcggtctgc gagttaccga tggtccagac 28440
gacgaccgac tgaaccctga gttagctatt aatgctgccg ctaagcaact tgcaggtctg 28500
gtagggaagt ttgatggcga tgaactcaaa gctgcccttg cgtacaacca aggcgaggga 28560
cgcttgggta atccacaact tgaggcgtac tctaagggag acttcgcatc aatctctgag 28620
gagggacgta actacatgcg taaccttctg gatgttgcta agtcacctat ggctggacag 28680
ttggaaactt ttggtggcat aaccccaaag ggtaaaggca ttccggctga ggtaggattg 28740
gctggaattg gtcacaagca gaaagtaaca caggaacttc ctgagtccac aagttttgac 28800
gttaagggta tcgaacagga ggctacggcg aaaccattcg ccaaggactt ttgggagacc 28860
cacggagaaa cacttgacga gtacaacagt cgttcaacct tcttcggatt caaaaatgct 28920
gccgaagctg aactctccaa ctcagtcgct gggatggctt tccgtgctgg tcgtctcgat 28980
aatggttttg atgtgtttaa agacaccatt acgccgactc gctggaactc tcacatctgg 29040
actccagagg agttagagaa gattcgaaca gaggttaaga accctgcgta catcaacgtt 29100
gtaactggtg gttcccctga gaacctcgat gacctcatta aattggctaa cgagaacttt 29160
gagaatgact cccgcgctgc cgaggctggc ctaggtgcca aactgagtgc tggtattatt 29220
ggtgctggtg tggacccgct tagctatgtt cctatggtcg gtgtcactgg taagggcttt 29280
aagttaatca ataaggctct tgtagttggt gccgaaagtg ctgctctgaa cgttgcatcc 29340
gaaggtctcc gtacctccgt agctggtggt gacgcagact atgcgggtgc tgccttaggt 29400
ggctttgtgt ttggcgcagg catgtctgca atcagtgacg ctgtagctgc tggactgaaa 29460
cgcagtaaac cagaagctga gttcgacaat gagttcatcg gtcctatgat gcgattggaa 29520
gcccgtgaga cagcacgaaa cgccaactct gcggacctct ctcggatgaa cactgagaac 29580
atgaagtttg aaggtgaaca taatggtgtc ccttatgagg acttaccaac agagagaggt 29640
gccgtggtgt tacatgatgg ctccgttcta agtgcaagca acccaatcaa ccctaagact 29700
ctaaaagagt tctccgaggt tgaccctgag aaggctgcgc gaggaatcaa actggctggg 29760
ttcaccgaga ttggcttgaa gaccttgggg tctgacgatg ctgacatccg tagagtggct 29820
atcgacctcg ttcgctctcc tactggtatg cagtctggtg cctcaggtaa gttcggtgca 29880
acagcttctg acatccatga gagacttcat ggtactgacc agcgtactta taatgacttg 29940
tacaaagcaa tgtctgacgc tatgaaagac cctgagttct ctactggcgg cgctaagatg 30000
tcccgtgaag aaactcgata cactatctac cgtagagcgg cactagctat tgagcgtcca 30060
gaactacaga aggcactcac tccgtctgag agaatcgtta tggacatcat taagcgtcac 30120
tttgacacca agcgtgaact tatggaaaac ccagcaatat tcggtaacac aaaggctgtg 30180
agtatcttcc ctgagagtcg ccacaaaggt acttacgttc ctcacgtata tgaccgtcat 30240
gccaaggcgc tgatgattca acgctacggt gccgaaggtt tgcaggaagg gattgcccgc 30300
tcatggatga acagctacgt ctccagacct gaggtcaagg ccagagtcga tgagatgctt 30360

-continued

```
aaggaattac acggggtgaa ggaagtaaca ccagagatgg tagagaagta cgctatggat  30420
aaggcttatg gtatctccca ctcagaccag ttcaccaaca gttccataat agaagagaac  30480
attgagggct tagtaggtat cgagaataac tcattccttg aggcacgtaa cttgtttgat  30540
tcggacctat ccatcactat gccagacgga cagcaattct cagtgaatga cctaagggac  30600
ttcgatatgt tccgcatcat gccagcgtat gaccgccgtg tcaatggtga catcgccatc  30660
atggggtcta ctggtaaaac cactaaggaa cttaaggatg agattttggc tctcaaagcg  30720
aaagctgagg gagacggtaa gaagactggc gaggtacatg ctttaatgga taccgttaag  30780
attcttactg gtcgtgctag acgcaatcag gacactgtgt gggaaacctc actgcgtgcc  30840
atcaatgacc tagggttctt cgctaagaac gcctacatgg gtgctcagaa cattacggag  30900
attgctggga tgattgtcac tggtaacgtt cgtgctctag ggcatggtat cccaattctg  30960
cgtgatacac tctacaagtc taaaccagtt tcagctaagg aactcaagga actccatgcg  31020
tctctgttcg ggaaggaggt ggaccagttg attcggccta aacgtgctga cattgtgcag  31080
cgcctaaggg aagcaactga taccggacct gccgtggcga acatcgtagg gaccttgaag  31140
tattcaacac aggaactggc tgctcgctct ccgtggacta agctactgaa cggaaccact  31200
aactaccttc tggatgctgc gcgtcaaggt atgcttgggg atgttattag tgccacccta  31260
acaggtaaga ctacccgctg ggagaaagaa ggcttccttc gtggtgcctc cgtaactcct  31320
gagcagatgg ctggcatcaa gtctctcatc aaggaacata tggtacgcgg tgaggacggg  31380
aagtttaccg ttaaggacaa gcaagcgttc tctatggacc cacgggctat ggacttatgg  31440
agactggctg acaaggtagc tgatgaggca atgctgcgtc cacataaggt gtccttacag  31500
gattcccatg cgttcggagc actaggtaag atggttatgc agtttaagtc tttcactatc  31560
aagtccctta actctaagtt cctgcgaacc ttctatgatg gatacaagaa caaccgagcg  31620
attgacgctg cgctgagcat catcacctct atgggtctcg ctggtggttt ctatgctatg  31680
gctgcacacg tcaaagcata cgctctgcct aaggagaaac gtaaggagta cttggagcgt  31740
gcactggacc caaccatgat tgcccacgct gcgttatctc gtagttctca attgggtgct  31800
cctttggcta tggttgacct agttggtggt gttttagggt tcgagtcctc caagatggct  31860
cgctctacga ttctacctaa ggacaccgtg aaggaacgtg acccaaacaa accgtacacc  31920
tctagagagg taatgggcgc tatgggttca aaccttctgg aacagatgcc ttcggctggc  31980
tttgtggcta acgtaggggc taccttaatg aatgctgctg gcgtggtcaa ctcacctaat  32040
aaagcaaccg agcaggactt catgactggt cttatgaact ccacaaaaga gttagtaccg  32100
aacgacccat tgactcaaca gcttgtgttg aagatttatg aggcgaacgg tgttaacttg  32160
agggagcgta ggaaataata cgactcacta tagggagagg cgaaataatc ttctccctgt  32220
agtctcttag atttacttta aggaggtcaa atggctaacg taattaaaac cgttttgact  32280
taccagttag atggctccaa tcgtgatttt aatatcccgt ttgagtatct agcccgtaag  32340
ttcgtagtgg taactcttat tggtgtagac cgaaaggtcc ttacgattaa tacagactat  32400
cgctttgcta cacgtactac tatctctctg acaaaggctt ggggtccagc cgatggctac  32460
acgaccatcg agttacgtcg agtaacctcc actaccgacc gattggttga ctttacggat  32520
ggttcaatcc tccgcgcgta tgaccttaac gtcgctcaga ttcaaacgat gcacgtagcg  32580
gaagaggccc gtgacctcac tacggatact atcggtgtca ataacgatgg tcacttggat  32640
gctcgtggtc gtcgaattgt gaacctagcg aacgccgtgg atgaccgcga tgctgttccg  32700
```

-continued

```
tttggtcaac taaagaccat gaaccagaac tcatggcaag cacgtaatga agccttacag  32760
ttccgtaatg aggctgagac tttcagaaac caagcggagg gctttaagaa cgagtccagt  32820
accaacgcta cgaacacaaa gcagtggcgc gatgagacca agggtttccg agacgaagcc  32880
aagcggttca agaatacggc tggtcaatac gctacatctg ctgggaactc tgcttccgct  32940
gcgcatcaat ctgaggtaaa cgctgagaac tctgccacag catccgctaa ctctgctcat  33000
ttggcagaac agcaagcaga ccgtgcggaa cgtgaggcag acaagctgga aaattacaat  33060
ggattggctg gtgcaattga taaggtagat ggaaccaatg tgtactggaa aggaaatatt  33120
cacgctaacg ggcgccttta catgaccaca aacggttttg actgtggcca gtatcaacag  33180
ttctttggtg gtgtcactaa tcgttactct gtcatggagt ggggagatga gaacggatgg  33240
ctgatgtatg ttcaacgtag agagtggaca acagcgatag gcggtaacat ccagttagta  33300
gtaaacggac agatcatcac ccaaggtgga gccatgaccg gtcagctaaa attgcagaat  33360
gggcatgttc ttcaattaga gtccgcatcc gacaaggcgc actatattct atctaaagat  33420
ggtaacagga ataactggta cattggtaga gggtcagata acaacaatga ctgtaccttc  33480
cactcctatg tacatggtac gaccttaaca ctcaagcagg actatgcagt agttaacaaa  33540
cacttccacg taggtcaggc cgttgtggcc actgatggta atattcaagg tactaagtgg  33600
ggaggtaaat ggctggatgc ttacctacgt gacagcttcg ttgcgaagtc caaggcgtgg  33660
actcaggtgt ggtctggtag tgctggcggt ggggtaagtg tgactgtttc acaggatctc  33720
cgcttccgca atatctggat taagtgtgcc aacaactctt ggaacttctt ccgtactggc  33780
cccgatggaa tctacttcat agcctctgat ggtggatggt tacgattcca aatacactcc  33840
aacggtctcg gattcaagaa tattgcagac agtcgttcag tacctaatgc aatcatggtg  33900
gagaacgagt aattggtaaa tcacaaggaa agacgtgtag tccacggatg gactctcaag  33960
gaggtacaag gtgctatcat tagactttaa caacgaattg attaaggctg ctccaattgt  34020
tgggacgggt gtagcagatg ttagtgctcg actgttcttt gggttaagcc ttaacgaatg  34080
gttctacgtt gctgctatcg cctacacagt ggttcagatt ggtgccaagg tagtcgataa  34140
gatgattgac tggaagaaag ccaataagga gtgatatgta tggaaaagga taagagcctt  34200
attacattct tagagatgtt ggacactgcg atggctcagc gtatgcttgc ggacctttcg  34260
gaccatgagc gtcgctctcc gcaactctat aatgctatta acaaactgtt agaccgccac  34320
aagttccaga ttggtaagtt gcagccggat gttcacatct taggtggcct tgctggtgct  34380
cttgaagagt acaaagagaa agtcggtgat aacggtctta cggatgatga tatttacaca  34440
ttacagtgat atactcaagg ccactacaga tagtggtctt tatggatgtc attgtctata  34500
cgagatgctc ctacgtgaaa tctgaaagtt aacgggaggc attatgctag aatttttacg  34560
taagctaatc ccttgggttc tcgctgggat gctattcggg ttaggatggc atctagggtc  34620
agactcaatg gacgctaaat ggaaacagga ggtacacaat gagtacgtta agagagttga  34680
ggctgcgaag agcactcaaa gagcaatcga tgcggtatct gctaagtatc aagaagacct  34740
tgccgcgctg gaagggagca ctgataggat tatttctgat ttgcgtagcg acaataagcg  34800
gttgcgcgtc agagtcaaaa ctaccggaac ctccgatggt cagtgtggat tcgagcctga  34860
tggtcgagcc gaacttgacg accgagatgc taaacgtatt ctcgcagtga cccagaaggg  34920
tgacgcatgg attcgtgcgt tacaggatac tattcgtgaa ctgcaacgta agtaggaaat  34980
caagtaagga ggcaatgtgt ctactcaatc caatcgtaat gcgctcgtag tggcgcaact  35040
gaaaggagac ttcgtggcgt tcctattcgt cttatggaag gcgctaaacc taccggtgcc  35100
```

```
cactaagtgt cagattgaca tggctaaggt gctggcgaat ggagacaaca agaagttcat  35160
cttacaggct ttccgtggta tcggtaagtc gttcatcaca tgtgcgttcg ttgtgtggtc  35220
cttatggaga gaccctcagt tgaagatact tatcgtatca gcctctaagg agcgtgcaga  35280
cgctaactcc atctttatta agaacatcat tgacctgctg ccattcctat ctgagttaaa  35340
gccaagaccc ggacagcgtg actcggtaat cagctttgat gtaggcccag ccaatcctga  35400
ccactctcct agtgtgaaat cagtaggtat cactggtcag ttaactggta gccgtgctga  35460
cattatcatt gcggatgacg ttgagattcc gtctaacagc gcaactatgg gtgcccgtga  35520
gaagctatgg actctggttc aggagttcgc tgcgttactt aaaccgctgc cttcctctcg  35580
cgttatctac cttggtacac ctcagacaga gatgactctc tataaggaac ttgaggataa  35640
ccgtgggtac acaaccatta tctggcctgc tctgtaccca aggacacgtg aagagaacct  35700
ctattactca cagcgtcttg ctcctatgtt acgcgctgag tacgatgaga accctgaggc  35760
acttgctggg actccaacag acccagtgcg ctttgaccgt gatgacctgc gcgagcgtga  35820
gttggaatac ggtaaggctg gctttacgct acagttcatg cttaacccta accttagtga  35880
tgccgagaag tacccgctga ggcttcgtga cgctatcgta gcggccttag acttagagaa  35940
ggccccaatg cattaccagt ggcttccgaa ccgtcagaac atcattgagg accttcctaa  36000
cgttggcctt aagggtgatg acctgcatac gtaccacgat tgttccaaca actcaggtca  36060
gtaccaacag aagattctgg tcattgaccc tagtggtcgc ggtaaggacg aaacaggtta  36120
cgctgtgctg tacacactga acggttacat ctaccttatg gaagctggag gtttccgtga  36180
tggctactcc gataagaccc ttgagttact cgctaagaag gcaaagcaat ggggagtcca  36240
gacggttgtc tacgagagta acttcggtga cggtatgttc ggtaaggtat tcagtcctat  36300
ccttcttaaa caccacaact gtgcgatgga agagattcgt gcccgtggta tgaaagagat  36360
gcgtatttgc gatacccttg agccagtcat gcagactcac cgccttgtaa ttcgtgatga  36420
ggtcattagg gccgactacc agtccgctcg tgacgtagac ggtaagcatg acgttaagta  36480
ctcgttgttc taccagatga cccgtatcac tcgtgagaaa ggcgctctgg ctcatgatga  36540
ccgattggat gcccttgcgt taggcattga gtatctccgt gagtccatgc agttggattc  36600
cgttaaggtc gagggtgaag tacttgctga cttccttgag gaacacatga tgcgtcctac  36660
ggttgctgct acgcatatca ttgagatgtc tgtgggagga gttgatgtgt actctgagga  36720
cgatgagggt tacggtacgt ctttcattga gtggtgattt atgcattagg actgcatagg  36780
gatgcactat agaccacgga tggtcagttc tttaagttac tgaaaagaca cgataaatta  36840
atacgactca ctatagggag aggagggacg aaaggttact atatagatac tgaatgaata  36900
cttatagagt gcataaagta tgcataatgg tgtacctaga gtgacctcta agaatggtga  36960
ttatattgta ttagtatcac cttaacttaa ggaccaacat aaagggagga gactcatgtt  37020
ccgcttattg ttgaacctac tgcggcatag agtcacctac cgatttcttg tggtactttg  37080
tgctgccctt gggtacgcat ctcttactgg agacctcagt tcactggagt ctgtcgtttg  37140
ctctatactc acttgtagcg attagggtct tcctgaccga ctgatggctc accgagggat  37200
tcagcggtat gattgcatca caccacttca tccctataga gtcaagtcct aaggtatacc  37260
cataaagagc ctctaatggt ctatcctaag gtctatacct aaagataggc catcctatca  37320
gtgtcaccta aagagggtct tagagagggc ctatggagtt cctatagggt cctttaaaat  37380
ataccataaa aatctgagtg actatctcac agtgtacgga cctaaagttc ccccataggg  37440
```

ggtacctaaa gcccagccaa tcacctaaag tcaaccttcg gttgaccttg agggttccct 37500
aagggttggg gatgaccctt gggtttgtct ttgggtgtta ccttgagtgt ctctctgtgt 37560
ccct 37564

<210> SEQ ID NO 71
<211> LENGTH: 164
<212> TYPE: PRT
<213> ORGANISM: Unknown
<220> FEATURE:
<223> OTHER INFORMATION: Description of Artificial Sequence: Bacteriophage polypeptide

<400> SEQUENCE: 71

Ala Lys Thr Gln Ala Glu Ile Asn Lys Arg Leu Asp Ala Tyr Ala Lys
1 5 10 15

Gly Thr Val Asp Ser Pro Tyr Arg Val Lys Lys Ala Thr Ser Tyr Asp
20 25 30

Pro Ser Phe Gly Val Met Glu Ala Gly Ala Ile Asp Ala Asp Gly Tyr
35 40 45

Tyr His Ala Gln Cys Gln Asp Leu Ile Thr Asp Tyr Val Leu Trp Leu
50 55 60

Thr Asp Asn Lys Val Arg Thr Trp Gly Asn Ala Lys Asp Gln Ile Lys
65 70 75 80

Gln Ser Tyr Gly Thr Gly Phe Lys Ile His Glu Asn Lys Pro Ser Thr
85 90 95

Val Pro Lys Lys Gly Trp Ile Ala Val Phe Thr Ser Gly Ser Tyr Glu
100 105 110

Gln Trp Gly His Ile Gly Ile Val Tyr Asp Gly Gly Asn Thr Ser Thr
115 120 125

Phe Thr Ile Leu Glu Gln Asn Trp Asn Gly Tyr Ala Asn Lys Lys Pro
130 135 140

Thr Lys Arg Val Asp Asn Tyr Tyr Gly Leu Thr His Phe Ile Glu Ile
145 150 155 160

Pro Val Lys Ala

<210> SEQ ID NO 72
<211> LENGTH: 20
<212> TYPE: PRT
<213> ORGANISM: Unknown
<220> FEATURE:
<223> OTHER INFORMATION: Description of Unknown: Bacterial outer membrane protein

<400> SEQUENCE: 72

Lys Lys Thr Ala Ile Ala Ile Ala Val Ala Leu Ala Gly Phe Ala Thr
1 5 10 15

Val Ala Gln Ala
20

<210> SEQ ID NO 73
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
tccctatcag tgatagagat tgacatccct atcagtgata gagatactga gcacatcagc 60
aggacgcact gacc 74

<210> SEQ ID NO 74
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
ccatcgaatg gctgaaatga gctgttgaca attaatcatc cggctcgtat aatgtgtgga 60
attgtgagcg gataacaatt tcacac 86

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
attaaagagg agaaa 15

<210> SEQ ID NO 76
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76 ggtacc 6

<210> SEQ ID NO 77
<211> LENGTH: 3
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77 atg 3

<210> SEQ ID NO 78
<211> LENGTH: 60
<212> TYPE: DNA
<213> ORGANISM: Unknown
<220> FEATURE:
<223> OTHER INFORMATION: Description of Unknown: Omp signal sequence

<400> SEQUENCE: 78
aaaaagacag ctatcgcgat tgcagtggca ctggctggtt tcgctaccgt agcgcaggcc 60

<210> SEQ ID NO 79
<211> LENGTH: 78
<212> TYPE: DNA
<213> ORGANISM: Pachycondyla goeldii

<400> SEQUENCE: 79
ggcatttggg gcaccctggc gaaaattggc attaaagcgg tgccgcgcgt gattagcatg 60
ctgaaaaaaa aaaaacag 78

<210> SEQ ID NO 80
<211> LENGTH: 72
<212> TYPE: DNA
<213> ORGANISM: Pachycondyla goeldii

<400> SEQUENCE: 80
ttttggggcg cgctgattaa aggcgcggcg aaactgattc cgagcgtggt gggcctgttt 60
aaaaaaaaac ag 72

<210> SEQ ID NO 81
<211> LENGTH: 75
<212> TYPE: DNA
<213> ORGANISM: Pachycondyla goeldii

<400> SEQUENCE: 81
tggctgggca gcgcgctgaa aattggcgcg aaactgctgc cgagcgtggt gggcctgttt 60
aaaaaaaaaa aacag 75

<210> SEQ ID NO 82
<211> LENGTH: 492
<212> TYPE: DNA
<213> ORGANISM: Unknown
<220> FEATURE:
<223> OTHER INFORMATION: Description of Unknown: Bacteriophage
polynucleotide

<400> SEQUENCE: 82
gctaagactc aagcagaaat aaataaacgt ttagatgctt atgcaaaagg aacagtagat 60
agcccttaca gagttaaaaa agctacaagt tatgacccat catttggtgt aatggaagca 120
ggagccattg atgcagatgg ttactatcac gctcagtgtc aagaccttat tacagactat 180
gttttatggt taacagataa taaagttaga acttggggta atgctaaaga ccaaattaaa 240
cagagttatg gtactggatt taaaatacat gaaaataaac cttctactgt acctaaaaaa 300
ggttggattg cggtatttac atccggtagt tatgaacagt ggggtcacat aggtattgta 360
tatgatggag gtaatacttc tacatttact attttagagc aaaactggaa tggttatgct 420
aataaaaaac ctacaaaacg tgtagataat tattacggat taactcactt cattgaaata 480
cctgtaaaag ca 492

<210> SEQ ID NO 83
<211> LENGTH: 3
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83 taa 3

<210> SEQ ID NO 84
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84 aagctt 6

<210> SEQ ID NO 85
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
ggcatcaaat aaaacgaaag gctcagtcga aagactgggc ctttcgtttt atctgttgtt 60
tgtcggtgaa cgctctcctg agtaggacaa atccgccgcc ctaga 105

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
ggtaccatgg gcatttgggg caccc 25

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
aagcttttac tgtttttttt ttttcagcat gctaatcacg cgcgg 45

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ggtaccatgt tttggggcgc 20

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
aagcttttac tgtttttttt taaacaggcc caccacgctc 40

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
ggtaccatgt ggctgggcag 20

<210> SEQ ID NO 91
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
aagcttttac tgtttttttt ttttaaacag gcccaccacg ctcg 44

<210> SEQ ID NO 92
<211> LENGTH: 589
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92
catatgatga aaaagacagc tatcgcgatt gcagtggcac tggctggttt cgctaccgta 60
gcgcaggccg ctaagactca agcagaaata aataaacgtt tagatgctta tgcaaaagga 120
acagtagata gcccttacag agttaaaaaa gctacaagtt atgacccatc atttggtgta 180
atggaagcag gagccattga tgcagatggt tactatcacg ctcagtgtca agaccttatt 240
acagactatg ttttatggtt aacagataat aaagttagaa cttggggtaa tgctaaagac 300
caaattaaac agagttatgg tactggattt aaaatacatg aaaataaacc ttctactgta 360
cctaaaaaag gttggattgc ggtatttaca tccggtagtt atgaacagtg gggtcacata 420
ggtattgtat atgatggagg taatacttct acatttacta ttttagagca aaactggaat 480
ggttatgcta ataaaaaacc tacaaaacgt gtagataatt attacggatt aactcacttc 540
attgaaatac ctgtaaaagc atagggatcc agctataggg atccagcta 589

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gaagggtacc atgaaaaaga c 21

<210> SEQ ID NO 94
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
gcagctttcg aactatgctt ttacaggtat ttcaatga 38

<210> SEQ ID NO 95
<211> LENGTH: 36
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 95
gcagctggta ccatggctaa gactcaagca gaaata 36

<210> SEQ ID NO 96
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
ggtaccatga aaaagacagc tatcgcgatt gcagtggcac tggctggttt cgctaccgta 60
gcgcaggccg gcatttgggg caccctggcg aaaattggca ttaaagcggt gccgcgcgtg 120
attagcatgc tgaaaaaaaa aaaacagtaa aagctt 156

<210> SEQ ID NO 97
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
ggtaccatga aaaagacagc tatcgcgatt gcagtggcac tggctggttt cgctaccgta 60
gcgcaggcct tttggggcgc gctgattaaa ggcgcggcga aactgattcc gagcgtggtg 120
ggcctgttta aaaaaaaaca gtaaaagctt 150

<210> SEQ ID NO 98
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
ggtaccatga aaaagacagc tatcgcgatt gcagtggcac tggctggttt cgctaccgta 60
gcgcaggcct ggctgggcag cgcgctgaaa attggcgcga aactgctgcc gagcgtggtg 120
ggcctgttta aaaaaaaaaa acagtaaaag ctt 153

<210> SEQ ID NO 99
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
ggtaccatga aaaagacagc tatcgcgatt gcagtggcac tggctggttt cgctaccgta 60
gcgcaggcca tgattctgcc gtggaaatgg ccgtggtggc cgtggcgccg ctaaaagctt 120

<210> SEQ ID NO 100
<211> LENGTH: 174
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 100
ggtaccatga aaaagacagc tatcgcgatt gcagtggcac tggctggttt cgctaccgta     60
gcgcaggcca tgagctggct gagcaaaacc gcgaaaaaac tggaaaacag cgcgaaaaaa    120
cgcattagcg aaggcattgc gattgcgatt cagggcggcc cgcgctaaaa gctt          174

<210> SEQ ID NO 101
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggtaccatga aaaagacagc tatcgcgatt gcagtggcac tggctggttt cgctaccgta     60
gcgcaggcc                                                             69

<210> SEQ ID NO 102
<211> LENGTH: 96
<212> TYPE: DNA
<213> ORGANISM: Pachycondyla goeldii

<400> SEQUENCE: 102
ggtaccatgg gcatttgggg caccctggcg aaaattggca ttaaagcggt gccgcgcgtg     60
attagcatgc tgaaaaaaaa aaaacagtaa aagctt                               96

<210> SEQ ID NO 103
<211> LENGTH: 90
<212> TYPE: DNA
<213> ORGANISM: Pachycondyla goeldii

<400> SEQUENCE: 103
ggtaccatgt tttggggcgc gctgattaaa ggcgcggcga aactgattcc gagcgtggtg     60
ggcctgttta aaaaaaaaca gtaaaagctt                                      90

<210> SEQ ID NO 104
<211> LENGTH: 93
<212> TYPE: DNA
<213> ORGANISM: Pachycondyla goeldii

<400> SEQUENCE: 104
ggtaccatgt ggctgggcag cgcgctgaaa attggcgcga aactgctgcc gagcgtggtg     60
ggcctgttta aaaaaaaaaa acagtaaaag ctt                                  93

<210> SEQ ID NO 105
<211> LENGTH: 45
<212> TYPE: DNA
<213> ORGANISM: Pachycondyla goeldii

<400> SEQUENCE: 105
atgattctgc cgtggaaatg gccgtggtgg ccgtggcgcc gctaa                     45

<210> SEQ ID NO 106
<211> LENGTH: 99
<212> TYPE: DNA
<213> ORGANISM: Pachycondyla goeldii

<400> SEQUENCE: 106
atgagctggc tgagcaaaac cgcgaaaaaa ctggaaaaca gcgcgaaaaa acgcattagc 60
gaaggcattg cgattgcgat tcagggcggc ccgcgctaa 99

<210> SEQ ID NO 107
<211> LENGTH: 492
<212> TYPE: DNA
<213> ORGANISM: Unknown
<220> FEATURE:
<223> OTHER INFORMATION: Description of Unknown: Bacteriophage polynucleotide

<400> SEQUENCE: 107
tgcttttaca ggtatttcaa tgaagtgagt taatccgtaa taattatcta cacgttttgt 60
aggtttttta ttagcataac cattccagtt ttgctctaaa atagtaaatg tagaagtatt 120
acctccatca tatacaatac ctatgtgacc ccactgttca taactaccgg atgtaaatac 180
cgcaatccaa cctttttag gtacagtaga aggtttattt tcatgtattt taaatccagt 240
accataactc tgtttaattt ggtctttagc attaccccaa gttctaactt tattatctgt 300
taaccataaa acatagtctg taataaggtc ttgacactga gcgtgatagt aaccatctgc 360
atcaatggct cctgcttcca ttacaccaaa tgatgggtca taacttgtag ctttttaac 420 tctgtaaggg ctatctactg ttccttttgc ataagcatct aaacgtttat ttatttctgc 480
ttgagtctta gc 492

<210> SEQ ID NO 108
<211> LENGTH: 7954
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
aatgctacta ctattagtag aattgatgcc accttttcag ctcgcgcccc aaatgaaaat 60
atagctaaac aggttattga ccatttgcga aatgtatcta atggtcaaac taaatctact 120
cgttcgcaga attgggaatc aactgttaca tggaatgaaa cttccagaca ccgtacttta 180
gttgcatatt taaaacatgt tgagctacag caccagattc agcaattaag ctctaagcca 240
tccgcaaaaa tgacctctta tcaaaaggag caattaaagg tactctctaa tcctgacctg 300
ttggagtttg cttccggtct ggttcgcttt gaagctcgaa ttaaaacgcg atatttgaag 360
tctttcgggc ttcctcttaa tctttttgat gcaatccgct ttgcttctga ctataatagt 420
cagggtaaag acctgatttt tgatttatgg tcattctcgt tttctgaact gtttaaagca 480
tttgaggggg attcaatgaa tatttatgac gattccgcag tattggacgc tatccagtct 540
aaacatttta ctattacccc ctctggcaaa acttcttttg caaaagcctc tcgctatttt 600
ggtttttatc gtcgtctggt aaacgagggt tatgatagtg ttgctcttac tatgcctcgt 660
aattcctttt ggcgttatgt atctgcatta gttgaatgtg gtattcctaa atctcaactg 720
atgaatcttt ctacctgtaa taatgttgtt ccgttagttc gttttattaa cgtagatttt 780
tcttcccaac gtcctgactg gtataatgag ccagttctta aaatcgcata aggtaattca 840
caatgattaa agttgaaatt aaaccatctc aagcccaatt tactactcgt tctggtgttc 900
tcgtcagggc aagccttatt cactgaatga gcagctttgt tacgttgatt tgggtaatga 960
atatccggtt cttgtcaaga ttactcttga tgaaggtcag ccagcctatg cgcctggtct 1020

-continued

```
gtacaccgtt catctgtcct ctttcaaagt tggtcagttc ggttccctta tgattgaccg   1080
tctgcgcctc gttccggcta agtaacatgg agcaggtcgc ggatttcgac acaatttatc   1140
aggcgatgat acaaatctcc gttgtacttt gtttcgcgct tggtataatc gctgggggtc   1200
aaagatgagt gttttagtgt attctttcgc ctctttcgtt ttaggttggt gccttcgtag   1260
tggcattacg tattttaccc gtttaatgga aacttcctca tgaaaaagtc tttagtcctc   1320
aaagcctctg tagccgttgc taccctcgtt ccgatgctgt ctttcgctgc tgagggtgac   1380
gatcccgcaa aagcggcctt taactccctg caagcctcag cgaccgaata tatcggttat   1440
gcgtgggcga tggttgttgt cattgtcggc gcaactatcg gtatcaagct gtttaagaaa   1500
ttcacctcga aagcaagctg ataaaccgat acaattaaag gctccttttg gagccttttt   1560
ttttggagat tttcaacgtg aaaaaattat tattcgcaat tcctttagtt gttcctttct   1620
attctcactc cgctgaaact gttgaaagtt gtttagcaaa accccataca gaaaattcat   1680
ttactaacgt ctggaaagac gacaaaactt tagatcgtta cgctaactat gagggttgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgaag   2220
atccattcgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgagggag gcggttccgg tggtggctct ggttccggtg   2400
attttgatta tgaaaagatg gcaaacgcta ataagggggc tatgaccgaa aatgccgatg   2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttag cgctggtaaa ccatatgaat tttctattga ttgtgacaaa ataaacttat   2760
tccgtggtgt ctttgcgttt cttttatatg ttgccacctt tatgtatgta ttttctacgt   2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcatttttga cgttaaacaa aaaatcgttt cttatttgga   3180
ttgggataaa taatatggct gtttattttg taactggcaa attaggctct ggaaagacgc   3240
tcgttagcgt tggtaagatt caggataaaa ttgtagctgg gtgcaaaata gcaactaatc   3300
ttgatttaag gcttcaaaac ctcccgcaag tcgggaggtt cgctaaaacg cctcgcgttc   3360
ttagaatacc ggataagcct tctatatctg atttgcttgc tattgggcgc ggtaatgatt   3420
```

```
cctacgatga aaataaaaac ggcttgcttg ttctcgatga gtgcggtact tggtttaata   3480
cccgttcttg gaatgataag gaaagacagc cgattattga ttggtttcta catgctcgta   3540
aattaggatg ggatattatt tttcttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt taaatatggc gattctcaat taagccctac tgttgagcgt tggctttata   3780
ctggtaagaa tttgtataac gcatatgata ctaaacaggc tttttctagt aattatgatt   3840
ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catatagtta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta aatgtaatta attttgtttt cttgatgttt   4260
gtttcatcat cttcttttgc tcaggtaatt gaaatgaata attcgcctct gcgcgatttt   4320
gtaacttggt attcaaagca atcaggcgaa tccgttattg tttctcccga tgtaaaaggt   4380
actgttactg tatattcatc tgacgttaaa cctgaaaatc tacgcaattt ctttatttct   4440
gttttacgtg ctaataattt tgatatggtt ggttcaattc cttccataat tcagaagtat   4500
aatccaaaca atcaggatta tattgatgaa ttgccatcat ctgataatca ggaatatgat   4560
gataattccg ctccttctgg tggtttcttt gttccgcaaa atgataatgt tactcaaact   4620
tttaaaatta ataacgttcg ggcaaaggat ttaatacgag ttgtcgaatt gtttgtaaag   4680
tctaatactt ctaaatcctc aaatgtatta tctattgacg gctctaatct attagttgtt   4740
agtgcaccta aagatatttt agataacctt cctcaattcc tttctactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aaatattgtc tgtgccacgt   5040
attcttacgc tttcaggtca gaagggttct atctctgttg gccagaatgt cccttttatt   5100
actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
actaatcaaa gaagtattgc tacaacggtt aatttgcgtg atggacagac tcttttactc   5340
ggtggcctca ctgattataa aaacacttct caagattctg gcgtaccgtt cctgtctaaa   5400
atccctttaa tcggcctcct gtttagctcc cgctctgatt ccaacgagga aagcacgtta   5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgacccca aaaaacttga   5700
tttgggtgat ggttcacgta gtgggccatc gccctgatag acggtttttc gccctttgac   5760
```

```
gttggagtcc acgttcttta atagtggact cttgttccaa actggaacaa cactcaaccc   5820
tatctcgggc tattcttttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcgctgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg ctttacactt tatgcttccg gctcgtatgt tgtgtggaat   6180
tgtgagcgga taacaatttc acacaggaaa cagctatgac catgattacg aattcgagct   6240
cctaatccct atcagtgata gagattgaca tccctatcag tgatagagat actgagcaca   6300
tcagcaggac gcactgaccg aattcattaa agaggagaaa ggtaccatga aagcgttaac   6360
ggccaggcaa caagaggtgt ttgatctcat ccgtgatcac atcagccaga caggtatgcc   6420
gccgacgcgt gcggaaatcg cgcagcgttt ggggttccgt tccccaaacg cggctgaaga   6480
acatctgaag gcgctggcac gcaaaggcgt tattgaaatt gtttccggcg catcacgcgg   6540
gattcgtctg ttgcaggaag aggaagaagg gttgccgctg gtaggtcgtg tggctgccga   6600
tgaaccactt ctggcgcaac agcatattga aggtcattat caggtcgatc cttccttatt   6660
caagccgaat gctgatttcc tgctgcgcgt cagcgggatg tcgatgaaag atatcggcat   6720
tatggatggt gacttgctgg cagtgcataa aactcaggat gtacgtaacg gtcaggtcgt   6780
tgtcgcacgt attgatgacg aagttaccgt taagcgcctg aaaaaacagg gcaataaagt   6840
cgaactgttg ccagaaaata gcgagtttaa accaattgtc gttgaccttc gtcagcagag   6900
cttcaccatt gaagggctgg cggttggggt tattcgcaac ggcgactggc tgtaaaagct   6960
tgatatcgaa ttcctgcagc ccgggggatc ccatggtacg cgtggcatca aataaaacga   7020
aaggctcagt cgaaagactg ggcctttcgt tttatctgtt gtttgtcggt gaacgctctc   7080
ctgagtagga caaatccgcc gccctagacg atcgcccttc ccaacagttg cgcagcctga   7140
atggcgaatg gcgctttgcc tggtttccgg caccagaagc ggtgccggaa agctggctgg   7200
agtgcgatct tcctgaggcc gatacggtcg tcgtcccctc aaactggcag atgcacggtt   7260
acgatgcgcc catctacacc aacgtaacct atcccattac ggtcaatccg ccgtttgttc   7320
ccacggagaa tccgacgggt tgttactcgc tcacatttaa tgttgatgaa agctggctac   7380
aggaaggcca gacgcgaatt atttttgatg gcgttcctat tggttaaaaa atgagctgat   7440
ttaacaaaaa tttaacgcga attttaacaa aatattaacg tttacaattt aaatatttgc   7500
ttatacaatc ttcctgtttt tggggctttt ctgattatca accggggtac atatgattga   7560
catgctagtt ttacgattac cgttcatcga ttctcttgtt tgctccagac tctcaggcaa   7620
tgacctgata gcctttgtag atctctcaaa aatagctacc ctctccggca ttaatttatc   7680
agctagaacg gttgaatatc atattgatgg tgatttgact gtctccggcc tttctcaccc   7740
ttttgaatct ttacctacac attactcagg cattgcattt aaaatatatg agggttctaa   7800
aaatttttat ccttgcgttg aaataaaggc ttctcccgca aaagtattac agggtcataa   7860
tgtttttggt acaaccgatt tagctttatg ctctgaggct ttattgctta attttgctaa   7920
ttctttgcct tgcctgtatg atttattgga tgtt                               7954
```

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 109

Leu Pro Xaa Thr Gly
1               5

<210> SEQ ID NO 110
<211> LENGTH: 5
<212> TYPE: PRT
<213> ORGANISM: Listeria monocytogenes

<400> SEQUENCE: 110

Thr Glu Ala Lys Asp
1               5

<210> SEQ ID NO 111
<211> LENGTH: 5
<212> TYPE: PRT
<213> ORGANISM: Lactococcus lactis

<400> SEQUENCE: 111

Val Tyr Ala Asp Thr
1               5

<210> SEQ ID NO 112
<211> LENGTH: 5
<212> TYPE: PRT
<213> ORGANISM: Bacillus anthracis

<400> SEQUENCE: 112

Ile Gln Ala Glu Val
1               5

<210> SEQ ID NO 113
<211> LENGTH: 5
<212> TYPE: PRT
<213> ORGANISM: Listeria monocytogenes

<400> SEQUENCE: 113

Ala Ser Ala Ser Thr
1               5

<210> SEQ ID NO 114
<211> LENGTH: 5
<212> TYPE: PRT
<213> ORGANISM: Listeria monocytogenes

<400> SEQUENCE: 114

Val Ser Ala Asp Glu
1               5

<210> SEQ ID NO 115
<211> LENGTH: 5
<212> TYPE: PRT
<213> ORGANISM: Bacillus anthracis

<400> SEQUENCE: 115

Ala Phe Ala Glu Asp
1               5

<210> SEQ ID NO 116
<211> LENGTH: 5
<212> TYPE: PRT
<213> ORGANISM: Staphylococcus aureus

<400> SEQUENCE: 116

Val Gln Ala Ala Glu
1 5

<210> SEQ ID NO 117
<211> LENGTH: 5
<212> TYPE: PRT
<213> ORGANISM: Listeria monocytogenes

<400> SEQUENCE: 117

Asp Lys Ala Leu Thr
1 5

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 118
aannnnnnnn nnnnnnnnnn ntt 23

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
tatatatata tatatatata 20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
tatatatata tatatata 18

<210> SEQ ID NO 121
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
cccccccccc 10

-continued

```
<210> SEQ ID NO 122
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

cccccccccc cc                                                        12
```

BACTERIOPHAGES EXPRESSING ANTIMICROBIAL PEPTIDES AND USES THEREOF

CROSS REFERENCE TO RELATED APPLICATIONS

This application is a continuation application under 35 U.S.C. § 120 of co-pending International Application PCT/US2010/026357, filed 5 Mar. 2010, which claims benefit under 35 U.S.C. 119(e) of U.S. Provisional Patent Application Ser. No. 61/157,773 filed Mar. 5, 2009, the contents of which are incorporated herein in its entirety by reference.

GOVERNMENT SUPPORT

This invention was made with the Government Support under Contract No: OD003644 awarded by the National Institutes of Health (NIH) and Contract No. W911NF-07-D-004 awarded by the U.S. Army Research Office. The Government has certain rights in the invention.

SEQUENCE LISTING

The instant application contains a Sequence Listing that has been submitted via EFS-Web and is hereby incorporated by reference in its entirety. Said ASCII copy, is a computer readable form under 37 C.F.R. § 1.821(e) created on Mar. 5, 2010, is named 701586PCT.txt, and is 399,011 bytes in size.

FIELD OF THE INVENTION

The present invention relates to the field of treatment and prevention of bacteria and bacterial infections. In particular, the present invention relates to engineered bacteriophages that have been engineered to express and secrete antimicrobial agents, such as antimicrobial peptides and naturally occurring antimicrobial peptides to potentiate the antimicrobial effect and bacterial killing of the bacteriophage.

BACKGROUND

Bacteria rapidly develop resistance to antibiotic drugs within years of first clinical use. Antibiotic resistance can be acquired by horizontal gene transfer or result from persistence, in which a small fraction of cells in a population exhibits a non-inherited tolerance to antimicrobials. Since antimicrobial drug discovery is increasingly lagging behind the evolution of antibiotic resistance, there is a pressing need for new antibacterial therapies.

Bacterial infections are responsible for significant morbidity and mortality in clinical settings. Though the advent of antibiotics has reduced the impact of bacterial diseases on human health, the constant evolution of antibiotic resistance poses a serious challenge to the usefulness of today's antibiotic drugs. Infections that would have been easily cured by antibiotics in the past are now able to survive to a greater extent, resulting in sicker patients and longer hospitalizations. The economic impact of antibiotic-resistant infections is estimated to be between US $5 billion and US $24 billion per year in the United States alone. Resistance to antibiotic drugs develops and spreads rapidly, often within a few years of first clinical use. However, the drug pipelines of pharmaceutical companies have not kept pace with the evolution of antibiotic resistance.

Acquired antibiotic resistance results from mutations in antibacterial targets or from genes encoding conjugative proteins that pump antibiotics out of cells or inactivate antibiotics. Horizontal gene transfer, which can occur via transformation, conjugative plasmids, or conjugative transposons, is a major mechanism for the spread of antibiotic resistance genes. For example, *Staphylococcus aureus* became quickly resistant to sulpha drugs in the 1940s, penicillin in the 1950s, and methicillin in the 1980s. In 2002, staphylococci developed resistance to vancomycin, the only uniformly effective antibiotic against staphylococci, by receiving vancomycin-resistance genes via conjugation from co-infecting *Enterococcus faecalis*, which itself became completely resistant to vancomycin in nosocomial settings by 1988. Drugs such as ciprofloxacin that induce the SOS response can even promote the horizontal dissemination of antibiotic resistance genes by mobilizing genetic elements. For example, *Streptococcus pneumoniae* and *Neisseria gonorrhoeae* have also obtained resistance to antibiotics (Morens, et al., (2004) Nature 430: 242-249). Sub-inhibitory concentrations or incomplete treatment courses can present evolutionary pressures for the development of antibiotic resistance. Use of antibiotics outside of clinical settings, for example in livestock for the agricultural industry, has contributed to the emergence of resistant organisms such as methicillin-resistant staphylococci and is unlikely to abate due to economic reasons and modern farming practices. Resistance genes that develop in non-clinical settings may be subsequently transmitted to bacterial populations which infect humans, worsening the antibiotic resistance problem.

In addition to acquiring antibiotic-resistance genes, a small subpopulation of cells known as persisters can survive antibiotic treatment by entering a metabolically-dormant state. Persister cells do not typically carry genetic mutations but rather exhibit phenotypic resistance to antibiotics. In *Escherichia coli*, the fraction of a population that represents persister cells increases dramatically in late-exponential and stationary phases. Chromosomally-encoded toxins may be important contributors to the persister phenotype but the underlying mechanisms that control the stochastic persistence phenomena are not well understood. Persisters constitute a reservoir of latent cells that can begin to regrow once antibiotic treatment ceases and may be responsible for the increased antibiotic tolerance observed in bacterial biofilms. By surviving treatment, persisters may play an important role in the development of mutations or acquisition of genes that confer antibiotic resistance.

Several strategies have been proposed for controlling antibiotic resistant infections. New classes of antibiotics would improve the arsenal of drugs available to fight antibiotic-resistant bacteria but few are in pharmaceutical pipelines. Surveillance and containment measures have been instituted in government and hospitals so that problematic infections are rapidly detected and isolated but do not address the fundamental evolution of resistance. Cycling antibiotics is one method of controlling resistant organisms but is costly and may not be efficacious. Reducing the overprescribing of antibiotics has only moderately reduced antibiotic resistance. Efforts have been also made to lessen the use of antibiotics in farming but some use is inevitable.

Using bacteriophage to kill bacteria has been in practice since the early $20^{th}$ century, particularly in Eastern Europe[16, 17]. Bacteriophage can be chosen to lyse and kill bacteria or can be modified to express lethal genes to cause cell death. However, bacteriophage which are directly lethal to their bacterial hosts can also produce phage-resistant bacteria in short amounts of time. In addition to the aforementioned approaches, novel methods for designing antimicrobial drugs are becoming more important to extending the lifespan of the antibiotic era. Combination therapy with different antibiotics or antibiotics with phage may enhance bacterial cell killing and thus reduce the incidence of antibiotic resistance, and reduce persisters. Unmodified filamentous bacteriophage have been shown to augment antibiotic efficacy. Systems biology analysis can be employed to identify pathways to target and followed by synthetic biology to devise methods to attack those pathways.

Bacterial biofilms are sources of contamination that are difficult to eliminate in a variety of industrial, environmental and clinical settings. Biofilms are polymer structures secreted by bacteria to protect bacteria from various environmental attacks, and thus result also in protection of the bacteria from disinfectants and antibiotics. Biofilms can be found on any environmental surface where sufficient moisture and nutrients are present. Bacterial biofilms are associated with many human and animal health and environmental problems. For instance, bacteria form biofilms on implanted medical devices, e.g., catheters, heart valves, joint replacements, and damaged tissue, such as the lungs of cystic fibrosis patients. Bacteria in biofilms are highly resistant to antibiotics and host defenses and consequently are persistent sources of infection.

Biofilms also contaminate surfaces such as water pipes and the like, and render also other industrial surfaces hard to disinfect. For example, catheters, in particular central venous catheters (CVCs), are one of the most frequently used tools for the treatment of patients with chronic or critical illnesses and are inserted in more than 20 million hospital patients in the USA each year. Their use is often severely compromised as a result of bacterial biofilm infection, which is associated with significant mortality and increased costs. Catheters are associated with infection by many biofilm-forming organisms such as *Staphylococcus epidermidis, Staphylococcus aureus, Pseudomonas aeruginosa, Enterococcus faecalis* and *Candida albicans*, which frequently result in generalized blood stream infection. Approximately 250,000 cases of CVC-associated bloodstream infections occur in the US each year with an associated mortality of 12%-25% and an estimated cost of treatment per episode of approximately $25, 000. Treatment of CVC-associated infections with conventional antimicrobial agents alone is frequently unsuccessful due to the extremely high tolerance of biofilms to these agents. Once CVCs become infected the most effective treatment still involves removal of the catheter, where possible, and the treatment of any surrounding tissue or systemic infection using antimicrobial agents. This is a costly and risky procedure and re-infection can quickly occur upon replacement of the catheter.

Bacteriophages (often known simply as "phages") are viruses that grow within bacteria. The name translates as "eaters of bacteria" and reflects the fact that as they grow, the majority of bacteriophages kill the bacterial host in order to release the next generation of bacteriophages. Naturally occurring bacteriophages are incapable of infecting anything other than specific strains of the target bacteria, undermining their potential for use as control agents.

Bacteriophages and their therapeutic uses have been the subject of much interest since they were first recognized early in the 20th century. Lytic bacteriophages are viruses that infect bacteria exclusively, replicate, disrupt bacterial metabolism and destroy the cell upon release of phage progeny in a process known as lysis. These bacteriophages have very effective antibacterial activity and in theory have several advantages over antibiotics. Most notably they replicate at the site of infection and are therefore available in abundance where they are most required; no serious or irreversible side effects of phage therapy have yet been described and selecting alternative phages against resistant bacteria is a relatively rapid process that can be carried out in days or weeks.

Bacteriophages (phages) prey on bacteria, infecting them, replicating and leaving the host, either by being shed non-lytically or lysing the host cell. The lytic property of bacteriophages led to them being discovered by Frederick Twort in 1915 (Twort Lancet 1915) and independently by Felix D'Herelle in 1917 (d'Herelle Comptes Rendus Hebdomadaires des Seances de L'academie des Sciences 1917), with D'Herelle recognizing the potential of these "bacteria-eaters" as a therapeutic modality. Bacteriophage therapy was successfully used to combat bacterial infections in Africa and India against cholera and to disinfect water wells. Historically, bacteriophage therapy predates the widespread use of antibiotics, but due to the advent of broad-spectrum antibiotics in the western world, this form of anti-infective treatment has not been pursued. Most, if not all, bacteriophage therapy is performed in the former Soviet Republic states due to the continued development and refinement of bacteriophage therapy approaches during the cold war (Stone Science 2002; Deresinski., Clin Infect. Diseases, 2009).

However, western practitioners have shied away from harnessing phage therapy, citing two primary concerns: i) the exquisite specificity of bacteriophages which means they can't be used like broad-spectrum antibiotics and necessitate a shift in clinical treatment protocol towards combination treatments, and ii) the quick development of phage resistance by strains of bacteria while they are being treated (Skurnik and Strauch., Int. J. Med. Microbiol. 2006).

Bacteriophages have been used in the past for treatment of plant diseases, such as fireblight as described in U.S. Pat. No. 4,678,750. Also, Bacteriophages have been used to destroy biofilms (e.g., U.S. Pat. No. 6,699,701). In addition, systems using natural bacteriophages that encode biofilm-destroying enzymes in general have been described. Art also provides a number of examples of lytic enzymes encoded by bacteriophages that have been used as enzyme dispersion to destroy bacteria (U.S. Pat. No. 6,335,012 and U.S. Patent Application Publication No. 2005/0004030).

The Eastern European research and clinical trials, particularly in treating human diseases, such as intestinal infections, has apparently concentrated on use of naturally occurring phages and their combined uses (Lorch, A. (1999), "Bacteriophages: An alternative to antibiotics?" Biotechnology and Development Monitor, No. 39, p. 14-17). For example, non-engineered bacteriophages have been used as carriers to deliver antibiotics (such as chloroamphenicol) (Yacoby et al., Antimicrobial agents and chemotherapy, 2006; 50; 2087-2097). Non-engineered bacteriophages have also had aminoglycosides antibiotics, such as chloroamphenicol, attached to the outside of filamentous non-engineered bacteriophage (Yacoby et al., Antimicrobial agents and chemotherapy, 2007; 51; 2156-2163). Non-engineered filamentous Pf3 bacteriophages have been reported to be administered with low concentration of gentamicin, where neither the filamentous Pf3 nor the gentamicin could eliminate the bacterial infection alone (Hagens et al, Microb. Drug resistance, 2006; 12; 164-8). Simultaneous administration of non-engineered bacteriophages and the antibiotic enrofloxacin have been reported, however the use of the antibiotic alone was reported to be more effective than the combination of the antibiotic and bacteriophage (see Table 1 in Huff et al., 2004; Poltry Sci, 83; 1994-1947).

Although there have been some reports of engineered bacteriophages, these have not been widely developed. For example, engineered M13 non-lytic bacteriophage that carry lethal cell death genes Gef and ChpBK. (Westwater et al., 2003, Antimicrobial agents and chemotherapy, 47; 1301-1307) have been reported.

Constant evolutionary pressure will ensure that antibiotic resistance bacteria will continue to grow in number. The lack of new antibacterial agents being developed in the last 25-30 years certainly bodes poorly for the future of the antibiotic era (Wise, R (2004) J Antimicrob Chemother 54: 306-310). As a result, there has been growing interest in phage therapy due to the advent of a greater number of antibiotic-resistant strains of bacteria (Merril, Scholl et al. Nature reviews Drug discovery). The specificity of bacteriophages is dependent on the specificity of the interaction between the tail fibers of the bacteriophage and the recognized domain(s) of the bacteria for which the bacteriophage exhibits tropism (Liu, Deora et al. Science 2002; Dai, Hodes et al. Proc Natl Acad Sci USA 2010). It is generally held to be true that bacteriophages are not able to infect more than a handful of closely related sub-species of bacteria, much less bacteria from different strains (Lederberg et al., Proc Natl Acad Sci USA 1996).

However, recent work has shown that the specificity of bacteriophages in common usage might be an artifact of historical isolation procedures used, which bias the isolation towards the most infective bacteriophage, with the greatest burst size (Rabinovitch, Hadas et al. J Bacteriol 1999). Specifically, it is feasible to change the protocols for isolation of phage to grow a desired phage on multiple hosts over multiple rounds. This ensures a broader selectivity of the phage throughout the passage from the initial input material. The isolation of bacteriophages with multiple specificities without great difficulty and only minor changes in the isolation protocols speaks to the enormous reservoir of variability in nature, and makes the use of single or low numbers of combinations of bacteriophages in an anti-infective setting more feasible (Jensen, Schrader et al. Appl Environ Microbiol 1998).

Similarly, it is considered a by-product of millions of years of co-evolution in the bacteria-bacteriophage predator-prey system that the prey (bacteria) have evolved the ability to quickly shift to a more resistant form in response to predation by bacteriophages. This prevents complete elimination of the prey species by the predating species, which would also result in a catastrophic extinction of the predating species. This fact has previously made phage therapy a less desirable alternative to antibiotic therapy.

Because antibiotic resistance in treating bacterial infections and biofilms poses a significant hurdle to eliminating or controlling or inhibiting bacteria and biofilms with conventional antimicrobial drugs, new anti-biofilm strategies, such as phage therapy, should be explored. Novel synthetic biology technologies are needed to enable the engineering of natural phage with biofilm-degrading enzymes to produce libraries of enzymatically-active phage, which can complement efforts to screen for new biofilm-degrading bacteriophages in the environment.

Thus, new methods for combating bacterial infections are needed in order to prolong the antibiotic age. For example, bacteriophage therapy or synthetic antibacterial peptides have been proposed as potential solutions (Loose et al., (2006) Nature 443: 867-869; Curtin, et al., (2006) Antimicrob Agents Chemother 50: 1268-1275).

SUMMARY OF THE INVENTION

Although bacteriophage therapy as been reported to be successful to combat bacterial infections in Africa and India against cholera and to disinfect water wells, the use of bacteriophage therapy to combat bacterial infection was not pursued due to the problem of rapid development of phage resistance by the bacteria and the advent of broad-spectrum antibiotics. Furthermore, two primary concerns: i) the host strain-specificity of bacteriophages which limits their use as broad-spectrum antimicrobial agents, and ii) the quick development of phage resistance by bacterial strains stemmed the development of phage therapy for use in killing or eliminating bacterial infections (Skurnik and Strauch Int J Med Microbiol 2006).

In particular, the development of phage resistance is a major problem for the effective use of bacteriophages to eliminate bacterial infections. In particular, because bacteria divide so rapidly, the mutant phage-resistant bacterial strains rapidly and exponentially grow to effectively eliminate any beneficial antimicrobial effects of the bacteriophage. As a result bacteriophage resistance by the bacteria occurs typically within a short period of time (e.g. 10 hrs or less), and has significantly limited the practical use of bacteriophages in therapy. In fact, the development of phage resistance is a major problem in real life settings where bacterial infections and bacterial contamination are common, such as hospitals and industrial settings, such as heating/cooling systems (e.g., HVAC systems).

The inventors have demonstrated, using an engineered bacteriophage expressing antimicrobial polypeptides (e.g. antimicrobial peptides or lytic enzymes), they are able to delay the development of bacteriophage resistance and have achieved long-term suppression of phage resistance of bacteria by at least 40 hours or more. Thus, the inventors have overcome these issues by engineering bacteriophages to express antimicrobial agents such as antimicrobial peptides (AMPs), such that the engineered bacteriophages have enhanced bacteriostatic or bacteriocidal properties, and have been demonstrated to eliminate numerous bacterial host strains simultaneously, and significantly circumvent the phage resistance by bacterial strains. The inventors have demonstrated that the engineered bacteriophages are self-renewing, achieving a high concentration locally of the bacteriophage as well as ampliees the antibacterial effect of the engineered bacteriophages.

The inventors demonstrate herein that engineered bacteriophages which have the ability for long term suppression of phage resistance of the host bacteria, and have the ability to inhibit bacterial infection of a broad range of bacterial host species. In particular, the present invention is directed to an engineered enzymatically active bacteriophage that is capable of killing the bacteria by lysis and expressing and secreting an antimicrobial agent such as an antimicrobial peptide (AMP). One aspect of the present invention is directed to engineered enzymatically active bacteriophages have been engineered to express an antimicrobial agent such as an antimicrobial peptide (AMP).

Accordingly, one aspect of the present invention relates to the engineered bacteriophages which express an antimicrobial agent, such as an antimicrobial peptide for use to inhibit bacteria and/or removing bacterial biofilms for bioremediation, such as in environmental, industrial, and clinical settings by administering a composition comprising at least one AMP-engineered bacteriophage. An engineered bacteriophage which express at least one antimicrobial agent, e.g. an antimicrobial peptide (AMP) are referred to as a "antimicrobial agent engineered bacteriophage" or "antimicrobial peptide engineered bacteriophage" or an "AMP-engineered bacteriophage" herein.

One aspect of the present invention relates to methods of using engineered bacteriophages, where the bacteriophage has been engineered to express an antimicrobial peptide (herein referred to as "AMP") to potentiate the antimicrobial effect of bacterial killing (i.e. eliminating or inhibiting the growth or controlling the bacteria) by the bacteriophage. Accordingly, the present invention relates to the discovery that an engineered bacteriophage expressing at least one antimicrobial peptide (Amp). In some embodiments, an Amp expressed by an engineered bacteriophage as discussed herein is a naturally occurring polypeptide, for example from an organism, for example natural antimicrobial peptides from frog's skin, human sweat or ant's venom.

In some embodiments, an AMP useful in being expressed by the engineered bacteriophages as disclosed herein includes, but it not limited to, at least one of the following different AmPs: Indolicidin (SEQ ID NO: 6), Cecropin P1 (SEQ ID NO: 11), Dermaseptin (SEQ ID NO: 14), Ponericin W1 (SEQ ID NO: 16), Ponericin W4 (SEQ ID NO: 18), Ponericin W5 (SEQ ID NO: 20), Ponericin W6 (SEQ ID NO: 22) or variants thereof. In some embodiments, an AMP-engineered bacteriophage expresses an AMP disclosed in Table 4, e.g. any AMP of SEQ ID NO: 10, or SEQ ID NO: 36-45. In some embodiments, an engineered bacteriophage expresses at least one of any of the following sequences, SEQ ID NO: 40 (J589.K4 or Ponericin W3), SEQ ID NO; 42 (J6084.H2 or Ponericin W5), SEQ ID NO: 44 (J6123.D7 or Ponericin W1), SEQ ID NO: 71 (LysK165 or CHAP165).

One aspect of the present invention relates to methods of using engineered bacteriophages, where the bacteriophage has been engineered to express an antimicrobial agent, such as an antimicrobial peptide as disclosed herein, which on expression of the antimicrobial agent by the bacteriophage-infected host bacterial cell, the antimicrobial agent is released from the lysis of the host bacterial cell.

Another aspect of the present invention relates to an engineered bacteriophage which comprises a nucleic acid encoding at least one antimicrobial agent. In some embodiments, an engineered bacteriophage comprises at least one of any of the following nucleic acid sequences; SEQ ID NO: 79 (which encodes J589.K4 or Ponericin W3 AMP), SEQ ID NO; 80 (which encodes J6084.H2 or Ponericin W5 AMP), SEQ ID NO: 81 (which encodes J6123.D7 or Ponericin W1 AMP), SEQ ID NO: 82 (which encodes LysK165 or CHAP165 antimicrobial polypeptide). In such and embodiment of this aspect of the invention, an engineered bacteriophage can comprise at least 2, 3, 4, 5 or even more, for example 10 of the same or different nucleic acids which encode an antimicrobial agent or AMP or antimicrobial polypeptide.

Another aspect of the present invention relates to an engineered bacteriophage which comprises a nucleic acid encoding an agent, such as but not limited to a protein, which has antimicrobial properties (i.e. reduces the viability of a bacteria). Such herein engineered bacteriophage which comprises a nucleic acid encoding an agent which is not a peptide but retains antimicrobial properties. For example, one such antimicrobial agent engineered bacteriophage expresses the antimicrobial polypeptide LysK165 (CHAP165) (SEQ ID NO: 71). In such an embodiment, then polypeptide-engineered bacteriophage comprises at least one nucleic acid sequence of SEQ ID NO: 82 (which encodes LysK165 or CHAP165 antimicrobial polypeptide of SEQ ID NO: 71).

In some embodiments, the expressed antimicrobial agent or AMP is released from the bacterial host cell by the host cells secretory pathway. In such an embodiment, the antimicrobial agent, such as an antimicrobial peptide or polypeptide expressed from the bacteriophage-infected host bacterial cell also contains a signal peptide such as a secretory signal sequence. Any signal peptide known to one of ordinary skill in the art can be used, where the signal peptide or secretory signal sequence allows intracellular transport of the antimicrobial peptide or polypeptide to the bacterial cell plasma membrane for its secretion from the bacteria. Accordingly, in such an embodiment, the expressed antimicrobial peptide is expressed as a pro-antimicrobial peptide comprising the signal sequence and antimicrobial peptide, where the signal sequence is subsequently cleaved as the peptide is secreted from the host bacteria to render the mature antimicrobial peptide in its active form without the signal sequence.

In one embodiment, an antimicrobial agent increases the entry of an antimicrobial agent into a bacterial cell, for example, a susceptibility agent is a porin or porin-like protein, such as but is not limited to, protein OmpF, and Beta barrel porins, or other members of the outer membrane porin (OMP)) functional superfamily which include, but are not limited to those disclosed in world wide web site: "//biocyc.org/ECOLI/NEW-IMAGE?object=BC-4.1.B", or a variant or fragment thereof. In some embodiments, the signal peptide is the bacterial signal sequence Omp (SEQ ID NO: 72) which is fused to the N-terminus of the AMP or antimicrobial polypeptide expressed by the engineered bacteriophage. Accordingly, in some embodiments, the nucleic acid encoding Omp (SEQ ID NO: 78) is located at the 5' and/or 3' end of the nucleic acid encoding the AMP or antimicrobial peptide to be expressed by the engineered bacteriophage.

One particular advantage of the antimicrobial agent, e.g. AMP-engineered bacteriophages as disclosed herein is the production and release (via either lysis or being secreted) of the expressed antimicrobial agent, e.g. AMP in the immediate vicinity and locality of the bacteriophage, thus allowing the antimicrobial peptide e.g. AMP to target and kill neighboring bacterial strains not necessarily infected by the antimicrobial agent-engineered bacteriophage. This allows for the antimicrobial agent, e.g. AMP-engineered bacteriophage to effectively killing a broad spectrum of different bacterial species, as the released antimicrobial agent, e.g. AMP targets and has efficacy on a variety of different bacterial species in the near vicinity which may otherwise be resistant to infection or lysis by the particular species of bacteriophage of the antimicrobial agent engineered bacteriophage. Thus, an antimicrobial agent engineered bacteriophage results in the release of the antimicrobial agent in the near vicinity of the bacteria to target a variety of different species of bacteria even if these species of bacteria have not, or are unable be infected with the antimicrobial agent engineered bacteriophage. Stated another way, a significant advantage of the antimicrobial agent-engineered bacteriophages, e.g. AMP-engineered bacteriophages is that they are effective at killing a broad spectrum of bacterial species, either through infection and lysis of specific bacterial strains or through release of antimicrobial agents, e.g, AMPs to kill either bacteriophage-resistant bacterial host cells or other bacterial strains in a heterogenous bacterial cell population.

Another advantage of the antimicrobial peptide-engineered bacteriophages of present invention is an improved delivery of antimicrobial agents in the vicinity of the bacterial infection. Additionally, another advantage of delivering the antimicrobial agents by being expressed by a bacteriophage is that it enables the antimicrobial agents to come into contact with the bacterial cells which may not be accessible using conventional antimicrobial agent delivery methods, due for example, the bacteria being located in a difficult to access location, such as a small space or between two pieces of material. As such, another advantage of the present invention which the present invention is an improved genetically engineered bacteriophage with an a broad spectrum target bacteria host range which can express and release antimicrobial agents within the near vicinity of bacterial cells, which may not be accessible to antimicrobial agent delivered by other means.

In some embodiments of this aspect, and all other aspects described herein, such an antimicrobial agent-engineered bacteriophage which decreases the viability of a bacteria refers to any bacteriophage expressing an antimicrobial agent, e.g. AMP or antimicrobial polypeptide (e.g. LysK165) which decreases the viability or a bacteria by at least about 10% or at least about 15%, or at least about 20% or at least about 30% or at least about 50% or more than 50%, or any integer between 10% and 50% or more, as compared to the absence of the antimicrobial agent-engineered bacteriophage alone or the presence of a non-engineered (e.g. wild-type) bacteriophage. In one embodiment, an antimicrobial agent-engineered bacteriophage specifically targets a particular bacterial strain. In another embodiment, an antimicrobial agent-engineered bacteriophage targets numerous bacterial strains simultaneously and reduces their viability.

In some embodiments, an antimicrobial agent, e.g. AMP or antimicrobial polypeptide modifies (i.e. inhibits or activates) a pathway which is specifically expressed in a bacterial cell. In one embodiment, an antimicrobial agent is an agent which has an additive effect of the efficacy of the bacteriophage to kill bacteria (i.e. the antimicrobial agent has an additive effect of the killing efficacy or inhibition of growth by the bacteriophage).

In some embodiments, an antimicrobial agent is not a chemotherapeutic agent. In another embodiment, an antimicrobial agent is not a toxin protein, and in another embodiment, an antimicrobial agent is not a bacterial toxin protein or bacterial toxin molecule.

Accordingly, the inventors have developed a modular design strategy in which bacteriophages are engineered to have enhanced capacity to kill bacteria to secrete a naturally occurring antimicrobial agent such as an antimicrobial peptide (AMP) or antimicrobial polypeptide.

In some embodiments, an antimicrobial-agent engineered bacteriophage can be engineered or modified to express (i) at least one antimicrobial agent such as an antimicrobial peptide (AmP). In some embodiments, an antimicrobial-agent engineered bacteriophage can be further modified to also express a biofilm degrading enzyme, such as dispersin B (DspB), an enzyme that hydrolyzes β-1,6-N-acetyl-D-glucosamine, or a SOS resistance gene such as LexA3, according to the methods as disclosed in U.S. patent application Ser. No. 12/337,677 and 11/662,551 and International Applications WO/2006/137847 and WO/2009/108406 which are incorporated herein in their entirety by reference.

In some embodiments, any one of these antimicrobial-agent engineered bacteriophages, used alone, or can be used in any combination. In some embodiments, an antimicrobial-agent engineered bacteriophage as disclosed herein can also be used with at least one additional antimicrobial-agent engineered bacteriophage. For example, one aspect discussed herein relates to an engineered bacteriophage which expresses an antimicrobial agents such as an AmP, such as, but not limited to Indolicidin (SEQ ID NO: 6), Cecropin P1 (SEQ ID NO: 11), Dermaseptin (SEQ ID NO: 14), Ponericin W1 (SEQ ID NO: 16), Ponericin W4 (SEQ ID NO: 18), Ponericin W5 (SEQ ID NO: 20), Ponericin W6 (SEQ ID NO: 22) and variants thereof. In some embodiments, an AMP-engineered bacteriophage expresses an AMP disclosed in Table 4, e.g. any AMP of SEQ ID NO: 10, or SEQ ID NO: 36-45. In some embodiments, an engineered bacteriophage expresses at least one of any of the following sequences, SEQ ID NO: 40 (J589.K4 or Ponericin W3), SEQ ID NO; 42 (J6084.H2 or Ponericin W5), SEQ ID NO: 44 (J6123.D7 or Ponericin W1), SEQ ID NO: 71 (LysK165 or CHAP165) and variants thereof.

The inventors also demonstrated that an antimicrobial-agent engineered bacteriophage as disclosed herein can reduce the number of bacteria in a population of bacteria.

In some embodiments of all aspects of the invention, any engineered bacteriophage disclosed herein which expresses an antimicrobial agent such as AmP can additionally comprise a least one of the degrading enzymes effective at degrading bacteria biofilms, such as effective EPS-degrading enzymes specific to the target biofilm, particularly, for example, dispersin B (DspB) which is discussed in PCT application Ser. No. 12/337,677 and 11/662,551 and International Applications WO/2006/137847 which is incorporated herein by reference.

Also discussed herein is the generation of a diverse library of antimicrobial-agent engineered bacteriophages described herein, such as a library of antimicrobial agent engineered bacteriophages which are capable of killing a wide variety of bacterial strains. This is advantageous than trying to isolate such different bacteriophages that have the ability to target and kill or reduce the viability of different bacterial strains Rapid bacteriophage (also referred to as "phage" herein) replication with subsequent bacterial lysis and expression of an antimicrobial agent, e.g. AMP, renders this a two-pronged attack strategy for killing bacteria and eliminating bacterial populations, and/or removing bacterial biofilms in environmental, industrial, and clinical settings. In some embodiments, a composition comprising an antimicrobial agent-engineered bacteriophage, e.g. an AMP-engineered bacteriophage is useful for bioremediation purposes, such as killing biofilms in heating and cooling systems, such as HVAC systems, industrial uses and the like.

The invention is further directed to the uses of such antimicrobial-agent engineered bacteriophage for reducing the viability of bacteria and/or killing bacteria within a mixed population of bacteria, such as a mixed (or heterogenous) population of bacterial host species. In some embodiments, the heterogenous bacterial population can comprise both phage-susceptible bacteria and phage-resistant bacteria.

Bacteriophages (often known simply as "phages") are viruses that grow within bacteria. The name translates as "eaters of bacteria" and reflects the fact that as they grow, the majority of bacteriophages kill the bacterial host in order to release the next generation of bacteriophages. Naturally occurring bacteriophages are incapable of infecting anything other than specific strains of the target bacteria, underlying their potential for use as control agents.

Bacteriophages and their therapeutic uses have been the subject of much interest since they were first recognized early in the 20th century. Lytic bacteriophages are viruses that infect bacteria exclusively, replicate, disrupt bacterial metabolism and destroy the cell upon release of phage progeny in a process known as lysis. These bacteriophages have very effective antibacterial activity and in theory have several advantages over antibiotics. Most notably they replicate at the site of infection and are therefore available in abundance where they are most required; no serious or irreversible side effects of phage therapy have yet been described and selecting alternative phages against resistant bacteria is a relatively rapid process that can be carried out in days or weeks.

Bacteriophage have been used in the past for treatment of plant diseases, such as fireblight as described in U.S. Pat. No. 4,678,750. Also, bacteriophages have been used to destroy biofilms (e.g., U.S. Pat. No. 6,699,701). In addition, systems using natural bacteriophages that encode biofilm destroying enzymes in general have been described. Art also provides a number of examples of lytic enzymes encoded by bacteriophages that have been used as enzyme dispersion to destroy bacteria (U.S. Pat. No. 6,335,012 and U.S. Patent Application Publication No. 2005/0004030). The Eastern European research and clinical trials, particularly in treating human diseases, such as intestinal infections, has apparently concentrated on use of naturally occurring phages and their combined uses (Lorch, A. (1999), "Bacteriophages: An alternative to antibiotics?" Biotechnology and Development Monitor, No. 39, p. 14-17).

For example, PCT Publication No. WO 2004/062677 provides a method of treating bacterial biofilm, wherein the method comprises use of a first bacteriophage that is capable of infecting a bacterium within said biofilm, and a first polysaccharide lyase enzyme that is capable of degrading a polysaccharide within said biofilm. However, other studies have showed that addition of alginate lyase to established *P. aeruginosa* biofilm caused no observable detachment of biofilm and the use of lyases would not be optimal for biofilm treatment (Christensen et al., 2001). WO/2006/137847 describes a bacteriophage that expresses a biofilm degrading enzyme attached to its surface.

However, one of the key problem associated with the use of bacteriophages as potential therapeutics are their high selectivity towards a specific strain of bacteria. Phages are often target and kill one particular strain of bacteria, leaving other strains unaffected. However, bacterial contamination, whether in food products or in patient infections or in biofilms on implantable devices, are typically composed of multiple different several strains of bacteria co-existing simultaneously. Thus, a bacterial infection comprises a heterogeneous population of bacterial strains. As a result, for phage therapy to be effective, a cocktail of different phages need to be used, typically combinations of up to 20 different phages need to be used. Herein, the inventors have discovered that a bacteriophage can be engineered to be effective in eliminating a bacterial infection comprising a heterogeneous population of bacteria, the bacteriophage should target multiple different bacterial strains or be effective at killing a variety of different bacterial strains.

Additionally, the FDA requires that each individual phage used for therapeutic purposes be tested and approved individually before it can be used in a combination with other bacteriophages as a therapy or antibacterial therapy. This significantly increases the cost and length of study of potential phage based therapeutic. It is thus highly desirable to increase the activity spectrum of individual bacteriophage to enable them to target a broad array of bacteria strains, rather than a single one.

The inventors have provides a novel modular design strategy in which phage that kill bacteria in a species-specific manner have been engineered to express antimicrobial agents, such as antimicrobial peptides (AmP) to generate engineered bacteriophages which have a broad activity spectrum to target and kill a variety of bacterial species and strains.

This strategy permits the development of a diverse library of antimicrobial-agent engineered bacteriophage rather than trying to isolate such phage from the environment. By multiplying within the bacterial population and hijacking the bacterial machinery, use of an antimicrobial-agent engineered bacteriophage achieves high local concentrations of both the lytic phage and the antimicrobial peptide in the zone of the bacterial population, even with small initial phage inoculations.

The inventors have demonstrated that an antimicrobial-agent engineered bacteriophage as disclosed herein are faster and have increased efficiency of killing bacteria, such as bacteria in biofilms as compared to use of a non-engineered bacteriophage alone (i.e. a bacteriophage which is not an engineered bacteriophage) (See FIG. 1). Additionally, the inventors have demonstrated that an antimicrobial-agent engineered bacteriophage as disclosed herein are more effective at killing a bacterial population comprising multiple different bacterial host strains as compared to use of a non-engineered bacteriophage alone (i.e. a bacteriophage which is not an engineered bacteriophage) (See FIG. 2). Thus, the inventors have demonstrated a significant and surprising improvement of such an antimicrobial-agent engineered bacteriophage as disclosed herein over the combined use of non-engineered bacteriophages as therapies described in prior art. Specifically, the inventors have also demonstrated that use of such an antimicrobial-agent engineered bacteriophage as disclosed herein are very effective at reducing the number of antibiotic resistant bacterial cells which can develop in the presence of sub-inhibitory antimicrobial drug concentrations.

Also, one significant advantage of an antimicrobial-agent engineered bacteriophage as disclosed herein as compared to methods using non-engineered bacteriophages is that the use of an antimicrobial-agent engineered bacteriophage as disclosed herein allows one to significantly reduce or eliminate a population of persister cells. For example, the administration or application of an antimicrobial-agent engineered bacteriophage as disclosed herein can reduce or eliminate a population of persister cells. Furthermore, the inventors have discovered that an antimicrobial-agent engineered bacteriophage as disclosed herein can reduce the number of antibiotic resistant mutant bacteria that survive in a bacterial population exposed to one or more antimicrobial agents, and therefore an antimicrobial-agent engineered bacteriophage described herein are effective at reducing the number of antibiotic resistant cells which develop in the presence of sub-inhibitory antimicrobial agent drug concentrations.

Another advantage of an antimicrobial-agent engineered bacteriophage as disclosed herein is that it allows one to reduce or eliminate multiple applications of the composition during the treatment of a surface having a bacterial biofilm.

One aspect of the present invention relates to engineering or modification of any bacteriophage strain or species to generate an antimicrobial-agent engineered bacteriophage disclosed herein. For example, an antimicrobial-agent engineered bacteriophage can be engineered from any bacteriophage known by a skilled artisan. For example, in one embodiment, the bacteriophage is a lysogenic bacteriophage, for example but not limited to a M13 bacteriophage. In another embodiment, the bacteriophage is a lytic bacteriophage such as, but not limited to T7 bacteriophage. In another embodiment, the bacteriophage is a phage K or a

*Staphyloccocus* phage K for use against bacterial infections of methicillin-resistant *S. aureus*.

One aspect of the present invention relates to an antimicrobial-agent engineered lysogenic M13 bacteriophage comprising a nucleic acid operatively linked to a M13 promoter, wherein the nucleic acid encodes at least one antimicrobial agent such as an antimicrobial peptide, including but not limited to Indolicidin, Cecropin P1, Dermaseptin, Ponericin W1, Ponericin W4, Ponericin W5, Ponericin W6, Ponercin W3 or antimicrobial polypeptide CHAP165.

Another aspect of the present invention relates to an antimicrobial-agent engineered lytic T7 bacteriophage comprising a nucleic acid operatively linked to a T7 promoter, wherein the nucleic acid encodes at least one antimicrobial agent such as an antimicrobial peptide, including but not limited to Indolicidin, Cecropin P1, Dermaseptin, Ponericin W1, Ponericin W4, Ponericin W5, Ponericin W6 Ponercin W3 or antimicrobial polypeptide CHAP165.

In some embodiments of all aspects described herein, an antimicrobial-agent engineered bacteriophage can comprise an agent which is selected from a group comprising, siRNA, antisense nucleic acid, asRNA, RNAi, miRNA and variants thereof. In some embodiments, the bacteriophage comprises an as RNA agent.

Another aspect of the present invention relates to a method to inhibit or eliminate a bacterial infection comprising administering to a surface infected with bacteria an antimicrobial-agent engineered bacteriophage comprising a nucleic acid operatively linked to a bacteriophage promoter, wherein the nucleic acid encodes at least one antimicrobial agent such as an antimicrobial peptide, including but not limited to Indolicidin, Cecropin P1, Dermaseptin, Ponericin W1, Ponericin W4, Ponericin W5, Ponericin W6, Ponericin W3 and CHAP165. The method can also optimally include administering at least one additional agent, such as an additional antimicrobial agent.

In some embodiments of all aspects described herein, a bacteriophage useful in the methods disclosed herein and used to generate an antimicrobial-agent engineered bacteriophage is any bacteriophage known by a skilled artisan. A non-limiting list of examples of bacteriophages which can be used are disclosed in Table 7F herein. In one embodiment, the bacteriophage is a lysogenic bacteriophage such as, for example a M13 lysogenic bacteriophage. In alternative embodiments, a bacteriophage useful in all aspects disclosed herein is a lytic bacteriophage, for example but not limited to a T7 lytic bacteriophage. In one embodiment, a bacteriophage useful in all aspects disclosed herein is a SP6 bacteriophage or a phage K, or a *staphylococcus* phage K bacteriophage.

In some embodiments, administration of any an antimicrobial-agent engineered bacteriophage as disclosed herein can occur substantially simultaneously with any additional agent, such as an additional antimicrobial agent. In alternative embodiments, the administration of an antimicrobial-agent engineered bacteriophage can occur prior to the administration of at least one additional antimicrobial agent. In other embodiments, the administration of an additional antimicrobial agent occurs prior to the administration of an antimicrobial-agent engineered bacteriophage.

In some embodiments, additional antimicrobial agents which can be administered with an antimicrobial-agent engineered bacteriophage as disclosed herein include, for example but not limited to, antimicrobial agents selected from a group comprising ciproflaxacin, levofloxacin, and ofloxacin, gatifloxacin, norfloxacin, lomefloxacin, trovafloxacin, moxifloxacin, sparfloxacin, gemifloxacin, pazufloxacin or variants or analogues thereof. In some embodiments, an antimicrobial agents useful in the methods as disclosed herein is ofloxacin or variants or analogues thereof. In some embodiments, antimicrobial agents useful in the methods as disclosed herein are aminoglycoside antimicrobial agents, for example but not limited to, antimicrobial agents selected from a group consisting of amikacin, gentamycin, tobramycin, netromycin, streptomycin, kanamycin, paromomycin, neomycin or variants or analogues thereof. In some embodiments, an antimicrobial agent useful in the methods as disclosed herein is gentamicin or variants or analogues thereof. In some embodiments, antimicrobial agents useful in the methods as disclosed herein are β-lactam antibiotic antimicrobial agents, such as for example but not limited to, antimicrobial agents selected from a group consisting of penicillin, ampicillin, penicillin derivatives, cephalosporins, monobactams, carbapenems, β-lactamase inhibitors or variants or analogues thereof. In some embodiments, an antimicrobial agent useful in the methods as disclosed herein is ampicillin or variants or analogues thereof.

Another aspect of the present invention relates to a composition comprising a lysogenic M13 antimicrobial-agent engineered bacteriophage comprising a nucleic acid operatively linked to a M13 promoter, wherein the nucleic acid encodes at least one antimicrobial agent, such as an antimicrobial peptide (AmP), for example but not limited to Indolicidin, Cecropin P1, Dermaseptin, Ponericin W1, Ponericin W4, Ponericin W5, Ponericin W6, Ponercin W3 or antimicrobial polypeptide CHAP165.

Another aspect of the present invention relates to a composition comprising a lytic T7 antimicrobial-agent engineered bacteriophage comprising a nucleic acid operatively linked to a T7 promoter, wherein the nucleic acid encodes at least one antimicrobial agent, such as an antimicrobial peptide (AmP), for example but not limited to Indolicidin, Cecropin P1, Dermaseptin, Ponericin W1, Ponericin W4, Ponericin W5, Ponericin W6, Ponercin W3 or antimicrobial polypeptide CHAP165.

In some embodiments, the composition can further comprise an additional agent, such as for example an antimicrobial agent such as, for example but not limited to, quinolone antimicrobial agents and/or aminoglycoside antimicrobial agents and/or β-lactam antimicrobial agent, for example, but not limited to, antimicrobial agents selected from a group comprising ciproflaxacin, levofloxacin, and ofloxacin, gatifloxacin, norfloxacin, lomefloxacin, trovafloxacin, moxifloxacin, sparfloxacin, gemifloxacin, pazufloxacin, amikacin, gentamycin, tobramycin, netromycin, streptomycin, kanamycin, paromomycin, neomycin, penicillin, ampicillin, penicillin derivatives, cephalosporins, monobactams, carbapenems, β-lactamase inhibitors or variants or analogues thereof.

In some embodiments, the composition comprises at least one antimicrobial-agent engineered bacteriophage as disclosed herein.

Another aspect of the present invention relates to a kit comprising a lysogenic M13 antimicrobial-agent engineered bacteriophage comprising the nucleic acid operatively linked to a M13 promoter, wherein the nucleic acid encodes at least one antimicrobial agent, such as an antimicrobial peptide (AmP), for example but not limited to Indolicidin, Cecropin P1, Dermaseptin, Ponericin W1, Ponericin W4, Ponericin W5, Ponericin W6, Ponercin W3 or antimicrobial polypeptide CHAP165.

Another aspect of the present invention relates a kit comprising a lytic T7 antimicrobial-agent engineered bacteriophage comprising the nucleic acid operatively linked to a T7 promoter, wherein the nucleic acid encodes at least one antimicrobial agent, such as an antimicrobial peptide (AmP), for example but not limited to Indolicidin, Cecropin P1, Dermaseptin, Ponericin W1, Ponericin W3, Ponericin W4, Ponericin W5, Ponericin W6, or antimicrobial polypeptide CHAP165.

In some embodiments, the methods and compositions as disclosed herein are administered to a subject. In some embodiments, the methods to inhibit or eliminate a bacterial infection comprising administering a composition comprising an antimicrobial-agent engineered bacteriophage as disclosed herein to a subject, wherein the bacteria are present in the subject. In some embodiments, the subject is a mammal, for example but not limited to a human.

In some embodiments, an antimicrobial-agent engineered bacteriophage as disclosed herein can be used to reduce the number of bacteria as compared to use of a non-engineered bacteriophage. In some embodiments, an antimicrobial-agent engineered bacteriophage as disclosed herein is useful in any combination to inhibit or eliminate a bacterial infection, such as for example inhibit or eliminate a bacteria present a biofilm.

Some aspects of the present invention are directed to use of an antimicrobial agent-engineered bacteriophage as an adjuvants to increase the effectiveness of the bacteriophage, where the a1 agent, where an antimicrobial agent-engineered bacteriophage encodes at least one antimicrobial agent which is expressed by the host bacteria.

Previous uses of antibiotics with bacteriophages have been used. For example, Hagens et al discuss a method for augmentation of antimicrobial efficacy of antibiotics by filamentous phage (Hagens et al., Microbial Drug resistance, 2006; 12; 164-168) and teaches treatment of resistant bacterial pathogens with a combination treatment of antibiotics and filamentous phages. However, in contrast to the present application, Hagens et al does not discuss modification of the filamentous phages to express and secrete an antimicrobial agent.

There have also been previous uses of genetically modified bacteriophages, which have been used in combination with antimicrobial agents. For instance, International Patent Application WO04/062677, which is incorporated herein by reference, and discloses bacteriophages which have been modified to comprise a heterologous gene encoding a lysase enzyme (e.g. alginate lyse), and are administered in a combination with a pharmaceutically acceptable antimicrobial agent (e.g. antibiotics and/or defensins). However, in contrast to the present application, the '677 application does not teach expressing and then release of the antimicrobial peptide from the bacteriophage.

Similarly, International Patent Applications WO02/034892 and WO04/046319, which are incorporated herein by reference, discloses genetically modified bacteriophages which comprise a KIL gene, such as a holin-gene which causes loss of viability to the cell which it is propagated, and can be used to effectively kill specific bacteria while simultaneously avoiding undesired side-effects due to cell debris. The '892 application also teaches that such a genetically-modified phages can also be used in the presence of an antimicrobial agent, such as other bacterial, virucial, etc. agents, e.g. antibiotics, chemical substances. However, in contrast to the present application, the '891 application does not teach expressing and then release of the antimicrobial peptide from the bacteriophage.

While there are some reports of modifying bacteriophages to increase their effectiveness of killing bacteria, previous studies have mainly focused on optimizing method to introduce a bacterial toxin gene. For example, Westwater et al (Antimicrobial agents and chemotherapy, 2003; 47; 1301-1307) discusses a genetically modified phage expressing a bacterial toxin such as pGef or ChpBK (i.e. the toxin component of the bacterial cell death "addiction module" pathway) to treat bacterial infections. The U.S. Pat. No. 6,759,229 teaches a genetically modified bacteriophage with a peptide to encode a peptide toxin which can be expressed from the bacteriophage-infected bacterial host cell. The '229 patent teaches that the toxic phage carries a intracellular peptide which when presented internally to a cell, kills the cell, such as Toxin A. Accordingly, these applications do not teach or suggest using engineering a bacteriophage to express an antimicrobial peptide which is released from the bacterial host cell via lysis or secretion.

Additionally, there are additional reports of modifying bacteriophages to increase their effectiveness of killing bacteria have also mainly focused on optimizing method to degrade bacteria biofilms, such as, for example introducing a lysase enzyme such as alginate lyse (discussed in International Application WO04/062677); or modifying bacteriophages to inhibit the cell which propagates the bacteriophage, such introducing a KIL gene such as the Holin gene in the bacteriophage (discussed in International Application WO02/034892 and WO04/046319), or introducing bacterial toxin genes such as pGef or ChpBK and Toxin A (discussed in U.S. Pat. No. 6,759,229 and Westwater et al., Antimicrobial agents and Chemotherapy, 2003, 47: 1301-1307). However, unlike the present invention the modified bacteriophages discussed in WO04/062677, WO02/034892, WO04/046319, U.S. Pat. No. 6,759,229 and Westwater et al., have not been modified to increase a bacteriophages' bacterial host species specificity, or to deliver antimicrobial agents or antimicrobial peptides to the site of bacterial infection by being expressed by the bacteriophage and released by bacterial host cell lysis or by secretion.

BRIEF DESCRIPTION OF FIGURES

This patent or application file contains at least one drawing executed in color. Copies of this patent or patent application publication with color drawing(s) will be provided by the Office upon request and payment of the necessary fee.

FIG. 1 shows the killing curve for wild-type T7 bacteriophages (T7.wt) and for the engineered T7 phages inducing the expression of OmpA secretion sequence and the AmP Indoliciditi (T7.Indol+OmpA) or Cecropin P1 (T7.CecPI+OmpA). The engineered phages T7.Indol+OmpA and T7.CecPI+OmpA show a faster and increased efficiency in killing the BL2I *E. coli* as compared to the T7.wt bacteriophages. The increased efficacy and killing of the BL2I *E. coli* by T7.Indol+OmpA and T7.CecPI+OmpA antimicrobial-agent engineered bacteriophages is due to the synthesis and secretion of the antimicrobial peptides from the host cell.

FIG. 2 shows $T7_{AMP}$ engineered phages are more effective than the wild type $T7_{WT}$ at slowing down the growth of *S. aureus*, whereas phages that express the AmP fused to the OmpA sequence are not as effective. The difference between killing efficacy of the $T7_{AMP}$ and the $T7_{AMP}+_{ompA}$ bacteriophages is due to that in $T7_{AMP}$ the AmPs are in their active form, whereas the AmP expressed from $T7_{AMP}+_{ompA}$ are inactive because they are fused with OmpA sequence until this sequence is cleaved by the host bacterial cell.

Note in FIGS. 3-14, the abbreviation SA denotes tests on *Staphylococcus aureus*, whereas EC denotes *Escherichia coli* bacteria. Experiments were run in duplicate. The nomenclature of the graphs in FIGS. 3-14 follows the pattern: Strain.AMP.Concentration(µg/mL).replicate #(1 or 2).

Figure 15B:
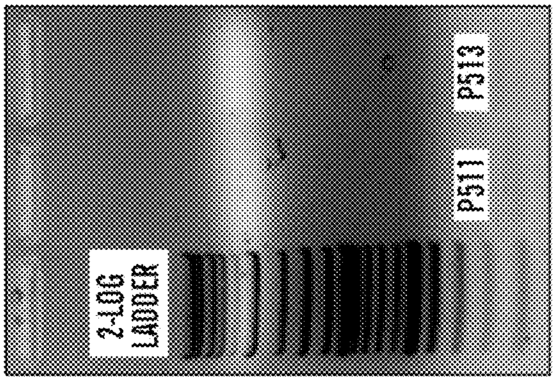
Figure 15A:

FIGS. 15A-15B are gel electrophoresis images showing PCR fragments for J589.K4(P511), J6084.H2 (P512) and J6123.D7 (P513) AMPs. FIG. 15A shows a band for the nucleic acid for the J6084.H2 (P512) AMP. FIG. 15B shows two bands for the nucleic acid for the J589.K4(P511) and J6123.D7 (P513) AMPs.

Figure 16B:
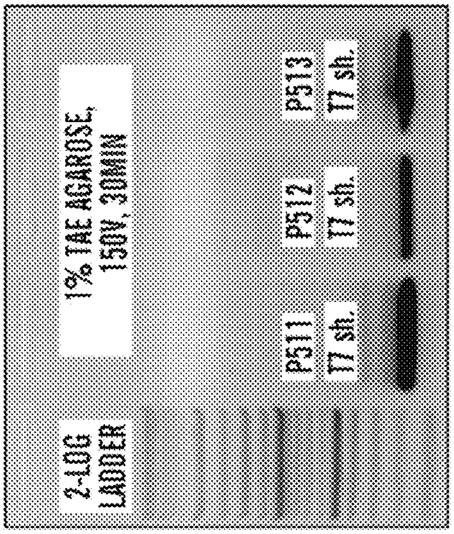
Figure 16A:
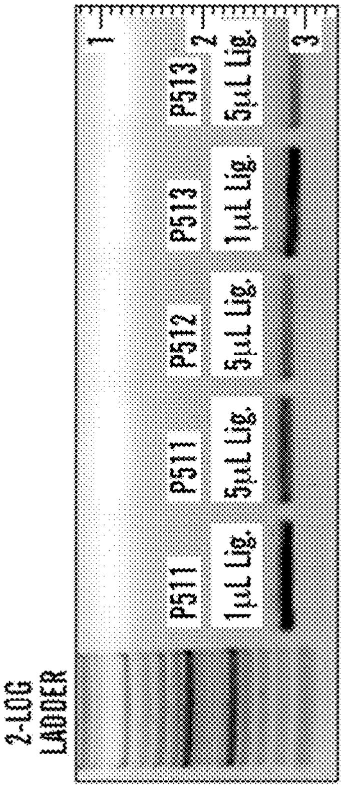
Figure 16C:
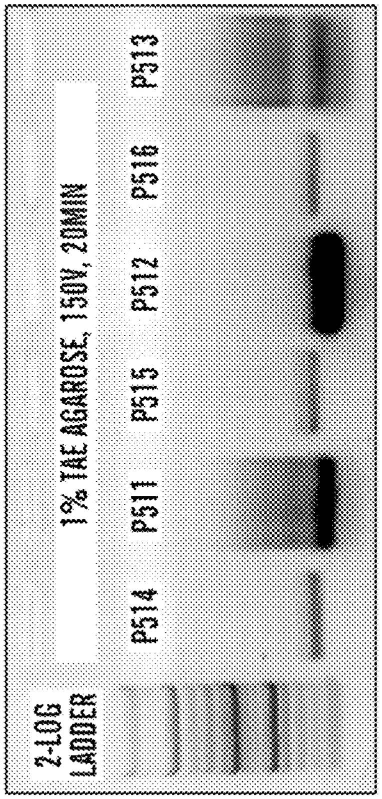

FIG. 16A-16C shows gel electrophoresis images of PCR fragments for J589.K4(P511), J6084.H2 (P512) and J6123.D7 (P513) AMPs amplified from the pET9a plasmid using D262 and D640 primers. FIG. 16A shows a gel of the PCR products of J589.K4 (P511), J6084.H2 (P512) and J6123.D7 (P513) fragments amplified from 1 µl or 5 µl pET9a plasmid. FIG. 16B shows the combined PCR products (1 µl and 5 µl fractions combined) from FIG. 16A. FIG. 16C shows the comparison of the T7 shuttle vector constructs with each of the J589.K4(P511), J6084.H2 (P512) and J6123.D7 (P513) and the nucleic acid insert J589.K4 (P511), J6084.H2 (P512), J6123.D7 (P513) fragments alone. FIG. 16C lanes are as follows: 1.10 µL 2-LOG ladder; 2. P514=P511 T7 shuttle; 3. P511 insert; 4. P515=P512 T7 shuttle; 5. P512 insert; 6. P516=P513 T7 shuttle.).

Figure 17B:
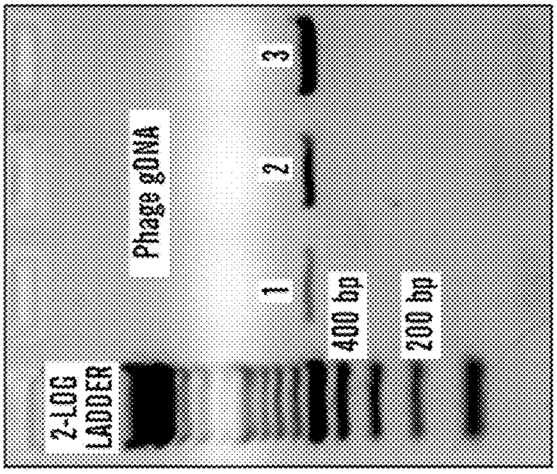
Figure 17A:
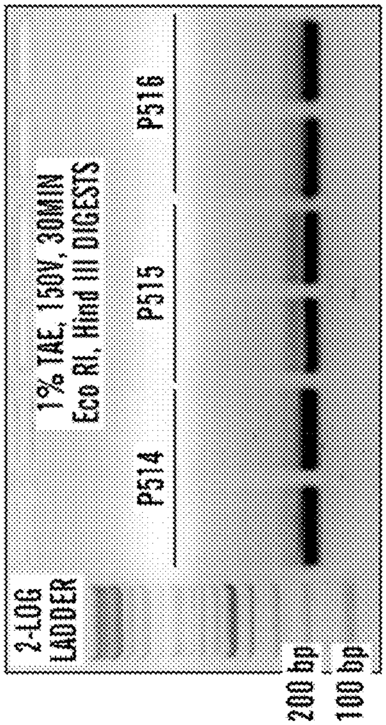

FIG. 17A-17B shows gel electrophoresis of the EcoRI/Hind III digested nucleic acid inserts J589.K4(P511), J6084.H2 (P512) and J6123.D7 (P513) AMPs, and the linear EcoRI/Hind III T7Select415-1b Shuttle vector. FIG. 17A shows EcoRI/Hind III digested nucleic acid inserts J589.K4 (P511), J6084.H2 (P512) and J6123.D7 (P513) AMPs, and FIG. 17B shows the linear EcoRI/Hind III T7Select415-1b Shuttle vector.

Figure 18:

FIG. 18 shows a gel electrophoresis image of PCR fragments for the short fragment of LysK (P8903) containing the CHAP domain digested with NdeI and BamHI for ligation into pET9a. The lanes in FIG. 18 are as follows: 1. 10 µL 2-LOG ladder; 2. LysK (R8903#1); 3. LysK (R8903#2); 4.LysK (R8903#3). The purified band was ligated into pET9a plasmid to generate pET9a-lysK165

Figure 19:
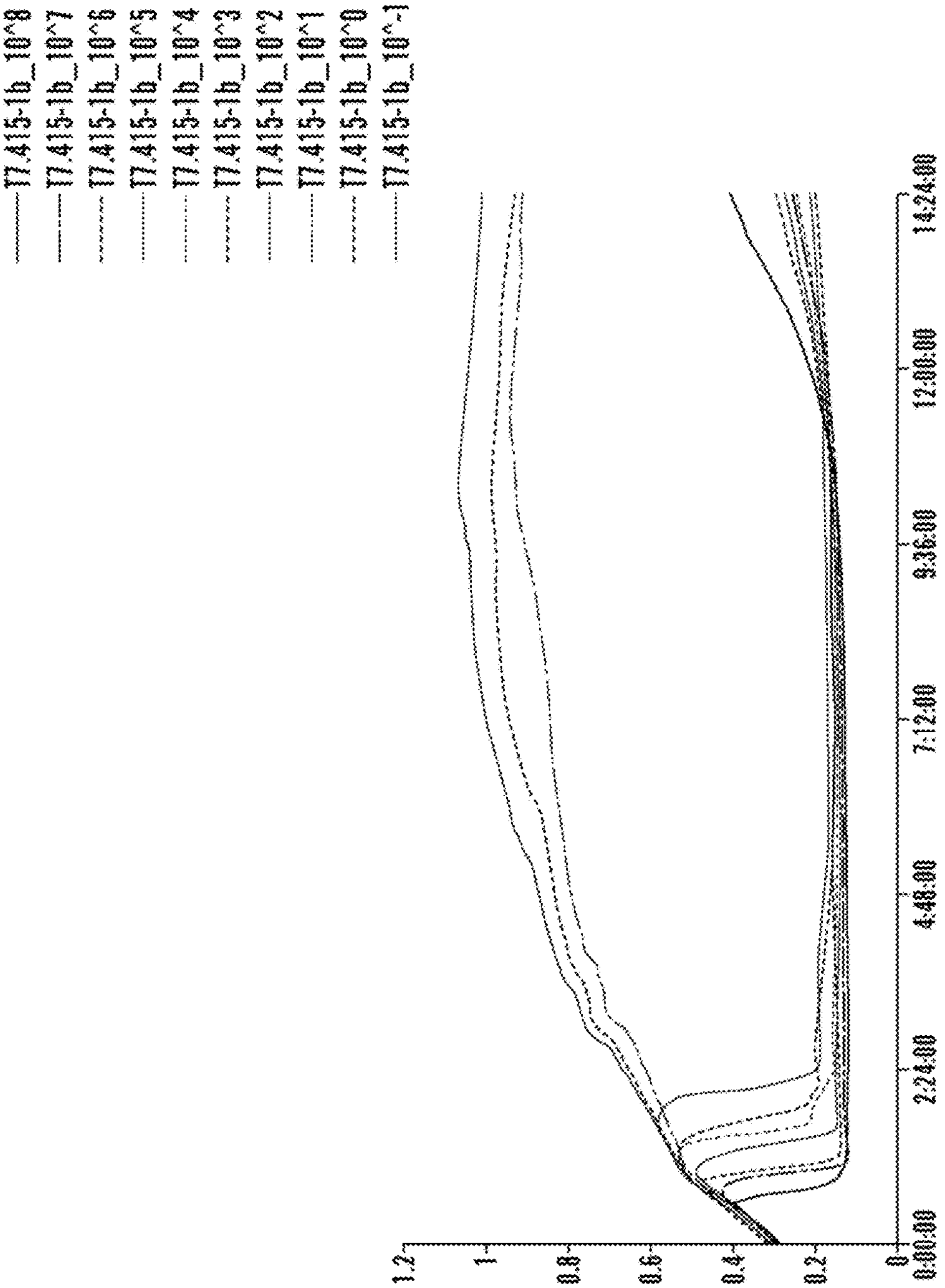

FIG. 19 is a graph showing the concentration dependence and kinetics of bacteriophage infection of *E. coli* BL21 with T7.415-1b. A strong concentration dependence in the onset of lysis of the culture was detected, and at least 10 PFU/mL of wild-type bacteriophage is necessary to effect complete lysis of the culture. In the control wild-type bacteriophages cultures, the lysed cultures start to show signs of re-growth at 12 h of incubation, demonstrating a small population of bacteria is able to evade bacteriophage-induced lysis, adapt to the bacteriophage in the environment and start to re-grow.

Figure 20:
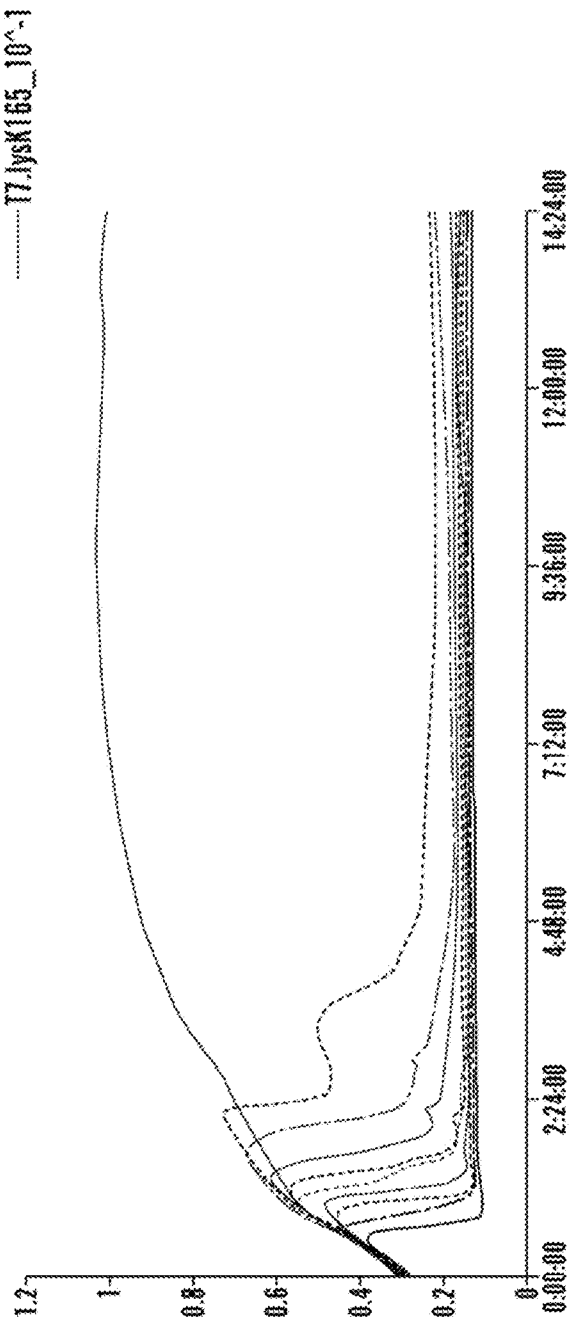

FIG. 20 is a graph showing the concentration dependence and kinetics of bacteriophage infection of *E. coli* BL21 with T7.lysK165. A concentration dependent infection and killing action of the engineered T7 bacteriophage expressing lysK165 AMP. The T7.lysK165 engineered bacteriophage has a slower kinetics of lysis than the wildtype, but is able to repress re-growth at 12 hours. Additionally, the T7.lysK165 engineered bacteriophage is active at 100-times lower concentrations, i.e. a theoretical concentration of 1 PFU/mL is able to sterilize an exponentially growing bacterial culture.

Figure 21:
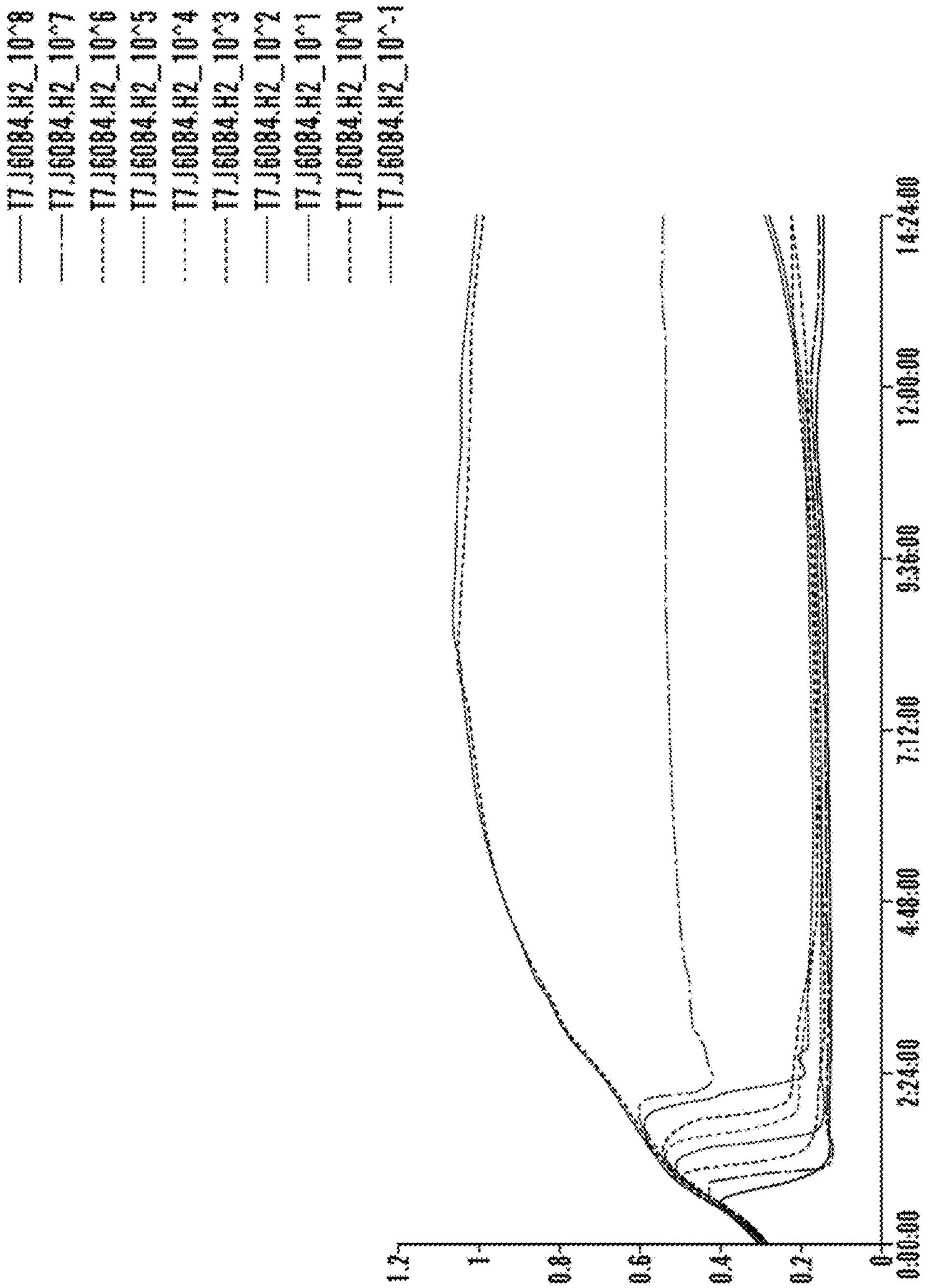

FIG. 21 is a graph showing the concentration dependence and kinetics of bacteriophage infection of *E. coli* BL21 with AMP expressing bacteriophage T7.J6084.H2. A concentration-dependent lysis of the culture with kinetics occurs between the rate with which the T7.415-1b non-engineered bacteriophage lyses bacteria and the rate at which T7.lysK165 engineered bacteriophage lyses bacteria. The engineered T7 bacteriophage expressing J6084.H2 AMP has a bacteriostatic effect of the AMP expression bacteriophage at least a 10-fold lower concentrations than for the non-engineered wildtype (control) bacteriophage. At 12-14 hrs of incubation with T7.lysK165 engineered bacteriophage, some regrowth may occur.

Figure 22:
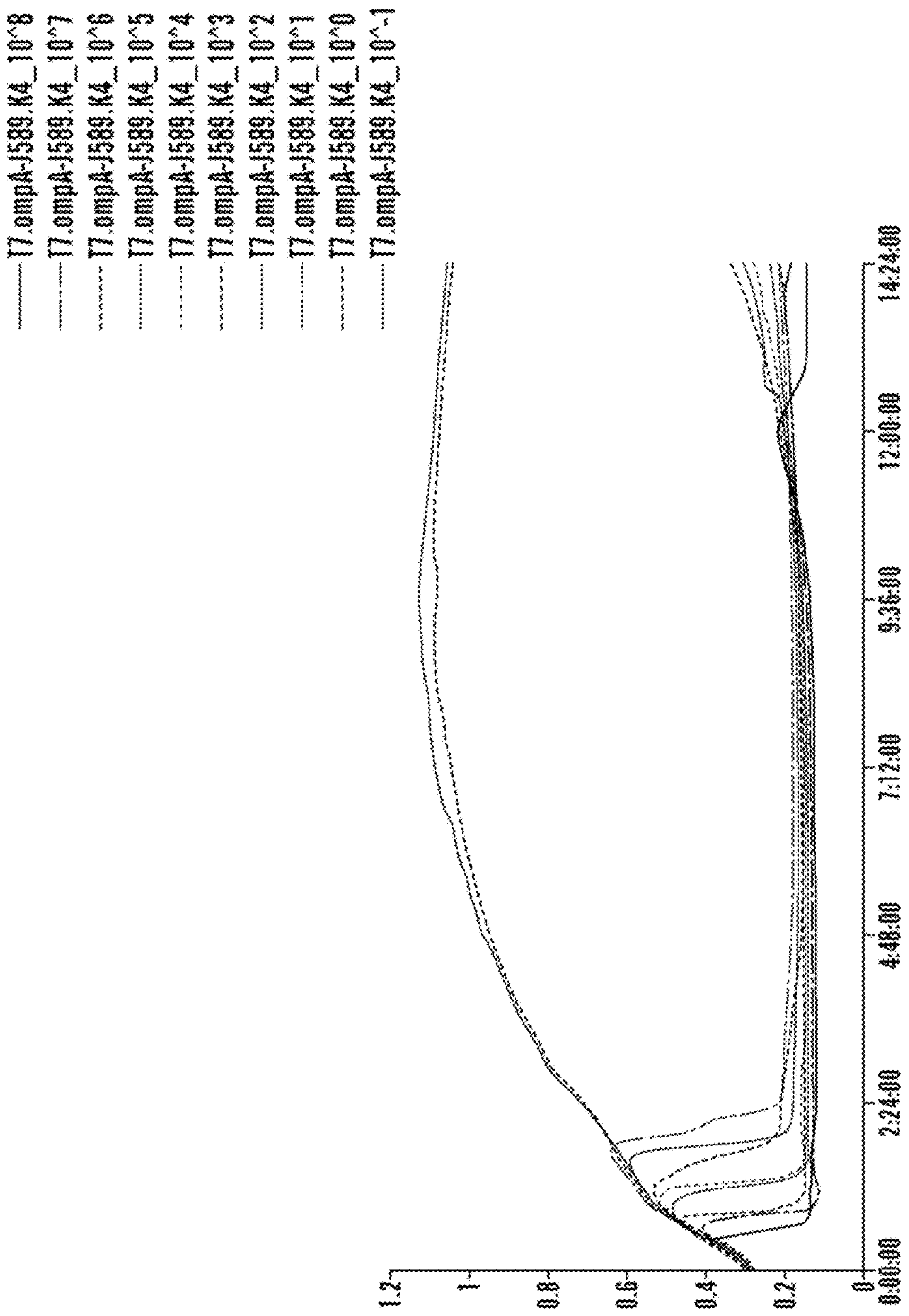

FIG. 22 is a graph showing the concentration dependence and kinetics of bacteriophage infection of *E. coli* BL21 with AMP expressing and exporting bacteriophage T7.ompA-J589.K4. A concentration-dependent lysis is detected with engineered T7 bacteriophage expressing ompA-J589.K4 AMP, and is able to lyse a culture at a ten-fold lower concentration than the non-engineered wildtype bacteriophage. At 12-14 hrs of incubation with T7. ompA-J589.K4 engineered bacteriophage, some regrowth may occur.

Figure 23:
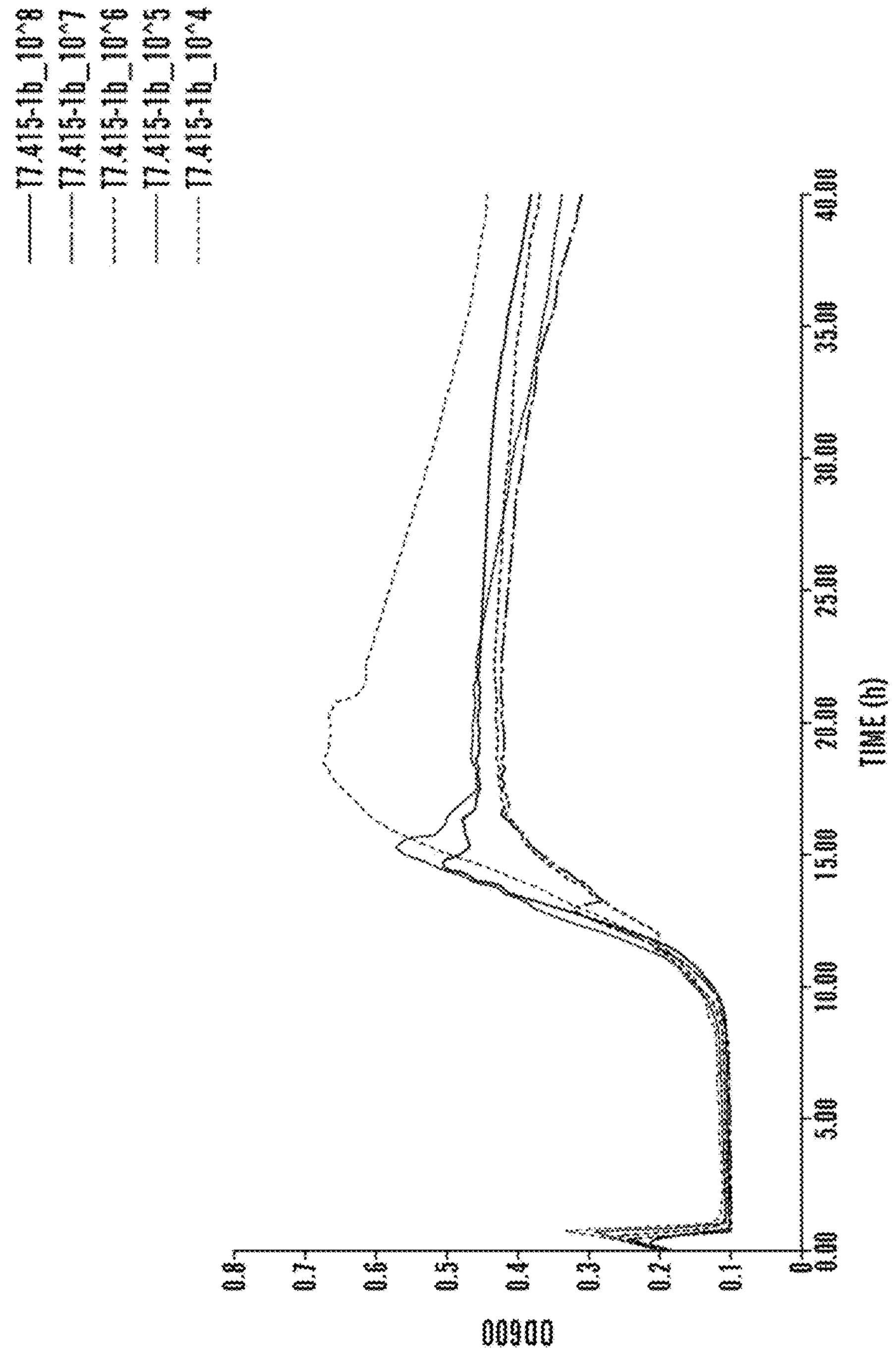

FIG. 23 is a graph showing the treatment of an exponentially growing culture of BL21 with the T7.415-1b wildtype bacteriophage for 40 h. Initial lysis is detected for 10 hours but consistent exponential regrowth occurs after about 12 hours. The culture then follows a well-documented pattern of increase in OD and subsequent decline as the culture age increases without influx of new media.

Figure 24:
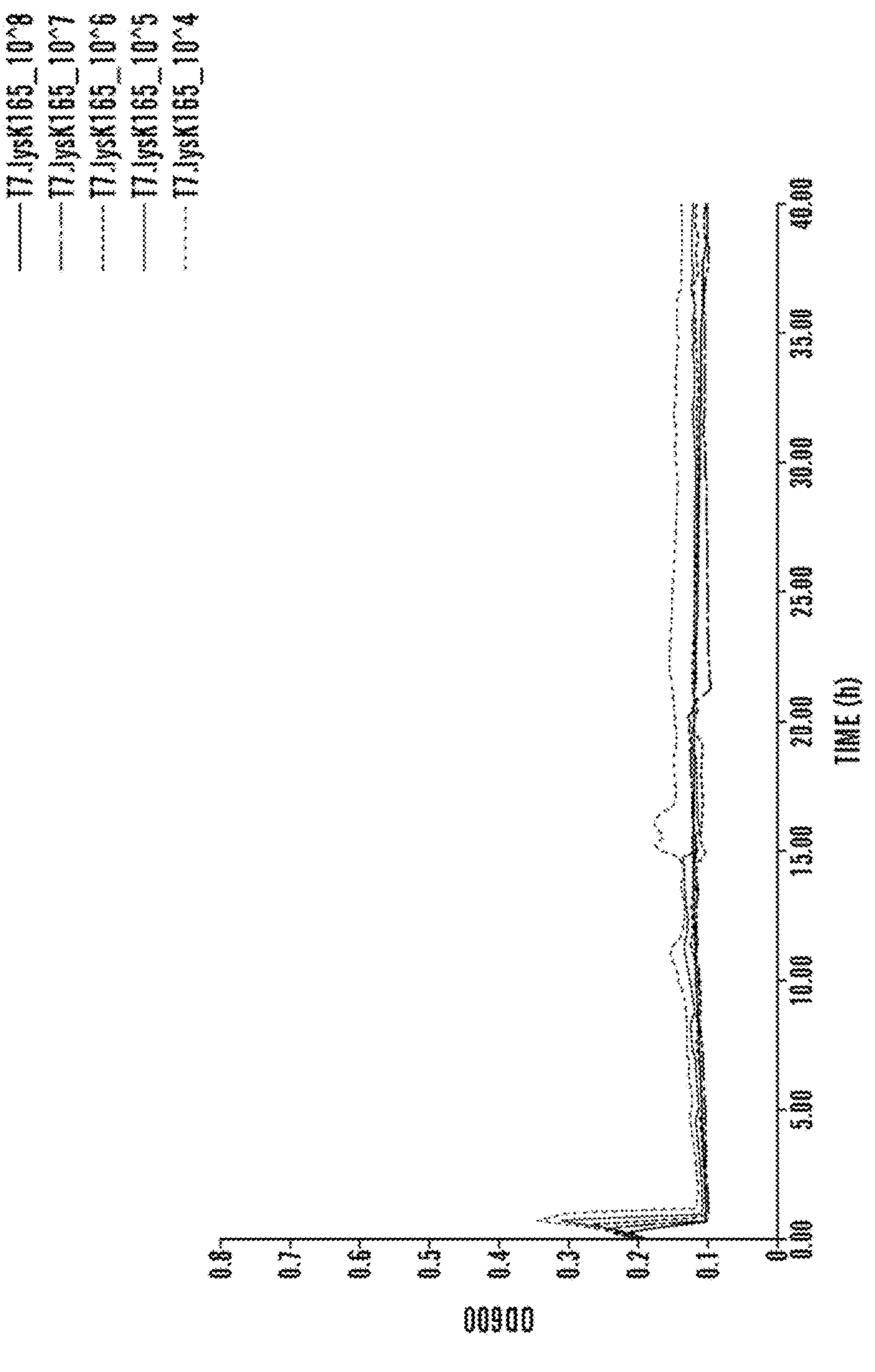

FIG. 24 is a graph showing the treatment of an exponentially growing culture of BL21 with the T7.lysK165 bacteriophage for 40 h. The T7.lysK165 expressing bacteriophage has a complete and lasting sterilization of the exponentially growing BL21 culture for at least 40 hours at all concentrations tested ($1\times10^4$ to $1\times10^8$ PFU/ml).

Figure 25:
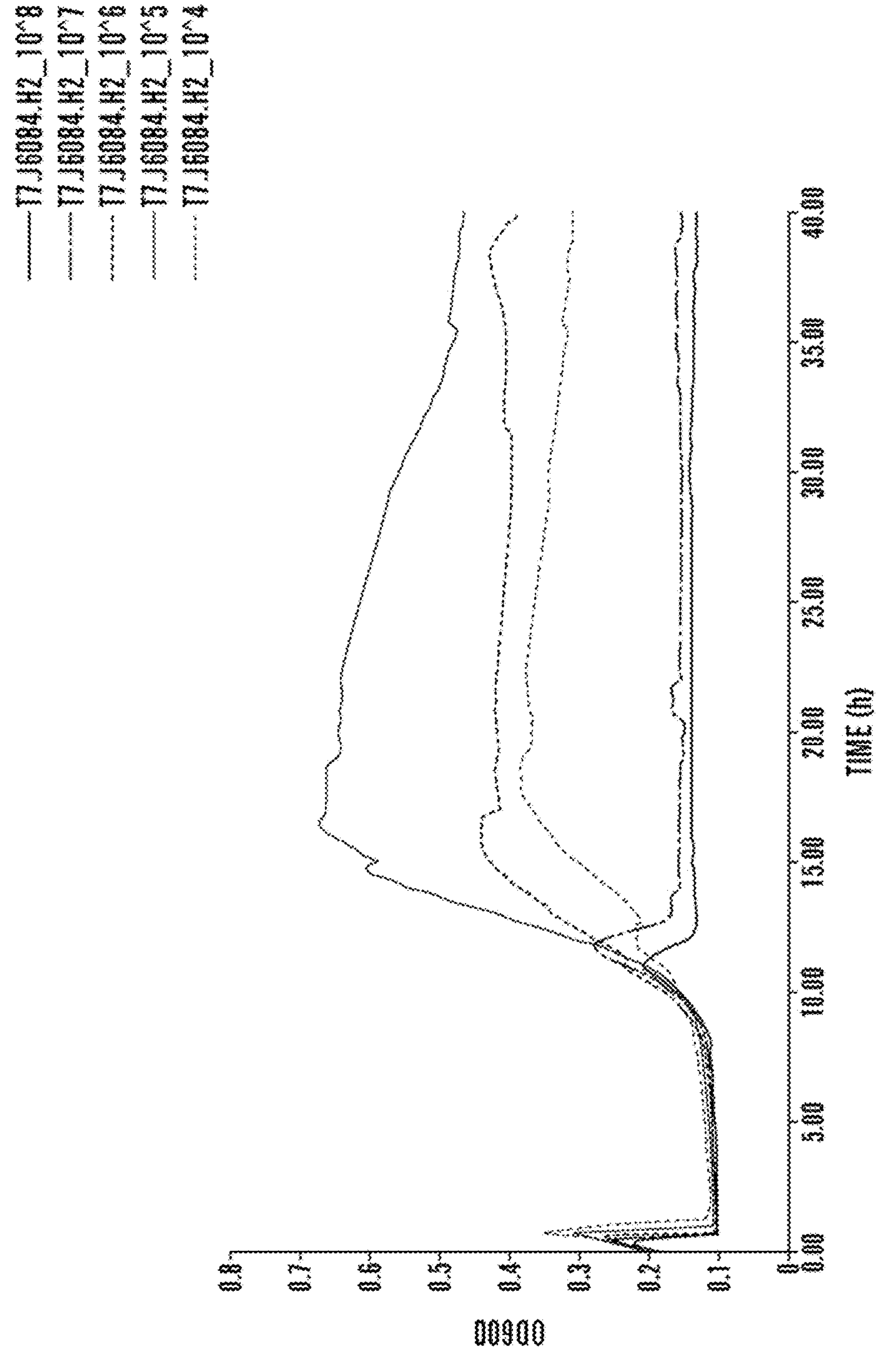

FIG. 25 is a graph showing the treatment of an exponentially growing culture of BL21 with the AMP-producing T7.J6084.H2 bacteriophage for 40 h. The T7.J6084.H2 expressing bacteriophage results in sterilization of the exponentially growing BL21 culture for at least 40 hours at concentrations $1\times10^7$ and $1\times10^8$ PFU/ml. Some re-growth of the culture occurs at a lower level and about the same time as for the non-engineered (wildtype) bacteriophage occurs at lower concentrations assessed ($1\times10^4$ to $1\times10^6$ PFU/ml), and this regrowth is concentration-dependent on the concentration of T7.J6084.H2 expressing bacteriophage.

Figure 26:
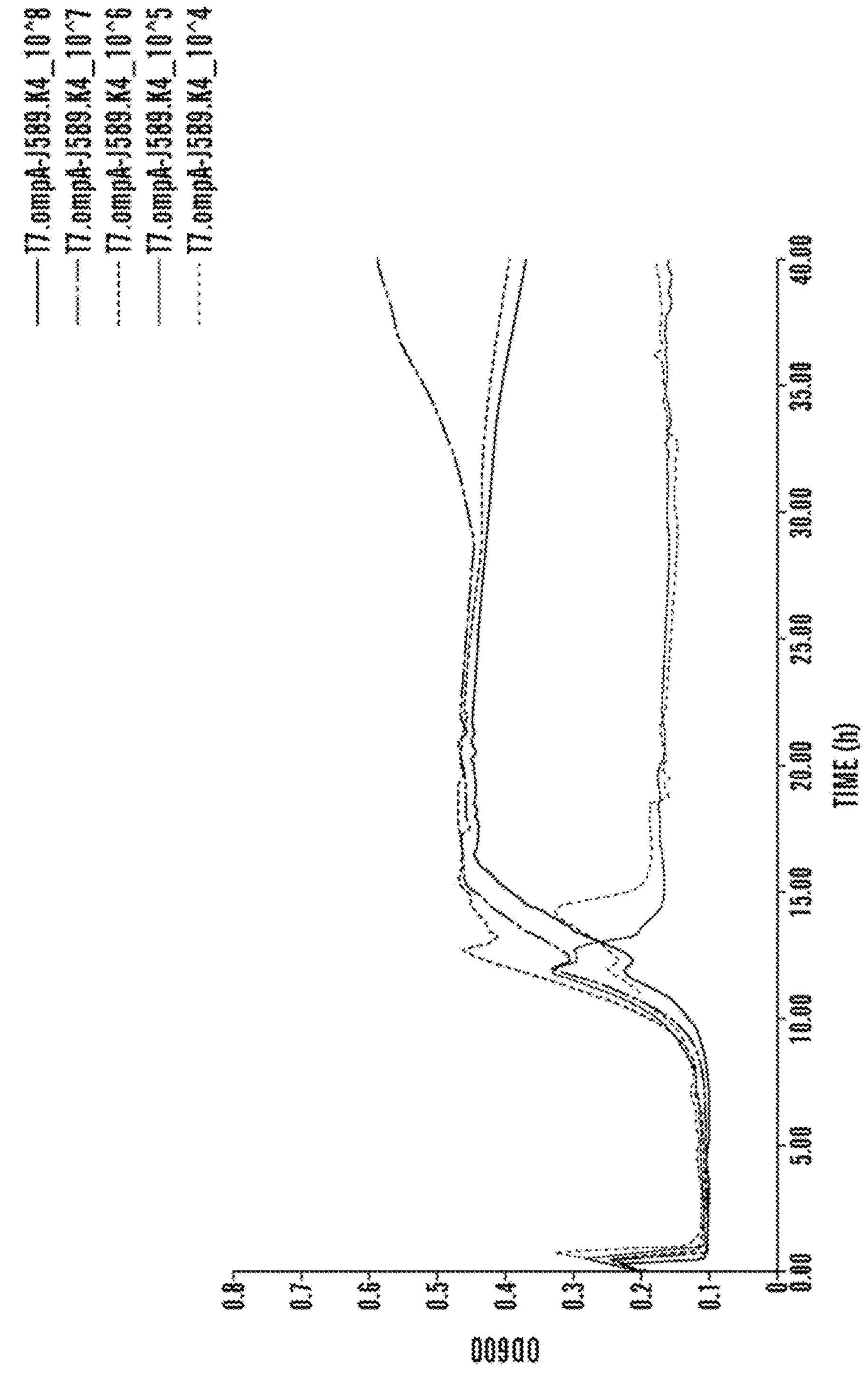

FIG. 26 is a graph showing the treatment of an exponentially growing culture of BL21 with the AMP-exporting bacteriophage T7.ompA-J589.K4 for 40 h. The ompA-J589.K4 expressing T7 bacteriophage results in sterilization of the exponentially growing BL21 culture for at least 40 hours at concentrations $1\times10^4$ and $1\times10^5$ PFU/ml. Some re-growth of the culture occurs at higher concentrations ($1\times10^6$ to $1\times10^8$ PFU/ml) at a lower level of regrowth but at about the same time as for the non-engineered (wildtype) bacteriophage.

Figure 27:
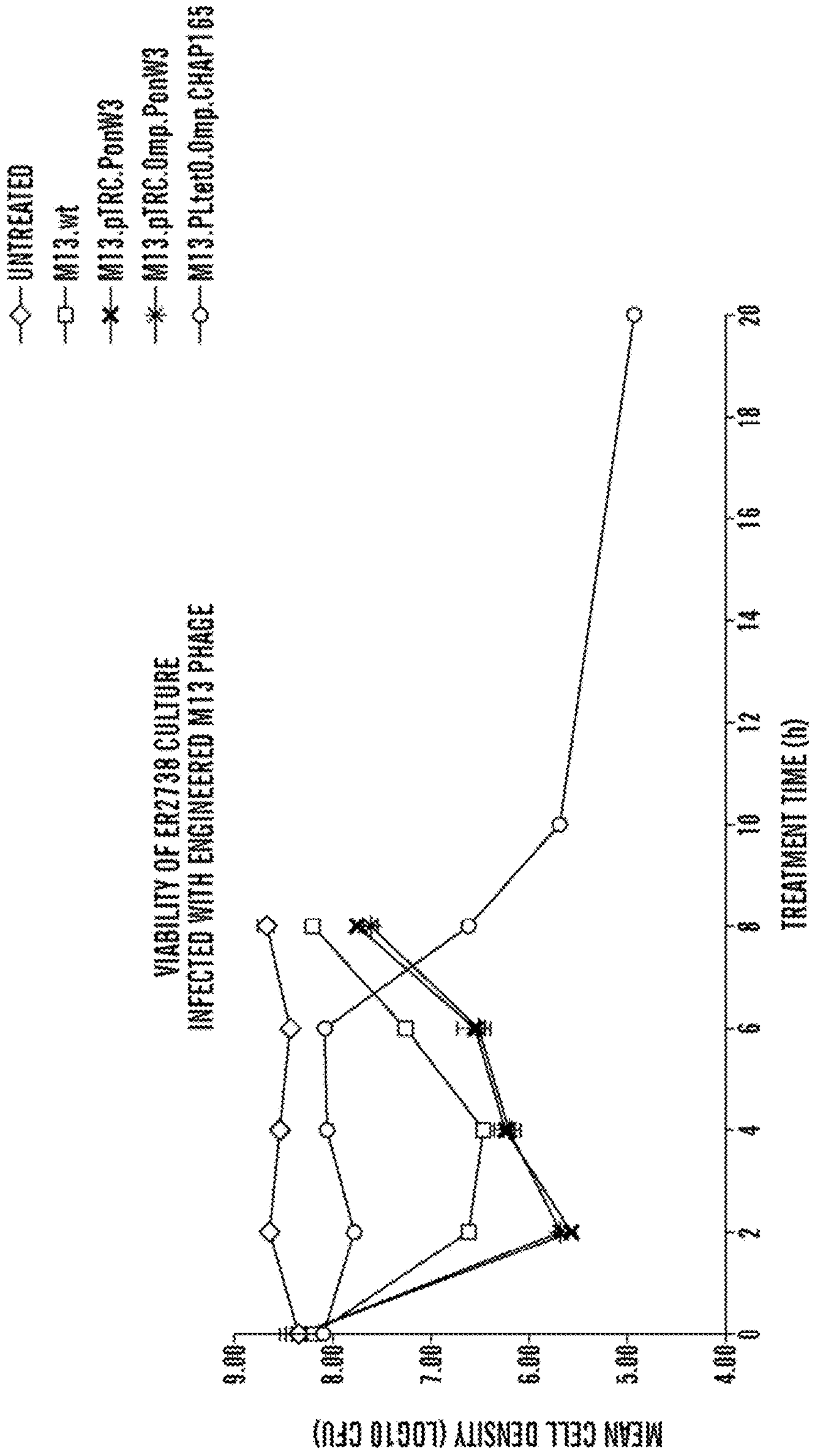

FIG. 27 is a graph of the time course treatment of *E. coli* ER2738 cultures with CHAP165 or AMP-expressing M13 phage. The engineered phage expressing CHAP165 (M13.PLtetO.Omp.CHAP165) and Ponericin W3 (M13.PonW3 and M13.Omp.PonW3) show 10,000- and 20-fold increases in killing efficacy over the wild-type non-engineered M13 phage (M13.wt), respectively.

Figure 28:
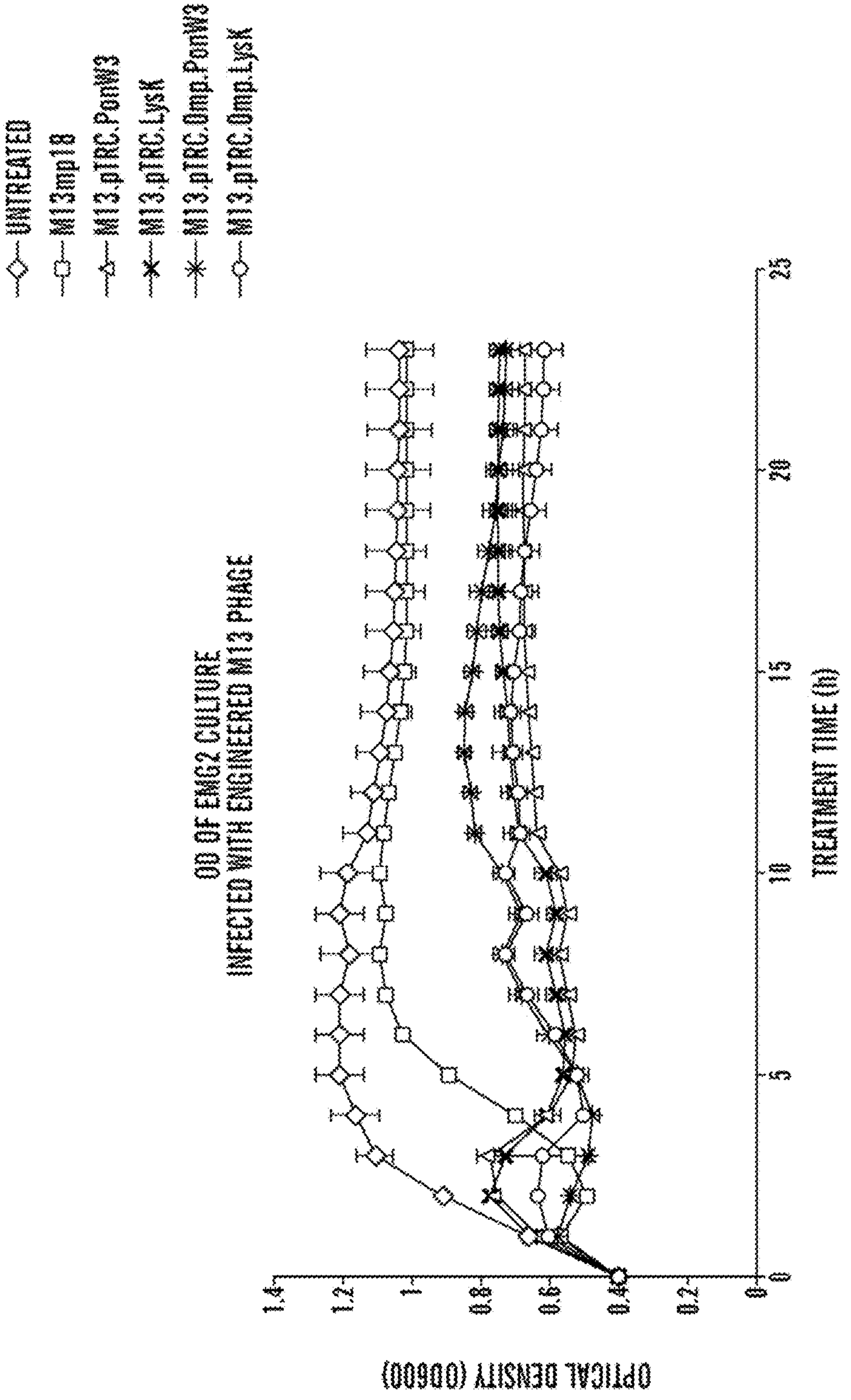

FIG. 28 is a graph showing the optical density of mid-log EMG2 culture treated untreated, treated with wild type M13mp18 or treated with various engineered M13 phages.

Figure 29:
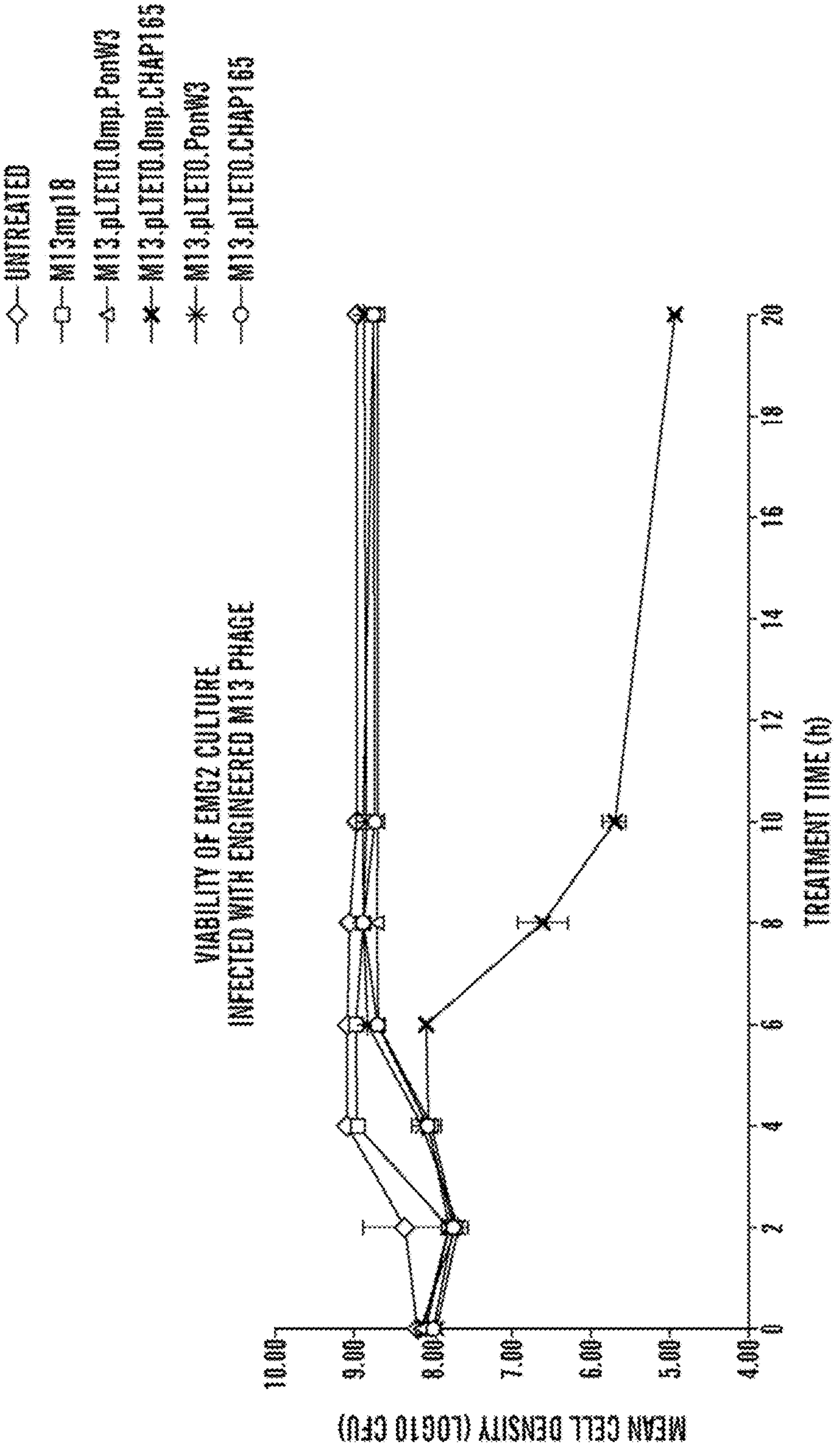

FIG. 29 is a graph showing the viability and time course treatment of *E. coli* EMG2 cultures with CHAP165 or AMP-expressing M13 phage. The engineered phage expressing CHAP165 (M13.PLtetO.Omp.CHAP165) show 10,000 increases in killing efficacy over the wild-type M13 phage (M13.wt).

Figure 30:
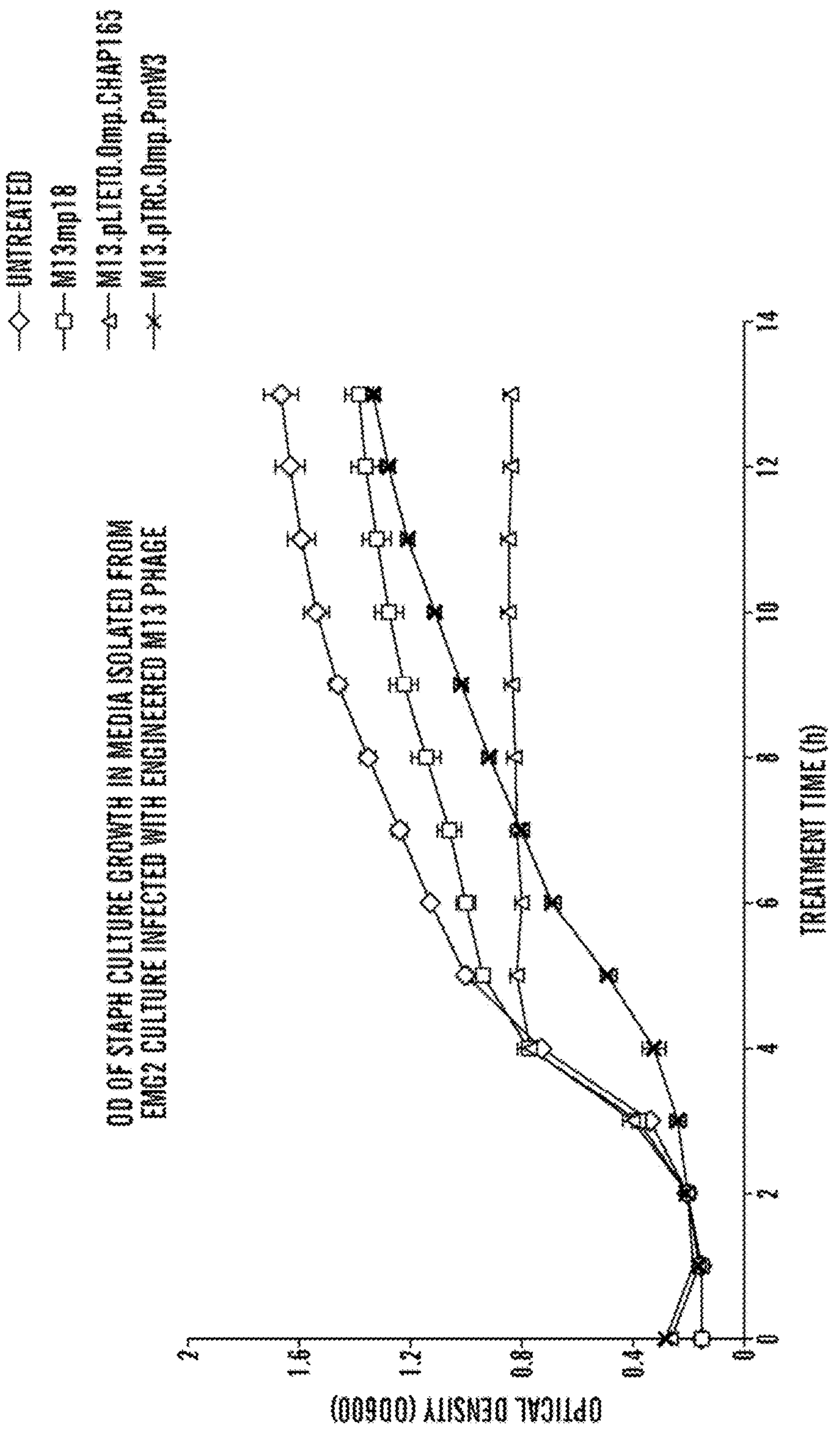

FIG. 30 is a graph showing the growth of *staph aureus* in media sterilized and isolated from after 6 hours infection of EMG2 cells with no phage, wild type phage or engineered phage. M13 phage are not able to infect *Staph aureus* and the growth effect are thus caused by agents released into the media. Media isolated from and EMG2 cultured infected with M13mp18 shows a slight slows growth retardation of the media from untreated EMG2. Media in which the AmP PonW3 was released lead to a 4 hours delay in the growth of *staph*. Media in which CHAP165 was released limited the growth of *Staph* to an OD of 0.8 as opposed to 1.6 of the untreated sample thereby causing decreasing the *staph* density which the phage are not able to affect.

DETAILED DESCRIPTION OF THE INVENTION

As disclosed herein, the inventors have discovered a two-pronged strategy to significantly reduce or eliminate a bacterial infection. In particular, the inventors have engineered bacteriophages to be express and secrete an antimicrobial peptide. Such engineered bacteriophages are referred to herein as an "antimicrobial-agent engineered bacteriophage" and in some embodiments, are an "antimicrobial-peptide engineered bacteriophage" or "AMP-engineered bacteriophage" where the antimicrobial agent expressed by the bacteriophage is an antimicrobial peptide (AMP) or antimicrobial polypeptide. In particular, the inventors have engineered bacteriophages to specifically express an antimicrobial agent, such as an antimicrobial peptide (AMP) or antimicrobial polypeptide, including but not limited to naturally occurring peptides to prevent the development of resistance of the host bacteria to the bacteriophage, and to allow for faster and more effective killing of bacteria in bacterial infections, such as bacterial infections comprising more than one different bacterial host species.

While theoretically bacteriophages provide an attractive antimicrobial agent for eliminating bacterial infections due to their amplification and predator-host mechanism, e.g. by propagating in the host bacteria and then killing the bacteria as lysis occurs to release the propagated bacteriophages which subsequently infect and kill the surrounding bacteria by the same mechanism), their practical use in eliminating bacterial infections is stemmed by significant limitations such as (i) a very narrow host bacteria selectivity of the bacteriophages and (ii) very rapid development of resistance against the bacteriophage by the bacteria. Thus, as seems common in many areas of science, the theoretical outcome is difficult to achieve in real life situations. Thus, while bacteriophages appear useful as antimicrobial agents in theory, in practice they have limited long-term antimicrobial properties, and their use for eliminating bacterial infections is very difficult to achieve due to the rapid development of host resistance to the bacteriophage. Thus, in the past bacteriophages have been ineffective at long-term elimination of the host bacteria.

Herein, the inventors have been surprisingly able to demonstrate long-term elimination of host bacteria and prevention of resistance to the bacteriophage by using bacteriophages that have been engineered to express antimicrobial polypeptide and peptides (AMPs). In contrast to existing bacteriophages, the inventors have demonstrated that the engineered bacteriophages actually work as proposed in theory, and are successful at both eliminating heterogenous populations and establishing a long-term antimicrobial activity.

Accordingly, one aspect of the present invention generally relates to an antimicrobial-agent engineered bacteriophage where the bacteriophage has modified or engineered to express and/or secrete an antimicrobial peptide (AMP). At least one, or any combination of different antimicrobial-agent engineered bacteriophage can be used alone, or in any combination to eliminate or kill a bacterial infection. In some embodiments, an antimicrobial-agent engineered bacteriophage can be used with and additional agent, such as the same or a different antimicrobial agent which is expressed by the bacteriophage. The antimicrobial peptide-engineered bacteriophages (or "AMP-engineered bacteriophages") can be used in combination with other engineered bacteriophages known to one of ordinary skill in the art.

Accordingly, one aspect of the present invention relates to the use of an antimicrobial-agent engineered bacteriophage in conjunction with (i.e. in combination with) at least one other agent, such as an antimicrobial agent or other engineered bacteriophages, e.g. but not limited to, bacteriophages expressing a biofilm-degrading enzyme such as DspB (which increases the ability of the phage to kill bacteria in a biofilm) (Lu and Collins Proc Natl Acad Sci USA 2007), and bacteriophages expressing a repressor protein (e.g. LexA3) of the SOS-response for enhancing the host bacteria's susceptibility to antibiotics (Lu and Collins Proc Natl Acad Sci USA 2009).

One aspect of the present invention relates to a method to kill and/or eliminate bacteria. In particular, one aspect of the present invention relates to methods and compositions comprising an antimicrobial-agent engineered bacteriophage, e.g. an AMP-engineered bacteriophage, to potentiate the effect of the bacteriophage in killing the bacteria. Another aspect of the present invention relates to the use of an antimicrobial-agent engineered bacteriophage to kill and/or eliminate a population of bacteria which comprises multiple (i.e. at least 2) different bacterial strains. In one embodiment of this aspect and all aspects described herein, an antimicrobial-agent engineered bacteriophage can comprise at least one or more than one antimicrobial agent, such as for example, at least 2, at least 3, at least 4, at least 5, least 6, at least 7, at least 8, at least 9 or at least 10 or more different antimicrobial agents at any one time. In some embodiments, an antimicrobial-agent engineered bacteriophage as disclosed herein can used in combination with at least one or more different antimicrobial-agent engineered bacteriophages, for example an antimicrobial-agent engineered bacteriophage as disclosed herein can used in combination with at least 2, 3, 4, 5, 6, 7, 8, 9 or 10 or more different antimicrobial-agent engineered bacteriophages.

In one aspect of the present invention, an antimicrobial-agent engineered bacteriophage as disclosed herein can comprise a nucleic acid encoding an antimicrobial agent which is an antimicrobial peptide, herein referred to as an "AmP". In another embodiment, an antimicrobial-agent engineered bacteriophage as disclosed herein can comprise a nucleic acid encoding a naturally occurring antimicrobial agent.

In some embodiments of this aspect and all aspects described herein, an antimicrobial-agent engineered bacteriophage as disclosed herein can comprise a nucleic acid encoding an antimicrobial peptide such as, for example but it not limited to, at least one of the following different AmPs: Indolicidin (SEQ ID NO: 6), Cecropin P1 (SEQ ID NO: 11), Dermaseptin (SEQ ID NO: 14), Ponericin W1 (SEQ ID NO: 16 or SEQ ID NO: 44), Ponericin W4 (SEQ ID NO: 18), Ponericin W5 (SEQ ID NO: 20 or SEQ ID NO: 42), Ponericin W6 (SEQ ID NO: 22), Ponercin W3 (SEQ ID NO: 40) or antimicrobial polypeptide CHAP165 (SEQ ID NO: 71) or variants thereof. AmPs useful in this aspect and all aspects as disclosed herein are listed in Table 1.

TABLE 1

Amino acid sequences of non-limiting AmPs useful to be expressed and secreted from antimicrobial-agent engineered bacteriophages of the invention. All sequences of the nucleic acid and protein accession numbers are herewith incorporated herein by reference.

| | Organism | mRNA Accession No | Protein Accession no | Signal peptide | Size of peptide | Mature peptide sequence |
|---|---|---|---|---|---|---|
| Lndolicidin (alisas Cathelicidin (CATHL4)) | Bos taurus (cattle) | BC133348 (SEQ ID NO: 1); X67340 (SEQ ID NO: 2) | AAI33481 (SEQ ID NO: 3); CAA47755 (SEQ ID NO: 4) | MQTQRASLSL GRWSLWLLLL GLVVPSAS A (SEQ ID NO: 5) | 14 aa | ILPWKWPWWP WRRG (SEQ ID NO: 6) |
| Cecropin P1 | Pig roundworm | AB186032 (SEQ ID NO: 7) | 58430587 (SEQ ID NO: 8) | MFLIYLFVQT AES (SEQ ID NO: 9) | 31 aa | SWLSKTAKKL ENSAKKRISE GIAIAIQGGPR (SEQ ID NO: 11) |
| Dermaseptin | Phyllomedusa sauvagii (painted-belly leaf frog) | 235324 (SEQ ID NO: 12) | AAB19757 (SEQ ID NO: 13) | | 34 aa | ALWKTMLKKL GTMALHAGKA ALGAAADTIS QGTQ (SEQ ID NO: 14) |
| Ponericin W1 | Pachycondyla goeldii (Ponerine ant) | | P82423 (SEQ ID NO: 15) | | 25 aa | WLGSALKIGA KLLPSVVGLF KKKKQ (SEQ ID NO: 16) |
| Ponericin W4 | Pachycondyla goeldii (Ponerine ant) | | P82426 (SEQ ID NO: 17) | | 26 aa | GIWGTALKWG VKLLPKLVGM AQTKKQ (SEQ ID NO: 18) |
| Ponericin W5 | Pachycondyla goeldii (Ponerine ant) | | 18202410 (SEQ ID NO: 19) | | 24 aa | FWGALIKGAA KLIPSVVGLF KKKQ (SEQ ID NO: 20) |
| Ponericin W6 | Pachycondyla goeldii (Ponerine ant) | | P82428 (SEQ ID NO: 21) | | 20 aa | FIGTALGIAS AIPAIVKLFK (SEQ ID NO: 22) |

In one embodiment of this aspect and all aspect described herein, an antimicrobial-agent engineered bacteriophage can comprise at least one or at least 2, 3, 4, 5 or even more, for example 10 or more of the same or different nucleic acids which encode an AmP, for example, at least 1, or 2, 3, 4, 5, 6, 7 or more of the following AmPs; Indolicidin (SEQ ID NO: 6), Cecropin P1 (SEQ ID NO: 11), Dermaseptin (SEQ ID NO: 14), Ponericin W1 (SEQ ID NO: 16 or SEQ ID NO: 44), Ponericin W4 (SEQ ID NO: 18 or SEQ ID NO: 42), Ponericin W5 (SEQ ID NO: 20 or SEQ ID NO: 42), Ponericin W6 (SEQ ID NO: 22), Ponercin W3 (SEQ ID NO: 40) or antimicrobial polypeptide CHAP165 (SEQ ID NO: 71), or any AMP of SEQ ID NO: 10, or SEQ ID NO: 36-45. In some embodiments, an engineered bacteriophage expresses at least one of any of the following sequences, SEQ ID NO: 40 (J589.K4 or Ponericin W3), SEQ ID NO: 42 (J6084.H2 or Ponericin W5), SEQ ID NO: 44 (J6123.D7 or Ponericin W1), SEQ ID NO: 71 (LysK165 or CHAP165) and variants thereof. In some embodiments, any or all different combinations of AmP can be present in an antimicrobial-agent engineered bacteriophage In another aspect of the present invention, an antimicrobial-agent engineered bacteriophage can comprise at least one nucleic acid encoding an antimicrobial agent, such as but not limited to a protein, which increases the susceptibility of a bacteria to the antimicrobial-agent engineered bacteriophage, e.g. AMP-engineered bacteriophage. In some embodiments of this aspect, and all other aspects described herein, such an antimicrobial agent which increases the susceptibility of a bacteria to an antimicrobial-agent engineered bacteriophage, e.g. AMP-engineered bacteriophage refers to any antimicrobial agent which increases the bacteria's susceptibility to the antimicrobial-agent engineered bacteriophage, e.g. AMP-engineered bacteriophage by at least about 10% or at least about 15%, or at least about 20% or at least about 30% or at least about 50% or more than 50%, or any integer between 10% and 50% or more, as compared to the use of the antimicrobial agent alone. Stated another way, the antimicrobial agent functions as an adjuvant to the engineered bacteriophage, aiding and increasing the bacteriophage to kill bacteria.

In one embodiment, an antimicrobial agent is an agent which specifically capable of decreasing the viability and/or killing a bacteria cell. Stated another way, an antimicrobial agent is specific to eliminating and/or killing a bacterial cell if it kills or eliminates such a bacterial cell more effectively that it kills or eliminates a non-bacterial cell (i.e. any cell which is not a bacteria cell).

In another embodiment, an antimicrobial agent modifies (i.e. inhibits or activates) a pathway which is specifically expressed in bacterial cells. In one embodiment, an antimicrobial agent has an additive effect of the efficacy of the antimicrobial-agent engineered bacteriophage (i.e. the antimicrobial agent expressed by the antimicrobial-agent engineered bacteriophage has an additive effect of the killing efficacy or inhibition of growth by the antimicrobial-agent engineered bacteriophage). In a preferred embodiment, an antimicrobial agent is an agent which has a synergistic effect on the efficacy of an antimicrobial-agent engineered bacteriophage (i.e. the antimicrobial agent has a synergistic effect of the killing efficacy or inhibition of growth of the bacterial by the antimicrobial-agent engineered bacteriophage).

Accordingly, another aspect of the invention relates to an improvement of a bacteriophage to kill bacteria. For instance, in one aspect and all aspects described herein, the bacteriophage is engineered to express and secrete an antimicrobial agent wherein the expression and secretion of an antimicrobial agent by the antimicrobial-agent engineered bacteriophage, e.g. AMP-engineered bacteriophage potentiate the bacteriophages bacterial killing effect and efficacy. Stated another way, the inventors have improved and enhanced the bacterial killing efficacy bacteriophages by engineering them to express and secrete antimicrobial agents. An antimicrobial agent expressed and secreted from an antimicrobial-agent engineered bacteriophage, e.g. AMP-engineered bacteriophage is considered to potentiate the effectiveness of the bacterial killing ability of said antimicrobial-agent engineered bacteriophage if the amount of antimicrobial-agent engineered bacteriophage as disclosed herein is reduced by at least about 10% without adversely affecting the result, for example, without adversely effecting the level of antimicrobial activity, as compared to a bacteriophage which has not been engineered to express and secrete such an antimicrobial agent. In some embodiments, the reduction of the amount of antimicrobial-agent engineered bacteriophage is a reduction of at least about 10%, . . . or at least about 15%, . . . or at least about 20%, . . . or at least about 25%, . . . or at least about 35%, . . . or at least about 50%, . . . or at least about 60%, . . . or at least about 90% and all integers in between 10-90% of the amount of the antimicrobial agent engineered bacteriophage without adversely effecting the killing efficacy when compared to a similar amount of a bacteriophage which has not been engineered to express an antimicrobial agent.

In another embodiment, the criteria used to select an antimicrobial agent to be expressed and secreted by an antimicrobial-agent engineered bacteriophage is an antimicrobial agent that potentiates (i.e. increases) the killing ability of such a bacteriophage (i.e. a bacteriophage which has not been engineered to express an antimicrobial agent). Stated another way, an antimicrobial agent expressed and secreted from an antimicrobial-agent engineered bacteriophage can increase the killing effectiveness of such bacteriophage by at least 10% (i.e. by 10% or more) as compared to the killing efficacy of the same type bacteriophage which has not been engineered to express or secrete an antimicrobial agent. An antimicrobial agent expressed and secreted from the antimicrobial-agent engineered bacteriophage can increase, for example by about 10%, or about 15%, . . . or about 20%, . . . or about 25%, . . . or about 35%, . . . or about 50%, . . . or about 60%, . . . or more than 60% the level of killing or reduction of a bacterial population by the antimicrobial-agent engineered bacteriophage as compared to the level of killing or reduction of a bacterial population which would occur with the same type of bacteriophage which has not been engineered to express and secrete an antimicrobial agent. Thus, in one embodiment, the antimicrobial agent functions as an adjuvant to enhance or increase the bacterial killing efficacy of the bacteriophage.

The inventors herein have demonstrated that an antimicrobial-agent engineered bacteriophage, e.g. AMP-engineered bacteriophage can target a variety of different bacterial host strains in a bacterial population. For example, an antimicrobial-agent engineered bacteriophage, e.g. AMP-engineered bacteriophage can target a variety of different bacterial host strains which are not normally targeted by the same type of bacteriophage which does not express an antimicrobial agent, and by doing so, greatly enhances the efficacy of the antimicrobial-agent engineered bacteriophage, e.g. AMP-engineered bacteriophage in a bacterial infection.

The inventors have also demonstrated herein in Examples that an antimicrobial-agent engineered bacteriophage, e.g. AMP-engineered bacteriophage which comprises at least one antimicrobial agent can reduce the number of bacteria in a mixed host bacterial population. For example, the inventors demonstrate that an antimicrobial-agent engineered bacteriophage, e.g. AMP-engineered bacteriophage as disclosed herein is effective at killing or reducing a heterogeneous population of bacteria comprising a variety of different bacterial host strains. Thus, the inventors have demonstrated that by expressing and secreting at least one antimicrobial agent, such as an antimicrobial peptide by a bacteriophage one can enhance the killing capability of the bacteriophage in killing a broad spectrum of bacterial host species, and thus have discovered a highly effective new antimicrobial-agent engineered bacteriophage, e.g. AMP-engineered bacteriophage mediated antimicrobial strategy.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "adjuvant" as used herein refers to an agent which enhances the pharmaceutical effect of another agent. As used herein, an antimicrobial agent expressed and secreted by an antimicrobial-agent engineered bacteriophage, e.g. AMP-engineered bacteriophage functions as an adjuvant to the killing efficacy of the bacteriophage, for example by enhancing the level of efficacy (i.e. the killing ability) of the bacteriophage by at least . . . 5%, . . . at least 10%, . . . at least 15%, . . . at least 20%, . . . at least 25%, . . . at least 35%, . . . at least 50%, . . . at least 60%, . . . at least 90% and all amounts in-between as compared to the level of efficacy of the same type of bacteriophage which has not been engineered to express and secrete an antimicrobial agent. Accordingly, the antimicrobial agent expressed and secreted by an antimicrobial-agent engineered bacteriophage function as an adjuvant to the antimicrobial-agent engineered bacteriophage.

As used herein, the term "antimicrobial-agent engineered bacteriophage" refers to a bacteriophage that have been genetically engineered to comprise a nucleic acid which encodes an agent which functions as an antimicrobial agent, for example, the antimicrobial agent reduces a population of bacterial host cells as compared to cells which are not bacterial cells. Such engineered bacteriophages as disclosed herein are termed "antimicrobial-agent engineered bacteriophage" as they comprise a nucleic acid which encodes at least one antimicrobial agent, such as but not limited to antimicrobial peptide (referred to herein as "AmP"), including naturally occurring AmPs, such as, but not limited to Indolicidin (SEQ ID NO: 6), Cecropin P1 (SEQ ID NO: 11), Dermaseptin (SEQ ID NO: 14), Ponericin W1 (SEQ ID NO: 16), Ponericin W4 (SEQ ID NO: 18), Ponericin W5 (SEQ ID NO: 20), Ponericin W6 (SEQ ID NO: 22) or variants thereof. Naturally, one can engineer a bacteriophage to comprise at least one nucleic acid which encodes more than one inhibitor, for example, two or more inhibitors to the same gene or to at least two different genes which can be used in the methods and compositions as disclosed herein.

The term "engineered bacteriophage" as used herein refers to an antimicrobial-agent engineered bacteriophage as this phrase is defined herein.

The term "additive" when used in reference to an antimicrobial agent having an additive effect of the efficacy of the bacteriophage refers to a total increase in antimicrobial efficacy (i.e. killing, or reducing the viability of a bacterial population or inhibiting growth of a bacterial population) with the expression and secretion from the antimicrobial-agent engineered bacteriophage, e.g. a AMP-engineered bacteriophage, over the single efficacy of each component alone. An additive effect to increase total antimicrobial effectiveness can be a result of an increase in antimicrobial effect of both components (i.e. the antimicrobial agent and the antimicrobial-agent engineered bacteriophage) or alternatively, it can be the result of the increase in activity of only one of the components (i.e. the antimicrobial agent or the antimicrobial-agent engineered bacteriophage). For clarification by way of a non-limiting illustrative example of a additive effect, if an antimicrobial agent is effective at reducing a bacterial population by 30%, and a non-engineered bacteriophage was effective at reducing a bacterial population by 20%, an additive effect of antimicrobial-agent engineered bacteriophage (i.e. the expression of the antimicrobial agent and the presence of an antimicrobial-agent engineered bacteriophage) could be, for example 35%. Stated another way, in this example, any total effect greater than 30% (i.e. greater than the highest antimicrobial efficacy (i.e. 30% which, in this example is displayed by the antimicrobial agent) would be indicative of an additive effect. In some embodiments of the present invention, the antimicrobial agent expressed and secreted by the antimicrobial-agent engineered bacteriophage show at least some additive anti-pathogenic activity. An additive effect of the combination of an antimicrobial agent expressed and secreted by the antimicrobial-agent engineered bacteriophage can be an increase in at least about 10% or at least about 20% or at least about 30% or at least about 40% or at least about 50% or more anti-pathogenic (or antimicrobial) efficacy as compared to the highest antimicrobial effect achieved with either the antimicrobial agent alone or a bacteriophage (which has not been engineered to express an antimicrobial agent) alone.

The term "antimicrobial agent" as used herein refers to any entity with antimicrobial activity, i.e. the ability to inhibit the growth and/or kill bacterium, for example gram positive- and gram negative bacteria. An antimicrobial agent is any agent which results in inhibition of growth or reduction of viability of a bacteria by at least about 30% or at least about 40%, or at least about 50% or at least about 60% or at least about 70% or more than 70%, or any integer between 30% and 70% or more, as compared to in the absence of the antimicrobial agent. Stated another way, an antimicrobial agent is any agent which reduces a population of antimicrobial cells, such as bacteria by at least about 30% or at least about 40%, or at least about 50% or at least about 60% or at least about 70% or more than 70%, or any integer between 30% and 70% as compared to in the absence of the antimicrobial agent. In one embodiment, an antimicrobial agent is an agent which specifically targets a bacteria cell. In another embodiment, an antimicrobial agent modifies (i.e. inhibits or activates or increases) a pathway which is specifically expressed in bacterial cells. In some embodiments, an antimicrobial agent does not include the following agents; chemotherapeutic agent, a toxin protein expressed by a bacteria or other microorganism (i.e. a bacterial toxin protein) and the like. An antimicrobial agent can include any chemical, peptide (i.e. an antimicrobial peptide), peptidomimetic, entity or moiety, or analogues of hybrids thereof, including without limitation synthetic and naturally occurring non-proteinaceous entities. In some embodiments, an antimicrobial agent is a small molecule having a chemical moiety. For example, chemical moieties include unsubstituted or substituted alkyl, aromatic or heterocyclyl moieties including macrolides, leptomycins and related natural products or analogues thereof. Antimicrobial agents can be any entity known to have a desired activity and/or property, or can be selected from a library of diverse compounds.

The term "agent" as used herein and throughout the application is intended to refer to any means such as an organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof.

The term "antimicrobial peptide" or "AMP" as used herein refers to any polypeptides or peptides with antimicrobial activity, i.e. the ability to inhibit the growth and/or kill bacterium, for example, gram positive- and gram-negative bacteria. The term antimicrobial peptides encompasses all peptides that have antimicrobial activity, and are typically, for example but not limited to, short proteins, generally between 12 and 50 amino acids long, however larger proteins with such as, for example lysozymes are also encompassed as antimicrobial peptides in the present invention. Also included in the term antimicrobial peptide are antimicrobial peptidomimetics, and analogues or fragments thereof. The term "antimicrobial peptide" also includes all cyclic and non-cyclic antimicrobial peptides, or derivatives or variants thereof, including tautomers, see Li et al. JACS, 2006, 128: 5776-85 and world-wide-web at //aps.unmc.edu, at /AP/main.php for examples, which are incorporated herein in their entirety by reference. In some embodiments, the antimicrobial peptide is a lipopeptide, and in some embodiments, the lipopeptide is a cyclic lipopeptide. The lipopeptides include, for example but not limited to, the polymyxin class of antimicrobial peptides.

The term "microorganism" includes any microscopic organism or taxonomically related macroscopic organism within the categories algae, bacteria, fungi, yeast and protozoa or the like. It includes susceptible and resistant microorganisms, as well as recombinant microorganisms. Examples of infections produced by such microorganisms are provided herein. In one aspect of the invention, the antimicrobial agents and enhancers thereof are used to target microorganisms in order to prevent and/or inhibit their growth, and/or for their use in the treatment and/or prophylaxis of an infection caused by the microorganism, for example multi-drug resistant microorganisms and gram-negative microorganisms. In some embodiments, gram-negative microorganisms are also targeted.

The anti-pathogenic aspects of the invention target the broader class of "microorganism" as defined herein. However, given that a multi-drug resistant microorganism is so difficult to treat, the antimicrobial agent and inhibitor-engineered bacteriophage and/or repressor-engineered bacteriophage in the context of the anti-pathogenic aspect of the invention is suited to treating all microorganisms, including for example multi-drug resistant microorganisms, such as bacterium and multi-drug resistant bacteria.

Unless stated otherwise, in the context of this specification, the use of the term "microorganism" alone is not limited to "multi-drug resistant organism", and encompasses both drug-susceptible and drug-resistant microorganisms. The term "multi-drug resistant microorganism" refers to those organisms that are, at the very least, resistant to more than two antimicrobial agents such as antibiotics in different antibiotic classes. This includes those microorganisms that have more resistance than those that are resistant to three or more antibiotics in a single antibiotic class. This also includes microorganisms that are resistant to a wider range of antibiotics, i.e. microorganisms that are resistant to one or more classes of antibiotics.

The term a "persistent cell" or a "persister" are used interchangeably herein and refer to a metabolically dormant subpopulation of microorganisms, typically bacteria, which are not sensitive to antimicrobial agents such as antibiotics. Persisters typically are not responsive (i.e. are not killed by the antibiotics) as they have non-lethally downregulated the pathways on which the antimicrobial agents act i.e. the persister cells have down regulated the pathways which are normally inhibited or corrupted by the antimicrobial agents, such as the transcription, translation, DNA replication and cell wall biosynthesis pathways. Persisters can develop at non-lethal (or sub-lethal) concentrations of the antimicrobial agent.

The term "release" or "released" from the host cell means that the expressed antimicrobial agent is moved to the external of the bacterial cell.

The term "secretion" refers to the process of, elaborating and releasing agents or chemicals from a cell, or an agent expressed by the cell. In contrast to excretion, the substance may have a certain function, rather than being a waste product.

The term "infection" or "microbial infection" which are used interchangeably herein refers to in its broadest sense, any infection caused by a microorganism and includes bacterial infections, fungal infections, yeast infections and protozomal infections.

The term "treatment" refers generally to afflicting a subject, tissue or cell to obtain a desired pharmacologic and/or physiologic effect, which in the case of the methods of this invention, include reduction or elimination of microbial or bacterial infections. The term "treatment", with respect to treatment of a bacterial infection or bacterial colonization, inter alia, is used to refer to inhibiting the development of the bacterial infection, or altering the course of the disease (for example, but not limited to, slowing the progression of the bacterial infection), or reversing a symptom of the bacterial infection, or preventing the worsening or progressing of symptoms of bacterial infection, as well as promoting recovery or improving prognosis. In some embodiments, treating can also be prophylactic treatment, such as to prevent the occurrence of a bacterial infection in a subject, such as a human subject. In some embodiments, treatment also refers to the prevention of microbial or bacterial infections, present in a subject, e.g. a human or non-human subject, or alternatively on the surface of a synthetic structure, such as prevention of bacterial infection for bioremediation purposes.

As used herein, the terms "prevent," "preventing" and "prevention" refer to the avoidance or delay in manifestation of one or more symptoms or measurable markers of a bacterial infection. A delay in the manifestation of a symptom of bacterial infection or a marker of a bacterial marker is a delay relative to the time at which such symptom of a bacterial infection manifests in a control or untreated subject with a similar likelihood or susceptibility of developing the bacterial infection. The terms "prevent," "preventing" and "prevention" include not only the complete avoidance or prevention of symptoms or marker of a bacterial infection, but also a reduced severity or degree of any one symptom of a bacterial infection, relative to those symptoms arising in a control or non-treated individual with a similar likelihood or susceptibility of developing the bacterial infection, or relative to a symptom of a bacterial infection likely to arise based on historical or statistical measures of populations affected by the same bacterial infection. By "reduced severity" is meant at least a 10% reduction in the severity or degree of a symptom of a bacterial infection or measurable disease marker of a bacterial infection, relative to a control or reference, e.g., at least 15%, 20%, 30%, 40%, 50%, 60%, 70%, 80%, 90%, 95%, 99% or even 100% (i.e., no symptoms of a bacterial infection or measurable marker of a bacterial infection).

In some embodiments, the methods as disclosed herein can be used prophylactically for example in instances where an individual is susceptible for infections or re-infection with a particular bacterial strain or a combination of such strains. For example, microbial infections such as bacterial infections such as biofilms can occur on any surface where sufficient moisture and nutrients are present. One such surface is the surface of implanted medical devices, such as catheters, heart valves and joint replacements. In particular, catheters are associated with infection by many biofilm-forming organisms such as *Staphylococcus epidermidis, Staphylococcus aureus, Pseudomonas aeruginosa, Enterococcus faecalis* and *Candida albicans* which frequently result in generalized blood stream infection. In a subject identified to have a catheter infected with bacterial, such as for example, a bacterial infected central venous catheter (CVC), the subject can have the infected catheter removed and can be treated by the methods and compositions as disclosed herein comprising an engineered bacteriophage and antimicrobial agent to eliminate the bacterial infection. Furthermore, on removal of the infected catheter and its replacement with a new catheter, the subject can also be administered the compositions comprising engineered bacteriophages and antimicrobial agents as disclosed herein on a prophylaxis basis to prevent re-infection or the re-occurrence of the bacterial infection. Alternatively, a subject can be administered the compositions as disclosed herein comprising engineered bacteriophages and antimicrobial agents on a prophylaxis basis on initial placement of the catheter to prevent any antimicrobial infection such as a bacterial biofilm infection. The effect can be prophylactic in terms of completely or partially preventing a disease or sign or symptom thereof, and/or can be therapeutic in terms of a partial or complete cure of a disease.

As used herein, the term "effective amount" is meant an amount of an antimicrobial-agent engineered bacteriophage, e.g. AMP-engineered bacteriophage effective to yield a desired decrease in bacteria. In terms of the effective amount of the antimicrobial agent to act as an adjuvant, i.e. to increase the efficacy of a bacteriophage as compared to the activity of the same type of bacteriophage which has not been engineered, is an amount of antimicrobial agent which increases the efficacy of the bacteriophage by a statistically significant amount as compared to in the absence of the antimicrobial agent. The term "effective amount" as used herein refers to that amount of composition comprising an antimicrobial agent engineered bacteriophage, e.g. an AMP-engineered bacteriophage necessary to achieve the indicated effect, i.e. a reduction or decrease in the number of viable microorganisms, such as bacteria, by at reduction of least 5%, at least 10%, by at least 20%, by at least 30% . . . at least 35%, . . . at least 50%, . . . at least 60%, . . . at least 90% or any decrease or reduction of viable microorganism in between, as compared to either the absence of an antimicrobial agent engineered bacteriophage or a wild-type non-engineered bacteriophage. The "effective amount" or "effective dose" will, obviously, vary with such factors, in particular, the strain of bacteria being treated, the strain of bacteriophage being used, the genetic modification of the bacteriophage being used, the antimicrobial agent, as well as the particular condition being treated, the physical condition of the subject, the type of subject being treated, the duration of the treatment, the route of administration, the type of antimicrobial agent and/or enhancer of antimicrobial agent, the nature of concurrent therapy (if any), and the specific formulations employed, and the level of expression and level of secretion of the antimicrobial agent from the antimicrobial-agent engineered bacteriophage components to each other. The term "effective amount" when used in reference to administration of the compositions comprising an antimicrobial-agent engineered bacteriophage as disclosed herein to a subject refers to the amount of the compositions to reduce or stop at least one symptom of the disease or disorder, for example a symptom or disorder of the microorganism infection, such as bacterial infection. For example, an effective amount using the methods as disclosed herein would be considered as the amount sufficient to reduce a symptom of the disease or disorder of the bacterial infection by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, a "pharmaceutical carrier" is a pharmaceutically acceptable solvent, suspending agent or vehicle for delivering an antimicrobial-agent engineered bacteriophage, e.g. AMP-engineered bacteriophage to the surface infected with bacteria or to a subject. The carrier can be liquid or solid and is selected with the planned manner of administration in mind. Each carrier must be pharmaceutically "acceptable" in the sense of being compatible with other ingredients of the composition and non injurious to the subject.

As used herein, "gene silencing" or "gene silenced" in reference to an activity of in RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein, an "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The terms "patient", "subject" and "individual" are used interchangeably herein, and refer to an animal, particularly a human, to whom treatment including prophylaxis treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. Suitable mammals also include members of the orders Primates, Rodentla, Lagomorpha, Cetacea, *Homo sapiens*, Carnivora, Perissodactyla and Artiodactyla. Members of the orders Perissodactyla and Artiodactyla are included in the invention because of their similar biology and economic importance, for example but not limited to many of the economically important and commercially important animals such as goats, sheep, cattle and pigs have very similar biology and share high degrees of genomic homology.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The term "inhibit" or "reduced" or "reduce" or "decrease" as used herein generally means to inhibit or decrease the expression of a gene or the biological function of the protein (i.e. an antibiotic resistance protein) by a statistically significant amount relative to in the absence of an inhibitor. The term "inhibition" or "inhibit" or "reduce" when referring to the activity of an antimicrobial-agent engineered bacteriophage, e.g. AMP-engineered bacteriophage as disclosed herein refers to prevention of a bacterial infection, or reduction in the rate of growth of the bacteria. However, for avoidance of doubt, "inhibit" means statistically significant decrease in growth of bacteria in the presence of an antimicrobial agent engineered bacteriophage by at least about 10% as compared to in the absence of an antimicrobial agent engineered bacteriophage or the presence of a wild-type non-engineered bacteriophage, for example a decrease by at least about 20%, at least about 30%, at least about 40%, at least about 50%, or least about 60%, or least about 70%, or least about 80%, at least about 90% or more, up to and including a 100% of the growth of bacteria, or any decrease in the rate of growth of bacteria between 10-100% as compared to either (i) the absence an antimicrobial agent engineered bacteriophage or (ii) the presence of a wild-type non-engineered bacteriophage.

The terms "activate" or "increased" or "increase" as used in the context of biological activity of a protein herein generally means an increase in the biological function of the protein by a statically significant amount relative to in a control condition. For the avoidance of doubt, an "increase", or "activation" of an antimicrobial activity of an antimicrobial agent engineered bacteriophage means a statistically significant increase of at least about 10% as compared to either (i) the absence an antimicrobial agent engineered bacteriophage or (ii) the presence of a wild-type non-engineered bacteriophage, including an increase of at least about 20%, at least about 30%, at least about 40%, at least about 50%, at least about 60%, at least about 70%, at least about 80%, at least about 90%, at least about 100% or more, including, for example at least 2-fold, at least 3-fold, at least 4-fold, at least 5-fold, at least 10-fold increase or greater of the antimicrobial activity as compared to either (i) the absence an antimicrobial agent engineered bacteriophage or (ii) the presence of a wild-type non-engineered bacteriophage.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, $NH_2$, NHR, $NR_2$ or CN, wherein R is C—C6 alkyl, alkenyl or alkynyl and halo is F. Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

As used herein, the terms "administering," and "introducing" are used interchangeably and refer to the placement of an antimicrobial-agent engineered bacteriophage, e.g. AMP-engineered bacteriophage as disclosed herein onto the surface colonized by bacteria or into a subject, such as a subject with a bacterial infection or other microorganism infection, by any method or route which results in at least partial localization of an antimicrobial-agent engineered bacteriophage, e.g. AMP-engineered bacteriophage at a desired site. The compositions as disclosed herein can be administered by any appropriate route which results in the effective killing, elimination or control of the growth of the bacteria.

The term "vectors" is used interchangeably with "plasmid" to refer to a nucleic acid molecule capable of transporting another nucleic acid to which it has been linked. A vector can be a plasmid, bacteriophage, bacterial artificial chromosome or yeast artificial chromosome. A vector can be a DNA or RNA vector. A vector can be either a self-replicating extrachromosomal vector or a vector which integrate into a host genome. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA.

The terms "polypeptide" and "protein" are be used interchangeably herein. A "peptide" is a relatively short polypeptide, typically between 2 and 60 amino acids in length, e.g., between 5 and 50 amino acids in length. Polypeptides (typically over 60 amino acids in length) and peptides described herein may be composed of standard amino acids (i.e., the 20 L-alpha-amino acids that are specified by the genetic code, optionally further including selenocysteine and/or pyrrolysine). Polypeptides and peptides may comprise one or more non-standard amino acids. Non-standard amino acids can be amino acids that are found in naturally occurring polypeptides, e.g., as a result of post-translational modification, and/or amino acids that are not found in naturally occurring polypeptides. Polypeptides and peptides may comprise one or more amino acid analogs known in the art can be used. Beta-amino acids or D-amino acids may be used. One or more of the amino acids in a polypeptide or peptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated may still be referred to as a "polypeptide". Polypeptides may be purified from natural sources, produced in vitro or in vivo in suitable expression systems using recombinant DNA technology, synthesized through chemical means such as conventional solid phase peptide synthesis and/or using methods involving chemical ligation of synthesized peptides. The term "polypeptide sequence" or "peptide sequence" or "amino acid sequence" as used herein can refer to the polypeptide material itself or the peptide material itself and/or to the sequence information (i.e. the succession of letters or three letter codes used as abbreviations for amino acid names) that biochemically characterizes a polypeptide. Polypeptide sequences herein are presented in an N-terminal to C-terminal direction unless otherwise indicated.

The term "analog" as used herein refers to a composition that retains the same structure or function (e.g., binding to a receptor) as a polypeptide or nucleic acid herein. Examples of analogs include peptidomimetics, peptide nucleic acids, small and large organic or inorganic compounds, as well as derivatives and variants of a polypeptide or nucleic acid herein. The term "analog" as used herein of antimicrobial peptide, such as an AMPs as disclosed herein, for example SEQ ID NOs: 6, 10, 11, 14, 16, 18, 20, 22, 36-45, 40, 42, 44 and 71 or any peptide derived from SEQ ID NOs: 6, 11, 14, 16, 18, 20, 22, 40, 42, 44 and 71 refers to a molecule similar in function to either the entire molecule of a fragment thereof. The term "analogue" is indented to include allelic, species and variants. Analogs typically differ from naturally occurring peptides at one or a few positions, often by virtue of conservative substitutions. Analogs typically exhibit at least 80 or 90% sequence identity with the natural peptides or the peptide sequence they are an analogue of. In some embodiments, analogs also include unnatural amino acids or modifications of N or C terminal amino acids. Examples of unnatural amino acids are acedisubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, δ-N-methylarginine. Fragments and analogs can be screened for prophylactic or therapeutic efficacy or ability to inhibit or reduce maintenance of amyloid formation as described herein in the Examples.

The term "variant" as used herein refers to any polypeptide or peptide differing from a naturally occurring polypeptide by amino acid insertion(s), deletion(s), and/or substitution(s), created using, e.g., recombinant DNA techniques. In some embodiments, amino acid "substitutions" are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, tyrosine, asparagine, and glutamine. The positively charged (basic) amino acids include arginine, lysine and histidine. The negatively charged (acidic) amino acids include aspartic acid and glutamic acid. In some embodiments, cysteine is considered a non-polar amino acid. In some embodiments, insertions or deletions may range in size from about 1 to 20 amino acids, e.g., 1 to 10 amino acids. In some instances, larger domains may be removed without substantially affecting function. In certain embodiments, the sequence of a variant can be obtained by making no more than a total of 1, 2, 3, 5, 10, 15, or 20 amino acid additions, deletions, or substitutions to the sequence of a naturally occurring polypeptide. In some embodiments, not more than 1%, 5%, 10%, or 20% of the amino acids in a peptide, polypeptide or fragment thereof are insertions, deletions, or substitutions relative to the original polypeptide. In some embodiments, guidance in determining which amino acid residues may be replaced, added, or deleted without eliminating or substantially reducing activities of interest, may be obtained by comparing the sequence of the particular polypeptide with that of orthologous polypeptides from other organisms and avoiding sequence changes in regions of high conservation or by replacing amino acids with those found in orthologous sequences since amino acid residues that are conserved among various species may more likely be important for activity than amino acids that are not conserved.

The term "derivative" as used herein refers to peptides which have been chemically modified by techniques such as adding additional side chains, ubiquitination, labeling, pegylation (derivatization with polyethylene glycol), and insertion, deletion or substitution of amino acids, including insertion, deletion and substitution of amino acids and other molecules (such as amino acid mimetics or unnatural amino acids) that do not normally occur in the peptide sequence that is basis of the derivative, for example but not limited to insertion of ornithine which do not normally occur in human proteins. The term "derivative" is also intended to encompass all modified variants of the antimicrobial peptides (AMPs), variants, functional derivatives, analogues and fragments thereof, as well as peptides with substantial identity as compared to the reference peptide to which they refer to. The term derivative is also intended to encompass aptamers, peptidomimetics and retro-inverso peptides of the reference peptide to which they refer to. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size.

Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments, amino acid substitutions are conservative.

A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A. and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides or amino acid residues, usually from about 75% to 99%, and more preferably at least about 98 to 99% of the nucleotides or amino acid residues. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan. Homologous sequences can be the same functional gene in different species.

The term "substantial identity" as used herein refers to two peptide sequences, when optimally aligned, such as by the programs GAP or BESTFIT using default gap weights, share at least about 65%, at least about . . . 70%, at least about . . . 80%, at least about . . . 90% sequence identity, at least about . . . 95% sequence identity or more (e.g., 99% sequence identity or higher). In some embodiments, residue positions which are not identical differ by conservative amino acid substitutions.

A "glycoprotein" as use herein is protein to which at least one carbohydrate chain (oligopolysaccharide) is covalently attached. A "proteoglycan" as used herein is a glycoprotein where at least one of the carbohydrate chains is a glycosaminoglycan, which is a long linear polymer of repeating disaccharides in which one member of the pair usually is a sugar acid (uronic acid) and the other is an amino sugar.

Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments, amino acid substitutions are conservative.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Antimicrobial-Agent Engineered Bacteriophages

One aspect of the present invention relates to an antimicrobial-agent engineered bacteriophage, e.g. AMP-engineered bacteriophage which comprises a nucleic acid which encodes an antimicrobial agent.

In some embodiments, an antimicrobial-agent engineered bacteriophage, e.g. AMP-engineered bacteriophage can comprise a nucleic acid encoding any type of antimicrobial agent, such as an antimicrobial peptide (AmP) as that term is defined herein. In alternative embodiments, an antimicrobial agent can be a nucleic acid inhibitor. Nucleic acid inhibitors include, for example but are not limited to antisense nucleic acid inhibitors, oligonucleotides, RNA interference (RNAi) and paired termini (PT) antisense and variants thereof.

In some embodiments of this aspect of the invention, an antimicrobial-agent engineered bacteriophage can encode an antimicrobial agent commonly known by persons of ordinary skill in the art, such as, a natural antimicrobial peptide (AMPs) from frog's skin, human sweat or ant's venom.

The use of two classes of broadly antibiotic proteins in combination with bacteriophage infection can act as a generalizable solution to the generally stated caveats against bacteriophage therapy. Those two classes are small, cationic antimicrobial peptides (AMPs) and lytic enzymes of the lysin superfamily. AMPs range between 6 and 40 amino acids in length and possess many different mechanisms to effect bacteriocidality, such as disruption of the membrane, destruction of membrane potential, translocation into the interior of the bacteria and interference with intracellular processes, to name just a few (Brogden Nat Rev Microbiol 2005; Hancock and Sahl Nat Biotechnol 2006). Lytic enzymes on the other hand range in size from 50 to several hundreds of amino acids, and are predominantly used by bacteriophages and bacteria in inter- and intraspecies bacteriocidal warfare (Keller and Surette Nat Rev Microbiol 2006; Cegelski, Marshall et al. Nat Rev Microbiol 2008).

The inventors assessed several different AMPs in vitro before choosing two exemplary AMPs to encode separately in an engineered bacteriophage. As disclosed herein, the inventors encoded a truncated, more active lysin K (lysK) from a bacteriophage specific for *S. aureus* (O'Flaherty, Coffey et al. J Bacteriol 2005; Becker, Foster-Frey et al. FEMS Microbiol Lett 2008; Horgan, O'Flynn et al. Appl Environ Microbiol 2009) into engineered bacteriophage to test the effect of a larger gene product during infection, and replication. Additionally, the inventors demonstrate the effects of the outer membrane protein A (ompA) translocation signal on the kinetics and efficacy of bacterial killing during and after bacteriophage infection and replication, by creating fusion proteins of the AMPs with the ompA signal, as well as the lysin with the ompA signal (Movva, Nakamura et al. J Biol Chem 1980).

In some embodiments, an Amp useful in being expressed by an antimicrobial-agent engineered bacteriophage as disclosed herein includes, but it not limited to, at least one of the following different AmPs: Indolicidin (SEQ ID NO: 6), Cecropin P1 (SEQ ID NO: 11), Dermaseptin (SEQ ID NO: 14), Ponericin W1 (SEQ ID NO: 16), Ponericin W4 (SEQ ID NO: 18), Ponericin W5 (SEQ ID NO: 20), Ponericin W6 (SEQ ID NO: 22) or variants thereof.

In some embodiments, one can use a modular design strategy in which bacteriophage kill bacteria in a species-specific manner are engineered to express at least one antimicrobial agent. For example, in some embodiments, an antimicrobial-agent engineered bacteriophage, e.g. AMP-engineered bacteriophage can express and secrete an anti-microbial peptide, or alternatively an antimicrobial-agent engineered bacteriophage can express and secrete a nucleic acid inhibitor, such as an antisense nucleic acid inhibitor or antisense RNA (asRNA).

Modification of an Antimicrobial-Agent Engineered Bacteriophage

In another embodiment, an antimicrobial-agent engineered bacteriophage, e.g. AMP-engineered bacteriophage can be further be modified to comprise nucleic acids which encode phage resistant genes, for example any phage resistant gene known by persons of ordinary skill in the art, such as, but not limited to AbiZ (as disclosed in U.S. Pat. No. 7,169,911 which is incorporated herein by reference), $sie_{2009}$, $sie_{IL409}$, $sie_{F2/2A}$, orf2, orf258, orf2(M), orfD, orf304, orfB, orf142, orf203, orf3ψ, orf2ψgp34, gp33, gp32, gp25, glo, orf1, SieA, SieB, imm, sim, rexB (McGrath et al., Mol Microbiol, 2002, 43; 509-520).

In another embodiment, an antimicrobial-agent engineered bacteriophage, e.g. AMP-engineered bacteriophage can be further be modified to comprise nucleic acids which encode enzymes which assist in breaking down or degrading the biofilm matrix, for example any phage resistant gene known as a biofilm degrading enzyme by persons of ordinary skill in the art, such as, but not limited to Dispersin D aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase or lyase. In other embodiments, the enzyme is selected from the group consisting of cellulases, such as glycosyl hydroxylase family of cellulases, such as glycosyl hydroxylase 5 family of enzymes also called cellulase A; polyglucosamine (PGA) depolymerases; and colonic acid depolymerases, such as 1,4-L-fucodise hydrolase (see, e.g., Verhoef R. et al., Characterisation of a 1,4-beta-fucoside hydrolase degrading colanic acid, Carbohydr Res. 2005 Aug. 15; 340(11):1780-8), depolymerazing alginase, and DNase I, or combinations thereof, as disclosed in the methods as disclosed in U.S. patent application Ser. No. 11/662,551 and International Patent Application WO2006/137847 and provisional patent application 61/014,518, which are specifically incorporated herein in their entirety by reference.

In another embodiment, an antimicrobial-agent engineered bacteriophage, e.g. AMP-engineered bacteriophage can be further be modified in a species-specific manner, for example, one can modify or select the bacteriophage on the basis for its infectivity of specific bacteria.

A bacteriophage to be engineered or developed into an antimicrobial-agent engineered bacteriophage, e.g. AMP-engineered bacteriophage can be any bacteriophage as known by a person of ordinary skill in the art. In some embodiments, an antimicrobial-agent engineered bacteriophage, e.g. AMP-engineered bacteriophage is derived from any or a combination of bacteriophages listed in Table 7F.

In some embodiments, a bacteriophage which is engineered to become an antimicrobial-agent engineered bacteriophage, e.g. AMP-engineered bacteriophage as disclosed herein is a lytic bacteriophage or lysogenic bacteriophage, or any bacteriophage that infects *E. coli, P. aeriginosa, S. aureaus, E. facalis* and the like. Such bacteriophages are well known to one skilled in the art and are listed in Table 7F, and include, but are not limited to, lambda phages, M13, T7, T3, and T-even and T-even like phages, such as T2, and T4, and RB69; also phages such as Pf1, Pf4, *Bacteroides fragilis* phage B40-8 and coliphage MS-2 can be used. For example, lambda phage attacks *E. coli* by attaching itself to the outside of the bacteria and injecting its DNA into the bacteria. Once injected into its new host, a bacteriophage uses *E. coli*'s genetic machinery to transcribe its genes. Any of the known phages can be engineered to express an antimicrobial agent as described herein.

In some embodiments, bacteriophages which have been engineered to be more efficient cloning vectors or naturally lack a gene important in infecting all bacteria, such as male and female bacteria can be used to generate an antimicrobial-agent engineered bacteriophage, e.g. AMP-engineered bacteriophage as disclosed herein. Typically, bacteriophages have been engineered to lack genes for infecting all variants and species of bacteria can have reduced capacity to replicate in naturally occurring bacteria thus limiting the use of such phages in degradation of biofilm produced by the naturally occurring bacteria.

For example, the capsid protein of phage T7, gene 10, comes in two forms, the major product 10A (36 kDa) and the minor product 10B (41 kDa) (Condron, B. G., Atkins, J. F., and Gesteland, R. F. 1991. Frameshifting in gene 10 of bacteriophage T7. J. Bacteriol. 173:6998-7003). Capsid protein 10B is produced by frameshifting near the end of the coding region of 10A. NOVAGEN® modified gene 10 in T7 to remove the frameshifting site so that only 10B with the attached user-introduced peptide for surface display is produced (U.S. Pat. No. 5,766,905. 1998. Cytoplasmic bacteriophage display system, which is incorporated in its entirety herein by reference). The 10B-enzyme fusion product is too large to make up the entire phage capsid because the enzymes that are typically introduced into phages, such as T7, are large (greater than a few hundred amino acids). As a result, T7select 10-3b must be grown in host bacterial strains that produce wild-type 10A capsid protein, such as BLT5403 or BLT5615, so that enough 10A is available to be interspersed with the 10B-enzyme fusion product to allow replication of phage (U.S. Pat. No. 5,766,905. 1998. Cytoplasmic bacteriophage display system, which is incorporated in its entirety herein by reference). However, because most biofilm-forming *E. coli* do not produce wild-type 10A capsid protein, this limits the ability of T7select 10-3b displaying large enzymes on their surface to propagate within and lyse some important strains of *E. coli*. Accordingly, in some embodiments, the present invention provides genetically antimicrobial-agent engineered bacteriophage, e.g. AMP-engineered bacteriophages that in addition to comprising a nucleic acid encoding an antimicrobial agent and being capable of expressing and secreting the gene product (i.e. the antimicrobial agent nucleic acid and/or antimicrobial protein or peptide), also express all the essential genes for virus replication in naturally occurring bacterial strains. In one embodiment, the invention provides an engineered T7select 10-3b phage that expresses both cellulase and 10A capsid protein.

It is known that wild-type T7 does not productively infect male (F plasmid-containing) *E. coli* because of interactions between the F plasmid protein PifA and T7 genes 1.2 or 10 (Garcia, L. R., and Molineux, I. J. 1995. Incomplete entry of bacteriophage T7 DNA into F plasmid-containing *Escheri-*

*chia coli*. J. Bacteriol. 177:4077-4083). F plasmid-containing *E. coli* infected by T7 die but do not lyse or release large numbers of T7 (Garcia, L. R., and Molineux, I. J. 1995. Incomplete entry of bacteriophage T7 DNA into F plasmid-containing *Escherichia coli*. J. Bacteriol. 177:4077-4083). Wild-type T3 grows normally on male cells because of T3's gene 1.2 product (Garcia, L. R., and Molineux, I. J. 1995, Id.). When T3 gene 1.2 is expressed in wild-type T7, T7 is able to productively infect male cells (Garcia, L. R., and Molineux, I. J. 1995. Id).

Because many biofilm-producing *E. coli* contain the F plasmid (Ghigo, et al., 2001. Natural conjugative plasmids induce bacterial biofilm development. Nature. 412:442-445), it is important, although not necessary, for an antimicrobial-agent engineered bacteriophage, e.g. AMP-engineered bacteriophage to be able to productively infect also male cells. Therefore, in addition to an antimicrobial-agent engineered bacteriophage, e.g. AMP-engineered bacteriophage expressing and secreting the antimicrobial agent, one can also engineer it to express the gene necessary for infecting the male bacteria. For example, one can use the modification described by Garcia and Molineux (Garcia, L. R., and Molineux, I. J. 1995. Incomplete entry of bacteriophage T7 DNA into F plasmid-containing *Escherichia coli*. J. Bacteriol. 177:4077-4083) to express T3 gene 1.2 in T7.

Protein or Peptide Based Antimicrobial Agents.

In some embodiments of aspects of the invention, an antimicrobial-agent engineered bacteriophage, e.g. AMP-engineered bacteriophage can express and secrete an antimicrobial agent which is a protein or peptide.

In this aspect and all aspects as described herein, the nucleic acid encoding the antimicrobial agent is also operatively linked to a nucleic acid encoding a signal sequence, where the signal sequence is a secretion sequence. Thus, this allows for secretion of the antimicrobial peptide out of the bacterial cell. In some embodiments, the signal sequence is an Omp secretion sequence.

In some embodiments of this aspect of the invention, a protein or peptide based is any antimicrobial agent commonly known by persons of ordinary skill in the art, such as, a natural antimicrobial peptide from frog's skin, human sweat or ant's venom. In some embodiments, an Amp useful in being expressed by an antimicrobial-agent engineered bacteriophage, e.g. AMP-engineered bacteriophage as disclosed herein includes, but it not limited to, at least one of the following different AmPs: Indolicidin (SEQ ID NO: 6), Cecropin P1 (SEQ ID NO: 11), Dermaseptin (SEQ ID NO: 14), Ponericin W1 (SEQ ID NO: 44), Ponericin W4 (SEQ ID NO: 18), Ponericin W5 (SEQ ID NO: 42), Ponericin W6 (SEQ ID NO: 22) or variants thereof. In some embodiments, an AMP-engineered bacteriophage expresses an AMP disclosed in Table 4, e.g. any AMP of SEQ ID NO: 10, or SEQ ID NO: 36-45. In some embodiments, an engineered bacteriophage expresses at least one of any of the following sequences, SEQ ID NO: 40 (J589.K4 or Ponericin W3), SEQ ID NO; 42 (J6084.H2 or Ponericin W5), SEQ ID NO: 44 (J6123.D7 or Ponericin W1), SEQ ID NO: 71 (LysK165 or CHAP165) and variants thereof.

One aspect of the present invention relates to the killing or inhibiting the growth of bacteria using an antimicrobial-agent engineered bacteriophage, e.g. AMP-engineered bacteriophage. Accordingly, one aspect of the present invention relates to methods and compositions comprising an antimicrobial-agent engineered bacteriophage, e.g. AMP-engineered bacteriophage which expresses and secretes an antimicrobial agent to potentiate the bacterial killing function or inhibition of growth function of bacteriophage.

Accordingly in some embodiments of this aspect of the present invention relates to the use of an antimicrobial-agent engineered bacteriophage, e.g. AMP-engineered bacteriophage to potentiate the killing effect of the bacteriophage. Stated another way, the antimicrobial agent expressed and secreted from an antimicrobial-agent engineered bacteriophage, e.g. AMP-engineered bacteriophage can be used to enhance the efficacy of at least one bacteriophage.

An antimicrobial agent expressed and secreted from an antimicrobial-agent engineered bacteriophage, e.g. AMP-engineered bacteriophage is considered to potentiate the effectiveness of the bacteriophage if the amount of bacteriophage as disclosed herein is reduced by at least 10% as compared to a non-engineered bacteriophage without adversely affecting the result, for example, without adversely affecting the level of antimicrobial activity. In another embodiment, the criteria used to select an antimicrobial agent for expression and secretion in an antimicrobial-agent engineered bacteriophage, e.g. AMP-engineered bacteriophage is one which can potentiate or increase the efficacy (i.e. the killing ability) of a non-engineered bacteriophage (i.e. one which has not been engineered to express and secrete an antimicrobial agent) by at least about 10%, . . . or at least about 15%, . . . or at least about 20%, . . . or at least about 25%, . . . or at least about 35%, . . . or at least about 50%, . . . or at least about 60%, . . . or at least about 90% and all integers in between 10-90% of the amount (i.e. dose).

In some embodiments, any antimicrobial agent can be used which is know by persons of ordinary skill in the art can be expressed and secreted in an antimicrobial-agent engineered bacteriophage. In some embodiments, an antimicrobial agent is an antibiotic. Thus, in some embodiments, an antimicrobial-agent engineered bacteriophage as disclosed expresses for example, an antimicrobial agent, such as but not limited to, gentamicin, amikacin, gentamycin, tobramycin, netromycin, streptomycin, kanamycin, paromomycin, and neomycin. In some embodiments, an antimicrobial-agent engineered bacteriophage as disclosed herein secretes and expresses an antibiotic such as a β-lactam antibiotic, such as but not limited to, ampicillin, penicillin, penicillin derivatives, cephalosporins, monobactams, carbapenems and β-lactamase inhibitors. In some embodiments, an antimicrobial-agent engineered bacteriophage as disclosed herein expresses and secretes a quinolones antimicrobial agent, such as, but not limited to, ofloxacin, ciproflaxacin, levofloxacin, gatifloxacin, norfloxacin, lomefloxacin, trovafloxacin, moxifloxacin, sparfloxacin, gemifloxacin, and pazufloxacin.

In alternative embodiments, an antimicrobial agent can be, for example, but not limited to, a small molecule, a peptide, a peptidomimetic, a chemical, a compound and any entity that inhibits the growth and/or kills a microorganism. In some embodiments, an antimicrobial agent can include, but is not limited to; antibodies (polyclonal or monoclonal), neutralizing antibodies, antibody fragments, chimeric antibodies, humanized antibodies, recombinant antibodies, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. An antimicrobial agent can also be selected from a group of a chemical, small molecule, chemical entity, nucleic acid sequences, nucleic acid analogues or protein or polypeptide or analogue or fragment thereof.

In all aspects of the invention as disclosed herein, an antimicrobial agent is an antimicrobial peptide, for example but not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

In some embodiments, an antimicrobial agent which can be selected to be expressed and secreted by an antimicrobial-agent engineered bacteriophage as described herein includes, but are not limited to aminoglycosides, carbapenemes, cephalosporins, cephems, glycoproteins fluoroquinolones/quinolones, oxazolidinones, penicillins, streptogramins, sulfonamides and/or tetracyclines.

Aminoglycosides are a group of antibiotics found to be effective against gram-negative. Aminoglycosides are used to treat complicated urinary tract infections, septicemia, peritonitis and other severe intra-abdominal infections, severe pelvic inflammatory disease, endocarditis, mycobacterium infections, neonatal sepsis, and various ocular infections. They are also frequently used in combination with penicillins and cephalosporins to treat both gram-positive and gram-negative bacteria. Examples of aminoglycosides include amikacin, gentamycin, tobramycin, netromycin, streptomycin, kanamycin, paromomycin, and neomycin.

Carbapenems are a class of broad spectrum antibiotics that are used to fight gram-positive, gram-negative, and anaerobic microorganisms. Carbapenems are available for intravenous administration, and as such are used for serious infections which oral drugs are unable to adequately address. For example, carbapenems are often used to treat serious single or mixed bacterial infections, such as lower respiratory tract infections, urinary tract infections, intra-abdominal infections, gynecological and postpartum infections, septicemia, bone and joint infections, skin and skin structure infections, and meningitis. Examples of carbapenems include imipenem/cilastatin sodium, meropenem, ertapenem, and panipenem/betamipron.

Cephalosporins and cephems are broad spectrum antibiotics used to treat gram-positive, gram-negative, and spirochaetal infections. Cephems are considered the next generation Cephalosporins with newer drugs being stronger against gram negative and older drugs better against gram-positive. Cephalosporins and cephems are commonly substituted for penicillin allergies and can be used to treat common urinary tract infections and upper respiratory infections (e.g., pharyugitis and tonsillitis).

Cephalosporins and cephems are also used to treat otitis media, some skin infections, bronchitis, lower respiratory infections (pneumonia), and bone infection (certain; members), and are a preferred antibiotic for surgical prophylaxis. Examples of Cephalosporins include cefixime, cefpodoxime, ceftibuten, cefdinir, cefaclor, cefprozil, loracarbef, cefadroxil, cephalexin, and cephradineze. Examples of cephems include cefepime, cefpirome, cefataxidime pentahydrate, ceftazidime, ceftriaxone, ceftazidime, cefotaxime, cefteram, cefotiam, cefuroxime, cefamandole, cefuroxime axetil, cefotetan, cefazolin sodium, cefazolin, cefalexin.

Fluoroquinolones/quinolones are antibiotics used to treat gram-negative infections, though some newer agents have activity against gram-positive bacteria and anaerobes. Fluoroquinolones/quinolones are often used to treat conditions such as urinary tract infections, sexually transmitted diseases (e.g., *gonorrhea*, chlamydial urethritis/cervicitis, pelvic inflammatory disease), gram-negative gastrointestinal infections, soft tissue infections, pphthalmic infections, dermatological infections, sinusitis, and respiratory tract infections (e.g., bronchitis, pneumonia, and tuberculosis). Fluoroquinolones/quinolones are used in combination with other antibiotics to treat conditions, such as multi-drug resistant tuberculosis, neutropenic cancer patients with fever, and potentially anthrax. Examples of fluoroquinolones/quinolones include ciproflaxacin, levofloxacin, and ofloxacin, gatifloxacin, norfloxacin, lomefloxacin, trovafloxacin, moxifloxacin, sparfloxacin, gemifloxacin, and pazufloxacin.

Glycopeptides and streptogramins represent antibiotics that are used to treat bacteria that are resistant to other antibiotics, such as methicillin-resistant *Staphylococcus aureus* (MRSA). They are also be used for patients who are allergic to penicillin. Examples of glycopeptides include vancomycin, teicoplanin, and daptomycin.

β-lactam antibiotics are a broad class of antibiotics which include penicillin derivatives, cephalosporins, monobactams, carbapenems and β-lactamase inhibitors; basically, any antibiotic or agent or antimicrobial agent which contains a β-lactam nucleus in its molecular structure. Without being bound by theory, β-Lactam antibiotics are bactericidal, and act by inhibiting the synthesis of the peptidoglycan layer of bacterial cell walls. The peptidoglycan layer is important for cell wall structural integrity, especially in Gram-positive organisms. The final transpeptidation step in the synthesis of the peptidoglycan is facilitated by transpeptidases known as penicillin binding proteins (PBPs). β-lactam antibiotics are analogues of D-alanyl-D-alanine—the terminal amino acid residues on the precursor NAM/NAG-peptide subunits of the nascent peptidoglycan layer. The structural similarity between β-lactam antibiotics and D-alanyl-D-alanine facilitates their binding to the active site of penicillin binding proteins (PBPs). The β-lactam nucleus of the molecule irreversibly binds to (acylates) the Ser403 residue of the PBP active site. This irreversible inhibition of the PBPs prevents the final crosslinking (transpeptidation) of the nascent peptidoglycan layer, disrupting cell wall synthesis. Under normal circumstances peptidoglycan precursors signal a reorganization of the bacterial cell wall and consequently trigger the activation of autolytic cell wall hydrolyses. Inhibition of cross-linkage by β-lactams causes a build-up of peptidoglycan precursors which triggers the digestion of existing peptidoglycan by autolytic hydrolases without the production of new peptidoglycan. This as a result further enhances the bactericidal action of β-lactam antibiotics.

Carbapenems are used to treat gram-positive, gram-negative, and/or anaerobes.

Oxazolidinones are commonly administered to treat gram-positive infections. Oxazolidinones are commonly used as an alternative to other antibiotic classes for bacteria that have developed resistance. Examples of oxazolidinones include linezolid.

Penicillins are broad spectrum used to treat gram-positive, gram-negative, and spirochaetal infections. Conditions that are often treated with penicillins include pneumococcal and meningococcal meningitis, dermatological infections, ear infections, respiratory infections, urinary tract infections, acute sinusitis, pneumonia, and Lyme disease. Examples of penicillins include penicillin, amoxicillin, amoxicillin-clavulanate, ampicillin, ticarcillin, piperacillin-tazobactam, carbenicillin, piperacillin, mezocillin, benzathin penicillin G. penicillin V potassium, methicillin, nafcillin, oxacillin, cloxacillin, and dicloxacillin.

Streptogramins are antibiotics developed in response to bacterial resistance that diminished effectiveness of existing antibiotics. Streptogramins are a very small class of drugs and are currently very expensive. Examples of streptogramins include quinupristin/dafopristin and pristinamycin.

Sulphonamides are broad spectrum antibiotics that have had reduced usage due to increase in bacterial resistance to them. Suphonamides are commonly used to treat recurrent attacks of rheumatic fever, urinary tract infections, prevention of infections of the throat and chest, traveler's diarrhea, whooping cough, meningococcal disease, sexually transmitted diseases, toxoplasmosis, and rhinitis. Examples of sulfonamides include co-trimoxazole, sulfamethoxazole trimethoprim, sulfadiazine, sulfadoxine, and trimethoprim.

Tetracyclines are broad spectrum antibiotics that are often used to treat gram-positive, gram-negative, and/or spirochaetal infections. Tetracyclines are often used to treat mixed infections, such as chronic bronchitis and peritonitis, urinary tract infections, rickets, *Chlamydia, gonorrhea*, Lyme disease, and periodontal disease. Tetracyclines are an alternative therapy to penicillin in syphilis treatment and are also used to treat acne and anthrax. Examples of tetracyclines include tetracycline, demeclocycline, minocycline, and doxycycline.

Other antimicrobial agents and antibiotics contemplated herein useful to be expressed and secreted by an antimicrobial-agent engineered bacteriophage as disclosed herein include (some of which can be redundant with the list above), but are not limited to; abrifam; acrofloxacin; aptecin, amoxicillin plus clavulonic acid; apalcillin; apramycin; astromicin; arbekacin; aspoxicillin; azidozillin; azlocillin; aztreonam; bacitracin; benzathine penicillin; benzylpenicillin; clarithromycin, carbencillin; cefaclor; cefadroxil; cefalexin; cefamandole; cefaparin; cefatrizine; cefazolin; cefbuperazone; cefcapene; cefdinir; cefditoren; cefepime; cefetamet; cefixime; cefinetazole; cefminox; cefoperazone; ceforanide; cefotaxime; cefotetan; cefotiam; cefoxitin; cefpimizole; cefpiramide; cefpodoxime; cefprozil; cefradine; cefroxadine; cefsulodin; ceftazidime; ceftriaxone; cefuroxime; cephalexin; chloramphenicol; chlortetracycline; ciclacillin; cinoxacin; clemizole penicillin; cleocin, cleocin-T, cloxacillin; corifam; daptomycin; daptomycin; demeclocycline; desquinolone; dibekacin; dicloxacillin; dirithromycin; doxycycline; enoxacin; epicillin; ethambutol; gemifloxacin; fenampicin; finamicina; fleroxacin; flomoxef; flucloxacillin; flumequine; flurithromycin; fosfomycin; fosmidomycin; fusidic acid; gatifloxacin; gemifloxaxin; isepamicin; isoniazid; josamycin; kanamycin; kasugamycin; kitasamycin; kalrifam, latamoxef; levofloxacin, levofloxacin; lincomycin; linezolid; lomefloxacin; loracarbaf; lymecycline; mecillinam; methacycline; methicillin; metronidazole; mezlocillin; midecamycin; minocycline; miokamycin; moxifloxacin; nafcillin; nafcillin; nalidixic acid; neomycin; netilmicin; norfloxacin; novobiocin; oflaxacin; oleandomycin; oxacillin; oxolinic acid; oxytetracycline; paromycin; pazufloxacin; pefloxacin; penicillin g; penicillin v; phenethicillin; phenoxymethyl penicillin; pipemidic acid; piperacillin and tazobactam combination; piromidic acid; procaine penicillin; propicillin; pyrimethamine; rifadin; rifabutin; rifamide; rifampin; rifapentene; rifomycin; rimactane, rofact; rokitamycin; rolitetracycline; roxithromycin; rufloxacin; sitafloxacin; sparfloxacin; spectinomycin; spiramycin; sulfadiazine; sulfadoxine; sulfamethoxazole; sisomicin; streptomycin; sulfamethoxazole; sulfisoxazole; quinupristan-dalfopristan; teicoplanin; temocillin; gatifloxacin; tetracycline; tetroxoprim; telithromycin; thiamphenicol; ticarcillin; tigecycline; tobramycin; tosufloxacin; trimethoprim; trimetrexate; trovafloxacin; vancomycin; verdamicin; azithromycin; and linezolid.

Secretion of an Antimicrobial Peptide from the Host Bacterial Cell

In some embodiments, the antimicrobial agent expressed from the host bacterial cell is released when the bacterial host cell lyses in the lytic cycle process of bacteriophage infection. In alternative embodiment, the expressed antimicrobial agent is released from the bacterial host cell by the bacterial host cell via the secretory pathway. In such an embodiment, the antimicrobial agent, such as an antimicrobial peptide expressed from the bacteriophage-infected host bacterial cell also contains a signal peptide such as a secretory signal sequence. Such a secretory signal sequence allows intracellular transport of the antimicrobial peptide to the bacterial cell plasma membrane for its secretion from the bacteria. Accordingly, in such an embodiment, the expressed antimicrobial peptide is expressed as a pro-antimicrobial peptide comprising the signal sequence and antimicrobial peptide, where the signal sequence is subsequently cleaved as the peptide is secreted from the host bacteria to render the mature antimicrobial peptide in its active form without the signal sequence.

One particular benefit of an antimicrobial agent engineered bacteriophage expressing an antimicrobial agent such as an antimicrobial peptide, and a method of using it according to methods disclosed herein is the presence of the antimicrobial peptide in the immediate locality of the bacteriophage, thus the antimicrobial agent is released from bacterial host cells infected with the bacteriophage, via either lysis or being secreted, allowing the antimicrobial peptide to target and kill bacterial strains which are not infected by the antimicrobial agent-engineered bacteriophage, this providing a strategy for killing efficacy of a broad spectrum of bacterial host species. This is possible because the released antimicrobial agent, such as an antimicrobial peptide can target and have efficacy on a variety of different bacterial host species in the near local which may otherwise be resistant to infection or lysis by the species of bacteriophage of the antimicrobial agent engineered bacteriophage. Therefore, an antimicrobial agent engineered bacteriophage results in the release of the antimicrobial agent in the near vicinity of the bacteriophage to target a variety of different species of bacteria even if these species of bacteria have not or cannot be infected with the antimicrobial agent bacteriophage. Thus, the present invention provides an improved delivery of antimicrobial agents in the vicinity of the bacterial infection. Additionally, another advantage of delivering the antimicrobial agents by being expressed by a bacteriophage is that it enables the antimicrobial agents to come into contact with the bacterial cells which may not be accessible using conventional antimicrobial agent delivery methods, due for example, the bacteria being located in a difficult to access location, such as a small space or between two pieces of material. As such, another advantage of the present invention which the present invention is an improved genetically engineered bacteriophage with an a broad spectrum target bacteria host range which can express and release antimicrobial agents within the near vicinity of bacterial cells, which may not be accessible to antimicrobial agent delivered by other means.

Signal Sequence:

Without wishing to be bound to theory, when proteins are expressed by a cell, including a bacterial cell, the proteins are targeted to a particular part in the cell or secreted from the cell. Thus, protein targeting or protein sorting is the mechanism by which a cell transports proteins to the appropriate positions in the cell or outside of it. Sorting targets can be the inner space of an organelle, any of several interior membranes, the cell's outer membrane, or its exterior via secretion. This delivery process is carried out based on information contained in the protein itself. Correct sorting is crucial for the cell; errors can lead to diseases.

With some exceptions, Bacteria lack membrane-bound organelles as found in eukaryotes, but they may assemble proteins onto various types of inclusions such as gas vesicles and storage granules. Also, depending on the species of bacteria, bacteria may have a single plasma membrane (Gram-positive bacteria), or both an inner (plasma) membrane and an outer cell wall membrane, with an aqueous space between the two called the periplasm (Gram-negative bacteria). Proteins can be secreted into the environment, according to whether or not there is an outer membrane. The basic mechanism at the plasma membrane is similar to the eukaryotic one. In addition, bacteria may target proteins into or across the outer membrane. Systems for secreting proteins across the bacterial outer membrane may be quite complex and play key roles in pathogenesis. These systems may be described as type I secretion, type II secretion, etc.

In most Gram-positive bacteria, certain proteins are targeted for export across the plasma membrane and subsequent covalent attachment to the bacterial cell wall. A specialized enzyme, sortase, cleaves the target protein at a characteristic recognition site near the protein C-terminus, such as an LPXTG motif (SEQ ID NO:109) (where X can be any amino acid), then transfers the protein onto the cell wall. A system analogous to sortase/LPXTG (SEQ ID NO:109), termed exosortase/PEP-CTERM, is proposed to exist in a broad range of Gram-negative bacteria.

A. Secretion in Gram Negative Bacteria

By way of background but not wishing to be bound by theory, secretion is present in bacteria and archaea as well. ATP binding cassette (ABC) type transporters are common to all the three domains of life. The secretory system in bacteria, also referred to in the art as the "Sec system" is a conserved secretion system which generally requires the presence of an N-terminal signal peptide on the secreted protein. Gram negative bacteria have two membranes, thus making secretion topologically more complex. There are at least six specialized secretion systems (Type I-VI) in Gram negative bacteria.

1. Type I Secretion System (T1SS or TOSS):

It is similar to the ABC transporter, however it has additional proteins that, together with the ABC protein, form a contiguous channel traversing the inner and outer membranes of Gram-negative bacteria. It is a simple system, which consists of only three protein subunits: the ABC protein, membrane fusion protein (MFP), and outer membrane protein (OMP). Type I secretion system transports various molecules, from ions, drugs, to proteins of various sizes (20-900 kDa). The molecules secreted vary in size from the small *Escherichia coli* peptide colicin V, (10 kDa) to the *Pseudomonas* fluorescence cell adhesion protein LapA of 900 kDa. The best characterized are the RTX toxins and the lipases. Type I secretion is also involved in export of non-proteinaceous substrates like cyclic β-glucans and polysaccharides. Many secreted proteins are particularly important in bacterial pathogenesis. [Wooldridge K (2009). Bacterial Secreted Proteins: Secretory Mechanisms and Role in Pathogenesis. Caister Academic Press]

2. Type II Secretion System (T2SS):

Proteins secreted through the type II system, or main terminal branch of the general secretory pathway, depend on the Sec system for initial transport into the periplasm. Once there, they pass through the outer membrane via a multimeric complex of secretin proteins. In addition to the secretin protein, 10-15 other inner and outer membrane proteins compose the full secretion apparatus, many with as yet unknown function. Gram-negative type IV pili use a modified version of the type II system for their biogenesis, and in some cases certain proteins are shared between a pilus complex and type II system within a single bacterial species.

3. Type III Secretion System (T3SS or 11SS):

It is homologous to bacterial flagellar basal body. It is like a molecular syringe through which a bacterium (e.g. certain types of *Salmonella, Shigella, Yersinia*) can inject proteins into eukaryotic cells. The low $Ca^{2+}$ concentration in the cytosol opens the gate that regulates T3SS. One such mechanism to detect low calcium concentration has been illustrated by the lcrV (Low Calcium Response) antigen utilized by *Y. pestis*, which is used to detect low calcium concentrations and elicits T3SS attachment. (Salyers et al, 2002; Bacterial Pathogenesis: A Molecular Approach, 2nd ed., Washington, D.C.: ASM Press)

4. Type IV Secretion System (T4SS or TFSS):

It is homologous to conjugation machinery of bacteria (and archaeal flagella). It is capable of transporting both DNA and proteins. It was discovered in *Agrobacterium tumefaciens*, which uses this system to introduce the Ti plasmid and proteins into the host which develops the crown gall (tumor). [[*Helicobactor pylori*]] uses a type IV secretion system to deliver CagA into gastric epithelial cells. *Bordetella pertussis*, the causative agent of whooping cough, secretes the pertussis toxin partly through the type IV system. *Legionella pneumophila*, the causing agent of legionellosis (Legionnaires' disease) utilizes type IV secretion system, known as the icm/dot (intracellular multiplication/defect in organelle trafficking genes) system, to translocate numerous effector proteins into its eukaryotic host. (Cascales et al., (2003), Nat Rev Microbiol 1 (2): 137-149). The prototypic Type IV secretion system is the VirB complex of *Agrobacterium tumefaciens* (Christie et al. 2005; Ann Rev Microbiol 59: 451-485).

5. Type V Secretion System (T5SS):

Also know in the art as the "autotransporter system" (Thanassi, et al., 2005; Mol. Membrane Biol. 22 (1): 63-72). type V secretion involves use of the Sec system for crossing the inner membrane. Proteins which use this pathway have the capability to form a beta-barrel with their C-terminus which inserts into the outer membrane, allowing the rest of the peptide (the passenger domain) to reach the outside of the cell. Often, autotransporters are cleaved, leaving the beta-barrel domain in the outer membrane and freeing the passenger domain.

6. Type VI Secretion System (T6SS):

Proteins secreted by the type VI system lack N-terminal signal sequences and therefore presumably do not enter the Sec pathway. (Pukatzki et al., (2006), PNAS 103 (5): 1528-33; Mougous et al., (2006) Science 312 (5779): 1526-30). Type VI secretion systems are now known to be widespread in Gram-negative bacteria. (Bingle et al., 2008; Curr. Opin. Microbiol. 11 (1): 3-8; Cascales E (2008), EMBO Reports 9 (8): 735-741).

7. Twin-Arginine Translocation:

Bacteria as well as mitochondria and chloroplasts also use many other special transport systems such as the twin-arginine translocation (Tat) pathway which, in contrast to Sec-dependent export, transports fully folded proteins across the membrane. The signal sequence requires two consecutive arginines for targeting to this system.

8. Release of Outer Membrane Vesicles:

In addition to the use of the multiprotein complexes listed above, Gram-negative bacteria possess another method for release of material: the formation of outer membrane vesicles. [Chatterjee, et al., J. Gen. Microbiol." "49": 1-11 (1967); Kuehn et al., Genes Dev. 19(22):2645-55 (2005)]. Portions of the outer membrane pinch off, forming spherical structures made of a lipid bilayer enclosing periplasmic materials. Vesicles from a number of bacterial species have been found to contain virulence factors, some have immunomodulatory effects, and some can directly adhere to and intoxicate host cells. While release of vesicles has been demonstrated as a general response to stress conditions, the process of loading cargo proteins seems to be selective. [McBroom, et al., Mol. Microbiol. 63(2):545-58 (2007)]

B. Secretion in Gram Positive Bacteria

Proteins with appropriate N-terminal targeting signals are synthesized in the cytoplasm and then directed to a specific protein transport pathway. During, or shortly after its translocation across the cytoplasmic membrane, the protein is processed and folded into its active form. Then the translocated protein is either retained at the extracytoplasmic side of the cell or released into the environment. Since the signal peptides that target proteins to the membrane are key determinants for transport pathway specificity, these signal peptides are classified according to the transport pathway to which they direct proteins. Signal peptide classification is based on the type of signal peptidase (SPase) that is responsible for the removal of the signal peptide. The majority of exported proteins are exported from the cytoplasm via the general "Secretory (Sec) pathway". Most well known virulence factors (e.g. exotoxins of *Staphylococcus aureus*, protective antigen of *Bacillus anthracis*, lysteriolysin 0 of *Listeria monocytogenes*) that are secreted by Gram-positive pathogens have a typical N-terminal signal peptide that would lead them to the Sec-pathway. Proteins that are secreted via this pathway are translocated across the cytoplasmic membrane in an unfolded state. Subsequent processing and folding of these proteins takes place in the cell wall environment on the trans-side of the membrane. In addition to the Sec system, some Gram-positive bacteria also contain the Tat-system that is able to translocate folded proteins across the membrane. Pathogenic bacteria may contain certain special purpose export systems that are specifically involved in the transport of only a few proteins. For example, several gene clusters have been identified in mycobacteria that encode proteins that are secreted into the environment via specific pathways (ESAT-6) and are important for mycobacterial pathogenesis. Specific ATP-binding cassette (ABC) transporters direct the export and processing of small antibacterial peptides called bacteriocins. Genes for endolysins that are responsible for the onset of bacterial lysis are often located near genes that encode for holin-like proteins, suggesting that these holins are responsible for endolysin export to the cell wall. [Wooldridge K (2009). Bacterial Secreted Proteins: Secretory Mechanisms and Role in Pathogenesis. Caister Academic Press]

In some embodiments, the signal sequence useful in the present invention is OmpA Signal sequence, however any signal sequence commonly known by persons of ordinary skill in the art which allows the transport and secretion of antimicrobial agents outside the bacteriophage infected cell are encompassed for use in the present invention.

Signal sequence that direct secretion of proteins from bacterial cells are well known in the art, for example as disclosed in International application WO2005/071088, which is herein incorporated in its entirety by reference.

For example, one can use some of the non-limited examples of signal peptide shown in Table 2 which can be attached to the amino-terminus or carboxyl terminus of the antimicrobial peptide (Amp) or antimicrobial polypeptide to be expressed by the antimicrobial-agent engineered bacteriophage, e.g. AMP-engineered bacteriophage. Attachment can be via fusion or chimera composition with selected antimicrobial peptides (AmP) resulting in the secretion from the bacterium infected with the antimicrobial-agent engineered bacteriophage, e.g. AMP-engineered bacteriophage.

TABLE 2

Some exemplary signal peptides to direct secretion of an antimicrobial peptide out of a bacterial cell.

| Secretion Pathway | Signal Peptide Amino Acid sequence ($NH_2$—$CO_2$) | Signal peptidase Site (cleavage site representedby ') | Gene | Genus/Species |
|---|---|---|---|---|
| secA1 | MKKIMLVITLILVSPIAQQTEAKD (SEQ ID NO: 23) | TEA'KD (SEQ ID NO: 110) | Hly (LLO) | *Listeria monocytogenes* |
| | MKKKIISAILMSTVILSAAAPLSGVYADT (SEQ ID NO: 24) | VYA'DT (SEQ ID NO: 111) | Usp45 | *Lactococcus lactis* |
| | MKKRKVLIPLMALSTILVSSTGNLEVIQAEV (SEQ ID NO: 25) | IQA'EV (SEQ ID NO: 112) | Pag (protective antigen) | *Bacillus anthracis* |
| secA2 | MNMKKATIAATAGIAVTAFAAPTIASAST (SEQ ID NO: 26) | ASA'ST (SEQ ID NO: 113) | Iap (invasion-associated protein p60) | *Listeria monocytogenes* |
| | MQKTRKERILEALQEEKKNKKSKKFKTGATIAGVTA IATSITVPGIEVIVSADE (SEQ ID NO: 27) | VSA'DE (SEQ ID NO: 114) | NamA Imo2691 (autolysin) | *Listeria monocytogenes* |
| | MKKLKMASCALVAGLMFSGLTPNAFAED (SEQ ID NO: 28) | AFA'ED (SEQ ID NO: 115) | *BA_0281 (NLP/P60 family) | *Bacillus anthracis* |

TABLE 2 -continued

Some exemplary signal peptides to direct secretion of an antimicrobial peptide out of a bacterial cell.

| Secretion Pathway | Signal Peptide Amino Acid sequence ($NH_2$–$CO_2$) | Signal peptidase Site (cleavage site representedby ') | Gene | Genus/Species |
|---|---|---|---|---|
| | MAKKFNYKLPSMVALTLVGSAVTAHQVQAAE (SEQ ID NO: 29) | VQA'AE (SEQ ID NO: 116) | *atl (autolysin) | *Staphylococcus aureus* |
| Tat | MTDKKSENQTEKTETKENKGMTRREMLKLSAVAGT GIAVGATGLGTILNVVDQVDKALT (SEQ ID NO: 30) | DKA'LT (SEQ ID NO: 117) | Imo0367 | *Listeria monocytogenes* |
| | MAYDSRFDEWVQKLKEESFQNNTFDRRKFIQGAGKI AGLGLGLTIAQSVGAFG (SEQ ID NO: 31) | | PhoD (alkaline phosphatase) | *Bacillus subtillis* |

*Signal peptidase cleavage site represented by '

In alternative embodiments, one of ordinary skill in the art can use synthetic bacterial sequences, such as those discussed in Clérico et al., Biopolymers. 2008; 90(3):307-19, which is incorporated herein by reference. Alternatively, one can use methods to secrete peptides without the use of signal (or secretory) sequences, such as the methods disclosed in International Application WO2007/018853, which is incorporated herein by reference. Bacterial protein secretion is discussed in Driessen et al., Nat Struct Biol. 2001 June; 8(6):492-8, which is incorporated herein by reference. The localization of signal sequences, such as secretory signal sequences can be located anywhere on the peptide, so long as the signal is exposed on the peptide and its placement does not disrupt the antimicrobial effect of the peptide or AmP. For example, it can be placed at the carboxy or amino terminus or even sometimes within the peptide, providing it satisfies the above conditions. Some signal sequences which can be used are disclosed in Table 1 of U.S. Pat. No. 6,072,039 which is incorporated herein in its entirety by reference.

Nucleic Acid Based Antimicrobial Agents.

In some embodiments of aspects of the invention, an antimicrobial-agent engineered bacteriophage can express and secrete an antimicrobial agent which is an nucleic acid, for example an antimicrobial agent which functions by "gene silencing" commonly known bacterial genes known by persons of ordinary skill in the art. A nucleic acid-based antimicrobial agent includes for example, but is not limited to, RNA interference-inducing (RNAi) molecules, for example but are not limited to siRNA, dsRNA, stRNA, shRNA, miRNA and modified versions thereof, where the RNA interference molecule gene silences the expression of a gene expressed and important for viability (i.e. survival) of the bacteria. In some embodiments, a nucleic acid-based antimicrobial agent is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, a nucleic acid-based antimicrobial agent is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid inhibitors include for example, but are not limited to, a nucleic acid sequence encoding a protein that is a transcriptional repressor, or an antisense molecule, or a ribozyme, or a small inhibitory nucleic acid sequence such as a RNAi, an shRNAi, an siRNA, a micro RNAi (miRNA), an antisense oligonucleotide etc.

In some embodiments, a nucleic acid-based antimicrobial agent can be for example, but not are limited to, paired termini antisense, an example which is disclosed in Nakashima, et al., (2006) Nucleic Acids Res 34: e138, which in incorporated herein in its entirety by reference.

In some embodiments of this aspect and all aspects described herein, a single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of a target genes, such an antibiotic resistance gene and/or cell survival gene and/or non-SOS defense gene. As used herein, "inhibition of target gene expression" includes any decrease in expression or protein activity or level of the target gene (i.e. antibiotic resistance gene) or protein encoded by the target gene (i.e. antibiotic resistance protein) as compared to the level in the absence of an RNA interference (RNAi) molecule. The decrease in expression or protein level as result of gene silencing can be of at least 30%, 40%, 50%, 60%, 70%, 80%, 90%, 95% or 99% or more as compared to the expression of a target gene or the activity or level of the protein (i.e. expression of the antibiotic resistance gene or antibiotic resistance protein) encoded by a target gene which has not been targeted and gene silenced by an RNA interfering (RNAi) agent.

As used herein, the term "short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. In some embodiments, the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

Typically a target gene or sequence targeted by gene silencing by an RNA interfering (RNAi) agent can be a cellular gene or genomic sequence encoding an antibiotic resistant protein or a cell survival protein. In some embodiments, an siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST (Basic Local Alignment Search Tool available from or at NIBI).

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196, which is incorporated herein by reference). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly D-arabinose (U.S. Pat. No. 5,177,196, which is incorporated herein in its entirety by reference).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful can be readily designed and tested. Accordingly, siRNAs useful for the methods described herein include siRNA molecules of about 15 to about 40 or about 15 to about 28 nucleotides in length. Preferably, the siRNA molecules have a length of about 19 to about 25 nucleotides. More preferably, the siRNA molecules have a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the RNA molecule is double stranded—one strand has a 3' overhang and the other strand can be blunt-ended or have an overhang. In the embodiment in which the RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

In some embodiments, bacterial cell viability can be determined by using commercially available kits. Others can be readily prepared by those of skill in the art based on the known sequence of the target mRNA.

siRNA sequences are chosen to maximize the uptake of the antisense (guide) strand of the siRNA into RISC and thereby maximize the ability of the inhibitor to target RISC to target antibiotic resistance gene or cell survival gene mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the targeted mRNA.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836, which are incorporated herein by reference, teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In one embodiment, the nucleic acid inhibitors of antibiotic resistance genes and/or cell survival genes can be obtained synthetically, for example, by chemically synthesizing a nucleic acid by any method of synthesis known to the skilled artisan. The synthesized nucleic acid inhibitors of antibiotic resistance genes and/or cell survival genes can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro'phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci., USA*

98:8012-8017; and Tuschl, T. et al. (1999) *Genes & Development* 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) *Genes Dev.* 16:948-958; McManus, M. T. et al. (2002) *RNA* 8:842-850; Paul, C. P. et al. (2002) *Nat. Biotechnol.* 20:505-508; Miyagishi, M. et al. (2002) *Nat. Biotechnol.* 20:497-500; Sui, G. et al. (2002) *Proc. Natl. Acad. Sci., USA* 99:5515-5520; Brummelkamp, T. et al. (2002) *Cancer Cell* 2:243; Lee, N. S., et al. (2002) *Nat. Biotechnol.* 20:500-505; Yu, J. Y., et al. (2002) *Proc. Natl. Acad. Sci., USA* 99:6047-6052; Zeng, Y., et al. (2002) *Mol. Cell* 9:1327-1333; Rubinson, D. A., et al. (2003) *Nat. Genet.* 33:401-406; Stewart, S. A., et al. (2003) *RNA* 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., an antibiotic resistance genes and/or cell survival genes coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide) (SEQ ID NO: 118), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as OLIGOENGINE®, can also be used to select siRNA sequences against EST libraries to ensure that only one gene is targeted.

Accordingly, the RNAi molecules functioning as nucleic acid inhibitors of antibiotic resistance genes and/or cell survival genes as disclosed herein are for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of antibiotic resistance genes and/or cell survival genes is any agent which binds to and inhibits the expression of antibiotic resistance genes and/or cell survival gene mRNA, where the expression of the antibiotic resistance genes and/or cell survival mRNA or a product of transcription of nucleic acid encoded by antibiotic resistance genes and/or cell survival gene is inhibited.

In another embodiment of the invention, agents inhibiting antibiotic resistance genes and/or cell survival genes are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of antibiotic resistance genes and/or cell survival genes or homologues or variants thereof can be achieved by techniques well known to those skilled in the art (for example Lleber and Strauss, (1995) Mol Cell Biol 15:540.551, the disclosure of which is incorporated herein by reference).

Promoters of the Engineered Bacteriophages

In some embodiments of all aspects described herein, an antimicrobial-agent engineered bacteriophage, e.g. AMP-engineered bacteriophage can express and secrete an antimicrobial agent, whether the antimicrobial agent is a protein-based (such as a peptide) or a nucleic-acid based antimicrobial agent. In this aspect and all aspects as described herein, the antimicrobial agent is also linked to a signal sequence (also known in the art as a signal peptide), such as a secretion sequence, allowing translocation of the antimicrobial agent to the bacterial cell layer and secretion of the antimicrobial peptide out of the bacterial cell. An antimicrobial agent which comprises a signal sequence allowing it to be secreted from the host bacterial cell is referred to herein as a "secretable antimicrobial agent". In some embodiments, the signal sequence is an Omp secretion sequence. Thus, the nucleic acid encoding the antimicrobial agent is operatively linked to the nucleic acid encoding the signal sequence.

In all aspects of the invention, gene expression from the nucleic acid encoding the antimicrobial agent is regulated by a promoter to which the nucleic acid is operatively linked to. In some embodiments, a promoter is a bacteriophage promoter. One can use any bacteriophage promoter known by one of ordinary skill in the art, for example but not limited to, any promoter listed in Table 7G or disclosed in world-wide web site "partsregistry.org/cgi/partsdb/pgroup.cgi?pgroup=other_regulator&show=1".

In some embodiments, an antimicrobial agent is protein or polypeptide or RNAi agent, as disclosed herein. In such embodiments a bacteriophage can be engineered (e.g. by homologous recombination) to become an antimicrobial-agent engineered bacteriophage and to express a secretable form of an antimicrobial agent, for example by replacing, in whole or in part, the naturally occurring bacteriophage promoter with all or part of a heterologous promoter so that the bacteriophage and/or the bacteriophage infected-host cell expresses a high level of the secretable antimicrobial agent. In some embodiments, a heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems, which are incorporated herein in their entirety by reference.

In some embodiments, a bacteriophage can be engineered as disclosed herein to express an antimicrobial agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al, which are all incorporated herein in their entirety by reference.

Other exemplary examples of promoter which can be used include, for example but not limited, Anhydrotetracycline (aTc) promoter, PLtetO-1 (Pubmed Nucleotide # U66309), Arabinose promoter (PBAD), IPTG inducible promoters PTAC (in vectors such as Pubmed Accession # EU546824), PTrc-2, Plac (in vectors such as Pubmed Accession # EU546816), PLlacO-1, PA1lacO-1, and Arabinose and IPTG promoters, such as Plac/ara-a. Examples of these promoters are as follows:

Modification of Engineered Bacteriophages.

In some embodiments of all aspects described herein, an antimicrobial-agent engineered bacteriophage, e.g. AMP-engineered bacteriophage can also be designed for example, for optimal enzyme activity or to delay cell lysis or using multiple phage promoters to allow for increased enzyme production, or targeting multiple biofilm EPS components with different proteins. In some embodiments, one can also target multi-species bacterial infections or biofilm with a cocktail of different species-specific an antimicrobial-agent engineered bacteriophage, e.g. an AMP-engineered bacteriophage, and combination therapy with other agents that are well known to one skilled in the art and phage to improve the efficacy of both types of treatment.

In some embodiments of all aspects described herein, an antimicrobial-agent engineered bacteriophage, e.g. AMP-engineered bacteriophage can also be used together with other antibacterial or bacteriofilm degrading agents or chemicals such as EGTA, a calcium-specific chelating agent, effected the immediate and substantial detachment of a *P. aeruginosa* biofilm without affecting microbial activity, NaCl, $CaCl_2$ or $MgCl_2$, surfactants and urea.

Phage therapy or bacteriophage therapy has begun to be accepted in industrial and biotechnological settings. For example, the FDA has previously approved the use of phage targeted at *Listeria monocytogenes* as a food additive. Phage therapy has been used successfully for therapeutic purposes in Eastern Europe for over 60 years. The development and use of phage therapy in clinical settings in Western medicine, in particular for treating mammals such as humans has been delayed due to the lack of properly designed clinical trials to date as well as concerns with (i) development of phage resistance, (ii) phage immunogenicity in the human body and clearance by the reticuloendothelial system (RES), (iii) the release of toxins upon bacterial lysis, and (iv) phage specificity. Many of these concerns are currently being

```
Anhydrotetracycline (aTc) promoter, such as PLtetO-1
(Pubmed Nucleotide # U66309):
                                                  (SEQ ID NO: 32)
GCATGCTCCCTATCAGTGATAGAGATTGACATCCCTATCAGTGATAGAGATACTGAGCACATCAGCAGGA

CGCACTGACCAGGA;

Arabinose promoter (PBAD): or modified versions which can be found at
world-wide web site: partsregistry.org/wild/index.php?title=Part:BBa_I13453"
                                                  (SEQ ID NO: 33)
AAGAAACCAATTGTCCATATTGCATCAGACATTGCCGTCACTGCGTCTTTTACTGGCTCTTCTCGCTAACC

AAACCGGTAACCCCGCTTATTAAAAGCATTCTGTAACAAAGCGGGACCAAAGCCATGACAAAAACGCGT

AACAAAAGTGTCTATAATCACGGCAGAAAAGTCCACATTGATTATTTGCACGGCGTCACACTTTGCTATG

CCATAGCATTTTTATCCATAAGATTAGCGGATCCTACCTGACGCTTTTTATCGCAACTCTCTACTGTTTCTC

CATA;

IPTG promoters: (i) PTAC (in vectors such as Pubmed Accession #EU546824,
which is incorporated herein by reference), (ii) PTrc-2:
                                                  (SEQ ID NO: 34)
CCATCGAATGGCTGAAATGAGCTGTTGACAATTAATCATCCGGCTCGTATAATGTGTGGAATTGTGAGCG

GATAACAATTTCACACAGGA
and

temperature sensitive promoters such as PLs1con,
                                                  (SEQ ID NO: 35)
GCATGCACAGATAACCATCTGCGGTGATAAATTATCTCTGGCGGTGTTGACATAAATACCACTGGCGGTtA

TAaTGAGCACATCAGCAGGGTATGCAAAGGA
and modified variants thereof.
```

studied and addressed, such as the isolation and development of long-circulating phage that can avoid RES clearance for increased in vivo efficacy. Accordingly, in all aspects described herein, the methods of the present invention are applicable to human treatment as the engineered bacteriophages can be designed to prevent the development of phage resistance in bacteria. A skilled artisan can also develop and carry out an appropriate clinical trial for use in clinical applications, such as therapeutic purposes as well as in human subjects. In some instances, a skilled artisan could establish and set up a clinical trial to establish the specific tolerance of the engineered bacteriophage in human subjects. The inventors have already demonstrated herein that an antimicrobial-agent engineered bacteriophage, e.g. AMP-engineered bacteriophage are effective at killing or reducing a bacterial population comprising a heterologous population of different bacterial host strains. Additionally, an antimicrobial-agent engineered bacteriophage, e.g. AMP-engineered bacteriophage as disclosed herein is also effective in dispersing biofilms, including biofilms present in human organs, such as colon or lungs and other organs in a subject prone to bacterial infection such as bacterial biofilm infection.

Another aspect relates to a pharmaceutical composition comprising at least one antimicrobial-agent engineered bacteriophage, e.g. AMP-engineered bacteriophage. In some embodiments of this and all aspects described herein, the composition comprising an antimicrobial-agent engineered bacteriophage, e.g. AMP-engineered bacteriophage can be administered as a co-formulation with one or more other non-antimicrobial or therapeutic agents.

In a further embodiment, the invention provides methods of administration of the compositions and/or pharmaceutical formulations comprising an antimicrobial-agent engineered bacteriophage, e.g. AMP-engineered bacteriophage and include any means commonly known by persons skilled in the art. In some embodiments, the subject is any organism, including for example a mammalian, avian or plant. In some embodiments, the mammalian is a human, a domesticated animal and/or a commercial animal.

While clearance issue is not significant in treatment of chronic diseases, the problem of phage clearance is an important one that needs to be solved as it can make phage therapy more useful for treating transient infections rather than chronic ones. Non-lytic and non-replicative phage have been engineered to kill bacteria while minimizing endotoxin release. Accordingly, the present invention encompasses modification of an antimicrobial-agent engineered bacteriophage, e.g. AMP-engineered bacteriophage with minimal endotoxin release or toxin-free bacteriophage preparation.

The specificity of phage for host bacteria is both an advantage and a disadvantage for phage therapy. Specificity allows human cells as well as innocuous bacteria to be spared, potentially avoiding serious issues such as drug toxicity. Antibiotic therapy is believed to alter the microbial flora in the colon due to lack of target specificity, and in some instances allowing resistant *C. difficile* to proliferate and cause disease such as diarrhea and colitis. In some embodiments, the antimicrobial-agent engineered bacteriophage, e.g. AMP-engineered bacteriophage as disclosed herein are capable of inhibiting the local bacterial synthetic machinery which normally circumvent antimicrobial effect to result in persistent bacteria.

For host specificity, a skilled artisan can generate a well-characterized library of antimicrobial-agent engineered bacteriophage, e.g. AMP-engineered bacteriophages, where specific antimicrobial-agent engineered bacteriophage can be selected and for specific types of bacterial infection.

While one aspect of the present invention provides a method to increase (i.e. broadening) the ability of bacteriophages to target and be effective against multiple bacterial species, the diversity of bacterial infections may result in some instances where a single antimicrobial-agent engineered bacteriophage as disclosed herein is not effective at killing all the different bacterial species in a given bacterial population. Thus, to circumvent this problem, one can administer a variety of different antimicrobial-agent engineered bacteriophage, e.g. AMP-engineered bacteriophage to a bacterial population in order to be effective in killing all the different bacterial species in the heterologous bacterial population. One can do this by having the same bacterial species expressing different antimicrobial agents, or alternatively, generating different an antimicrobial-agent engineered bacteriophage, e.g. AMP-engineered bacteriophage from the same bacteriophage species expressing the same antimicrobial agent. In this way, one of ordinary skill in the art can use a combination of antimicrobial-agent engineered bacteriophage, e.g. AMP-engineered bacteriophages as disclosed herein to be effective at killing a bacterial population comprising multiple different bacterial strains. Accordingly, in one embodiment, the invention provides use of a variety of different engineered bacteriophages in combination (i.e. a cocktail of engineered bacteriophages discussed herein) to cover a range of target bacteria.

One skilled in the art can generate a collection or a library of the antimicrobial-agent engineered bacteriophage, e.g. AMP-engineered bacteriophages as disclosed herein by new cost-effective, large-scale DNA sequencing and DNA synthesis technologies. Sequencing technologies allows the characterization of collections of natural phage that have been used in phage typing and phage therapy for many years. Accordingly, a skilled artisan can use synthesis technologies as described herein to add different antimicrobial agents to produce a variety of new antimicrobial-agent engineered bacteriophage, e.g. AMP-engineered bacteriophages.

In particular embodiments, an antimicrobial-agent engineered bacteriophage, e.g. AMP-engineered bacteriophage as described herein can be engineered to express an endogenous gene, such as a repressor protein, or a nucleic acid inhibitor of an antibiotic resistance gene or cell survival gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al, which are all incorporated herein in their entirety by reference.

Furthermore, rational engineering methods with new synthesis technologies can be employed to broaden an antimicrobial-agent engineered bacteriophage, e.g. AMP-engineered bacteriophage host range. For example, a T7 antimicrobial-agent engineered bacteriophage, e.g AMP-engineered bacteriophage, can be modified to express K1-5 endosialidase, allowing it to effectively replicate in *E. coli* that produce the K1 polysaccharide capsule. In some embodiments, the gene 1.2 from phage T3 can be used to extend an antimicrobial-agent engineered bacteriophage, e.g. a AMP-engineered bacteriophage to be able to transfect a host range to include *E. coli* that contain the F plasmid, thus demonstrating that multiple modifications of a phage genome can be done without significant impairment of the phage's ability to replicate. *Bordetella* bacteriophage use a reverse-transcriptase-mediated mechanism to produce diversity in host tropism which can also be used according to the methods of the present invention to create an antimicrobial-agent engineered bacteriophage, e.g. an AMP-engineered bacteriophage, and is lytic to the target bacterium or bacteria. The many biofilm-promoting factors required by *E. coli* K-12 to produce a mature biofilm are likely to be shared among different biofilm-forming bacterial strains and are thus also targets for an antimicrobial-agent engineered bacteriophage as disclosed herein.

Uses of the Engineered Bacteriophages

Accordingly, the inventors have demonstrated that an antimicrobial-agent engineered bacteriophage, e.g. AMP-engineered bacteriophage as disclosed herein is more effective at killing bacteria, such as a bacterial infection or a bacteria biofilm than use of a bacteriophage which has not been engineered to express and secrete an antimicrobial agent. The inventors have also discovered that an antimicrobial-agent engineered bacteriophage, e.g. AMP-engineered bacteriophage can be adapted to express a variety of different antimicrobial agents, and can be further optionally modified, for example to express other biofilm-degrading enzymes to target a wide range of bacteria and bacteria biofilms. In some embodiments, an antimicrobial-agent engineered bacteriophage, e.g. AMP-engineered bacteriophage can be used in combination with at least one other an antimicrobial-agent engineered bacteriophage as disclosed herein, and optionally a different bacteriophage (engineered or non-engineered) or a different antimicrobial-agent engineered bacteriophage, e.g. a AMP-engineered bacteriophage, as well as a bacteriophage which is modified to express a therapeutic gene or a toxin gene or a biofilm degrading gene. Such bacteriophages are well known in the art and are encompassed for use in the methods and compositions as disclosed herein.

Bacterial Infections

One aspect of the present invention relates to the use of the methods and compositions comprising an antimicrobial-agent engineered bacteriophage, e.g. AMP-engineered bacteriophage to inhibit the growth and/or kill (or reduce the cell viability) of a microorganism, such as a bacteria. In some embodiments of this aspect and all aspects described herein, a microorganism is a bacterium. In some embodiments, the bacteria are gram positive and gram negative bacteria. In some embodiments, the bacteria are multi-drug resistant bacterium. In further embodiments, the bacteria are polymyxin-resistant bacterium. In some embodiments, the bacterium is a persister bacterium. Examples of gram-negative bacteria are for example, but not limited to *P. aeruginosa, A. bumannii, Salmonella* spp, *Klebsiella pneumonia, Shigeila* spp. and/or *Stenotrophomonas maltophilia*. In one embodiment, the bacteria to be targeted using the phage of the invention include *E. coli, S. epidermidis, Yersina pestis* and *Pseudomonas fluorescens.*

In some embodiments, the methods and compositions as disclosed herein can be used to kill or reduce the viability of a bacterium, for example a bacterium such as, but not limited to: *Bacillus cereus, Bacillus anbhracis, Bacillus cereus, Bacillus anthracis, Clostridium botulinum, Clostridium difficle, Clostridium tetani, Clostridium perfringens, Corynebacteria diptheriae, Enterococcus* (*Streptococcus* D), *Listeria* monocytogenes, Pneumoccocal infections (*Streptococcus pneumoniae*), Staphylococcal infections and Streptococcal infections; Gram-negative bacteria including *Bacteroides, Bordetella pertussis, Brucella, Campylobacter* infections, enterohaemorrhagic *Escherichia coli* (EHEC/*E. coli* 0157:17), enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulars, Myobacterium johnei, Mycobacterium leprae*, atypical bacteria, *Chlamydia, Myoplasma, Rickettsia, Spirochetes, Treponema pallidum, Borrelia recurrentis, Borrelia burgdorfii* and *Leptospira icterohemorrhagiae, Actinomyces, Nocardia, P. aeruginosa, A. bumannii, Salmonella* spp., *Klebsiella pneumonia, Shigeila* spp. and/or *Stenotrophomonas maltophilia* and other miscellaneous bacteria.

Bacterial infections include, but are not limited to, infections caused by *Bacillus cereus, Bacillus anbhracis, Bacillus cereus, Bacillus anthracis, Clostridium botulinum, Clostridium difficle, Clostridium tetani, Clostridium perfringens, Corynebacteria diptheriae, Enterococcus* (*Streptococcus* D), *Listeria* monocytogenes, Pneumococcal infections (*Streptococcus pneumoniae*), Staphylococcal infections and Streptococcal infections/Gram-negative bacteria including *Bacteroides, Bordetella pertussis, Brucella, Campylobacter* infections, enterohaemorrhagic *Escherichia coli* (EHEC/*E. coli* 0157:17) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium*-intracellulars, *Myobacterium johnei, Mycobacterium leprae*, atypical bacteria, *Chlamydia, Myoplasma, Rickettsia, Spirochetes, Treponema pallidum, Borrelia recurrentis, Borrelia burgdorfii* and *Leptospira icterohemorrhagiae* and other miscellaneous bacteria, including *Actinomyces* and *Nocardia.*

In some embodiments, the microbial infection is caused by gram-negative bacterium, for example, *P. aeruginosa, A. bumannii, Salmonella* spp, *Klebsiella pneumonia, Shigeila* spp. and/or *Stenotrophomonas maltophilia*. Examples of microbial infections include bacterial wound infections, mucosal infections, enteric infections, septic conditions, pneumonia, trachoma, onithosis, trichomoniasis and salmonellosis, especially in veterinary practice.

Examples of infections caused by *P. aeruginosa* include: A) Nosocomial infections; 1. Respiratory tract infections in cystic fibrosis patients and mechanically-ventilated patients; 2. Bacteraemia and sepsis; 3, Wound infections, particularly in burn wound patients; 4. Urinary tract infections; 5. Post-surgery infections on invasive devises 5. Endocarditis by intravenous administration of contaminated drug solutions; 7, Infections in patients with acquired immunodeficiency syndrome, cancer chemotherapy, steroid therapy, hematological malignancies, organ transplantation, renal replacement therapy, and other situations with severe neutropenia. B) Community-acquired infections; 1. Community-acquired respiratory tract infections; 2. Meningitis; 3. Folliculitis and infections of the ear canal caused by contaminated waters; 4. Malignant otitis externa in the elderly and diabetics; 5. Osteomyelitis of the caleaneus in children; Eye infections commonly associated with contaminated contact lens; 6. Skin infections such as nail infections in people whose hands are frequently exposed to water; 7. Gastrointestinal tract infections; 8. Muscoskeletal system infections.

Examples of infections caused by *A. baumannii* include: A) Nosocomial infections 1. Bacteraemia and sepsis, 2. Respiratory tract infections in mechanically ventilated patients;—3. Post-surgery infections on invasive devices; 4. Wound infectious, particularly in burn wound patients; 5. infection in patients with acquired immunodeficiency syndrome, cancer chemotherapy, steroid therapy, hematological malignancies, organ transplantation, renal replacement therapy, and other situations with severe neutropenia; 6. Urinary tract infections; 7. Endocarditis by intravenous administration of contaminated drug solutions; 8. Cellulitis. B) Community-acquired infections; a. community-acquired pulmonary infections; 2. Meningitis; Cheratitis associated with contaminated contact lens; 4. War-zone community-acquired infections. C) Atypical infections: 1. Chronic gastritis.

Examples of infections caused by *Stenotrophomonas maltophilia* include Bacteremia, pneumonia, meningitis, wound infections and urinary tract infections. Some hospital breaks are caused by contaminated disinfectant solutions, respiratory devices, monitoring instruments and ice machines. Infections usually occur in debilitated patients with impaired host defense mechanisms.

Examples of infections caused by *Klebsiella pneumoniae* include community-acquired primary lobar pneumonia, particularly in people with compromised pulmonary function and alcoholics. It also caused wound infections, soft tissue infections and urinary tract infections.

Examples of infections caused by *Salmonella* app. are acquired by eating contaminated food products. Infections include enteric fever, enteritis and bacteremia.

Examples of infections caused by *Shigella* spp. include gastroenteritis (shigellosis).

The methods and compositions as disclosed herein comprising an antimicrobial-agent engineered bacteriophage, e.g. AMP-engineered bacteriophage can also be used in various fields as where antiseptic treatment or disinfection of materials it required, for example, surface disinfection, including for use in bioremediation, such as industry settings, including cleaning of heating and cooling systems, such as HVAC systems and the like.

The methods and compositions as disclosed herein comprising an antimicrobial-agent engineered bacteriophage, e.g. AMP-engineered bacteriophage can be used to treat microorganisms infecting a cell, group of cells, or a multicellular organism.

In one embodiment, an antimicrobial-agent engineered bacteriophage, e.g. AMP-engineered bacteriophage as described herein can be used to reduce the rate of proliferation and/or growth of microorganisms. In some embodiments, the microorganism are either or both gram-positive or gram-negative bacteria, whether such bacteria are cocci (spherical), rods, *vibrio* (comma shaped), or spiral. Other uses of the antimicrobial-agent engineered bacteriophage, e.g. AMP-engineered bacteriophages include elimination or bioremediation of water-borne pathogens and bacterial, such as, but not limited to *legionella* and *pseudomonas*. *Legionella* are endemic in HVAC systems, cooling towers and other man-made, humid structures around the world. The most recent US case happened in December 2009, where a man died in a Miami Beach hotel and 300 people were infected. *Pseudomonas* on the other hand is an opportunistic pathogen that gained notoriety by being the morbidity and mortality-causing agent of cystic fibrosis. Like *Legionella, Pseudomonas* is also endemic and has through the years acquired resistance to many commonly used antibiotics.

Without wishing to be bound by theory, in the United States, the disease affects between 8,000 to 18,000 individuals a year. Person-to-person transmission of *Legionella* has not been demonstrated. *Legionella* live within amoebae in the natural environment. *Legionella* species are the causative agent of the human Legionnaires' disease and the lesser form, Pontiac fever. *Legionella* transmission is via aerosols—the inhalation of mist droplets containing the bacteria. Common sources include cooling towers, domestic hot-water systems, fountains, and similar disseminators that tap into a public water supply. Natural sources of *Legionella* include freshwater ponds and creeks. Once inside a host, incubation may take up to two weeks. Initial symptoms are flu-like, including fever, chills, and dry cough. Advanced stages of the disease cause problems with the gastrointestinal tract and the nervous system and lead to diarrhea and nausea. Other advanced symptoms of pneumonia may also present. However, the disease is generally not a threat to most healthy individuals, and tends to lead to harmful symptoms only in those with a compromised immune system and the elderly. Consequently, it should be actively checked for in the water systems of hospitals and nursing homes. According to the journal "Infection Control and Hospital Epidemiology," Hospital-acquired *Legionella* pneumonia has a fatality rate of 28%, and the source is the water distribution system The present invention can be used to treat and reduce bacterial infections in all transmitting parts of HVAC systems possibly to being contaminated, as well as the entire water distribution and storage system. For water distribution system, it has been established that quantitative counts of *Legionella* from the distal fixtures (faucets) do not correlate with the incidence of the disease in hospitals. On the other hand, 4 studies have found that when distal site positivity is 30% or higher, cases of hospital-acquired Legionnaires' disease occur. Many incidents of Legionnaires' disease in the workplace have been reported: Legionnaires' disease in the work environment: implications for environmental health, and Legionnaires' disease outbreak in an automobile engine manufacturing plant.

Of the cocci bacteria, *micrococcus* and *staphylococcus* species are commonly associated with the skin, and *Streptococcus* species are commonly associated with tooth enamel and contribute to tooth decay. Of the rods family, bacteria *Bacillus* species produce endospores seen in various stages of development in the photograph and *B. cereus* cause a relatively mild food poisoning, especially due to reheated fried food. Of the *vibrio* species, *V. cholerae* is the most common bacteria and causes cholera, a severe diarrhea disease resulting from a toxin produced by bacterial growth in the gut. Of the spiral bacteria, *rhodospirillum* and *Treponema pallidum* are the common species to cause infection (e.g., *Treponema pallidum* causes syphilis). Spiral bacteria typically grow in shallow anaerobic conditions and can photosynthesize to obtain energy from sunlight.

Moreover, the present invention relates to the use of an antimicrobial-agent engineered bacteriophage, e.g. a AMP-engineered bacteriophage, or a composition comprising an antimicrobial-agent engineered bacteriophage, e.g. AMP-engineered bacteriophage to reduce the rate of growth and/or kill either gram positive, gram negative, or mixed flora bacteria or other microorganisms. In one embodiment, a composition consists essentially of an antimicrobial-agent engineered bacteriophage, e.g. AMP-engineered bacteriophage as disclosed herein for the use to reduce the rate of growth and/or kill either gram positive, gram negative, or mixed flora bacteria or other microorganisms. In another embodiment, the composition contains at least one antimicrobial-agent engineered bacteriophage, e.g. AMP-engineered bacteriophage as disclosed herein for the use to reduce the rate of growth and/or kill either gram positive, gram negative, or mixed flora bacteria or other microorganisms.

Such bacteria are for example, but are not limited to, listed in Table 7A. Further examples of bacteria are, for example but not limited to *Baciccis Antracis; Enterococcus faecalis; Corynebacterium; diphtheriae; Escherichia coli; Streptococcus coelicolor; Streptococcus pyogenes; Streptobacillus oniliformis; Streptococcus agalactiae; Streptococcus pneurmoniae; Salmonella typhi; Salmonella paratyphi; Salmonella schottmulleri; Salmonella hirshieldii; Staphylococcus epidermidis; Staphylococcus aureus; Klebsiella pneumoniae; Legionella pneumophila; Helicobacter pylori; Mycoplasma pneumonia; Mycobacterium tuberculosis; Mycobacterium leprae; Yersinia enterocolitica; Yersinia pestis; Vibrio cholerae; Vibrio parahaemolyticus; Rickettsia prowozekii; Rickettsia rickettsii; Rickettsia akari; Clostridium difficile; Clostridium tetani; Clostridium perfringens; Clostridianz novyii; Clostridianz septicum; Clostridium botulinum; Legionella pneumophila; Hemophilus influenzue; Hemophilus parainfluenzue; Hemophilus aegyptus; Chlamydia psittaci; Chlamydia trachonZatis; Bordetella pertcsis; Shigella* spp.; *Campylobacter jejuni; Proteus* spp.; *Citrobacter* spp.; *Enterobacter* spp.; *Pseudomonas aeruginosa; Propionibacterium* spp.; *Bacillus anthracis; Pseudomonas syringae; Spirrilum minus; Neisseria meningitidis; Listeria monocytogenes; Neisseria gonorrheae; Treponema pallidum; Francisella tularensis; Brucella* spp.; *Borrelia recurrentis; Borrelia hermsii; Borrelia turicatue; Borrelia burgdorferi; Mycobacterium avium; Mycobacterium smegmatis*; Methicillin-resistant *Staphyloccus aureus*; Vanomycin-resistant *enterococcus*; and multi-drug resistant bacteria (e.g., bacteria that are resistant to more than 1, more than 2, more than 3, or more than 4 different drugs).

In some embodiments, an antimicrobial-agent engineered bacteriophage, e.g. AMP-engineered bacteriophage as described herein can be used to treat an already drug resistant bacterial strain such as Methicillin-resistant *Staphylococcus aureus* (MRSA) or Vancomycin-resistant *enterococcus* (VRE) of variant strains thereof.

In some embodiments, the present invention also contemplates the use and methods of use of an antimicrobial-agent engineered bacteriophage, e.g. AMP-engineered bacteriophage as described herein in all combinations with other agents, such as other antimicrobial agents and/or antibiotics to fight gram-positive bacteria that maintain resistance to certain drugs.

In some embodiments, an antimicrobial-agent engineered bacteriophage, e.g. AMP-engineered bacteriophage as disclosed herein can be used to treat infections, for example bacterial infections and other conditions such as urinary tract infections, ear infections, sinus infections, bacterial infections of the skin, bacterial infections of the lungs, sexually transmitted diseases, tuberculosis, pneumonia, Lyme disease, and Legionnaire's disease. Thus any of the above conditions and other conditions resulting from a microorganism infection, for example a bacterial infection or a biofilm can be prevented or treated by the compositions of the invention herein.

Biofilms

Another aspect of the present invention relates to the use of an antimicrobial-agent engineered bacteriophage, e.g. AMP-engineered bacteriophage to eliminate or reduce a bacterial biofilm, for example a bacterial biofilm in a medical, or industrial, or biotechnological setting.

For instance, some bacteria, including *P. aeruginosa*, actively form tightly arranged multi-cell structures in vivo known as biofilm. The production of biofilm is important for the persistence of infectious processes such as seen in pseudomonal lung-infections in patients with cystic fibrosis and diffuse panbronchiolitis and many other diseases. A biofilm is typically resistant to phagocytosis by host immune cells and the effectiveness of antibiotics at killing bacteria in biofilm structures can be reduced by 10 to 1000 fold. Biofilm production and arrangement is governed by quorum sensing systems. The disruption of the quorum sensing system in bacteria such as *P. aeruginosa* is an important anti-pathogenic activity as it disrupts the biofilm formation and also inhibits alginate production Selection of Subjects Administered a Composition Comprising an Engineered Bacteriophage In some embodiments, a subject amenable for the method described herein or for the administration with a composition comprising at least one antimicrobial-agent engineered bacteriophage, e.g. AMP-engineered bacteriophage is selected based on the desired treatment regime. For instance, a subject is selected for treatment if the subject has a bacterial infection where the bacteria form a biofilm, or where the subject has been non-responsive to prior therapy or administration with an antimicrobial agent.

Accordingly, in some embodiments, a subjects is administered an antimicrobial-agent engineered bacteriophage, e.g. AMP-engineered bacteriophage to potentiate the effect of the bacteriophage.

In some embodiments, a subject can be administered a composition comprising at an antimicrobial-agent engineered bacteriophage, e.g. AMP-engineered bacteriophage which expresses and secretes, for example at least one, 2, 3, or 4 or as many of 10 different antimicrobial agents. In some embodiments, a subject is administered at least one antimicrobial-agent engineered bacteriophage, e.g. AMP-engineered bacteriophage as disclosed herein, or more, for example, for example at least 2, 3, or 4 or as many of 10 different antimicrobial-agent engineered bacteriophage, e.g. AMP-engineered bacteriophage as disclosed herein. In some embodiments, the composition can comprise an antimicrobial-agent engineered bacteriophage, e.g. AMP-engineered bacteriophage with at least one or a variety of different other bacteriophages, or different antimicrobial-agent engineered bacteriophage. In alternative embodiments, the composition can comprise at least two, or at least 3, 4, 5 or as many of 10 different antimicrobial-agent engineered bacteriophage, e.g. a AMP-engineered bacteriophage, wherein each of the antimicrobial-agent engineered bacteriophages comprise a nucleic acid which encodes at least different antimicrobial agent. Any combination and mixture of antimicrobial-agent engineered bacteriophage, e.g. AMP-engineered bacteriophages are useful in the compositions and methods of the present invention.

In some embodiments, an antimicrobial-agent engineered bacteriophage, e.g. AMP-engineered bacteriophage is administered to a subject at the same time, prior to, or after the administration of an additional agent. In some embodiments, an antimicrobial-agent engineered bacteriophage, e.g. AMP-engineered bacteriophage can be formulated to a specific time-release for activity, such as an antimicrobial-agent engineered bacteriophage is present in a time-release capsule. In such embodiments, an antimicrobial agent that is formulated for time-release can be administered to a subject at the same time, concurrent with, or prior to, or after the administration of an additional agent, such as an additional therapeutic or antimicrobial agent. Methods of formulation of an antimicrobial-agent engineered bacteriophage, e.g. AMP-engineered bacteriophage for release in a time-dependent manner are disclosed herein as "sustained release pharmaceutical compositions" in the section entitled "pharmaceutical formulations and compositions." Accordingly, in such embodiments, a time-release an antimicrobial-agent engineered bacteriophage can be administered to a subject at the same time (i.e. concurrent with), prior to or after the administration of an additional agent, such as an additional therapeutic agent or therapeutic agent.

In some embodiments, an additional agent administered at the same or different time as an antimicrobial-agent engineered bacteriophage, e.g. AMP-engineered bacteriophage can be a pro-drug, where it is activated by a second agent. Accordingly, in such embodiments, a pro-drug agent can be administered to a subject at the same time, concurrent with, or prior to, or after the administration of an antimicrobial-agent engineered bacteriophage, e.g. AMP-engineered bacteriophage, e.g. a AMP-engineered bacteriophage, and administration of an agent which activates the pro-drug into its active form can be administered the same time, concurrent with, or prior to, or after the administration of the antimicrobial-agent engineered bacteriophage.

In some embodiments, a subject is selected for the administration with the compositions comprising an antimicrobial-agent engineered bacteriophage, e.g. AMP-engineered bacteriophage as disclosed herein by identifying a subject that needs a specific treatment regimen, and is administered an antimicrobial-agent engineered bacteriophage, e.g. AMP-engineered bacteriophage concurrently with, or prior to, or after administration with an additional therapeutic agent.

Using a subject with cystic fibrosis as an exemplary example, a subject could be administered an antimicrobial-agent engineered bacteriophage, e.g. AMP-engineered bacteriophage to avoid chronic endobronchial infections, such as those caused by *pseudomonas aeruginosis* or *stentrophomonas maltophilia*.

Pharmaceutical Formulations and Compositions

The antimicrobial-agent engineered bacteriophage, e.g. AMP-engineered bacteriophage as disclosed herein can be formulated in combination with one or more pharmaceutically acceptable agents. In some embodiments, combinations of different an antimicrobial-agent engineered bacteriophage, e.g. AMP-engineered bacteriophage can be tailored to be combined, where different antimicrobial-agent engineered bacteriophages are designed to target different (or the same) species of microorganisms or bacteria, which contribute towards morbidity and mortality. A pharmaceutically acceptable composition comprising an antimicrobial-agent engineered bacteriophage, e.g. AMP-engineered bacteriophage as disclosed herein, are suitable for internal administration to an animal, for example human.

In some embodiments, an antimicrobial-agent engineered bacteriophage, e.g. AMP-engineered bacteriophage as disclosed herein can be used for industrial sterilizing, sterilizing chemicals such as detergents, disinfectants, and ammonium-based chemicals (e.g. quaternary ammonium compounds such as QUATAL, which contains 10.5% N-alkyldimethyl-benzlammonium HCl and 5.5% gluteraldehyde as active ingredients, Ecochimie Ltée, Quebec, Canada), and can be used in concurrently with, or prior to or after the treatment or administration of an antimicrobial agent. Such sterilizing chemicals are typically used in the art for sterilizing industrial work surfaces (e.g. in food processing, or hospital environments), and are not suitable for administration to an animal.

In another aspect of the present invention relates to a pharmaceutical composition comprising an antimicrobial-agent engineered bacteriophage, e.g. AMP-engineered bacteriophage and a pharmaceutically acceptable excipient. Suitable carriers for the an antimicrobial-agent engineered bacteriophage, e.g. AMP-engineered bacteriophage of the invention, and their formulations, are described in Remington's Pharmaceutical Sciences, 16$^{th}$ ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of an antimicrobial-agent engineered bacteriophage being administered.

Administration to human can be accomplished by means determined by the underlying condition. For example, if an antimicrobial-agent engineered bacteriophage, e.g. AMP-engineered bacteriophage is to be delivered into lungs of an individual, inhalers can be used. If the composition is to be delivered into any part of the gut or colon, coated tablets, suppositories or orally administered liquids, tablets, caplets and so forth can be used. A skilled artisan will be able to determine the appropriate way of administering the phages of the invention in view of the general knowledge and skill in the art.

Compounds as disclosed herein, can be used as a medicament or used to formulate a pharmaceutical composition with one or more of the utilities disclosed herein. They can be administered in vitro to cells in culture, in vivo to cells in the body, or ex vivo to cells outside of a subject that can later be returned to the body of the same subject or another subject. Such cells can be disaggregated or provided as solid tissue in tissue transplantation procedures.

Compositions comprising at least one antimicrobial-agent engineered bacteriophage, e.g. AMP-engineered bacteriophage as disclosed herein can be used to produce a medicament or other pharmaceutical compositions. Use of the compositions as disclosed herein comprising an antimicrobial-agent engineered bacteriophage, e.g. AMP-engineered bacteriophage can further comprise a pharmaceutically acceptable carrier. The composition can further comprise other components or agents useful for delivering the composition to a subject are known in the art. Addition of such carriers and other components to the agents as disclosed herein is well within the level of skill in this art.

In some embodiments, the composition comprising an antimicrobial-agent engineered bacteriophage, e.g. AMP-engineered bacteriophage is a composition for sterilization of a physical object, that is infected with bacteria, such as sterilization of hospital equipment, industrial equipment, medical devices and food products. In another embodiment, a composition comprising an antimicrobial-agent engineered bacteriophage, e.g. AMP-engineered bacteriophage is a pharmaceutical composition useful to treat a bacterial infection in a subject, for example a human or animal subject.

In some embodiments, a pharmaceutical composition comprising an antimicrobial-agent engineered bacteriophage, e.g. AMP-engineered bacteriophage as disclosed herein can be administered as a formulation adapted for passage through the blood-brain barrier or direct contact with the endothelium. In some embodiments, the pharmaceutical composition comprising an antimicrobial-agent engineered bacteriophage, e.g. AMP-engineered bacteriophage can be administered as a formulation adapted for systemic delivery. In some embodiments, the compositions can be administered as a formulation adapted for delivery to specific organs, for example but not limited to the liver, bone marrow, or systemic delivery.

Alternatively, pharmaceutical compositions comprising an antimicrobial-agent engineered bacteriophage, e.g. AMP-engineered bacteriophage can be added to the culture medium of cells ex vivo. In addition to an antimicrobial-agent engineered bacteriophage, e.g. a AMP-engineered bacteriophage, such compositions can contain pharmaceutically-acceptable carriers and other ingredients or agents known to facilitate administration and/or enhance uptake (e.g., saline, dimethyl sulfoxide, lipid, polymer, affinity-based cell specific-targeting systems). In some embodiments, a pharmaceutical composition can be incorporated in a gel, sponge, or other permeable matrix (e.g., formed as pellets or a disk) and placed in proximity to the endothelium for sustained, local release. The composition comprising an antimicrobial-agent engineered bacteriophage, e.g. AMP-engineered bacteriophage can be administered in a single dose or in multiple doses which are administered at different times.

Pharmaceutical compositions comprising an antimicrobial-agent engineered bacteriophage, e.g. AMP-engineered bacteriophage can be administered to a subject by any known route. By way of example, a composition comprising an antimicrobial-agent engineered bacteriophage can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example, the carrier does not decrease the impact of the agent on the treatment. In other words, a carrier is pharmaceutically inert.

Suitable choices in amounts and timing of doses, formulation, and routes of administration can be made with the goals of achieving a favorable response in the subject with a bacterial infection or infection with a microorganism, for example, a favorable response is killing or elimination of the microorganism or bacteria, or control of, or inhibition of growth of the bacterial infection in the subject or a subject at risk thereof (i.e., efficacy), and avoiding undue toxicity or other harm thereto (i.e., safety). Therefore, "effective" refers to such choices that involve routine manipulation of conditions to achieve a desired effect or favorable response.

A bolus of the pharmaceutical composition comprising an antimicrobial-agent engineered bacteriophage, e.g. AMP-engineered bacteriophage can be administered to a subject over a short time, such as once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the composition in the subject, especially in and around the area of the bacterial infection or infection with a microorganism, and to result in the desired therapeutic response or protection. It is also within the skill of the art to start doses at levels lower than required to achieve the desired therapeutic effect and to gradually increase the dosage until the desired effect is achieved.

The amount of a pharmaceutical composition comprising an antimicrobial-agent engineered bacteriophage, e.g. AMP-engineered bacteriophage to be administered to a subject is dependent upon factors known to a persons of ordinary skill in the art such as bioactivity and bioavailability of the antimicrobial agent (e.g., half-life in the body, stability, and metabolism of the engineered bacteriophage); chemical properties of the antimicrobial agent (e.g., molecular weight, hydrophobicity, and solubility); route and scheduling of administration, and the like. It will also be understood that the specific dose level of the composition comprising an antimicrobial-agent engineered bacteriophage, e.g. AMP-engineered bacteriophage as disclosed herein to be achieved for any particular subject can depend on a variety of factors, including age, gender, health, medical history, weight, combination with one or more other drugs, and severity of disease, and bacterial strain or microorganism the subject is infected with, such as infection with multi-resistant bacterial strains.

In another embodiment, an antimicrobial-agent engineered bacteriophage, e.g. AMP-engineered bacteriophage and compositions thereof can be used in bioremediation, or to eliminate bacterial infections, such as bacterial infections from a solution. The solution may be, e.g., water or a body fluid such as blood, plasma, serum, etc. The fluid is contacted with an antimicrobial-agent engineered bacteriophage, e.g. AMP-engineered bacteriophage or compositions thereof. In some embodiments, the concentration of an antimicrobial-agent engineered bacteriophage, e.g. AMP-engineered bacteriophage to be effective at inhibiting bacterial infection, for example, in solution is about at least $1\times10^2$ PFU/ml, or about at least $1\times10^3$ PFU/ml, or about at least $1\times10^4$ PFU/ml, or about at least $1\times10^5$ PFU/ml, or about at least $1\times10^6$ PFU/ml, or about at least $1\times10^7$ PFU/ml, or about at least $1\times10^8$ PFU/ml, or about at least $1\times10^9$ PFU/ml, or about at least $1\times10^{10}$ PFU/ml, or more than about at least $1\times10^{10}$ PFU/ml. In some embodiments, if the antimicrobial-agent engineered bacteriophage, e.g. AMP-engineered bacteriophage is a non-replicating bacteriophage (i.e. does not infect cells and proliferate in the host bacteria via lysis), then the concentration of an antimicrobial-agent engineered bacteriophage, e.g. AMP-engineered bacteriophage to be effective at reducing a bacterial infection, for example, a bacteria or a bacteria biofilm in solution is about at least $1\times10^{7}$-$1\times10^{15}$ PFU/ml, for example, at least $1\times10^{7}$ PFU/ml, or about at least $1\times10^{8}$ PFU/ml, or about at least $1\times10^{9}$ PFU/ml, or about at least $1\times10^{10}$ PFU/ml, or about at least $1\times10^{11}$ PFU/ml, or about at least $1\times10^{12}$ PFU/ml, or about at least $1\times10^{13}$ PFU/ml, or about at least $1\times10^{14}$ PFU/ml, or about at least $1\times10^{15}$ PFU/ml, or more than about at least $1\times10^{15}$ PFU/ml.

In some embodiments, the concentration of the antimicrobial-agent engineered bacteriophage, e.g. AMP-engineered bacteriophage for inhibiting bacterial infection is administered at a concentration threshold which enables the bacteriophage to replicate and self-renew. As shown in FIG. 25, T7.J6084.H2 administered at the threshold concentrations of $1\times10^{7}$ or above results in long-term suppression of phase resistance by the bacteria, whereas lower concentrations below the threshold concentration are less effective at long-term suppression of phage resistance. Alternatively, shown in FIG. 26, T7.omp-J589.K4 decreases bacterial infection and suppresses phage resistance at a threshold of $1\times10^{5}$ or below, whereas phage resistance begins to occur at concentrations above the threshold concentration level.

In one embodiment, an antimicrobial-agent engineered bacteriophage, e.g. AMP-engineered bacteriophage and compositions thereof are useful in a method to treat a subject either ex vivo or in vivo. In one embodiment, an antimicrobial-agent engineered bacteriophage, e.g. AMP-engineered bacteriophage and a composition thereof can be used to inhibit bacterial infection in a subject or eliminate a bacterial infection in a subject. In some embodiments, the subject is suffering from, or at risk of developing a bacterial infection. In some embodiments, the subject has an immune comprised system, or is in hospital or in long-term care, or is recovering from surgery, or is about to have a surgical procedure.

In some embodiments, an antimicrobial-agent engineered bacteriophage, e.g. AMP-engineered bacteriophage and compositions thereof is contacted with a blood product from the subject. In another embodiment, an antimicrobial-agent engineered bacteriophage, e.g. AMP-engineered bacteriophage and compositions thereof is administered to a subject. In one embodiment an antimicrobial-agent engineered bacteriophage, e.g. AMP-engineered bacteriophage and compositions thereof is contacted with the surface of an organ to be transplanted into a subject. The organ may be bathed in an antimicrobial-agent engineered bacteriophage, e.g. AMP-engineered bacteriophage and compositions thereof prior to transplantation. In one embodiment, methods, antimicrobial-agent engineered bacteriophage, e.g. AMP-engineered bacteriophage and compositions thereof can be used to inhibit bacterial infection from a body fluid in a subject undergoing dialysis.

In some embodiments, the concentration of antimicrobial-agent engineered bacteriophage, e.g. AMP-engineered bacteriophage for treatment of a subject to inhibit a bacterial infection in a solution for example, in a biological sample (such as blood or other biological solution) of the subject can be about at least $1\times10^{7}$-$1\times10^{15}$ PFU/ml, for example, at least $1\times10^{7}$ PFU/ml, or about at least $1\times10^{8}$ PFU/ml, or about at least $1\times10^{9}$ PFU/ml, or about at least $1\times10^{10}$ PFU/ml, or about at least $1\times10^{11}$ PFU/ml, or about at least $1\times10^{12}$ PFU/ml, or about at least $1\times10^{13}$ PFU/ml, or about at least $1\times10^{14}$ PFU/ml, or about at least $1\times10^{15}$ PFU/ml, or more than about at least $1\times10^{15}$ PFU/ml.

In some embodiments, where an antimicrobial-agent engineered bacteriophage, e.g. AMP-engineered bacteriophage is used to treat a subject, the dose is at least $1\times10^{7}$ PFU/ml or in some embodiments higher than $1\times10^{7}$ PFU/ml. In some embodiments, where an antimicrobial-agent engineered bacteriophage, e.g. AMP-engineered bacteriophage is used to treat a subject, such as a human subject with, or at risk of developing a bacterial infection, an antimicrobial-agent engineered bacteriophage, e.g. AMP-engineered bacteriophage can be administered multiple times (i.e. repeated doses). Should the bacteriophage and/or AMP or expressed antimicrobial agent (e.g. polypeptide) to be immunogenic, then repeated dosing with the antimicrobial-agent engineered bacteriophage, e.g. AMP-engineered bacteriophage would result in the plaques being cleared from the system. Typically, antimicrobial-agent engineered bacteriophage, e.g. AMP-engineered bacteriophage is used to treat a subject or administered to a subject are non-replicating bacteriophages. Such bacteriophages are known to one of ordinary skill in the art and are disclosed herein.

In some embodiments, a subject amenable for the methods as described herein or for the administration with a composition comprising at least one antimicrobial engineered bacteriophage, e.g. AMP-engineered bacteriophage is selected based on the desired treatment regime. For instance, a subject is selected for treatment if the subject suffers from, or is at risk of a bacterial infection.

In some embodiments, a subject amenable to treatment as disclosed herein is a subject with, or likely to develop a bacterial infection where the bacteria form a biofilm, or where the subject has been non-responsive to prior therapy or administration with conventional antibiotics or other antimicrobial agents.

In some embodiments, efficacy of treatment can be measured as an improvement in morbidity or mortality (e.g., lengthening of survival curve for a selected population). Prophylactic methods (e.g., preventing or reducing the incidence of relapse) are also considered treatment.

Dosages, formulations, dosage volumes, regimens, and methods for analyzing results aimed at reducing the number of viable bacteria and/or activity can vary. Thus, minimum and maximum effective dosages vary depending on the method of administration. Suppression of the clinical changes associated with bacterial infections or infection with a microorganism can occur within a specific dosage range, which, however, varies depending on the organism receiving the dosage, the route of administration, whether the antimicrobial agents are administered in conjunction with the engineered bacteriophages as disclosed herein, and in some embodiments with other co-stimulatory molecules, and the specific regimen administration. For example, in general, nasal administration requires a smaller dosage than oral, enteral, rectal, or vaginal administration.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982, which are incorporated herein in their entirety by reference.

Examples of solid carriers include starch, sugar, bentonite, silica, and other commonly used carriers. Further non-limiting examples of carriers and diluents which can be used in the formulations of the present invention include saline, syrup, dextrose, and water.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

In some embodiments of the present invention may be defined in any of the following numbered paragraphs:

1. A method to reduce a population of bacterial cells comprising administering to a surface infected with the bacterial cells at least one bacteriophage comprising a nucleic acid operatively linked to a promoter, wherein the nucleic acid encodes at least one antimicrobial polypeptide.
2. The method of paragraph 1, wherein the antimicrobial polypeptide is an antimicrobial peptide.
3. The method of paragraph 1 or 2, wherein the antimicrobial peptide is a naturally occurring bacterial peptide.
4. The method of any of paragraphs 1 to 3, wherein the antimicrobial peptide is selected from the group comprising: Indolicidin (SEQ ID NO: 6), Cecropin P1 (SEQ ID NO: 11), Dermaseptin (SEQ ID NO: 14), Ponericin W1 (SEQ ID NO: 44), Ponericin W3 (SEQ ID NO: 40), Ponericin W4 (SEQ ID NO: 18), Ponericin W5 (SEQ ID NO: 42), Ponericin W6 (SEQ ID NO: 22) or variants thereof
5. The method of any of paragraphs 1 to 4, wherein the antimicrobial peptide is Ponericin W1 (SEQ ID NO: 44) or a variant thereof.
6. The method of any of paragraphs 1 to 4, wherein the antimicrobial peptide is Ponericin W3 (SEQ ID NO: 40) or a variant thereof.
7. The method of any of paragraphs 1 to 4, wherein the antimicrobial peptide is Ponericin W5 (SEQ ID NO: 42) or variants thereof
8. The method of paragraph 1, wherein the antimicrobial polypeptide is a lytic enzyme.
9. The method of paragraphs 1 or 8, wherein the lytic enzyme is LysK or a functional fragment thereof.
10. The method of 9, wherein the functional fragment of LysK is CHAP165 (SEQ ID NO: 71) or a variant thereof.
11. The method of paragraph 1, wherein the bacteria is present in a subject.
12. The method of any of paragraphs 1 or 11, wherein the subject is a mammal.
13. The method of any of paragraph 1 to 12, wherein the mammal is a human.
14. The method of any of paragraphs 1 to 13, wherein the bacteria is in a biofilm.
15. The method of any of paragraphs 1 to 14, further comprising adding an additional agent to the surface infected with the bacterial cells.
16. The method of any of paragraph 1 to 15, wherein the bacteriophage is administered at a concentration of at least 1×104 PFU/ml.
17. The method of any of paragraph 1 to 16, wherein the bacteriophage is administered at a concentration of at least 1×105 PFU/ml.
18. The method of any of paragraph 1 to 17, wherein the bacteriophage is administered at a concentration of at least 1×106 PFU/ml.
19. The method of any of paragraph 1 to 18, wherein the bacteriophage is administered at a concentration of at least 1×107 PFU/ml.
20. The method of any of paragraph 1 to 19, wherein the bacteriophage is administered at a concentration of at least 1×108 PFU/ml.
21. The method any of paragraphs 1 to 20, wherein the surface is a wound.
22. The method any of paragraphs 1 to 21, wherein the bacteriophage is administered by way of an inoculant.
23. The method any of paragraphs 1 to 22, wherein the bacteriophage is administered by a spray or wound dressing or gel.
24. The method any of paragraphs 1 to 22, wherein the bacteriophage is administered prophylatically to a location where a bacterial infection is likely to develop.
25. The method of any of paragraphs 1 to 24, wherein the bacteriophage is a T7 bacteriophage.
26. The method of any of paragraphs 1 to 24, wherein the bacteriophage is a M13 bacteriophage.
27. An engineered bacteriophage comprising a nucleic acid operatively linked to a promoter, wherein the nucleic acid encodes at least one antimicrobial polypeptide.
28. The bacteriophage of paragraph 27, wherein the antimicrobial polypeptide is an antimicrobial peptide.
29. The bacteriophage of any of paragraphs 27 or 28, wherein the antimicrobial peptide is a naturally occurring bacterial peptide.
30. The bacteriophage of any of paragraphs 27 to 29, wherein the antimicrobial peptide is selected from the group comprising: Indolicidin (SEQ ID NO: 6), Cecropin P1 (SEQ ID NO: 11), Dermaseptin (SEQ ID NO: 14), Ponericin W1 (SEQ ID NO: 44), Ponericin W3 (SEQ ID NO: 40), Ponericin W4 (SEQ ID NO: 18), Ponericin W5 (SEQ ID NO: 42), Ponericin W6 (SEQ ID NO: 22) or variants thereof
31. The bacteriophage of any of paragraphs 27 to 30, wherein the antimicrobial peptide is Ponericin W1 (SEQ ID NO: 44) or a variant thereof.
32. The bacteriophage of any of paragraphs 27 to 30, wherein the antimicrobial peptide is Ponericin W3 (SEQ ID NO: 40) or a variant thereof.

33. The bacteriophage of any of paragraphs 27 to 30, wherein the antimicrobial peptide is Ponericin W5 (SEQ ID NO: 42) or variants thereof
34. The bacteriophage of paragraph 27, wherein the antimicrobial polypeptide is a lytic enzyme.
35. The bacteriophage of paragraph 27 or 34, wherein the lytic enzyme is LysK or a functional fragment thereof.
36. The bacteriophage of any of paragraphs 27 or 35, wherein the functional fragment of LysK is CHAP165 (SEQ ID NO: 71) or a variant thereof.
37. The bacteriophage of any of the paragraphs 27 to 36, wherein the antimicrobial polypeptide or antimicrobial peptide is released from a bacterial host cell infected by the engineered bacteriophage.
38. The bacteriophage of any of the paragraphs 27 to 37, wherein the antimicrobial peptide is released from a bacterial host cell infected by the engineered bacteriophage by lysis of the bacterial cell.
39. The bacteriophage of any of the paragraphs 27 to 37, wherein the antimicrobial peptide is released from a bacterial host cell infected by the engineered bacteriophage by secretion by the bacterial host cell.
40. The bacteriophage of any of paragraphs 27 to 37, wherein the nucleic acid encoding at least one antimicrobial agent also encodes a signal sequence.
41. The bacteriophage of any of paragraphs 27 to 40, wherein the signal sequence is a secretory sequence.
42. The bacteriophage of any of paragraphs 27 to 41, wherein the secretory sequence is cleaved from the antimicrobial agent or antimicrobial peptide.
43. The bacteriophage of any of paragraphs 27 to 42, wherein the antimicrobial agent is selected from a group comprising, siRNA, antisense nucleic acid, asRNA, RNAi, miRNA and variants thereof.
44. The bacteriophage of any of paragraphs 27 to 43, wherein the bacteriophage is a T7 bacteriophage.
45. The bacteriophage of any of paragraphs 27 to 43, wherein the bacteriophage is a M13 bacteriophage.
46. A kit comprising a bacteriophage comprising the nucleic acid operatively linked to a promoter, wherein the nucleic acid encodes at least one antimicrobial agent.
47. The engineered bacteriophage of any of paragraphs 27 to 45 for use in reducing a heterogeneous population of bacterial host strains.
48. The use of the engineered bacteriophage of paragraph 47, for treating wound infections on the surface of a subject.
49. The use of the engineered bacteriophage of paragraph 48, for reducing bacterial infections in hospitals.

The following Examples are provided to illustrate the present invention, and should not be construed as limiting thereof.

EXAMPLES

The examples presented herein relate to the methods and compositions comprising inhibitor-engineered bacteriophages, repressor-engineered bacteriophages or susceptibility-agent engineered bacteriophages and antimicrobial agents. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

The inventors have genetically engineered T7 bacteriophages (phages) to give them broad spectrum activity by inducing the expression and secretion of natural antimicrobial peptide from the host bacteria. The engineered phage show improved killing activity against bacteria, for example when the bacteria are in solution.

One of the key problem associated with bacteriophages and their usage as potential therapeutics are their high selectivity towards specific strain of bacteria. Phages are often target and kill one particular strain of bacteria, leaving other strains unaffected. However, bacterial contamination, whether in food products or in patient infections or in biofilms on implantable devices, are typically composed of several strains of bacteria co-existing. As a result for phage therapy to be effective, a cocktail of different phages need to be used, typically combinations of up to 20 different phages need to be used.

The FDA requires that each Individual phage used in the combination be tested and approved individually before the combination therapy be tested as a whole. This significantly increases the cost and length of study of potential phage based therapeutic. It is thus highly desirable to increase the activity spectrum of individual bacteriophage to enable them to target a broad array of bacteria strains, rather than a single one. The inventors have discovered that by genetically engineering the bacteriophage to induce the expression and secretion of antimicrobial peptides, they can generate bacteriophages with a broad spectrum of bacterial species activity.

Antimicrobial peptides (AmPs) are small peptides, typically composed of 15 to 30 amino acids that are found in many organisms act nature, such as the secretions from frog's skin, human sweat, or ant's venom. These natural peptides have strong antimicrobial properties and a large activity spectrum against many different types of bacteria. They can also be expressed in new living organisms, such as bacteria, yeasts and plants, using genetic engineering techniques.

The inventors have combined the broad activity spectrum of antimicrobial peptides with advantages such as exponential growth and low toxicity of bacteriophages. Phages multiply and replicate in the presence of host cells while typical AmPs therapies would require that the correct amount of AmPs be delivered systemically such appropriate therapeutic concentration are reached the site of infection; this poses toxicity issues for AmPs. The engineered bacteriophages include a DNA sequence inducing the expression (and secretion in some case) of different AmPs such that AmPs are synthesized and delivered only in the presence of bacteria.

This approach is extremely advantageous for future therapeutic applications and we show that these engineered bacteriophages have increased killing activity in solution.

The inventors have engineered bacteriophages to induce expression of the following 7 different AmPs: Indolicidin (SEQ ID NO: 6), Cecropin P1 (SEQ ID NO: 11), Dermaseptin (SEQ ID NO: 14), Ponericin W1 (SEQ ID NO: 16), Ponericin W4 (SEQ ID NO: 18), Ponericin W5 (SEQ ID NO: 20), Ponericin W6 (SEQ ID NO: 22). Each of these AmPs was expressed in the phages with and in some cases without an expression sequence obtained from OmpA. The DNA sequence encoding for the AmPs and the OmpA secretion sequence were synthesized commercially. The engineering of the genome was carried out using conventional genetic engineering techniques.

Bacteriophage Plaque Assay.

1. Inoculate the appropriate host strain in LB medium and incubate with shaking at 37° C. to an OD600=1.0. 2. Store the host cells at 4° C. until needed. Do not use host cells that have been stored for longer than 48 h. 3.Melt a sufficient volume of top agarose to provide 5 ml for each dilution being plated. Transfer the molten agarose to a 45-50° C. water bath. 4. Prepare a series of dilutions of the sample using sterile LB or TB medium as the diluent. Generally, the appropriate dilution for recombinant phage is 103-106. When the T7Select® Packaging Control DNA is used, dilutions should be made to 1:107. The initial 1:100 dilution can be prepared by adding 10 μL of sample to 990 μL of medium. Serial dilutions can be made by adding 100 μL of the 1:100 dilution to 900 μL medium (103 dilution), 100 μL of the 103 dilution to 900 μL medium (104 dilution), and so on. 5. Prepare a series of 4 ml sterile tubes by pipetting 250 μL of host cells into each tube. Starting with the highest dilution, add 100 μL of the phage dilution to each tube. Be sure to replace the pipet tip between samples to avoid cross contamination. 6. Add 3 ml top agarose to the tube and pour the contents onto a prewarmed (37° C.) LB or LB/carbenicillin or LB/carbenicillin/kanamycin agar plate. Immediately swirl the plate (gently) to spread the agarose evenly. 7.Allow the plate to sit undisturbed for several min until the top agarose hardens, then invert and incubate for 3-4 h at 37° C. or overnight at room temperature. 8.

Count the plaques and calculate the phage titer. The phage titer, described in plaque forming units (pfu) per unit volume is the number of plaques on the plate times the dilution times 10 (to account for the 0.1 ml of dilution plated). For example, if there are 200 plaques on a plate from a 1/106 dilution, then the titer of the sample is 200×106×10=2×109 pfu/ml. The total number of phage in a sample is determined by multiplying the titer by the total sample volume. For example, if the sample were a packaging reaction where 1 μg of vector DNA was.

OD600 AMP or Bacteriophage Killing Assay

1. Inoculate the appropriate host strain in LB medium with the appropriate selective marker and incubate with shaking at 37° C. overnight. 2. Re-dilute the culture 1:5000 into LB with the appropriate selective marker and grow at 300 rpm and 37° C. to an OD600 between 0.2 and 0.4.3. Add the appropriate amount of AMP or bacteriophage to the wells, running at least duplicate samples, preferably triplicates, and always carrying a no treatment control to control for phage contamination. 4. Sample points every 5 minutes using an automated 96-well assay plate capable heated and shaking plate reader.

Example 1

The inventors used a modified T7 strain of bacteriophage (Novagen T7select4IS-1) targeting 8L21 *E. coli* strains with deletions of several nonessential genes. The inventors cloned the gene coding for OmpA secretion sequence (when applicable) followed by the AmP gene sequence under the control of the strong T7Φ1O promoter so that the inserted genes would be strongly transcribed by T7 RNA polymerase during host cell infection. The AmPs are expressed intracellularly by the bacteria upon infection by the phages. The AmPs are then either secreted out when the OmpA secretion sequence is included or the AmPs are release from the cell upon cell lysis by the phage lysins and holins enzymes. The phages were names $T7_{AMP}$ and $T7_{AmP+ompA}$ where $_{Amp}$ reflects the nature of the antimicrobial peptide expressed and $_{OmpA}$ indicated whether the OmpA sequence was inserted.

Figure 1:
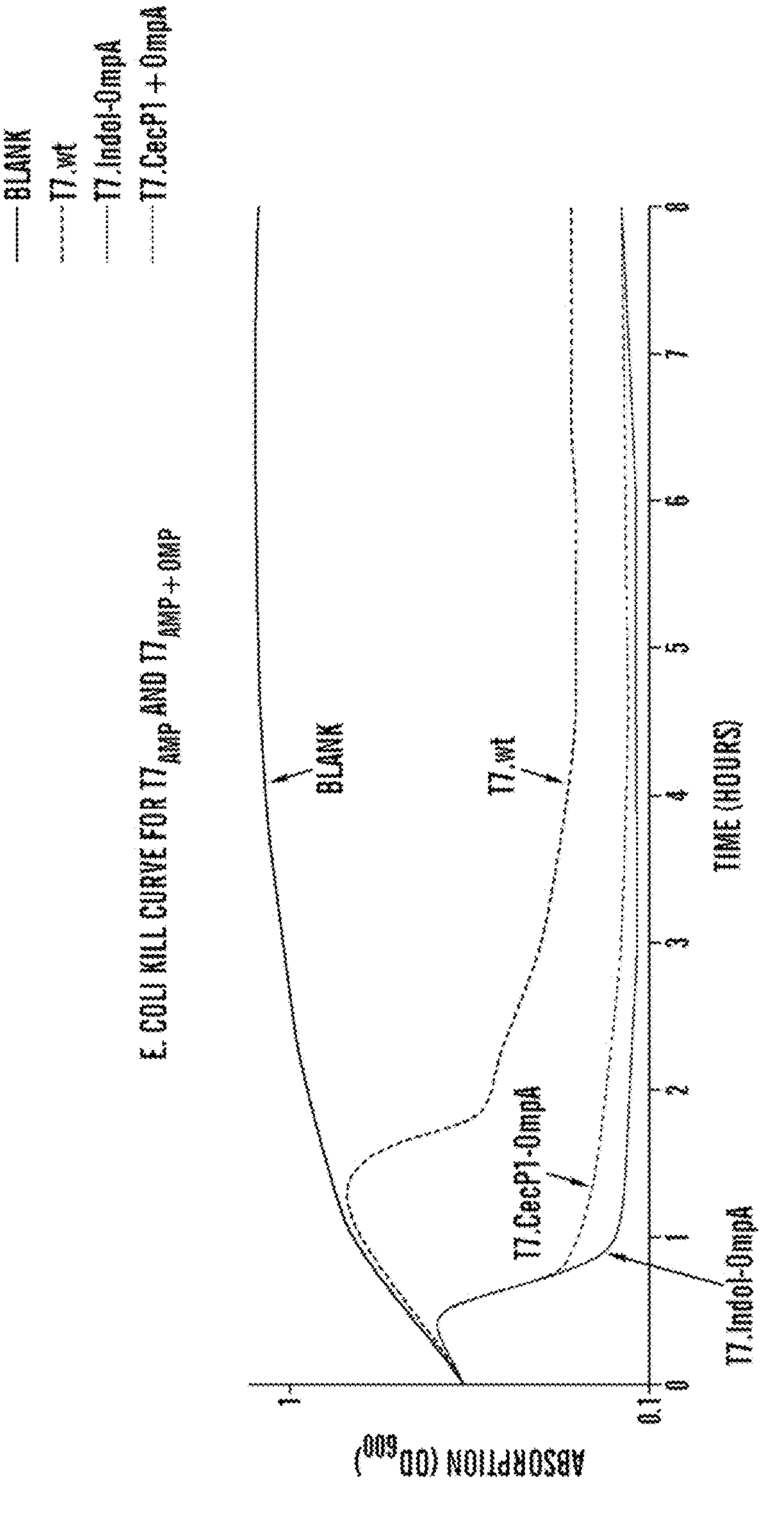
FIG. 1 shows *E. Coli* Kill curve for $T7_{AMP}$ and $T7_{AMP-OMP}$

Firstly, to determine assess the killing efficacy of the engineered phages, the inventors performed killing assay in LB media against BL2I. *E. coli* at an 0D600 of 0.4. The time profile of the decrease in optical density was monitored continuously. The inventors demonstrated that the engineered phages killed and lysed the culture bacteria faster than the wild type phages. As shown in FIG. 1, the killing curve for wild-type T7 bacteriophages (T7.wt) and for the engineered T7 phages inducing the expression of OmpA secretion sequence and the AmP Indolicidiri (T7.Indol+OmpA) or Cecropin P1 (T7.CecPI+OmpA) demonstrated that the engineered phages show a significantly faster and increased efficiency in killing the BL2I *E. coli*. Thus, the inventors have discovered that bacteriophages which express and secrete AmPs are more effective at killing bacteria due to the synthesis and secretion of the antimicrobial peptides from the host bacterial cell.

Example 2

Secondly, to assess whether our engineered phages were more effective against bacterial biofilms, the inventors grew uniform *E. coli* 8121 biofilms onto polypropylene pegs for 24 hours in LB media. The biofilms were then treated with the engineered and wild-type phages for another 24 hours after which the remaining biofilms were rinsed and sonicated from the pegs. The remaining live bacteria cells were grown on LB agar plates over night and counted to determine the killing efficiency of the phages.

Both wild type phages T7, wt and the engineered phages T7.CecP1+OmpA and T7.Indol+OmpA showed high activity against uniform biofilms since it was composed only of BL21, a particular strain which indecently forms rather weak biofilms. Both wild type and engineered phages killed all bacteria in the films and no colonies were observed after plating from the sonicated pegs. The inventors then repeated the experiment with a mixed culture of BL21 bacteria and another strain of bacteria to differentiate wild type and engineered phages.

Figure 2:
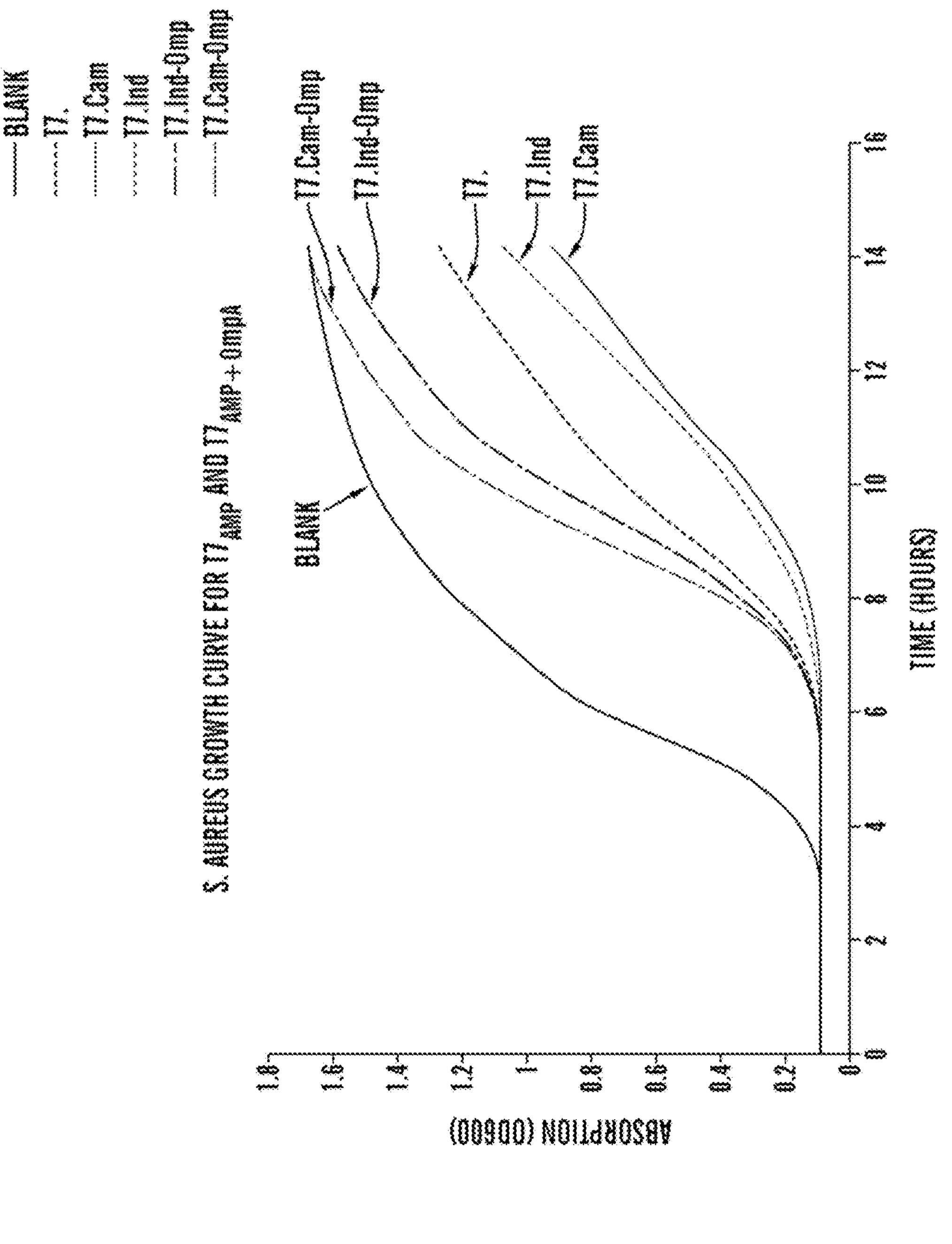
FIG. 2 shows *S. aureus* growth curve for $T7_{AMP}$ and $T7_{AMP-OMP}$

Finally, the media from a lysate culture of wild type and engineered phages was used to grow *S. aureus* bacteria. The media that contained T7 phages did not infect *S. aureus*, and the media of engineered phages contained released AmPs, active against *S. aureus*, and possibly also uncleaved fusion OmpA-AmP peptide inactive against *S. aureus*. FIG. 2 demonstrated that the engineered $T7_{AMP}$ phages are more effective than the wild type $T7_{WT}$ at slowing down the growth of *S. aureus* while the phages that included the OmpA sequence where not as effective. Thus, the inventors have demonstrated that $T7_{AMP}$ and the $T7_{AMP}+_{ompA}$ have different killing ability, due to the fact when AmP is expressed by $T7_{AMP}$, the AmPs are in their active form, whereas when AmPs are expressed by $T7_{AMP}+_{ompA}$ they are inactive due to being fused with OmpA sequence until cleaved by the cell.

The inventors have discovered that a method to increase the bacterial host range spectrum of T7 bacteriophages by engineering T7 phages to express at least one antimicrobial peptide. This is the first demonstration of a technology aimed at addressing one of the main drawbacks of phage technology, namely limited bacterial host specificity. The inventors have discovered that the engineered bacteriophages can be adapted to express any natural or designed antimicrobial peptide in any bacteriophage species to target a wide range of different bacterial hosts. Accordingly, the inventors have discovered expressing an antimicrobial peptide, both natural and designed peptides with broad spectrum antimicrobial activity, with and without secretion sequence, OmpA and any other secretion sequences, in a bacteriophage, such as T7 or any other bacteriophage. The engineered bacteriophage which have been modified to express AmPs and secretion sequence can optionally be further engineered to express additional genes, such as for example but not as a limitation, a Dispersin B enzyme, or other biofilm degrading enzyme.

Example 3

Testing of Bacteriocidality of Several AMPs In Vitro

The inventors tested a panel of AMPs, shown in Table 3 to assess which AMP has the greatest bacteriocidality against both *E. coli* and *S. aureus*. Cultures were grown to an optical density measured at 600 nm between 0.3-0.6 and then the AMPs were added in the respective concentrations. The decrease in OD600 is assessed as the killing of bacterial cells by the AMP, if the OD600 drops, other results cannot be inferred, as the information gained is from the OD600 is limited. The abbreviation SA denotes tests on *Staphylococcus aureus*, whereas EC denotes *Escherichia coli* bacteria. Experiments were run in duplicate. The nomenclature of these graphs follows the pattern: Strain.AMP.Concentration (μg/mL).replicate #(1 or 2).

know that other concentrations can be used, and that these concentrations are not in the physiological range, if either produced endogenously or if they are being delivered.

Figure 3:
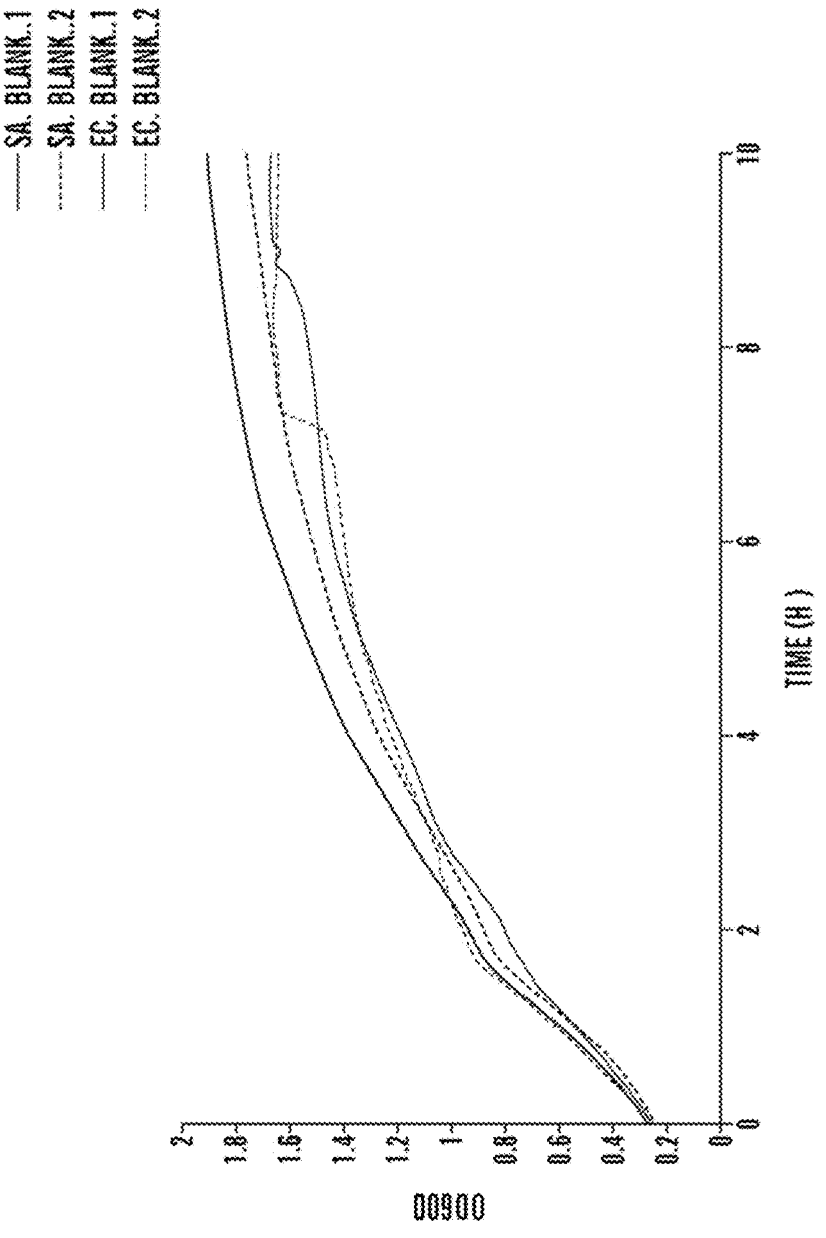
FIG. 3 shows the growth kinetics of duplicate *S. aureus* and *E. coli* cultures to reference the killing activity of the AMPs.
Figure 4:
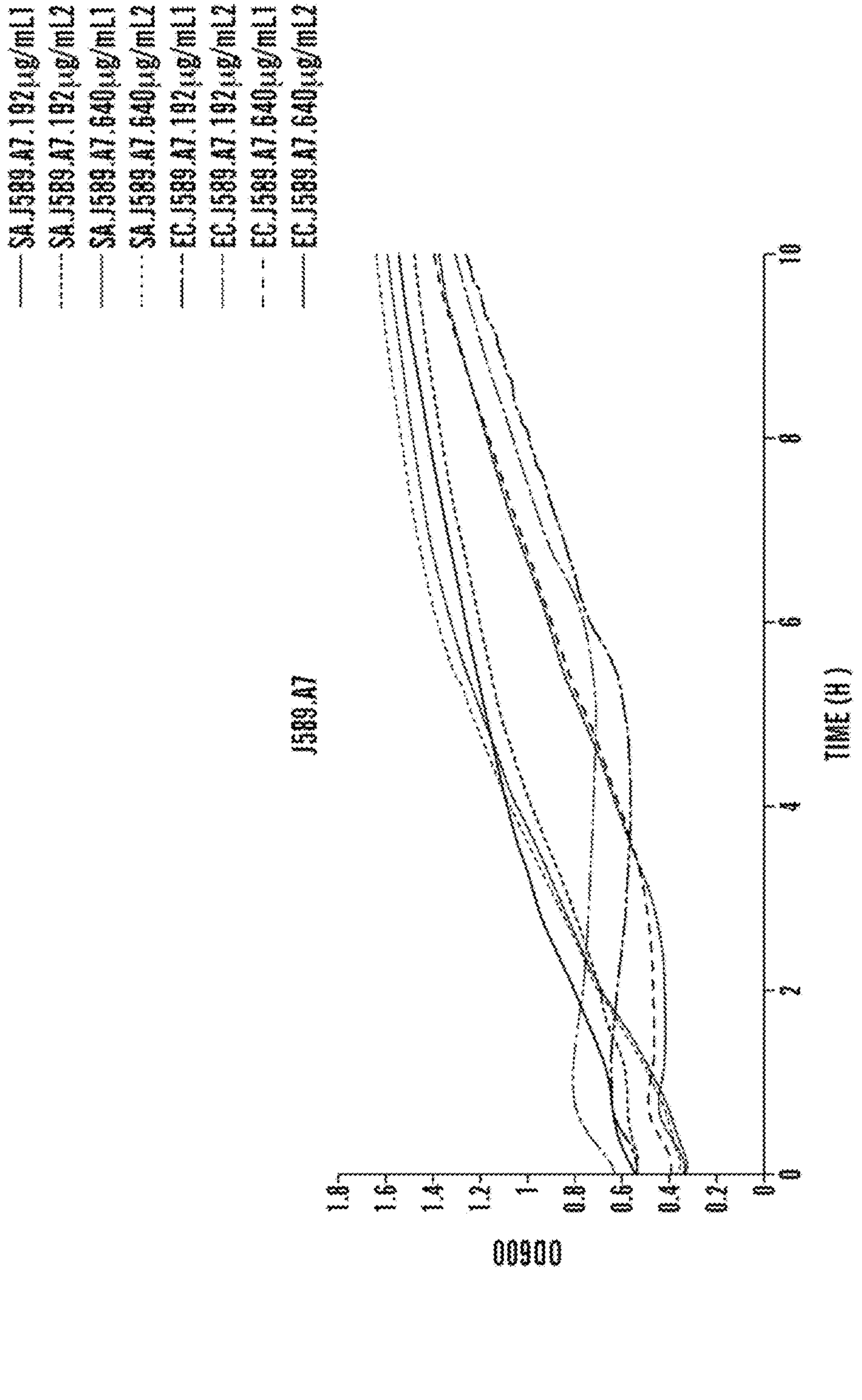
FIG. 4 shows the bacteriocidal action of J589.A7 AMP on *S. aureus* and *E. coli* bacteria, showing an intermediate bacteriocidal action of J589.A7 on *E. coli*, moderately concentration dependent; no effects can be seen on *S. aureus*, even at high concentrations.
Figure 5:
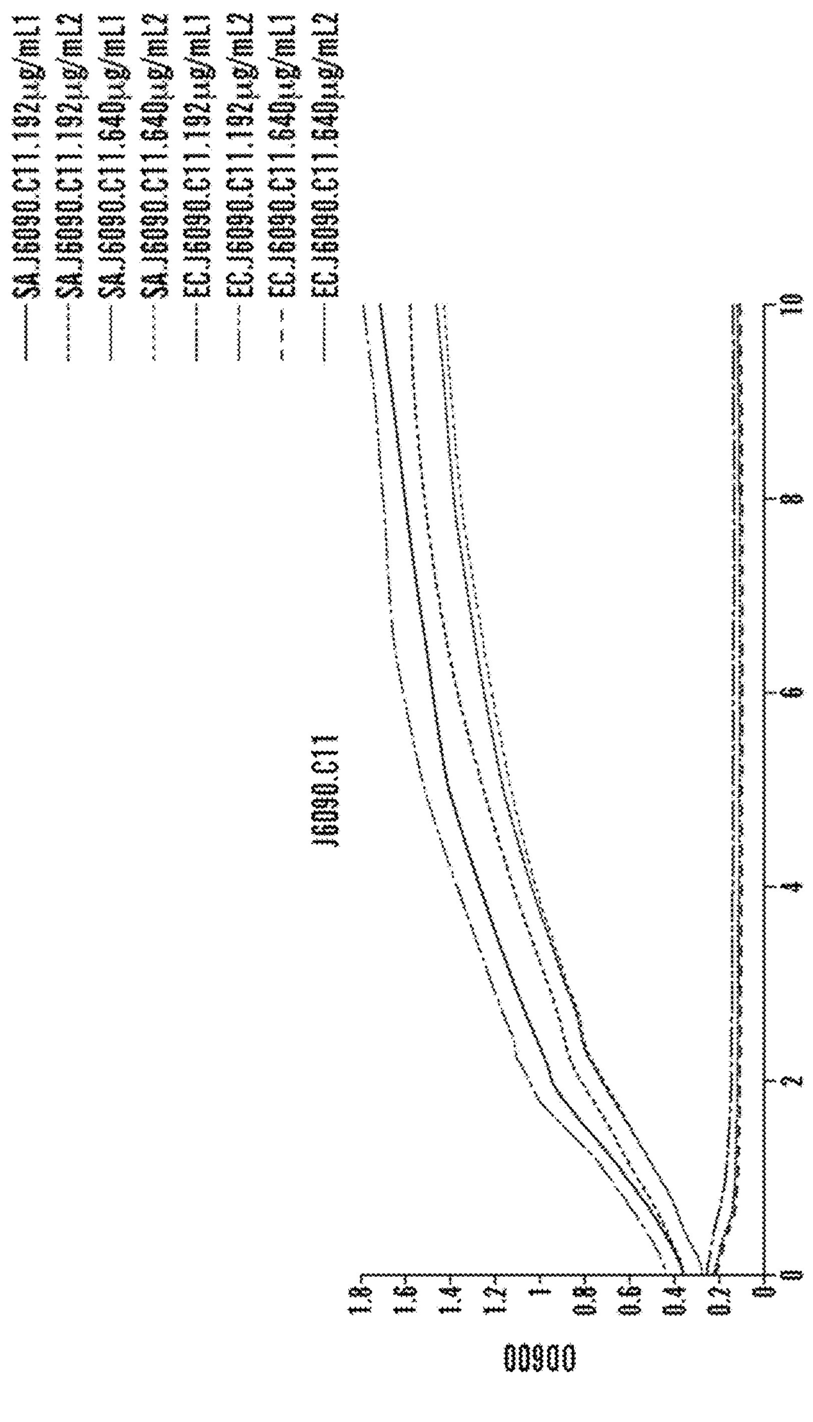
FIG. 5 shows the bacteriocidal action of J690.C11 AMP on *S. aureus* and *E. Coli* bacteria, showing killing of *E. coli* by AMP J690.C11, but only at high levels of AMP (640 µg/mL); no effect on *S. aureus*.
Figure 6:
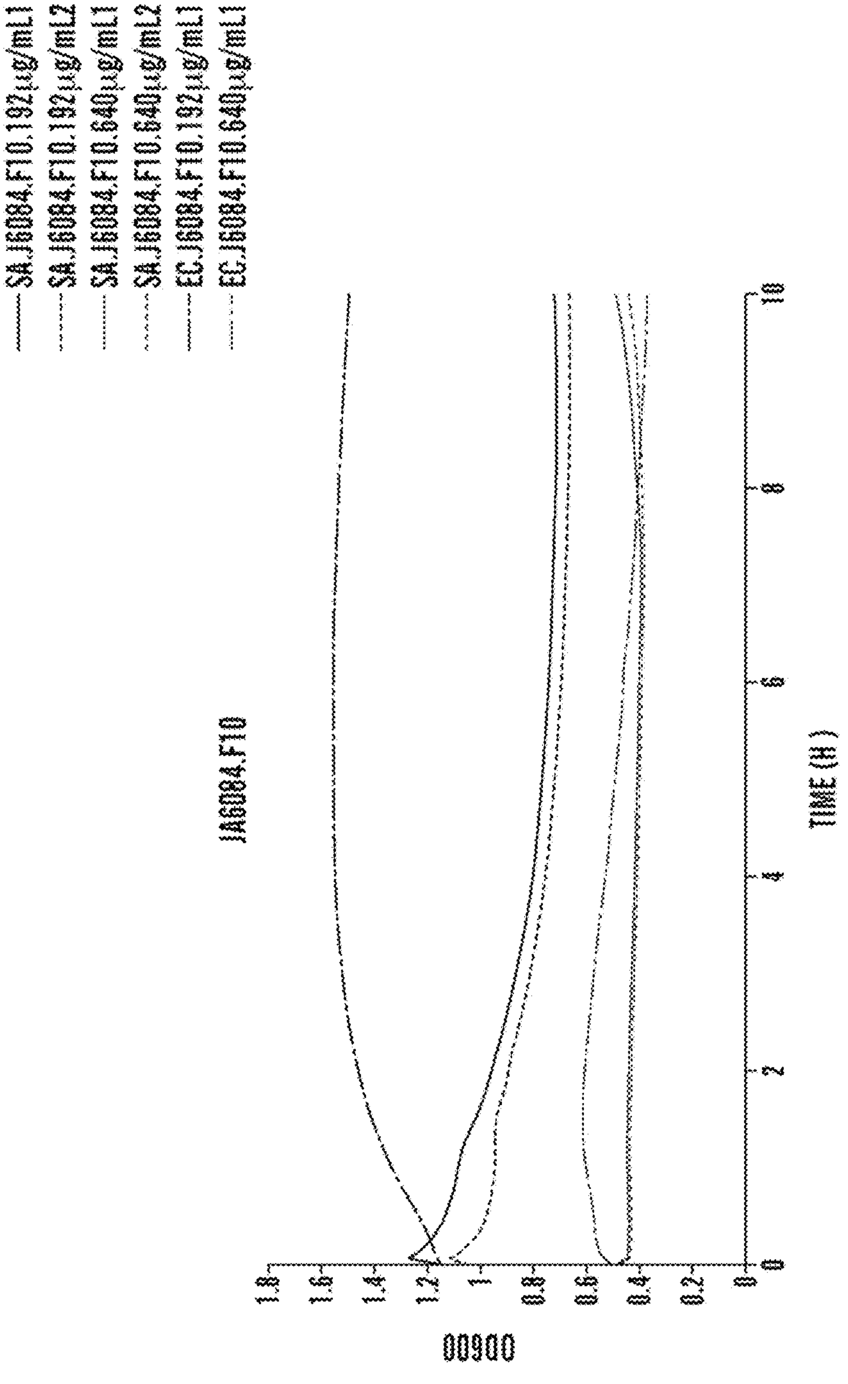
FIG. 6 shows moderate killing of *S. aureus* by J6084.F10 at intermediate concentrations, no effect on *E. coli* at intermediate concentrations. Killing of both *S. aureus* and *E. coli* occurs at high concentrations.
Figure 7:
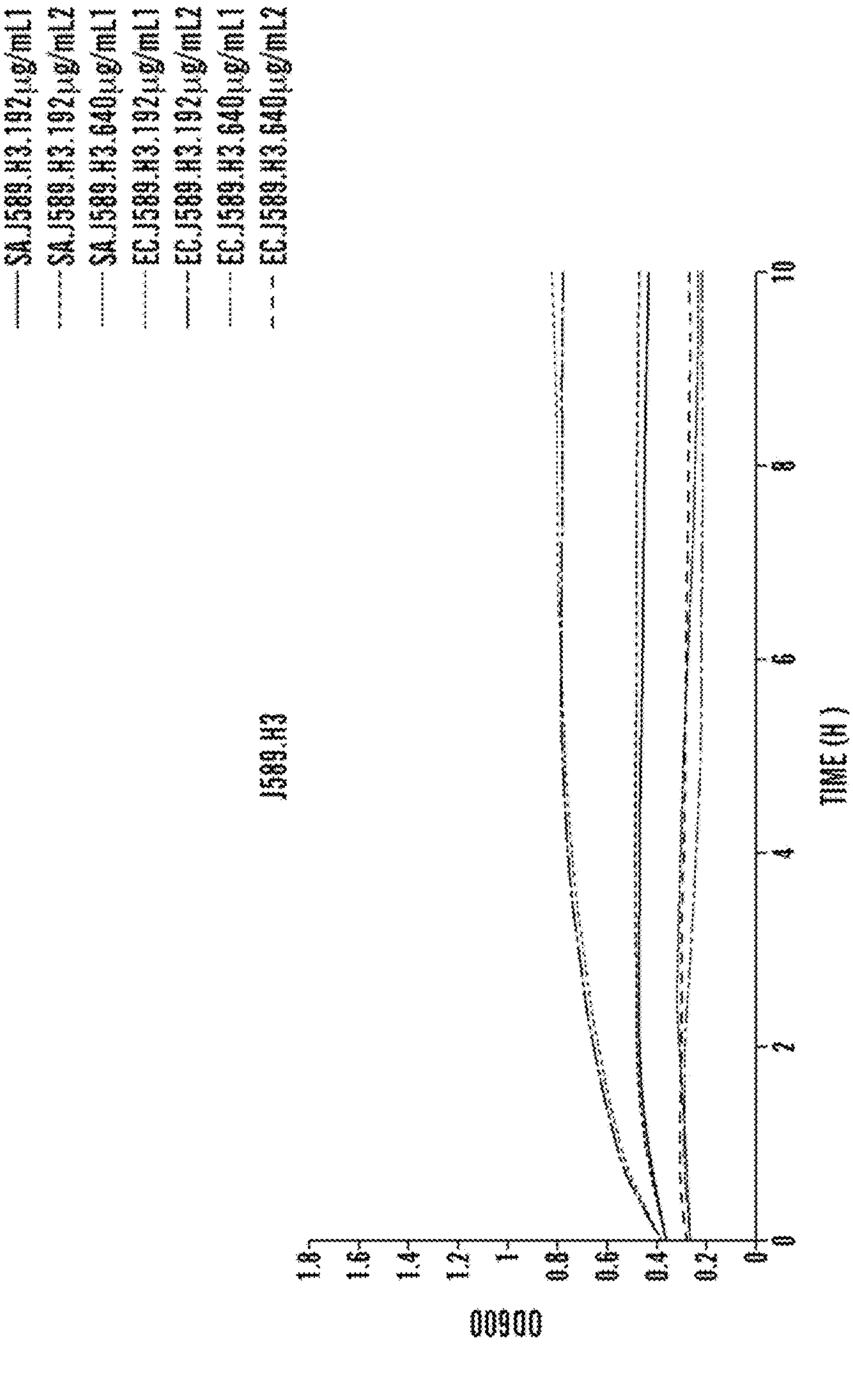
FIG. 7 shows bacteriostatic activity of J589.H3 on *S. aureus* and *E. coli*. The magnitude of the effect is concentration dependent and similar for both strains.
Figure 8:
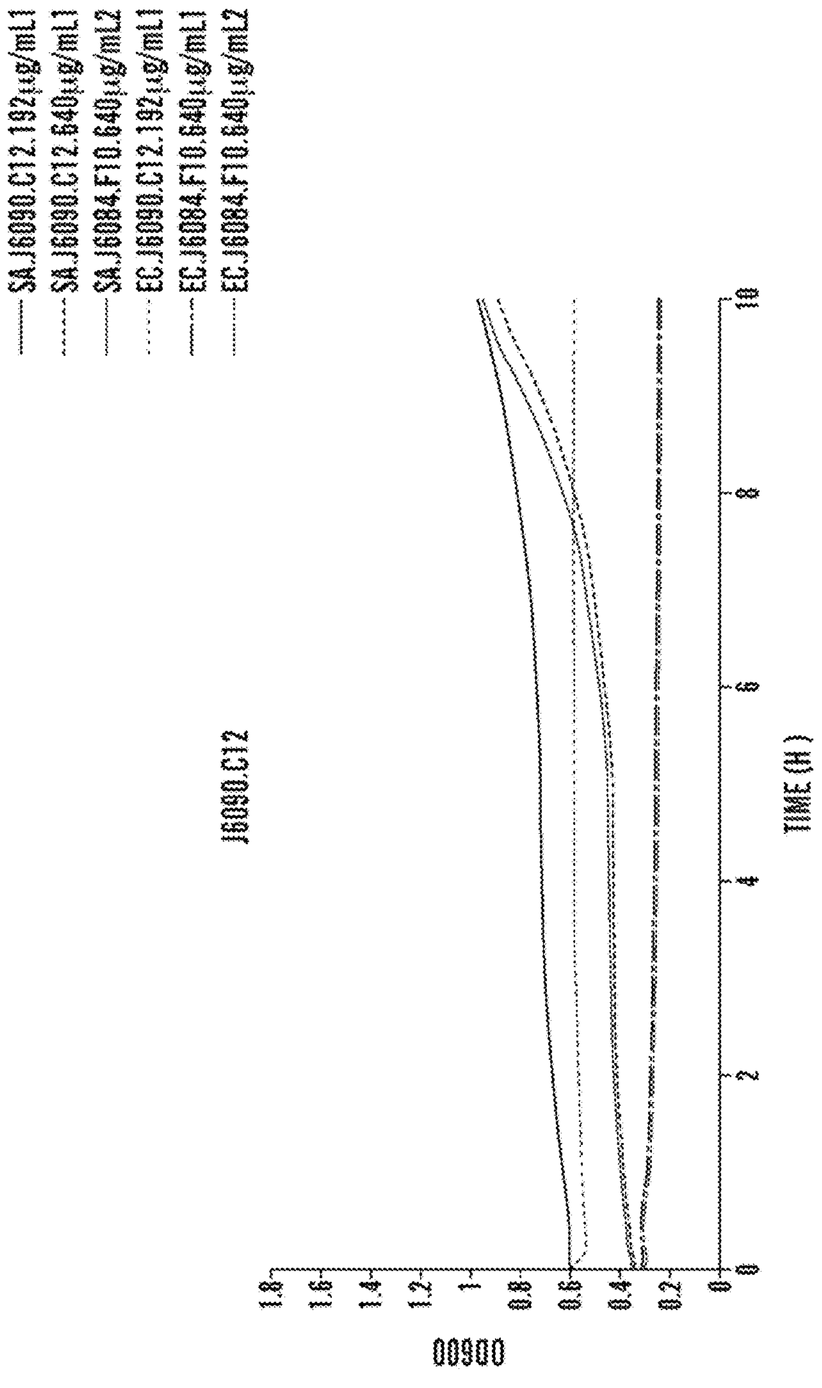
FIG. 8 shows bacteriostatic, time-limited effect of J6090.C12. Both *S. aureus* and *E. coli* are repressed by the AMP, however the effect is time-limited, as re-growth is being observed starting at hour 7.
Figure 9:
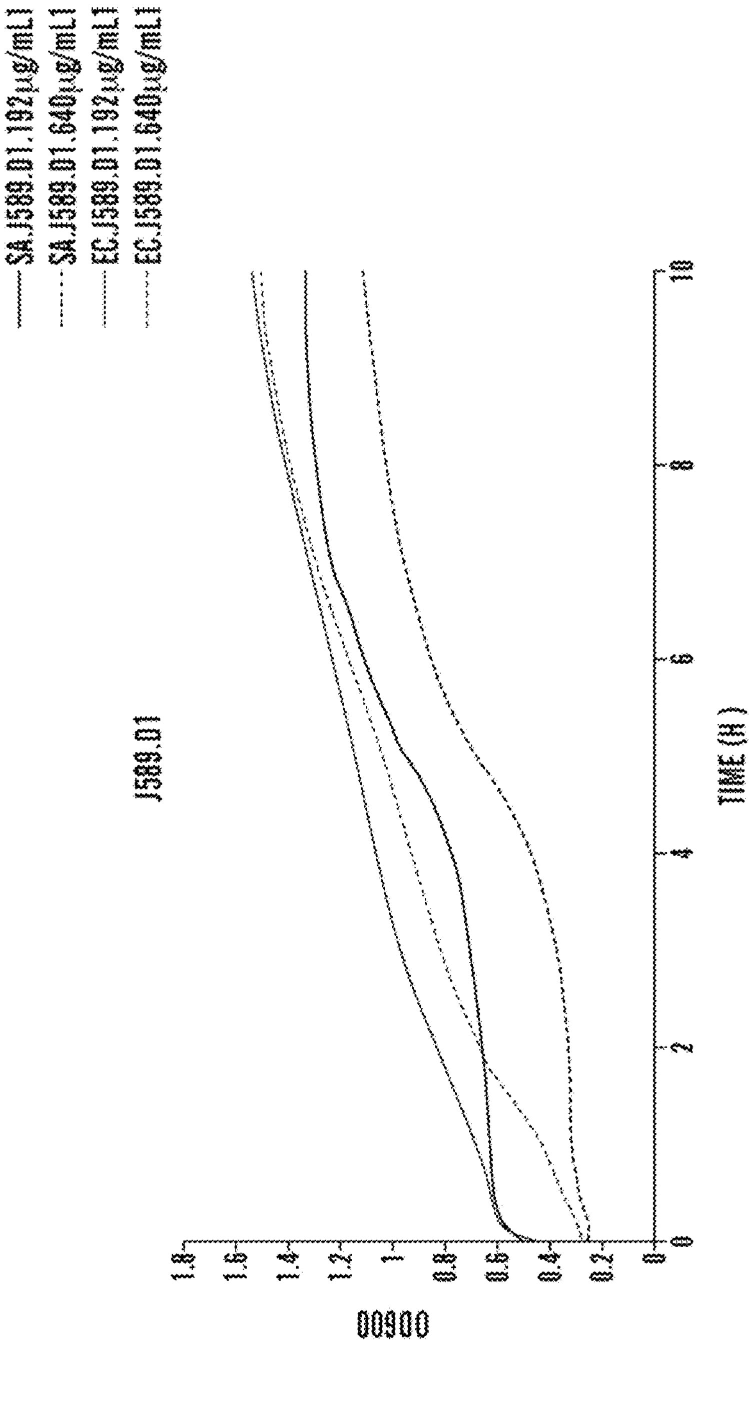
FIG. 9 shows inefficient bacteriostatic or bacteriocidal activity of J589.D1. Neither *E. coli* nor *S. aureus* are inhibited.
Figure 10:
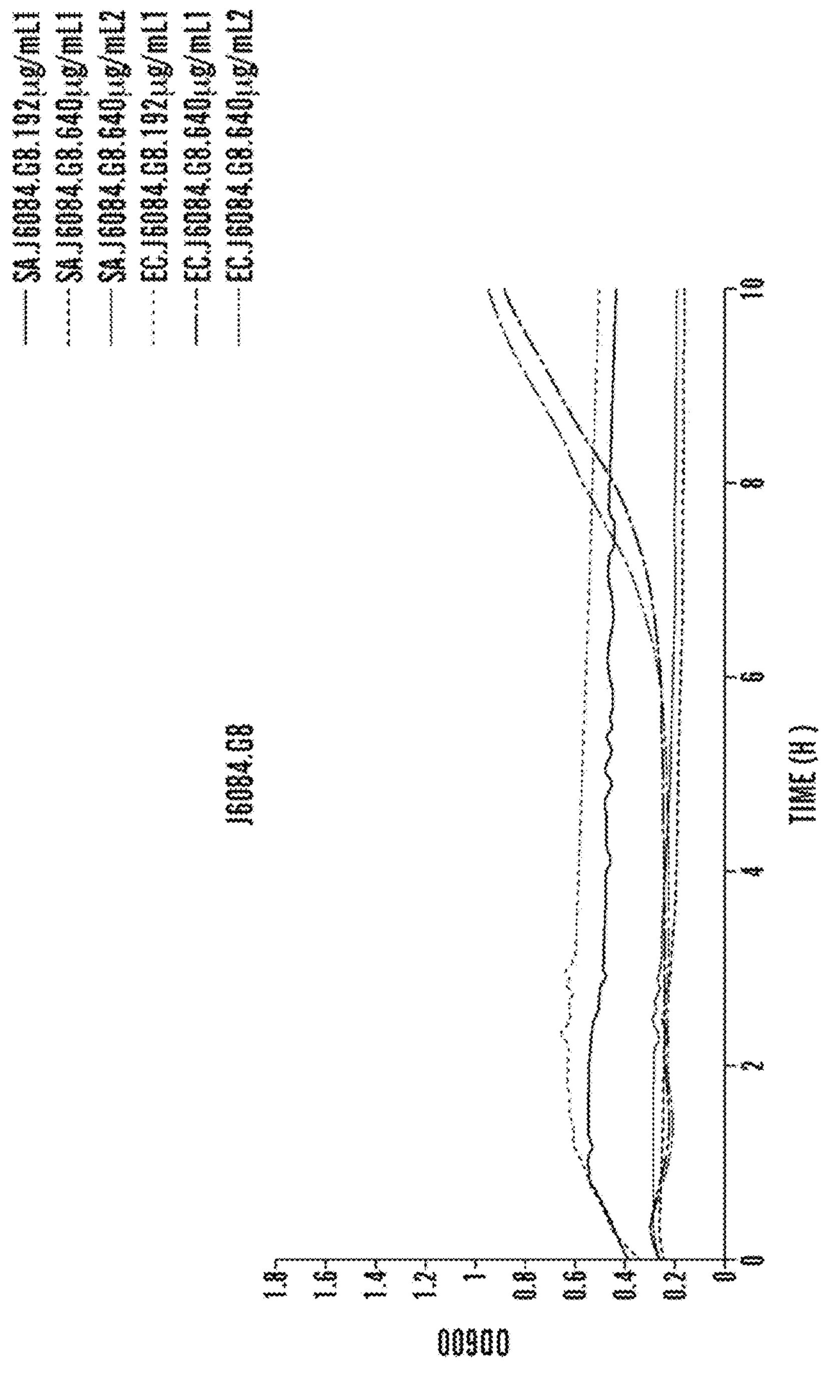
FIG. 10 shows both *S. aureus* and *E. coli* are growth arrested using AMP J6084.G8, with the effect being concentration dependent. Again, the inventors demonstrate a time limit on the repression, starting with re-growth after about 6 hours.
Figure 11:
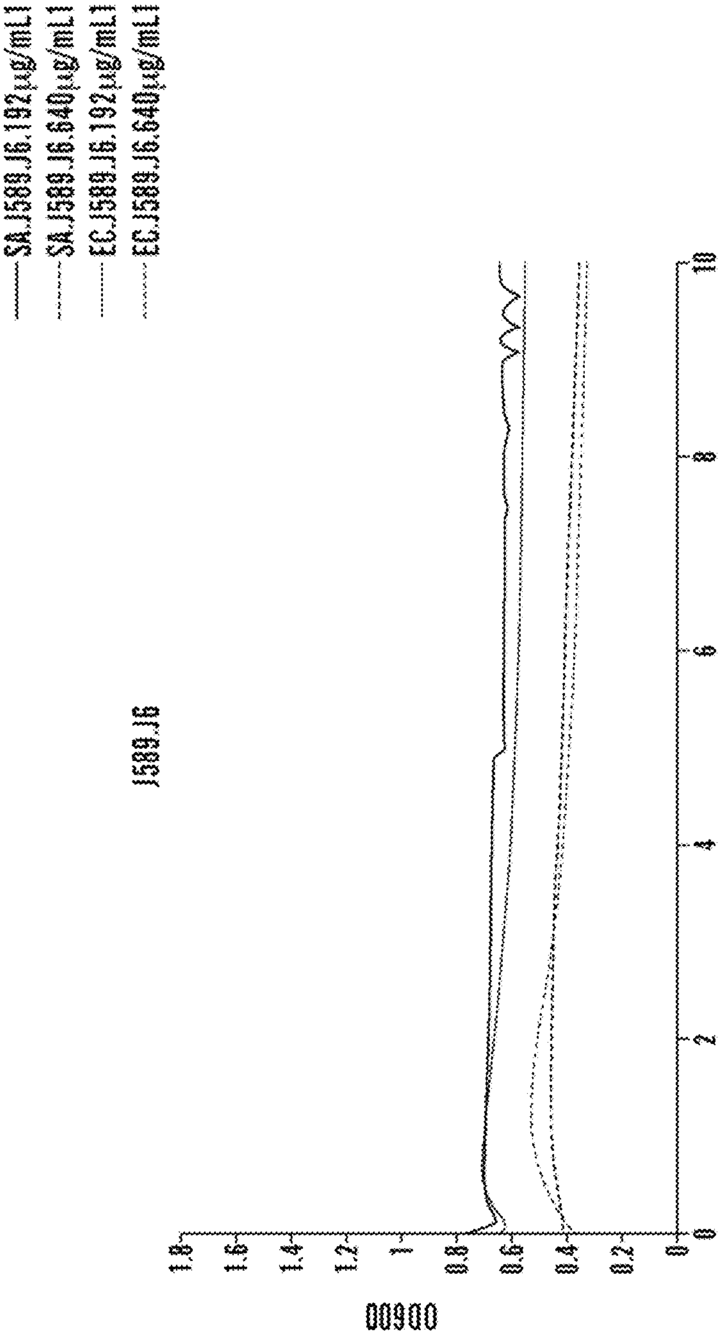
FIG. 11 shows AMP J589.J6 displays good bacteriostatic activity against *E. coli* and *S. aureus*.
Figure 12:
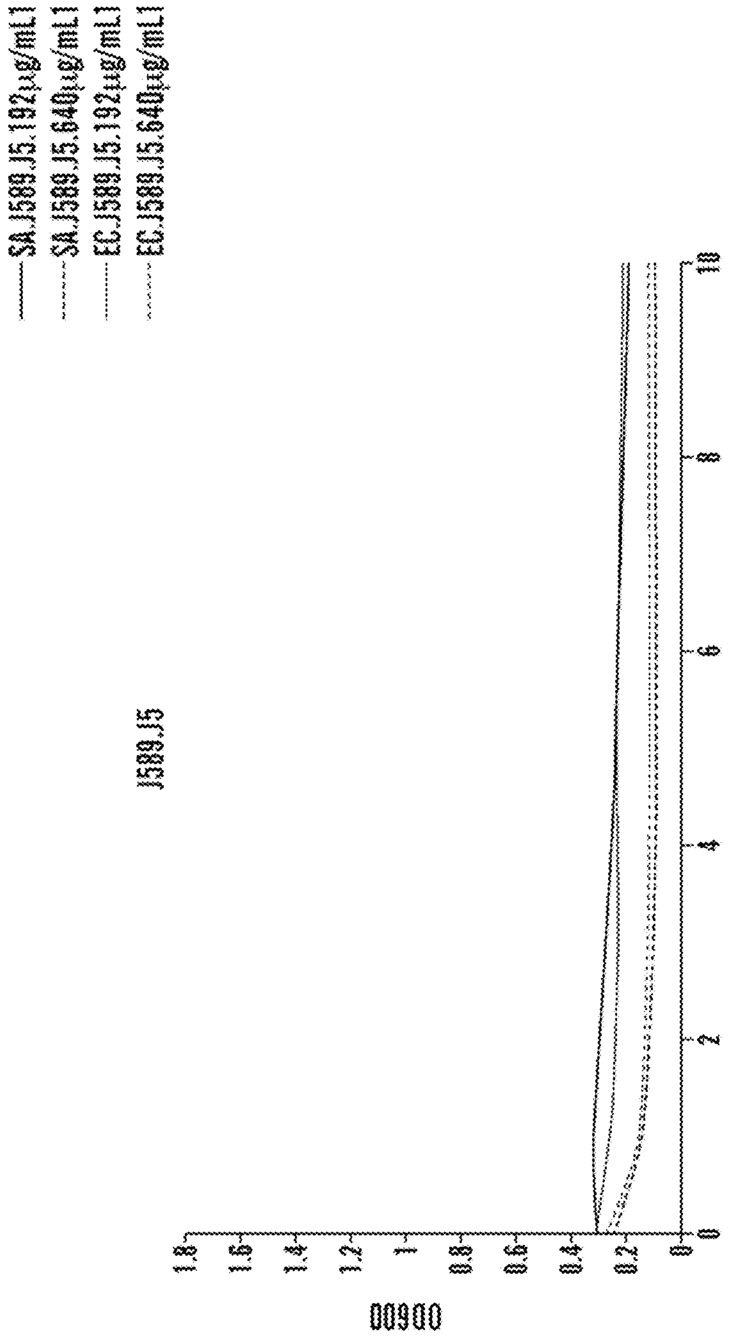
FIG. 12 shows bacteriostatic behavior from AMP J589.J5 on *E. coli* and *S. aureus* at the intermediate concentration, while we see killing and no re-growth at the higher concentration.

FIG. 3 shows the growth kinetics of duplicate *S. aureus* and *E. coli* cultures to reference the killing activity of the AMPs. FIG. 4 shows intermediate bacteriocidal action of J589.A7 on *E. coli*, moderately concentration dependent; no effects can be seen on *S. aureus*, even at high concentrations. FIG. 5 shows killing of *E. coli* by AMP J690.C11, but only at high levels of AMP (640 μg/mL); no effect on *S. aureus*. FIG. 6 shows moderate killing of *S. aureus* by J6084.F10 at intermediate concentrations, no effect on *E. coli* at intermediate concentrations. Killing of both *S. aureus* and *E. coli* occurs at high concentrations. FIG. 7 shows bacteriostatic activity of J589.H3 on *S. aureus* and *E. coli*. The magnitude of the effect is concentration dependent and similar for both strains. FIG. 8 shows bacteriostatic, time-limited effect of J6090.C12. Both *S. aureus* and *E. coli* are repressed by the AMP, however the effect is time-limited, as re-growth is being observed starting at hour 7. FIG. 9 shows inefficient bacteriostatic or bacteriocidal activity of J589.D1. Neither *E. coli* nor *S. aureus* are inhibited. FIG. 10 shows both *S. aureus* and *E. coli* are growth arrested using AMP J6084.G8, with the effect being concentration dependent. Again, the inventors demonstrated a time limit on the repression, starting with re-growth at hour 6. FIG. 11 shows AMP J589.J6 displays good bacteriostatic activity against *E. coli* and *S. aureus*. FIG. 12 shows bacteriostatic behavior from AMP

TABLE 3

AMPs tested in the exponential phase killing assay.

| Label | Amino Acid Sequence | Length | MIC *E. coli* | | MIC *S. aureus* | | Toxicity | |
|---|---|---|---|---|---|---|---|---|
| J589_A7 | RLCRIVVIRVCR (SEQ ID NO: 10) | 12 | 64 | 64 | 64 | 64 | 256 | 256 |
| J589_D1 | LLLFLLKKRKKRKY (SEQ ID NO: 36) | 14 | 32 | 64 | 16 | 16 | 512 | 512 |
| J589_H3 | FFHHIFRGIVHVGKTIHKLVTG (SEQ ID NO: 37) | 22 | 32 | 64 | 32 | 32 | 128 | 128 |
| J589_J5 | WLGSALKIGAKLLPSVVGLFQKKKK (SEQ ID NO: 38) | 25 | 32 | 32 | 4 | 4 | 32 | 32 |
| J589_J6 | FFGWLIKGAIHAGKAIHGLIHRRRH (SEQ ID NO: 39) | 25 | 8 | 8 | 4 | 4 | 16 | 16 |
| **J589_K4** | **GIWGTLAKIGIKAVPRVISMLKKKKQ** (SEQ ID NO: 40) | 26 | 16 | 16 | 8 | 8 | 64 | 64 |
| J6084_F10 | KWKLFKKILKFLHLAKKF (SEQ ID NO: 41) | 18 | 8 | 4 | 16 | 16 | 32 | 32 |
| **J6084_H2** | **FWGALIKGAAKLIPSVVGLFKKKQ** (SEQ ID NO: 42) | 24 | 64 | 64 | 4 | 4 | 32 | 32 |
| J6123_C11 | FLGALFKVASKVLPSVFCAITKKC (SEQ ID NO: 43) | 24 | 64 | 64 | 4 | 8 | 16 | 16 |
| **J6123_D7** | **WLGSALKIGAKLLPSVVGLFKKKKQ** (SEQ ID NO: 44) | 25 | 32 | 32 | 4 | 4 | 64 | 64 |
| J6090_C11 | RWKFFKKIERVGQNVRDGLIKAGPAIQVLGAAKAL (SEQ ID NO: 45) | 35 | 2 | 4 | 256 | 256 | 256 | 256 |

Figure 13:
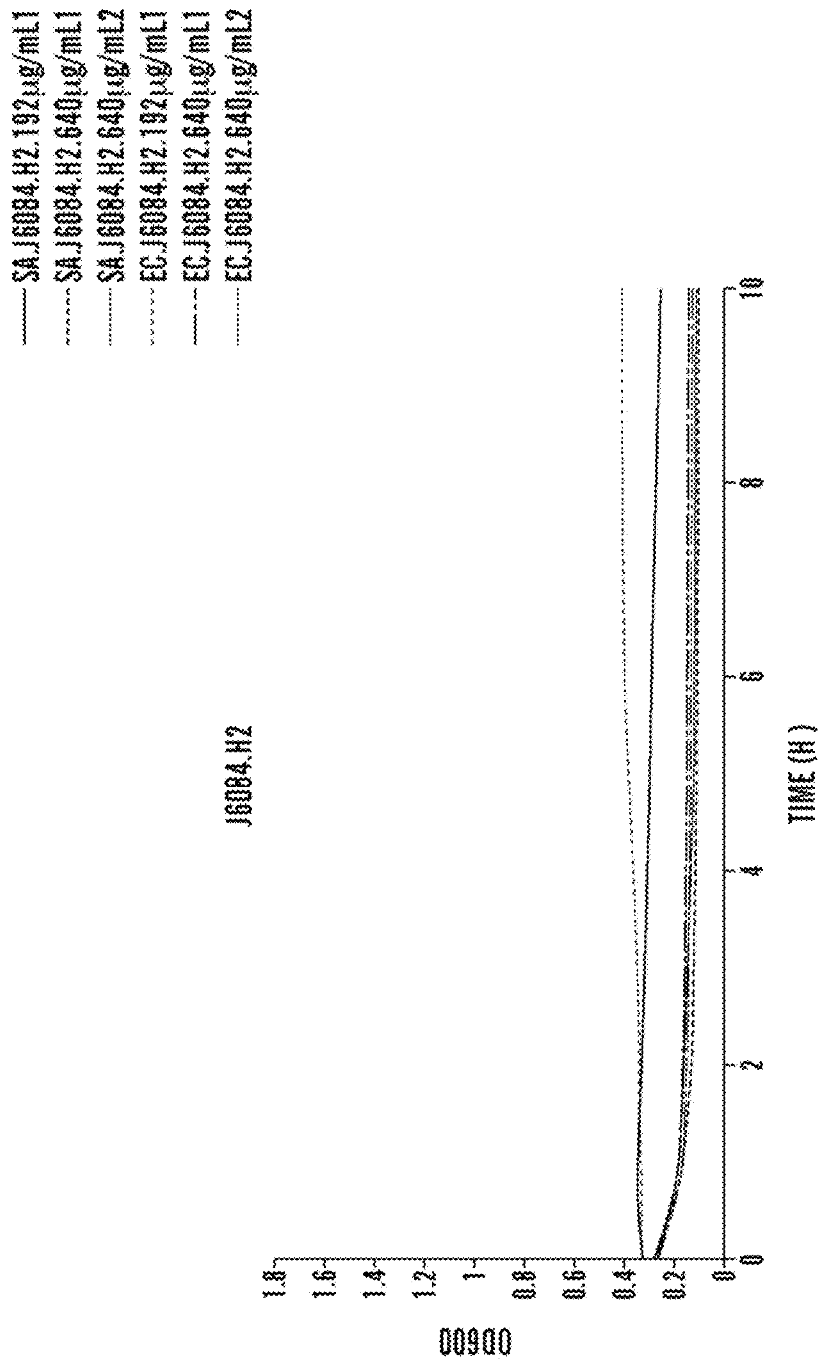
FIG. 13 shows a growth arrest from AMP J6084.H2 on *E. coli* and *S. aureus* at the intermediate concentration, while killing and no re-growth at the higher concentration.
Figure 14:
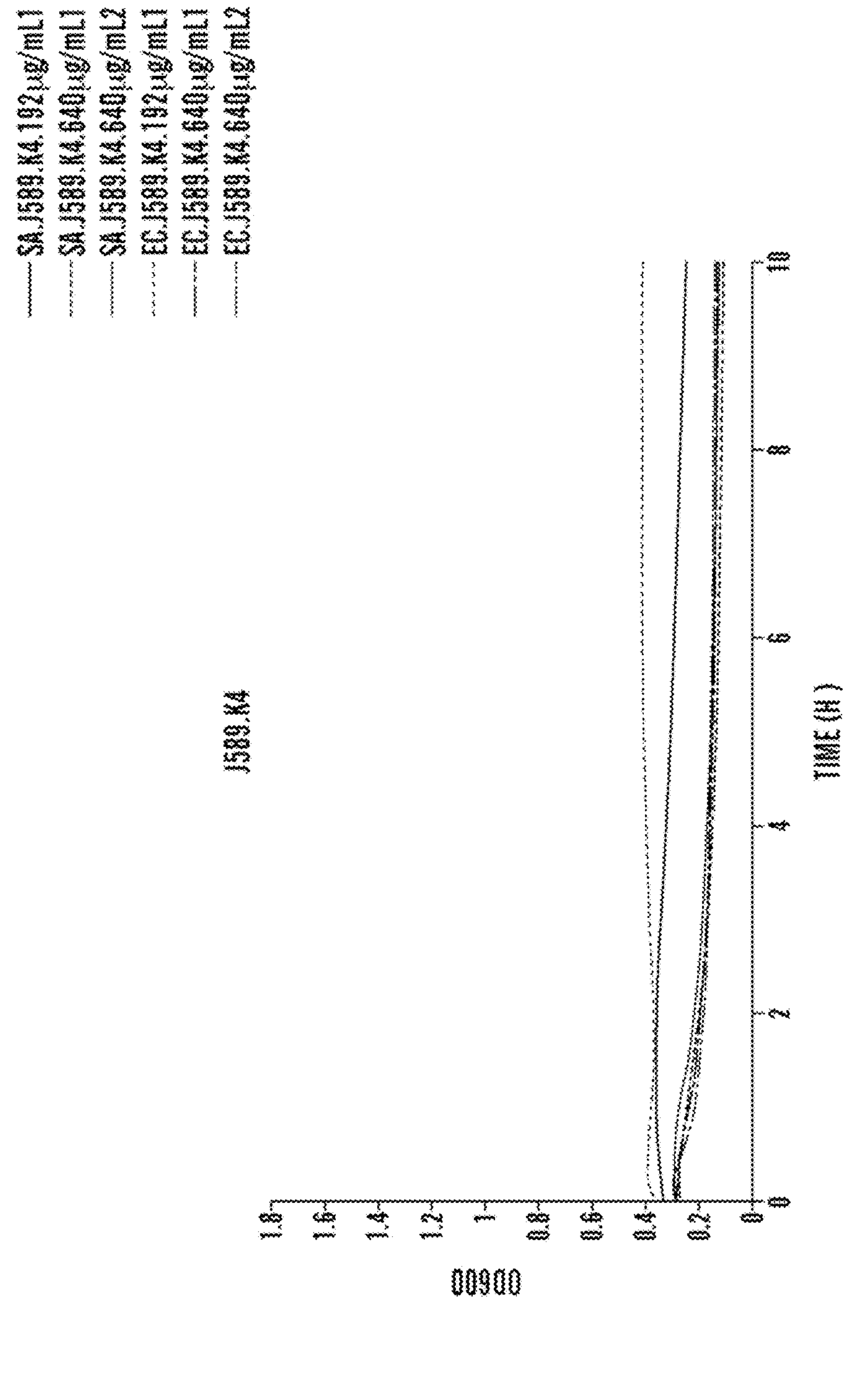
FIG. 14 shows growth arrest from AMP J6084.H2 on *E. coli* and *S. aureus* at the intermediate concentration, and decrease of OD towards the end of the treatment period, and also shows killing and no re-growth at the higher concentration.

Table 3 shows AMPs assessed for bacterial killing activity for both *E. coli* and *Staphylococcus aureus*. These AMPs were previously tested for the minimal inhibitory condition (MIC), which informed the concentrations that were used in this killing assay. The inventors used an intermediate concentration of 192 μg/mL and a high concentration of 640 μg/mL, to ensure that the greatest activity of the AMP was observed. However, one of ordinary skill in the art would J589.J5 on *E. coli* and *S. aureus* at the intermediate concentration, while we see killing and no re-growth at the higher concentration. FIG. 13 shows a growth arrest from AMP J6084.H2 on *E. coli* and *S. aureus* at the intermediate concentration, while killing and no re-growth at the higher concentration. FIG. 14 shows growth arrest from AMP J6084.H2 on *E. coli* and *S. aureus* at the intermediate concentration, and decrease of OD towards the end of the treatment period, and also shows killing and no re-growth at the higher concentration.

Example 4

Cloning Strategy for the Construction of Recombinant Bacteriophage T7 Expressing Antimicrobial Peptides Based on these results from Example 3, the inventors chose the AMPs J589.K4 (SEQ ID NO: 40), J6084.H2 (SEQ ID NO: 42) and J6123.D7 (SEQ ID NO: 44) (also shown in bold in Table 4) as exemplary AMPs to clone into bacteriophages delivery system for co-expression and to generate engineered bacteriophages expressing AMPs. Note that AMP J6123.D7 efficacy is not shown, however was separately assayed and found to possess good killing capabilities of both *E. coli* and *S. aureus* at both high and intermediate concentrations (data not shown).

In general it is a well-established procedure to clone small to medium size DNA fragments into T7 for expression in *E. coli* BL21 (the cell line recommended by Novagen). The cloning of the three AMPs that are deemed to be most cidal against *E. coli* and *S. aureus* is described in the following section and the AMPs are: J589.K4, J6084.H2 and J6123.D7.

The inventors PCR amplified the AMP inserts. Shown in Table 5 are the primers used to clone the nucleic acid sequences encoding J589.K4, J6084.H2 and J6123.D7 into pET9a plasmid.

Nucleic acid sequence P511 (SEQ ID NO: 45) was used to design primers I301_4 (SEQ ID NO: 46) and I301_1 (SEQ ID NO: 47) to amplify nucleic acid which encodes AMP J589.K2 (SEQ ID NO: 40), and can inserted into pET9a plasmid. The PCR resulted in a PCR band of the appropriate size of 86 bp (see middle lane, FIG. 15B).

Nucleic acid sequence P512 (SEQ ID NO: 48) was used to design primers I301_4 (SEQ ID NO: 46) and I302_1 (SEQ ID NO: 49) and I302_4 (SEQ ID NO: 51) to amplify nucleic acid which encodes AMP J6084.H2 (SEQ ID NO: 42), and can inserted into pET9a plasmid. The PCR resulted in a PCR band the appropriate size of 80 bp (see middle lane, FIG. 15A).

Nucleic acid sequence P513 (SEQ ID NO: 52) was used to design primers I303_4 (SEQ ID NO: 53) and I303_1 (SEQ ID NO: 54) to amplify nucleic acid which encodes AMP J6123 D7 (SEQ ID NO: 44), and can inserted into pET9a plasmid. The PCR resulted in a PCR band of the appropriate size of 83 bp (see middle lane, FIG. 15B)

The PCR bands were excised from the gel and purified using methods commonly known by ordinary skill in the art, and then restriction digested with NdeI and BamHI and then electrophoresis (data not shown) and then purified using standard PCR cleanup procedure. Measurement of concentration on the Nanodrop yielded the following concentrations: (1) P511 cut Nde I Bam HI: 7.8 ng/μL, 86 bp; (2) P512 cut Nde I Bam HI: 14.3 ng/μL, 80 bp; (3) P513 cut Nde I Bam HI: 3.7 ng/μL, 83 bp (4) pET9a cut Nde I Bam HI: 4.7 ng/μL, 4301 bp.

The NdeI-BamHI excised J589.K4 (P511), J6084.H2 (P512), J6123.D7 (P513) nucleic acid sequences were then cloned into a ligated pET9a plasmid. The pET9a vector backbone was used at 23.5 ng (~5 ng/μl) and 70 ng of the insert DNA.

PCR Build of T7 Shuttle Constructs

To transfer the J589.K4 (P511), J6084.H2 (P512), J6123.D7 (P513) inserts from pET9a plasmid into a T7 plasmid, the bands were amplified by PCR with primers D262 (SEQ ID NO: 55) and D640 (SEQ ID NO: 56). FIG. 16A shows a gel of the PCR products of J589.K4 (P511), J6084.H2 (P512) and J6123.D7 (P513) fragments in pET9a plasmid, using D262 and D640 primers, where the P511-pET9a, P512-pET9a, P513-pET9a are used at 1 μl or 5 μl respectively. FIG. 16B shows the combined PCR products from FIG. 16A. FIG. 16C shows the comparison of the T7 shuttle vector constructs and insert J589.K4 (P511), J6084.H2 (P512), J6123.D7 (P513) DNA fragments. (FIG. 16C lanes are as follows: 1.10 μL 2-LOG ladder; 2. P514=P511 T7 shuttle; 3. P511 insert; 4. P515=P512 T7 shuttle; 5. P512 insert; 6. P516=P513 T7 shuttle.)

T7 Shuttle

The T7 shuttle vector constructs comprising the J589.K4 (P511), J6084.H2 (P512), J6123.D7 (P513) DNA fragments are inserted into T7Select415-1b shuttle plasmid. The P511-T7, P512-T7, P513-T7 shuttle constructs and the T7Select415-1b are digested with Eco RI/Hind III digestion, and then ligated to insert the J589.K4 (P511), J6084.H2 (P512), J6123.D7 (P513) into the T7Select415-1b plasmid to generate P511-T7Select415-1b; P512-T7Select415-1b; P513-T7Select415-1b. FIG. 17A shows the EcoRI/Hind III digestion of the inserts from the T7Select145-1b plasmids.

In Vitro Packaging

Ligation reactions were added directly to T7 Packaging Extracts for in vitro packaging. The inventors used one method which is as follows: 1. Allow the T7Select® Packaging Extract to thaw on ice. The volume of the extract is 25 μL and will package up to 1 μg of vector DNA without a loss in efficiency. The extract can be subdivided into several prechilled tubes for testing several DNA samples at once. If performing smaller scale packaging tests, the amount of ligation reaction added must be reduced proportionately. 2. Add 5 μL ligation reaction per 25 μL extract. Mix gently by stirring with a pipet tip; do not vortex. A vial of T7Select Packaging Control DNA is provided with the system. To test the packaging efficiency independently, add 0.5 μg of the control DNA to 25 μL extract. 3. Incubate the reaction at room temperature (22° C.) for 2 h. 4. Stop the reaction by adding 270 μL sterile LB or TB medium. If the packaging reaction will be stored for more than 24 h prior to amplification, add 20 μL chloroform and mix gently by inversion. The packaging reaction can be stored for up to one week at 4° C. without significant losses in titer. For longer term storage, the packaged phage must be amplified by plate or liquid culture methods. 5. Perform a plaque assay as described below to determine the number of recombinants generated.

Cloning Strategy for the Construction of Recombinant Bacteriophage T7 Expressing a lysK Fragment PCR was performed from *S. aureus* Phage K gDNA using PCR primers D8901 (SEQ ID NO: 57) and D8902 (SEQ ID NO: 58) or D8901 (SEQ ID NO: 57) and D8903 (SEQ ID NO: 64; 5'-TAGCTGGATCCCTATGCTTTTACAGGT-ATTTCAATGA 3') for the short fragment of LysK containing the CHAP domain. The P8903 PCR products are shown in FIG. 18. The P8903 PCR products were subject to restriction digestion with NdeI and BamHI for ligation into pET9a, and the purified band shown in FIG. 18. (The lanes in FIG. 18 are as follows; 1. 10 μL 2-LOG ladder; 2. R8903#1; 3. R8903#2; 4.R8903#3). The purified band was ligated into pET9a plasmid to generate pET9a-lysK165.

To transfer the D8901 inserts from pET9a plasmid (pET9a-lysK165) into a T7 plasmid, the bands were amplified by PCR with primers D262 (SEQ ID NO: 55) and D640 (SEQ ID NO: 56) (data not shown).

Construction of the ompA-Signal Peptide Sequence.

The inventors added an OmpA signal sequence to the N-terminus of the lysK165. The OmpA full length DNA is as follows: 5'-ATGAAAAAGACAGCTATCGCGATT-GCAGTGGCACTGGCTGGTTTCGCTACCG-TAGCGCAGGCC-3' (SEQ ID NO: 59). The four overlapping primers (D8904-D8907; SEQ ID NO: 60-63) are used to sequentially add the OmpA sequence to the LysK165 fragment (or other lysK fragment).

Construction of the ompA-Signal Peptide Sequence on the Various AMPs

The inventors also added OmpA to AMP constructs for the pET9a expression vector, using the universal D8907 primer system originally developed for the ompA-lysK. For addition of OmpA to J589.K4 (P511), primers D8907 (SEQ ID NO: 63) and I301_4 (SEQ ID NO: 46) were used. For addition of OmpA to J6084.H2 (P512), primers D8907 (SEQ ID NO: 63) and I302_4 (SEQ ID NO: 51) were used. For addition of OmpA to J6123.D7 (P513), primers D8907 (SEQ ID NO: 63) and I303_4 (SEQ ID NO: 53) were used.

Example 5

Suppression of Resistance—Demonstration of the Feasibility of Using T7 Expressing LysK165 or AMPs for Long-Term Sterilization of a Culture The inventors assessed a large range of dilutions of antimicrobial peptide-engineered bacteriophages to determine the effects of inoculum on the effectiveness of the treatment. The inventors used a starting concentration of 100,000,000 phage particles per milliliter (PFU/ml) and diluted those ten-fold until reaching a concentration of 0.1 PFU/mL. As demonstrated in FIGS. 19-26, the effect of the antimicrobial peptide-engineered phages on killing and eliminating bacteria was assessed. Note, the no phage controls are not shown, as these had the same efficacy as the 10-1 PFU/mL sample (data not shown). As demonstrated in FIG. 19 for the wildtype non-engineered bacteriophage (control), an inoculum of more than 10 phages (i.e. 100+ phages/mL) is necessary to initially sterilize the culture. The inventors used T7.415-1b bacteriophage as the control, which is referred to as the wildtype bacteriophage which is used as a baseline efficacy which is used to compare improved efficacy or killing of the antimicrobial peptide-engineered phages. All samples were run in duplicate and SD calculated (data not shown). FIGS. 20 and 21 demonstrate killing by T7.LysK165 and T7.J6084.H2 respectively.

Improvements in Repression of Culture Over Long Periods of Time.

The inventors demonstrate that the phage concentrations used to guarantee complete initial sterilization of the culture must be at least 10,000 phages/mL in order to determine the phage and the inserted gene product beneficial effects. Utilizing a starter culture at an OD600-0.2 the inventors assayed the effect of the different dilutions from about 10,0000,000 PFU/ml to 10,000 phages per mL.

The inventors assessed three exemplary representative recombinant chimeric T7 bacteriophages as well as the non-engineered control bacteriophage T7.415-1b. The assay time was 40 hrs in order to properly assess the effect of the AMP expressed by the engineered bacteriophage to suppress the evolution and outgrowth of resistant strains of bacteria.

The inventors used BL21 *E. coli* bacteria, a reference strain that can be easily infected with T7 bacteriophage, yet does develop a fast onset resistance, as can be seen in FIG. 23, where the bacteria start entering the exponential growth phase again after roughly 10-11 h of lag phase. Also, it is important to note that this regrowth, i.e. the emergence of the resistant form of the bacteria is not concentration dependent. Furthermore the decline in optical density after 20-23 h can be attributed to any number of factors known to people skilled in the art and enumerated in the literature, such as, for example, but not limited to evaporation, nutrient limitation and cannibalism in the culture, changes in the physical makeup of the cells, which increases scatter and affects transmission.

The inventors demonstrate that the engineered T7.lysK165 bacteriophage was effective at completely sterilize the culture 100% of the time with the addition of at least about 10,000 PFU/mL (See FIG. 24). T7.J6084.H2 and T7.ompA-J589.K4 were also demonstrated to be effective at sterilizing the cultures for a long time period (e.g. over 40 hrs) at higher concentrations (see FIG. 25 and FIG. 26).

Example 6

Treatment of a Mixed Culture Containing Variants of the Same Species of Bacteria that are not Able to be Infected as Well as a Susceptible Population The inventors demonstrated that engineering of bacteriophages to express AMPS enables the long-term sterilization of cultures with low concentrations of non-lytic as well as lytic antimicrobial peptide-engineered bacteriophages. The expression of the genomic payload of lytic peptides and proteins increases the utility of the engineered bacteriophage to treat heterologous infections. The inventors demonstrate this capability by co-culturing an *E. coli* host strain with an *E. coli* strain that expresses capsular polysaccharide K which protects that strain from bacteriophage infection. The inventors demonstrate that the expressed, lytic protein lysK165 expressed from the antimicrobial peptide-engineered bacteriophage was able to lyse the *E. coli* strain that expresses capsular polysaccharide K, as well and sterilize the heterogeneous *E. coli* culture completely.

Example 7

Sterilization of Heterologous Cultures Containing Gram-Negative and Gram-Positive Bacteria The inventors also demonstrate the feasibility of treating mixed gram-negative and gram-positive infections, by co-culturing *E. coli* with *Staphylococcus aureus*. The bacteriophage is not able to infect *S. aureus*, but lysK165 is able to complete lyse the staphylococcal population.

Sequences of Genetically Engineered Lytic Bacteriophages are disclosed in the Sequence Listing. The starting sequence used for restriction cloning all fragment into is the T7 Select System's T7.415-1b vector from Novagen, according to the manufactures instructions. The form in which the starting genetic material was provided were two arms made out of the linear T7 genome, digested with the restriction endonucleases Eco RI and Hind III, respectively, yielding fragments of 21498 bp and 15797 bp, respectively.

SEQ ID NO: 64 is the nucleic acid sequence for the vector for T7.LysK165. SEQ ID NO: 65 is the nucleic acid sequence for the vector for T7.J6084.H2. SEQ ID NO: 66 is the nucleic acid sequence for the vector for T7.J589.K4; SEQ ID NO: 67 is the nucleic acid sequence for the vector for T7.J6123.D7; SEQ ID NO: 68 is the nucleic acid sequence for the vector for T7.ompA-J589.K4; SEQ ID NO: 69 is the nucleic acid sequence for the vector for T7.ompA- J6084.H2 and SEQ ID NO: 70 is the nucleic acid sequence for the vector for T7.ompA-J6123.D7.

Example 8

Design of the Engineered M13 Phages

In addition to developing resistance to antibiotics, bacteria are also able to develop resistance to phage themselves. To address this issue we have encoded DNA sequences that induce the expression of antimicrobial agents, which are toxic to the host bacteria. We are thus using phage as a delivery vehicle for toxic antimicrobial peptides that can act on the extracellular surfaces of bacteria. In essence, this transforms host cells into mini antimicrobial peptide factories. Once enough peptide has accumulated inside the host cell to kill it, the host cell lyses and releases the peptides into its surroundings and induces lysis of other surrounding bacterial cells.

The inventors engineered non-lytic M13 bacteriophages to express and release prospective antimicrobial agents, such as AMPs during infection. The inventors cloned sequences encoding for three selected antimicrobial peptides in the genome of the M13 bacteriophage and under the regulation of promoters of various strengths. As a proof of concept, the inventors demonstrated that expressing three different ponericin antimicrobial peptides[1]; Ponericin W3 (SEQ ID NO: 40), Ponericin W5 (SEQ ID NO: 42), Ponericin W1 (SEQ ID NO: 44) from M13 bacteriophages resulted in strong growth inhibition as well as strong bactericidal properties. These AmPs induced cellular lysis by targeting and disrupting the bacterial cell membrane of both gram positive and gram-negative bacteria. The minimum inhibitory concentration (MIC) of these AmPs was measured and reported in Table 4.

The inventors also encoded for the expression of CHAP165 (SEQ ID NO: 71), an optimized version of the phage lysine, LysK[2], isolated from staphylococcal phage K and truncated to the first 165 amino acid of its cysteine- and histidine-dependent amidohydrolase/peptidase domain[3]. This CHAP165 truncated version has an MIC of ~0.3 ug/ml (ROSS 2009) and has been reported to be a potential new enzybiotics[4] and demonstrates twice stronger lytic activity against antibiotic-resistant staphylococci than the natural LysK enzyme. The enzyme targets and degraded the bacterial cell wall peptidoglycan, and forms a hole in the cell's membrane.

The expression of these antimicrobial peptides (AMPs) and antimicrobial polypeptide enzymes were placed under the regulation of either the pLtetO promoter (SEQ ID NO: 73) constitutively expressed in EMG2 *E. coli* or under the regulation of the strong pTRC promoter induced by IPTG. The pLtetO promoter is inducible in the presence of the TetR repressor and is thus constitutively on in EMG2 cells, which lack TetR[5].

Finally, the engineered phages were built with or without an Omp signaling sequence (SEQ ID NO: 78) fused to the antimicrobial peptides/enzyme. The Omp signaling portion directs the translated precursor peptides/enzyme (also referred herein as "pro-antimicrobial peptide") for exogenous secretion from the cell. Upon secretion, the Omp sequence is cleaved and the AmP or enzyme are released in the media surrounding the bacteria. The inventors demonstrated the presence of the Omp sequence influenced the resulting cidal activity of the engineered phages.

TABLE 4

MIC and amino acid sequence of the peptides and enzymes used.

| Label | Name | Amino Acid Sequence | $MIC_{EC}$ | $MIC_{SA}$ |
|---|---|---|---|---|
| J589_K4 | Ponericin W3 | GIWGTLAKIGIKAVPRVISMLKKKKQ (SEQ ID NO: 40) | 16 ug/ml | 8 ug/ml |
| J6084_H2 | Ponericin W5 | FWGALIKGAAKLIPSVVGLFKKKQ (SEQ ID NO: 42) | 64 ug/ml | 4 ug/ml |
| J6123_D7 | Ponericin W1 | WLGSALKIGAKLLPSVVGLFKKKKQ (SEQ ID NO: 44) | 32 ug/ml | 4 ug/ml |
| LysK165 | CHAP165 | AKTQAEINKRLDAYAKGTVDSPYRVKKATSYDPSFGVMEAGAIDADGYYHAQCQDLITDYVLWLTDNKVRTWGNAKDQIKQSYGTGFKIHENKPSTVPKKGWIAVFTSGSYEQWGHIGIVYDGGNTSTFTILEQNWNGYANKKPTKRVDNYYGLTHFIEIPVKA (SEQ ID NO: 71) | Not available | 0.3 ug/ml |
| Omp | Omp | KKTAIAIAVALAGFATVAQA (SEQ ID NO: 72) | For signaling only | |

Construction of the Engineered M13 Phages

The inventors our engineered M13 phage using the natural M13mp18 commercially available through Novogen as a starting point. The DNA cassette encoding for the functions described above is cloned with the vector multiple cloning site between the unique site Kpn I and the unique HindIII cut site. Table 5 shows the nucleic acid sequences encoding elements useful in engineering of AMP or antimicrobial polypeptide-expressing bacteriophages, with or without the OMP signal sequence at the 5' end of the AMP or antimicrobial enzyme (e.g. CHAP165). The circular single stranded DNA sequence composing the M13mp18 genome is shown as SEQ ID NO: 108.

TABLE 5

| Nucleotide sequence for different engineered components | | |
|---|---|---|
| Label | Function | DNA encoding Sequence |
| pLtetO | Promoter | Tccctatcagtgatagagattgacatccctatcagtgatagagatactgagca catcagcaggacgcactgacc (SEQ ID NO: 73) |
| pTRC | Promoter | ccatcgaatggctgaaatgagctgttgaca attaatcatccggctcgtataatgtgtggaattgtgagcggataacaatttca cac (SEQ ID NO: 74) |
| RBS | Ribosome binding sequence | Attaaagaggagaaa (SEQ ID NO: 75) |
| KpnI | Cut site | Ggtacc (SEQ ID NO: 76) |
| atg | Start codon | Atg (SEQ ID NO: 77) |
| Omp | Signaling sequence | Aaaaagacagctatcgcgattgcagtggcactggctggtttcgctaccgtagc gcaggcc (SEQ ID NO: 78) |
| J589_K4 Ponericin W3 | Antimicrobial peptide | Ggcatttggggcaccctggcgaaaattggcattaaagcggtgccgcgcgtgat tagcatgctgaaaaaaaaaaaacag (SEQ ID NO: 79) |
| J6084_H2 Ponericin W5 | Antimicrobial peptide | Ttttggggcgcgctgattaaaggcgcggcgaaactgattccgagcgtggtggg cctgtttaaaaaaaaacag (SEQ ID NO: 80) |
| J6123_D7 Ponericin W1 | Antimicrobial peptide | Tggctgggcagcgcgctgaaaattggcgcgaaactgctgccgagcgtggtggg cctgtttaaaaaaaaaaaacag (SEQ ID NO: 81) |
| LysK165 CHAP165 | Antimicrobial Enzyme | Gctaagactcaagcagaaataaataaacgatagatgcttatgcaaaaggaaca gtagatagccatacagagttaaaaaagctacaagttatgacccatcatttggt gtaatggaagcaggagccattgatgcagatggttactatcacgctcagtgtca agaccttattacagactatgttttatggttaacagataataaagttagaactt ggggtaatgctaaagaccaaattaaacagagttatggtactggatttaaaata catgaaaataaaccttctactgtacctaaaaaaggaggattgeggtatttaca tccggtagttatgaacagtggggtcacataggtattgtatatgatggaggtaa tacttctacatttactattttagagcaaaactggaatggttatgctaataaaa aacctacaaaacgtgtagataattattacggattaactcacttcattgaaata cctgtaaaagca (SEQ ID NO: 82) |
| Stop | Stopcodon | Taa (SEQ ID NO: 83) |
| HindIII | Cut site | Aagctt (SEQ ID NO: 84) |
| Terminator T1 | terminator | Ggcatcaaataaaacgaaaggctcagtcgaaagactgggccatcgattatctg agtagtcggtgaacgctctcctgagtaggacaaatccgccgccctaga (SEQ ID NO: 85) |

Cloning Steps for the Construction of the M13 Phage Stock

AMP sequences were generated using PCT amplification with correct KpnI/HindIII cut sites. The sequences shown in cut sites required for cloning in the M13 genome. Table 7E shows the primer combination in order to amplify AMPs with OmpA signal sequence attached.

TABLE 10

| | Template 1 ul | F primer 0.5 ul | R primer 0.5 ul | Expected PCR product |
|---|---|---|---|---|
| 1 | P525 (SEQ ID NO: 45) | D9001 (SEQ ID NO: 93) | D9002 (SEQ ID NO: 87) | OmpA-Amp1 |
| 2 | P529 (SEQ ID NO: 48) | D9001 (SEQ ID NO: 93) | D9003 (SEQ ID NO: 88) | OmpA-Amp2 |
| 3 | P533 (SEQ ID NO: 42) | D9001 (SEQ ID NO: 93) | D9003 (SEQ ID NO: 88) | OmpA-Amp3 |
| 4 | M8906 (SEQ ID NO: 92) | D9001 (SEQ ID NO: 93) | D9007 (SEQ ID NO: 94) | OmpA-LysK |
| 5 | M8906 (SEQ ID NO: 92) | D9008 (SEQ ID NO: 95) | D9007 (SEQ ID NO: 94) | LysK |

Table 7C demonstrate template DNA for generating DNA encoding AMPs. The sequence in Table 7D are the primers used to amplify the original NdeI and BamHI cut sides to the KpnI and HindIII cut sites required for cloning in the M13 genome. For cloning of the OmpA-LysK and LysK with correct KpnI/HindIII cut sites, the template of SEQ ID NO: 92 was amplified using primers of SEQ ID NO: 93, 94 and 95 to amplify CHAP165 and Omp.CHAP165 to change the original NdeI and BamHI cut sides to the KpnI and HindIII Preparation of the M13 Vector To prepare the M13 vector for the AMP inserts, the inventors performed a restriction digest of M13ΔLexA3 vector (SEQ ID NO: 108) with KpnI and HindIII. The inventors PCR amplified the inserts from Table 10, and digested with KpnI and HindIII for insertion and ligation into the KpnI/Hind III linearized M13ΔLexA3 vector. The ligated M13ΔLexA3 vector with inserted nucleic acid encoding AMPs (or antimicrobial polypeptide/enzyme) was used to transform XL-1 Blue supercompetent cells according to ordinary methods known in the art.

For clarity purposes, the nucleic acid sequences encoding the AMPS, wither with or without the OmpA signal sequence which are expressed by the engineered bacteriophages is shown in Table 6. The AMP-engineered M13 phages were amplified overnight in a mid-log culture of XL-10 *E. coli* cells. Infective phage solutions were obtained by centrifuging infected cultures for 5 min at 16,100 g and collecting supernatants followed by filtration through a Nalge #190-2520 0.2 μm filters.

The infective phage solutions were tittered to obtain the PFUs count by serial dilutions of phage performed in 1×PBS to 200 μl of overnight XL-10 cells in 3 ml top agar, 1 mM IPTG, and 40 μl of 20 mg/ml X-Gal, and poured the mixture onto LB agar chloramphenicol (30 ug/ml) plates. After overnight incubation at 37° C., plaques were counted. All infective phage solution were then standardized to a phage concentration of $10^9$ PFU/ml by dilution in LB media.

TABLE 6

| DNA | Sequence | Length |
|---|---|---|
| OmpA | atgAAAAAGACAGCTATCGCGATTGCAGTGGCACTGGCTGGTTTCGCTACCGT AGCGCAGGCC (SEQ ID NO: 59) | 63 |
| OmpA-AMP1 | Ggtaccatgaaaaagacagctatcgcgattgcagtggcactggctggtttcgc taccgtagcgcaggccggcatttggggcaccctggcgaaaattggcattaaag cggtgccgcgcgtgattagcatgctgaaaaaaaaaaaacagtaaaagat (SEQ IDNO: 96) | 156 |
| OmpA-AMP2 | Ggtaccatgaaaaagacagctatcgcgattgcagtggcactggctggtttcgc taccgtagcgcaggcctttggggcgcgctgattaaaggcgcggcgaaactga ttccgagcgtggtgggcctgataaaaaaaaacagtaaaagat (SEQ ID NO:97) | 150 |
| OmpA-AMP3 | Ggtaccatgaaaaagacagctatcgcgattgcagtggcactggctggtttcgc taccgtagcgcaggcctggctgggcagcgcgctgaaaattggcgcgaaactgc tgccgagcgtggtgggcctgataaaaaaaaaaaacagtaaaagat (SEQ ID NO: 98) | 153 |
| OmpA-AMP4 | ggtaccatgaaaaagacagctatcgcgattgcagtggcactggctggtttcgc taccgtagcgcaggccatgATTCTGCCGTGGAAATGGCCGTGGTGGCCGTGGC GCCGCTAAaagctt (SEQ ID NO: 99) | 120 |
| OmpA-AMP5 | ggtaccatgaaaaagacagctatcgcgattgcagtggcactggctggtttcgc taccgtagcgcaggccatgAGCTGGCTGAGCAAAACCGCGAAAAAACTGGAAA ACAGCGCGAAAAAACGCATTAGCGAAGGCATTGCGATTGCGATTCAGGGCGGC CCGCGCTAAaagctt (SEQ ID NO: 100) | 174 |
| OmpA-Lysk | Ggtaccatgaaaaagacagctatcgcgattgcagtggcactggctggtttcgc taccgtagcgcaggcc (SEQ ID NO: 101) | 555 |
| AMP1-only | Ggtaccatgggcataggggcaccctggcgaaaattggcattaaagcggtgccg cgcgtgattagcatgctgaaaaaaaaaaaacagtaaaagctt (SEQ ID NO: 102) | 96 |
| AMP2-only | Ggtaccatgttttggggcgcgctgattaaaggcgcggcgaaactgattccgag cgtggtgggcctgtttaaaaaaaaacagtaaaagctt (SEQ ID NO: 103) | 90 |
| AMP3-only | Ggtaccatgtggctgggcagcgcgctgaaaattggcgcgaaactgctgccgag cgtggtgggcctgtttaaaaaaaaaaaacagtaaaagctt (SEQ ID NO: 104) | 93 |
| AMP4-only | atgATTCTGCCGTGGAAATGGCCGTGGTGGCCGTGGCGCCGCTAA_(SEQ ID NO: 105) | 45 |
| AMP5-only | atgAGCTGGCTGAGCAAAACCGCGAAAAAACTGGAAAACAGCGCGAAAAAA CGCATTAGCGAAGGCATTGCGATTGCGATTCAGGGCGGCCCGCGCTAA (SEQ ID NO: 106) | 99 |
| LysK-only | TGCTTTTACAGGTATTTCAATGAAGTGAGTTAATCCGTAATAATTATCTACA CGTTTTGTAGGTTTTTTATTAGCATAACCATTCCAGTTTTGCTCTAAAATAGT AAATGTAGAAGTATTACCTCCATCATATACAATACCTATGTGACCCCACTGT TCATAACTACCGGATGTAAATACCGCAATCCAACCTTTTTTAGGTACAGTAG AAGGTTTATTTTCATGTATTTTAAATCCAGTACCATAACTCTGTTTAATTTGG TCTTTAGCATTACCCCAAGTTCTAACTTTATTATCTGTTAACCATAAAACATA GTCTGTAATAAGGTCTTGACACTGAGCGTGATAGTAACCATCTGCATCAATG GCTCCTGCTTCCATTACACCAAATGATGGGTCATAACTTGTAGCTTTTTTAAC TCTGTAAGGGCTATCTACTGTTCCTTTTGCATAAGCATCTAAACGTTTATTTA TTTCTGCTTGAGTCTTAGC (SEQ ID NO: 107) | 492 |

Example 9

Antimicrobial Activity of the Engineered M13 Phages

The M13 phage is non-lytic lysogenic bacteriophages specific to *E. coli*. Infection with filamentous phages is not lethal, however the infection causes turbid plaques in *E. coli* and decreases the rate of cell growth seen in the infected cells. The M13 phage infects the cell by attaching to the receptor at the tip of the F pilus of the host *E. coli* cells. In the absence of the F pilus, M13 phages are no able to infect and replicate in *E. coli* cells.

Therefore, the inventors first measured the antimicrobial activity of our engineered phages activity against the strain ER2738 *E. coli* strain in which the F' pilus is selected for using tetracycline. Treatment of a mid-log culture of *E. coli* ER2738 with wild type M13 bacteriophage (M13.wt) reduced the bacterial culture from 8.4 to 6.6 $\log_{10}$(CFU/mL) at 2 hours post treatment (27). The AMP-engineered M13 phages expressing CHAP165 (M13.PLtetO.Omp.CHAP165) provided a 10,000-fold improvement over the wild-type (non-engineered) M13 phage and reduced the bacterial culture to 4.9 $\log_{10}$ (CFU/ml) at 20 hours post treatment. The engineered M13 phage expressing PonW3 (M13.PTRC.PonW3 and M13.PRTC.Omp.PonW3) provided a 20-fold improvement over wild-type M13 phage and reduced bacterial counts to 5.5 $\log_{10}$ (CFU/ml) in the first 2 hours. Thus, FIG. 27 demonstrates the strong antimicrobial activity of the AMP-engineered, or CHAP165-engineered M13 phages in ER2738, an *E. coli* strain engineered to maintain the F pilus.

The inventors then demonstrate that the engineered M13 bacteriophages is also effective in wild type and clinically relevant EMG2 *E. coli* strain that evolves freely and is subject to potentially losing the F-pilus necessary for infection by M13. FIG. 28 demonstrates the optical density measure at absorbance 600 nm of a mid-log growing culture of *E. coli* EMG2 infected with different M13 phages. Treatment with the natural M13mp18 phages (M13mp18) delays the growth of EMG2 starting 2 hours post infection. The cells then adapt and resist to the presence of the phage and continue their growth starting at 3 hours. After 10 hours post infection, the culture treated with M13mp18 have reached the same density as the untreated culture. The mechanism by which the cells adapt and resist the wild type M13mp18 involved a long term genetic change since cells isolated after 25 post infection and regrown to mid-log phase are entirely resistant to the wild type M13mp18 (data not shown). This demonstrates resistance to wild type *E. coli* due to a loss in F pilus.

The AMP or CHAP165-engineered M13 phages were demonstrated to have an enhanced antimicrobial and inhibitory effect on the EMG2 culture. The initial decrease in the cell growth takes longer to manifest itself, likely due to the additional a load on the phage genome to produce the added peptides and enzyme at high rate slows the phage's rate of replication in the cell and extend the life cycle. The density of the culture then decreases slightly and stabilizes around 10 hours post-infection at an OD of ~0.6 instead of an OD of ~1 for the culture untreated or treated with wild type M13mp18. The growth inhibition of the culture is attributed to the expression and release of the antimicrobial peptides or antimicrobial enzyme by the host *E. coli* cells. Thus the inventors have demonstrated, as shown in FIG. 28, that by engineering antimicrobial agents in the M13 phage genome, the inventors can inhibit the growth and proliferation of a wild type clinically relevant *E. coli* strain and reduce extent of resistance to the M13 phage by decreasing the density of resistant bacteria.

Next, the inventors demonstrate that not only the density but also the viability of the resistant EMG2 is upon engineering of the M13 phage. FIG. 29 shows the count in viable of cells over time post treatment with the engineered and wild type phage. While the viable cell count of all engineered-M13 treated cultures dips in the $1^{st}$ hour, after 2 hours, the count for the culture treated with the wild type phage reaches that of the untreated sample indicating that resistance to the wild-type M13 phage has formed. It should also be noted that the time require for resistance to occur is less for the EMG2 culture (~4 hours) than it is for the ER2738 culture (>8 hours) since the EMG2 cells are able to loose the F pilus necessary for M13 infection and propagation. The AMP or CHAP165-engineered M13 phages results in a 4 to 6 hours delay before the viable count reaches that of the untreated control. Most strikingly, the AMP or CHAP165-engineered M13 phages expressing Omp and the truncated LysK, CHAP165 (M13.pLTETO.Omp.CHA165) shows a very strong and long term bactericidal effect on the EMG2 culture. Even at 20 hours post treatment, the count of resistant cells is stable and at 10^5 CFU/ml for M13.pLTETO.Omp.CHA165 treated cells instead of 10^9 CFU/ml for untreated or wild-type treated culture samples.

Broad Spectrum Bacterial Killing Properties of AMP and Antimicrobial Polypeptide/Enzyme Engineered M13 Phages The inventors also demonstrate that the release of antimicrobial peptides/enzyme from the host bacterial cells increases and broadens the bacterial host activity spectrum and inhibit growth cells that the M13 phages cannot infect, allowing the AMP and antimicrobial polypeptide/enzyme engineered M13 phages to kill and eliminate M13 resistant cells and/or cells form another bacterial strain such as *Staph aureus* in which the M13 phage cannot replicate.

The inventors isolated the media in which the antimicrobial agents were released. The inventors next infected a growing mid-log culture of EMG2 with the different wild-type and engineered M13 phage. At 6 hours post infection, the EMG2 cells were centrifuged at 13,000 g and filtered through a 0.2 um membrane to collect sterile media with the released AmP and enzyme. The media was replenished in nutrients by adding 5× concentrated LB solution. Mid-log *Staph* bacteria where then inoculated in the media at a concentration of $10^5$ CFU/ml. The *staph* growth was monitored by OD and the results are shown in FIG. 30.

The media from untreated EMG2 shows and shown as the "No Phage" control shows results in the typical inhibited *staph* growth curve. Media containing M13mp18 shows a similar growth profile but with a slightly *staph* growth inhibition for densities above OD600=1. On the other hand, media in which PonW3 (SEQ ID NO: 40) has been released by the host EMG2 cells result in a clear delay in the growth of *staph aureus*. For example, the "no phage" or the "m13 mp 18" *staph* culture reach an OD of 0.8 within 4 hours whereas the "M13.pTRC.Omp.PonW3" media containing PonW3 (SEQ ID NO: 40) causes a growth delay by another 4 hours, the culture reaches the same OD of 0.8 only after 8 hours of growth. Finally, release of CHAP165 in the surrounding media due to phage reengineering limited *staph* growth to an OD level of 0.8 while compared to 1.6 for the no phage control and 1.2 for the wild M13mp18. These results show that inducing production of antimicrobial peptides/enzymes from a host cells via bacteriophage reengineering results in growth inhibition and reduce bacterial cell densities for all surrounding bacteria including those bacteria that are resistant to or unaffected by the phage. Therefore, the inventors have demonstrated an orthogonal antimicrobial properties to the engineered M13 phage, and effectively broadened its effect to a range of bacterial species host cells.

One key advantage of the discovery of the antimicrobial-agent engineered bacteriophage, e.g. AMP-engineered bacteriophage technology disclosed herein is the ability to yield bacteriophages with improved antimicrobial activity and a broader spectrum of bacterial host species activity. Accordingly, this enables a new array of applications and greatly facilitates the FDA approval process for the use of bacteriophages. For example, current strategies using bacteriophages to target bacterial infections require natural non-engineered bacteriophages to be used in phage cocktails, i.e. combinations of different phages to target a variety of different bacterial strains. The inventors gave discovered herein that bacteriophages with the ability to target and kill a broad spectrum of host bacteria can be obtained without the need of bacteriophage combination cocktails, but instead through the genetic engineering of one single bacteriophage to increase the antimicrobial activity and infectivity of a broad range of bacterial host cells. Accordingly, the inventors have generated an antimicrobial-agent engineered bacteriophage, e.g. AMP-engineered bacteriophage which can be used to treat and eliminate a heterogeneous bacterial population comprising a variety of different bacterial host species, thus making the FDA approval process faster, easier and less costly by eliminating the need to multiple FDA approvals for a cocktail of bacteriophages to target each bacteria host species separately. The antimicrobial agent engineered bacteriophages can be used in, for example, but not limited to, the medical industry, the food processing industry, the defense sector, the agricultural sector, the sanitation sector and other such industries where elimination of bacterial populations which contain multiple bacterial species is desirable.

The antimicrobial-agent engineered bacteriophages can also be used in specific products and services. For example, the antimicrobial-agent engineered bacteriophage, e.g. AMP-engineered bacteriophages can be formulated in liquid or tablet forms for medical, food processing, agricultural, sanitization and defense purposes. The engineered phages can also be packaged in tablets sold for sterilization of water storage tanks or in liquid forms used for various sterilization purposes ranging from open wounds, sites of surgery in patients or even the clinical operating rooms. Such antimicrobial-agent engineered bacteriophage, e.g. AMP-engineered bacteriophages can be used in the farming industry to replace current antibiotics and prevent the rise of drug resistant bacteria in food stocks. Similarly the antimicrobial-agent engineered bacteriophage, e.g. AMP-engineered bacteriophages can be used to prevent bacterial contamination by food borne pathogens of crops or food products and would be used in food processing plants for meat, dairies and fresh vegetables.

TABLE 7

Non-Limiting Examples of Bacteria, Primers, Bacteriophages, and Templates

TABLE 7A: Examples of Bacteria

| | | |
|---|---|---|
| *Staphylococcus aureus* | *Nisseria menigintidis* | *Helicobacter pylori* |
| *Bacillus anthracis* | *Nisseria gonerrhoeae* | *Legionella pnemophilia* |
| *Bacillus cereus* | *Vibrio cholerae* | *Borrelia burgdorferi* |
| *Bacillus subtillis* | *Escherichia coli* K12 | *Ehrlichia chaffeensis* |
| *Streptococcus pneumoniae* | *Bartonella henselae* | *Treponema pallidum* |
| *Streptococcus pyogenes* | *Haemophilus influenzae* | *Chlamydia trachomatis* |
| *Clostridium tetani* | *Salmonella typhi* | |
| *Listeria monocytogenes* | *Shigella dysentriae* | |
| *Mycobacterium tuberculosis* | *Yersinia pestis* | |
| *Staphylococcus epidermidis* | *Pseudomonas aeruginosa* | |

TABLE 7B

| Primers used in generation of the antimicrobial peptide engineered bacteriophages | |
|---|---|
| P511 | AGTAAACATATGGGCATTTGGGGCACCCTGGCGAAAATTGGCATTAAAGCGGTGCCGCG**CGTGATTAGCATGCTGAAAAAAAAAAAACAGTAAGGATCCTCGAT** (SEQ ID NO: 45) |
| I301_4 | **ATCGAGGATCCTTACTGTTTTTTTTTTTTCAGCATGCTAATCACG** (SEQ ID NO: 46) |
| I301_1 | AGTAAACATATGGGCATTTGGGGCACCCTGGCGAAA (SEQ ID NO: 47) |
| P512 | AGTAAACATATGTTTTGGGGCGCGCTGATTAAAGGCGCGGCGAAACTGATTCC**GAGCGTGGTGGGCCTGTTTAAAAAAAAACAGTAAGGATCCTCGAT** (SEQ ID NO: 48) |
| I302_1 | **AGTAAACATATGTTTTGGGGCGCGCTGATTAAAG** (SEQ ID NO: 49) |
| I303_4 | 5' ATCGAGGATCCTTACTGTTTTTTTTTTTTAAACAGGCCCACCACG (SEQ ID NO: 50) |
| I302_4 | 5' ATCGAGGATCCTTACTGTTTTTTTTTAAACAGGCCCACCACGCTC (SEQ ID NO: 51) |

TABLE 7B -continued

Primers used in generation of the antimicrobial peptide engineered bacteriophages P513　　AGTAAACATATGTGGCTGGGCAGCGCGCTGAAAATTGGCGCGAAACTGCTGCC
　　　　 GAGCGTGGTGGGCCTGTTTAAAAAAAAAAAACAGTAAGGATCCTCGAT
　　　　 (SEQ ID NO: 52)

I303_4　ATCGAGGATCCTTACTGTTTTTTTTTTTAAACAGGCCCACCACG (SEQ ID
　　　　 NO: 53)

I303_1　AGTAAACATATGTGGCTGGGCAGCGCGCTGAAAATTGG (SEQ ID NO: 54)

D262　　tactcGAATTCTTAAgTAAcTAAcgaaattaatacgactc (SEQ ID NO: 55)

D640　　AAATATaagcttCGGGCTTTGTTAGCAGCC (SEQ ID NO: 56)

D8901　 AGTAAACATATGGCTAAGACTCAAGCAGAAATA 3' (SEQ ID NO: 57)

D8902　 TAGCTGGATCCTTTGAATACTCCCCAGGCA 3' (SEQ ID NO: 58)

ompA full　ATGAAAAAGACAGCTATCGCGATTGCAGTGGCACTGGCTGGTTTCGCTACCGTA
length　　GCGCAGGCC-3' (SEQ ID NO: 59)

D8904　 CGTAGCGCAGGCCATGGCTAAGACTCAAGCAGAAATA (SEQ ID NO: 60)

D8905　 GCACTGGCTGGTTTCGCTACCGTAGCGCAGGCCatggctaag (SEQ ID NO: 61)

D8906　 CAGCTATCGCGATTGCAGTG GCACTGGCTGGTTTCGCTAC (SEQ ID NO: 62)

D8907　 agtaaacatatgAAAAAGA CAGCTATCGC GATTGCAGTG (SEQ ID NO: 63)

TABLE 7C

Template and Primers used in generation of the antimicrobial peptide engineered bacteriophages

| Ultramer Code | Sequence | AmP |
| --- | --- | --- |
| P511 | AGTAAACATATGGGCATTTGGGGCACCCTGGCGAAAATTGGCA TTAAAGCGGTGCCGCGCGTGATTAGCATGCTGAAAAAAAAAAA ACAGTAAGGATCCTCGAT (SEQ ID NO: 45) | AmP1 (J589_K4) |
| P512 | AGTAAACATATGTTTTGGGGCGCGCTGATTAAAGGCGCGGCGA AACTGATTCCGAGCGTGGTGGGCCTGTTTAAAAAAAAAACAGTA AGGATCCTCGAT (SEQ ID NO: 48) | AmP2 (J6084_H2) |
| P513 | AGTAAACATATGTGGCTGGGCAGCGCGCTGAAAATTGGCGCGA AACTGCTGCCGAGCGTGGTGGGCCTGTTTAAAAAAAAAAAACA GTAAGGATCCTCGAT (SEQ ID NO: 49) | AmP3 (J6123_D7) |
| M8906-TMC | CATATGatgAAAAAGACAGCTATCGCGATTGCAGTGGCACTGGCT GGTTTCGCTACCGTAGCGCAGGCCGCTAAGACTCAAGCAGAAA TAAATAAACGTTTAGATGCTTATGCAAAAGGAACAGTAGATAG CCCTTACAGAGTTAAAAAAGCTACAAGTTATGACCCATCATTTG GTGTAATGGAAGCAGGAGCCATTGATGCAGATGGTTACTATCA CGCTCAGTGTCAAGACCTTATTACAGACTATGTTTTATGGTTAA CAGATAATAAAGTTAGAACTTGGGGTAATGCTAAAGACCAAAT TAAACAGAGTTATGGTACTGGATTTAAAATACATGAAAATAAA CCTTCTACTGTACCTAAAAAAGGTTGGATTGCGGTATTTACATC CGGTAGTTATGAACAGTGGGGTCACATAGGTATTGTATATGATG GAGGTAATACTTCTACATTTACTATTTTAGAGCAAAACTGGAAT GGTTATGCTAATAAAAAACCTACAAAACGTGTAGATAATTATTA CGGATTAACTCACTTCATTGAAATACCTGTAAAAGCATAGGGAT CCAGCTATAGGGATCCAGCTA (SEQ ID NO: 92) | OmpA-lysK165 |

TABLE 7D

| Template and Primers used in generation of the antimicrobial peptide engineered bacteriophages | | | |
|---|---|---|---|
| Code | Primer | Sequence | Tm |
| D9001 | AmP1-F | **GGTACC**ATGGGCATTTGGGGCACCC (SEQ ID NO: 86) | 61/45 |
| D9002 | AmP1-R | **AAGCTT**TTACTGTTTTTTTTTTTTC AGCATGCTAATCACGCGCGG (SEQ ID NO: 87) | 70/67 |
| D9003 | AmP2-F | **GGTACC**ATGTTTTGGGGCGC (SEQ ID NO: 88) | 54/34 |
| D9004 | AmP2-R | **AAGCTT**TTACTGTTTTTTTTTAAAC AGGCCCACCACGCTC (SEQ ID NO: 89) | 66/63 |
| D9005 | AmP3-F | **GGTACC**ATGTGGCTGGGCAG (SEQ ID NO: 90) | 56/35 |
| D9006 | AmP3-R | **AAGCTT**TTACTGTTTTTTTTTTTTA AACAGGCCCACCACGCTCG (SEQ ID NO: 91) | 68/65 |
| D9001 | KpnI-OmpA-F | GAAGGGTACC**ATGAAAAAGAC** (SEQ ID NO: 93) | 48/14 |
| D9007 | LysK-HindIII-R | GCAGCTttcgaa**CTA**TGCTTTTACA GGTATTTCAATGA (SEQ ID NO: 94) | 65/50 |
| D9008 | KpnI-LysK-F | GCAGCTggtacc**ATG**GCTAAGACTC AAGCAGAAATA (SEQ ID NO: 95) | 61/50 |

TABLE 7E

| shows the primer combination in order to amplify AMPs with OmpA signl sequence attached. | | | |
|---|---|---|---|
| Template 1 ul | F primer 0.5 ul | R primer 0.5 ul | Expected PCR product |
| P525 (SEQ ID NO: 45) | D9001 (SEQ ID NO: 93) | D9002 (SEQ ID NO: 87) | OmpA-Amp1 |
| P529 (SEQ ID NO: 48) | D9001 (SEQ ID NO: 93) | D9003 (SEQ ID NO: 88) | OmpA-Amp2 |
| P533 (SEQ ID NO: 42) | D9001 (SEQ ID NO: 93) | D9003 (SEQ ID NO: 88) | OmpA-Amp3 |
| M8906 (SEQ ID NO: 92) | D9001 (SEQ ID NO: 93) | D9007 (SEQ ID NO: 94) | OmpA-LysK |
| M8906 (SEQ ID NO: 92) | D9008 (SEQ ID NO: 95) | D9007 (SEQ ID NO: 94) | LysK |

TABLE 7F

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Acholeplasma* phage L2 | NC_001447 | 11965 nt | 14 | 0 | 14 |
| *Acholeplasma* phage MV-L1 | NC_001341 | 4491 nt | 4 | 0 | 4 |
| *Acidianus* bottle-shaped virus | NC_009452 | 23814 nt | 57 | 0 | 57 |
| *Acidianus* filamentous virus 1 | NC_005830 | 20869 nt | 40 | 0 | 40 |
| *Acidianus* filamentous virus 2 | NC_009884 | 31787 nt | 52 | 1 | 53 |
| *Acidianus* filamentous virus 3 | NC_010155 | 40449 nt | 68 | 0 | 68 |
| *Acidianus* filamentous virus 6 | NC_010152 | 39577 nt | 66 | 0 | 66 |
| *Acidianus* filamentous virus 7 | NC_010153 | 36895 nt | 57 | 0 | 57 |
| *Acidianus* filamentous virus 8 | NC_010154 | 38179 nt | 61 | 0 | 61 |
| *Acidianus* filamentous virus 9 | NC_010537 | 41172 nt | 73 | 0 | 73 |
| *Acidianus* rod-shaped virus 1 | NC_009965 | 24655 nt | 41 | 0 | 41 |
| *Acidianus* two-tailed virus | NC_007409 | 62730 nt | 72 | 0 | 72 |
| *Acinetobacter* phage AP205 | NC_002700 | 4268 nt | 4 | 0 | 4 |
| *Actinomyces* phage Av-1 | NC_009643 | 17171 nt | 22 | 1 | 23 |
| *Actinoplanes* phage phiAsp2 | NC_005885 | 58638 nt | 76 | 0 | 76 |
| *Acyrthosiphon pisum* secondary endosymbiont phage 1 | NC_000935 | 36524 nt | 54 | 0 | 54 |
| *Aeromonas* phage 25 | NC_008208 | 161475 nt | 242 | 13 | 242 |
| *Aeromonas* phage 31 | NC_007022 | 172963 nt | 247 | 15 | 262 |
| *Aeromonas* phage 44RR2.8t | NC_005135 | 173591 nt | 252 | 17 | 269 |
| *Aeromonas* phage Aeh1 | NC_005260 | 233234 nt | 352 | 23 | 375 |
| *Aeromonas* phage phiO18P | NC_009542 | 33985 nt | 45 | 0 | 45 |
| *Archaeal* BJ1 virus | NC_008695 | 42271 nt | 70 | 1 | 71 |
| *Azospirillum* phage Cd | NC_010355 | 62337 nt | 95 | 0 | 95 |
| *Bacillus* phage 0305phi8-36 | NC_009760 | 218948 nt | 246 | 0 | 246 |
| *Bacillus* phage AP50 | NC_011523 | 14398 nt | 31 | 0 | 31 |
| *Bacillus* phage B103 | NC_004165 | 18630 nt | 17 | 0 | 17 |
| *Bacillus* phage BCJA1c | NC_006557 | 41092 nt | 58 | 0 | 58 |
| *Bacillus* phage Bam35c | NC_005258 | 14935 nt | 32 | 0 | 32 |
| *Bacillus* phage Cherry | NC_007457 | 36615 nt | 51 | 0 | 51 |
| *Bacillus* phage Fah | NC_007814 | 37974 nt | 50 | 0 | 50 |
| *Bacillus* phage GA-1 | NC_002649 | 21129 nt | 35 | 1 | 52 |
| *Bacillus* phage GIL16c | NC_006945 | 14844 nt | 31 | 0 | 31 |
| *Bacillus* phage Gamma | NC_007458 | 37253 nt | 53 | 0 | 53 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Bacillus* phage IEBH | NC_011167 | 53104 nt | 86 | 0 | 86 |
| *Bacillus* phage SPBc2 | NC_001884 | 134416 nt | 185 | 0 | 185 |
| *Bacillus* phage SPO1 | NC_011421 | 132562 nt | 204 | 5 | 209 |
| *Bacillus* phage SPP1 | NC_004166 | 44010 nt | 101 | 0 | 101 |
| *Bacillus* phage TP21-L | NC_011645 | 37456 nt | 56 | 0 | 56 |
| *Bacillus* phage WBeta | NC_007734 | 40867 nt | 53 | 0 | 53 |
| *Bacillus* phage phBC6A51 | NC_004820 | 61395 nt | 75 | 0 | 75 |
| *Bacillus* phage phBC6A52 | NC_004821 | 38472 nt | 49 | 0 | 49 |
| *Bacillus* phage phi105 | NC_004167 | 39325 nt | 51 | 0 | 51 |
| *Bacillus* phage phi29 | NC_011048 | 19282 nt | 27 | 0 | 27 |
| *Bacillus* virus 1 | NC_009737 | 35055 nt | 54 | 0 | 54 |
| *Bacteriophage* APSE-2 | NC_011551 | 39867 nt | 41 | 1 | 42 |
| *Bacteroides* phage B40-8 | NC_011222 | 44929 nt | 46 | 0 | 46 |
| *Bdellovibrio* phage phiMH2K | NC_002643 | 4594 nt | 11 | 0 | 11 |
| *Bordetella* phage BIP-1 | NC_005809 | 42638 nt | 48 | 0 | 48 |
| *Bordetella* phage BMP-1 | NC_005808 | 42663 nt | 47 | 0 | 47 |
| *Bordetella* phage BPP-1 | NC_005357 | 42493 nt | 49 | 0 | 49 |
| *Burkholderia ambifaria* phage BcepF1 | NC_009015 | 72415 nt | 127 | 0 | 127 |
| *Burkholderia* phage Bcep1 | NC_005263 | 48177 nt | 71 | 0 | 71 |
| *Burkholderia* phage Bcep176 | NC_007497 | 44856 nt | 81 | 0 | 81 |
| *Burkholderia* phage Bcep22 | NC_005262 | 63879 nt | 81 | 1 | 82 |
| *Burkholderia* phage Bcep43 | NC_005342 | 48024 nt | 65 | 0 | 65 |
| *Burkholderia* phage Bcep781 | NC_004333 | 48247 nt | 66 | 0 | 66 |
| *Burkholderia* phage BcepB1A | NC_005886 | 47399 nt | 73 | 0 | 73 |
| *Burkholderia* phage BcepC6B | NC_005887 | 42415 nt | 46 | 0 | 46 |
| *Burkholderia* phage BcepGomr | NC_009447 | 52414 nt | 75 | 0 | 75 |
| *Burkholderia* phage BcepMu | NC_005882 | 36748 nt | 53 | 0 | 53 |
| *Burkholderia* phage BcepNY3 | NC_009604 | 47382 nt | 70 | 1 | 70 |
| *Burkholderia* phage BcepNazgul | NC_005091 | 57455 nt | 73 | 0 | 73 |
| *Burkholderia* phage KS10 | NC_011216 | 37635 nt | 49 | 0 | 49 |
| *Burkholderia* phage phi1026b | NC_005284 | 54865 nt | 83 | 0 | 83 |
| *Burkholderia* phage phi52237 | NC_007145 | 37639 nt | 47 | 0 | 47 |
| *Burkholderia* phage phi644-2 | NC_009235 | 48674 nt | 71 | 0 | 71 |
| *Burkholderia* phage phiE12-2 | NC_009236 | 36690 nt | 50 | 0 | 50 |
| *Burkholderia* phage phiE125 | NC_003309 | 53373 nt | 71 | 0 | 71 |
| *Burkholderia* phage phiE202 | NC_009234 | 35741 nt | 48 | 0 | 48 |
| *Burkholderia* phage phiE255 | NC_009237 | 37446 nt | 55 | 0 | 55 |
| *Chlamydia* phage 3 | NC_008355 | 4554 nt | 8 | 0 | 8 |
| *Chlamydia* phage 4 | NC_007461 | 4530 nt | 8 | 0 | 8 |
| *Chlamydia* phage CPAR39 | NC_002180 | 4532 nt | 7 | 0 | 7 |
| *Chlamydia* phage Chp1 | NC_001741 | 4877 nt | 12 | 0 | 12 |
| *Chlamydia* phage Chp2 | NC_002194 | 4563 nt | 8 | 0 | 7 |
| *Chlamydia* phage phiCPG1 | NC_001998 | 4529 nt | 9 | 0 | 9 |
| *Clostridium* phage 39-O | NC_011318 | 38753 nt | 62 | 0 | 62 |
| *Clostridium* phage c-st | NC_007581 | 185683 nt | 198 | 0 | 198 |
| *Clostridium* phage phi CD119 | NC_007917 | 53325 nt | 79 | 0 | 79 |
| *Clostridium* phage phi3626 | NC_003524 | 33507 nt | 50 | 0 | 50 |
| *Clostridium* phage phiC2 | NC_009231 | 56538 nt | 82 | 0 | 82 |
| *Clostridium* phage phiCD27 | NC_011398 | 50930 nt | 75 | 0 | 75 |
| *Clostridium* phage phiSM101 | NC_008265 | 38092 nt | 53 | 1 | 54 |
| *Corynebacterium* phage BFK20 | NC_009799 | 42969 nt | 54 | 0 | 54 |
| *Corynebacterium* phage P1201 | NC_009816 | 70579 nt | 97 | 4 | 101 |
| *Enterobacteria* phage 13a | NC_011045 | 38841 nt | 55 | 0 | 55 |
| *Enterobacteria* phage 933W | NC_000924 | 61670 nt | 80 | 4 | 84 |
| *Enterobacteria* phage BA14 | NC_011040 | 39816 nt | 52 | 0 | 52 |
| *Enterobacteria* phage BP-4795 | NC_004813 | 57930 nt | 85 | 0 | 85 |
| *Enterobacteria* phage BZ13 | NC_001426 | 3466 nt | 4 | 0 | 4 |
| *Enterobacteria* phage EPS7 | NC_010583 | 111382 nt | 170 | 0 | 171 |
| *Enterobacteria* phage ES18 | NC_006949 | 46900 nt | 79 | 0 | 79 |
| *Enterobacteria* phage EcoDS1 | NC_011042 | 39252 nt | 53 | 0 | 53 |
| *Enterobacteria* phage FI sensu lato | NC_004301 | 4276 nt | 4 | 0 | 4 |
| *Enterobacteria* phage Felix 01 | NC_005282 | 86155 nt | 131 | 22 | 153 |
| *Enterobacteria* phage Fels-2 | NC_010463 | 33693 nt | 47 | 0 | 48 |
| *Enterobacteria* phage G4 sensu lato | NC_001420 | 5577 nt | 11 | 0 | 13 |
| *Enterobacteria* phage HK022 | NC_002166 | 40751 nt | 57 | 0 | 57 |
| *Enterobacteria* phage HK620 | NC_002730 | 38297 nt | 58 | 0 | 58 |
| *Enterobacteria* phage HK97 | NC_002167 | 39732 nt | 61 | 0 | 62 |
| *Enterobacteria* phage I2-2 | NC_001332 | 6744 nt | 9 | 0 | 9 |
| *Enterobacteria* phage ID 18 sensu lato | NC_007856 | 5486 nt | 11 | 0 | 11 |
| *Enterobacteria* phage ID2 Moscow/ID/2001 | NC_007817 | 5486 nt | 11 | 0 | 11 |
| *Enterobacteria* phage If1 | NC_001954 | 8454 nt | 10 | 0 | 10 |
| *Enterobacteria* phage Ike | NC_002014 | 6883 nt | 10 | 0 | 10 |
| *Enterobacteria* phage JK06 | NC_007291 | 46072 nt | 82 | 0 | 82 |
| *Enterobacteria* phage JS98 | NC_010105 | 170523 nt | 266 | 3 | 269 |
| *Enterobacteria* phage K1-5 | NC_008152 | 44385 nt | 52 | 0 | 52 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Enterobacteria* phage K1E | NC_007637 | 45251 nt | 62 | 0 | 62 |
| *Enterobacteria* phage K1F | NC_007456 | 39704 nt | 43 | 0 | 41 |
| *Enterobacteria* phage M13 | NC_003287 | 6407 nt | 10 | 0 | 10 |
| *Enterobacteria* phage MS2 | NC_001417 | 3569 nt | 4 | 0 | 4 |
| *Enterobacteria* phage Min27 | NC_010237 | 63395 nt | 83 | 3 | 86 |
| *Enterobacteria* phage Mu | NC_000929 | 36717 nt | 55 | 0 | 55 |
| *Enterobacteria* phage N15 | NC_001901 | 46375 nt | 60 | 0 | 60 |
| *Enterobacteria* phage N4 | NC_008720 | 70153 nt | 72 | 0 | 72 |
| *Enterobacteria* phage P1 | NC_005856 | 94800 nt | 110 | 4 | 117 |
| *Enterobacteria* phage P2 | NC_001895 | 33593 nt | 43 | 0 | 43 |
| *Enterobacteria* phage P22 | NC_002371 | 41724 nt | 72 | 2 | 74 |
| *Enterobacteria* phage P4 | NC_001609 | 11624 nt | 14 | 5 | 19 |
| *Enterobacteria* phage PRD1 | NC_001421 | 14927 nt | 31 | 0 | 31 |
| *Enterobacteria* phage Phi1 | NC_009821 | 164270 nt | 276 | 0 | 276 |
| *Enterobacteria* phage PsP3 | NC_005340 | 30636 nt | 42 | 0 | 42 |
| *Enterobacteria* phage Qbeta | NC_001890 | 4215 nt | 4 | 0 | 4 |
| *Enterobacteria* phage RB32 | NC_008515 | 165890 nt | 270 | 8 | 270 |
| *Enterobacteria* phage RB43 | NC_007023 | 180500 nt | 292 | 1 | 292 |
| *Enterobacteria* phage RB49 | NC_005066 | 164018 nt | 279 | 0 | 279 |
| *Enterobacteria* phage RB69 | NC_004928 | 167560 nt | 273 | 2 | 275 |
| *Enterobacteria* phage RTP | NC_007603 | 46219 nt | 75 | 0 | 75 |
| *Enterobacteria* phage SP6 | NC_004831 | 43769 nt | 52 | 0 | 52 |
| *Enterobacteria* phage ST104 | NC_005841 | 41391 nt | 63 | 0 | 63 |
| *Enterobacteria* phage ST64T | NC_004348 | 40679 nt | 65 | 0 | 65 |
| *Enterobacteria* phage Sf6 | NC_005344 | 39043 nt | 66 | 2 | 70 |
| *Enterobacteria* phage SfV | NC_003444 | 37074 nt | 53 | 0 | 53 |
| *Enterobacteria* phage T1 | NC_005833 | 48836 nt | 78 | 0 | 78 |
| *Enterobacteria* phage T3 | NC_003298 | 38208 nt | 55 | 0 | 56 |
| *Enterobacteria* phage T4 | NC_000866 | 168903 nt | 278 | 10 | 288 |
| *Enterobacteria* phage T5 | NC_005859 | 121750 nt | 162 | 33 | 195 |
| *Enterobacteria* phage T7 | NC_001604 | 39937 nt | 60 | 0 | 60 |
| *Enterobacteria* phage TLS | NC_009540 | 49902 nt | 87 | 0 | 87 |
| *Enterobacteria* phage VT2-Sakai | NC_000902 | 60942 nt | 83 | 3 | 86 |
| *Enterobacteria* phage WA13 sensu lato | NC_007821 | 6068 nt | 10 | 0 | 10 |
| *Enterobacteria* phage YYZ-2008 | NC_011356 | 54896 nt | 75 | 0 | 75 |
| *Enterobacteria* phage alpha3 | NC_001330 | 6087 nt | 10 | 0 | 10 |
| *Enterobacteria* phage epsilon15 | NC_004775 | 39671 nt | 51 | 0 | 51 |
| *Enterobacteria* phage lambda | NC_001416 | 48502 nt | 73 | 0 | 92 |
| *Enterobacteria* phage phiEco32 | NC_010324 | 77554 nt | 128 | 1 | 128 |
| *Enterobacteria* phage phiEcoM-GJ1 | NC_010106 | 52975 nt | 75 | 1 | 76 |
| *Enterobacteria* phage phiP27 | NC_003356 | 42575 nt | 58 | 2 | 60 |
| *Enterobacteria* phage phiV10 | NC_007804 | 39104 nt | 55 | 0 | 55 |
| *Enterobacteria* phage phiX174 sensu lato | NC_001422 | 5386 nt | 11 | 0 | 11 |
| *Enterococcus* phage phiEF24C | NC_009904 | 142072 nt | 221 | 5 | 226 |
| *Erwinia* phage Era103 | NC_009014 | 45445 nt | 53 | 0 | 53 |
| *Erwinia* phage phiEa21-4 | NC_011811 | 84576 nt | 118 | 26 | 144 |
| *Escherichia* phage rv5 | NC_011041 | 137947 nt | 233 | 6 | 239 |
| *Flavobacterium* phage 11b | NC_006356 | 36012 nt | 65 | 0 | 65 |
| *Geobacillus* phage GBSV1 | NC_008376 | 34683 nt | 54 | 0 | 54 |
| *Geobacillus* virus E2 | NC_009552 | 40863 nt | 71 | 0 | 71 |
| *Haemophilus* phage Aaphi23 | NC_004827 | 43033 nt | 66 | 0 | 66 |
| *Haemophilus* phage HP1 | NC_001697 | 32355 nt | 42 | 0 | 42 |
| *Haemophilus* phage HP2 | NC_003315 | 31508 nt | 37 | 0 | 37 |
| *Haloarcula* phage SH1 | NC_007217 | 30889 nt | 56 | 0 | 56 |
| *Halomonas* phage phiHAP-1 | NC_010342 | 39245 nt | 46 | 0 | 46 |
| *Halorubrum* phage HF2 | NC_003345 | 77670 nt | 114 | 5 | 119 |
| *Halovirus* HF1 | NC_004927 | 75898 nt | 102 | 4 | 106 |
| His1 virus | NC_007914 | 14462 nt | 35 | 0 | 35 |
| His2 virus | NC_007918 | 16067 nt | 35 | 0 | 35 |
| Iodobacteriophage phiPLPE | NC_011142 | 47453 nt | 84 | 0 | 84 |
| *Klebsiella* phage K11 | NC_011043 | 41181 nt | 51 | 0 | 51 |
| *Klebsiella* phage phiKO2 | NC_005857 | 51601 nt | 64 | 0 | 63 |
| *Kluyvera* phage Kvp1 | NC_011534 | 39472 nt | 47 | 1 | 48 |
| *Lactobacillus johnsonii* prophage LJ771 | NC_010179 | 40881 nt | 56 | 0 | 56 |
| *Lactobacillus* phage A2 | NC_004112 | 43411 nt | 61 | 0 | 64 |
| *Lactobacillus* phage KC5a | NC_007924 | 38239 nt | 61 | 0 | 61 |
| *Lactobacillus* phage LL-H | NC_009554 | 34659 nt | 51 | 0 | 51 |
| *Lactobacillus* phage LP65 | NC_006565 | 131522 nt | 165 | 14 | 179 |
| *Lactobacillus* phage Lc-Nu | NC_007501 | 36466 nt | 51 | 0 | 51 |
| *Lactobacillus* phage Lrm1 | NC_011104 | 39989 nt | 54 | 0 | 54 |
| *Lactobacillus* phage Lv-1 | NC_011801 | 38934 nt | 47 | 0 | 47 |
| *Lactobacillus* phage phiAT3 | NC_005893 | 39166 nt | 55 | 0 | 55 |
| *Lactobacillus* phage phiJL-1 | NC_006936 | 36674 nt | 46 | 0 | 46 |
| *Lactobacillus* phage phiadh | NC_000896 | 43785 nt | 63 | 0 | 63 |
| *Lactobacillus* phage phig1e | NC_004305 | 42259 nt | 50 | 0 | 62 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Lactobacillus* prophage Lj928 | NC_005354 | 38384 nt | 50 | 1 | 50 |
| *Lactobacillus* prophage Lj965 | NC_005355 | 40190 nt | 46 | 4 | 46 |
| *Lactococcus* phage 1706 | NC_010576 | 55597 nt | 76 | 0 | 76 |
| *Lactococcus* phage 712 | NC_008370 | 30510 nt | 55 | 0 | 55 |
| *Lactococcus* phage BK5-T | NC_002796 | 40003 nt | 63 | 0 | 63 |
| *Lactococcus* phage KSY1 | NC_009817 | 79232 nt | 130 | 3 | 131 |
| *Lactococcus* phage P008 | NC_008363 | 28538 nt | 58 | 0 | 58 |
| *Lactococcus* phage P335 sensu lato | NC_004746 | 36596 nt | 49 | 0 | 49 |
| *Lactococcus* phage Q54 | NC_008364 | 26537 nt | 47 | 0 | 47 |
| *Lactococcus* phage TP901-1 | NC_002747 | 37667 nt | 56 | 0 | 56 |
| *Lactococcus* phage Tuc2009 | NC_002703 | 38347 nt | 56 | 0 | 56 |
| *Lactococcus* phage asccphi28 | NC_010363 | 18762 nt | 28 | 0 | 27 |
| *Lactococcus* phage bIBB29 | NC_011046 | 29305 nt | 54 | 0 | 54 |
| *Lactococcus* phage bIL170 | NC_001909 | 31754 nt | 64 | 0 | 64 |
| *Lactococcus* phage bIL285 | NC_002666 | 35538 nt | 62 | 0 | 62 |
| *Lactococcus* phage bIL286 | NC_002667 | 41834 nt | 61 | 0 | 61 |
| *Lactococcus* phage bIL309 | NC_002668 | 36949 nt | 56 | 0 | 56 |
| *Lactococcus* phage bIL310 | NC_002669 | 14957 nt | 29 | 0 | 29 |
| *Lactococcus* phage bIL311 | NC_002670 | 14510 nt | 22 | 0 | 22 |
| *Lactococcus* phage bIL312 | NC_002671 | 15179 nt | 27 | 0 | 27 |
| *Lactococcus* phage bIL67 | NC_001629 | 22195 nt | 37 | 0 | 0 |
| *Lactococcus* phage c2 | NC_001706 | 22172 nt | 39 | 2 | 41 |
| *Lactococcus* phage jj50 | NC_008371 | 27453 nt | 49 | 0 | 49 |
| *Lactococcus* phage phiLC3 | NC_005822 | 32172 nt | 51 | 0 | 51 |
| *Lactococcus* phage r1t | NC_004302 | 33350 nt | 50 | 0 | 50 |
| *Lactococcus* phage sk1 | NC_001835 | 28451 nt | 56 | 0 | 56 |
| *Lactococcus* phage ul36 | NC_004066 | 36798 nt | 61 | 0 | 61 |
| *Leuconostoc* phage L5 | NC_009534 | 2435 nt | 0 | 0 | 0 |
| *Listeria* phage 2389 | NC_003291 | 37618 nt | 59 | 1 | 58 |
| *Listeria* phage A006 | NC_009815 | 38124 nt | 62 | 0 | 62 |
| *Listeria* phage A118 | NC_003216 | 40834 nt | 72 | 0 | 72 |
| *Listeria* phage A500 | NC_009810 | 38867 nt | 63 | 0 | 63 |
| *Listeria* phage A511 | NC_009811 | 137619 nt | 199 | 16 | 215 |
| *Listeria* phage B025 | NC_009812 | 42653 nt | 65 | 0 | 65 |
| *Listeria* phage B054 | NC_009813 | 48172 nt | 80 | 0 | 80 |
| *Listeria* phage P35 | NC_009814 | 35822 nt | 56 | 0 | 56 |
| *Listeria* phage P40 | NC_011308 | 35638 nt | 62 | 0 | 62 |
| *Listonella* phage phiHSIC | NC_006953 | 37966 nt | 47 | 0 | 47 |
| *Mannheimia* phage phiMHaA1 | NC_008201 | 34525 nt | 49 | 0 | 50 |
| *Methanobacterium* phage psiM2 | NC_001902 | 26111 nt | 32 | 0 | 32 |
| *Methanothermobacter* phage psiM100 | NC_002628 | 28798 nt | 35 | 0 | 35 |
| *Microbacterium* phage Min1 | NC_009603 | 46365 nt | 77 | 0 | 77 |
| *Microcystis* phage Ma-LMM01 | NC_008562 | 162109 nt | 184 | 2 | 186 |
| *Morganella* phage MmP1 | NC_011085 | 38233 nt | 47 | 0 | 47 |
| *Mycobacterium* phage 244 | NC_008194 | 74483 nt | 142 | 2 | 144 |
| *Mycobacterium* phage Adjutor | NC_010763 | 64511 nt | 86 | 0 | 86 |
| *Mycobacterium* phage BPs | NC_010762 | 41901 nt | 63 | 0 | 63 |
| *Mycobacterium* phage Barnyard | NC_004689 | 70797 nt | 109 | 0 | 109 |
| *Mycobacterium* phage Bethlehem | NC_009878 | 52250 nt | 87 | 0 | 87 |
| *Mycobacterium* phage Boomer | NC_011054 | 58037 nt | 105 | 0 | 105 |
| *Mycobacterium* phage Brujita | NC_011291 | 47057 nt | 74 | 0 | 74 |
| *Mycobacterium* phage Butterscotch | NC_011286 | 64562 nt | 86 | 0 | 86 |
| *Mycobacterium* phage Bxb1 | NC_002656 | 50550 nt | 86 | 0 | 86 |
| *Mycobacterium* phage Bxz1 | NC_004687 | 156102 nt | 225 | 28 | 253 |
| *Mycobacterium* phage Bxz2 | NC_004682 | 50913 nt | 86 | 3 | 89 |
| *Mycobacterium* phage Cali | NC_011271 | 155372 nt | 222 | 35 | 257 |
| *Mycobacterium* phage Catera | NC_008207 | 153766 nt | 218 | 34 | 253 |
| *Mycobacterium* phage Chah | NC_011284 | 68450 nt | 104 | 0 | 104 |
| *Mycobacterium* phage Che12 | NC_008203 | 52047 nt | 98 | 3 | 101 |
| *Mycobacterium* phage Che8 | NC_004680 | 59471 nt | 112 | 0 | 112 |
| *Mycobacterium* phage Che9c | NC_004683 | 57050 nt | 84 | 1 | 85 |
| *Mycobacterium* phage Che9d | NC_004686 | 56276 nt | 111 | 0 | 111 |
| *Mycobacterium* phage Cjw1 | NC_004681 | 75931 nt | 141 | 1 | 142 |
| *Mycobacterium* phage Cooper | NC_008195 | 70654 nt | 99 | 0 | 99 |
| *Mycobacterium* phage Corndog | NC_004685 | 69777 nt | 122 | 0 | 122 |
| *Mycobacterium* phage D29 | NC_001900 | 49136 nt | 79 | 5 | 84 |
| *Mycobacterium* phage DD5 | NC_011022 | 51621 nt | 87 | 0 | 87 |
| *Mycobacterium* phage Fruitloop | NC_011288 | 58471 nt | 102 | 0 | 102 |
| *Mycobacterium* phage Giles | NC_009993 | 54512 nt | 79 | 1 | 80 |
| *Mycobacterium* phage Gumball | NC_011290 | 64807 nt | 88 | 0 | 88 |
| *Mycobacterium* phage Halo | NC_008202 | 42289 nt | 65 | 0 | 65 |
| *Mycobacterium* phage Jasper | NC_011020 | 50968 nt | 94 | 0 | 94 |
| *Mycobacterium* phage KBG | NC_011019 | 53572 nt | 89 | 0 | 89 |
| *Mycobacterium* phage Konstantine | NC_011292 | 68952 nt | 95 | 0 | 95 |
| *Mycobacterium* phage Kostya | NC_011056 | 75811 nt | 143 | 2 | 145 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Mycobacterium* phage L5 | NC_001335 | 52297 nt | 85 | 3 | 88 |
| *Mycobacterium* phage Llij | NC_008196 | 56852 nt | 100 | 0 | 100 |
| *Mycobacterium* phage Lockley | NC_011021 | 51478 nt | 90 | 0 | 90 |
| *Mycobacterium* phage Myrna | NC_011273 | 164602 nt | 229 | 41 | 270 |
| *Mycobacterium* phage Nigel | NC_011044 | 69904 nt | 94 | 1 | 95 |
| *Mycobacterium* phage Omega | NC_004688 | 110865 nt | 237 | 2 | 239 |
| *Mycobacterium* phage Orion | NC_008197 | 68427 nt | 100 | 0 | 100 |
| *Mycobacterium* phage PBI1 | NC_008198 | 64494 nt | 81 | 0 | 81 |
| *Mycobacterium* phage PG1 | NC_005259 | 68999 nt | 100 | 0 | 100 |
| *Mycobacterium* phage PLot | NC_008200 | 64787 nt | 89 | 0 | 89 |
| *Mycobacterium* phage PMC | NC_008205 | 56692 nt | 104 | 0 | 104 |
| *Mycobacterium* phage Pacc40 | NC_011287 | 58554 nt | 101 | 0 | 101 |
| *Mycobacterium* phage Phaedrus | NC_011057 | 68090 nt | 98 | 0 | 98 |
| *Mycobacterium* phage Pipefish | NC_008199 | 69059 nt | 102 | 0 | 102 |
| *Mycobacterium* phage Porky | NC_011055 | 76312 nt | 147 | 2 | 149 |
| *Mycobacterium* phage Predator | NC_011039 | 70110 nt | 92 | 0 | 92 |
| *Mycobacterium* phage Pukovnik | NC_011023 | 52892 nt | 88 | 1 | 89 |
| *Mycobacterium* phage Qyrzula | NC_008204 | 67188 nt | 81 | 0 | 81 |
| *Mycobacterium* phage Ramsey | NC_011289 | 58578 nt | 108 | 0 | 108 |
| *Mycobacterium* phage Rizal | NC_011272 | 153894 nt | 220 | 35 | 255 |
| *Mycobacterium* phage Rosebush | NC_004684 | 67480 nt | 90 | 0 | 90 |
| *Mycobacterium* phage ScottMcG | NC_011269 | 154017 nt | 221 | 36 | 257 |
| *Mycobacterium* phage Solon | NC_011267 | 49487 nt | 86 | 0 | 86 |
| *Mycobacterium* phage Spud | NC_011270 | 154906 nt | 222 | 35 | 257 |
| *Mycobacterium* phage TM4 | NC_003387 | 52797 nt | 89 | 0 | 89 |
| *Mycobacterium* phage Troll4 | NC_011285 | 64618 nt | 84 | 0 | 84 |
| *Mycobacterium* phage Tweety | NC_009820 | 58692 nt | 109 | 0 | 109 |
| *Mycobacterium* phage U2 | NC_009877 | 51277 nt | 81 | 0 | 81 |
| *Mycobacterium* phage Wildcat | NC_008206 | 78441 nt | 148 | 23 | 171 |
| *Mycoplasma* phage MAV1 | NC_001942 | 15644 nt | 15 | 0 | 15 |
| *Mycoplasma* phage P1 | NC_002515 | 11660 nt | 11 | 0 | 11 |
| *Mycoplasma* phage phiMFV1 | NC_005964 | 15141 nt | 15 | 0 | 17 |
| *Myxococcus* phage Mx8 | NC_003085 | 49534 nt | 86 | 0 | 85 |
| *Natrialba* phage PhiCh1 | NC_004084 | 58498 nt | 98 | 0 | 98 |
| *Pasteurella* phage F108 | NC_008193 | 30505 nt | 44 | 0 | 44 |
| Phage Gifsy-1 | NC_010392 | 48491 nt | 58 | 1 | 59 |
| Phage Gifsy-2 | NC_010393 | 45840 nt | 55 | 0 | 56 |
| Phage cdtI | NC_009514 | 47021 nt | 60 | 0 | 60 |
| Phage phiJL001 | NC_006938 | 63649 nt | 90 | 0 | 90 |
| *Phormidium* phage Pf-WMP3 | NC_009551 | 43249 nt | 41 | 0 | 41 |
| *Phormidium* phage Pf-WMP4 | NC_008367 | 40938 nt | 45 | 0 | 45 |
| *Prochlorococcus* phage P-SSM2 | NC_006883 | 252401 nt | 329 | 1 | 330 |
| *Prochlorococcus* phage P-SSM4 | NC_006884 | 178249 nt | 198 | 0 | 198 |
| *Prochlorococcus* phage P-SSP7 | NC_006882 | 44970 nt | 53 | 0 | 53 |
| *Propionibacterium* phage B5 | NC_003460 | 5804 nt | 10 | 0 | 10 |
| *Propionibacterium* phage PA6 | NC_009541 | 29739 nt | 48 | 0 | 48 |
| *Pseudoalteromonas* phage PM2 | NC_000867 | 10079 nt | 22 | 0 | 22 |
| *Pseudomonas* phage 119X | NC_007807 | 43365 nt | 53 | 0 | 53 |
| *Pseudomonas* phage 14-1 | NC_011703 | 66235 nt | 90 | 0 | 90 |
| *Pseudomonas* phage 201phi2-1 | NC_010821 | 316674 nt | 461 | 1 | 462 |
| *Pseudomonas* phage 73 | NC_007806 | 42999 nt | 52 | 0 | 52 |
| *Pseudomonas* phage B3 | NC_006548 | 38439 nt | 59 | 0 | 59 |
| *Pseudomonas* phage D3 | NC_002484 | 56425 nt | 95 | 4 | 99 |
| *Pseudomonas* phage D3112 | NC_005178 | 37611 nt | 55 | 0 | 55 |
| *Pseudomonas* phage DMS3 | NC_008717 | 36415 nt | 52 | 0 | 52 |
| *Pseudomonas* phage EL | NC_007623 | 211215 nt | 201 | 0 | 201 |
| *Pseudomonas* phage F10 | NC_007805 | 39199 nt | 63 | 0 | 63 |
| *Pseudomonas* phage F116 | NC_006552 | 65195 nt | 70 | 0 | 70 |
| *Pseudomonas* phage F8 | NC_007810 | 66015 nt | 91 | 0 | 91 |
| *Pseudomonas* phage LBL3 | NC_011165 | 64427 nt | 87 | 0 | 87 |
| *Pseudomonas* phage LKA1 | NC_009936 | 41593 nt | 56 | 0 | 56 |
| *Pseudomonas* phage LKD16 | NC_009935 | 43200 nt | 53 | 0 | 53 |
| *Pseudomonas* phage LMA2 | NC_011166 | 66530 nt | 93 | 0 | 93 |
| *Pseudomonas* phage LUZ19 | NC_010326 | 43548 nt | 54 | 0 | 54 |
| *Pseudomonas* phage LUZ24 | NC_010325 | 45625 nt | 68 | 0 | 68 |
| *Pseudomonas* phage M6 | NC_007809 | 59446 nt | 85 | 0 | 85 |
| *Pseudomonas* phage MP22 | NC_009818 | 36409 nt | 51 | 0 | 51 |
| *Pseudomonas* phage MP29 | NC_011613 | 36632 nt | 51 | 0 | 51 |
| *Pseudomonas* phage MP38 | NC_011611 | 36885 nt | 51 | 0 | 51 |
| *Pseudomonas* phage PA11 | NC_007808 | 49639 nt | 70 | 0 | 70 |
| *Pseudomonas* phage PAJU2 | NC_011373 | 46872 nt | 79 | 0 | 79 |
| *Pseudomonas* phage PB1 | NC_011810 | 65764 nt | 93 | 0 | 94 |
| *Pseudomonas* phage PP7 | NC_001628 | 3588 nt | 4 | 0 | 4 |
| *Pseudomonas* phage PRR1 | NC_008294 | 3573 nt | 4 | 0 | 4 |
| *Pseudomonas* phage PT2 | NC_011107 | 42961 nt | 54 | 0 | 54 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Pseudomonas* phage PT5 | NC_011105 | 42954 nt | 52 | 0 | 52 |
| *Pseudomonas* phage PaP2 | NC_005884 | 43783 nt | 58 | 0 | 58 |
| *Pseudomonas* phage PaP3 | NC_004466 | 45503 nt | 71 | 4 | 75 |
| *Pseudomonas* phage Pf1 | NC_001331 | 7349 nt | 14 | 0 | 14 |
| *Pseudomonas* phage Pf3 | NC_001418 | 5833 nt | 9 | 0 | 9 |
| *Pseudomonas* phage SN | NC_011756 | 66390 nt | 92 | 0 | 92 |
| *Pseudomonas* phage YuA | NC_010116 | 58663 nt | 77 | 0 | 77 |
| *Pseudomonas* phage gh-1 | NC_004665 | 37359 nt | 42 | 0 | 42 |
| *Pseudomonas* phage phi12 | NC_004173 | 6751 nt | 6 | 0 | 6 |
| *Pseudomonas* phage phi12 | NC_004175 | 4100 nt | 5 | 0 | 5 |
| *Pseudomonas* phage phi12 | NC_004174 | 2322 nt | 4 | 0 | 4 |
| *Pseudomonas* phage phi13 | NC_004172 | 6458 nt | 4 | 0 | 4 |
| *Pseudomonas* phage phi13 | NC_004171 | 4213 nt | 5 | 0 | 5 |
| *Pseudomonas* phage phi13 | NC_004170 | 2981 nt | 4 | 0 | 4 |
| *Pseudomonas* phage phi6 | NC_003715 | 6374 nt | 4 | 0 | 4 |
| *Pseudomonas* phage phi6 | NC_003716 | 4063 nt | 4 | 0 | 4 |
| *Pseudomonas* phage phi6 | NC_003714 | 2948 nt | 5 | 0 | 5 |
| *Pseudomonas* phage phi8 | NC_003299 | 7051 nt | 7 | 0 | 7 |
| *Pseudomonas* phage phi8 | NC_003300 | 4741 nt | 6 | 0 | 6 |
| *Pseudomonas* phage phi8 | NC_003301 | 3192 nt | 6 | 0 | 6 |
| *Pseudomonas* phage phiCTX | NC_003278 | 35580 nt | 47 | 0 | 47 |
| *Pseudomonas* phage phiKMV | NC_005045 | 42519 nt | 49 | 0 | 49 |
| *Pseudomonas* phage phiKZ | NC_004629 | 280334 nt | 306 | 0 | 306 |
| *Pyrobaculum* spherical virus | NC_005872 | 28337 nt | 48 | 0 | 48 |
| *Pyrococcus abyssi* virus 1 | NC_009597 | 18098 nt | 25 | 0 | 25 |
| *Ralstonia* phage RSB1 | NC_011201 | 43079 nt | 47 | 0 | 47 |
| *Ralstonia* phage RSL1 | NC_010811 | 231256 nt | 345 | 2 | 346 |
| *Ralstonia* phage RSM1 | NC_008574 | 8999 nt | 15 | 0 | 15 |
| *Ralstonia* phage RSM3 | NC_011399 | 8929 nt | 14 | 0 | 14 |
| *Ralstonia* phage RSS1 | NC_008575 | 6662 nt | 12 | 0 | 12 |
| *Ralstonia* phage p12J | NC_005131 | 7118 nt | 9 | 0 | 9 |
| *Ralstonia* phage phiRSA1 | NC_009382 | 38760 nt | 51 | 0 | 51 |
| *Rhizobium* phage 16-3 | NC_011103 | 60195 nt | 110 | 0 | 109 |
| *Rhodothermus* phage RM378 | NC_004735 | 129908 nt | 146 | 0 | 146 |
| *Roseobacter* phage SIO1 | NC_002519 | 39898 nt | 34 | 0 | 34 |
| *Salmonella* phage E1 | NC_010495 | 45051 nt | 51 | 0 | 52 |
| *Salmonella* phage Fels-1 | NC_010391 | 42723 nt | 52 | 0 | 52 |
| *Salmonella* phage KS7 | NC_006940 | 40794 nt | 59 | 0 | 59 |
| *Salmonella* phage SE1 | NC_011802 | 41941 nt | 67 | 0 | 67 |
| *Salmonella* phage SETP3 | NC_009232 | 42572 nt | 53 | 0 | 53 |
| *Salmonella* phage ST64B | NC_004313 | 40149 nt | 56 | 0 | 56 |
| *Salmonella* phage phiSG-JL2 | NC_010807 | 38815 nt | 55 | 0 | 55 |
| *Sinorhizobium* phage PBC5 | NC_003324 | 57416 nt | 83 | 0 | 83 |
| *Sodalis* phage phiSG1 | NC_007902 | 52162 nt | 47 | 0 | 47 |
| *Spiroplasma kunkelii* virus SkV1_CR2-3x | NC_009987 | 7870 nt | 13 | 0 | 13 |
| *Spiroplasma* phage 1-C74 | NC_003793 | 7768 nt | 13 | 0 | 13 |
| *Spiroplasma* phage 1-R8A2B | NC_001365 | 8273 nt | 12 | 0 | 12 |
| *Spiroplasma* phage 4 | NC_003438 | 4421 nt | 9 | 0 | 9 |
| *Spiroplasma* phage SVTS2 | NC_001270 | 6825 nt | 13 | 0 | 13 |
| Sputnik virophage | NC_011132 | 18343 nt | 21 | 0 | 21 |
| *Staphylococcus aureus* phage P68 | NC_004679 | 18227 nt | 22 | 0 | 22 |
| *Staphylococcus* phage 11 | NC_004615 | 43604 nt | 53 | 0 | 53 |
| *Staphylococcus* phage 187 | NC_007047 | 39620 nt | 77 | 0 | 77 |
| *Staphylococcus* phage 2638A | NC_007051 | 41318 nt | 57 | 0 | 57 |
| *Staphylococcus* phage 29 | NC_007061 | 42802 nt | 67 | 0 | 67 |
| *Staphylococcus* phage 37 | NC_007055 | 43681 nt | 70 | 0 | 70 |
| *Staphylococcus* phage 3A | NC_007053 | 43095 nt | 67 | 0 | 67 |
| *Staphylococcus* phage 42E | NC_007052 | 45861 nt | 79 | 0 | 79 |
| *Staphylococcus* phage 44AHJD | NC_004678 | 16784 nt | 21 | 0 | 21 |
| *Staphylococcus* phage 47 | NC_007054 | 44777 nt | 65 | 0 | 65 |
| *Staphylococcus* phage 52A | NC_007062 | 41690 nt | 60 | 0 | 60 |
| *Staphylococcus* phage 53 | NC_007049 | 43883 nt | 74 | 0 | 74 |
| *Staphylococcus* phage 55 | NC_007060 | 41902 nt | 77 | 0 | 77 |
| *Staphylococcus* phage 66 | NC_007046 | 18199 nt | 27 | 0 | 27 |
| *Staphylococcus* phage 69 | NC_007048 | 42732 nt | 69 | 0 | 69 |
| *Staphylococcus* phage 71 | NC_007059 | 43114 nt | 67 | 0 | 67 |
| *Staphylococcus* phage 77 | NC_005356 | 41708 nt | 69 | 0 | 69 |
| *Staphylococcus* phage 80alpha | NC_009526 | 43864 nt | 73 | 0 | 73 |
| *Staphylococcus* phage 85 | NC_007050 | 44283 nt | 71 | 0 | 71 |
| *Staphylococcus* phage 88 | NC_007063 | 43231 nt | 66 | 0 | 66 |
| *Staphylococcus* phage 92 | NC_007064 | 42431 nt | 64 | 0 | 64 |
| *Staphylococcus* phage 96 | NC_007057 | 43576 nt | 74 | 0 | 74 |
| *Staphylococcus* phage CNPH82 | NC_008722 | 43420 nt | 65 | 0 | 65 |
| *Staphylococcus* phage EW | NC_007056 | 45286 nt | 77 | 0 | 77 |
| *Staphylococcus* phage G1 | NC_007066 | 138715 nt | 214 | 0 | 214 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Staphylococcus* phage K | NC_005880 | 127395 nt | 115 | 0 | 115 |
| *Staphylococcus* phage PH15 | NC_008723 | 44041 nt | 68 | 0 | 68 |
| *Staphylococcus* phage PT1028 | NC_007045 | 15603 nt | 22 | 0 | 22 |
| *Staphylococcus* phage PVL | NC_002321 | 41401 nt | 62 | 0 | 62 |
| *Staphylococcus* phage ROSA | NC_007058 | 43155 nt | 74 | 0 | 74 |
| *Staphylococcus* phage SAP-2 | NC_009875 | 17938 nt | 20 | 0 | 20 |
| *Staphylococcus* phage Twort | NC_007021 | 130706 nt | 195 | 0 | 195 |
| *Staphylococcus* phage X2 | NC_007065 | 43440 nt | 77 | 0 | 77 |
| *Staphylococcus* phage phi 12 | NC_004616 | 44970 nt | 49 | 0 | 49 |
| *Staphylococcus* phage phi13 | NC_004617 | 42722 nt | 49 | 0 | 49 |
| *Staphylococcus* phage phi2958PVL | NC_011344 | 47342 nt | 60 | 0 | 59 |
| *Staphylococcus* phage phiETA | NC_003288 | 43081 nt | 66 | 0 | 66 |
| *Staphylococcus* phage phiETA2 | NC_008798 | 43265 nt | 69 | 0 | 69 |
| *Staphylococcus* phage phiETA3 | NC_008799 | 43282 nt | 68 | 0 | 68 |
| *Staphylococcus* phage phiMR11 | NC_010147 | 43011 nt | 67 | 0 | 67 |
| *Staphylococcus* phage phiMR25 | NC_010808 | 44342 nt | 70 | 0 | 70 |
| *Staphylococcus* phage phiN315 | NC_004740 | 44082 nt | 65 | 0 | 64 |
| *Staphylococcus* phage phiNM | NC_008583 | 43128 nt | 64 | 0 | 64 |
| *Staphylococcus* phage phiNM3 | NC_008617 | 44061 nt | 65 | 0 | 65 |
| *Staphylococcus* phage phiPVL108 | NC_008689 | 44857 nt | 59 | 0 | 59 |
| *Staphylococcus* phage phiSLT | NC_002661 | 42942 nt | 61 | 0 | 61 |
| *Staphylococcus* phage phiSauS-IPLA35 | NC_011612 | 45344 nt | 62 | 0 | 62 |
| *Staphylococcus* phage phiSauS-IPLA88 | NC_011614 | 42526 nt | 60 | 0 | 61 |
| *Staphylococcus* phage tp310-1 | NC_009761 | 41407 nt | 59 | 0 | 59 |
| *Staphylococcus* phage tp310-2 | NC_009762 | 45710 nt | 67 | 0 | 67 |
| *Staphylococcus* phage tp310-3 | NC_009763 | 41966 nt | 58 | 0 | 58 |
| *Staphylococcus* prophage phiPV83 | NC_002486 | 45636 nt | 65 | 0 | 65 |
| *Stenotrophomonas* phage S1 | NC_011589 | 40287 nt | 48 | 0 | 48 |
| *Stenotrophomonas* phage phiSMA9 | NC_007189 | 6907 nt | 7 | 0 | 7 |
| *Streptococcus* phage 2972 | NC_007019 | 34704 nt | 44 | 0 | 44 |
| *Streptococcus* phage 7201 | NC_002185 | 35466 nt | 46 | 0 | 46 |
| *Streptococcus* phage 858 | NC_010353 | 35543 nt | 46 | 0 | 46 |
| *Streptococcus* phage C1 | NC_004814 | 16687 nt | 20 | 0 | 20 |
| *Streptococcus* phage Cp-1 | NC_001825 | 19343 nt | 25 | 0 | 25 |
| *Streptococcus* phage DT1 | NC_002072 | 34815 nt | 45 | 0 | 45 |
| *Streptococcus* phage EJ-1 | NC_005294 | 42935 nt | 73 | 0 | 73 |
| *Streptococcus* phage MM1 | NC_003050 | 40248 nt | 53 | 0 | 53 |
| *Streptococcus* phage O1205 | NC_004303 | 43075 nt | 57 | 0 | 57 |
| *Streptococcus* phage P9 | NC_009819 | 40539 nt | 53 | 0 | 53 |
| *Streptococcus* phage PH15 | NC_010945 | 39136 nt | 60 | 0 | 60 |
| *Streptococcus* phage SM1 | NC_004996 | 34692 nt | 56 | 0 | 56 |
| *Streptococcus* phage SMP | NC_008721 | 36216 nt | 48 | 0 | 48 |
| *Streptococcus* phage Sfi11 | NC_002214 | 39807 nt | 53 | 0 | 53 |
| *Streptococcus* phage Sfi19 | NC_000871 | 37370 nt | 45 | 0 | 45 |
| *Streptococcus* phage Sfi21 | NC_000872 | 40739 nt | 50 | 0 | 50 |
| *Streptococcus* phage phi3396 | NC_009018 | 38528 nt | 64 | 0 | 64 |
| *Streptococcus pyogenes* phage 315.1 | NC_004584 | 39538 nt | 56 | 0 | 56 |
| *Streptococcus pyogenes* phage 315.2 | NC_004585 | 41072 nt | 60 | 1 | 61 |
| *Streptococcus pyogenes* phage 315.3 | NC_004586 | 34419 nt | 52 | 0 | 52 |
| *Streptococcus pyogenes* phage 315.4 | NC_004587 | 41796 nt | 64 | 0 | 64 |
| *Streptococcus pyogenes* phage 315.5 | NC_004588 | 38206 nt | 55 | 0 | 55 |
| *Streptococcus pyogenes* phage 315.6 | NC_004589 | 40014 nt | 51 | 0 | 51 |
| *Streptomyces* phage VWB | NC_005345 | 49220 nt | 61 | 0 | 61 |
| *Streptomyces* phage mu1/6 | NC_007967 | 38194 nt | 52 | 0 | 52 |
| *Streptomyces* phage phiBT1 | NC_004664 | 41831 nt | 55 | 1 | 56 |
| *Streptomyces* phage phiC31 | NC_001978 | 41491 nt | 53 | 1 | 54 |
| Stx1 converting phage | NC_004913 | 59866 nt | 167 | 0 | 166 |
| Stx2 converting phage I | NC_003525 | 61765 nt | 166 | 0 | 166 |
| Stx2 converting phage II | NC_004914 | 62706 nt | 170 | 0 | 169 |
| Stx2-converting phage 1717 | NC_011357 | 62147 nt | 77 | 0 | 81 |
| Stx2-converting phage 86 | NC_008464 | 60238 nt | 81 | 3 | 80 |
| *Sulfolobus islandicus* filamentous virus | NC_003214 | 40900 nt | 73 | 0 | 73 |
| *Sulfolobus islandicus* rod-shaped virus 1 | NC_004087 | 32308 nt | 45 | 0 | 45 |
| *Sulfolobus islandicus* rod-shaped virus 2 | NC_004086 | 35450 nt | 54 | 0 | 54 |
| *Sulfolobus* spindle-shaped virus 4 | NC_009986 | 15135 nt | 34 | 0 | 34 |
| *Sulfolobus* spindle-shaped virus 5 | NC_011217 | 15330 nt | 34 | 0 | 34 |
| *Sulfolobus* turreted icosahedral virus | NC_005892 | 17663 nt | 36 | 0 | 36 |
| *Sulfolobus* virus 1 | NC_001338 | 15465 nt | 32 | 0 | 33 |
| *Sulfolobus* virus 2 | NC_005265 | 14796 nt | 34 | 0 | 34 |
| *Sulfolobus* virus Kamchatka 1 | NC_005361 | 17385 nt | 31 | 0 | 31 |
| *Sulfolobus* virus Ragged Hills | NC_005360 | 16473 nt | 37 | 0 | 37 |
| *Sulfolobus* virus STSV1 | NC_006268 | 75294 nt | 74 | 0 | 74 |
| *Synechococcus* phage P60 | NC_003390 | 47872 nt | 80 | 0 | 80 |
| *Synechococcus* phage S-PM2 | NC_006820 | 196280 nt | 236 | 1 | 238 |
| *Synechococcus* phage Syn5 | NC_009531 | 46214 nt | 61 | 0 | 61 |

TABLE 7F-continued

Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Synechococcus* phage syn9 | NC_008296 | 177300 nt | 226 | 6 | 232 |
| Temperate phage phiNIH1.1 | NC_003157 | 41796 nt | 55 | 0 | 55 |
| *Thalassomonas* phage BA3 | NC_009990 | 37313 nt | 47 | 0 | 47 |
| *Thermoproteus tenax* spherical virus 1 | NC_006556 | 20933 nt | 38 | 0 | 38 |
| *Thermus* phage IN93 | NC_004462 | 19603 nt | 40 | 0 | 32 |
| *Thermus* phage P23-45 | NC_009803 | 84201 nt | 117 | 0 | 117 |
| *Thermus* phage P74-26 | NC_009804 | 83319 nt | 116 | 0 | 116 |
| *Thermus* phage phiYS40 | NC_008584 | 152372 nt | 170 | 3 | 170 |
| *Vibrio* phage K139 | NC_003313 | 33106 nt | 44 | 0 | 44 |
| *Vibrio* phage KSF-1phi | NC_006294 | 7107 nt | 12 | 0 | 12 |
| *Vibrio* phage KVP40 | NC_005083 | 244834 nt | 381 | 29 | 415 |
| *Vibrio* phage VGJphi | NC_004736 | 7542 nt | 13 | 0 | 13 |
| *Vibrio* phage VHML | NC_004456 | 43198 nt | 57 | 0 | 57 |
| *Vibrio* phage VP2 | NC_005879 | 39853 nt | 47 | 0 | 47 |
| *Vibrio* phage VP5 | NC_005891 | 39786 nt | 48 | 0 | 48 |
| *Vibrio* phage VP882 | NC_009016 | 38197 nt | 71 | 0 | 71 |
| *Vibrio* phage VSK | NC_003327 | 6882 nt | 14 | 0 | 14 |
| *Vibrio* phage Vf12 | NC_005949 | 7965 nt | 7 | 0 | 7 |
| *Vibrio* phage Vf33 | NC_005948 | 7965 nt | 7 | 0 | 7 |
| *Vibrio* phage VfO3K6 | NC_002362 | 8784 nt | 10 | 0 | 10 |
| *Vibrio* phage VfO4K68 | NC_002363 | 6891 nt | 8 | 0 | 8 |
| *Vibrio* phage fs1 | NC_004306 | 6340 nt | 15 | 0 | 15 |
| *Vibrio* phage fs2 | NC_001956 | 8651 nt | 9 | 0 | 9 |
| *Vibrio* phage kappa | NC_010275 | 33134 nt | 45 | 0 | 45 |
| Vibriophage VP4 | NC_007149 | 39503 nt | 31 | 0 | 31 |
| Vibriophage VpV262 | NC_003907 | 46012 nt | 67 | 0 | 67 |
| *Xanthomonas* phage Cf1c | NC_001396 | 7308 nt | 9 | 0 | 9 |
| *Xanthomonas* phage OP1 | NC_007709 | 43785 nt | 59 | 0 | 59 |
| *Xanthomonas* phage OP2 | NC_007710 | 46643 nt | 62 | 0 | 62 |
| *Xanthomonas* phage Xop411 | NC_009543 | 44520 nt | 58 | 0 | 58 |
| *Xanthomonas* phage Xp10 | NC_004902 | 44373 nt | 60 | 0 | 60 |
| *Xanthomonas* phage Xp15 | NC_007024 | 55770 nt | 84 | 0 | 84 |
| *Yersinia pestis* phage phiA1122 | NC_004777 | 37555 nt | 50 | 0 | 50 |
| *Yersinia* phage Berlin | NC_008694 | 38564 nt | 45 | 0 | 45 |
| *Yersinia* phage L-413C | NC_004745 | 30728 nt | 40 | 0 | 40 |
| *Yersinia* phage PY54 | NC_005069 | 46339 nt | 67 | 0 | 66 |
| *Yersinia* phage Yepe2 | NC_011038 | 38677 nt | 46 | 0 | 46 |
| *Yersinia* phage phiYeO3-12 | NC_001271 | 39600 nt | 59 | 0 | 59 |

TABLE 7G

Examples of promoters which can be operatively linked to the nucleic acid in the engineered bacteriophages.

| Name | Description | Length |
|---|---|---|
| BBa_I0500 | Inducible pBad/araC promoter | 1210 |
| BBa_I13453 | Pbad promoter | 130 |
| BBa_I712004 | CMV promoter | 654 |
| BBa_I712074 | T7 promoter (strong promoter from T7 bacteriophage) | 46 |
| BBa_I714889 | OR21 of PR and PRM | 101 |
| BBa_I714924 | RecA_DlexO_DLacO1 | 862 |
| BBa_I714927 | RecA_S_WTlexO_DLacO | 862 |
| BBa_I714929 | RecA_S_WTlexO_DLacO3 | 862 |
| BBa_I714930 | RecA_D_consenLexO_lacO1 | 862 |
| BBa_I714933 | WT_sulA_Single_LexO_double_LacO1 | 884 |
| BBa_I714935 | WT_sulA_Single_LexO_double_LacO2 | 884 |
| BBa_I714936 | WT_sulA_Single_LexO_double_LacO3 | 884 |
| BBa_I714937 | sluA_double_lexO_LacO1 | 884 |
| BBa_I714938 | sluA_double_lexO_LacO2 | 884 |
| BBa_I714939 | sluA_double_lexO_LacO3 | 884 |
| BBa_I715038 | pLac-RBS-T7 RNA Polymerase | 2878 |
| BBa_I716014 | yfbE solo trial 2 | 302 |
| BBa_I716102 | pir (Induces the R6K Origin) | 918 |
| BBa_I719005 | T7 Promoter | 23 |
| BBa_I732205 | NOT Gate Promoter Family Member (D001O55) | 124 |
| BBa_J13002 | TetR repressed POPS/RIPS generator | 74 |
| BBa_J13023 | 3OC6HSL + LuxR dependent POPS/RIPS generator | 117 |
| BBa_J23100 | constitutive promoter family member | 35 |
| BBa_J23101 | constitutive promoter family member | 35 |
| BBa_J23102 | constitutive promoter family member | 35 |
| BBa_J23103 | constitutive promoter family member | 35 |

TABLE 7G-continued

Examples of promoters which can be operatively linked to the nucleic acid in the engineered bacteriophages.

| Name | Description | Length |
|---|---|---|
| BBa_J23104 | constitutive promoter family member | 35 |
| BBa_J23105 | constitutive promoter family member | 35 |
| BBa_J23106 | constitutive promoter family member | 35 |
| BBa_J23107 | constitutive promoter family member | 35 |
| BBa_J23108 | constitutive promoter family member | 35 |
| BBa_J23109 | constitutive promoter family member | 35 |
| BBa_J23110 | constitutive promoter family member | 35 |
| BBa_J23111 | constitutive promoter family member | 35 |
| BBa_J23112 | constitutive promoter family member | 35 |
| BBa_J23113 | constitutive promoter family member | 35 |
| BBa_J23114 | constitutive promoter family member | 35 |
| BBa_J23115 | constitutive promoter family member | 35 |
| BBa_J23116 | constitutive promoter family member | 35 |
| BBa_J23117 | constitutive promoter family member | 35 |
| BBa_J23118 | constitutive promoter family member | 35 |
| BBa_J44002 | pBAD reverse | 130 |
| BBa_J52010 | NFkappaB -dependent promoter | 814 |
| BBa_J52034 | CMV promoter | 654 |
| BBa_J61043 | [fdhF2] Promoter | 269 |
| BBa_J63005 | yeast ADH1 promoter | 1445 |
| BBa_J63006 | yeast GAL1 promoter | 549 |
| BBa_K082017 | general recombine system | 89 |
| BBa_K091110 | LacI Promoter | 56 |
| BBa_K091111 | LacIQ promoter | 56 |
| BBa_K094120 | pLacI/ara-1 | 103 |
| BBa_K100000 | Natural Xylose Regulated Bi-Directional Operator | 303 |
| BBa_K100001 | Edited Xylose Regulated Bi-Directional Operator 1 | 303 |
| BBa_K100002 | Edited Xylose Regulated Bi-Directional Operator 2 | 303 |
| BBa_K118011 | PcstA (glucose-repressible promoter) | 131 |
| BBa_K135000 | pCpxR (CpxR responsive promoter) | 55 |
| BBa_K137029 | constitutive promoter with (TA)10 between (SEQ ID NO: 119) −10 and −35 elements | 39 |
| BBa_K137030 | constitutive promoter with (TA)9 (SEQ ID NO: 120) between −10 and −35 elements | 37 |
| BBa_K137046 | 150 bp inverted tetR promoter | 150 |
| BBa_K137047 | 250 bp inverted tetR promoter | 250 |
| BBa_K137048 | 350 bp inverted tetR promoter | 350 |
| BBa_K137049 | 450 bp inverted tetR promoter | 450 |
| BBa_K137050 | 650 bp inverted tetR promoter | 650 |
| BBa_K137051 | 850 bp inverted tetR promoter | 850 |
| BBa_R0010 | promoter (lacI regulated) | 200 |
| BBa_R0011 | Promoter (lacI regulated, lambda pL hybrid) | 55 |
| BBa_R0053 | Promoter (p22 cII regulated) | 54 |
| BBa_I1010 | cI(1) fused to tetR promoter | 834 |
| BBa_I1051 | Lux cassette right promoter | 68 |
| BBa_I12006 | Modified lamdba Prm promoter (repressed by 434 cI) | 82 |
| BBa_I12036 | Modified lamdba Prm promoter (cooperative repression by 434 cI) | 91 |
| BBa_I12040 | Modified lambda P(RM) promoter: −10 region from P(L) and cooperatively repressed by 434 cI | 91 |
| BBa_I13005 | Promoter R0011 w/YFP (−LVA) TT | 920 |
| BBa_I13006 | Promoter R0040 w/YFP (−LVA) TT | 920 |
| BBa_I14015 | P(Las) TetO | 170 |
| BBa_I14016 | P(Las) CIO | 168 |
| BBa_I14017 | P(Rhl) | 51 |
| BBa_I14018 | P(Bla) | 35 |
| BBa_I14033 | P(Cat) | 38 |
| BBa_I14034 | P(Kat) | 45 |
| BBa_I714890 | OR321 of PR and PRM | 121 |
| BBa_I714925 | RecA_DlexO_DLacO2 | 862 |
| BBa_I714926 | RecA_DlexO_DLacO3 | 862 |
| BBa_I714928 | RecA_S_WTlexO_DLacO2 | 862 |
| BBa_I714931 | RecA_D_consenLexO_lacO2 | 862 |
| BBa_I718018 | dapAp promoter | 81 |
| BBa_I720001 | AraBp−>rpoN | 1632 |
| BBa_I720002 | glnKp−>lacI | 1284 |
| BBa_I720003 | NifHp−>cI (lambda) | 975 |
| BBa_I720005 | NifA lacI RFP | 3255 |
| BBa_I720006 | GFP glnG cI | 2913 |
| BBa_I720007 | araBp−>rpoN (leucine landing pad) | 51 |
| BBa_I720008 | Ara landing pad (pBBLP 6) | 20 |
| BBa_I720009 | Ara landing pad (pBBLP 7) | 23 |
| BBa_I720010 | Ara landing pad (pBBLP 8) | 20 |
| BBa_I721001 | Lead Promoter | 94 |
| BBa_I723020 | Pu | 320 |
| BBa_I728456 | MerRT: Mercury-Inducible Promoter + RBS (MerR + part of MerT) | 635 |

TABLE 7G-continued

Examples of promoters which can be operatively linked to the nucleic acid in the engineered bacteriophages.

| Name | Description | Length |
|---|---|---|
| BBa_I741018 | Right facing promoter (for xylF) controlled by xylR and CRP-cAMP | 221 |
| BBa_I742124 | Reverse complement Lac promoter | 203 |
| BBa_I746104 | P2 promoter in agr operon from *S. aureus* | 96 |
| BBa_I746360 | PF promoter from P2 phage | 91 |
| BBa_I746361 | PO promoter from P2 phage | 92 |
| BBa_I746362 | PP promoter from P2 phage | 92 |
| BBa_I746364 | Psid promoter from P4 phage | 93 |
| BBa_I746365 | PLL promoter from P4 phage | 92 |
| BBa_I748001 | Putative Cyanide Nitrilase Promoter | 271 |
| BBa_I752000 | Riboswitch(theophylline) | 56 |
| BBa_I761011 | CinR, CinL and glucose controlled promoter | 295 |
| BBa_I761014 | cinr + cinl (RBS) with double terminator | 1661 |
| BBa_I764001 | Ethanol regulated promoter AOX1 | 867 |
| BBa_I765000 | Fe promoter | 1044 |
| BBa_I765001 | UV promoter | 76 |
| BBa_I765007 | Fe and UV promoters | 1128 |
| BBa_J13210 | pOmpR dependent POPS producer | 245 |
| BBa_J22106 | rec A (SOS) Promoter | 192 |
| BBa_J23119 | constitutive promoter family member | 35 |
| BBa_J24669 | Tri-Stable Toggle (Arabinose induced component) | 3100 |
| BBa_J3902 | PrFe (PI + PII rus operon) | 272 |
| BBa_J58100 | AND-type promoter synergistically activated by cI and CRP | 106 |
| BBa_J61051 | [Psal1] | 1268 |
| BBa_K085005 | (lacI)promoter->key3c->Terminator | 405 |
| BBa_K088007 | GlnRS promoter | 38 |
| BBa_K089004 | phaC Promoter (−663 from ATG) | 663 |
| BBa_K089005 | −35 to Tc start site of phaC | 49 |
| BBa_K089006 | −663 to Tc start site of phaC | 361 |
| BBa_K090501 | Gram-Positive IPTG-Inducible Promoter | 107 |
| BBa_K090504 | Gram-Positive Strong Constitutive Promoter | 239 |
| BBa_K091100 | pLac_lux hybrid promoter | 74 |
| BBa_K091101 | pTet_Lac hybrid promoter | 83 |
| BBa_K091104 | pLac/Mnt Hybrid Promoter | 87 |
| BBa_K091105 | pTet/Mnt Hybrid Promoter | 98 |
| BBa_K091106 | LsrA/cI hybrid promoter | 141 |
| BBa_K091107 | pLux/cI Hybrid Promoter | 57 |
| BBa_K091114 | LsrAR Promoter | 248 |
| BBa_K091115 | LsrR Promoter | 100 |
| BBa_K091116 | LsrA Promoter | 126 |
| BBa_K091117 | pLas promoter | 126 |
| BBa_K091143 | pLas/cI Hybrid Promoter | 164 |
| BBa_K091146 | pLas/Lux Hybrid Promoter | 126 |
| BBa_K091184 | pLux/cI + RBS + LuxS + RBS + Mnt + TT + pLac/Mnt + RBS + LuxS + RBS + cI + TT | 2616 |
| BBa_K093000 | pRecA with LexA binding site | 48 |
| BBa_K101017 | MioC Promoter (DNAa-Repressed Promoter) | 319 |
| BBa_K101018 | MioC Promoter (regulating tetR) | 969 |
| BBa_K105020 | tetR - operator | 29 |
| BBa_K105021 | cI - operator | 27 |
| BBa_K105022 | lex A - operator | 31 |
| BBa_K105023 | lac I - operator | 25 |
| BBa_K105024 | Gal4 - operator | 27 |
| BBa_K105026 | Gal1 promoter | 549 |
| BBa_K105027 | cyc100 minimal promoter | 103 |
| BBa_K105028 | cyc70 minimal promoter | 103 |
| BBa_K105029 | cyc43 minimal promoter | 103 |
| BBa_K105030 | cyc28 minimal promoter | 103 |
| BBa_K105031 | cyc16 minimal promoter | 103 |
| BBa_K108014 | PR | 234 |
| BBa_K108016 | PP | 406 |
| BBa_K108025 | Pu | 200 |
| BBa_K109200 | AraC and TetR promoter (hybrid) | 132 |
| BBa_K110005 | Alpha-Cell Promoter MF(ALPHA)2 | 500 |
| BBa_K110006 | Alpha-Cell Promoter MF(ALPHA)1 | 501 |
| BBa_K110016 | A-Cell Promoter STE2 (backwards) | 500 |
| BBa_K112118 | rrnB P1 promoter | 503 |
| BBa_K112318 | {<bolA promoter>} in BBb format | 436 |
| BBa_K112319 | {<ftsQ promoter>} in BBb format | 434 |
| BBa_K112320 | {<ftsAZ promoter>} in BBb format | 773 |
| BBa_K112322 | {Pdps} in BBb format | 348 |
| BBa_K112323 | {H-NS!} in BBb format | 414 |
| BBa_K112400 | Promoter for grpE gene - Heat Shock and Ultrasound Sensitive | 98 |
| BBa_K112401 | Promoter for recA gene - SOS and Ultrasound Sensitive | 286 |
| BBa_K112402 | promoter for FabA gene - Membrane Damage and Ultrasound Sensitive | 256 |
| BBa_K112405 | Promoter for CadA and CadB genes | 370 |

TABLE 7G-continued

Examples of promoters which can be operatively linked to the nucleic acid in the engineered bacteriophages.

| Name | Description | Length |
|---|---|---|
| BBa_K112406 | cadC promoter | 2347 |
| BBa_K112407 | Promoter for ygeF pseudogene | 494 |
| BBa_K113009 | pBad/araC | 1210 |
| BBa_K116001 | nhaA promoter, that can be regulated by pH and nhaR protein. | 274 |
| BBa_K116401 | external phosphate sensing promoter | 506 |
| BBa_K116500 | OmpF promoter that is activated or repressed by OmpR according to osmolarity. | 126 |
| BBa_K116603 | pRE promoter from λ phage | 48 |
| BBa_K117002 | LsrA promoter (indirectly activated by AI-2) | 102 |
| BBa_K117004 | pLacI-GFP | 1086 |
| BBa_K117005 | pLacI-RBS | 220 |
| BBa_K119002 | RcnR operator (represses RcnA) | 83 |
| BBa_K122000 | pPGK1 | 1497 |
| BBa_K122002 | pADH1 (truncated) | 701 |
| BBa_K123002 | LacIQ ERE TetR | 742 |
| BBa_K123003 | ER | 1849 |
| BBa_K125110 | nir promoter + rbs (0.6) | 111 |
| BBa_K128006 | *L. bulgaricus* LacS Promoter | 197 |
| BBa_K133044 | TetR(RBS) | 35 |
| BBa_K136006 | flgA promoter followed by its natural RBS | 202 |
| BBa_K136008 | flhB promoter followed by its natural RBS | 203 |
| BBa_K136009 | fliL promoter followed by its natural RBS | 154 |
| BBa_K136010 | fliA promoter | 345 |
| BBa_K137031 | constitutive promoter with (C)10 (SEQ ID NO: 121) between −10 and −35 elements | 62 |
| BBa_K137032 | constitutive promoter with (C)12 (SEQ ID NO: 122) between −10 and −35 elements | 64 |
| BBa_K137125 | LacI-repressed promoter B4 | 103 |
| BBa_K145150 | Hybrid promoter: HSL-LuxR activated, P22 C2 repressed | 66 |
| BBa_K149001 | Prp22 promoter | 1006 |
| BBa_K165001 | pGAL1+ w/XhoI sites | 672 |
| BBa_K165011 | Zif268-HIV binding sites (3) | 46 |
| BBa_K165012 | Gli1 binding sites | 127 |
| BBa_K165013 | YY1 binding sites | 51 |
| BBa_K165016 | mCYC1 minimal yeast promoter | 245 |
| BBa_K165030 | mCYC promoter plus Zif268-HIV binding sites | 307 |
| BBa_K165031 | mCYC promoter plus LexA binding sites | 403 |
| BBa_K165032 | mCYC promoter plus Gli1 binding sites | 411 |
| BBa_K165033 | YY1 binding sites + mCYC promoter | 304 |
| BBa_K165034 | Zif268-HIV bs + LexA bs + mCYC promoter | 457 |
| BBa_K165035 | Gli1 bs + Zif268-HIV bs + mCYC promoter | 442 |
| BBa_K165036 | Gli1 bs + LexA bs + mCYC promoter | 538 |
| BBa_K165038 | Gli1 binding sites + ADH1 constitutive yeast promoter | 1580 |
| BBa_K165039 | Zif268-HIV binding sites + ADH1 yeast promoter | 1499 |
| BBa_K165040 | Gli1 binding sites + TEF constitutive yeast promoter | 538 |
| BBa_K165041 | Zif268-HIV binding sites + TEF constitutive yeast promoter | 457 |
| BBa_K165042 | Gli1 binding sites + MET25 inducible yeast promoter | 522 |
| BBa_K165043 | Zif268-HIV binding sites + MET25 constitutive yeast promoter | 441 |
| BBa_K165045 | pGAL1+ LexA binding sites | 785 |
| BBa_K165048 | Lex A op8 mCYC1 | 393 |
| BBa_R0050 | Promoter (HK022 cI regulated) | 55 |
| BBa_R0052 | Promoter (434 cI regulated) | 46 |
| BBa_R0061 | Promoter (HSL-mediated luxR repressor) | 30 |
| BBa_R0063 | Promoter (luxR & HSL regulated - lux pL) | 151 |
| BBa_R0065 | Promoter (lambda cI and luxR regulated - hybrid) | 97 |
| BBa_R0071 | Promoter (RhlR & C4-HSL regulated) | 53 |
| BBa_R0073 | Promoter (Mnt regulated) | 67 |
| BBa_R0074 | Promoter (PenI regulated) | 77 |
| BBa_R0075 | Promoter (TP901 cI regulated) | 117 |
| BBa_R0077 | Promoter (cinR and HSL regulated, RBS+) | 231 |
| BBa_R0078 | Promoter (cinR and HSL regulated) | 225 |
| BBa_R0081 | Inhibitor (AraC loop attachment with O2 site) | 183 |
| BBa_R0082 | Promoter (OmpR, positive) | 108 |
| BBa_R0083 | Promoter (OmpR, positive) | 78 |
| BBa_R0084 | Promoter (OmpR, positive) | 108 |
| BBa_R1050 | Promoter, Standard (HK022 cI regulated) | 56 |
| BBa_R1051 | Promoter, Standard (lambda cI regulated) | 49 |
| BBa_R1052 | Promoter, Standard (434 cI regulated) | 46 |
| BBa_R1053 | Promoter, Standard (p22 cII regulated) | 55 |
| BBa_R1062 | Promoter, Standard (luxR and HSL regulated -- lux pR) | 56 |
| BBa_R2000 | Promoter, Zif23 regulated, test: between | 45 |
| BBa_R2001 | Promoter, Zif23 regulated, test: after | 52 |
| BBa_R2002 | Promoter, Zif23 regulated, test: between and after | 52 |
| BBa_R2109 | Promoter with operator site for C2003 | 72 |
| BBa_R2114 | Promoter with operator site for C2003 | 72 |

TABLE 7G-continued

Examples of promoters which can be operatively linked to the nucleic acid in the engineered bacteriophages.

| Name | Description | Length |
|---|---|---|
| BBa_I10498 | Oct-4 promoter | 1417 |
| BBa_I12001 | Promoter (PRM+) | 96 |
| BBa_I12003 | Lambda Prm Promoter | 88 |
| BBa_I12005 | lambda Prm Inverted Antisense (No start codon) | 85 |
| BBa_I12008 | Barkai-Leibler design experiment part A (p22cII) | 1154 |
| BBa_I12010 | Modified lamdba Prm promoter (repressed by p22 cII) | 78 |
| BBa_I12014 | Repressor, 434 cI (RBS− LVA−) | 636 |
| BBa_I12021 | Inducible Lambda cI Repressor Generator (Controlled by IPTG and LacI) | 2370 |
| BBa_I12031 | Barkai-Leibler design experiment Part A (Lambda cI) wth cooperativity | 1159 |
| BBa_I12032 | Modified lamdba Prm promoter (repressed by p22 cI with cooperativity) RBS+ | 106 |
| BBa_I12034 | Modified lamdba Prm promoter (repressed by 434 cI with cooperativity) RBS+ | 102 |
| BBa_I12035 | Modified lamdba Prm promoter (repressed by p22 cI without cooperativity) RBS+ | 106 |
| BBa_I12037 | Reporter 3 for Barkai-Leibler oscillator | 1291 |
| BBa_I12044 | Activator for BL oscillator with reporter protein, (cooperativity) | 2112 |
| BBa_I12045 | BL oscillator, cooperativity, reporter protein, kickstart | 4139 |
| BBa_I12046 | Activator for BL oscillator with reporter protein, (cooperativity and L-strain −10 region) | 2112 |
| BBa_I12047 | BL oscillator, cooperativity + replaced −10 region (Llac), reporter protein, kickstart | 4139 |
| BBa_I12210 | plac Or2-62 (positive) | 70 |
| BBa_I12212 | TetR - TetR-4C heterodimer promoter (negative) | 61 |
| BBa_I12219 | Wild-type TetR(B) promoter (negative) | 71 |
| BBa_I13062 | LuxR QPI | 822 |
| BBa_I13267 | Intermediate part from assembly 317 | 1769 |
| BBa_I13406 | Pbad/AraC with extra REN sites | 1226 |
| BBa_I14021 | plTetO1 · RBS · CinI | 810 |
| BBa_I20255 | Promoter-RBS | 57 |
| BBa_I20256 | Promoter-RBS | 56 |
| BBa_I20258 | Promoter-RBS | 56 |
| BBa_I714932 | RecA_D_consenLexO_lacO3 | 862 |
| BBa_I715003 | hybrid pLac with UV5 mutation | 55 |
| BBa_I715052 | Trp Leader Peptide and anti-terminator/terminator | 134 |
| BBa_I715053 | Trp Leader Peptide and anti-terminator/terminator with hixC insertion | 159 |
| BBa_I717002 | Pr from lambda switch | 177 |
| BBa_I723011 | pDntR (estimated promoter for DntR) | 26 |
| BBa_I723013 | pDntA (estimated promoter for DntA) | 33 |
| BBa_I723018 | Pr (promoter for XylR) | 410 |
| BBa_I731004 | FecA promoter | 90 |
| BBa_I732021 | Template for Building Primer Family Member | 159 |
| BBa_I732200 | NOT Gate Promoter Family Member (D001O1wt1) | 125 |
| BBa_I732201 | NOT Gate Promoter Family Member (D001O11) | 124 |
| BBa_I732202 | NOT Gate Promoter Family Member (D001O22) | 124 |
| BBa_I732203 | NOT Gate Promoter Family Member (D001O33) | 124 |
| BBa_I732204 | NOT Gate Promoter Family Member (D001O44) | 124 |
| BBa_I732206 | NOT Gate Promoter Family Member (D001O66) | 124 |
| BBa_I732207 | NOT Gate Promoter Family Member (D001O77) | 124 |
| BBa_I732270 | Promoter Family Member with Hybrid Operator (D001O12) | 124 |
| BBa_I732271 | Promoter Family Member with Hybrid Operator (D001O16) | 124 |
| BBa_I732272 | Promoter Family Member with Hybrid Operator (D001O17) | 124 |
| BBa_I732273 | Promoter Family Member with Hybrid Operator (D001O21) | 124 |
| BBa_I732274 | Promoter Family Member with Hybrid Operator (D001O24) | 124 |
| BBa_I732275 | Promoter Family Member with Hybrid Operator (D001O26) | 124 |
| BBa_I732276 | Promoter Family Member with Hybrid Operator (D001O27) | 124 |
| BBa_I732277 | Promoter Family Member with Hybrid Operator (D001O46) | 124 |
| BBa_I732278 | Promoter Family Member with Hybrid Operator (D001O47) | 124 |
| BBa_I732279 | Promoter Family Member with Hybrid Operator (D001O61) | 124 |
| BBa_I732301 | NAND Candidate (U073O26D001O16) | 120 |
| BBa_I732302 | NAND Candidate (U073O27D001O17) | 120 |
| BBa_I732303 | NAND Candidate (U073O22D001O46) | 120 |
| BBa_I732304 | NAND Candidate (U073O22D001O47) | 120 |
| BBa_I732305 | NAND Candidate (U073O22D059O46) | 178 |
| BBa_I732306 | NAND Candidate (U073O11D002O22) | 121 |
| BBa_I732351 | NOR Candidate (U037O11D002O22) | 85 |
| BBa_I732352 | NOR Candidate (U035O44D001O22) | 82 |
| BBa_I732400 | Promoter Family Member (U097NUL + D062NUL) | 165 |
| BBa_I732401 | Promoter Family Member (U097O11 + D062NUL) | 185 |
| BBa_I732402 | Promoter Family Member (U085O11 + D062NUL) | 173 |
| BBa_I732403 | Promoter Family Member (U073O11 + D062NUL) | 161 |
| BBa_I732404 | Promoter Family Member (U061O11 + D062NUL) | 149 |
| BBa_I732405 | Promoter Family Member (U049O11 + D062NUL) | 137 |
| BBa_I732406 | Promoter Family Member (U037O11 + D062NUL) | 125 |

TABLE 7G-continued

Examples of promoters which can be operatively linked
to the nucleic acid in the engineered bacteriophages.

| Name | Description | Length |
|---|---|---|
| BBa_I732407 | Promoter Family Member (U097NUL + D002O22) | 125 |
| BBa_I732408 | Promoter Family Member (U097NUL + D014O22) | 137 |
| BBa_I732409 | Promoter Family Member (U097NUL + D026O22) | 149 |
| BBa_I732410 | Promoter Family Member (U097NUL + D038O22) | 161 |
| BBa_I732411 | Promoter Family Member (U097NUL + D050O22) | 173 |
| BBa_I732412 | Promoter Family Member (U097NUL + D062O22) | 185 |
| BBa_I732413 | Promoter Family Member (U097O11 + D002O22) | 145 |
| BBa_I732414 | Promoter Family Member (U097O11 + D014O22) | 157 |
| BBa_I732415 | Promoter Family Member (U097O11 + D026O22) | 169 |
| BBa_I732416 | Promoter Family Member (U097O11 + D038O22) | 181 |
| BBa_I732417 | Promoter Family Member (U097O11 + D050O22) | 193 |
| BBa_I732418 | Promoter Family Member (U097O11 + D062O22) | 205 |
| BBa_I732419 | Promoter Family Member (U085O11 + D002O22) | 133 |
| BBa_I732420 | Promoter Family Member (U085O11 + D014O22) | 145 |
| BBa_I732421 | Promoter Family Member (U085O11 + D026O22) | 157 |
| BBa_I732422 | Promoter Family Member (U085O11 + D038O22) | 169 |
| BBa_I732423 | Promoter Family Member (U085O11 + D050O22) | 181 |
| BBa_I732424 | Promoter Family Member (U085O11 + D062O22) | 193 |
| BBa_I732425 | Promoter Family Member (U073O11 + D002O22) | 121 |
| BBa_I732426 | Promoter Family Member (U073O11 + D014O22) | 133 |
| BBa_I732427 | Promoter Family Member (U073O11 + D026O22) | 145 |
| BBa_I732428 | Promoter Family Member (U073O11 + D038O22) | 157 |
| BBa_I732429 | Promoter Family Member (U073O11 + D050O22) | 169 |
| BBa_I732430 | Promoter Family Member (U073O11 + D062O22) | 181 |
| BBa_I732431 | Promoter Family Member (U061O11 + D002O22) | 109 |
| BBa_I732432 | Promoter Family Member (U061O11 + D014O22) | 121 |
| BBa_I732433 | Promoter Family Member (U061O11 + D026O22) | 133 |
| BBa_I732434 | Promoter Family Member (U061O11 + D038O22) | 145 |
| BBa_I732435 | Promoter Family Member (U061O11 + D050O22) | 157 |
| BBa_I732436 | Promoter Family Member (U061O11 + D062O22) | 169 |
| BBa_I732437 | Promoter Family Member (U049O11 + D002O22) | 97 |
| BBa_I732438 | Promoter Family Member (U049O11 + D014O22) | 109 |
| BBa_I732439 | Promoter Family Member (U049O11 + D026O22) | 121 |
| BBa_I732440 | Promoter Family Member (U049O11 + D038O22) | 133 |
| BBa_I732441 | Promoter Family Member (U049O11 + D050O22) | 145 |
| BBa_I732442 | Promoter Family Member (U049O11 + D062O22) | 157 |
| BBa_I732443 | Promoter Family Member (U037O11 + D002O22) | 85 |
| BBa_I732444 | Promoter Family Member (U037O11 + D014O22) | 97 |
| BBa_I732445 | Promoter Family Member (U037O11 + D026O22) | 109 |
| BBa_I732446 | Promoter Family Member (U037O11 + D038O22) | 121 |
| BBa_I732447 | Promoter Family Member (U037O11 + D050O22) | 133 |
| BBa_I732448 | Promoter Family Member (U037O11 + D062O22) | 145 |
| BBa_I732450 | Promoter Family Member (U073O26 + D062NUL) | 161 |
| BBa_I732451 | Promoter Family Member (U073O27 + D062NUL) | 161 |
| BBa_I732452 | Promoter Family Member (U073O26 + D062O61) | 181 |
| BBa_I735008 | ORE1X Oleate response element | 273 |
| BBa_I735009 | ORE2X oleate response element | 332 |
| BBa_I735010 | This promoter encoding for a thiolase involved in beta-oxidation of fatty acids. | 850 |
| BBa_I739101 | Double Promoter (constitutive/TetR, negative) | 83 |
| BBa_I739102 | Double Promoter (cI, negative/TetR, negative) | 97 |
| BBa_I739103 | Double Promoter (lacI, negative/P22 cII, negative) | 87 |
| BBa_I739104 | Double Promoter (LuxR/HSL, positive/P22 cII, negative) | 101 |
| BBa_I739105 | Double Promoter (LuxR/HSL, positive/cI, negative) | 99 |
| BBa_I739106 | Double Promoter (TetR, negative/P22 cII, negative) | 84 |
| BBa_I739107 | Double Promoter (cI, negative/LacI, negative) | 78 |
| BBa_I741015 | two way promoter controlled by XylR and Crp-CAmp | 301 |
| BBa_I741017 | dual facing promoter controlled by xylR and CRP-cAMP (1741015 reverse complement) | 302 |
| BBa_I741019 | Right facing promoter (for xylA) controlled by xylR and CRP-cAMP | 131 |
| BBa_I741020 | promoter to xylF without CRP and several binding sites for xylR | 191 |
| BBa_I741021 | promoter to xylA without CRP and several binding sites for xylR | 87 |
| BBa_I741109 | Lambda Or operator region | 82 |
| BBa_I742126 | Reverse lambda cI-regulated promoter | 49 |
| BBa_I746363 | PV promoter from P2 phage | 91 |
| BBa_I746665 | Pspac-hy promoter | 58 |
| BBa_I751500 | pcI (for positive control of pcI-lux hybrid promoter) | 77 |
| BBa_I751501 | plux-cI hybrid promoter | 66 |
| BBa_I751502 | plux-lac hybrid promoter | 74 |
| BBa_I756002 | Kozak Box | 7 |
| BBa_I756014 | LexAoperator-MajorLatePromoter | 229 |
| BBa_I756015 | CMV Promoter with lac operator sites | 663 |
| BBa_I756016 | CMV-tet promoter | 610 |
| BBa_I756017 | U6 promoter with tet operators | 341 |
| BBa_I756018 | Lambda Operator in SV-40 intron | 411 |

TABLE 7G-continued

Examples of promoters which can be operatively linked to the nucleic acid in the engineered bacteriophages.

| Name | Description | Length |
|---|---|---|
| BBa_I756019 | Lac Operator in SV-40 intron | 444 |
| BBa_I756020 | Tet Operator in SV-40 intron | 391 |
| BBa_I756021 | CMV promoter with Lambda Operator | 630 |
| BBa_I760005 | Cu-sensitive promoter | 16 |
| BBa_I761000 | cinr + cinl (RBS) | 1558 |
| BBa_I761001 | OmpR binding site | 62 |
| BBa_I766200 | pSte2 | 1000 |
| BBa_I766214 | pGal1 | 1002 |
| BBa_I766555 | pCyc (Medium) Promoter | 244 |
| BBa_I766556 | pAdh (Strong) Promoter | 1501 |
| BBa_I766557 | pSte5 (Weak) Promoter | 601 |
| BBa_I766558 | pFig1 (Inducible) Promoter | 1000 |
| BBa_I9201 | lambda cI operator/binding site | 82 |
| BBa_J01005 | pspoIIE promoter (spo0A J01004, positive) | 206 |
| BBa_J01006 | Key Promoter absorbs 3 | 59 |
| BBa_J03007 | Maltose specific promoter | 206 |
| BBa_J03100 | -- No description -- | 847 |
| BBa_J04700 | Part containing promoter, riboswitch mTCT8-4 theophylline aptamer (J04705), and RBS | 258 |
| BBa_J04705 | Riboswitch designed to turn "ON" a protein | 38 |
| BBa_J04800 | J04800 (RevAptRibo) contains a theophylline aptamer upstream of the RBS that should act as a riboswitch | 258 |
| BBa_J04900 | Part containing promoter, 8 bp, RBS, and riboswitch mTCT8-4 theophylline aptamer (J04705) | 258 |
| BBa_J05209 | Modified Pr Promoter | 49 |
| BBa_J05210 | Modified Prm + Promoter | 82 |
| BBa_J05215 | Regulator for R1-CREBH | 41 |
| BBa_J05216 | Regulator for R3-ATF6 | 41 |
| BBa_J05217 | Regulator for R2-YAP7 | 41 |
| BBa_J05218 | Regulator for R4-cMaf | 41 |
| BBa_J05221 | Triple Binding Site for R3-ATF6 | 62 |
| BBa_J05222 | ZF-2*e2 Binding Site | 37 |
| BBa_J05500 | Sensing Device A (cI) | 2371 |
| BBa_J05501 | Sensing Device B (cI + LVA) | 2337 |
| BBa_J06403 | RhIR promoter repressible by CI | 51 |
| BBa_J07007 | ctx promoter | 145 |
| BBa_J07010 | ToxR_inner (aa's 1-198; cytoplasm + TM) | 594 |
| BBa_J07019 | FecA Promoter (with Fur box) | 86 |
| BBa_J07041 | POPS/RIPS generator (R0051::B0030) | 72 |
| BBa_J07042 | POPS/RIPS generator (R0040::B0030) | 77 |
| BBa_J11003 | control loop for PI controller with BBa_J11002 | 961 |
| BBa_J13211 | R0040.B0032 | 75 |
| BBa_J13212 | R0040.B0033 | 73 |
| BBa_J15301 | Pars promoter from *Escherichia coli* chromosomal ars operon. | 127 |
| BBa_J15502 | copA promoter | 287 |
| BBa_J16101 | BanAp - Banana-induced Promoter | 19 |
| BBa_J16105 | HelPp - "Help" Dependant promoter | 26 |
| BBa_J16400 | Iron sensitive promoter (test delete later) | 26 |
| BBa_J21002 | Promoter + LuxR | 998 |
| BBa_J21003 | Promoter + TetR | 904 |
| BBa_J21004 | Promoter + LacL | 1372 |
| BBa_J21006 | LuxR, TetR Generator | 1910 |
| BBa_J21007 | LuxR, TetR, LacL Generator | 3290 |
| BBa_J22052 | Pcya | 65 |
| BBa_J22086 | pX (DnaA binding site) | 125 |
| BBa_J22126 | Rec A (SOS) promoter | 186 |
| BBa_J23150 | 1 bp mutant from J23107 | 35 |
| BBa_J23151 | 1 bp mutant from J23114 | 35 |
| BBa_J24000 | CafAp (Cafeine Dependant promoter) | 14 |
| BBa_J24001 | WigLp (Wiggle-dependent Promotor) | 46 |
| BBa_J24670 | Tri-Stable Toggle (Lactose induced component) | 1877 |
| BBa_J24671 | Tri-Stable Toggle (Tetracycline induced component) | 2199 |
| BBa_J24813 | URA3 Promoter from *S. cerevisiae* | 137 |
| BBa_J26003 | Mushroom Activated Promoter | 23 |
| BBa_J31013 | pLac Backwards [cf. BBa_R0010] | 200 |
| BBa_J31014 | crRNA | 38 |
| BBa_J3102 | pBad: RBS | 153 |
| BBa_J31020 | produces taRNA | 295 |
| BBa_J31022 | comK transcription activator from *B. subtilis* | 578 |
| BBa_J33100 | ArsR and Ars Promoter | 472 |
| BBa_J34800 | Promoter tetracycline inducible | 94 |
| BBa_J34806 | promoter lac induced | 112 |
| BBa_J34809 | promoter lac induced | 125 |
| BBa_J34814 | T7 Promoter | 28 |
| BBa_J45503 | hybB Cold Shock Promoter | 393 |

TABLE 7G-continued

Examples of promoters which can be operatively linked to the nucleic acid in the engineered bacteriophages.

| Name | Description | Length |
|---|---|---|
| BBa_J45504 | htpG Heat Shock Promoter | 405 |
| BBa_J45992 | Full-length stationary phase osmY promoter | 199 |
| BBa_J45993 | Minimal stationary phase osmY promoter | 57 |
| BBa_J45994 | Exponential phase transcriptional control device | 1109 |
| BBa_J48103 | Iron promoter | 140 |
| BBa_J48104 | NikR promoter, a protein of the ribbon helix-helix family of transcription factors that repress expression | 40 |
| BBa_J48106 | vnfH | 891 |
| BBa_J48107 | UGT008-3 Promoter/Met32p | 588 |
| BBa_J48110 | Fe Promoter + mRFP1 | 1009 |
| BBa_J48111 | *E. coli* NikR | 926 |
| BBa_J48112 | vnfH: vanadium promoter | 1816 |
| BBa_J49000 | Roid Rage | 4 |
| BBa_J49001 | Testosterone dependent promoter for species *Bicyclus Bicyclus* | 89 |
| BBa_J49006 | Nutrition Promoter | 3 |
| BBa_J4906 | WrooHEAD2 (Wayne Rooney's Head dependent promoter) | 122 |
| BBa_J54015 | Protein Binding Site_LacI | 42 |
| BBa_J54016 | promoter_lacq | 54 |
| BBa_J54017 | promoter_always | 98 |
| BBa_J54018 | promoter_always | 98 |
| BBa_J54101 | deltaP-GFP(A) | |
| BBa_J54102 | DeltaP-GFP(A) | 813 |
| BBa_J54110 | MelR_regulated promoter | 76 |
| BBa_J54120 | EmrR_regulated promoter | 46 |
| BBa_J54130 | BetI_regulated promoter | 46 |
| BBa_J54200 | lacq_Promoter | 50 |
| BBa_J54210 | RbsR_Binding_Site | 37 |
| BBa_J54220 | FadR_Binding_Site | 34 |
| BBa_J54230 | TetR_regulated | 38 |
| BBa_J54250 | LacI_Binding_Site | 42 |
| BBa_J56012 | Invertible sequence of dna includes Ptrc promoter | 409 |
| BBa_J56015 | lacIQ - promoter sequence | 57 |
| BBa_J61045 | [spv] spv operon (PoPS out) | 1953 |
| BBa_J61054 | [HIP-1] Promoter | 53 |
| BBa_J61055 | [HIP-1fnr] Promoter | 53 |
| BBa_J64000 | rhlI promoter | 72 |
| BBa_J64001 | psicA from *Salmonella* | 143 |
| BBa_J64010 | lasI promoter | 53 |
| BBa_J64065 | cI repressed promoter | 74 |
| BBa_J64067 | LuxR + 3OC6HSL independent R0065 | 98 |
| BBa_J64068 | increased strength R0051 | 49 |
| BBa_J64069 | R0065 with lux box deleted | 84 |
| BBa_J64700 | Trp Operon Promoter | 616 |
| BBa_J64712 | LasR/LasI Inducible & RHLR/RHLI repressible Promoter | 157 |
| BBa_J64750 | SPI-1 TTSS secretion-linked promoter from *Salmonella* | 167 |
| BBa_J64800 | RHLR/RHLI Inducible & LasR/LasI repressible Promoter | 53 |
| BBa_J64804 | The promoter region (inclusive of regulator binding sites) of the *B. subtilis* RocDEF operon | 135 |
| BBa_J64931 | glnKp promoter | 147 |
| BBa_J64951 | *E. Coli* CreABCD phosphate sensing operon promoter | 81 |
| BBa_J64979 | glnAp2 | 151 |
| BBa_J64980 | OmpR-P strong binding, regulatory region for Team Challenge March 2007 | |
| BBa_J64981 | OmpR-P strong binding, regulatory region for Team Challenge March 2007 | 82 |
| BBa_J64982 | OmpR-P strong binding, regulatory region for Team Challenge March 2007 | 25 |
| BBa_J64983 | Strong OmpR Binding Site | 20 |
| BBa_J64986 | LacI Consensus Binding Site | 20 |
| BBa_J64987 | LacI Consensus Binding Site in sigma 70 binding region | 32 |
| BBa_J64991 | TetR | 19 |
| BBa_J64995 | Phage −35 site | 6 |
| BBa_J64997 | T7 consensus −10 and rest | 19 |
| BBa_J64998 | consensus −10 and rest from SP6 | 19 |
| BBa_J70025 | Promoter for tetM gene, from pBOT1 plasmid, pAMbeta1 | 345 |
| BBa_J72005 | {Ptet} promoter in BBb | 54 |
| BBa_K076017 | Ubc Promoter | 1219 |
| BBa_K078101 | aromatic compounds regulatory pcbC promoter | 129 |
| BBa_K079017 | Lac symmetric - operator library member | 20 |
| BBa_K079018 | Lac 1 - operator library member | 21 |
| BBa_K079019 | Lac 2 - operator library member | 21 |
| BBa_K079036 | Tet O operator library member | 15 |
| BBa_K079037 | TetO-4C - operator library member | 15 |
| BBa_K079038 | TetO-wt/4C5G - operator library member | 15 |
| BBa_K079039 | LexA 1 - operator library member | 16 |
| BBa_K079040 | LexA 2 - operator library member | 16 |
| BBa_K079041 | Lambda OR1 - operator library member | 17 |
| BBa_K079042 | Lambda OR2 - operator library member | 17 |

TABLE 7G-continued

Examples of promoters which can be operatively linked to the nucleic acid in the engineered bacteriophages.

| Name | Description | Length |
|---|---|---|
| BBa_K079043 | Lambda OR3 - operator library member | 17 |
| BBa_K079045 | Lac operator library | 78 |
| BBa_K079046 | Tet operator library | 61 |
| BBa_K079047 | Lambda operator library | 67 |
| BBa_K079048 | LexA operator library | 40 |
| BBa_K080000 | TCFbs-BMP4 | 1582 |
| BBa_K080001 | A20/alpha cardiac actin miniPro-BMP4 | 1402 |
| BBa_K080003 | CMV-rtTA | 1413 |
| BBa_K080005 | TetO (TRE)-nkx2.5-fmdv2A-dsRed | 2099 |
| BBa_K080006 | TetO (TRE)-gata4-fmdv2A-dsRed | 2447 |
| BBa_K080008 | TetO (TRE)-nkx-2.5-fmdv2A-gata4-fmdv2A-dsRed | 3497 |
| BBa_K085004 | riboswitch system with GFP | 1345 |
| BBa_K085006 | pTet−>lock3d−>GFP−>Ter | 932 |
| BBa_K086017 | unmodified Lutz-Bujard LacO promoter | 55 |
| BBa_K086018 | modified Lutz-Bujard LacO promoter, with alternative sigma factor σ24 | 55 |
| BBa_K086019 | modified Lutz-Bujard LacO promoter, with alternative sigma factor σ24 | 55 |
| BBa_K086020 | modified Lutz-Bujard LacO promoter, with alternative sigma factor σ24 | 55 |
| BBa_K086021 | modified Lutz-Bujard LacO promoter, with alternative sigma factor σ24 | 55 |
| BBa_K086022 | modified Lutz-Bujard LacO promoter, with alternative sigma factor σ28 | 55 |
| BBa_K086023 | modified Lutz-Bujard LacO promoter, with alternative sigma factor σ28 | 55 |
| BBa_K086024 | modified Lutz-Bujard LacO promoter, with alternative sigma factor σ28 | 55 |
| BBa_K086025 | modified Lutz-Bujard LacO promoter, with alternative sigma factor σ28 | 55 |
| BBa_K086026 | modified Lutz-Bujard LacO promoter, with alternative sigma factor σ32 | 55 |
| BBa_K086027 | modified Lutz-Bujard LacO promoter, with alternative sigma factor σ32 | 55 |
| BBa_K086028 | modified Lutz-Bujard LacO promoter, with alternative sigma factor σ32 | 55 |
| BBa_K086029 | modified Lutz-Bujard LacO promoter, with alternative sigma factor σ32 | 55 |
| BBa_K086030 | modified Lutz-Bujard LacO promoter, with alternative sigma factor σ38 | 55 |
| BBa_K086031 | modified Lutz-Bujard LacO promoter, with alternative sigma factor σ38 | 55 |
| BBa_K086032 | modified Lutz-Bujard LacO promoter, with alternative sigma factor σ38 | 55 |
| BBa_K086033 | modified Lutz-Bujard LacO promoter, with alternative sigma factor σ38 | 55 |
| BBa_K090502 | Gram-Positive Xylose-Inducible Promoter | 126 |
| BBa_K090503 | Gram-Positive General Constitutive Promoter | 91 |
| BBa_K091112 | pLacIQ1 promoter | 56 |
| BBa_K091156 | pLux | 55 |
| BBa_K091157 | pLux/Las Hybrid Promoter | 55 |
| BBa_K093008 | reverse BBa_R0011 | 55 |
| BBa_K094002 | plambda P(O-R12) | 100 |
| BBa_K094140 | pLacIq | 80 |
| BBa_K100003 | Edited Xylose Regulated Bi-Directional Operator 3 | 303 |
| BBa_K101000 | Dual-Repressed Promoter for p22 mnt and TetR | 61 |
| BBa_K101001 | Dual-Repressed Promoter for LacI and LambdacI | 116 |
| BBa_K101002 | Dual-Repressed Promoter for p22 cII and TetR | 66 |
| BBa_K102909 | TA11 gate from synthetic algorithm v1.1 | 134 |
| BBa_K102910 | TA12 gate from synthetic algorithm v1.1 | 107 |
| BBa_K102911 | TA13 gate from synthetic algorithm v1.2 | 90 |
| BBa_K102912 | TA12 plus pause sequence | 108 |
| BBa_K102950 | TA0In null anti-sense input | 175 |
| BBa_K102951 | TA1In anti-sense input to TA1 (BBa_K102901) | 157 |
| BBa_K102952 | TA2In anti-sense input to BBa_K102952 | 168 |
| BBa_K102953 | TA13n anti-sense input to TA3 (BBa_K102903) | 168 |
| BBa_K102954 | TA6In anti-sense input to BBa_K102904 | 169 |
| BBa_K102955 | TA7In anti-sense input to BBa_K102905 | 168 |
| BBa_K102956 | TA8In anti-sense input to BBa_K102906 | 168 |
| BBa_K102957 | TA9In anti-sense input to BBa_K102907 | 173 |
| BBa_K102958 | TA10In anti-sense input to BBa_K102908 | 183 |
| BBa_K102959 | TA11In anti-sense input to BBa_K102909 | 178 |
| BBa_K102960 | TA12In anti-sense input to anti-terminator BBa_K102910 | 173 |
| BBa_K102961 | TA13In anti-sense input to BBa_K102911 | 171 |
| BBa_K102962 | TA14In anti-sense input to BBa_K102912 | 180 |
| BBa_K103021 | modified T7 promoter with His-Tag | 166 |
| BBa_K103022 | Plac with operator and RBS | 279 |
| BBa_K106673 | 8xLexAops-Cyc1p | 418 |
| BBa_K106680 | 8xLexAops-Fig1P | 1169 |
| BBa_K106694 | Adh1P! (Adh1 Promoter, A! end) | 1511 |
| BBa_K106699 | Gal1 Promoter | 686 |
| BBa_K109584 | this is a test part, disregard it | |
| BBa_K110004 | Alpha-Cell Promoter Ste3 | 501 |
| BBa_K110007 | A-Cell Promoter MFA2 | 501 |
| BBa_K110008 | A-Cell Promoter MFA1 | 501 |
| BBa_K110009 | A-Cell Promoter STE2 | 501 |
| BBa_K110014 | A-Cell Promoter MFA2 (backwards) | 550 |
| BBa_K110015 | A-Cell Promoter MFA1 (RtL) | 436 |
| BBa_K112139 | oriR6K conditional replication origin | 408 |
| BBa_K112148 | phoPp1 magnesium promoter | 81 |
| BBa_K112149 | PmgtCB Magnesium promoter from *Salmonella* | 280 |

TABLE 7G-continued

Examples of promoters which can be operatively linked to the nucleic acid in the engineered bacteriophages.

| Name | Description | Length |
|---|---|---|
| BBa_K112321 | {H-NS!} using MG1655 reverse oligo in BBb format | 414 |
| BBa_K112701 | hns promoter | 669 |
| BBa_K112706 | Pspv2 from *Salmonella* | 474 |
| BBa_K112707 | Pspv from *Salmonella* | 1956 |
| BBa_K112708 | PfhuA | 210 |
| BBa_K112711 | rbs.spvR! | 913 |
| BBa_K112900 | Pbad | 1225 |
| BBa_K112904 | PconB5 | 41 |
| BBa_K112905 | PconC5 | 41 |
| BBa_K112906 | PconG6 | 41 |
| BBa_K112907 | Pcon | 41 |
| BBa_K113010 | overlapping T7 promoter | 40 |
| BBa_K113011 | more overlapping T7 promoter | 37 |
| BBa_K113012 | weaken overlapping T7 promoter | 40 |
| BBa_K116201 | ureD promoter from *P mirabilis* | |
| BBa_K119000 | Constitutive weak promoter of lacZ | 38 |
| BBa_K119001 | Mutated LacZ promoter | 38 |
| BBa_K120010 | Triple_lexO | 114 |
| BBa_K120023 | lexA_DBD | 249 |
| BBa_K121011 | promoter (lacI regulated) | 232 |
| BBa_K121014 | promoter (lambda cI regulated) | 90 |
| BBa_K124000 | pCYC Yeast Promoter | 288 |
| BBa_K124002 | Yeast GPD (TDH3) Promoter | 681 |
| BBa_K125100 | nir promoter from *Synechocystis* sp. PCC6803 | 88 |
| BBa_K131017 | p_qrr4 from *Vibrio harveyi* | 275 |
| BBa_K137085 | optimized (TA) repeat constitutive promoter with 13 bp between −10 and −35 elements | 31 |
| BBa_K137086 | optimized (TA) repeat constitutive promoter with 15 bp between −10 and −35 elements | 33 |
| BBa_K137087 | optimized (TA) repeat constitutive promoter with 17 bp between −10 and −35 elements | 35 |
| BBa_K137088 | optimized (TA) repeat constitutive promoter with 19 bp between −10 and −35 elements | 37 |
| BBa_K137089 | optimized (TA) repeat constitutive promoter with 21 bp between −10 and −35 elements | 39 |
| BBa_K137090 | optimized (A) repeat constitutive promoter with 17 bp between −10 and −35 elements | 35 |
| BBa_K137091 | optimized (A) repeat constitutive promoter with 18 bp between −10 and −35 elements | 36 |
| BBa_K137124 | LacI-repressed promoter A81 | 103 |
| BBa_K143010 | Promoter ctc for *B. subtilis* | 56 |
| BBa_K143011 | Promoter gsiB for *B. subtilis* | 38 |
| BBa_K143012 | Promoter veg a constitutive promoter for *B. subtilis* | 97 |
| BBa_K143013 | Promoter 43 a constitutive promoter for *B. subtilis* | 56 |
| BBa_K143014 | Promoter Xyl for *B. subtilis* | 82 |
| BBa_K143015 | Promoter hyper-spank for *B. subtilis* | 101 |
| BBa_K145152 | Hybrid promoter: P22 c2, LacI NOR gate | 142 |
| BBa_K157042 | Eukaryotic CMV promoter | 654 |
| BBa_K165000 | MET 25 Promoter | 387 |
| BBa_K165015 | pADH1 yeast constitutive promoter | 1445 |
| BBa_K165017 | LexA binding sites | 393 |
| BBa_K165037 | TEF2 yeast constitutive promoter | 403 |
| BBa_M13101 | M13K07 gene I promoter | 47 |
| BBa_M13102 | M13K07 gene II promoter | 48 |
| BBa_M13103 | M13K07 gene III promoter | 48 |
| BBa_M13104 | M13K07 gene IV promoter | 49 |
| BBa_M13105 | M13K07 gene V promoter | 50 |
| BBa_M13106 | M13K07 gene VI promoter | 49 |
| BBa_M13108 | M13K07 gene VIII promoter | 47 |
| BBa_M13110 | M13110 | 48 |
| BBa_M31201 | Yeast CLB1 promoter region, G2/M cell cycle specific | 500 |
| BBa_M31232 | Redesigned M13K07 Gene III Upstream | 79 |
| BBa_M31252 | Redesigned M13K07 Gene V Upstream | 72 |
| BBa_M31272 | Redesigned M13K07 Gene VII Upstream | 50 |
| BBa_M31282 | Redesigned M13K07 Gene VIII Upstream | 146 |
| BBa_M31292 | Redesigned M13K07 Gene IX Upstream | 69 |
| BBa_M31302 | Redesigned M13K07 Gene X Upstream | 115 |
| BBa_M31370 | tacI Promoter | 68 |
| BBa_M31519 | Modified promoter sequence of g3. | 60 |
| BBa_R0001 | HMG-CoA Dependent RBS Blocking Segment | 53 |
| BBa_R00100 | Tet promoter and sRBS | 67 |
| BBa_R00101 | VM1.0 to RiPS converter | 36 |
| BBa_R0085 | T7 Consensus Promoter Sequence | 23 |
| BBa_R0180 | T7 RNAP promoter | 23 |
| BBa_R0181 | T7 RNAP promoter | 23 |

TABLE 7G-continued

Examples of promoters which can be operatively linked to the nucleic acid in the engineered bacteriophages.

| Name | Description | Length |
|---|---|---|
| BBa_R0182 | T7 RNAP promoter | 23 |
| BBa_R0183 | T7 RNAP promoter | 23 |
| BBa_R0184 | T7 promoter (lacI repressible) | 44 |
| BBa_R0185 | T7 promoter (lacI repressible) | 44 |
| BBa_R0186 | T7 promoter (lacI repressible) | 44 |
| BBa_R0187 | T7 promoter (lacI repressible) | 44 |
| BBa_R1028 | Randy Rettberg Standardillator | |
| BBa_R1074 | Constitutive Promoter I | 49 |
| BBa_R1075 | Constitutive Promoter II | 49 |
| BBa_R2108 | Promoter with operator site for C2003 | 72 |
| BBa_R2110 | Promoter with operator site for C2003 | 72 |
| BBa_R2111 | Promoter with operator site for C2003 | 72 |
| BBa_R2112 | Promoter with operator site for C2003 | 72 |
| BBa_R2113 | Promoter with operator site for C2003 | 72 |
| BBa_R2182 | RiPS generator | 44 |
| BBa_R2201 | C2006-repressible promoter | 45 |
| BBa_R6182 | RiPS generator | 36 |
| BBa_S03331 | --Specify Parts List-- | 30 |
| BBa_S03385 | Cold-sensing promoter (hybB) | |
| BBa_Z0251 | T7 strong promoter | 35 |
| BBa_Z0252 | T7 weak binding and processivity | 35 |
| BBa_Z0253 | T7 weak binding promoter | 35 |
| BBa_Z0294 | A1, A2, A3, boxA | 435 |

REFERENCES

All references cited herein, in the specification and Examples are incorporated in their entirety by reference.

1. Orivel et al., Ponericins, New Antibacterial and Insecticidal Peptides from the Venom of the Ant Pachycondyla goeldii. 2001, JBC, 276; 17823-17829.
2. S. O'Flaherty, et al., The Recombinant Phage Lysin LysK Has a Broad Spectrum of Lytic Activity against Clinically Relevant Staphylococci, Including Methicillin-Resistant *Staphylococcus aureus*. J. Bacteriol. 2005 October; 187 (20):7161-4.
3. Horgan M et al., Phage lysin LysK can be truncated to its CHAP domain and retain lytic activity against live antibiotic-resistant staphylococci. Appl Environ Microbiol. 2009, 75(3): 872-874
4. Fischetti et al., Phage antibacterials make a comeback, Nature Biotechnology 19, 734-735 (1 Aug. 2001)
5. Bujard et al., Independent and tight regulation of transcriptional units in *Escherichia coli* via the LacR/O, the TetR/O and AraC/I1-I2 regulatory elements. Nucleic Acids Res. 1997; 15; 25(6):1203-10.
6. Enzybiotics: Antibiotic Enzymes as Drugs and Therapeutics; Enzybiotics: Antibiotic Enzymes as Drugs and Therapeutics, 2010. Ed. Villa and Veiga Crespo
7. Becker, S.C., J. Foster-Frey, et al. (2008). "The phage K lytic enzyme LysK and lysostaphin act synergistically to kill MRSA." FEMS Microbiol Lett 287(2): 185-91.
8. Brogden, K. A. (2005). "Antimicrobial peptides: pore formers or metabolic inhibitors in bacteria?" Nat Rev Microbiol 3(3): 238-50.
9. Cegelski, L., G. R. Marshall, et al. (2008). "The biology and future prospects of antivirulence therapies." Nat Rev Microbiol 6(1): 17-27.
10. d'Herelle, F. (1917). "An invisible antagonist microbe of dysentery *bacillus*." Comptes Rendus Hebdomadaires des Seances de L'academie des Sciences (165): 373-5.
11. Dai, W., A. Hodes, et al. (2010). "Three-dimensional structure of tropism-switching *Bordetella* bacteriophage." Proc Natl Acad Sci USA.
12. Deresinski, S. (2009). "Bacteriophage Therapy: Exploiting Smaller Fleas." CLIN INFECT DIS.—
13. Hancock, R. E. W. and H.-G. Sahl (2006). "Antimicrobial and host-defense peptides as new anti-infective therapeutic strategies." Nat Biotechnol 24(12): 1551-7.
14. Horgan, M., G. O'Flynn, et al. (2009). "Phage lysin LysK can be truncated to its CHAP domain and retain lytic activity against live antibiotic-resistant staphylococci." Appl Environ Microbiol 75(3): 872-4.
15. Jensen, E. C., H. S. Schrader, et al. (1998). "Prevalence of broad-host-range lytic bacteriophages of *Sphaerotilus natans, Escherichia coli*, and *Pseudomonas aeruginosa*." Appl Environ Microbiol 64(2): 575-80.
16. Keller, L. and M. G. Surette (2006). "Communication in bacteria: an ecological and evolutionary perspective." Nat Rev Microbiol 4(4): 249-58.
17. Lederberg, J. (1996). "Smaller fleas . . . ad infinitum: therapeutic bacteriophage redux." Proc Natl Acad Sci USA 93(8): 3167-8.
18. Liu, M., R. Deora, et al. (2002). "Reverse transcriptase-mediated tropism switching in *Bordetella* bacteriophage." Science 295(5562): 2091-4.
19. Lu and J. J. Collins (2007). "Dispersing biofilms with engineered enzymatic bacteriophage." Proc Natl Acad Sci USA.
20. Lu, T. and J. Collins (2009). "Engineered bacteriophage targeting gene networks as adjuvants for antibiotic therapy." Proc Natl Acad Sci USA.
21. Merril, C. R., D. Scholl, et al. (2003). "The prospect for bacteriophage therapy in Western medicine." Nature reviews Drug discovery 2(6): 489-97.
22. Movva, N. R., K. Nakamura, et al. (1980). "Amino acid sequence of the signal peptide of ompA protein, a major outer membrane protein of *Escherichia coli*." J Biol Chem 255(1): 27-9.
23. O'Flaherty, S., A. Coffey, et al. (2005). "The recombinant phage lysin LysK has a broad spectrum of lytic activity against clinically relevant staphylococci, including methicillin-resistant *Staphylococcus aureus*." J Bacteriol 187(20): 7161-4.

24. Rabinovitch, A., H. Hadas, et al. (1999). "Model for bacteriophage T4 development in *Escherichia coli*." J Bacteriol 181(5): 1677-83.

25. Skurnik, M. and E. Strauch (2006). "Phage therapy: facts and fiction." Int J Med Microbiol 296(1): 5-14.

26. Stone, R. (2002). "Bacteriophage therapy. Stalin's forgotten cure." Science 298(5594): 728-31.

27. Twort, F. W. (1915). "An investigation on the nature of ultra-microscopic viruses." Lancet (2): 1241-3.

The invention claimed is:

1. An engineered bacteriophage comprising a heterologous nucleic acid operatively linked to a promoter, wherein the nucleic acid encodes at least one antimicrobial polypeptide fused to an N-terminal secretory signal sequence, the antimicrobial peptide having antimicrobial properties when outside a bacterial cell.

2. The bacteriophage of claim 1, wherein the antimicrobial polypeptide is an antimicrobial peptide or a naturally occurring bacterial peptide.

3. The bacteriophage of claim 1, wherein the antimicrobial peptide is selected from: lndolicidin (SEQ ID NO: 6), Cecropin PI (SEQ ID NO: 11), Dermaseptin (SEQ ID NO: 14), Ponericin WI (SEQ ID NO: 44), Ponericin W3 (SEQ ID NO: 40), Ponericin W4 (SEQ ID NO: 18), Ponericin W5 (SEQ ID NO: 42), Ponericin W6 (SEQ ID NO: 22) and variants thereof.

4. The bacteriophage of claim 1, wherein the antimicrobial polypeptide is a lytic enzyme.

5. The bacteriophage of claim 4, wherein the lytic enzyme is LysK or a functional fragment thereof.

6. The bacteriophage of claim 5, wherein the functional fragment of LysK is CHAP165 (SEQ ID NO: 71) or a variant thereof.

7. The bacteriophage of claim 1, wherein the bacteriophage is a T7 or M13 bacteriophage.

8. The bacteriophage of claim 1, wherein the bacteriophage is a lysogenic bacteriophage.

9. The bacteriophage of claim 1, wherein the bacteriophage is a lytic bacteriophage.

10. The bacteriophage of claim 1, wherein the bacteriophage infects a bacteria selected from *Escherichia coli, Pseudomonas aeruginosa, Staphylococcus aureus*, and *Enterococcus faecalis.*

11. The bacteriophage of claim 1, wherein the bacteriophage encodes an antimicrobial peptide having from 12-50 amino acids.

12. The bacteriophage of claim 1, wherein the bacteriophage encodes an antimicrobial peptide having from 15-30 amino acids.

13. The bacteriophage of claim 1, wherein the N-terminal secretory signal sequence is recognized by a Type I, Type II, or Type V bacterial secretion system.

14. The bacteriophage of claim 1, wherein the secretory signal sequence is recognized by a secA1, secA2 or Tat secretion pathway.

15. The bacteriophage of claim 1, wherein the secretory signal sequence is an Omp signal sequence.

16. The bacteriophage of claim 15, wherein the secretory signal sequence is an OmpA signal sequence.

17. The bacteriophage of claim 1, wherein the antimicrobial peptide has antimicrobial properties against one or both of gram positive and gram negative bacteria.

18. An engineered bacteriophage comprising a heterologous nucleic acid operatively linked to a promoter, the nucleic acid encoding an antimicrobial peptide (AMP) of 12 to 50 amino acids in length fused to an N-terminal bacterial secretion signal sequence, the AMP having antimicrobial properties when outside a bacterial cell.

19. The engineered bacteriophage of claim 1, wherein the antimicrobial peptide, when secreted from a host bacterial cell, reduces the viability of a heterogeneous bacterial population not infected with the engineered bacteriophage.

* * * * *